United States Patent
Yang et al.

(10) Patent No.: US 11,084,808 B2
(45) Date of Patent: *Aug. 10, 2021

(54) OXOPICOLINAMIDE DERIVATIVE, PREPARATION METHOD THEREFOR AND PHARMACEUTICAL USE THEREOF

(71) Applicants: Jiangsu Hengrui Medicine Co., Ltd., Jiangsu (CN); Shanghai Hengrui Pharmaceutical Co., Ltd., Shanghai (CN)

(72) Inventors: Fanglong Yang, Shanghai (CN); Weimin Wang, Shanghai (CN); Xiaodong Li, Shanghai (CN); Gang Chen, Shanghai (CN); Feng He, Shanghai (CN); Weikang Tao, Shanghai (CN)

(73) Assignees: Jiangsu Hengrui Medicine Co., Ltd., Jiangsu (CN); Shanghai Hengrui Pharmaceutical Co., Ltd., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/804,180

(22) Filed: Feb. 28, 2020

(65) Prior Publication Data

US 2020/0199115 A1    Jun. 25, 2020

Related U.S. Application Data

(63) Continuation of application No. 16/328,128, filed as application No. PCT/CN2017/099579 on Aug. 30, 2017, now Pat. No. 10,633,375.

(30) Foreign Application Priority Data

Aug. 31, 2016  (CN) .......................... 201610789384.9
Jan. 9, 2017  (CN) .......................... 201710014133.8

(51) Int. Cl.
*C07D 413/14*  (2006.01)
*C07D 401/14*  (2006.01)
(Continued)

(52) U.S. Cl.
CPC ........ *C07D 413/14* (2013.01); *A61K 31/4439* (2013.01); *A61P 7/02* (2018.01); *A61P 9/10* (2018.01); *A61P 11/00* (2018.01); *C07D 213/02* (2013.01); *C07D 213/89* (2013.01); *C07D 401/06* (2013.01); *C07D 401/12* (2013.01); *C07D 401/14* (2013.01); *C07D 405/06* (2013.01); *C07D 405/10* (2013.01); *C07D 405/12* (2013.01); *C07D 405/14* (2013.01); *C07D 409/12* (2013.01); *C07D 413/12* (2013.01); *C07D 417/12* (2013.01); *C07D 487/04* (2013.01)

(58) Field of Classification Search
CPC .. C07D 413/14; C07D 487/04; C07D 401/14; C07D 401/12; C07D 213/02; C07D 213/89; C07D 401/06; C07D 405/12; C07D 405/14; C07D 413/12; C07D 417/12; A61K 31/4439; A61P 9/10; A61P 7/02
USPC .......................................................... 514/230
See application file for complete search history.

(56) References Cited

U.S. PATENT DOCUMENTS 5,981,529 A    11/1999  Baker et al.
10,633,375 B2 *  4/2020  Yang .................... C07D 401/12
(Continued)

FOREIGN PATENT DOCUMENTS

CN    103450146 A1    12/2013
CN    103804358 A      5/2014
(Continued)

OTHER PUBLICATIONS

Chowdhury et al., "Tetracyclic spirooxindole blockers of hNav1.7: activity in vitro and in CFA-induced inflammatory pain model," Med. Chem. Res., vol. 22, pp. 1825-1836 (2013).
(Continued)

*Primary Examiner* — Tracy Vivlemore
*Assistant Examiner* — Ebenezer O Sackey
(74) *Attorney, Agent, or Firm* — Ice Miller LLP

(57) ABSTRACT

The present invention relates to an oxopicolinamide derivative, a preparation method therefor and the pharmaceutical use thereof. In particular, the present invention relates to an oxopicolinamide derivative as shown in the general formula (AI), a preparation method therefor and a pharmaceutical composition comprising the derivative, and to the use thereof as a therapeutic agent, in particular as an inhibitor of blood coagulation factor XIa (Factor XIa, FXIa for short) and the use thereof in the preparation of a drug for treating diseases such as thromboembolism, wherein the definition of each substituent in the general formula (AI) is the same as defined in the description.

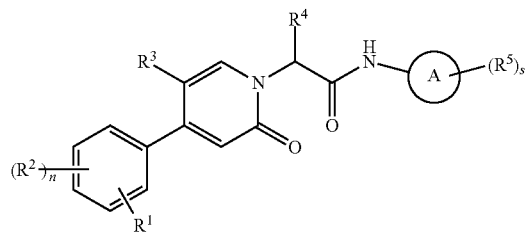

(AI)

8 Claims, No Drawings

(51) Int. Cl.

| | | |
|---|---|---|
| C07D 401/12 | (2006.01) | |
| C07D 213/02 | (2006.01) | |
| C07D 213/89 | (2006.01) | |
| C07D 401/06 | (2006.01) | |
| C07D 405/06 | (2006.01) | |
| C07D 405/10 | (2006.01) | |
| C07D 405/12 | (2006.01) | |
| C07D 405/14 | (2006.01) | |
| C07D 409/12 | (2006.01) | |
| C07D 413/12 | (2006.01) | |
| C07D 417/12 | (2006.01) | |
| C07D 487/04 | (2006.01) | |
| A61P 7/02 | (2006.01) | |
| A61K 31/4439 | (2006.01) | |
| A61P 9/10 | (2006.01) | |
| A61P 11/00 | (2006.01) | |

(56) References Cited

U.S. PATENT DOCUMENTS

| | | |
|---|---|---|
| 2005/0171148 A1 | 8/2005 | Mjalli et al. |
| 2010/0216783 A1 | 8/2010 | Bhat et al. |
| 2014/0349990 A1 | 11/2014 | Blank et al. |
| 2016/0271105 A1 | 9/2016 | Hadida-Ruah et al. |
| 2016/0282369 A1 | 9/2016 | Cravatt et al. |

FOREIGN PATENT DOCUMENTS

| | | | |
|---|---|---|---|
| CN | 104136431 | A | 11/2014 |
| CN | 105348251 | A | 2/2016 |
| CN | 106242941 | A | 12/2016 |
| JP | 2008013527 | A | 1/2008 |
| WO | 9630396 | A1 | 10/1996 |
| WO | 9941276 | A1 | 8/1999 |
| WO | 2003095438 | A1 | 11/2003 |
| WO | 2004002405 | A2 | 1/2004 |
| WO | 2006/067445 | A2 | 6/2006 |
| WO | 2007048070 | A2 | 4/2007 |
| WO | 2009079767 | A9 | 10/2009 |
| WO | 2010146881 | A1 | 12/2010 |
| WO | 2011100285 | A1 | 8/2011 |
| WO | 2012044090 | A2 | 4/2012 |
| WO | 2012087519 | A1 | 6/2012 |
| WO | 2012092880 | A1 | 7/2012 |
| WO | 2012118216 | A1 | 9/2012 |
| WO | 2012162482 | A1 | 11/2012 |
| WO | 2012177638 | A1 | 12/2012 |
| WO | 2013006792 | A1 | 1/2013 |
| WO | 2013042782 | A1 | 3/2013 |
| WO | 2013056034 | A1 | 4/2013 |
| WO | 2013056060 | A1 | 4/2013 |
| WO | 2013068467 | A1 | 5/2013 |
| WO | 2013093484 | A1 | 6/2013 |
| WO | 2013142266 | A1 | 9/2013 |
| WO | 2013146963 | A1 | 10/2013 |
| WO | 2014065413 | A1 | 5/2014 |
| WO | 2014100833 | A1 | 6/2014 |
| WO | 2014135095 | A1 | 9/2014 |
| WO | 2014160592 | A2 | 10/2014 |
| WO | 2015063093 | A1 | 5/2015 |
| WO | 2015090599 | A1 | 6/2015 |
| WO | 2015110435 | A1 | 7/2015 |
| WO | 2015120777 | A1 | 8/2015 |
| WO | 2015120786 | A1 | 8/2015 |
| WO | 2015129926 | A1 | 9/2015 |
| WO | 2015143380 | A1 | 9/2015 |
| WO | 2016044626 | A1 | 3/2016 |
| WO | 2016045125 | A1 | 3/2016 |
| WO | 2016046156 | A1 | 3/2016 |
| WO | 2016046159 | A1 | 3/2016 |
| WO | 2016053794 | A1 | 4/2016 |
| WO | 2017005725 | A1 | 1/2017 |

OTHER PUBLICATIONS

Kim et al., "Novel JAK1-selective benzimidazole inhibitors with enhanced membrane permeability," Bioorganic & Medicinal Chemistry Letters, vol. 26, pp. 3213-3215 (2016).
Liu et al., "Practical Synthesis of a Peptide Deformylase (PDF) Inhibitor," Organic Process Research & Development, vol. 12, pp. 183-191 (2008).
Ross et al., "A straightforward prepartation of primary alkyl triflates and their utility in the synthesis of derivatives of ethidium," J. Chem. Soc., Perkin Trans., vol. 1, pp. 571-574 (2000).
Minoshima et al., "DNA Alkylation by Pyrrole-Imidazole seco-CBI Conjugates with an Indole Linker: Sequence-Specific DNA Alkylation with 10-Base-Pair Recognition through Heterodimer Formation," J. Am. Chem. Soc., vol. 129, pp. 5384-5390 (2007).
Prybylski et al., "Regioselective synthesis of 2-O-acyl-3-O-(1-acyloxyalkyl) prodrugs of 5,6-isopropylidene-L-ascorbic acid," Tetrahedron Letter, vol. 57, pp. 1619-1621 (2016).
Zhong et al., "Substituted indolin-2-ones as p90 ribosomal S6 protein kinase 2 (RSK2) inhibitors: Molecular docking simulation and structure-activity relationship analysis," Bioorganic & Medicinal Chemistry, vol. 21, pp. 1724-1734 (2013).
Ferlin et al., "Synthesis and in Vitro and in Vivo Antitumor Activity of 2-Phenylpyrroloquinolin-4-ones," J. Med. Chem., vol. 48, pp. 3417-3427 (2005).
Dey et al., "Highly selective reduction of nitroarenes by iron(0) nanoparticles in water," Chem. Commun., vol. 48, pp. 7982-7984 (2012).
Son et al., "High-Potency Phenylquinoxalinone Cystic Fibrosis Transmembrane Conductance Regulator (CRTR) Activators," Journal of Medicinal Chemistry, vol. 60, pp. 2401-2410 (2017).
Jiang et al., "CuI/4-Hydro-L-proline as a More Effective Catalytic System for Coupling of Aryl Bromides with N-Boc -Hydrazine and Aqueous Ammonia," J. Org. Chem., vol. 74, pp. 4542-4546 (2009).
Chatterjee et al., "A Metal and Base-Free Chemoselective Primary Amination of Boronic Acids Using Cyanamidyl/Arylcyanamidyl Radical as Aminating Species: Synthesis and Mechanistic Studies by Density Functional Theory," The Journal of Organic Chemistry, vol. 81, pp. 5120-5127 (2016).
Doherty et al., "Discovery of Potent, Orally Available Vanilloid Receptor-1 Antagonists. Structure-Activity Relationship of N-Aryl Cinnamides," J. Med. Chem., vol. 48, pp. 71-90 (2005).
O'Connor et al., "Second-Generation Peptidomimetic Inhibitors of Protein Farnesyltransferase Demonstrating Improved Cellular Potency and Significant in Vivo Efficacy," J. Med. Chem., vol. 42, pp. 3701-3710 (1999).
Argade et al., "Design, synthesis of diaminopyrimidine inhibitors targeting IgE—and IgG-mediated activation of Fc receptor signaling," Bioorganic & Medicinal Chemistry Letters, vol. 25, pp. 2122-2128 (2015).
Fu et al., "Mechanism of Inactivation of g-Aminobutyric Acid Aminotransferase by (S)-4-Amino-4,5-dihydro-2-tiophenecarboxylic Acid," J. Am. Chem. Soc., vol. 121, pp. 7751-7759 (1999).
International Search Report dated Dec. 1, 2017 in International Application No. PCT/CN2017/099579.
International Preliminary Report on Patentability dated Mar. 5, 2019 in International Application No. PCT/CN2017/099579; dated Mar. 14, 2019.
Corte et al., "Pyridine and pyridinone-based factor XIa inhibitors" Bioorganic & Medicinal Chemistry Letters, 29, pp. 925-930, 2015.
Quan et al., "Tetrahydroquinoline Derivaties as Potent and Selective Factor XIa Inhibitors", Medicinal Chemistry, 57, pp. 955-969, 2014.
Al-Horani et al., "Factor XIa inhibitors: A review of the patent literature" Expert Opinion, vol. 26, No. pages 323-345, 2016.
Eriksson et al., "Novel Oral Factor Xa and Thrombin Inhibitors in the Management of Thromboembolism," Annual Review of Medicine, vol. 62, pp. 41-57 (2011).
Asakai et al., "Factor Xi in Ashkenazi Jews in Israel," The New England Journal of Medicine, vol. 325, No. 3, pp. 153-158 (Jul. 18, 1991).

(56) References Cited

OTHER PUBLICATIONS

Salomon et al., "Prevalence, causes, and characterization of factor Xi inhibitors in patients with inherited factor Xi deficiency," Blood, vol. 101, No. 12, pp. 4783-4788 (Jun. 15 2003).
Schumacher et al., "Inhibition of Factor Xia as a New Approach to Anticoagulation," Arteriosclerosis, Thrombosis, and Vascular Biology, vol. 30, pp. 388-392 (Mar. 2010).
Cheng et al., "A role for factor Xiia-mediated factor Xi activation in thrombus formation in vivo," Blood, vol. 116, No. 19, pp. 3981-3989 (2010).
Cushman et al., "Coagulation factors Ix through Xiii and the risk of future venous thrombosis: the Longitudinal Investigation of Thromboembolism Etiology," Blood, vol. 114, No. 14, pp. 2878-2883 (Oct. 1 2009).
Salomon et al., "Patients with severe factor Xi deficiency have a reduced incidence of deep-vein thrombosis," Thrombosis and Haemostasis, vol. 105, pp. 269-273 (2011).
Crosby et al., "Antithrombotic Effect of Antisense Factor Xi Oligonucleotide Treatment in Primates," Arteriosclerosis, Thrombosis, and Vascular Biology, vol. 33, No. 7, pp. 1670-1678 (Jul. 2013).
Zhao et al., "Synthesis and Biological Evaluation of Antibody Conjugates of Phosphate Prodrugs of Cytotoxic DNA Alkylators for the Targeted Treatment of Cancer," Journal of Medicinal Chemistry, vol. 55, No. 2, pp. 766-782 (2012).
Nishikawa et al., "Chiral Pyridinium Phosphoramide as a Dual Brønsted Acid Catalyst for Enantioselective Diels-Alder Reaction," Organic Letters, vol. 18, pp. 2004-2007 (2016).
Discekici et al., "A highly reducing metal-free photoredox catalyst: design and application in radical dehalogenations," Chemical Communications, vol. 51, No. 58, pp. 11705-11708 (2015).
Yamamoto et al., "Asymmetric addition of arylboronic acids to glyoxylate catalyzed by a ruthenium/Me-BIPAM complex," Chemical Communications, vol. 48, No. 22, pp. 2803-2805 (2012).
Nitti et al., "Conjugated Thiophene-Fused Isatin Dyes through Intramolecular Direct Arylation," Journal of Organic Chemistry, vol. 81, No. 22, pp. 11035-11042 (2016).
Dudnik et al., "A General Strategy Toward Aromatic 1,2-Ambiphilic Synthons: Palladium-Catalyzed ortho-Halogenation of PyDipSi-Arenes," Angewandte Chemie, International Edition, vol. 49, No. 46, pp. 8729-8732 (2010).
Shimizu et al., "Microwave-Assisted Deacylation of Unactivated Amides Using Ammonium-Salt-Accelerated Transamidation," Angewandte Chemie, International Edition, vol. 51, No. 34, pp. 8564-8567 (2012).
Granchi et al., "Structural Optimization of 4-Chlorobenzoylpiperidine Derivatives for the Development of Potent, Reversible, and Selective Monoacylglycerol Lipase (MAGL) Inhibitors," Journal of Medicinal Chemistry, vol. 59, No. 22, pp. 10299-10314 (2016).
Thomas et al., "Overcoming steric effects in the coupling reaction of alkyloxycarbonyloxymethyl (AOCOM) halides with phenols: an efficient synthesis of AOCOM phenolic prodrugs," Tetrahedron Letters, vol. 48, No. 1, pp. 109-112 (2007).
Champagne et al., "Friedel-Crafts Reaction of Benzyl Fluorides: Selective Activation of C F Bonds as Enabled by Hydrogen Bonding," Angewandte Chemie, International Edition, vol. 53, No. 50, pp. 13835-13839 (2014).
Khazdooz et al., "An efficient and selective method for the iodination and bromination of alcohols under mild conditions," Tetrahedron Letters, vol. 57, No. 2, pp. 168-171 (2016).
Partridge et al., "Enantioenriched synthesis of Escitalopram using lithiation-borylation methodology," Tetrahedron, vol. 67, No. 52, pp. 10082-10088 (2011).
Cheng et al., "Unparalleled Ease of Access to a Library of Biheteroaryl Fluorophores via Oxidative Cross-Coupling Reactions: Discovery of Photostable NIR Probe for Mitochondria," Journal of the American Chemical Society, vol. 138, No.14, pp. 4730-4738 (2016).
Sun et al., "6,6-Fused heterocyclic ureas as highly potent TRPV1 antagonists," Bioorganic & Medicinal Chemistry Letters, vol. 25, No. 4, pp. 803-806 (2015).
Morse et al., "Bulk iron pyrite as a catalyst for the selective hydrogenation of nitroarenes," Chemical Communications, vol. 53, No. 35, pp. 4807-4810 (2017).
Quinn et al, "Rapid reduction of heteroaromatic nitro groups using catalytic transfer hydrogenation with microwave heating," Tetrahedron Letters, vol. 51, No. 5, pp. 786-789 (2010).
Jagadeesh et al., "Efficient and highly selective iron-catalyzed reduction of nitroarenes," Chemical Communications, vol. 47, No. 39, pp. 10972-10974 (2011).
Zhao et al., "Palladium-Catalyzed Beta-Mesylation of Simple Amide via Primary sp3 C-H Activation," Organic Letters, vol. 19, No. 7, pp. 1768-1771 (2017).
Reddy Battu et al, "Siderophore-mediated Antibiosis of rhizobacterial fluorescent Pseudomonads against Rice fungal pathogens," International Journal of PharmTech Research, vol. 1, No. 2, pp. 227-229 (2009).
Choi et al., "Azobenzene-based chloride transporters with light-controllable activities," Chemical Communications, vol. 50, No. 97, pp. 15305-15308 (2014).
Elancheran et al., "Design and development of oxobenzimidazoles as novel androgen receptor antagonists," Medicinal Chemistry Research, vol. 25, No. 4, pp. 539-552 (2016).
Sharma et al., "Metal-Free Transfer Hydrogenation of Nitroarenes in Water with Vasicine: Revelation of Organocatalytic Facet of an Abundant Alkaloid," Journal of Organic Chemistry, vol. 79, No. 19, pp. 9433-9439 (2014).
Suh et al., "Novel Potent Antagonists of Transient Receptor Potential Channel, Vanilloid Subfamily Member 1: Structure-Activity Relationship of 1,3-Diarylalkyl Thioureas Possessing New Vanilloid Equivalents," Journal of Medicinal Chemistry, vol. 48, No. 18, pp. 5823-5836 (2005).
Alonso et al., "Structure-activity relationships (SAR) and structure-kinetic relationships (SKR) of bicyclic heteroaromatic acetic acids as potent CRTh2 antagonists III: The role of a hydrogen-bond acceptor in long receptor residence times," Bioorganic & Medicinal Chemistry Letters, vol. 24, No. 21, pp. 5127-5133 (2014).
Cantillo et al., "A Scalable Procedure for Light-Induced Benzylic Brominations in Continuous Flow," Journal of Organic Chemistry, vol. 79, No. 1, pp. 223-229 (2014).
Mao et al., "Palladium(0)-catalyzed cyclopropanation of benzyl bromides via C(sp3)-H bond activation," Chemical Communications, vol. 50, No. 28, pp. 3692-3694 (2014).
Kabalka et al., "Reductive bromination of aromatic aldehydes using alkylboron dibromides," Tetrahedron Letters, vol. 41, pp. 5161-5164 (2000).
Ajvazi et al., "Direct halogenation of alcohols with halosilanes under catalyst—and organic solvent-free reaction conditions," Tetrahedron Letters, vol. 57, No. 22, pp. 2430-2433 (2016).
Tan et al., "Silver-Catalyzed Decarboxylative Bromination of Aliphatic Carboxylic Acids," Organic Letters, vol. 19, No. 7, pp. 1634-1637 (2017).
Doni et al., "Overturning Established Chemoselectivities: Selective Reduction of Arenes over Malonates and Cyanoacetates by Photoactivated Organic Electron Donors," Journal of the American Chemical Society, vol. 135, No. 30, pp. 10934-10937 (2013).
Zhiquan et al., "Russian Nesting Doll Complexes of Molecular Baskets and Zinc Containing TPA Ligands," Journal of the American Chemical Society, vol. 138, No. 26, pp. 8253-8258 (2016).
Lin et al., "A Rising Star: Truxene as a Promising Hole Transport Material in Perovskite Solar Cells," Journal of Physical Chemistry, vol. 121, pp. 21729-21739 (2017).
Liu et al., "Semiconductor quantum dots photosensitizing release of anticancer drug," Chemical Communications, vol. 47, No. 5, pp. 1482-1484 (2011).
Xu et al., "Substituted 5,6,11,12-Tetradehydrodibenzo[a,e]cyclooctenes: Syntheses, Properties, and DFT Studies of Substituted Sondheimer-Wong Diynes," The Journal of Organic Chemistry, vol. 79, No. 23, pp. 11592-11608 (2014).
Quattropani et al., "Pharmacophore-Based Design of Novel Oxadiazoles as Selective Sphingosine-1-phosphate (S1P) Receptor Agonists with in vivo Efficacy," ChemMedChem, vol. 10, No. 4, pp. 688-714 (2015).

(56) References Cited

OTHER PUBLICATIONS

Ashokkumar et al., "One-pot synthesis of alpha,beta-epoxy ketones through domino reaction between alkenes and aldehydes catalyzed by proline based chiral organocatalysts," Organic & Biomolecular Chemistry, vol. 15, No. 12, pp. 2551-2561 (2017).

Crowley et al., "Development of Glucose Regulated Protein 94-Selective Inhibitors Based on the Bnlm and Radamide Scaffold," Journal of Medicinal Chemistry, vol. 59, No. 7, pp. 3471-3488 (2016).

Sasaki et al., "Sequence-Specific Alkylation of Double-Strand Human Telomere Repeat Sequence by Pyrrole-Imidazole Polyamides with Indole Linkers," Journal of the American Chemical Society, vol. 128, No. 37, pp. 12162-12168 (2006).

Rajule et al., "Perturbing pro-survival proteins using quinoxaline derivatives: A structure-activity relationship study," Bioorganic & Medicinal Chemistry Letters, vol. 20, No. 7, pp. 2227-2234 (2012).

Hu et al., "Palladium-Catalyzed Ring-Forming Aminoalkenylation of Alkenes with Aldehydes Initiated by Intramolecular Aminopalladation," Agnew. Chem. Int. Ed., vol. 56, pp. 2473-2477 (2017).

Zhang et al., "Synthesis of Dibenzo[c,e]oxepin-5(7H)-ones from Benzyl Thioethers and Carboxylic Acids: Rhodium-Catalyzed Double C-H Activation Controlled by Different Directing Groups," Agnew. Chem., vol. 127, pp. 5568-5572 (2015).

van der Klei et al., "Synthesis and Spectroscopic Characterization of [1'-14C]Ubiquinone-2 [1'-14C]-5-Demethoxy-5-hydroxyubiquinone-2, and [1'-14C]-5-Demethoxyubiquinone-2," Eur. J. Org. Chem., pp. 3015-3023 (2002).

* cited by examiner

OXOPICOLINAMIDE DERIVATIVE, PREPARATION METHOD THEREFOR AND PHARMACEUTICAL USE THEREOF

CROSS-REFERENCE TO RELATED APPLICATION

This application is a Continuation of co-pending U.S. patent application Ser. No. 16/328,128, filed Feb. 25, 2019, which was a Section 371 of International Application No. PCT/CN2017/099579, filed Aug. 30, 2017, which was published in the Chinese language on Mar. 8, 2018, under International Publication No. WO 2018/041122 A1, which claims priority under 35 U.S.C. § 119(b) to Chinese Application Nos. 201610789384.9, filed Aug. 31, 2016 and 201710014133.8, filed Jan. 9, 2017, the disclosures of which are incorporated herein by reference in their entirety.

FIELD OF THE INVENTION

The present invention relates to a novel class of oxopyridinyl amide derivatives, a preparation method thereof, and a pharmaceutical composition comprising the same, and use thereof as a therapeutic agent, in particular as an inhibitor of blood coagulation factor XIa (Factor XIa, abbreviated as FXIa) and use thereof in the preparation of a medicament for treating and/or preventing diseases such as thromboembolism.

BACKGROUND OF THE INVENTION

Every year, cardiovascular and cerebrovascular diseases such as cerebrovascular, cerebral infarction, myocardial infarction, coronary heart disease and arteriosclerosis take nearly 12 million lives, which are close to ¼ of the total death toll in the world, and become the number one enemy of human health. The number of people dying from cardiovascular disease in China each year is more than 2.6 million, and 75% of surviving patients are disabled, and more than 40% of them are severely disabled. The problem of thrombosis caused by cardiovascular and cerebrovascular diseases and diabetes and complications thereof has become an urgent problem to be solved today.

According to Datamonitor 2011 data from independent market analysts, with the production of generic drugs, the share of cardiovascular and metabolic diseases in the seven major markets will peak in 2011 and then gradually decrease. The sales will decrease from $109 billion in 2010 to $101 billion in 2019. The thrombus market remained basically stable, from $19.5 billion in 2010 to $18.9 billion in 2019 (Datamonitor: HC00034-001, HC00139-001). Guangzhou Punctuation 2011 research report also showed that China's anti-thrombotic drug market scale in 2011 reached 8.135 billion yuan, year-on-year growth of 20.52%, with huge market potential (anti-thrombotic drug market research report: Guangzhou Punctuation (2011)).

The process of human blood coagulation, consisting of an intrinsic pathway, an extrinsic pathway, and a common pathway (Annu. Rev. Med. 2011.62:41-57), is a chain reaction in which the process is continuously enhanced and amplified by sequential activation of multiple zymogens. The coagulation cascade is initiated by the endogenous pathway (also known as the contact activation pathway) and the exogenous pathway (also known as the tissue factor pathway) to produce FXa, which then forms thrombin (FIIa) by a common pathway, and fibrin is finally formed.

The endogenous pathway refers to the process from the activation of factor XII to the formation of XIa-VIIIa-Ca2+PL complex and the activation of factor X, and the exogenous coagulation pathway refers to the process from the release of tissue factor (TF) to the formation of TF-VIIaCa2+ complex and the activation of factor X. The common pathway refers to the process in which after the formation of factor Xa, the two pathways are combined into one, prothrombin is activated, and fibrin is finally formed, and FXI is necessary for maintaining the endogenous pathway and plays a key role in the amplification of the coagulation cascade. In the coagulation cascade, thrombin feedback activates FXI, and activated FXI (FXIa) in turn promotes the mass production of thrombin, thereby amplifying the coagulation cascade. Therefore, antagonists of FXI have been extensively developed for the treatment of various thrombi.

Traditional anticoagulant drugs such as warfarin, heparin, low molecular weight heparin (LMWH), and new drugs marketed in recent years, such as FXa inhibitors (rivaroxaban, apixaban, etc.) and thrombin inhibitors (dabigatran etexilate, hirudin, etc.,) have a good effect on reducing thrombosis, and occupy the majority of cardiovascular and cerebrovascular market with their remarkable effectiveness, but their side effects are also more and more significant, of which "bleeding risk" is one of the most serious problems (N. Engl. J. Med. 1991; 325: 153-8, Blood. 2003; 101: 4783-4788).

Human FXI deficiency (FXI activity<15 U/dL) is also known as type C hemophilia. This type of patient has a mild bleed phenotype and seldom spontaneous bleeding. Even in the case of injury or surgery, the body's hemostatic function is not affected. Patients with type C hemophilia can be pregnant normally (Arterioscler Thromb. Vasc. Biol. 2010; 30: 388-392). This shows that the safety of FXIa is significantly better than that of FXa. Therefore, the target FXIa has become a hot research topic among major companies and research institutions. In the thrombus model, inhibition of FXIa factor can effectively inhibit thrombus formation, but in the case of more severe thrombosis, FXIa has little effect (Blood. 2010; 116 (19): 3981-3989). Clinical statistics show that increasing the amount of FXIa increases the prevalence of VTE (Blood 2009: 114: 2878-2883), while those with severe FXIa deficiency have a reduced risk of suffering from DVT (Thromb. Haemost. 2011; 105: 269-273).

FXIa is an emerging target, and patents disclosing compounds having FXIa inhibitory activity include WO9630396, WO9941276, WO2013093484, WO2004002405, WO2013056060, WO2017005725, and US20050171148. Among them, only Bayer's antisense oligonucleotides (ASO) BAY-2306001 entered the clinical phase II study and achieved good results. In the clinical Phase I trial of the drug, the subject's FXI activity showed a sustained, dose-dependent decrease, accompanied by a prolongation of aPTT, even if the FXI in the body fell to an undetectable level, there would be no drug-related hemorrhagic symptoms. The results show the potential of FXIa as an emerging target (Arterioscler Thromb. Vasc. Biol., 2013, 33(7) 1670-1678). However, FXI ASO is administered by injection and has a slow onset of action. It takes several weeks to form an antithrombotic effect, which may be limited as a preventive drug. In terms of small molecule inhibitors, only FXIa inhibitors (BMS company) entered clinical Phase I in 2014. So far, no clinical results have been reported, therefore, the research of new FXIa inhibitors is of great significance.

The present invention devises a novel small molecule FXIa antagonist having the structure of formula (AI), wherein R¹ in the formula is C(O)R⁷, which has a significant improvement on the anticoagulant effect and pharmacological absorption of the entire compound. The compounds of the present invention have higher activity than the disclosed patented compounds having a similar core structure. In particular, the compound of the present invention exhibits excellent anticoagulant action against human blood, and has good pharmacokinetic activity, and can be used for effectively treating and/or preventing cardiovascular and cerebrovascular diseases and thrombotic symptoms.

SUMMARY OF THE INVENTION

The object of the present invention is to provide a compound of the formula (AI):

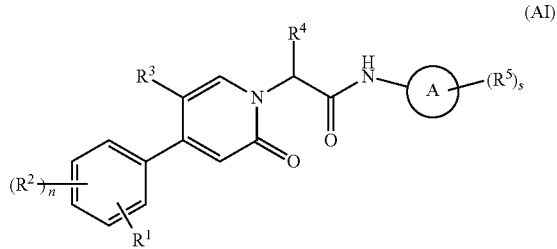

or a tautomer, mesomer, racemate, enantiomer, diastereomer thereof, or mixture thereof, or a pharmaceutically acceptable salt thereof, or a prodrug thereof, wherein:

ring A is an aryl or a heteroaryl;

R¹ is —C(O)R⁷;

each R² is identical or different and each is independently selected from the group consisting of hydrogen, halogen, alkyl, haloalkyl, alkoxy, haloalkoxy, amino, nitro, cyano, hydroxy, hydroxyalkyl, cycloalkyl, heterocyclyl, aryl and heteroaryl;

R³ is selected from the group consisting of halogen, alkyl, haloalkyl, alkoxy, cycloalkyloxy, haloalkoxy, amino, nitro, cyano, hydroxy, hydroxyalkyl and alkylthio, wherein the alkyl, alkoxy, haloalkyl, haloalkoxy, hydroxyalkyl and alkylthio are each optionally substituted by one or more groups selected from the group consisting of deuterium, halogen, alkoxy, haloalkoxy, amino, nitro, cyano, hydroxy, and hydroxyalkyl;

R⁴ is selected from the group consisting of hydrogen, alkyl, alkoxy, haloalkyl, hydroxyalkyl, cycloalkyl, cycloalkyloxy, heterocyclyl, aryl and heteroaryl, wherein the alkyl, cycloalkyl, heterocyclyl, aryl and heteroaryl are each optionally substituted by one or more R⁹ groups:

each R⁵ is identical or different and each is independently selected from the group consisting of hydrogen, alkyl, alkoxy, oxo, halogen, haloalkyl, haloalkoxy, amino, nitro, cyano, hydroxy, hydroxyalkyl, cycloalkyl, heterocyclyl, aryl, heteroaryl, —C(O)R⁸, —C(O)OR⁸, —NHC(O)R⁸, —NHC(O)OR⁸, —NR¹⁰R¹¹, —C(O)NR¹⁰R¹¹, —CH₂NHC(O)OR⁸, —CH₂NR¹⁰R¹¹, —C(O)OCH(R¹⁰)R¹¹ and —S(O)ₘR⁸, wherein the alkyl is optionally substituted by one or more groups selected from the group consisting of deuterium, halogen, alkoxy, haloalkoxy, amino, nitro, cyano, hydroxy, hydroxyalkyl, —NR¹⁰R¹¹ and —NHC(O)OR⁸;

R⁷ is selected from the group consisting of hydrogen, alkyl, haloalkyl, alkoxy, haloalkoxy, amino, hydroxy, hydroxyalkyl, cycloalkyl, heterocyclyl, aryl and heteroaryl, wherein the alkyl, alkoxy, cycloalkyl, heterocyclyl, aryl and heteroaryl are each optionally substituted by one or more groups selected from the group consisting of hydrogen, deuterium, halogen, alkyl, alkoxy, haloalkoxy, amino, nitro, cyano, hydroxy, hydroxyalkyl, cycloalkyl, cycloalkyloxy, heterocyclyl, aryl and heteroaryl;

R⁸ is selected from the group consisting of hydrogen, alkyl, haloalkyl, hydroxy, amino, cycloalkyl, heterocyclyl, aryl and heteroaryl;

R⁹ is selected from the group consisting of hydrogen, deuterium, halogen, alkyl, alkoxy, haloalkyl, amino, nitro, cyano, hydroxy, hydroxyalkyl, cycloalkyl, cycloalkyloxy, heterocyclyl, aryl and heteroaryl, wherein the cycloalkyl, heterocyclyl, aryl and heteroaryl are each optionally substituted by one or more groups selected from the group consisting of deuterium, halogen, alkyl, alkoxy, haloalkyl, amino, nitro, cyano, hydroxy, hydroxyalkyl, cycloalkyl, cycloalkyloxy, heterocyclyl, —NHC(O)R¹² and R¹³;

R¹⁰ and R¹¹ are identical or different, and each is independently selected from the group consisting of hydrogen, alkyl, haloalkyl, cycloalkyl, heterocyclyl, —C(O)OR⁸ and —OC(O)OR¹², wherein the cycloalkyl and heterocyclyl are each optionally substituted by one or more groups selected from the group consisting of deuterium, halogen, alkyl, alkoxy, haloalkyl, oxo, amino, nitro, cyano, hydroxy and hydroxyalkyl;

R¹² is selected from the group consisting of hydrogen, alkyl, alkoxy, haloalkyl, haloalkoxy, amino, cycloalkyl, heterocyclyl, aryl and heteroaryl;

R¹³ is aryl or heteroaryl, wherein the aryl and heteroaryl are each optionally substituted by one or more groups selected from the group consisting of hydrogen, deuterium, halogen, alkyl, alkoxy, haloalkyl, amino, nitro, cyano, hydroxy, hydroxyalkyl, cycloalkyl, cycloalkyloxy and heterocyclyl;

n is 0, 1, 2, 3 or 4;

m is 0, 1 or 2; and s is 0, 1, 2, 3 or 4.

In a preferred embodiment of the present invention, the compound of formula (AI) is a compound of formula (I):

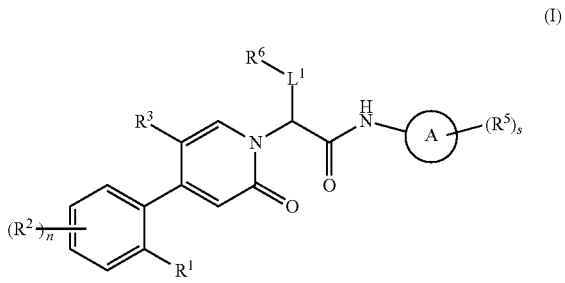

or a tautomer, mesomer, racemate, enantiomer, diastereomer thereof, or mixture thereof, or a pharmaceutically acceptable salt thereof, or a prodrug thereof.

wherein:

$L^1$ is alkylene, wherein the alkylene is optionally substituted by one or more halogens or deuteriums:

$R^6$ is selected from the group consisting of hydrogen, deuterium, halogen, alkyl, alkoxy, amino, nitro, cyano, hydroxy, hydroxyalkyl, cycloalkyl, cycloalkyloxy, heterocyclyl, aryl and heteroaryl, wherein the cycloalkyl, heterocyclyl, aryl and heteroaryl are each optionally substituted by one or more groups selected from the group consisting of deuterium, halogen, alkyl, alkoxy, haloalkyl, amino, nitro, cyano, hydroxy, hydroxyalkyl, cycloalkyl, cycloalkyloxy, heterocyclyl, —NHC(O)$R^{12}$ and $R^{13}$;

$R^{12}$ is selected from the group consisting of hydrogen, alkyl, haloalkyl, amino, cycloalkyl, heterocyclyl, aryl and heteroaryl;

$R^{13}$ is aryl or heteroaryl, wherein the aryl and heteroaryl are each optionally substituted by one or more groups selected from the group consisting of hydrogen, deuterium, halogen, alkyl, alkoxy, haloalkyl, amino, nitro, cyano, hydroxy, hydroxyalkyl, cycloalkyl, cycloalkyloxy and heterocyclyl; and ring A, $R^1$~$R^3$, $R^5$, n and s are as defined in formula (AI).

In a preferred embodiment of the present invention, the compound of formula (AI) is a compound of formula (Iaa):

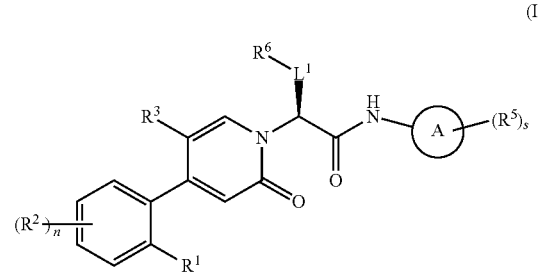

(Iaa)

or a tautomer, mesomer, racemate, enantiomer, diastereomer thereof, or mixture thereof, or a pharmaceutically acceptable salt thereof, or a prodrug thereof, wherein:

ring A, $L^1$, $R^1$~$R^3$, $R^5$—$R^6$, n and s are as defined in formula (I).

In a preferred embodiment of the present invention, in the compound of formula (AI).

is selected from the group consisting of:

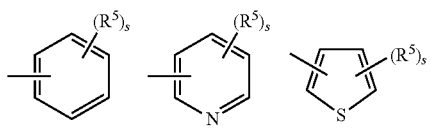

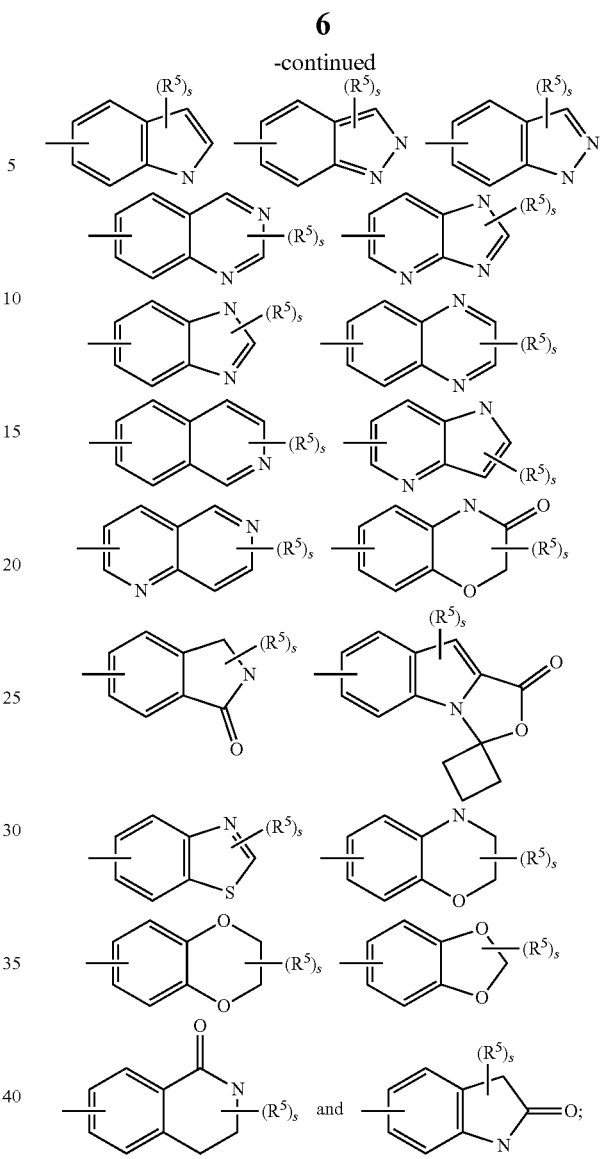

wherein $R^5$ and s are as defined in formula (AI).

In a preferred embodiment of the present invention, the compound of formula (AI) is a compound of formula (II):

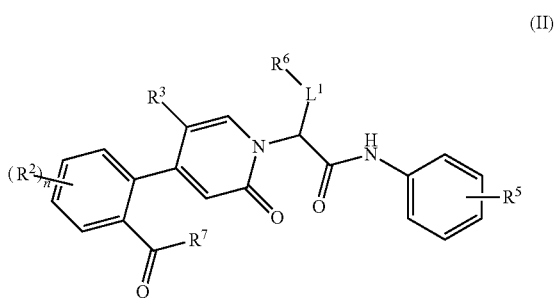

(II)

wherein:

$R^7$ is selected from the group consisting of alkyl, cycloalkyl and haloalkyl, wherein the alkyl and cycloalkyl are each optionally substituted by one or more groups selected from the group consisting of deuterium, halogen, alkyl and cycloalkyl; and $L^1$, $R^2$, $R^3$, $R^5$, $R^6$ and n are as defined in formula (I).

In a preferred embodiment of the present invention, in the compound of formula (AI), each $R^5$ is identical or different and each is independently selected from the group consisting of alkyl, alkoxy, oxo, halogen, haloalkyl, cyano, hydroxy, —C(O)OR$^8$, —NHC(O)OR$^8$, —C(O)NR$^{10}$R$^{11}$, —CH$_2$NHC(O)OR$^8$, —CH$_2$NR$^{10}$R$^{11}$, —C(O)OCH(R$^{10}$)R$^{11}$ and —S(O)$_m$R$^8$; R$^8$ is selected from the group consisting of hydrogen, alkyl, hydroxy and amino; R$^{10}$ and R$^{11}$ are identical or different and each is independently selected from the group consisting of hydrogen, alkyl, haloalkyl, cycloalkyl, heterocyclyl, —C(O)OR$^8$ and —OC(O)OR$^{12}$, wherein the cycloalkyl and heterocyclyl are each optionally substituted by one or more groups selected from the group consisting of deuterium, halogen, alkyl, alkoxy, haloalkyl, oxo, amino, nitro, cyano, hydroxy and hydroxyalkyl; and R$^{12}$ is alkyl.

In a preferred embodiment of the present invention, in the compound of formula (AI), R$^1$ is —C(O)R$^7$; R$^7$ is selected from the group consisting of alkyl, cycloalkyl and haloalkyl, wherein the alkyl and cycloalkyl are each optionally substituted by one or more groups selected from the group consisting of deuterium, halogen, alkyl and cycloalkyl. In a preferred embodiment of the present invention, the compound of formula (AI) is a compound of formula (III):

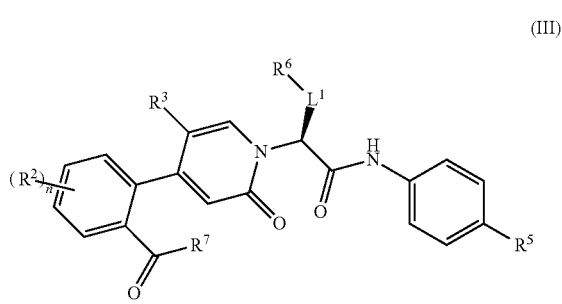

(III)

wherein:
each R$^5$ is identical or different and each is independently selected from the group consisting of alkyl, alkoxy, oxo, halogen, haloalkyl, cyano, hydroxy,. —C(O)OR$^8$, —NHC(O)OR$^8$, —C(O)NR$^{10}$R$^{11}$, —CH$_2$NHC(O)OR$^8$, —CH$_2$NR$^{10}$R$^{11}$, —C(O)OCH(R$^{10}$)R$^{11}$ and —S(O)$_m$R$^8$; R$^8$ is selected from the group consisting of hydrogen, alkyl, hydroxy and amino; R$^{10}$ and R$^{11}$ are identical or different and each is independently selected from the group consisting of hydrogen, alkyl, haloalkyl, cycloalkyl, heterocyclyl, —C(O)OR$^8$ and —OC(O)OR$^{12}$, wherein the cycloalkyl and heterocyclyl are each optionally substituted by one or more groups selected from the group consisting of deuterium, halogen, alkyl, alkoxy, haloalkyl, oxo, amino, nitro, cyano, hydroxy and hydroxyalkyl; and R$^{12}$ is alkyl;

R$^7$ is selected from the group consisting of alkyl, cycloalkyl and haloalkyl, wherein the alkyl and cycloalkyl are each optionally substituted by one or more groups selected from the group consisting of deuterium, halogen, alkyl and cycloalkyl; and L$^1$, R$^2$, R$^3$, R$^6$ and n are as defined in formula (I).

In a preferred embodiment of the present invention, the compound of formula (AI) is a compound of formula (IV):

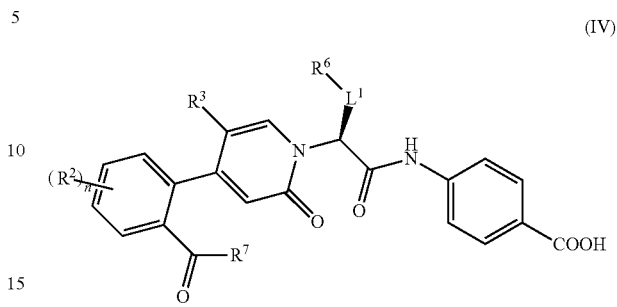

(IV)

wherein:
L$^1$, R$^2$, R$^3$, R$^6$, R$^7$ and n are as defined in formula (III).

In a preferred embodiment of the present invention, in the compound of formula (AI), wherein R$^2$ is halogen; and n is 0, 1 or 2.

In a preferred embodiment of the present invention, in the compound of formula (AI), R$^3$ is alkoxy, wherein the alkoxy is optionally substituted by one or more deuteriums or halogens.

In a preferred embodiment of the present invention, in the compound of formula (I), L$^1$ is —(CR$^{14}_2$)$_x$—, x is an integer of 1~4; R$^4$ is hydrogen or deuterium; R$^6$ is selected from the group consisting of hydrogen, deuterium, halogen, alkyl, alkoxy, cycloalkyl, cycloalkyloxy, heterocyclyl, aryl and heteroaryl; wherein the cycloalkyl, heterocyclyl, aryl and heteroaryl are each optionally substituted by one or more groups selected from the group consisting of deuterium, halogen, alkyl, alkoxy, cycloalkyl, heterocyclyl, —NHC(O)R$^{12}$ and R$^{13}$; R$^{12}$ is alkyl or cycloalkyl; R$^{13}$ is aryl or heteroaryl, wherein the aryl and heteroaryl are each optionally substituted by one or more groups selected from the group consisting of deuterium, halogen, alkyl, alkoxy, haloalkyl, amino, nitro, cyano and hydroxy.

In a preferred embodiment of the present invention, in the compound of formula (AI), L$^1$ is —CH$_2$— or -CD$_2$-, wherein D is deuterium; R$^6$ is selected from the group consisting of cycloalkyl, heterocyclyl, aryl and heteroaryl; wherein the cycloalkyl, heterocyclyl, aryl and heteroaryl are each optionally substituted by one or more groups selected from the group consisting of deuterium, halogen, alkyl, alkoxy, cycloalkyl, heterocyclyl, —NHC(O)R$^{12}$ and R$^{13}$; R$^{12}$ is alkyl or cycloalkyl; R$^{13}$ is aryl or heteroaryl, wherein the aryl and heteroaryl are each optionally substituted by one or more groups selected from the group consisting of deuterium, halogen, alkyl, alkoxy, haloalkyl, amino, nitro, cyano and hydroxy.

In a preferred embodiment of the present invention, in the compound of formula (AI), L$^1$ is —CH$_2$CH$_2$—; and R$^6$ is alkyl, alkoxy or cycloalkyloxy.

Typical compounds of formula (AI), include, but are not limited to:

| Example No. | Structure and Name |
|---|---|
| 1 | 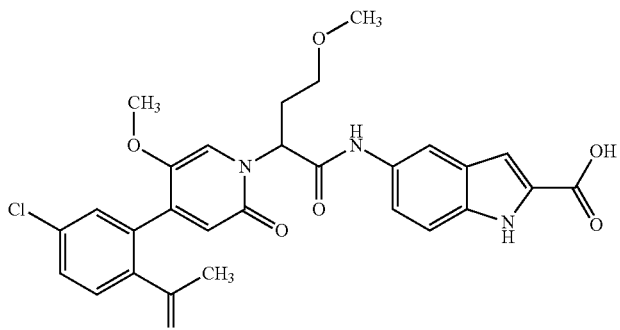
1
5-(2-(4-(2-acetyl-5-chlorophenyl)-5-methoxy-2-oxopyridin-1(2H)-yl)-4-methoxybutanamido)-1H-indole-2-carboxylic acid |
| 1i | 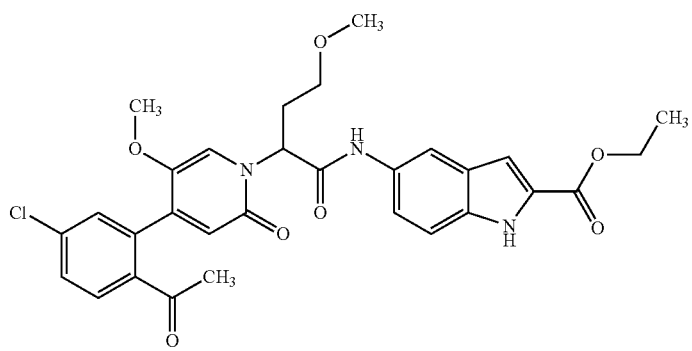
1i
ethyl 5-(2-(4-(2-acetyl-5-chlorophenyl)-5-methoxy-2-oxopyridin-1(2H)-yl)-4-methoxybutanamido)-1H-indole-2-carboxylate 1i |
| 2 | 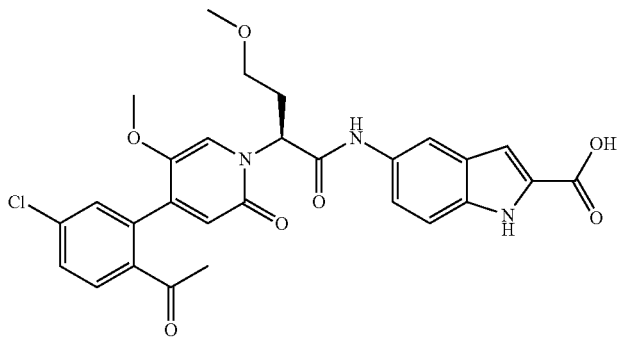
2
(S)-5-(2-(4-(2-acetyl-5-chlorophenyl)-5-methoxy-2-oxopyridin-1(2H)-yl)-4-methoxybutanamido)-1H-indole-2-carboxylic acid 2 |

-continued
| Example No. | Structure and Name |
|---|---|
| 3 | 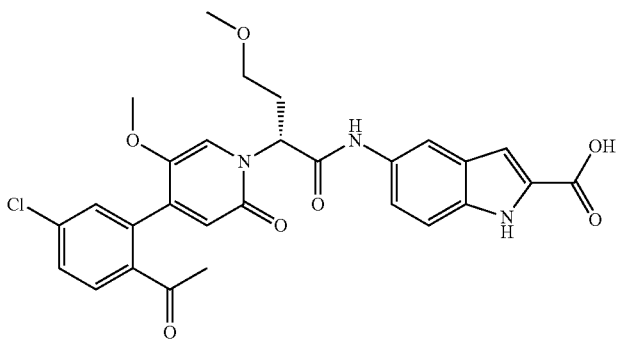<br>(R)-5-(2-(4-(2-acetyl-5-chlorophenyl)-5-methoxy-2-oxopyridin-1(2H)-yl)-4-methoxybutanamido)-1H-indole-2-carboxylic acid 3 |
| 4d | 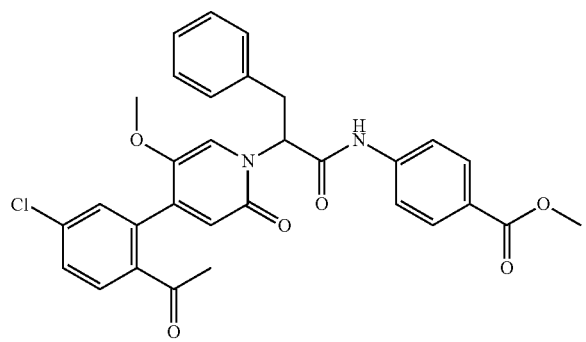<br>methyl 4-(2-(4-(2-acetyl-5-chlorophenyl)-5-methoxy-2-oxopyridin-1(2H)-yl)-3-phenylpropanamido)benzoate 4d |
| 4 | 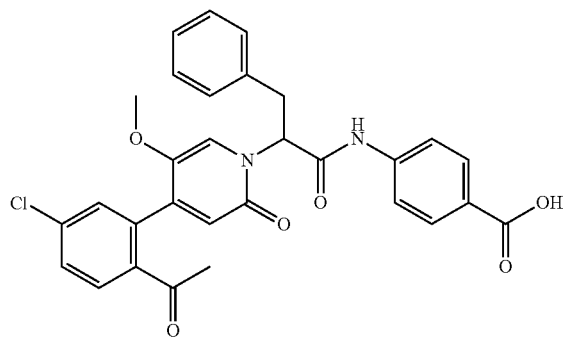<br>4-(2-(4-(2-acetyl-5-chlorophenyl)-5-methoxy-2-oxopyridin-1(2H)-yl)-3-phenylpropanamido)benzoic acid 4 |

-continued
| Example No. | Structure and Name |
|---|---|
| 5 | 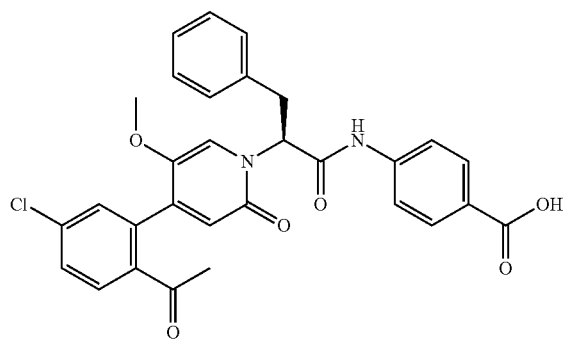
(S)-4-(2-(4-(2-acetyl-5-chlorophenyl)-5-methoxy-2-oxopyridin-1(2H)-yl)-3-phenylpropanamido)benzoic acid 5 |
| 6 | 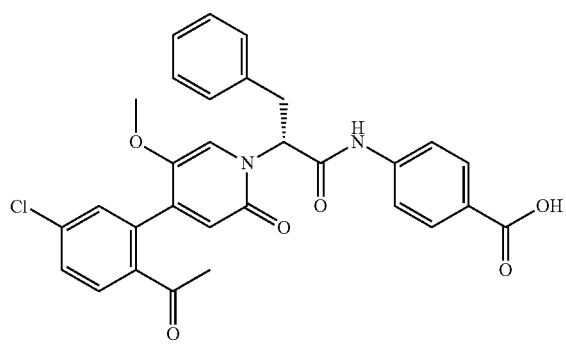
(R)-4-(2-(4-(2-acetyl-5-chlorophenyl)-5-methoxy-2-oxopyridin-1(2H)-yl)-3-phenylpropanamido)benzoic acid 6 |
| 7f | 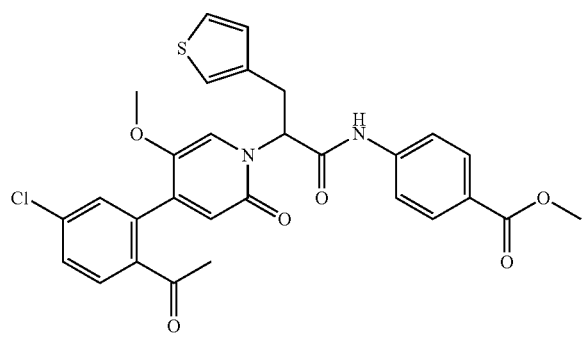
methyl 4-(2-(4-(2-acetyl-5-chlorophonyl)-5-methoxy-2-oxopyridin-1(2H)-yl)-3-(thiophen-3-yl)propanamido)benzoate 7f |

| Example No. | Structure and Name |
|---|---|
| 7 | 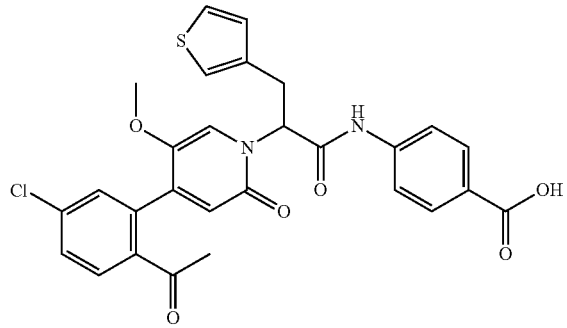
4-(2-(4-(2-acetyl-5-chlorophenyl)-5-methoxy-2-oxopyridin-1(2H)-yl)-3-(thiophen-3-yl)propanamido)benzoic acid 7 |
| 8 | 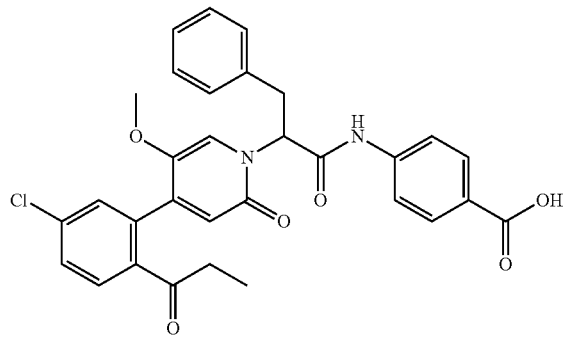
4-(2-(4-(5-chloro-2-propionylphenyl)-5-methoxy-2-oxopyridin-1(2H)-yl)-3-phenylpropanamido)benzoic acid 8 |
| 9 | 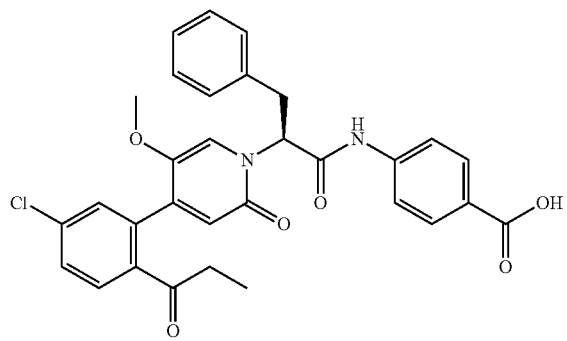
(S)-4-(2-(4-(5-chloro-2-propionylphenyl)-5-methoxy-2-oxopyridin-1(2H)-yl)-3-phenylpropanamido)benzoic acid 9 |

| Example No. | Structure and Name |
|---|---|
| 10 | 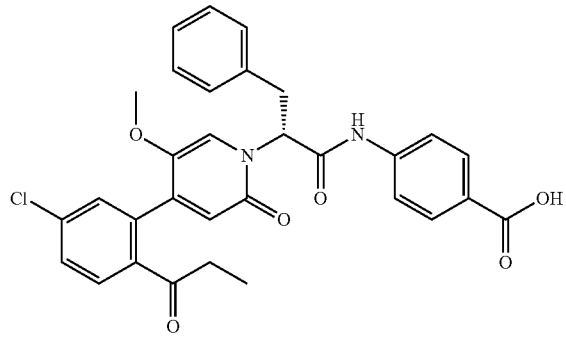
10
(R)-4-(2-(4-(5-chloro-2-propionylphenyl)-5-methoxy-2-oxopyridin-1(2H)-yl)-3-phenylpropanamido)benzoic acid 10 |
| 11 | 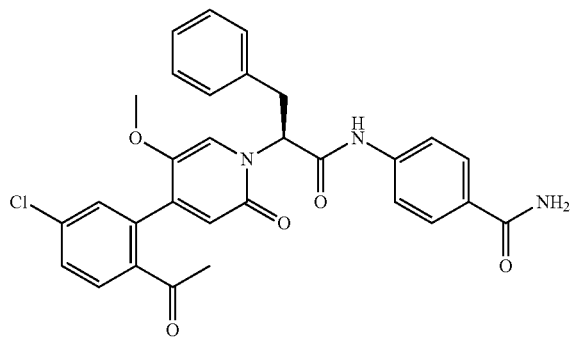
11
(S)-4-(2-(4-(2-acetyl-5-chlorophenyl)-5-methoxy-2-oxopyridin-1(2H)yl)-3-phenylpropanamido)benzamide 11 |
| 12 | 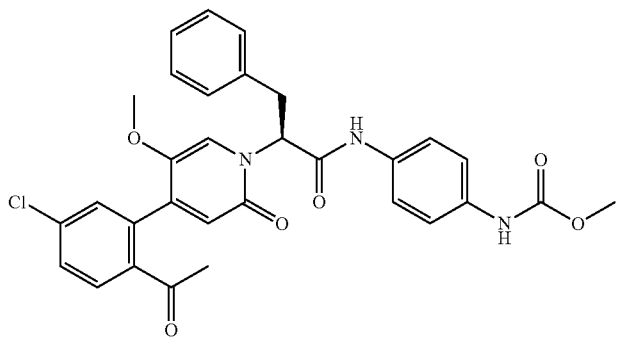
12
methyl (S)-(4-(2-(4-(2-acetyl-5-chlorophenyl)-5-methoxy-2-oxopyridin-1(2H)-yl)-3-phenylpropanamido)phenyl)carbamate 12 |

| Example No. | Structure and Name |
|---|---|
| 13 | 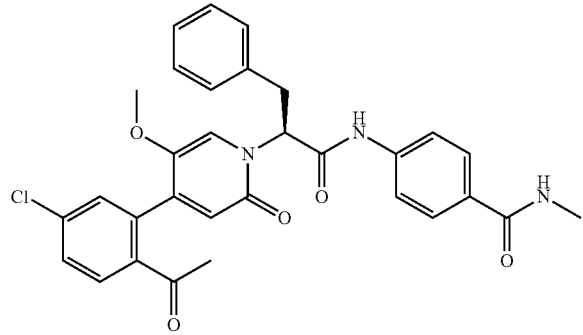
(S)-4-(2-(4-(2-acetyl-5-chlorophenyl)-5-methoxy-2-oxopyridin-1(2H)-yl)-3-phenylpropanamido)-N-methylbenzamide 13 |
| 14e | 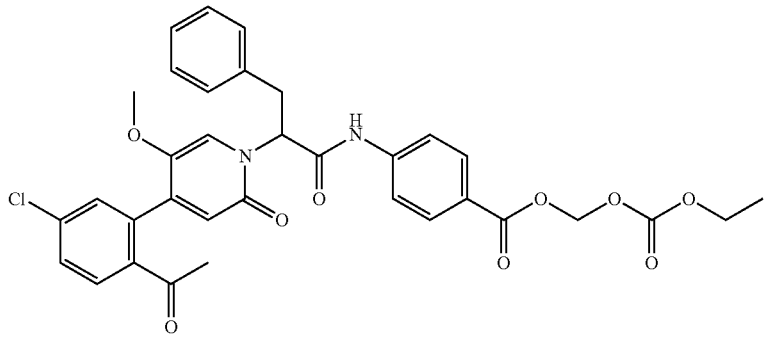
((ethoxycarbonyl)oxy)methyl 4-(2-(4-(2-acetyl-5-chlorophenyl)-5-methoxy-2-oxopyridin-1(2H)-yl)-3-phenylpropanamido)benzoate 14e |
| 14 | 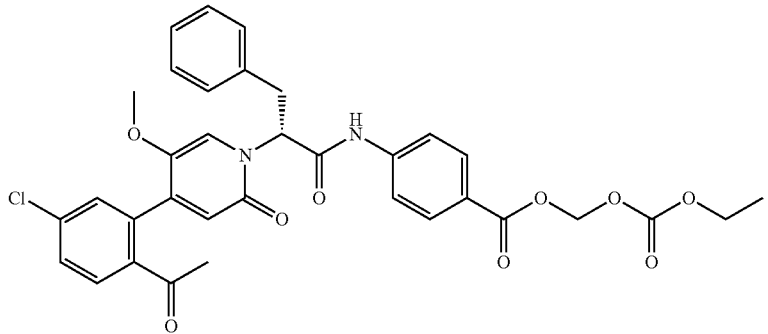
(R)-((ethoxycarbonyl)oxy)methyl 4-(2-(4-(2-acetyl-5-chlorophenyl)-5-methoxy-2-oxopyridin-1(2H)-yl)-3-phenylpropanamido)benzoate 14 |

| Example No. | Structure and Name |
|---|---|
| 15 | 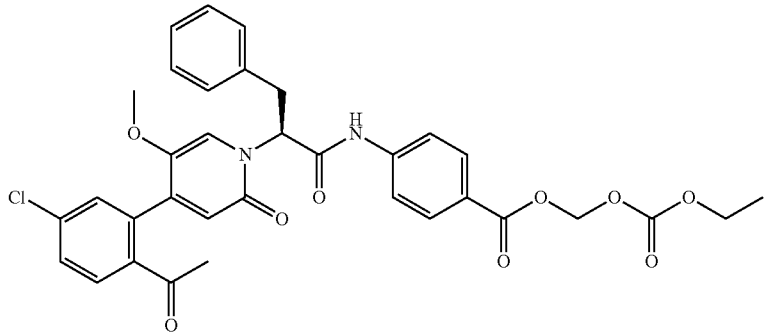
(S)-((ethoxycarbonyl)oxy)methyl 4-(2-(4-(2-acetyl-5-chlorophenyl)-5-methoxy-2-oxopyridin-1(2H)-yl)-3-phenylpropanamido)benzoate 15 |
| 16g | 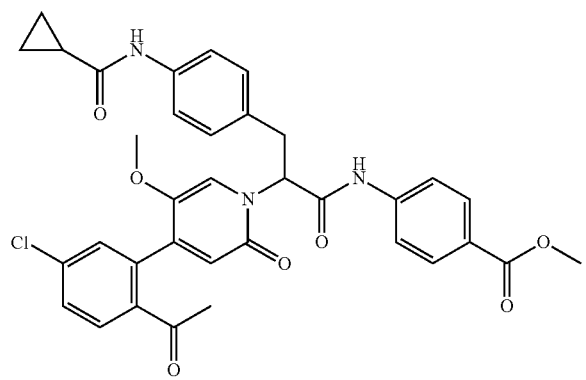
methyl 4-(2-(4-(2-acetyl-5-chlorophenyl)-5-methoxy-2-oxopyridin-1(2H)-yl)-3-(4-(cyclopropanecarboxamido)phenyl)propanamido)benzoate 16g |
| 16 | 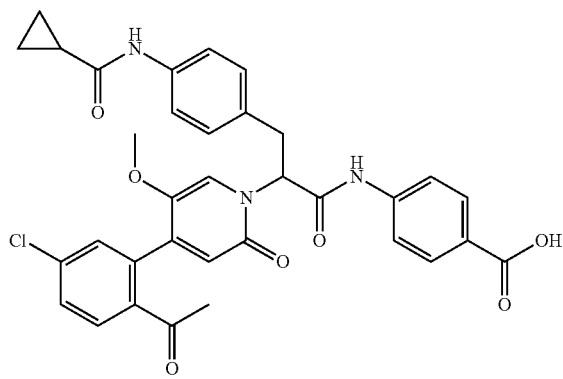
4-(2-(4-(2-acetyl-5-chlorophenyl)-5-methoxy-2-oxopyridin-1(2H)-yl)-3-(4-(cyclopropanecarboxamido)phenyl)propanamido)benzoic acid 16 |

-continued
| Example No. | Structure and Name |
|---|---|
| 17f | 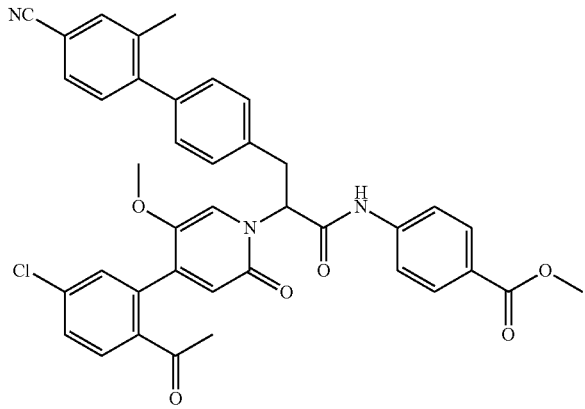
methyl 4-(2-(4-(2-acetyl-5-chlorophenyl)-5-methoxy-2-oxopyridin-1(2H)-yl)-3-(4'-cyano-2'-methyl-[1,1'-biphenyl]-4-yl)propanamido)benzoate 17f |
| 17 | 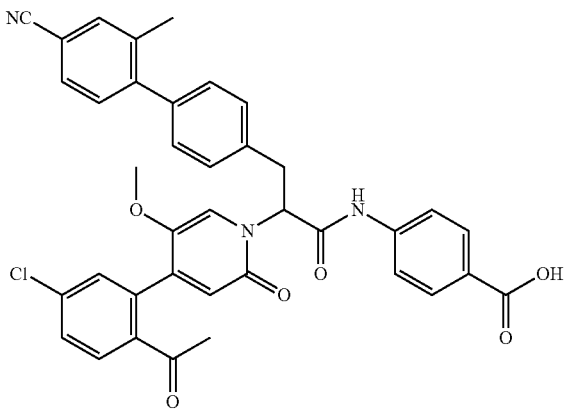
4-(2-(4-(2-acetyl-5-chlorophenyl)-5-methoxy-2-oxopyridin-1(2H)-yl)-3-(4'-cyano-2'-methyl-[1,1'-biphenyl]-4-yl)propanamido)benzoic acid 17 |
| 18 | 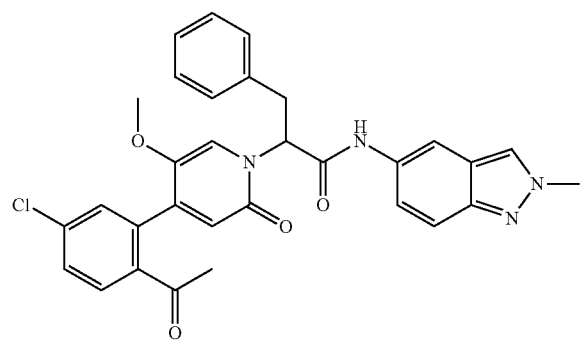
2-(4-(2-acetyl-5-chlorophenyl)-5-methoxy-2-oxopyridin-1(2H)-yl)-N-(2-methyl-2H-indazol-5-yl)-3-phenylpropanamide 18 |

| Example No. | Structure and Name |
|---|---|
| 19 | 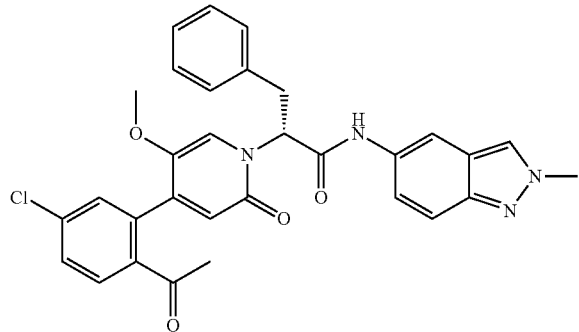<br>(R)-2-(4-(2-acetyl-5-chlorophenyl)-5-methoxy-2-oxopyridin-1(2H)-yl)-N-(2-methyl-2H-indazol-5-yl)-3-phenylpropanamide 19 |
| 20 | 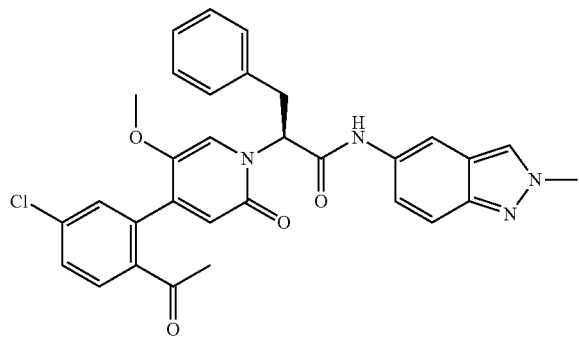<br>(S)-2-(4-(2-acetyl-5-chlorophenyl)-5-methoxy-2-oxopyridin-1(2H)-yl)-N-(2-methyl-2H-indazol-5-yl)-3-phenylpropanamide 20 |
| 21 | 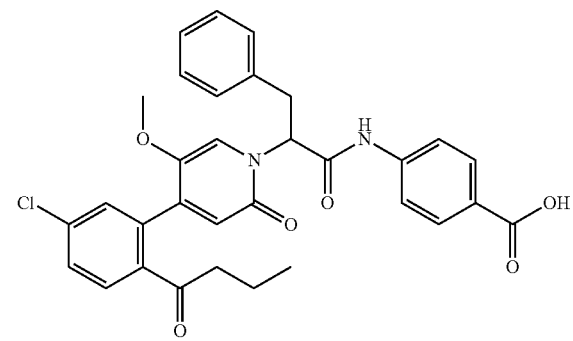<br>4-(2-(4-(2-butyryl-5-chlorophenyl)-5-methoxy-2-oxopyridin-1(2H)-yl)-3-phenylpropanamido)benzoic acid 21 |

| Example No. | Structure and Name |
|---|---|
| 22 | 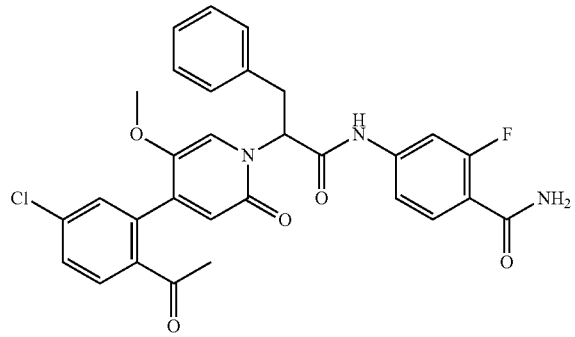<br>4-(2-(4-(2-acetyl-5-chlorophenyl)-5-methoxy-2-oxopyridin-1(2H)-yl)-3-phenylpropanamido)-2-fluorobenzamide 22 |
| 23 | 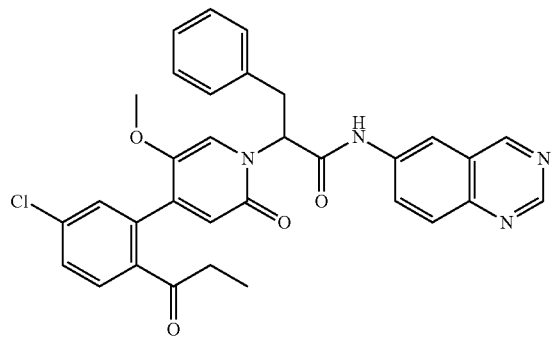<br>2-(4-(5-chloro-2-propionylphenyl)-5-methoxy-2-oxopyridin-1(2H)-yl)-3-phenyl-N-(quinazolin-6-yl)propanamide 23 |
| 24 | 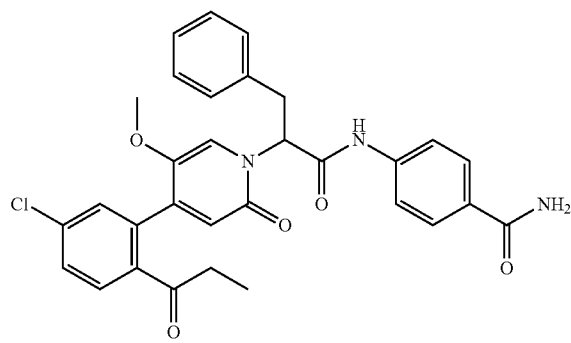<br>4-(2-(4-(5-chloro-2-propionylphenyl)-5-methoxy-2-oxopyridin-1(2H)-yl)-3-phenylpropanamido)benzamide 24 |

-continued
| Example No. | Structure and Name |
|---|---|
| 25 | 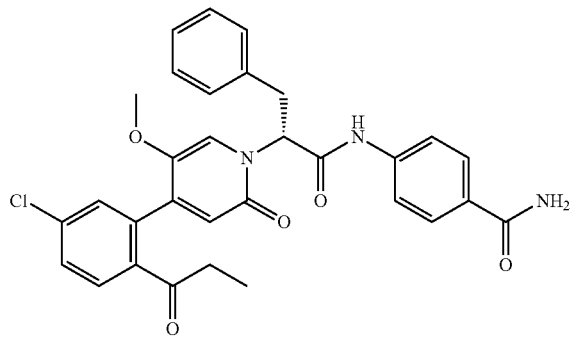<br>(R)-4-(2-(4-(5-chloro-2-propionylphenyl)-5-methoxy-2-oxopyridin-1(2H)-yl)-3-phenylpropanamido)benzamide 25 |
| 26 | 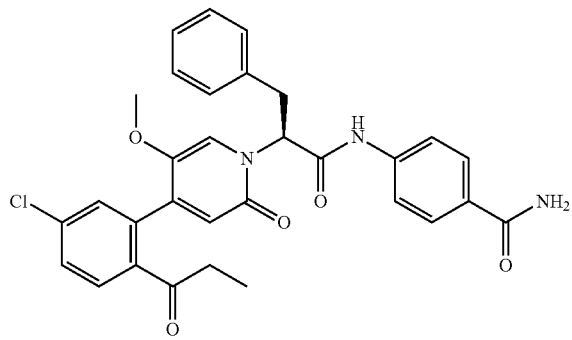<br>(S)-4-(2-(4-(5-chloro-2-propionylphenyl)-5-methoxy-2-oxopyridin-1(2H)-yl)-3-phenylpropanamido)benzamide 26 |
| 27 | 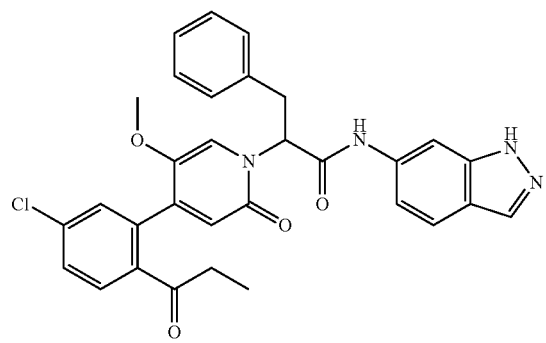<br>2-(4-(5-chloro-2-propionylphenyl)-5-methoxy-2-oxopyridin-1(2H)-yl)-N-(1H-indazol-6-yl)-3-phenylpropanamide 27 |

| Example No. | Structure and Name |
|---|---|
| 28 | 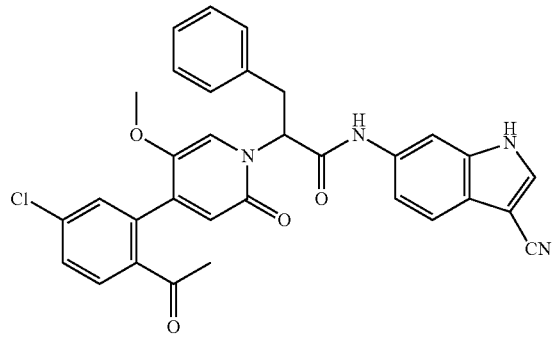
2-(4-(2-acetyl-5-chlorophenyl)-5-methoxy-2-oxopyridin-1(2H)-yl)-N-(3-cyano-1H-indole-6-yl)-3-phenylpropanamide 28 |
| 29 | 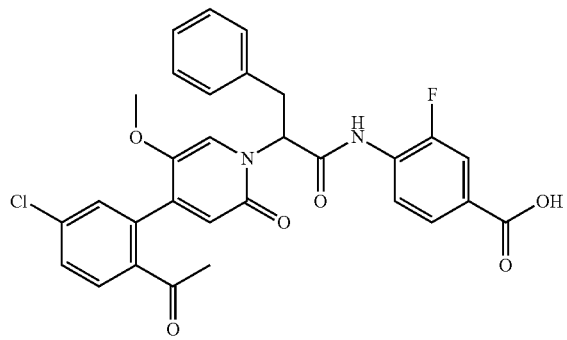
4-(2-(4-(2-acetyl-5-chlorophenyl)-5-methoxy-2-oxopyridin-1(2H)-yl)-3-phenylpropanamido)-3-fluorobenzoic acid 29 |
| 30e | 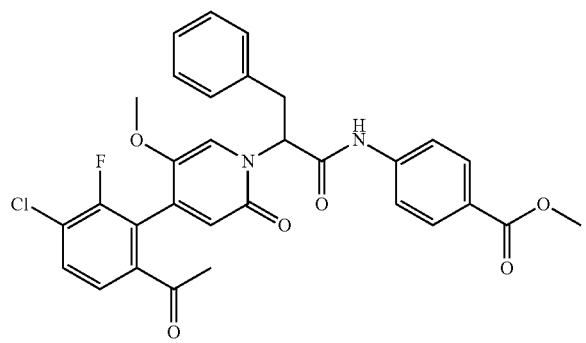
4-(2-(4-(6-acetyl-3-chloro-2-fluorophenyl)-5-methoxy-2-oxopyridin-1(2H)-yl)-3-phenylpropanamido)benzoate 30e |

| Example No. | Structure and Name |
|---|---|
| 30 | 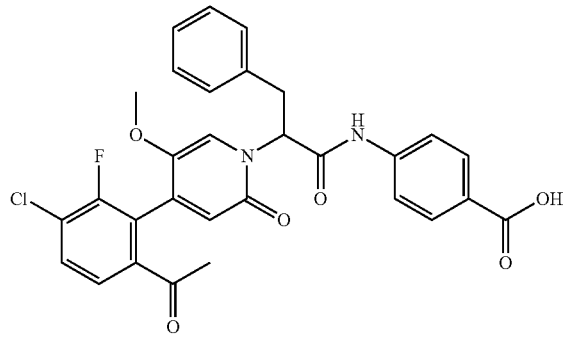<br>30<br>4-(2-(4-(6-acetyl-3-chloro-2-fluorophenyl)-5-methoxy-2-oxopyridin-1(2H)-yl)-3-phenylpropanamido)benzoic acid 30 |
| 31 | 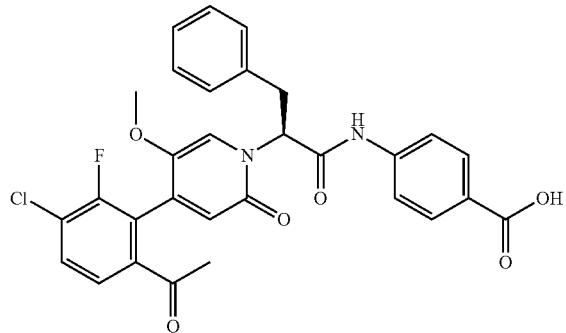<br>31<br>(S)-4-(2-(4-(6-acetyl-3-chloro-2-fluorophenyl)-5-methoxy-2-oxopyridin-1(2H)-yl)-3-phenylpropanamido)benzoic acid 31 |
| 32 | 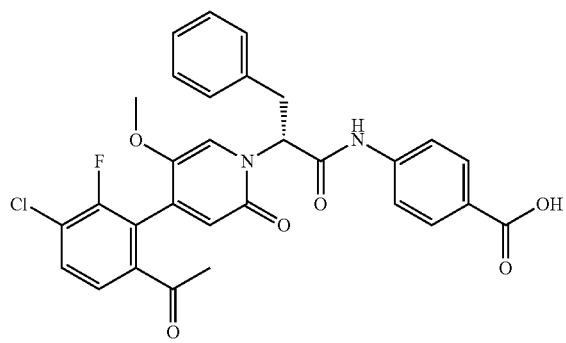<br>32<br>(R)-4-(2-(4-(6-acetyl-3-chloro-2-fluorophenyl)-5-methoxy-2-oxopyridin-1(2H)-yl)-3-phenylpropanamido)benzoic acid 32 |

-continued
| Example No. | Structure and Name |
|---|---|
| 33 | 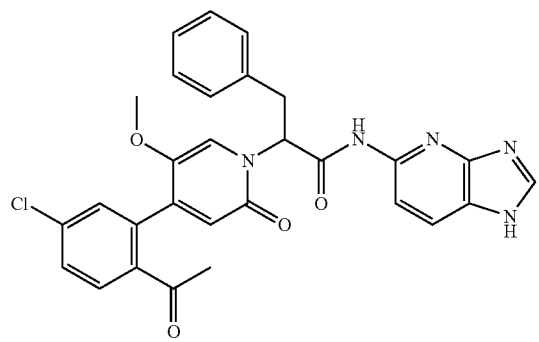<br>2-(4-(2-acetyl-5-chlorophenyl)-5-methoxy-2-oxopyridin-1(2H)-yl)-N-(1H-imidazo[4,5-b]pyridin-5-yl)-3-phenylpropanamide 33 |
| 34 | 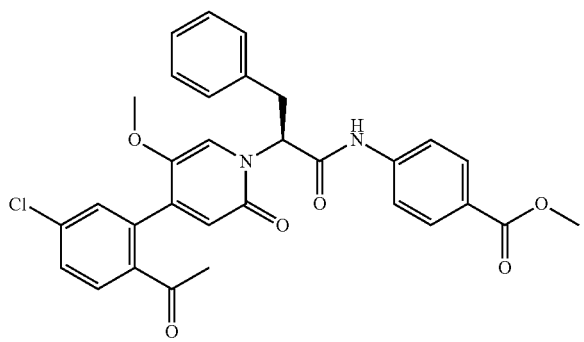<br>methyl (S)-4-(2-(4-(2-acetyl-5-chlorophenyl)-5-methoxy-2-oxopyridin-1(2H)-yl)-3-phenylpropanamido)benzoate 34 |
| 35 | 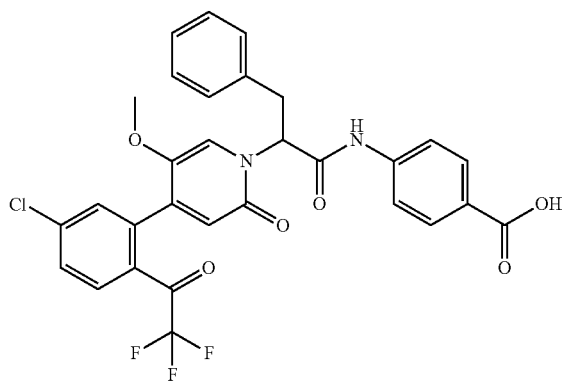<br>4-(2-(4-(5-chloro-2-(2,2,2-trifluoroacetyl)phenyl)-5-methoxy-2-oxopyridin-1(2H)-yl)-3-phenylpropanamido)benzoic acid 35 |

| Example No. | Structure and Name |
|---|---|
| 36 | 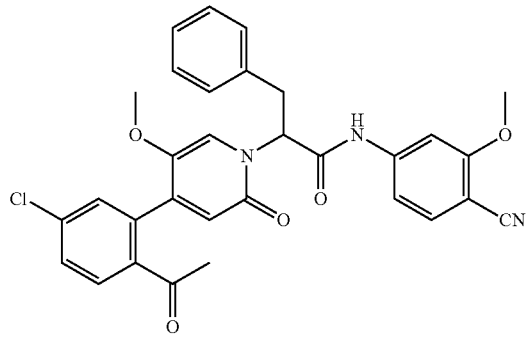<br>36<br>(4-(2-acetyl-5-chlorophenyl)-5-methoxy-2-oxopyridin-1(2H)-yl)-N-(4-cyano-3-methoxyphenyl)-3-phenylpropanamide 36 |
| 37 | 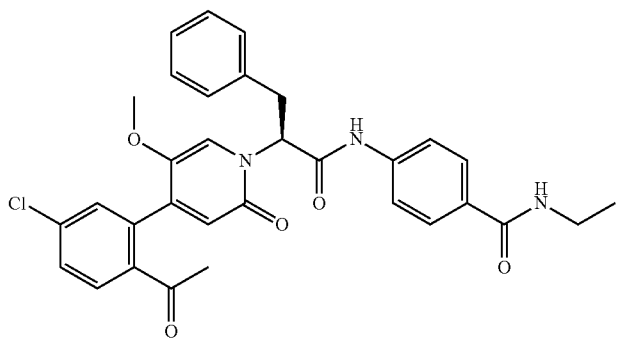<br>37<br>(S)-4-(2-(4-(2-acetyl-5-chlorophenyl)-5-methoxy-2-oxopyridin-1(2H)-yl)-3-phenylpropanamido)-N-ethylbenzamide 37 |
| 38 | 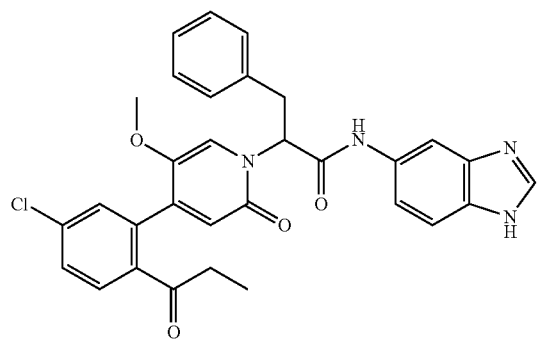<br>38<br>N-(1H-benzo[d]imidazol-5-yl)-2-(4-(5-chloro-2-propionylphenyl)-5-methoxy-2-oxopyridin-1(2H)-yl)-3-phenylpropanamide 38 |

| Example No. | Structure and Name |
|---|---|
| 39 | 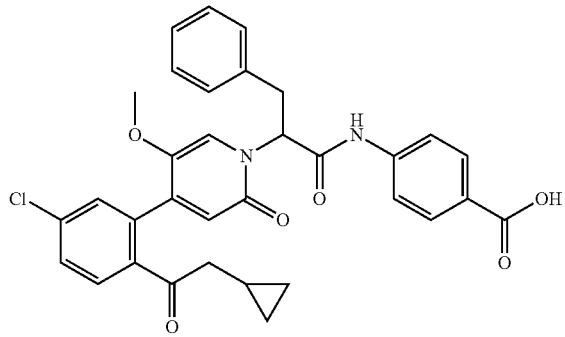<br>4-(2-(4-(5-chloro-2-(2-cyclopropylacetyl)phenyl)-5-methoxy-2-oxopyridin-1(2H)-yl)-3-phenylpropanamido)benzoic acid |
| 40 | 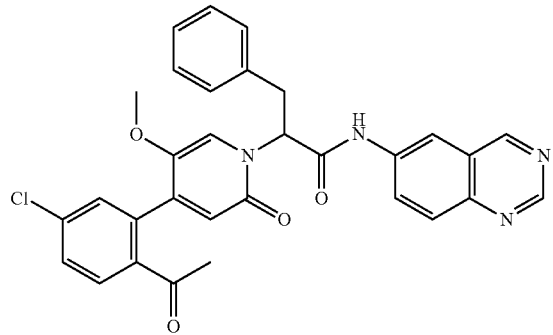<br>2-(4-(2-acetyl-5-chlorophenyl)-5-methoxy-2-oxopyridin-1(2H)-yl)-3-phenyl-N-(quinazolin-6-yl)propanamide 40 |
| 41 | 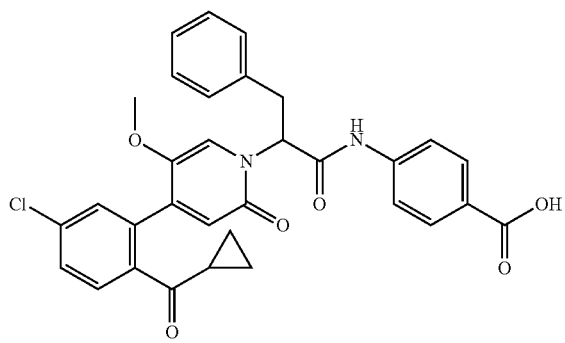<br>4-(2-(4-(5-chloro-2-(cyclopropanecarbonyl)phenyl)-5-methoxy-2-oxo-pyridin-1(2H)-yl)-3-phenylpropanamido)benzoic acid 41 |

| Example No. | Structure and Name |
|---|---|
| 42 | 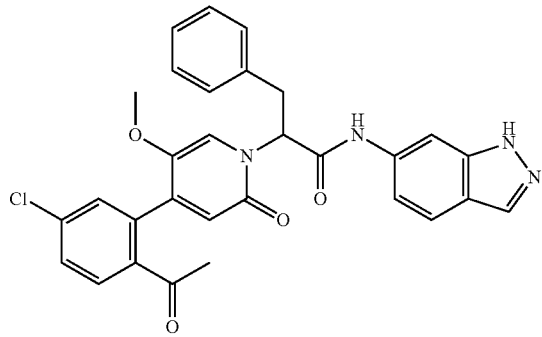<br>2-(4-(2-acetyl-5-chlorophenyl)-5-methoxy-2-oxopyridin-1(2H)-yl)-N-(1H-indazol-6-yl)-3-phenylpropanamide 42 |
| 43 | 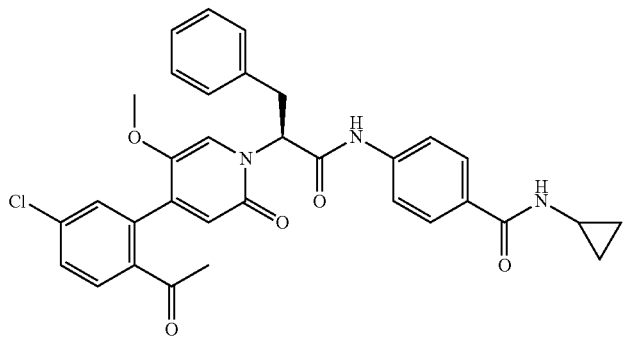<br>(S)-4-(2-(4-(2-acetyl-5-chlorophenyl)-5-methoxy-2-oxopyridin-1(2H)-yl)-3-phenylpropanamido)-N-cyclopropylbenzamide 43 |
| 44 | 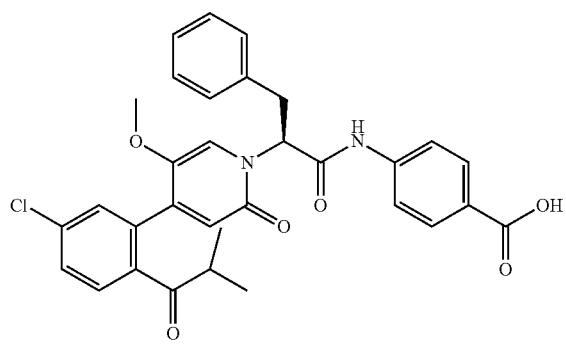<br>4-(2-(4-(5-chloro-2-isobutyrylphenyl)-5-methoxy-2-oxopyridin-1(2H)-yl)-3-phenylpropanamido)benzoic acid 44 |

| Example No. | Structure and Name |
|---|---|
| 45 | 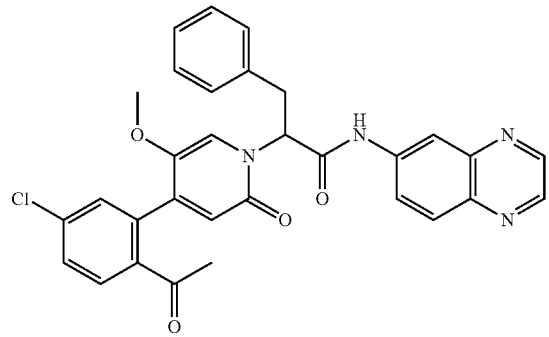
2-(4-(2-acetyl-5-chlorophenyl)-5-methoxy-2-oxopyridin-1(2H)-yl)-3-phenyl-N-(quinoxalin-6-yl)propanamide 45 |
| 46 | 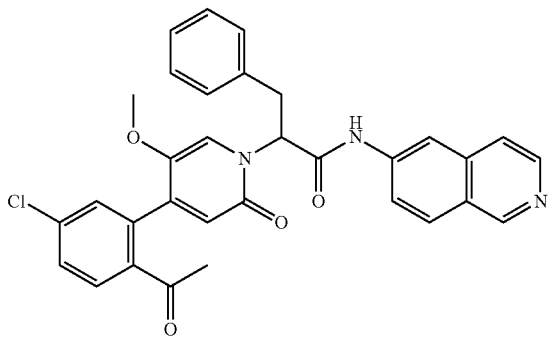
2-(4-(2-acetyl-5-chlorophenyl)-5-methoxy-2-oxopyridin-1(2H)-yl)-N-(isoquinolin-6-yl)-3-phenylpropanamide 46 |
| 47 | 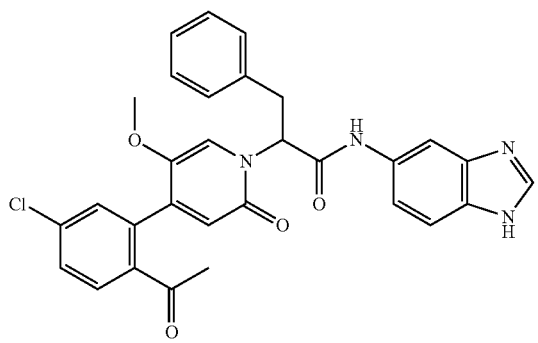 [SMILES: COc1cn(C(Cc2ccccc2)C(=O)Nc2cnc3[nH]cnc3c2)c(=O)cc1-c1cc(Cl)ccc1C(C)=O]
2-(4-(2-acetyl-5-chlorophenyl)-5-methoxy-2-oxopyridin-1(2H)-yl)-N-(1H-benzo[d]imidazol-5-yl)-3-phenylpropanamide 47 |

| Example No. | Structure and Name |
|---|---|
| 48 | 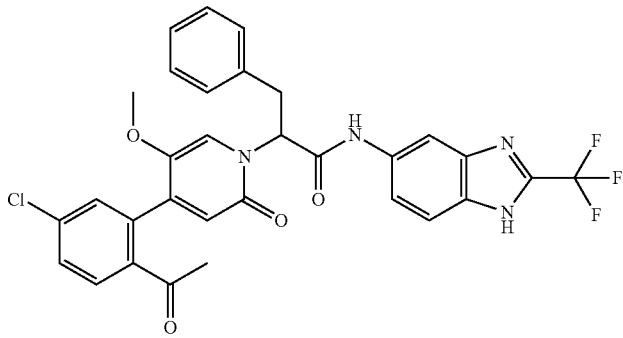<br>2-(4-(2-acetyl-5-chlorophenyl)-5-methoxy-2-oxopyridin-1(2H)-yl)-3-phenyl-N-(2-(trifluoromethyl)-1H-benzo[d]imidazol-5-yl)propanamide 48 |
| 49 | 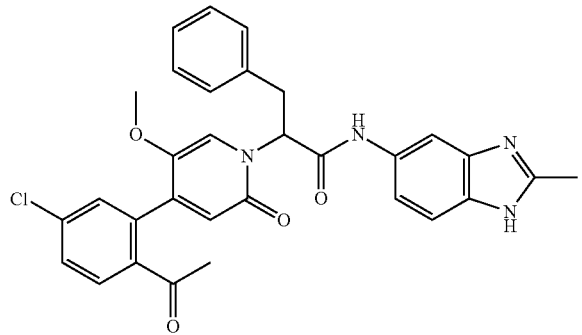<br>2-(4-(2-acetyl-5-chlorophenyl)-5-methoxy-2-oxopyridin-1(2H)-yl)-N-(2-methyl-1H-benzo[d]imidazol-5-yl)-3-phenylpropanamide 49 |
| 50 | 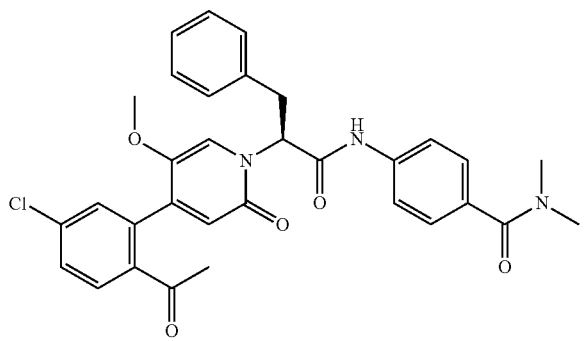<br>(S)-4-(2-(4-(2-acetyl-5-chlorophenyl)-5-methoxy-2-oxopyridin-1(2H)-yl)-3-phenylpropanamido)-N,N-dimethylbenzamide 50 |

| Example No. | Structure and Name |
|---|---|
| 51 | 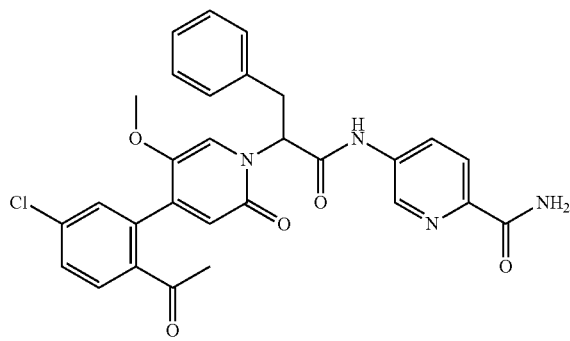
5-(2-(4-(2-acetyl-5-chlorophenyl)-5-methoxy-2-oxopyridin-1(2H)-yl)-3-phenylpropanamido)-2-picolinamide 51 |
| 52 | 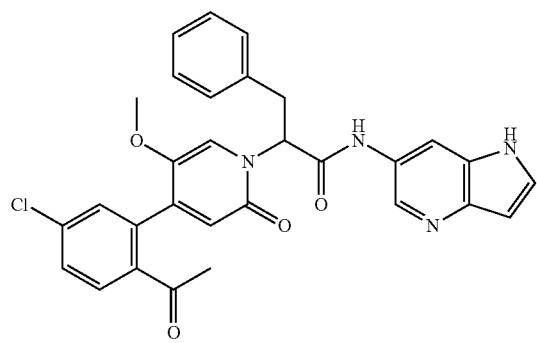
2-(4-(2-acetyl-5-chlorophenyl)-5-methoxy-2-oxopyridin-1(2H)-yl)-3-phenyl-N-(1H-pyrrolo[3,2-b]pyridin-6-yl)propanamide 52 |
| 53b | 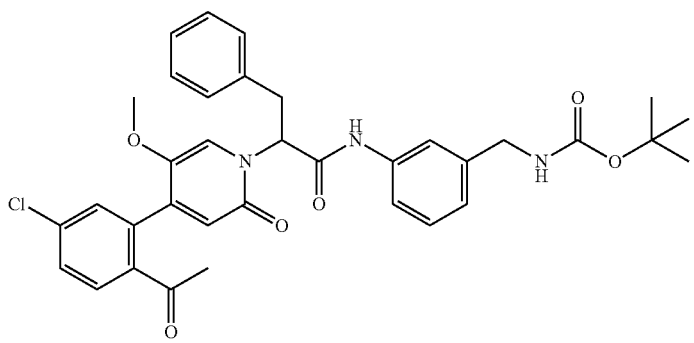
tert-butyl 3-(2-(4-(2-acetyl-5-chlorophenyl)-5-methoxy-2-oxopyridin-1(2H)-yl)-3-phenylpropanamido)benzylcarbamate 53b |

| Example No. | Structure and Name |
|---|---|
| 53c | 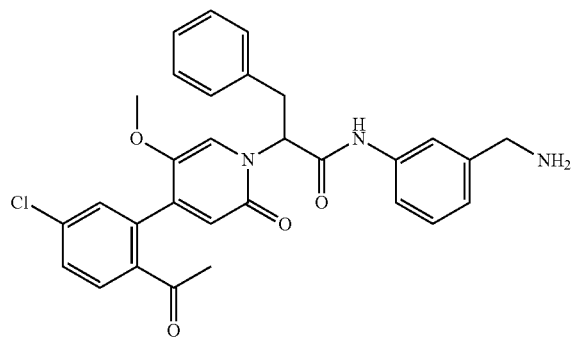<br>53c<br><br>2-(4-(2-acetyl-5-chlorophenyl)-5-methoxy-2-oxopyridin-1(2H)-yl)-N-(3-(aminomethyl)phenyl)-3-phenylpropanamide 53c |
| 53 | 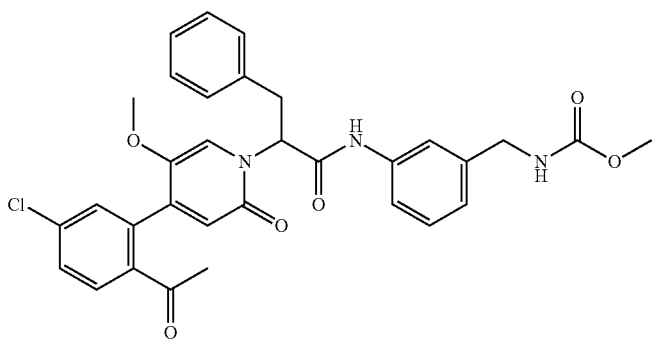<br>53<br><br>methyl 3-(2-(4-(2-acetyl-5-chlorophenyl)-5-methoxy-2-oxopyridin-1(2H)-yl)-3-phenylpropanamido)benzylcarbamate 53 |
| 54 | 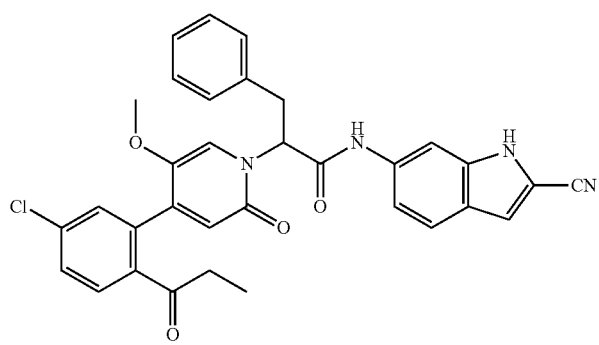<br>54<br><br>2-(4-(5-chloro-2-propionylphenyl)-5-methoxy-2-oxopyridin-1(2H)-yl)-N-(2-cyano-1H-indol-6-yl)-3-phenylpropanamide 54 |

-continued
| Example No. | Structure and Name |
|---|---|
| 55 | 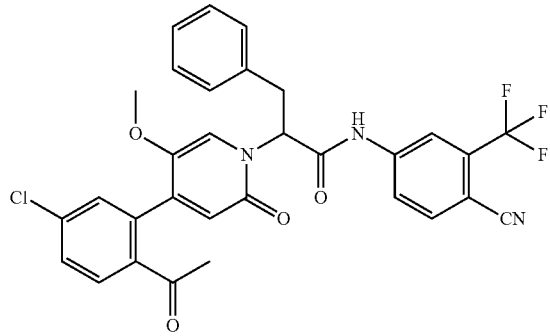 [SMILES: COc1cn(C(Cc2ccccc2)C(=O)Nc2ccc(C#N)c(C(F)(F)F)c2)c(=O)cc1-c1cc(Cl)ccc1C(C)=O]
55
2-(4-(2-acetyl-5-chlorophenyl)-5-methoxy-2-oxopyridin-1(2H)-yl)-N-(4-cyano-3-(trifluoromethyl)phenyl)-3-phenylpropanamide 55 |
| 56 | 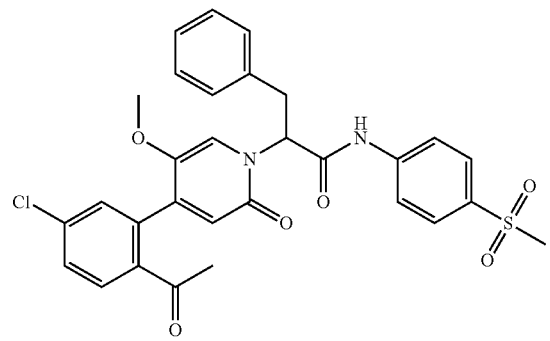
56
2-(4-(2-acetyl-5-chlorophenyl)-5-methoxy-2-oxopyridin-1(2H)-yl)-N-(4-(methylsulfonyl)phenyl)-3-phenylpropanamide 56 |
| 57 | 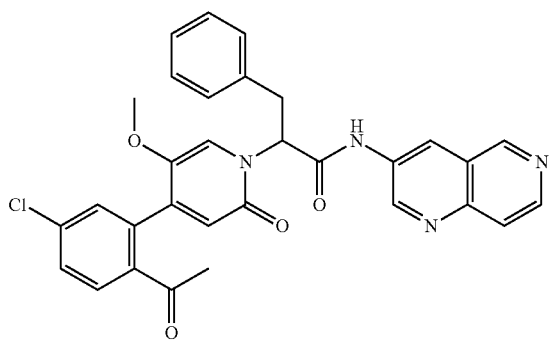
57
2-(4-(2-acetyl-5-chlorophenyl)-5-methoxy-2-oxopyridin-1(2H)-yl)-N-(1,6-naphthyridin-3-yl)-3-phenylpropanamide 57 |

| Example No. | Structure and Name |
|---|---|
| 58 | 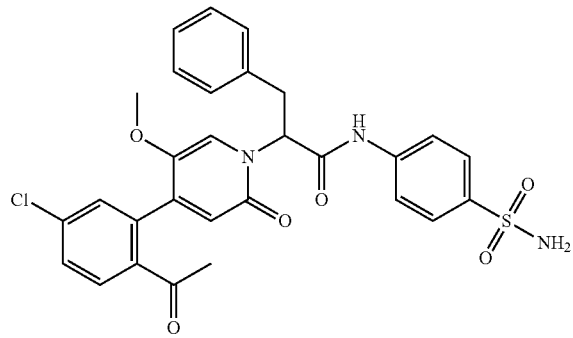<br>58<br>2-(4-(2-acetyl-5-chlorophenyl)-5-methoxy-2-oxopyridin-1(2H)-yl)-3-phenyl-N-(4-sulfamoylphenyl)propanamide 58 |
| 59 | 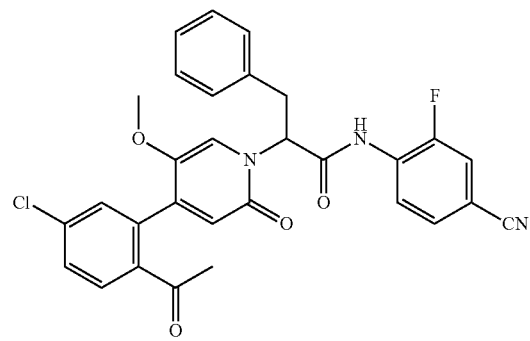<br>59<br>2-(4-(2-acetyl-5-chlorophenyl)-5-methoxy-2-oxopyridin-1(2H)-yl)-N-(4-cyano-2-fluorophenyl)-3-phenylpropanamide 59 |
| 60 | 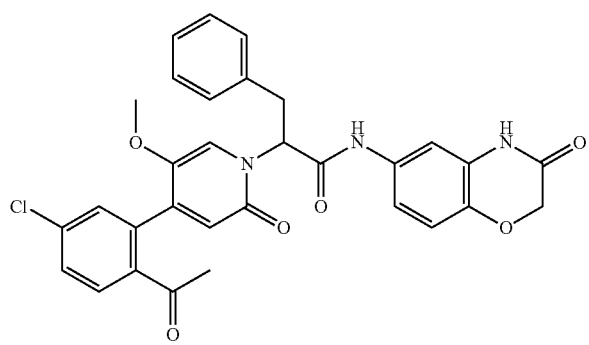<br>60<br>2-(4-(2-acetyl-5-chlorophenyl)-5-methoxy-2-oxopyridin-1(2H)-yl)-N-(3-oxo-3,4-dihydro-2H-benzo[b][1,4]oxazin-6-yl)-3-phenylpropanamide 60 |

| Example No. | Structure and Name |
|---|---|
| 61 | 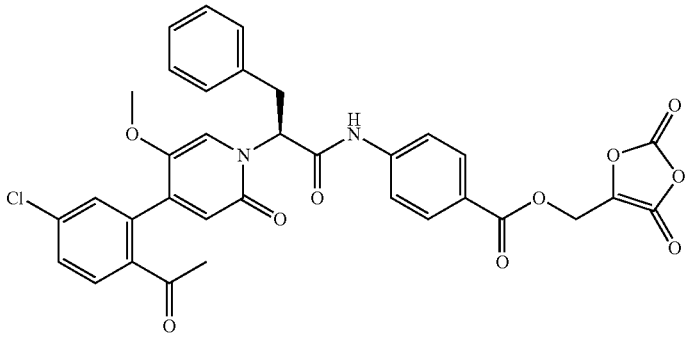
(S)-(5-methyl-2-oxo-1,3-dioxol-4-yl)methyl 4-(2-(4-(2-acetyl-5-chlorophenyl)-5-methoxy-2-oxopyridin-1(2H)-yl)-3-phenylpropanamido)benzoate 61 |
| 62 | 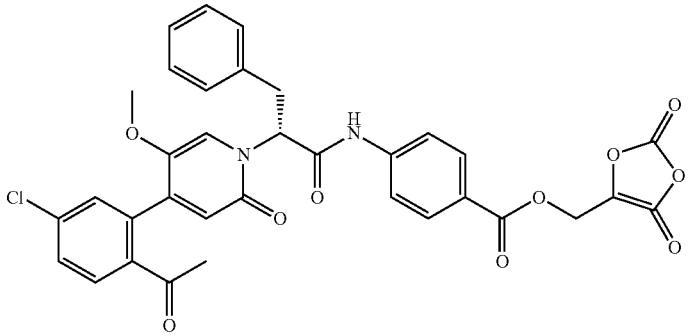
(R)-(5-methyl-2-oxo-1,3-dioxol-4-yl)methyl 4-(2-(4-(2-acetyl-5-chlorophenyl)-5-methoxy-2-oxopyridin-1(2H)-yl)-3-phenylpropanamido)benzoate 62 |
| 63 | 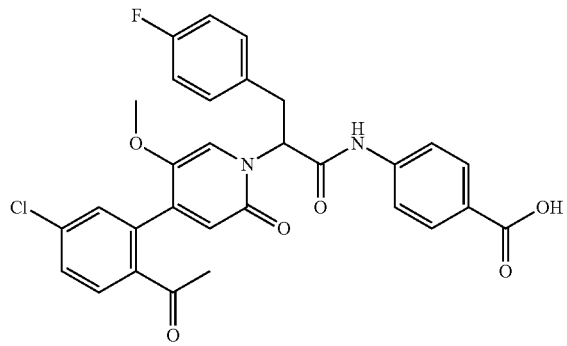
4-(2-(4-(2-acetyl-5-chlorophenyl)-5-methoxy-2-oxopyridin-1(2H)-yl)-3-(4-fluorophenyl)propanamido)benzoic acid 63 |

| Example No. | Structure and Name |
|---|---|
| 64 | 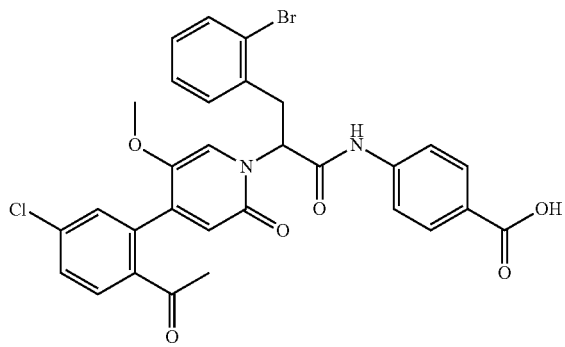
4-(2-(4-(2-acetyl-5-chlorophenyl)-5-methoxy-2-oxopyridin-1(2H)-yl)-
(2-bromophenyl)propanamido)benzoic acid 64 |
| 65 | 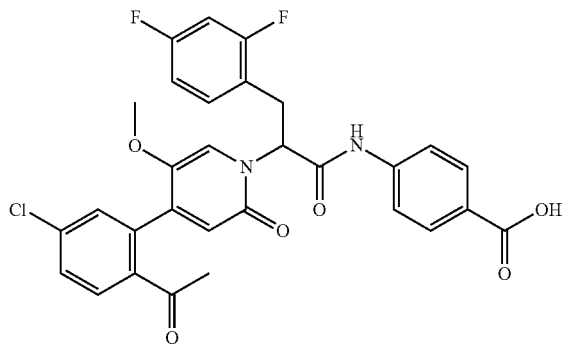
4-(2-(4-(2-acetyl-5-chlorophenyl)-5-methoxy-2-oxopyridin-1(2H)-yl)-
3-(2,4-difluorophenyl)propanamido)benzoic acid 65 |
| 66 | 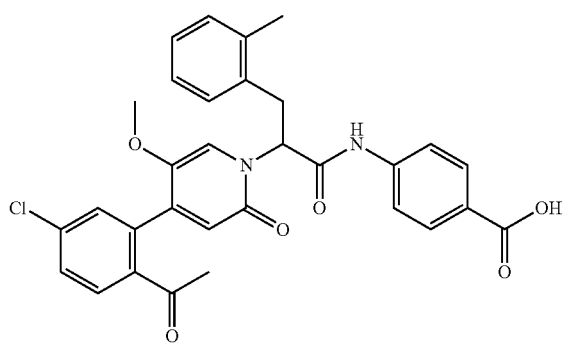
4-(2-(4-(2-acetyl-5-chlorophenyl)-5-methoxy-2-oxopyridin-1(2H)-yl)-
3-(o-tolyl)propanamido)benzoic acid 66 |

| Example No. | Structure and Name |
|---|---|
| 67 | 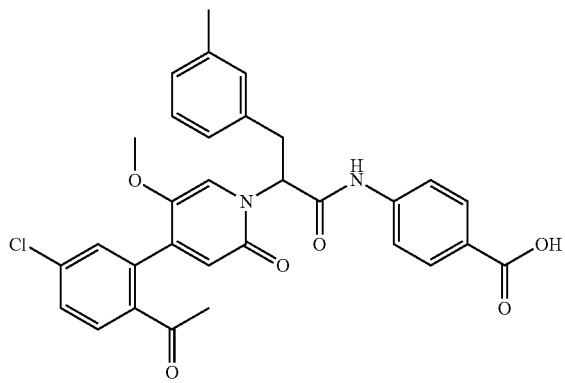
67
4-(2-(4-(2-acetyl-5-chlorophenyl)-5-methoxy-2-oxopyridin-1(2H)-yl)-3-(m-tolyl)propanamido)benzoic acid 67 |
| 68 | 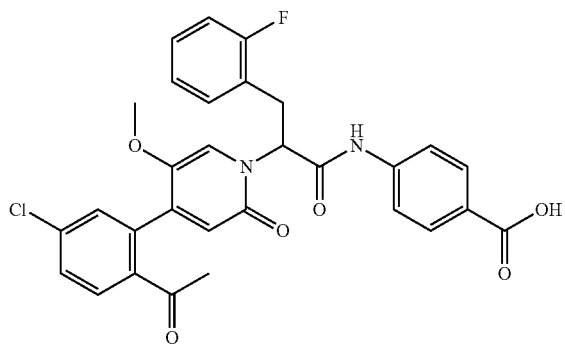
68
4-(2-(4-(2-acetyl-5-chlorophenyl)-5-methoxy-2-oxopyridin-1(2H)-yl)-3-(2-fluorophenyl)propanamido)benzoic acid 68 |
| 69 | 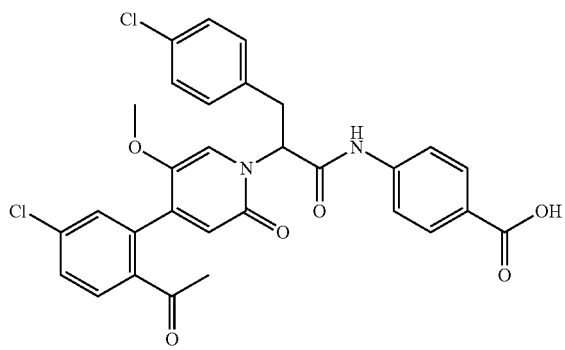
69
4-(2-(4-(2-acetyl-5-chlorophenyl)-5-methoxy-2-oxopyridin-1(2H)-yl)-3-(4-chlorophenyl)propanamido)benzoic acid 69 |

| Example No. | Structure and Name |
|---|---|
| 70 | 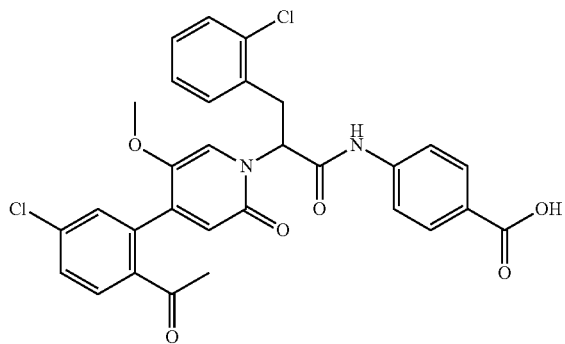<br>4-(2-(4-(2-acetyl-5-chlorophenyl)-5-methoxy-2-oxopyridin-1(2H)-yl)-3-(2-chlorophenyl)propanamido)benzoic acid 70 |
| 71 | 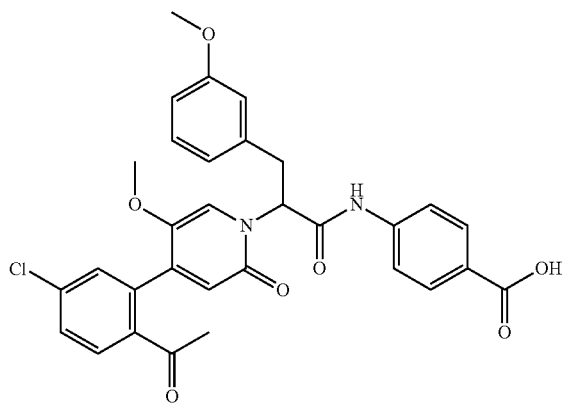<br>4-(2-(4-(2-acetyl-5-chlorophenyl)-5-methoxy-2-oxopyridin-1(2H)-yl)-3-(3-methoxyphenyl)propanamido)benzoic acid 71 |
| 72 | 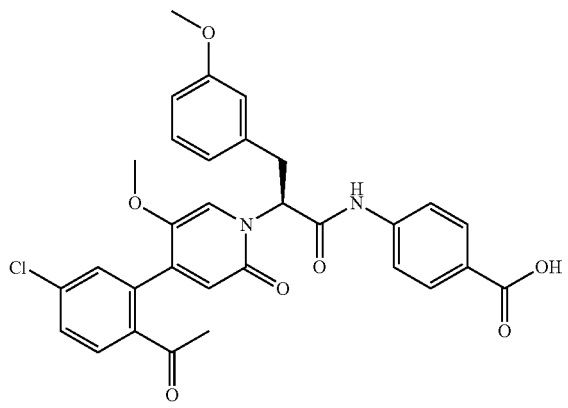<br>(S)-4-(2-(4-(2-acetyl-5-chlorophenyl)-5-methoxy-2-oxopyridin-1(2H)-yl)-3-(3-methoxyphenyl)propanamido)benzoic acid 72 |

| Example No. | Structure and Name |
|---|---|
| 73 | 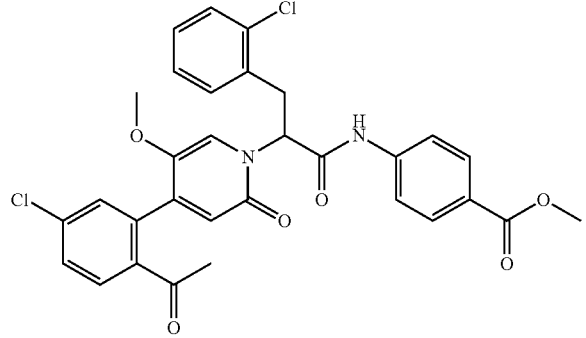<br>73<br>methyl 4-(2-(4-(2-acetyl-5-chlorophenyl)-5-methoxy-2-oxopyridin-1(2H)-yl)-3-(2-chlorophenyl)propanamido)benzoate 73 |
| 74 | 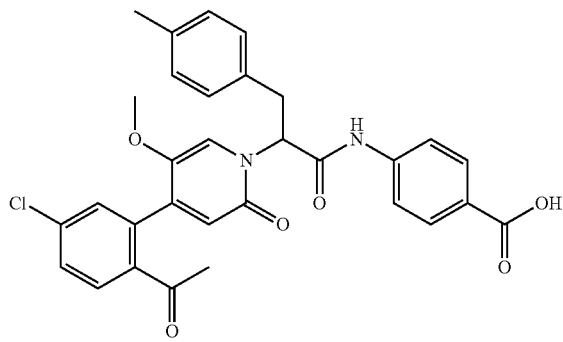<br>74<br>4-(2-(4-(2-acetyl-5-chlorophenyl)-5-methoxy-2-oxopyridin-1(2H)-yl)-3-(p-tolyl)propanamido)benzoic acid 74 |
| 75 | 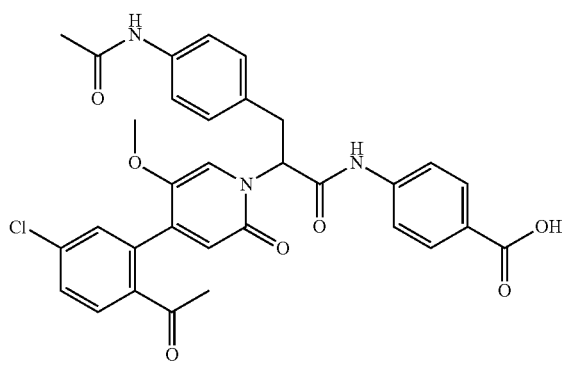<br>75<br>4-(3-(4-acetamidophenyl)-2-(4-(2-acetyl-5-chlorophenyl)-5-methoxy-2-oxopyridin-1(2H)-yl)propanamido)benzoic acid 75 |

| Example No. | Structure and Name |
|---|---|
| 76 | 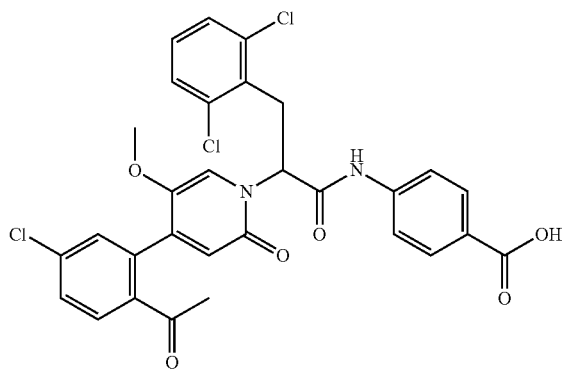<br>4-(2-(4-(2-acetyl-5-chlorophenyl)-5-methoxy-2-oxopyridin-1(2H)-yl)-3-(2,6-dichlorophenyl)propanamido)benzoic acid 76 |
| 77 | 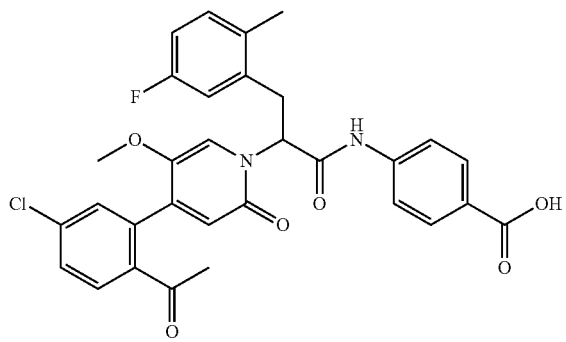<br>4-(2-(4-(2-acetyl-5-chlorophenyl)-5-methoxy-2-oxopyridin-1(2H)-yl)-3-(5-fluoro-2-methylphenyl)propanamido)benzoic acid 77 |
| 78 | 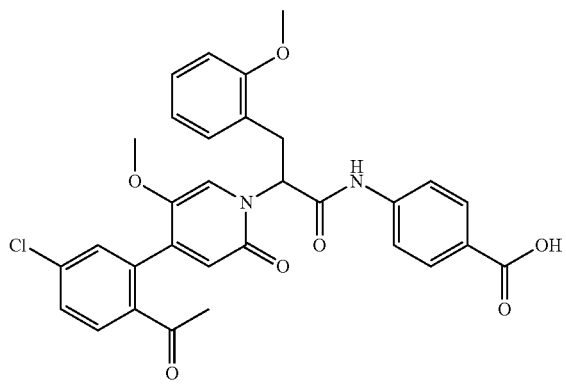<br>4-(2-(4-(2-acetyl-5-chlorophenyl)-5-methoxy-2-oxopyridin-1(2H)-yl)-3-(2-methoxyphenyl)propanamido)benzoic acid 78 |

| Example No. | Structure and Name |
|---|---|
| 79 | 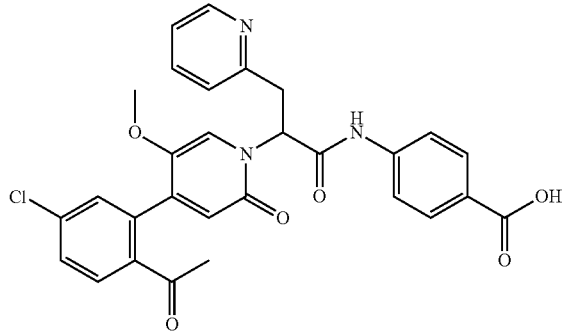<br>4-(2-(4-(2-acetyl-5-chlorophenyl)-5-methoxy-2-oxopyridin-1(2H)-yl)-3-(pyridin-2-yl)propanamido)benzoic acid 79 |
| 80 | 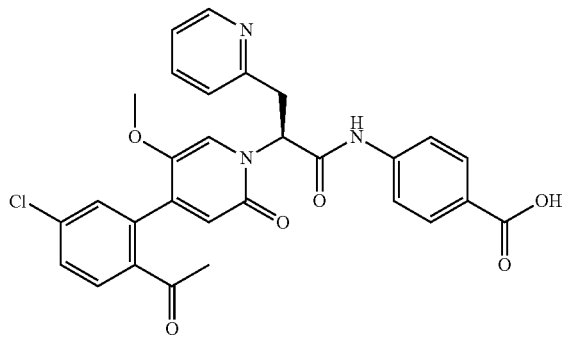<br>(S)-4-(2-(4-(2-acetyl-5-chlorophenyl)-5-methoxy-2-oxopyridin-1(2H)-yl)-3-(pyridin-2-yl)propanamido)benzoic acid 80 |
| 81 | 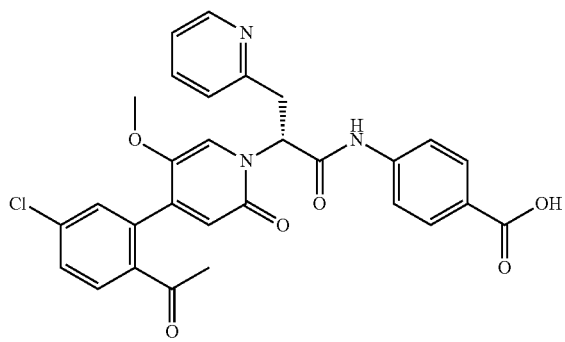<br>(R)-4-(2-(4-(2-acetyl-5-chlorophenyl)-5-methoxy-2-oxopyridin-1(2H)-yl)-3-(pyridin-2-yl)propanamido)benzoic acid 81 |

| Example No. | Structure and Name |
|---|---|
| 82 | 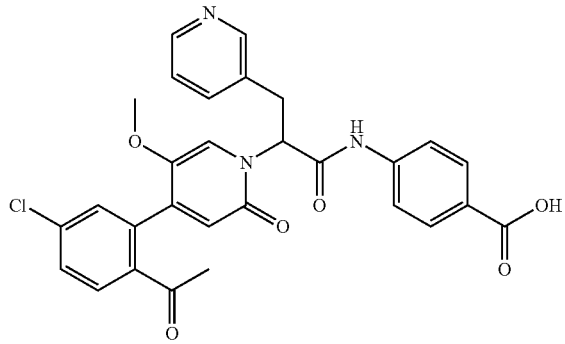
82
4-(2-(4-(2-acetyl-5-chlorophenyl)-5-methoxy-2-oxopyridin-1(2H)-yl)-3-(pyridin-3-yl)propanamido)benzoic acid 82 |
| 83 | 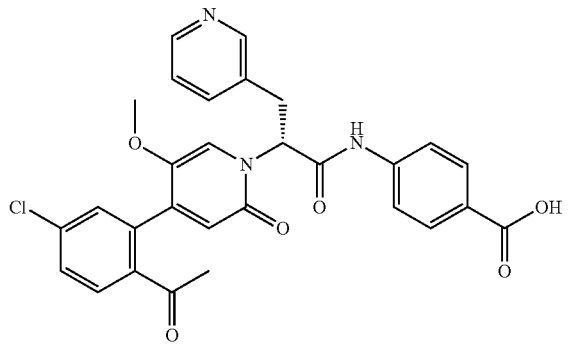
83
(R)-4-(2-(4-(2-acetyl-5-chlorophenyl)-5-methoxy-2-oxopyridin-1(2H)-yl)-3-(pyridin-3-yl)propanamido)benzoic acid 83 |
| 84 | 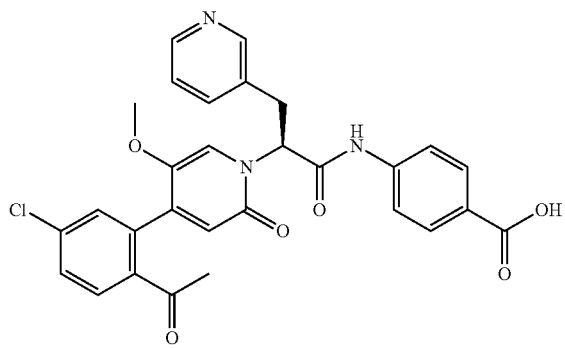
84
(S)-4-(2-(4-(2-acetyl-5-chlorophenyl)-5-methoxy-2-oxopyridin-1(2H)-yl)-3-(pyridin-3-yl)propanamido)benzoic acid 84 |

| Example No. | Structure and Name |
|---|---|
| 85 | 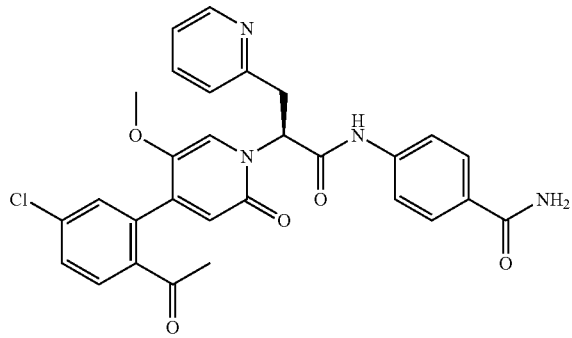
(S)-4-(2-(4-(2-acetyl-5-chlorophenyl)-5-methoxy-2-oxopyridin-1(2H)-yl)-3-(pyridin-2-yl)propanamido)benzamide 85 |
| 86 | 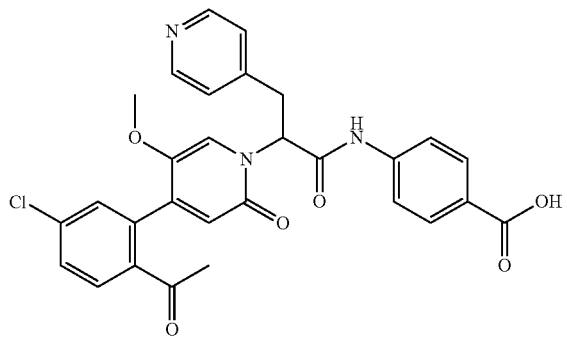
4-(2-(4-(2-acetyl-5-chlorophenyl)-5-methoxy-2-oxopyridin-1(2H)-yl)-3-(pyridin-4-yl)propanamido)benzoic acid 86 |
| 87 | 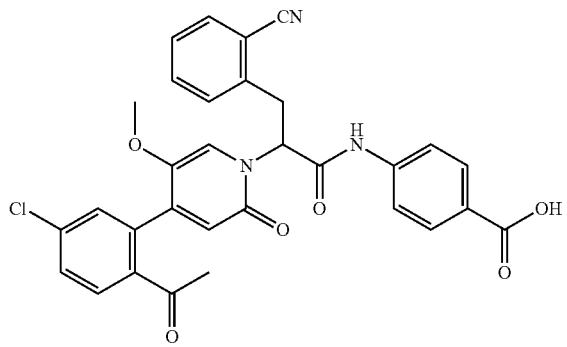
4-(2-(4-(2-acetyl-5-chlorophenyl)-5-methoxy-2-oxopyridin-1(2H)-yl)-3-(2-cyanophenyl)propanamido)benzoic acid 87 |

| Example No. | Structure and Name |
|---|---|
| 88 | 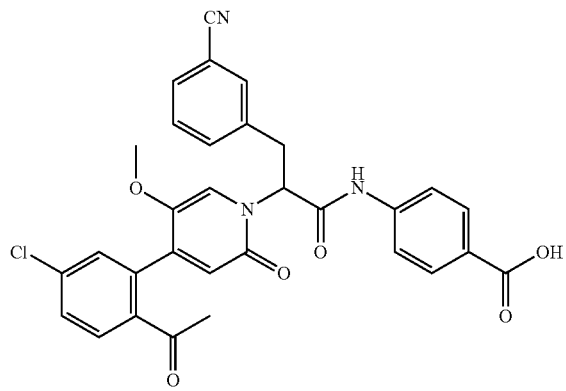<br>4-(2-(4-(2-acetyl-5-chlorophenyl)-5-methoxy-2-oxopyridin-1(2H)-yl)-3-(3-cyanophenyl)propanamido)benzoic acid 88 |
| 89 | 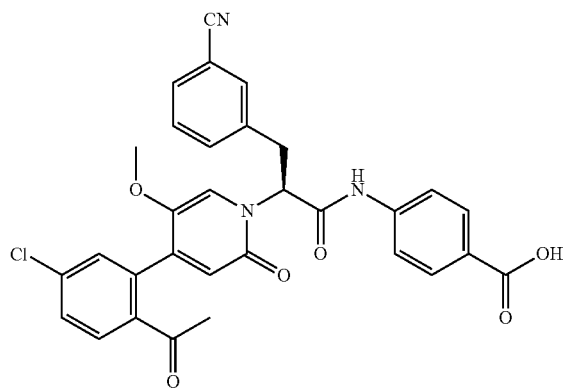<br>(S)-4-(2-(4-(2-acetyl-5-chlorophenyl)-5-methoxy-2-oxopyridin-1(2H)-yl)-3-(3-cyanophenyl)propanamido)benzoic acid 89 |
| 90 | 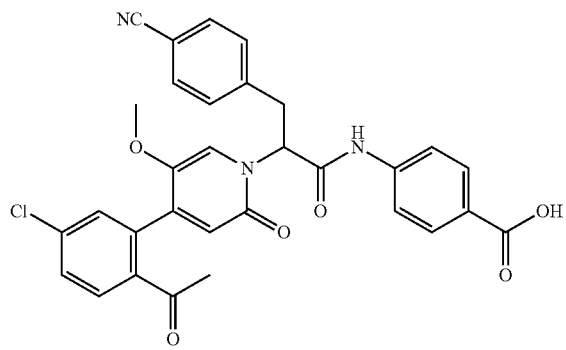<br>4-(2-(4-(2-acetyl-5-chlorophenyl)-5-methoxy-2-oxopyridin-1(2H)-yl)-3-(4-cyanophenyl)propanamido)benzoic acid 90 |

| Example No. | Structure and Name |
|---|---|
| 91 | 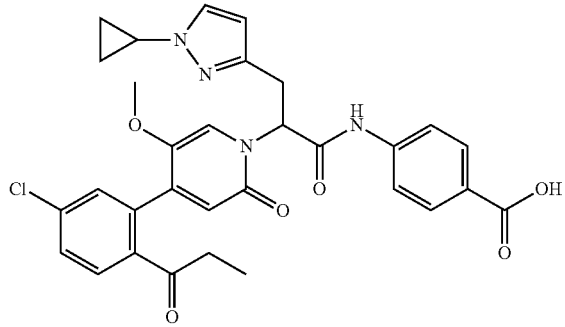
91
4-(2-(4-(5-chloro-2-propionylphenyl)-5-methoxy-2-oxopyridin-1(2H)-yl)-3-(1-cyclopropyl-1H-pyrazol-3-yl)propanamido)benzoic acid 91 |
| 92 | 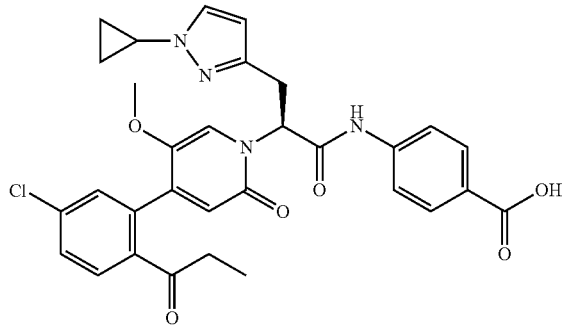
92
(S)-4-(2-(4-(5-chloro-2-propionylphenyl)-5-methoxy-2-oxopyridin-1(2H)-yl)-3-(1-cyclopropyl-1H-pyrazol-3-yl)propanamido)benzoic acid 92 |
| 93 | 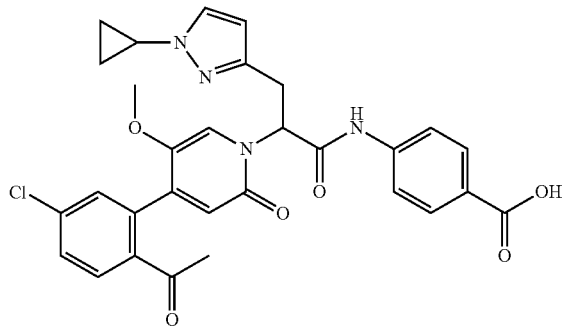
93
4-(2-(4-(2-acetyl-5-chlorophenyl)-5-methoxy-2-oxopyridin-1(2H)-yl)-3-(1-cyclopropyl-1H-pyrazol-3-yl)propanamido)benzoic acid 93 |

| Example No. | Structure and Name |
|---|---|
| 94 | 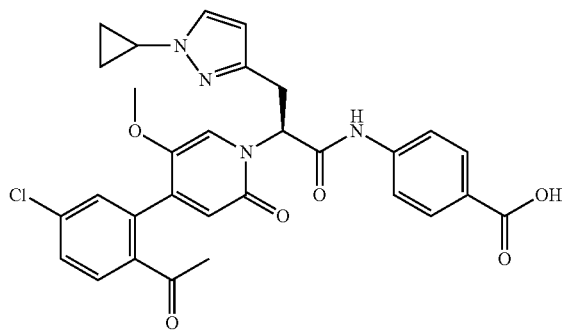<br>(S)-4-(2-(4-(2-acetyl-5-chlorophenyl)-5-methoxy-2-oxopyridin-1(2H)-yl)-3-(1-cyclopropyl-1H-pyrazol-3-yl)propanamido)benzoic acid 94 |
| 95 | 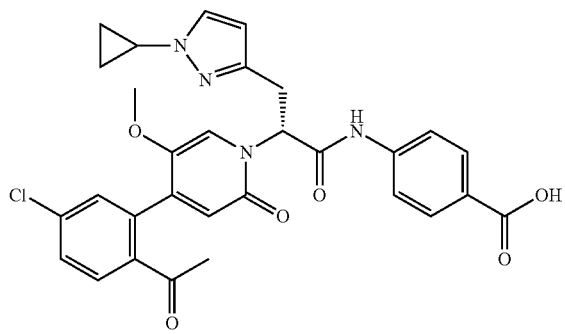<br>(R)-4-(2-(4-(2-acetyl-5-chlorophenyl)-5-methoxy-2-oxopyridin-1(2H)-yl)-3-(1-cyclopropyl-1H-pyrazol-3-yl)propanamido)benzoic acid 95 |
| 96 | 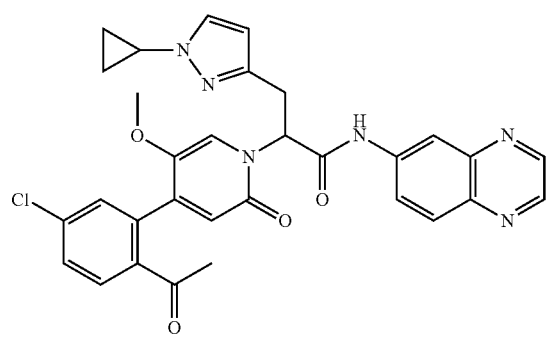<br>2-(4-(2-acetyl-5-chlorophenyl)-5-methoxy-2-oxopyridin-1(2H)-yl)-3-(1-cyclopropyl-1H-pyrazol-3-yl)-N-(quinoxalin-6-yl)propanamide 96 |

| Example No. | Structure and Name |
|---|---|
| 97 | 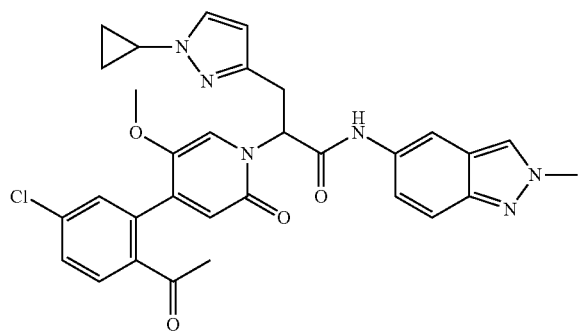<br>97<br><br>2-(4-(2-acetyl-5-chlorophenyl)-5-methoxy-2-oxopyridin-1(2H)-yl)-3-(1-cyclopropyl-1H-pyrazol-3-yl)-N-(2-methyl-2H-indazol-5-yl) propanamide 97 |
| 98 | 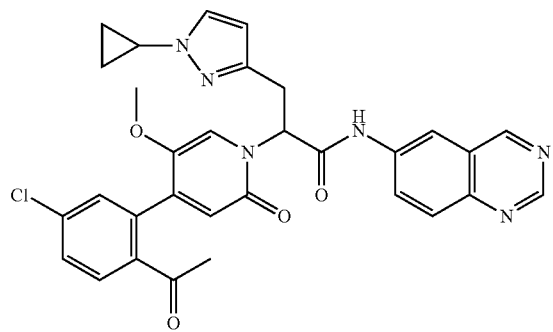<br>98<br><br>2-(4-(2-acetyl-5-chlorophenyl)-5-methoxy-2-oxopyridin-1(2H)-yl)-3-(1-cyclopropyl-1H-pyrazol-3-yl)-N-(quinazolin-6-yl)propanamide 98 |
| 99 | 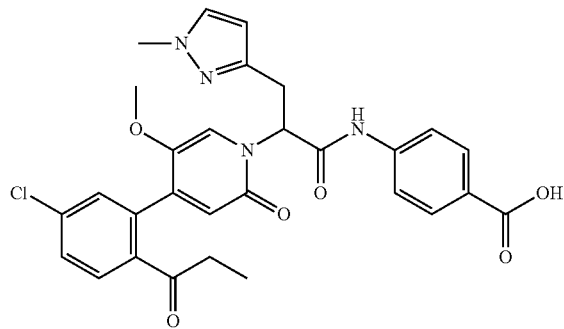<br>99<br><br>4-(2-(4-(5-chloro-2-propionylphenyl)-5-methoxy-2-oxopyridin-1(2H)-yl)-3-(1-methyl-1H-pyrazol-3-yl)propanamido)benzoic acid 99 |

| Example No. | Structure and Name |
|---|---|
| 100 | 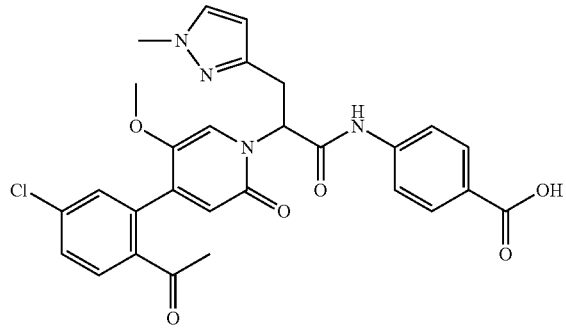<br>4-(2-(4-(2-acetyl-5-chlorophenyl)-5-methoxy-2-oxopyridin-1(2H)-yl)-3-(1-methyl-1H-pyrazol-3-yl)propanamido)benzoic acid 100 |
| 101 | 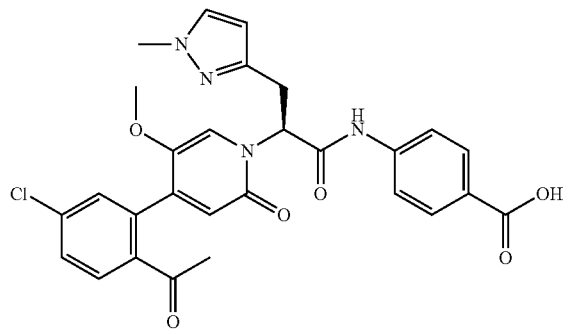<br>(S)-4-(2-(4-(2-acetyl-5-chlorophenyl)-5-methoxy-2-oxopyridin-1(2H)-yl)-3-(1-methyl-1H-pyrazol-3-yl)propanamido)benzoic acid 101 |
| 102 | 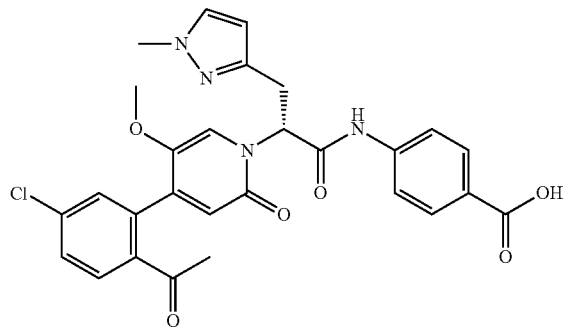<br>(R)-4-(2-(4-(2-acetyl-5-chlorophenyl)-5-methoxy-2-oxopyridin-1(2H)-yl)-3-(1-methyl-1H-pyrazol-3-yl)propanamido)benzoic acid 102 |

| Example No. | Structure and Name |
|---|---|
| 103 | 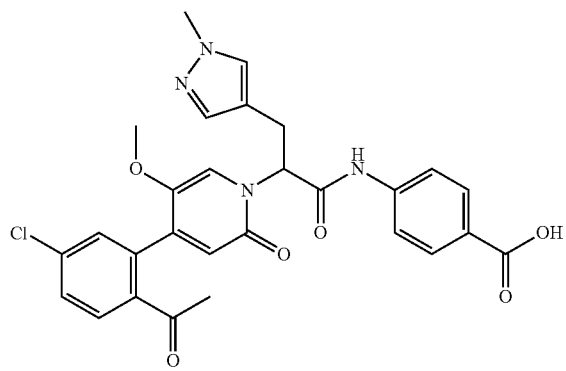
103
4-(2-(4-(2-acetyl-5-chlorophenyl)-5-methoxy-2-oxopyridin-1(2H)-yl)-
3-(1-methyl-1H-pyrazol-4-yl)propanamido)benzoic acid 103 |
| 104 | 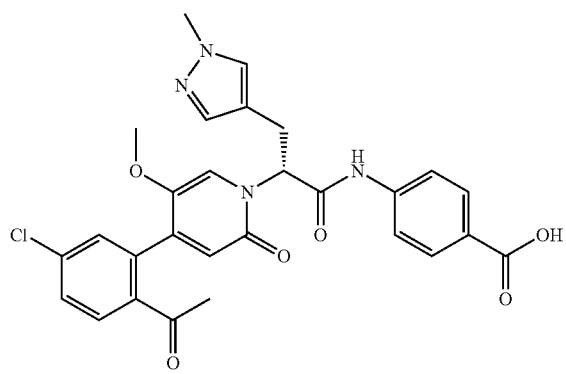
104
(R)-4-(2-(4-(2-acetyl-5-chlorophenyl)-5-methoxy-2-oxopyridin-1(2H)-
yl)-3-(1-methyl-1H-pyrazol-4-yl)propanamido)benzoic acid 104 |
| 105 | 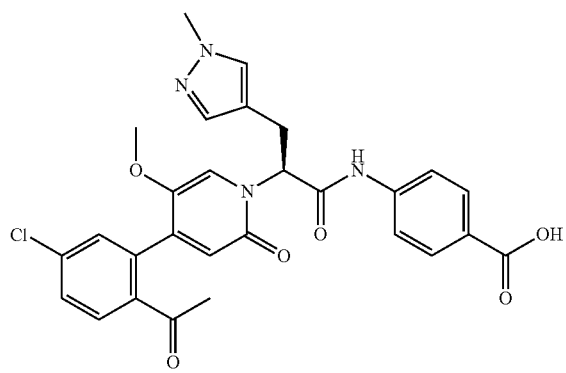
105
(S)-4-(2-(4-(2-acetyl-5-chlorophenyl)-5-methoxy-2-oxopyridin-1(2H)-
yl)-3-(1-methyl-1H-pyrazol-4-yl)propanamido)benzoic acid 105 |

| Example No. | Structure and Name |
|---|---|
| 106 | 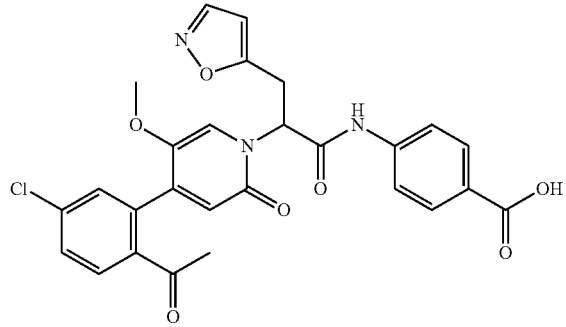<br>4-(2-(4-(2-acetyl-5-chlorophenyl)-5-methoxy-2-oxopyridin-1(2H)-yl)-3-(isoxazol-5-yl)propanamido)benzoic acid 106 |
| 107 | 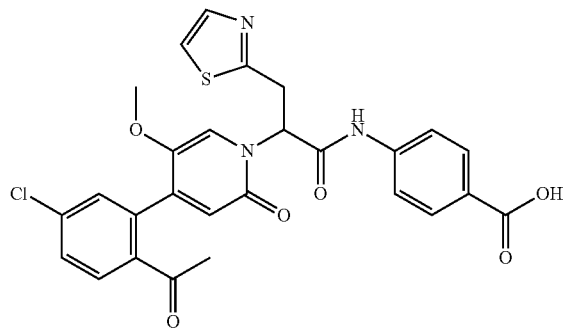<br>4-(2-(4-(2-acetyl-5-chlorophenyl)-5-methoxy-2-oxopyridin-1(2H)-yl)-3-(thiazol-2-yl)propanamido)benzoic acid 107 |
| 108e | 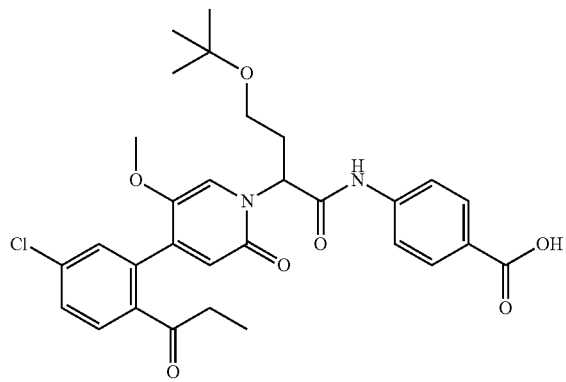<br>4-(4-(tert-butoxy)-2-(4-(5-chloro-2-propionylphenyl)-5-methoxy-2-oxopyridin-1(2H)-yl)butanamido)benzoic acid 108e |

| Example No. | Structure and Name |
|---|---|
| 108 | 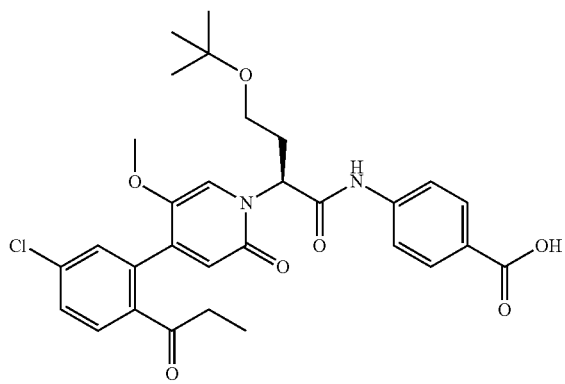<br>(S)-4-(4-(tert-butoxy)-2-(4-(5-chloro-2-propionylphenyl)-5-methoxy-2-oxopyridin-1(2H)-yl)butanamido)benzoic acid 108 |
| 109 | 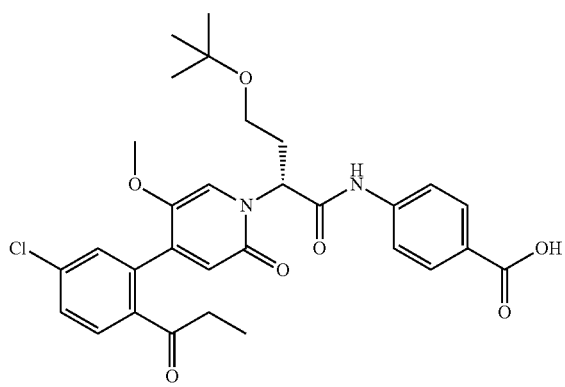<br>(R)-4-(4-tert-butoxy-2-(4-(5-chloro-2-propionylphenyl)-5-methoxy-2-oxopyridin-1(2H)-yl)butanamido)benzoic acid 109 |
| 110 | 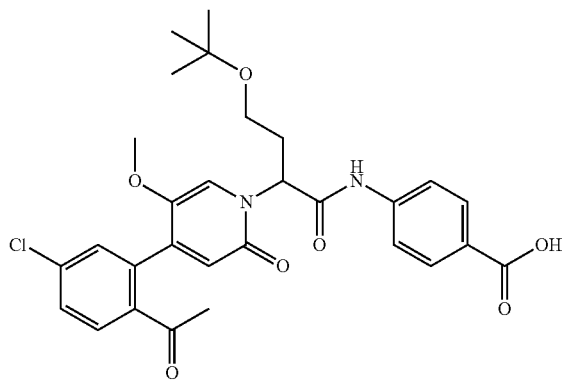<br>4-(2-(4-(2-acetyl-5-chlorophenyl)-5-methoxy-2-oxopyridin-1(2H)-yl)-4-(tert-butoxy)butanamido)benzoic acid 110 |

| Example No. | Structure and Name |
|---|---|
| 111 | 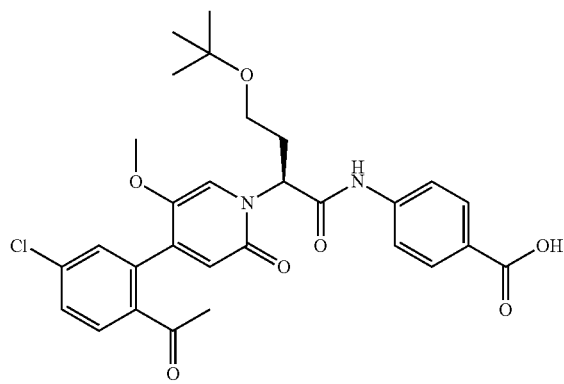<br>(S)-4-(2-(4-(2-acetyl-5-chlorophenyl)-5-methoxy-2-oxopyridin-1(2H)-yl)-4-(tert-butoxy)butanamido)benzoic acid 111 |
| 112 | 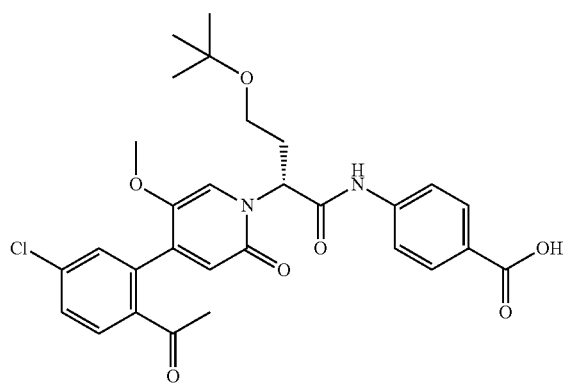<br>(R)-4-(2-(4-(2-acetyl-5-chlorophenyl)-5-methoxy-2-oxopyridin-1(2H)-yl)-4-(tert-butoxy)butanamido)benzoic acid 112 |
| 113 | 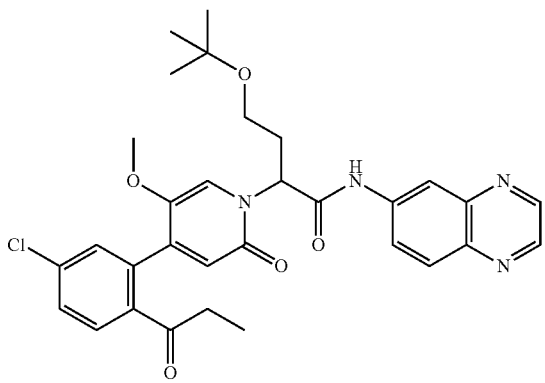<br>4-(tert-butoxy)-2-(4-(5-chloro-2-propionylphenyl)-5-methoxy-2-oxopyridin-1(2H)-yl)-N-(quinoxalin-6-yl)butanamide 113 |

| Example No. | Structure and Name |
|---|---|
| 114 | 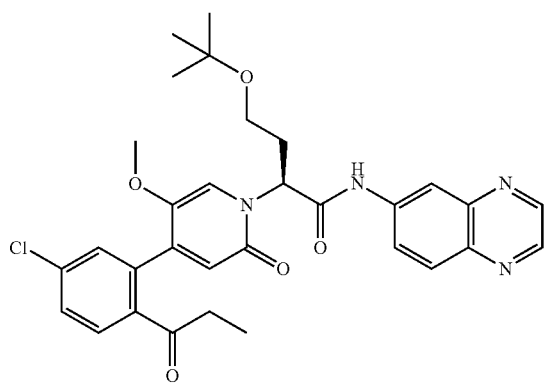<br>(S)-4-tert-butoxy-2-(4-(5-chloro-2-propionylphenyl)-5-methoxy-2-oxopyridin-1(2H)-yl)-N-(quinoxalin-6-yl)butanamide 114 |
| 115 | 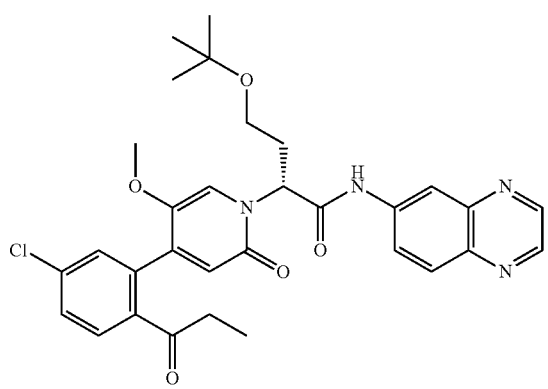<br>(R)-4-(tert-butoxy)-2-(4-(5-chloro-2-propionylphenyl)-5-methoxy-2-oxopyridin-1(2H)-yl)-N-(quinoxalin-6-yl)butanamide 115 |
| 116 | 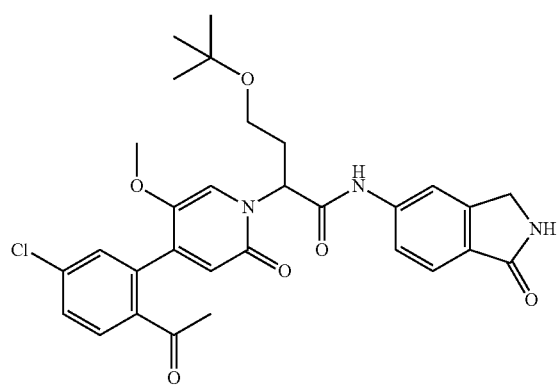<br>2-(4-(2-acetyl-5-chlorophenyl)-5-methoxy-2-oxopyridin-1(2H)-yl)-4-(tert-butoxy)-N-(1-oxoisoindolin-5-yl)butanamide 116 |

| Example No. | Structure and Name |
|---|---|
| 117d | 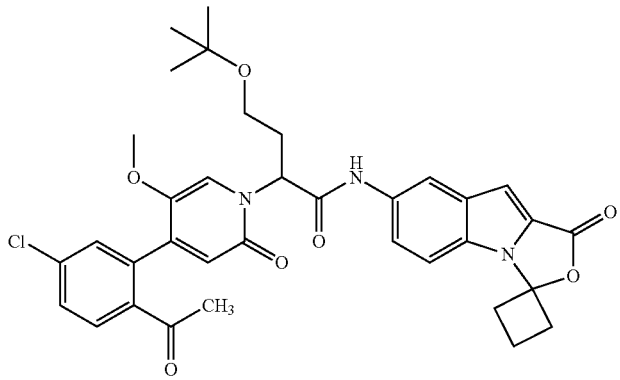

2-(4-(2-acetyl-5-chlorophenyl)-5-methoxy-2-oxopyridin-1(2H)-yl)-4-methoxy-N-(1'-oxo-1'H-spiro[cyclobutane-1,3'-oxazolo[3,4-a]indol]-7'-yl)butanamide 117d |
| 117 | 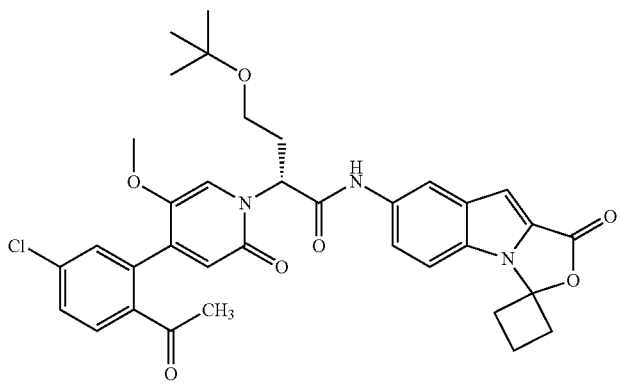

(R)-2-(4-(2-acetyl-5-chlorophenyl)-5-methoxy-2-oxopyridin-1(2H)-yl)-4-methoxy-N-(1'-oxo-1'H-spiro[cyclobutane-1,3'-oxazolo[3,4-a]indol]-7'-yl)butanamide 117 |
| 118 | 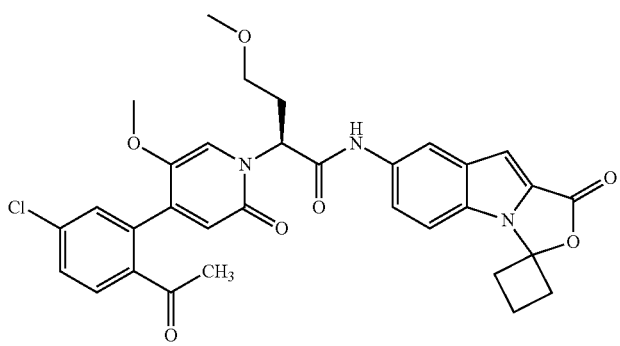

(S)-2-(4-(2-acetyl-5-chlorophenyl)-5-methoxy-2-oxopyridin-1(2H)-yl)-4-methoxy-N-(1'-oxo-1'H-spiro[cyclobutane-1,3'-oxazolo[3,4-a]indol]-7'-yl)butanamide 118 |

| Example No. | Structure and Name |
|---|---|
| 119 | 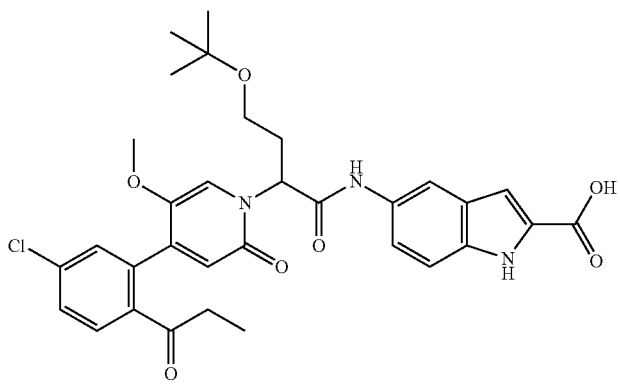
5-(4-(tert-butoxy)-2-(4-(5-chloro-2-propionylphenyl)-5-methoxy-2-oxopyridin-1(2H)-yl)butanamido)-1H-indole-2-carboxylic acid 119 |
| 120 | 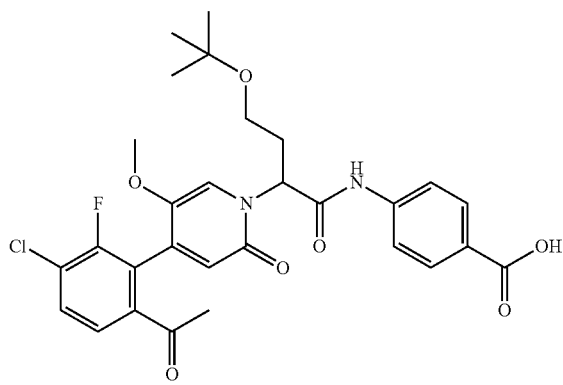
4-(2-(4-(6-acetyl-3-chloro-2-fluorophenyl)-5-methoxy-2-oxopyridin-1(2H)-yl)-4-(tert-butoxy)butanamido)benzoic acid 120 |
| 121 | 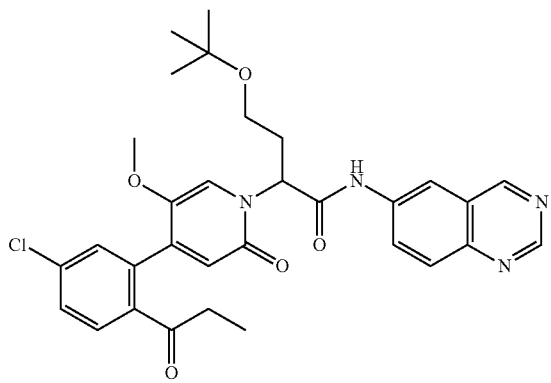
4-(tert-butoxy)-2-(4-(5-chloro-2-propionylphenyl)-5-methoxy-2-oxopyridin-1(2H)-yl)-N-(quinazolin-6-yl)butanamide 121 |

| Example No. | Structure and Name |
|---|---|
| 122 | 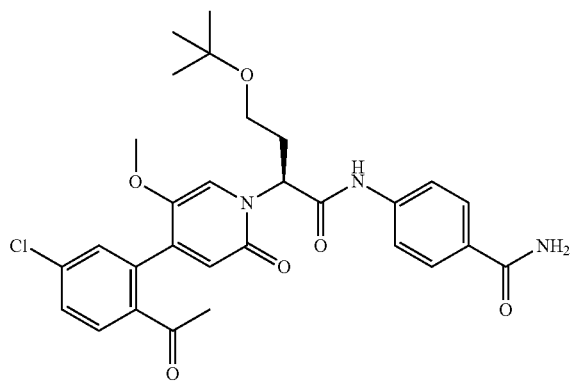<br>(S)-4-(2-(4-(2-acetyl-5-chlorophenyl)-5-methoxy-2-oxopyridin-1(2H)-yl)-4-(tert-butoxy)butanamido)benzamide 122 |
| 123 | 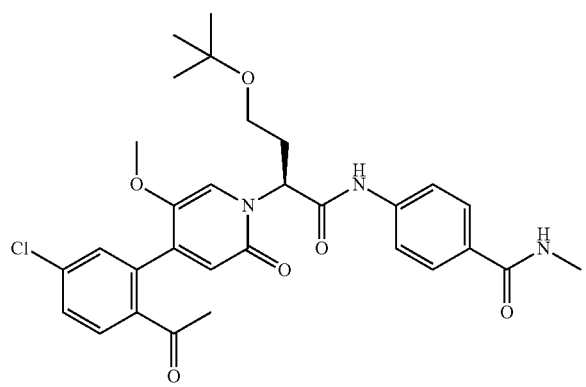<br>(S)-4-(2-(4-(2-acetyl-5-chlorophenyl)-5-methoxy-2-oxopyridin-1(2H)-yl)-4-(tert-butoxy)butanamido)-N-methylbenzamide 123 |
| 124 | 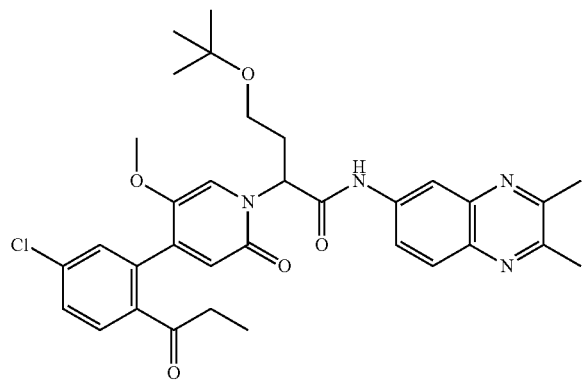<br>4-(tert-butoxy)-2-(4-(5-chloro-2-propionylphenyl)-5-methoxy-2-oxopyridin-1(2H)-yl)-N-(2,3-dimethylquinoxalin-6-yl)butanamide 124 |

| Example No. | Structure and Name |
|---|---|
| 125 | 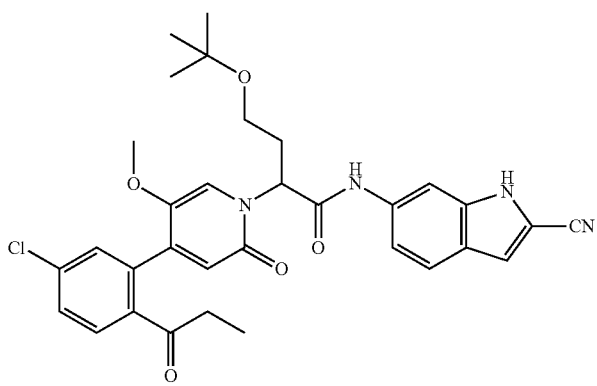
4-(tert-butoxy)-2-(4-(5-chloro-2-propionylphenyl)-5-methoxy-2-oxopyridin-1(2H)-yl)-N-(2-cyano-1H-indol-6-yl)butanamide 125 |
| 126 | 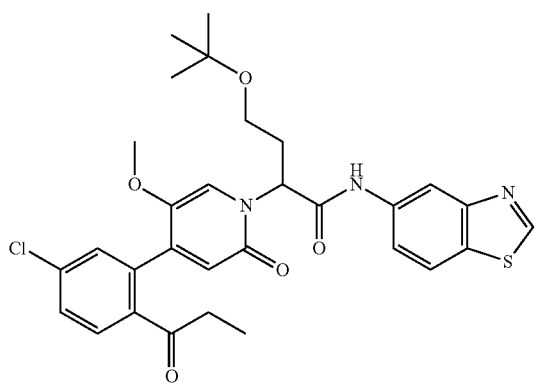
N-(benzo[d]thiazol-5-yl)-4-(tert-butoxy)-2-(4-(5-chloro-2-propionylphenyl)-5-methoxy-2-oxopyridin-1(2H)-yl)butanamide 126 |
| 127 | 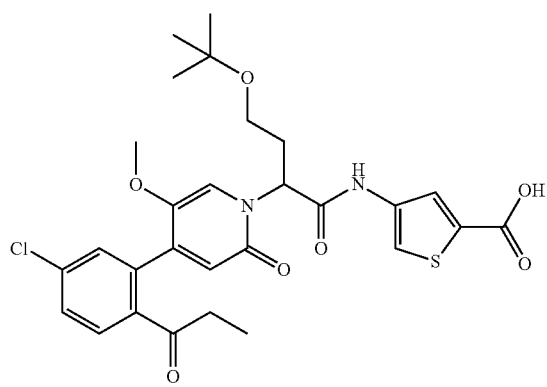
4-(4-(tert-butoxy)-2-(4-(5-chloro-2-propionylphenyl)-5-methoxy-2-oxopyridin-1(2H)-yl)butanamido)thiophene-2-carboxylic acid 127 |

| Example No. | Structure and Name |
|---|---|
| 128 | 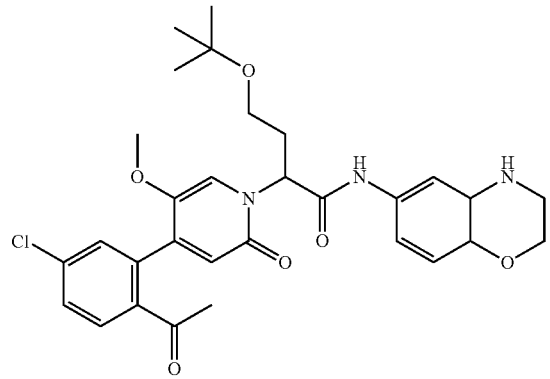
2-(4-(2-acetyl-5-chlorophenyl)-5-methoxy-2-oxopyridin-1(2H)-yl)-4-(tert-butoxy)-N-(3,4-dihydro-2H-benzo[b][1,4]oxazin-6-yl)butanamide 128 |
| 129 | 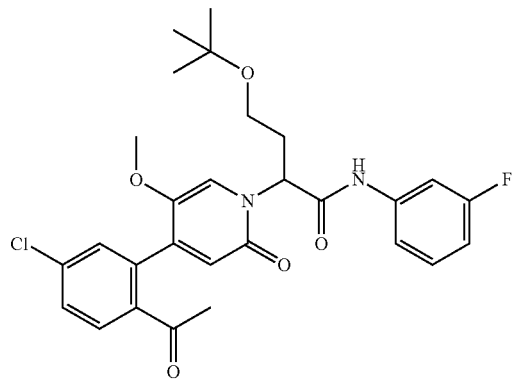
2-(4-(2-acetyl-5-chlorophenyl)-5-methoxy-2-oxopyridin-1(2H)-yl)-4-(tert-butoxy)-N-(3-fluorophenyl)butanamide 129 |
| 130 | 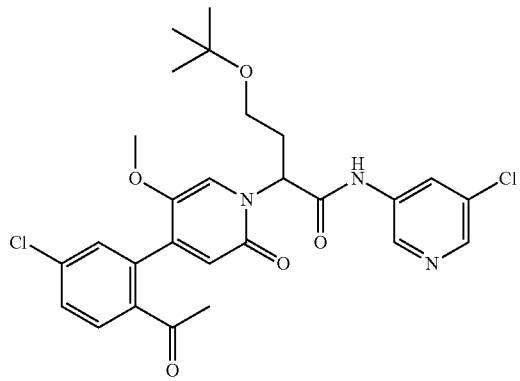
2-(4-(2-acetyl-5-chlorophenyl)-5-methoxy-2-oxopyridin-1(2H)-yl)-4-(tert-butoxy)-N-(5-chloropyridin-3-yl)butanamide 130 |

| Example No. | Structure and Name |
|---|---|
| 131 | 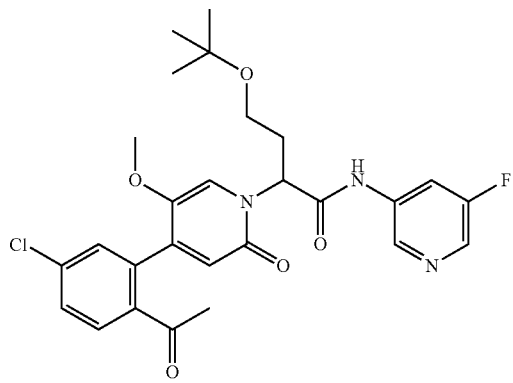
2-(4-(2-acetyl-5-chlorophenyl)-5-methoxy-2-oxopyridin-1(2H)-yl)-4-(tert-butoxy)-N-(5-fluoropyridin-3-yl)butanamide 131 |
| 132 | 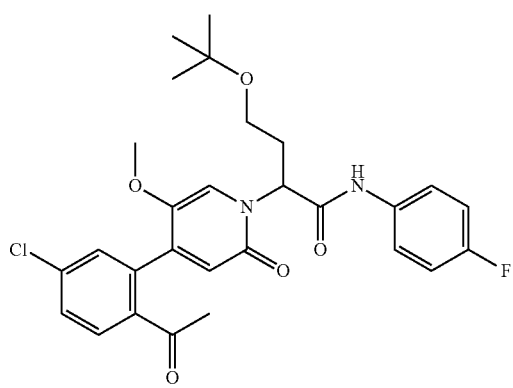
2-(4-(2-acetyl-5-chlorophenyl)-5-methoxy-2-oxopyridin-1(2H)-yl)-4-(tert-butoxy)-N-(4-fluorophenyl)butanamide 132 |
| 133 | 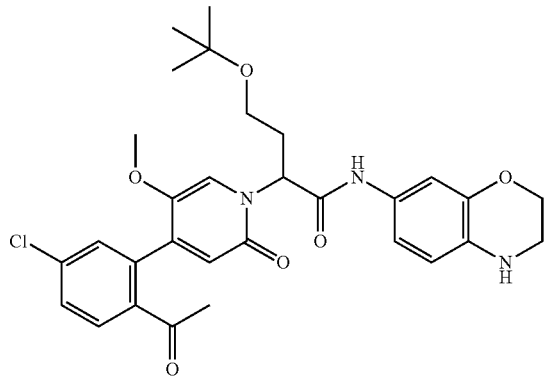
2-(4-(2-acetyl-5-chlorophenyl)-5-methoxy-2-oxopyridin-1(2H)-yl)-4-(tert-butoxy)-N-(3,4-dihydro-2H-benzo[b][1,4]oxazin-7-yl)butanamide 133 |

| Example No. | Structure and Name |
|---|---|
| 134 | 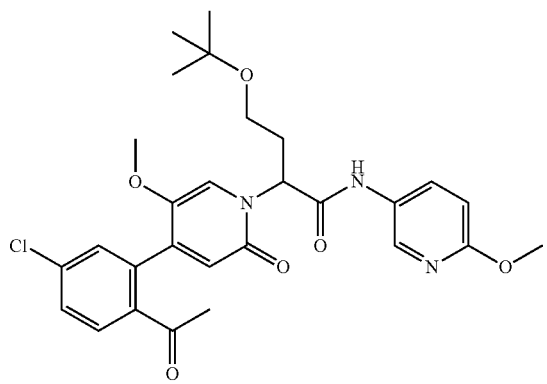<br>2-(4-(2-acetyl-5-chlorophenyl)-5-methoxy-2-oxopyridin-1(2H)-yl)-4-(tert-butoxy)-N-(6-methoxypyridin-3-yl)butanamide 134 |
| 135 | 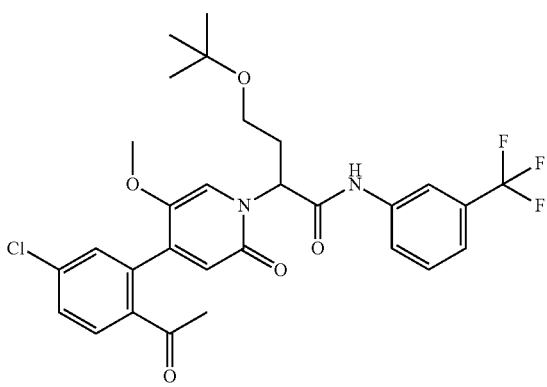<br>2-(4-(2-acetyl-5-chlorophenyl)-5-methoxy-2-oxopyridin-1(2H)-yl)-4-(tert-butoxy)-N-(3-(trifluoromethyl)phenyl)butanamide 135 |
| 136 | 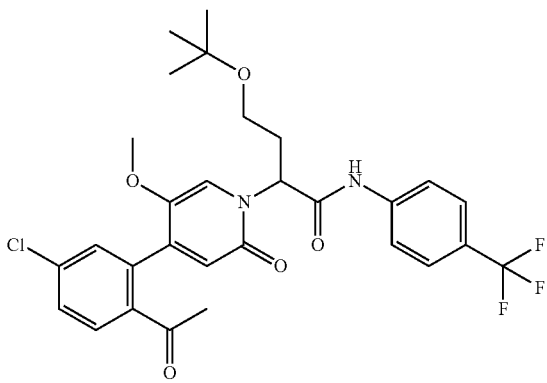<br>2-(4-(2-acetyl-5-chlorophenyl)-5-methoxy-2-oxopyridin-1(2H)-yl)-4-(tert-butoxy)-N-(4-(trifluoromethyl)phenyl)butanamide 136 |

| Example No. | Structure and Name |
|---|---|
| 137 | 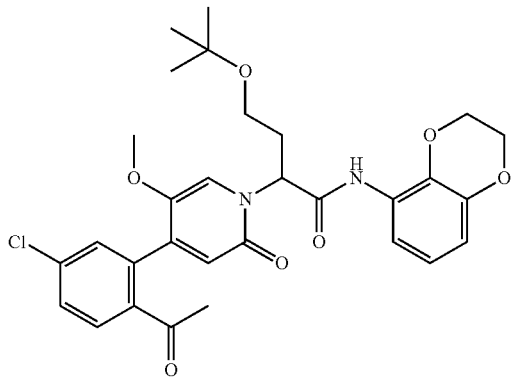<br>2-(4-(2-acetyl-5-chlorophenyl)-5-methoxy-2-oxopyridin-1(2H)-yl)-4-(tert-butoxy)-N-(2,3-dihydrobenzo[b][1,4]dioxin-5-yl)butanamide |
| 138 | 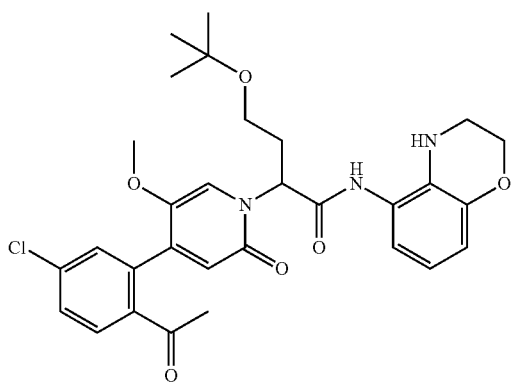<br>2-(4-(2-acetyl-5-chlorophenyl)-5-methoxy-2-oxopyridin-1(2H)-yl)-4-(tert-butoxy)-N-(3,4-dihydro-2H-benzo[b][1,4]oxazin-5-yl)butanamide |
| 139 | 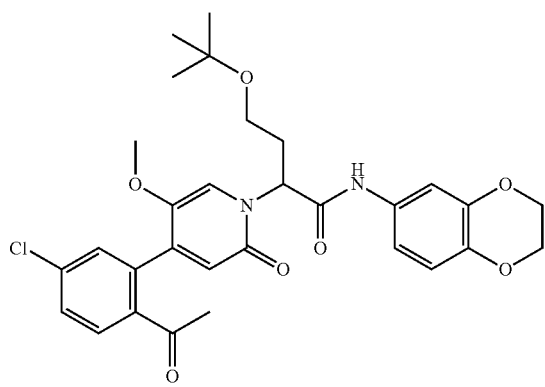<br>2-(4-(2-acetyl-5-chlorophenyl)-5-methoxy-2-oxopyridin-1(2H)-yl)-4-(tert-butoxy)-N-(2,3-dihydrobenzo[b][1,4]dioxin-6-yl)butanamide |

| Example No. | Structure and Name |
|---|---|
| 140 | 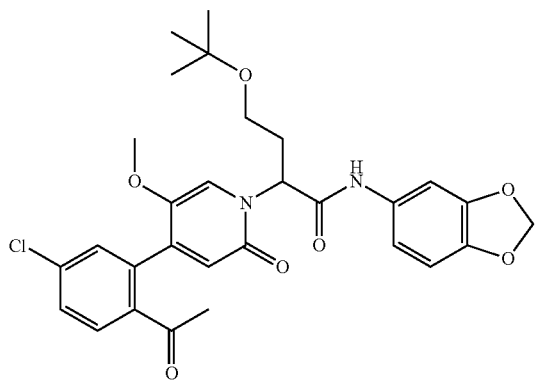<br>2-(4-(2-acetyl-5-chlorophenyl)-5-methoxy-2-oxopyridin-1(2H)-yl)-N-(benzo[d][1,3]dioxol-5-yl)-4-(tert-butoxy)butanamide 140 |
| 141 | 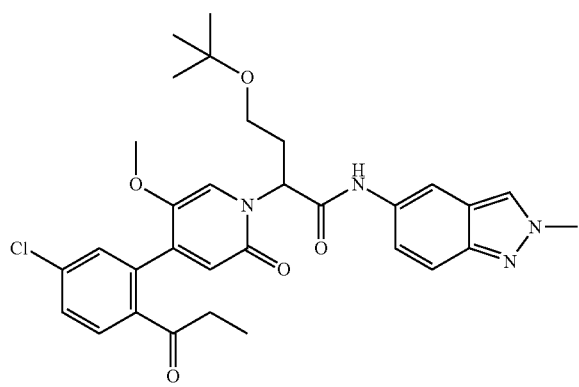<br>4-(tert-butoxy)-2-(4-(5-chloro-2-propionylphenyl)-5-methoxy-2-oxopyridin-1(2H)-yl)-N-(2-methyl-2H-carbazol-5-yl)butanamide 141 |
| 142 | 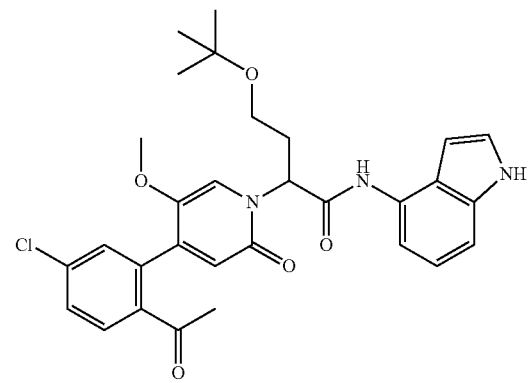<br>2-(4-(2-acetyl-5-chlorophenyl)-5-methoxy-2-oxopyridin-1(2H)-yl)-4-(tert-butoxy)-N-(1H-indol-4-yl)butanamide 142 |

| Example No. | Structure and Name |
|---|---|
| 143 | 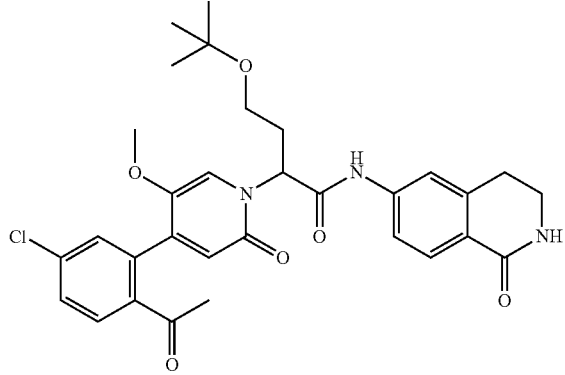<br>2-(4-(2-acetyl-5-chlorophenyl)-5-methoxy-2-oxopyridin-1(2H)-yl)-4-(tert-butoxy)-N-(1-oxo-1,2,3,4-tetrahydroisoquinolin-6-yl)butanamide 143 |
| 144 | 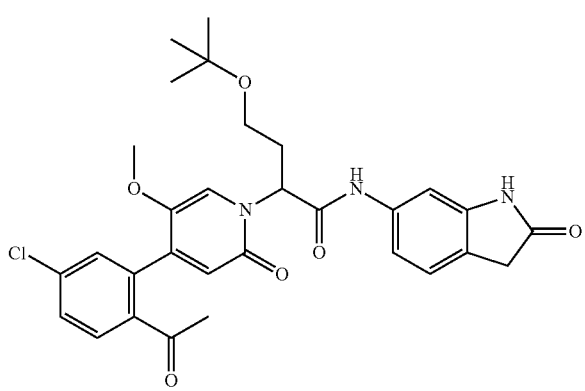<br>2-(4-(2-acetyl-5-chlorophenyl)-5-methoxy-2-oxopyridin-1(2H)-yl)-4-(tert-butoxy)-N-(2-oxoindolin-6-yl)butanamide 144 |
| 145 | 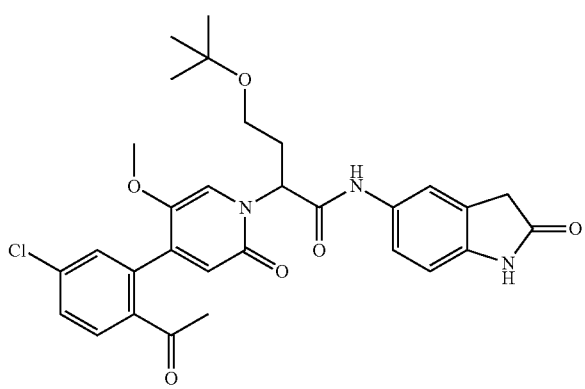<br>2-(4-(2-acetyl-5-chlorophenyl)-5-methoxy-2-oxopyridin-1(2H)-yl)-4-(tert-butoxy)-N-(2-oxoindolin-5-yl)butanamide 145 |

| Example No. | Structure and Name |
|---|---|
| 146 | 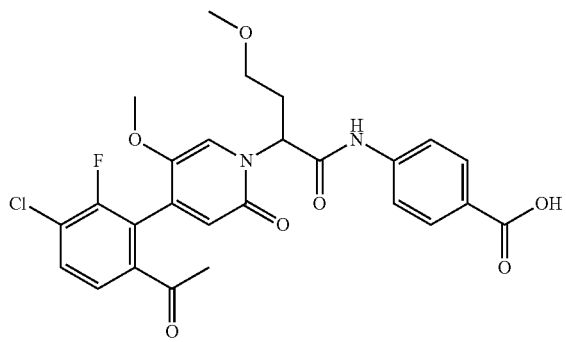<br>4-(2-(4-(6-acetyl-3-chloro-2-fluorophenyl)-5-methoxy-2-oxopyridin-1(2H)-yl)-4-methoxybutanamido)benzoic acid 146 |
| 147 | 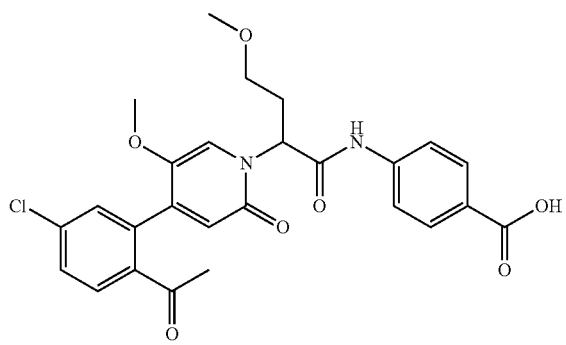<br>4-(2-(4-(2-acetyl-5-chlorophenyl)-5-methoxy-2-oxopyridin-1(2H)-yl)-4-methoxybutanamido)benzoic acid 147 |
| 148 | 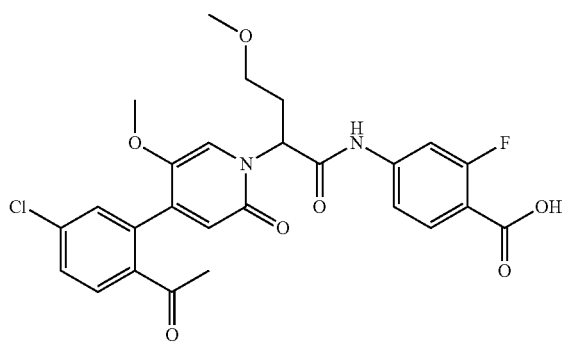<br>4-(2-(4-(2-acetyl-5-chlorophenyl)-5-methoxy-2-oxopyridin-1(2H)-yl)-4-methoxybutanamido)-2-fluorobenzoic acid 148 |

| Example No. | Structure and Name |
| --- | --- |
| 149 | 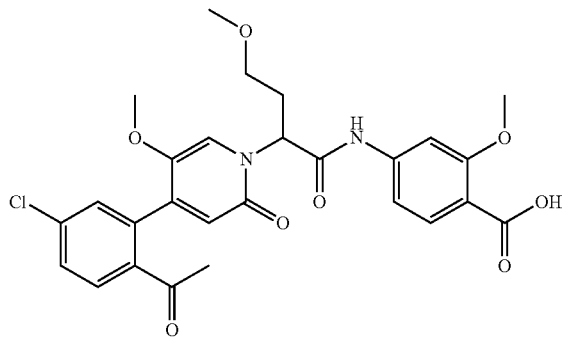<br><br>4-(2-(4-(2-acetyl-5-chlorophenyl)-5-methoxy-2-oxopyridin-1(2H)-yl)-<br>4-methoxybutanamido)-2-methoxybenzoic acid 149 |
| 150 | 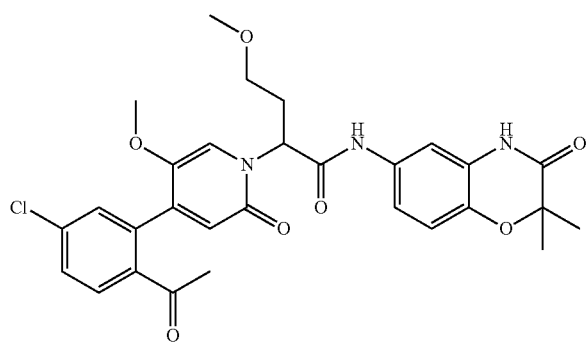<br><br>2-(4-(2-acetyl-5-chlorophenyl)-5-methoxy-2-oxopyridin-1(2H)-yl)-N-<br>(2,2-dimethyl-3-<br>oxo-3,4-dihydro-2H-benzo[b][1,4]oxazin-6-yl)-4-methoxybutanamide<br>150 |
| 151 | 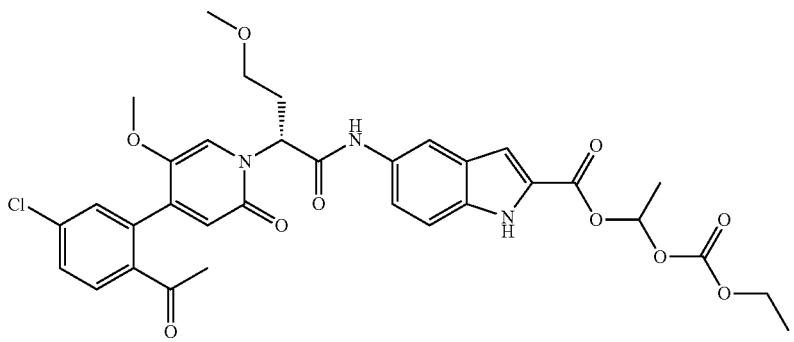<br><br>1-((ethoxycarbonyl)oxy)ethyl<br>5-((R)-2-(4-(2-acetyl-5-chlorophenyl)-5-methoxy-2-oxopyridin-1(2H)-<br>yl)-4-methoxybutanamido)-1H-indole-2-carboxylate 151 |

| Example No. | Structure and Name |
|---|---|
| 152 | 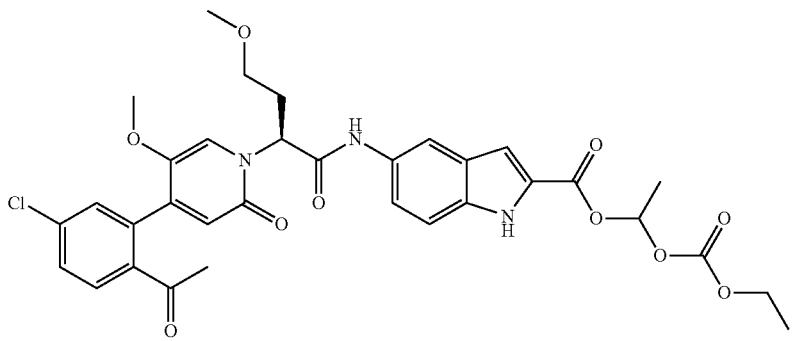

1-((ethoxycarbonyl)oxy)ethyl 5-((S)-2-(4-(2-acetyl-5-chlorophenyl)-5-methoxy-2-oxopyridin-1(2H)-yl)-4-methoxybutanamido)-1H-indole-2-carboxylate 152 |
| 153 | 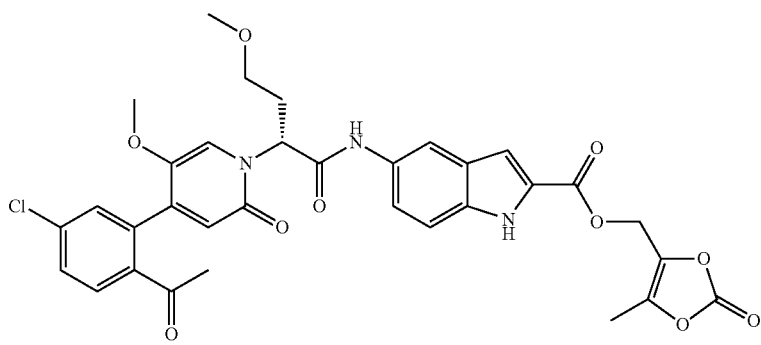

(5-methyl-2-oxo-1,3-dioxol-4-yl)methyl (R)-5-(2-(4-(2-acetyl-5-chlorophenyl))-5-methoxy-2-oxopyridin-1(2H)-yl)-4-methoxybutanamido)-1H-indole-2-carboxylate 153 |
| 154 | 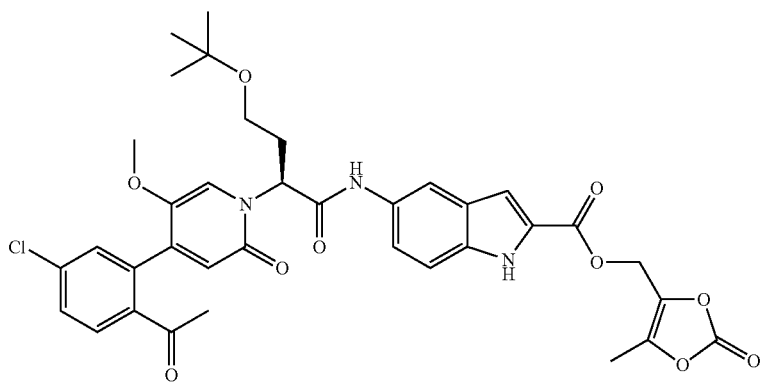

(5-methyl-2-oxo-1,3-dioxol-4-yl)methyl (S)-5-(2-(4-(2-acetyl-5-chlorophenyl))-5-methoxy-2-oxopyridin-1(2H)-yl)-4-methoxybutanamido)-1H-indole-2-carboxylate 154 |

-continued

| Example No. | Structure and Name |
|---|---|
| 155 | 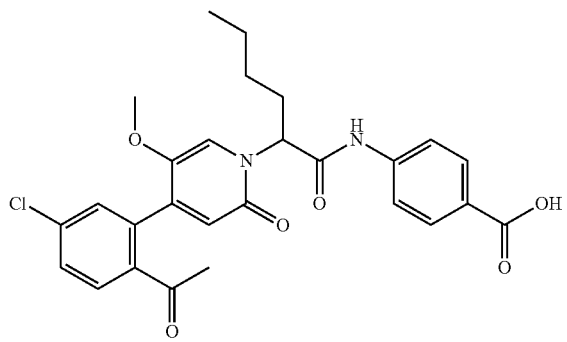<br>155<br>4-(2-(4-(2-acetyl-5-chlorophenyl)-5-methoxy-2-oxopyridin-1(2H)-yl) hexanamido)benzoic acid 155 |
| 156 | 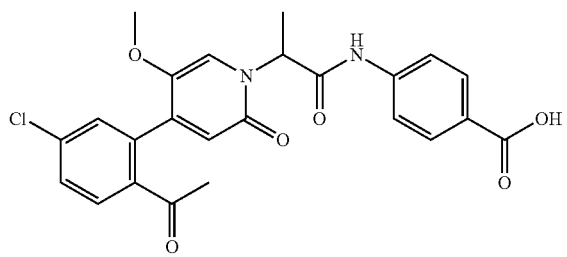<br>156<br>4-(2-(4-(2-acetyl-5-chlorophenyl)-5-methoxy-2-oxopyridin-1(2H)-yl) propanamido)benzoic acid 156 |
| 157 | 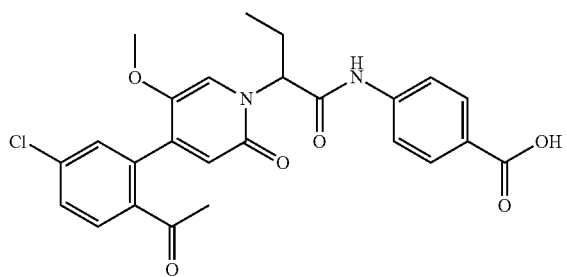<br>157<br>4-(2-(4-(2-acetyl-5-chlorophenyl)-5-methoxy-2-oxopyridin-1(2H)-yl) butanamido)benzoic acid 157 |
| 158 | 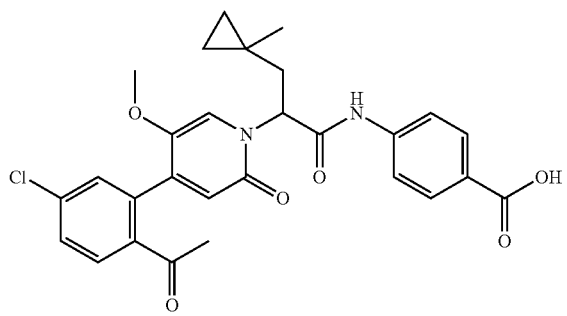<br>158<br>4-(2-(4-(2-acetyl-5-chlorophenyl)-5-methoxy-2-oxopyridin-1(2H)-yl)-3-(1-methylcyclopropyl)propanamido)benzoic acid 158 |

| Example No. | Structure and Name |
|---|---|
| 159 | 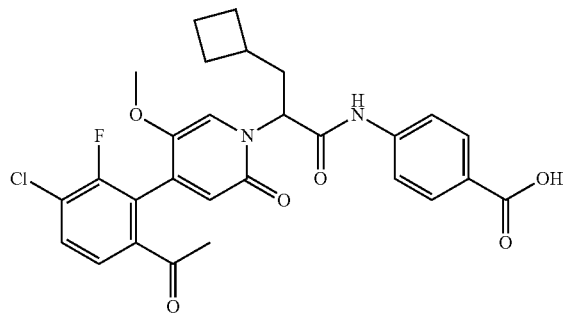
4-(2-(4-(6-chloro-2-fluorophenyl)-5-methoxy-2-oxopyridin-1(2H)-yl)-3-cyclobutylpropanamido)benzoic acid 159 |
| 160 | 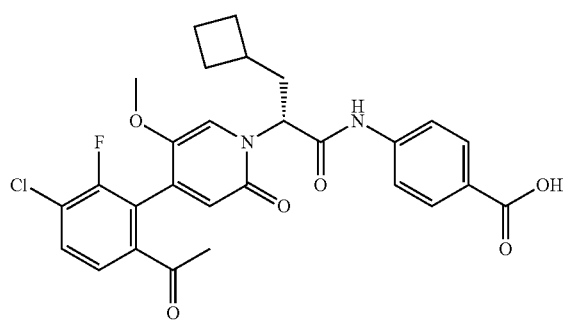
(R)-4-(2-(4-(6-acetyl-3-chloro-2-fluorophenyl)-5-methoxy-2-oxopyridin-1(2H)-yl)-3-cyclobutylpropanamido)benzoic acid 160 |
| 161 | 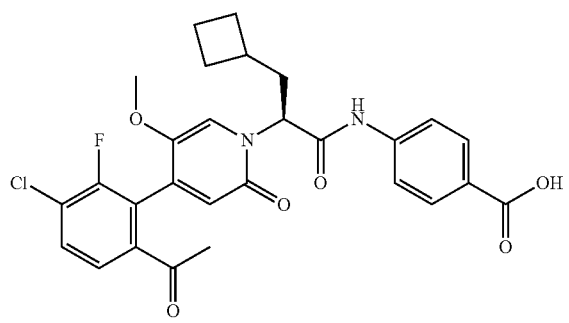
(S)-4-(2-(4-(6-acetyl-3-chloro-2-fluorophenyl)-5-methoxy-2-oxopyridin-1(2H)-yl)-3-cyclobutylpropanamido)benzoic acid 161 |

| Example No. | Structure and Name |
|---|---|
| 162 | 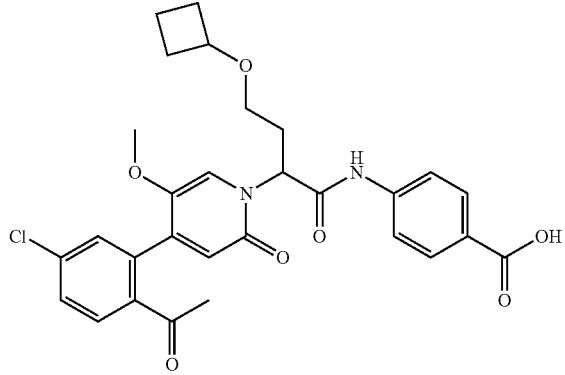<br>4-(2-(4-(2-acetyl-5-chlorophenyl)-5-methoxy-2-oxopyridin-1(2H)-yl)-4-cyclobutoxybutanamido)benzoic acid 162 |
| 163 | 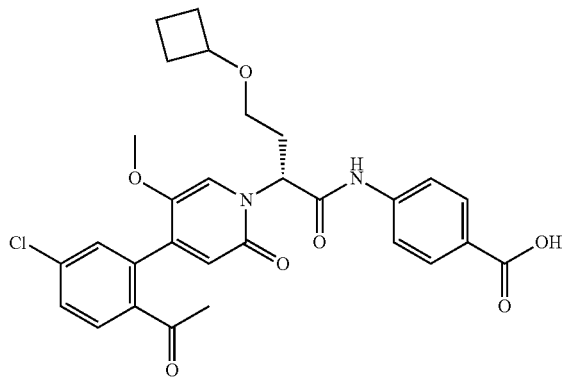<br>(R)-4-(2-(4-(2-acetyl-5-chlorophenyl)-5-methoxy-2-oxopyridin-1(2H)-yl)-4-cyclobutoxybutanamido)benzoic acid 163 |
| 164 | 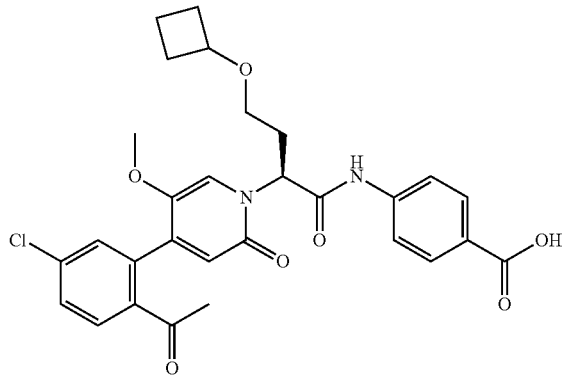<br>(S)-4-(2-(4-(2-acetyl-5-chlorophenyl)-5-methoxy-2-oxopyridin-1(2H)-yl)-4-cyclobutoxybutanamido)benzoic acid 164 |

| Example No. | Structure and Name |
|---|---|
| 165h | 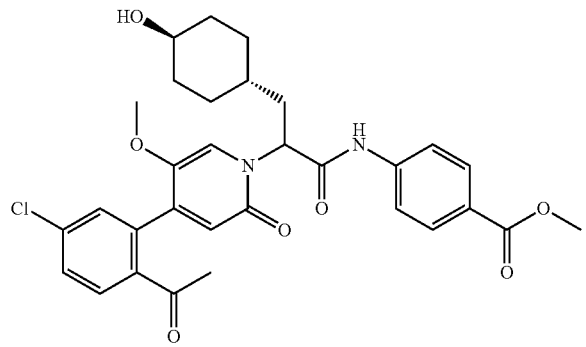<br>methyl 4-(2-(4-(2-acetyl-5-chlorophenyl)-5-methoxy-2-oxopyridin-1(2H)-yl)-3-((1R,4R)-4-hydroxycyclohexyl)propanamido)benzoate 165h |
| 165 | 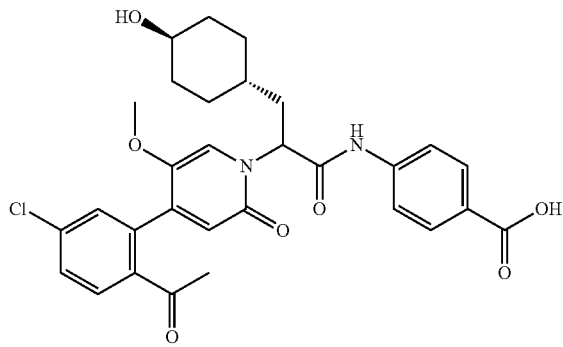<br>4-(2-(4-(2-acetyl-5-chlorophenyl)-5-methoxy-2-oxopyridin-1(2H)-yl)-3-((1r,4r)-4-hydroxycyclohexyl)propanamido)benzoic acid 165 |
| 166 | 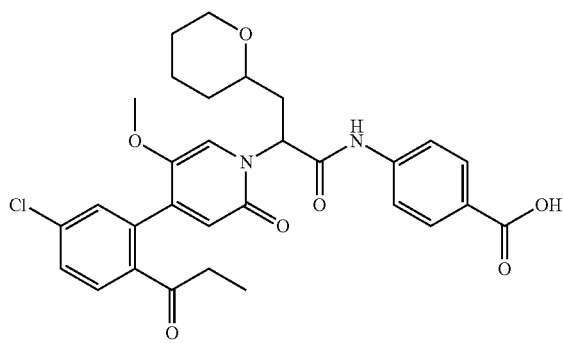<br>4-(2-(4-(5-chloro-2-propionylphenyl)-5-methoxy-2-oxopyridin-1(2H)-yl)-3-(tetrahydro-2H-pyran)-2-yl)propanamido)benzoic acid 166 |

| Example No. | Structure and Name |
|---|---|
| 167 | 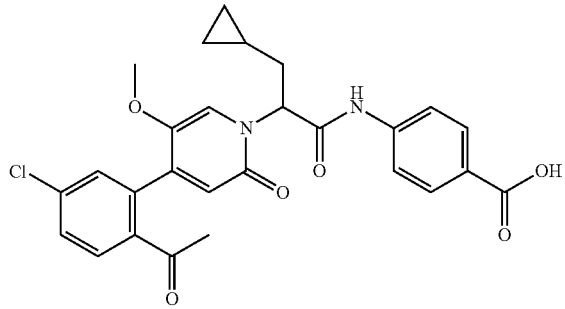<br>4-(2-(4-(2-acetyl-5-chlorophenyl)-5-methoxy-2-oxopyridin-1(2H)-yl)-3-cyclopropylpropanamido)benzoic acid 167 |
| 168 | 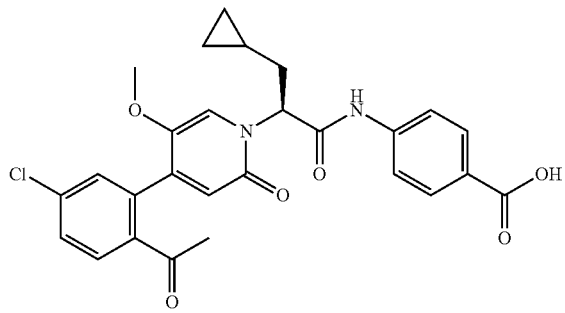<br>(S)-4-(2-(4-(2-acetyl-5-chlorophenyl)-5-methoxy-2-oxopyridin-1(2H)-yl)-3-cyclopropylpropanamido)benzoic acid 168 |
| 169 | 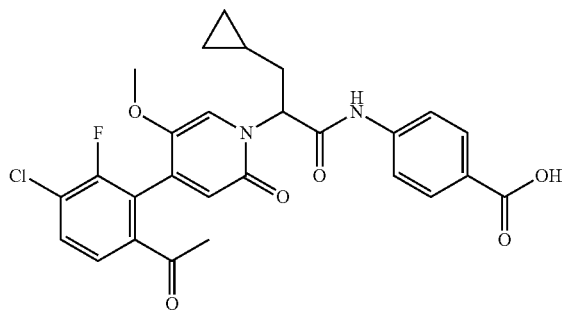<br>4-(2-(4-(6-acetyl-3-chloro-2-fluorophenyl)-5-methoxy-2-oxopyridin-1(2H)-yl)-3-cyclopropylpropanamido)benzoic acid 169 |

| Example No. | Structure and Name |
|---|---|
| 170 | 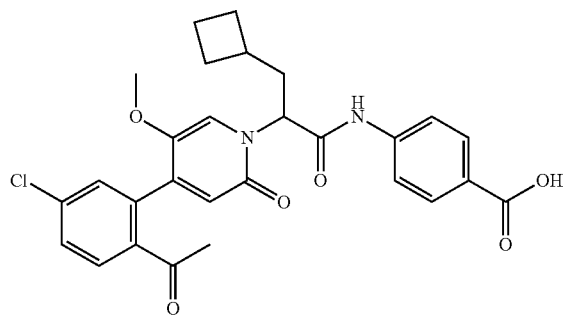<br>4-(2-(4-(2-acetyl-5-chlorophenyl)-5-methoxy-2-oxopyridin-1(2H)-yl)-3-cyclobutylpropanamido)benzoic acid 170 |
| 171 | 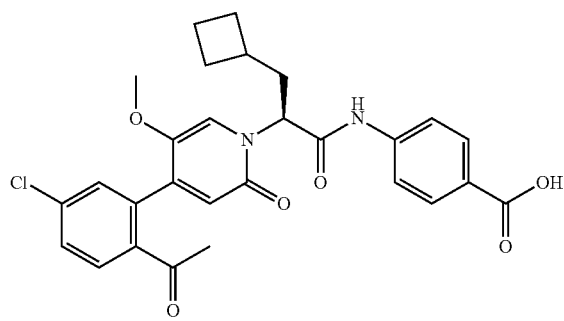<br>(S)-4-(2-(4-(2-acetyl-5-chlorophenyl)-5-methoxy-2-oxopyridin-1(2H)-yl)-3-cyclobutylpropanamido)benzoic acid 171 |
| 172 | 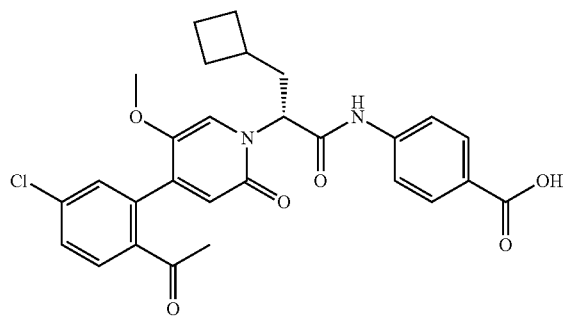<br>(R)-4-(2-(4-(2-acetyl-5-chlorophenyl)-5-methoxy-2-oxopyridin-1(2H)-yl)-3-cyclobutylpropanamido)benzoic acid 172 |

| Example No. | Structure and Name |
|---|---|
| 173 | 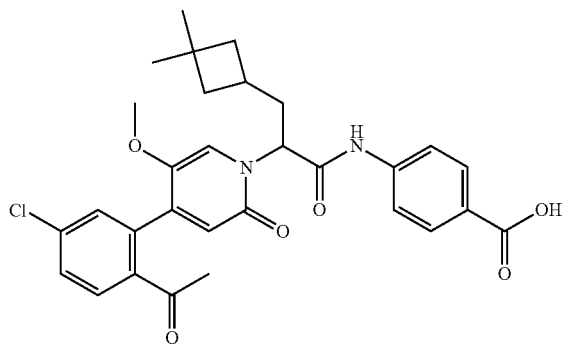<br>4-(2-(4-(2-acetyl-5-chlorophenyl)-5-methoxy-2-oxopyridin-1(2H)-yl)-3-(3,3-dimethylcyclobutyl)propanamido)benzoic acid 173 |
| 174 | 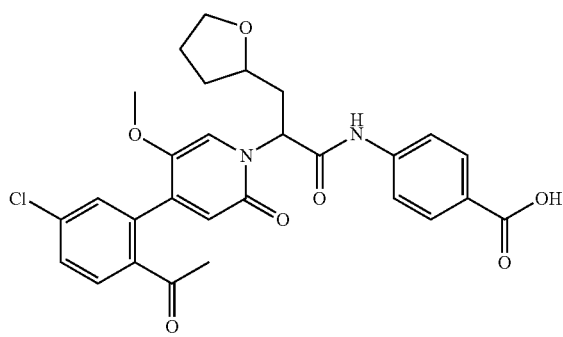<br>4-(2-(4-(2-acetyl-5-chlorophenyl)-5-methoxy-2-oxopyridin-1(2H)-yl)-3-(tetrahydrofuran-2-yl)propanamido)benzoic acid 174 |
| 175 | 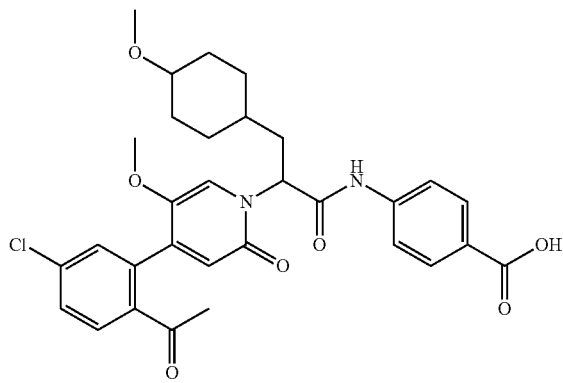<br>4-(2-(4-(2-acetyl-5-chlorophenyl)-5-methoxy-2-oxopyridin-1(2H)-yl)-3-(4-methoxycyclohexyl)propanamido)benzoic acid 175 |

-continued
| Example No. | Structure and Name |
|---|---|
| 176 | 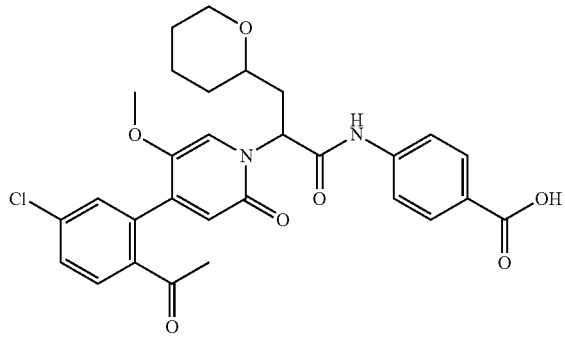<br>4-(2-(4-(2-acetyl-5-chlorophenyl)-5-methoxy-2-oxopyridin-1(2H)-yl)-3-(tetrahydro-2H-pyran-2-yl)propanamido)benzoic acid 176 |
| 177h | 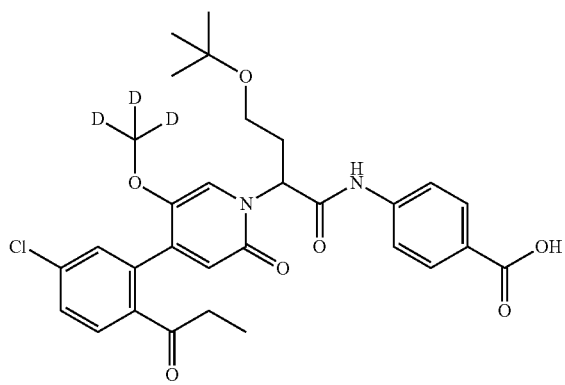<br>4-[[4-tert-butoxy-2-[4-(5-chloro-2-propionylphenyl)-2-oxo-5-(trideutero-methoxy)-1-pyridyl]butyryl]amino]benzoic acid 177h |
| 177 | 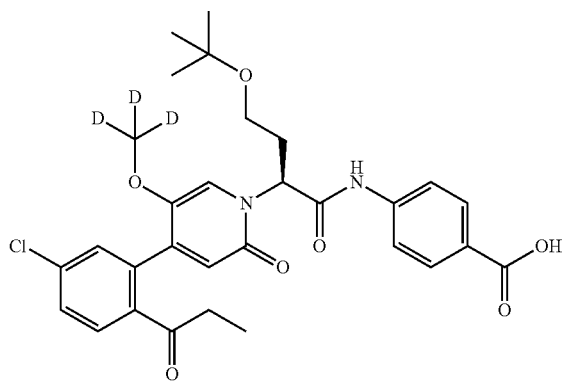<br>4-[[(2S)-4-tert-butoxy-2-[4-(5-chloro-2-propionyl-pheny-2-oxo-5-(trideuteromethoxy)-pyridyl]butyryl]amino]benzoic acid 177 |

| Example No. | Structure and Name |
|---|---|
| 178 | 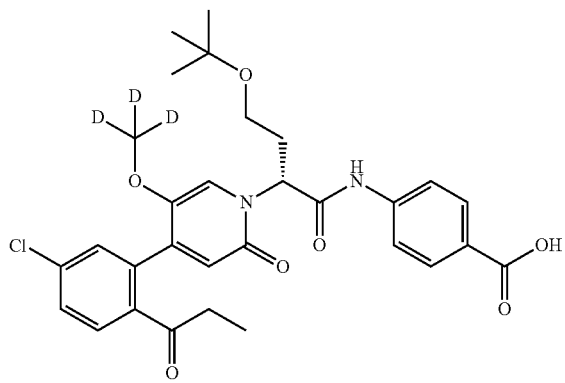<br>4-[[(2R)-4-tert-butoxy-2-[4-(5-chloro-2-propionyl-phenyl)-2-oxo-5-(trideuteromethoxy)-1-pyridyl]butyryl]amino]benzoic acid 178 |
| 179e | 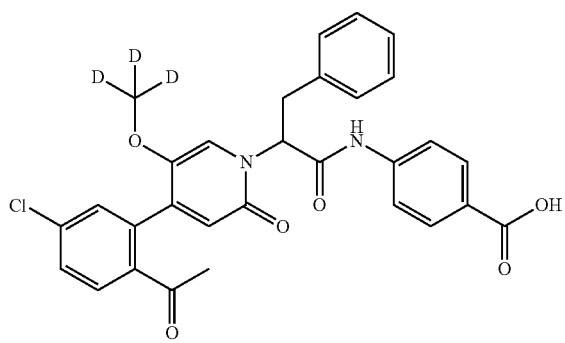<br>4-[[2-[4-(2-acetyl-5-chloro-phenyl)-2-oxo-5-(trideuteromethoxy)-1-pyridyl]-3-phenyl-propionyl]amino]benzoic acid 179e |
| 179 | 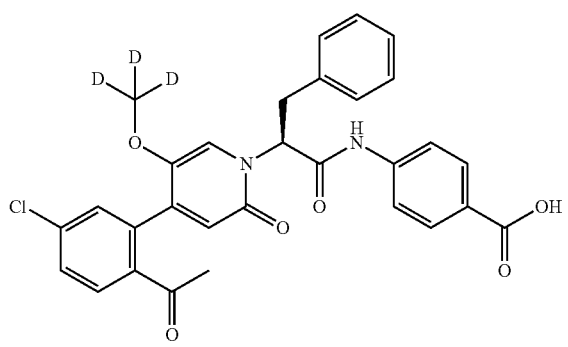<br>4-[[(2S)-2-[4-(2-acetyl-5-chloro-phenyl)-2-oxo-5-(trideuteromethoxy)-1-pyridyl]-3-phenyl-propionyl]amino]benzoic acid 179 |

| Example No. | Structure and Name |
|---|---|
| 180 | 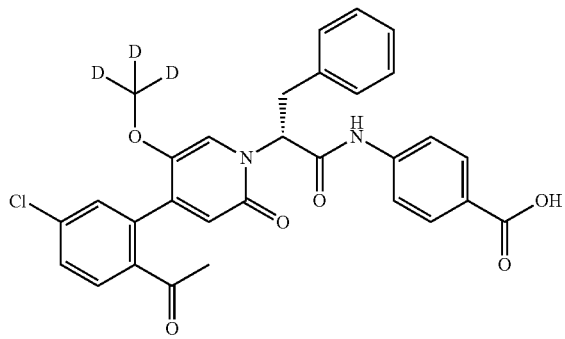
4-[[(2R)-2-[4-(2-acetyl-5-chloro-phenyl)-2-oxo-5-(trideuteromethoxy)-1-pyridyl]-3-phenyl-propionyl]amino]benzoic acid 180 |
| 181f | 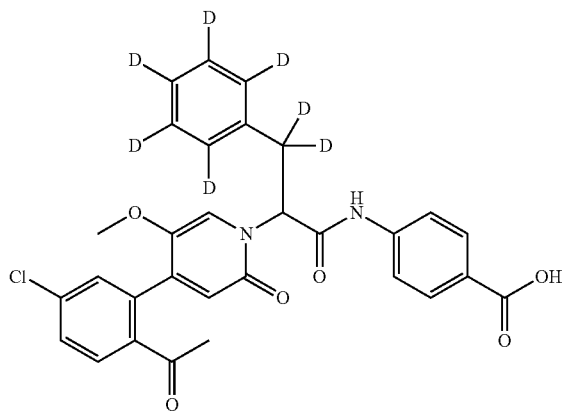
4-[[2-[4-(2-acetyl-5-chloro-phenyl)-5-methoxy-2-oxo-1-pyridyl]-3,3-dideutero-3-(2,3,4,5,6-pentadeuterophenyl)propionyl]amino]benzoic acid 181f |
| 181 | 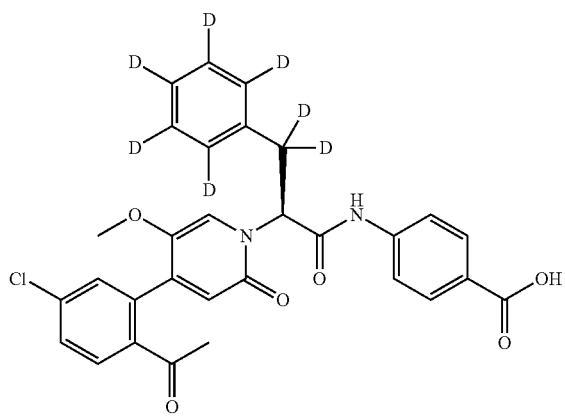
4-[[(2S)-2-[4-(2-acetyl-5-chloro-phenyl)-5-methoxy-2-oxo-1-pyridyl]-3,3-dideutero-3-(2,3,4,5,6-pentadeuterophenyl)propionyl]amino]benzoic acid 181 |

| Example No. | Structure and Name |
|---|---|
| 182 | 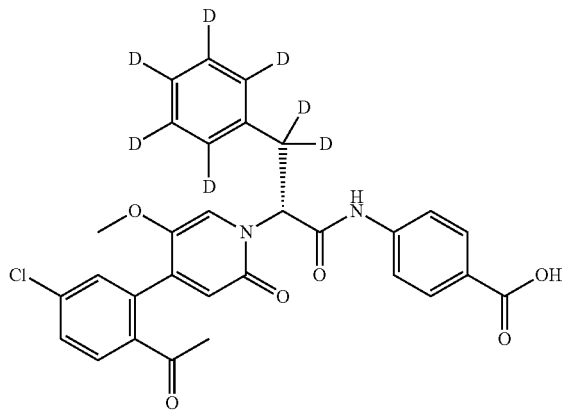
4-[[(2R)-2-[4-(2-acetyl-5-chloro-phenyl)-5-methoxy-2-oxo-1-pyridyl]-3,3-dideutero-3-(2,3,4,5,6-pentadeuterophenyl)propionyl]amino]benzoic acid 182 |
| 183g | 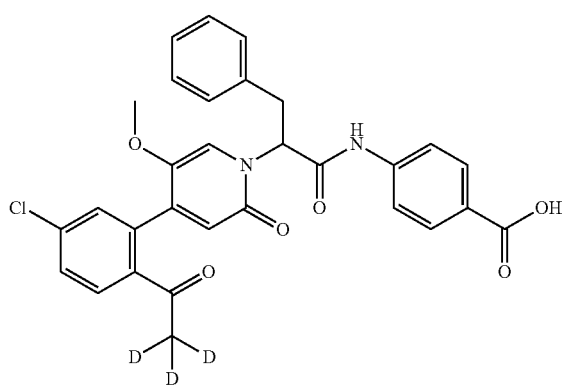
4-[[2-[4-[5-chloro-2-(2,2,2-trideuteroacetyl)phenyl]-5-methoxy-2-oxo-1-pyridyl]-3-phenyl-propionyl]amino]benzoic acid 183g |
| 183 | 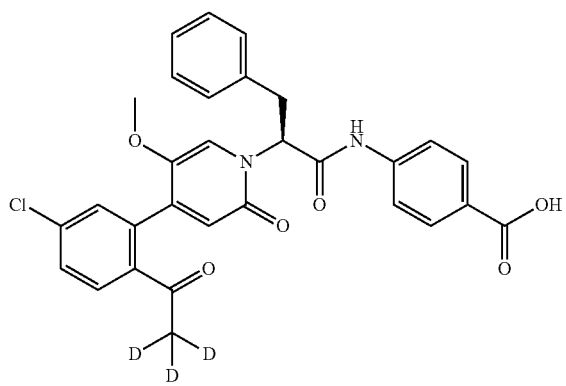
4-[[(2S)-2-[4-[5-chloro-2-(2,2,2-trideuteroacetyl)phenyl]-5-methoxy-2-oxo-1-pyridyl]-3-phenyl-propionyl]amino]benzoic acid 183 |

| Example No. | Structure and Name |
|---|---|
| 184 | 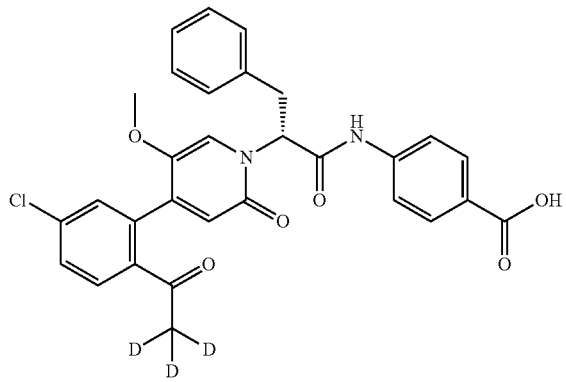<br>4-[[(2R)-2-[4-[5-chloro-2-(2,2,2-trideuteroacetyl)phenyl]-5-methoxy-2-oxo-1-pyridyl]-3-phenyl-propionyl]amino]benzoic acid 184 | or a tautomer, mesomer, racemate, enantiomer, diastereomer thereof, or mixture thereof, or a pharmaceutically acceptable salt thereof, or a prodrug thereof.

In a preferred embodiment of the present invention, the present invention is directed to a process for preparing the compound of formula (AI), comprising a step of:

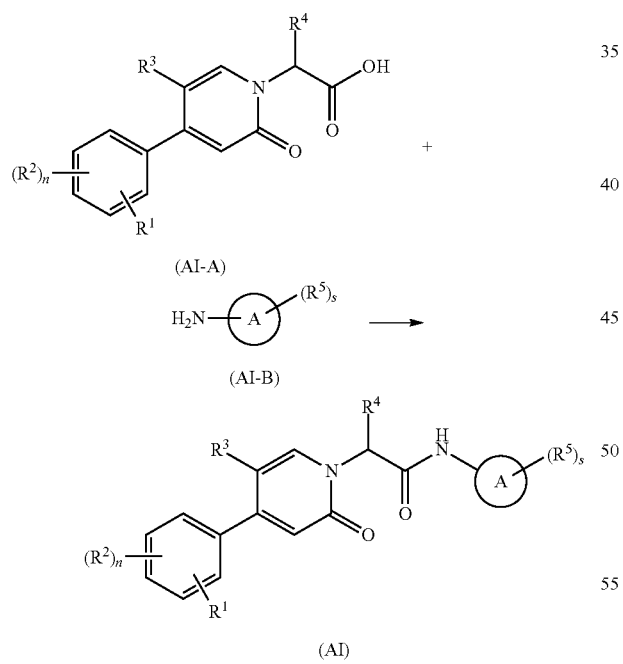

condensing a compound of formula (AI-A) with a compound of formula (AI-B) or a hydrochloride thereof under an alkaline condition, optionally hydrolyzing the condensation product under an alkaline condition to obtain a compound of formula (AI);

wherein:

ring A, $R^1 \sim R^5$, n and s are as defined in formula (AI).

In a preferred embodiment of the present invention, the present invention is directed to a process for preparing the compound of formula (I), comprising a step of:

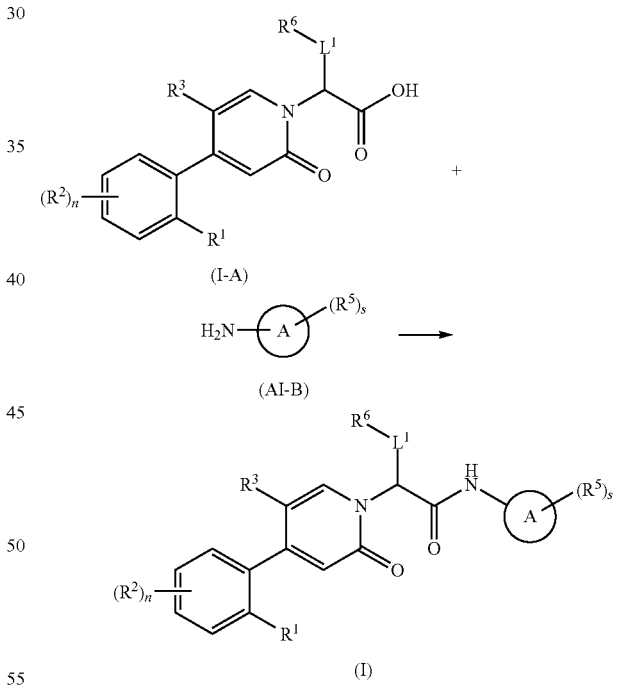

condensing a compound of formula (I-A) with a compound of formula (AI-B) or a hydrochloride thereof under an alkaline condition, optionally hydrolyzing the condensation product under an alkaline condition to obtain a compound of formula (I);

wherein:

ring A, $L^1$, $R^1 \sim R^3$, $R^1 \sim R^6$, n and s are as defined in formula (I).

In another aspect, the present invention is directed to a pharmaceutical composition comprising a therapeutically effective amount of the compound of formula (AI), or a tautomer, mesomer, racemate, enantiomer, diastereomer thereof, or mixture thereof, or a pharmaceutically acceptable salt thereof, and one or more pharmaceutically acceptable carriers, diluents or excipients.

In another aspect, the present invention is directed to the compound of formula (AI), or a tautomer, mesomer, racemate, enantiomer, diastereomer thereof, or mixture thereof, or a pharmaceutically acceptable salt thereof, or the pharmaceutical composition comprising the same for use as a medicament.

In another aspect, the present invention is directed to use of the compound of formula (AI), or a tautomer, mesomer, racemate, enantiomer, diastereomer thereof, or mixture thereof, or a pharmaceutically acceptable salt thereof, or the pharmaceutical composition comprising the same in the preparation of a medicament for inhibiting factor XIa.

In another aspect, the present invention is directed to the compound of formula (AI), or a tautomer, mesomer, racemate, enantiomer, diastereomer thereof, or mixture thereof, or a pharmaceutically acceptable salt thereof, or the pharmaceutical composition comprising the same for use as a factor XIa inhibitor.

In another aspect, the present invention is directed to use of the compound of formula (AI), or a tautomer, mesomer, racemate, enantiomer, diastereomer thereof, or mixture thereof, or a pharmaceutically acceptable salt thereof, or the pharmaceutical composition comprising the same in the preparation of a medicament for preventing and/or treating a factor XIa mediated disease.

In another aspect, the present invention is directed to use of the compound of formula (AI), or a tautomer, mesomer, racemate, enantiomer, diastereomer thereof, or mixture thereof, or a pharmaceutically acceptable salt thereof, or the pharmaceutical composition comprising the same in the preparation of a medicament for preventing and/or treating a cardiovascular and cerebrovascular disease, wherein the cardiovascular disease is preferably thromboembolic disease, and more preferably myocardial infarction, angina pectoris, angioplasty or reocclusion and restenosis after aortic coronary artery shunt, disseminated intravascular coagulation, stroke, transient ischemic attack, peripheral arterial occlusive disease, pulmonary embolism or deep vein thrombosis.

In another aspect, the present invention is directed to a method for preventing and/or treating a factor XIa mediated disease, comprising a step of administering to a patient in need thereof a therapeutically effective amount of the compound of formula (AI), or a tautomer, mesomer, racemate, enantiomer, diastereomer thereof, or mixture thereof, or a pharmaceutically acceptable salt thereof, or the pharmaceutical composition comprising the same.

In another aspect, the present invention is also directed to a method for preventing and/or treating a cardiovascular and cerebrovascular disease, comprising a step of administering to a patient in need thereof a therapeutically effective amount of the compound of formula (AI), or a tautomer, mesomer, racemate, enantiomer, diastereomer thereof, or mixture thereof, or a pharmaceutically acceptable salt thereof, or the pharmaceutical composition comprising the same, wherein the cardiovascular and cerebrovascular disease is selected from the group consisting of myocardial infarction, angina pectoris, angioplasty or reocclusion and restenosis after aortic coronary artery shunt, stroke, transient ischemic attack, peripheral arterial occlusive disease, pulmonary embolism or deep vein thrombosis.

In another aspect, the present invention is directed to a medicament for inhibiting factor XIa, comprising the compound of formula (AI), or a tautomer, mesomer, racemate, enantiomer, diastereomer thereof, or mixture thereof, or a pharmaceutically acceptable salt thereof, or the pharmaceutical composition comprising the same.

Pharmaceutical compositions containing the active ingredient can be in a form suitable for oral administration, for example, a tablet, troche, lozenge, aqueous or oily suspension, dispersible powder or granule, emulsion, hard or soft capsule, or syrup or elixir. Oral compositions can be prepared according to any method known in the art for the preparation of pharmaceutical compositions. Such compositions can contain one or more agents selected from the group consisting of sweetening agents, flavoring agents, coloring agents and preservatives, in order to provide a pleasing and palatable pharmaceutical formulation. The tablet contains the active ingredient in admixture with non-toxic pharmaceutically acceptable excipients suitable for the manufacture of a tablet. These excipients can be inert excipients, granulating agents, disintegrating agents, binders or lubricants. The tablet can be uncoated or coated by means of a known technique to mask drug taste or delay the disintegration and absorption of the active ingredient in the gastrointestinal tract, thereby providing sustained release over an extended period.

Oral formulations can be provided as soft gelatin capsules in which the active ingredient is mixed with an inert solid diluent, or the active ingredient is mixed with a water-soluble carrier or an oil medium or olive oil.

An aqueous suspension contains the active ingredient in admixture with excipients suitable for the manufacture of an aqueous suspension. Such excipients are suspending agents, dispersants or humectants. The aqueous suspension can also contain one or more preservatives, one or more coloring agents, one or more flavoring agents, or one or more sweetening agents.

An oil suspension can be formulated by suspending the active ingredient in a vegetable oil. The oil suspension can contain a thickener. The aforementioned sweetening agents and flavoring agents can be added to provide a palatable preparation. These compositions can be preserved by adding an antioxidant.

The active ingredient in admixture with the dispersing or wetting agents, suspending agents or one or more preservatives can be prepared as a dispersible powder or granule suitable for the preparation of an aqueous suspension by adding water. Suitable dispersant or wetting agents and suspending agents are exemplified by those already mentioned above. Additional excipients, such as sweetening, flavoring, and coloring agents, can also be added. These compositions can be preserved by adding an antioxidant such as ascorbic acid.

The present pharmaceutical composition of the present invention can also be in the form of an oil-in-water emulsion. The oil phase can be a vegetable oil, or a mineral oil, or a mixture thereof. Suitable emulsifying agents can be naturally occurring phospholipids. The emulsions can also contain sweetening agents, flavoring agents, preservatives and antioxidants. Such preparations may also contain demulcents, preservatives, coloring agents and antioxidants.

The pharmaceutical composition of the present invention can be in the form of a sterile aqueous solution. Acceptable vehicles or solvents that can be used are water, Ringer's solution or isotonic sodium chloride solution. The sterile injectable preparation can also be a sterile injectable oil-in-water microemulsion in which the active ingredient is dissolved in the oil phase. The injectable solution or microemulsion can be introduced into an individual's bloodstream by local bolus injection. Alternatively, the solution and microemulsion are preferably administered in a manner that maintains a constant circulating concentration of the compound of the present invention. In order to maintain this constant concentration, a continuous intravenous delivery device can be used. An example of such a device is Deltec CADD-PLUS. 5400 intravenous injection pump.

The pharmaceutical composition of the present invention can be in the form of a sterile injectable aqueous or oily suspension for intramuscular and subcutaneous administration. Such suspension can be formulated with suitable dispersants or wetting agents and suspending agents as described above according to known techniques. The sterile injectable preparation can also be a sterile injectable solution or suspension prepared in a nontoxic parenterally acceptable diluent or solvent. Moreover, sterile fixed oils can easily be used as a solvent or suspending medium. For this purpose, any blended fixed oil can be used. In addition, fatty acids can also be used to prepare injections.

The present compound can be administered in the form of a suppository for rectal administration. These pharmaceutical compositions can be prepared by mixing a drug with a suitable non-irritating excipient which is solid at ordinary temperatures but liquid in rectum, thereby melting in the rectum to release the drug.

It is well known to those skilled in the art that the dosage of a drug depends on a variety of factors including, but not limited to, the following factors: activity of a specific compound, age of the patient, weight of the patient, general health of the patient, behavior of the patient, diet of the patient, administration time, administration route, excretion rate, drug combination and the like. In addition, the best treatment, such as treatment mode, daily dose of the compound of formula (I) or the type of pharmaceutically acceptable salt thereof can be verified by traditional therapeutic regimens.

DETAILED DESCRIPTION OF THE INVENTION

Unless otherwise stated, the terms used in the specification and claims have the meanings described below.

The term "alkyl" refers to a saturated aliphatic hydrocarbon group including $C_1$ to $C_{20}$ linear chain and branched chain groups, preferably an alkyl having 1 to 12 carbon atoms, and more preferably an alkyl having 1 to 6 carbon atoms. Non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 33-diethylhexyl, 2,2-diethylhexyl, and branched isomers thereof. More preferably, an alkyl group is a lower alkyl having 1 to 6 carbon atoms, and non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, I-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, and the like. The alkyl group can be substituted or unsubstituted. When substituted, the substituent group(s) can be substituted at any available connection point. The substituent group(s) is preferably one or more groups independently selected from the group consisting of deuterium, alkyl, alkenyl, alkynyl, alkoxy, alkylthio, alkylamino, halogen, thiol, hydroxy, nitro, cyano, cycloalkyl, heterocyclyl, aryl, heteroaryl, cycloalkyloxy, heterocyclyloxy, cycloalkylthio, heterocyclylthio, oxo, —C(O)$R^8$, —C(O)O$R^8$ and —S(O)$_m$$R^8$.

The term "alkylene" refers to a saturated linear or branched aliphatic hydrocarbon group having two residues derived from the removal of two hydrogen atoms from the same carbon atom or two different carbon atoms of the parent alkane. The linear or branched alkylene has 1 to 20 carbon atoms, preferably 1 to 12 carbon atoms, and more preferably 1 to 6 carbon atoms. Non-limiting examples of alkylene groups include, but are not limited to, methylene (—CH$_2$—), 1,1-ethylene (—CH(CH$_3$)—), 1,2-ethylene (—CH$_2$CH$_2$)—, 1,1-propylene (—CH(CH$_2$CH$_3$)—), 1,2-propylene (—CH$_2$CH(CH$_3$)—), 1,3-propylene (—CH$_2$CH$_2$CH$_2$—), 1,4-butylene (—CH$_2$CH$_2$CH$_2$CH$_2$—), and the like. The alkylene group can be substituted or unsubstituted. When substituted, the substituent group(s) can be substituted at any available connection point. The substituent group(s) is preferably one or more groups independently selected from the group consisting of deuterium, alkyl, alkenyl, alkynyl, alkoxy, alkylthio, alkylamino, halogen, thiol, hydroxy, nitro, cyano, cycloalkyl, heterocyclyl, aryl, heteroaryl, cycloalkyloxy, heterocyclyloxy, cycloalkylthio, heterocyclylthio, oxo, —C(O)$R^8$, —C(O)O$R^8$ and —S(O)$_m$$R^8$.

The term "cycloalkyl" refers to a saturated or partially unsaturated monocyclic or polycyclic hydrocarbon group having 3 to 20 carbon atoms, preferably 3 to 12 carbon atoms, more preferably 3 to 8 carbon atoms, and most preferably 3 to 5 carbon atoms. Non-limiting examples of monocyclic cycloalkyls include cyclopropyl, cyclobutyl, cyclopentyl, cyclopentenyl, cyclohexyl, cyclohexenyl, cyclohexadienyl, cycloheptyl, cycloheptatrienyl, cyclooctyl, and the like, and preferably cycloalkyl. Polycyclic cycloalkyl includes a cycloalkyl having a spiro ring, fused ring or bridged ring.

The term "spiro cycloalkyl" refers to a 5 to 20 membered polycyclic group with rings connected through one common carbon atom (called a spiro atom), wherein one or more rings can contain one or more double bonds, but none of the rings has a completely conjugated pi-electron system, preferably 6 to 14 membered spiro cycloalkyl, and more preferably 7 to 10 membered spiro cycloalkyl. According to the number of the spiro atoms shared between the rings, spiro cycloalkyl can be divided into mono-spiro cycloalkyl, di-spiro cycloalkyl, or poly-spiro cycloalkyl, and preferably a mono-spiro cycloalkyl or di-spiro cycloalkyl, and more preferably 4-membered/4-membered, 4-membered/5-membered, 4-membered/6-membered, 5-membered/5-membered, or 5-membered/6-membered mono-spiro cycloalkyl. Non-limiting examples of spiro cycloalkyls include:

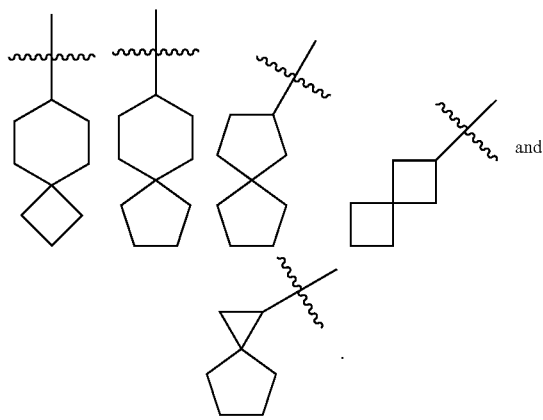

The term "fused cycloalkyl" refers to a 5 to 20 membered all-carbon polycyclic group, wherein each ring in the system shares an adjacent pair of carbon atoms with another ring, wherein one or more rings can contain one or more double bonds, but none of the rings has a completely conjugated pi-electron system, preferably 6 to 14 membered fused cycloalkyl, and more preferably 7 to 10 membered fused cycloalkyl. According to the number of membered rings, fused cycloalkyl can be divided into bicyclic, tricyclic, tetracyclic or polycyclic fused cycloalkyl, preferably bicyclic, or tricyclic fused cycloalkyl, and more preferably 5-membered/5-membered, or 5-membered/6-membered bicyclic fused cycloalkyl. Non-limiting examples of fused cycloalkyls include:

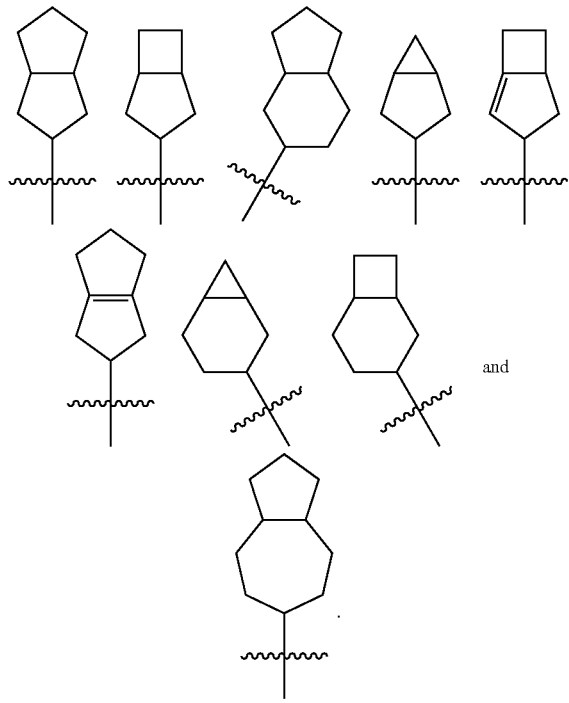

The term "bridged cycloalkyl" refers to a 5 to 20 membered all-carbon polycyclic group, wherein every two rings in the system share two disconnected carbon atoms, wherein the rings can have one or more double bonds, but none of the rings has a completely conjugated pi-electron system, preferably 6 to 14 membered bridged cycloalkyl, and more preferably 7 to 10 membered bridged cycloalkyl. According to the number of membered rings, bridged cycloalkyl can be divided into bicyclic, tricyclic, tetracyclic or polycyclic bridged cycloalkyl, and preferably bicyclic, tricyclic or tetracyclic bridged cycloalkyl, and more preferably bicyclic or tricyclic bridged cycloalkyl. Non-limiting examples of bridged cycloalkyls include:

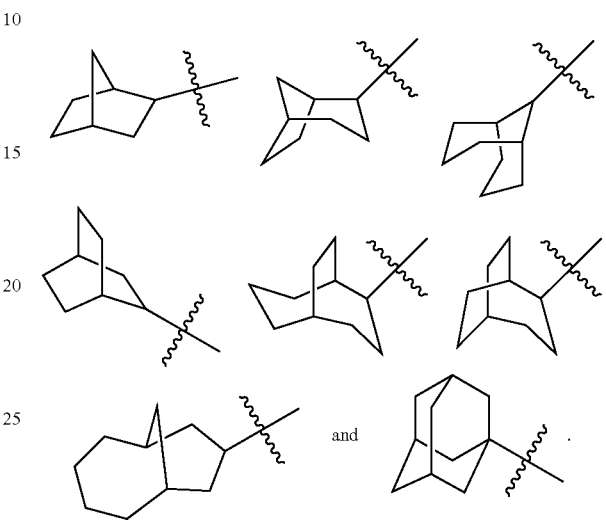

The ring of cycloalkyl can be fused to the ring of aryl, heteroaryl or heterocyclyl, wherein the ring bound to the parent structure is cycloalkyl. Non-limiting examples include indanyl, tetrahydronaphthyl, benzocycloheptyl and the like, preferably benzocyclopentyl, tetrahydronaphthyl. The cycloalkyl can be optionally substituted or unsubstituted. When substituted, the substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkyloxy, heterocyclyloxy, cycloalkylthio, heterocyclylthio, oxo, —C(O)R$^8$, —C(O)OR$^8$ and —S(O)$_m$R$^8$.

The term "heterocyclyl" refers to a 3 to 20 membered saturated or partially unsaturated monocyclic or polycyclic hydrocarbon group having one or more heteroatoms selected from the group consisting of N, O, and S(O)$_m$ (wherein m is an integer of 0 to 2) as ring atoms, but excluding —O—O—, —O—S— or —S—S— in the ring, with the remaining ring atoms being carbon atoms. Preferably, heterocyclyl has 3 to 12 atoms, wherein 1 to 4 atoms are heteroatoms, more preferably 3 to 8 atoms, wherein 1 to 3 atoms are heteroatoms, and most preferably 3 to 5 atoms, wherein 1 to 2 or 1 to 3 atoms are heteroatoms. Non-limiting examples of monocyclic heterocyclyls include pyrrolidinyl, imidazolidinyl, tetrahydrofuranyl, tetrahydropyranyl, tetrahydrothienyl, dihydroimidazolyl, dihydrofuranyl, dioxole, dihydropyrazolyl, dihydropyrrolyl, piperidyl, piperazinyl, morpholinyl, thiomorpholinyl, homopiperazinyl and the like. Polycyclic heterocyclyl includes a heterocyclyl having a spiro ring, fused ring or bridged ring.

The term "spiro heterocyclyl" refers to a 5 to 20 membered polycyclic heterocyclyl with rings connected through one common atom (called a spiro atom), wherein the rings have one or more heteroatoms selected from the group consisting of N, O, and S(O)$_m$ (wherein m is an integer of 0 to 2) as ring atoms, with the remaining ring atoms being carbon atoms, wherein one or more rings can contain one or more double bonds, but none of the rings has a completely conjugated pi-electron system, preferably 6 to 14 membered spiro heterocyclyl, and more preferably 7 to 10 membered spiro heterocyclyl. According to the number of the spiro atoms shared between the rings, spiro heterocyclyl can be divided into mono-spiro heterocyclyl, di-spiro heterocyclyl, or poly-spiro heterocyclyl, preferably mono-spiro heterocyclyl or di-spiro heterocyclyl, and more preferably 4-membered/4-membered, 4-membered/5-membered, 4-membered/6-membered, 5-membered/5-membered, or 5-membered/6-membered mono-spiro heterocyclyl. Non-limiting examples of spiro heterocyclyls include:

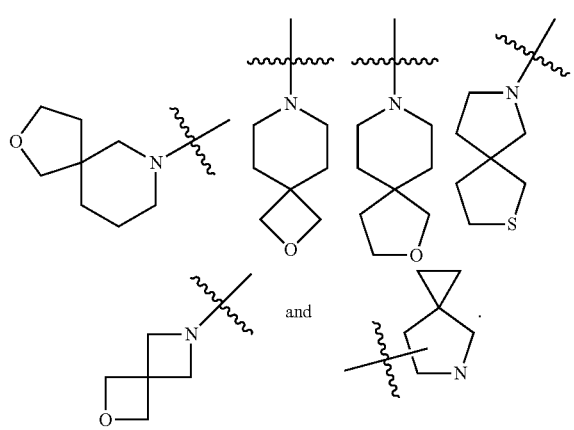

The term "fused heterocyclyl" refers to a 5 to 20 membered polycyclic heterocyclyl group, wherein each ring in the system shares an adjacent pair of atoms with another ring, wherein one or more rings can contain one or more double bonds, but none of the rings has a completely conjugated pi-electron system, and wherein the rings have one or more heteroatoms selected from the group consisting of N, O, and S(O)$_m$ (wherein m is an integer of 0 to 2) as ring atoms, with the remaining ring atoms being carbon atoms; preferably 6 to 14 membered fused heterocyclyl, and more preferably 7 to 10 membered fused heterocyclyl. According to the number of membered rings, fused heterocyclyl can be divided into bicyclic, tricyclic, tetracyclic or polycyclic fused heterocyclyl, preferably bicyclic or tricyclic fused heterocyclyl, and more preferably 5-membered/5-membered, or 5-membered/6-membered bicyclic fused heterocyclyl. Non-limiting examples of fused heterocyclyls include:

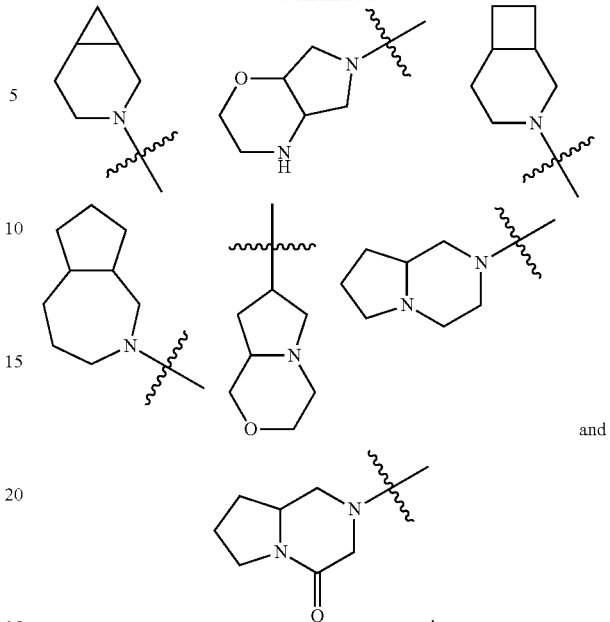

The term "bridged heterocyclyl" refers to a 5 to 14 membered polycyclic heterocyclyl group, wherein every two rings in the system share two disconnected atoms, wherein the rings can have one or more double bonds, but none of the rings has a completely conjugated pi-electron system, and the rings have one or more heteroatoms selected from the group consisting of N, O, and S (O)$_m$ (wherein m is an integer of 0 to 2) as ring atoms, with the remaining ring atoms being carbon atoms, preferably 6 to 14 membered bridged heterocyclyl, and more preferably 7 to 10 membered bridged heterocyclyl. According to the number of membered rings, bridged heterocyclyl can be divided into bicyclic, tricyclic, tetracyclic or polycyclic bridged heterocyclyl, and preferably bicyclic, tricyclic or tetracyclic bridged heterocyclyl, and more preferably bicyclic or tricyclic bridged heterocyclyl. Non-limiting examples of bridged heterocyclyls include:

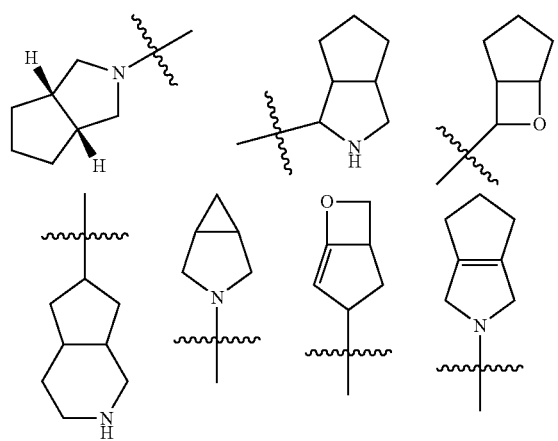

The heterocyclyl ring can be fused to the ring of an aryl, heteroaryl or cycloalkyl, wherein the ring bound to the parent structure is heterocyclyl. Non-limiting examples include:

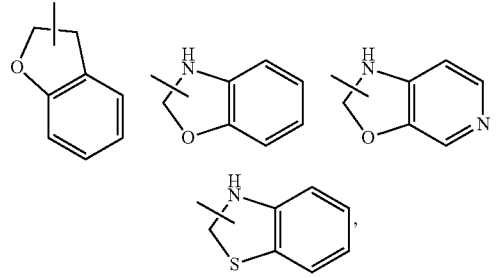

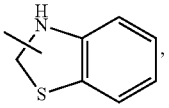

etc.

The heterocyclyl can be optionally substituted or unsubstituted. When substituted, the substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkyloxy, heterocyclyloxy, cycloalkylthio, heterocyclylthio, oxo, —C(O)R$^8$, —C(O)OR$^8$ and —S(O)$_m$R$^8$.

The term "aryl" refers to a 6 to 20 membered all-carbon monocyclic ring or polycyclic fused ring (i.e. each ring in the system shares an adjacent pair of carbon atoms with another ring in the system) having a completely conjugated pi-electron system, preferably 6 to 10 membered aryl, and more preferably 6 membered aryl, for example, phenyl and naphthyl. The aryl ring can be fused to the ring of heteroaryl, heterocyclyl or cycloalkyl, wherein the ring bound to the parent structure is the aryl ring. Non-limiting examples include:

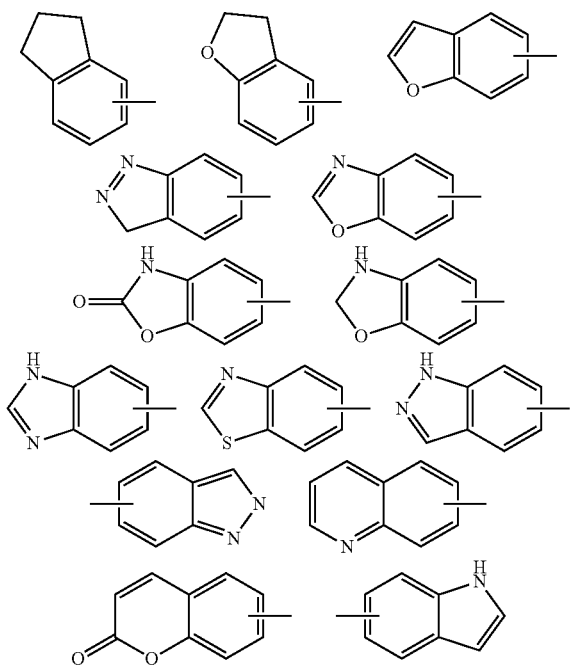

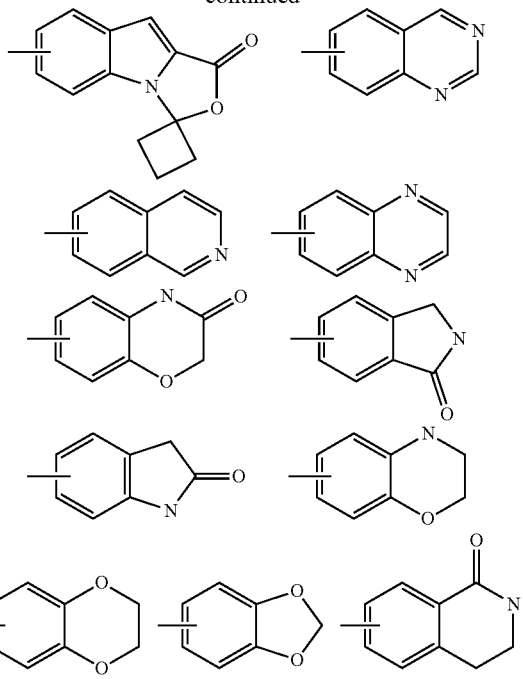

The aryl can be optionally substituted or unsubstituted. When substituted, the substituent group(s) is preferably one or more groups independently selected from the group consisting of deuterium, alkyl, alkenyl, alkynyl, alkoxy, alkylthio, alkylamino, halogen, thiol, hydroxy, nitro, cyano, cycloalkyl, heterocyclyl, aryl, heteroaryl, cycloalkyloxy, heterocyclyloxy, cycloalkylthio, heterocyclylthio, —C(O)R$^8$, —C(O)OR$^8$ and —S(O)$_m$R$^8$.

"Heteroaryl" refers to a 5 to 20 membered heteroaromatic system having 1 to 4 heteroatoms selected from the group consisting of O, S and N as ring atoms, preferably 5 to 10 membered heteroaryl having 1 to 3 heteroatoms, and more preferably 5 or 6 membered heteroaryl having 1 to 2 heteroatoms, for example, imidazolyl, furyl, thienyl, thiazolyl, pyrazolyl, oxazolyl, pyrrolyl, triazolyl, tetrazolyl, pyridyl, pyrimidinyl, thiadiazolyl, pyrazinyl and the like. The heteroaryl ring can be fused to the ring of an aryl, heterocyclyl or cycloalkyl, wherein the ring bound to the parent structure is heteroaryl ring. Non-limiting examples include:

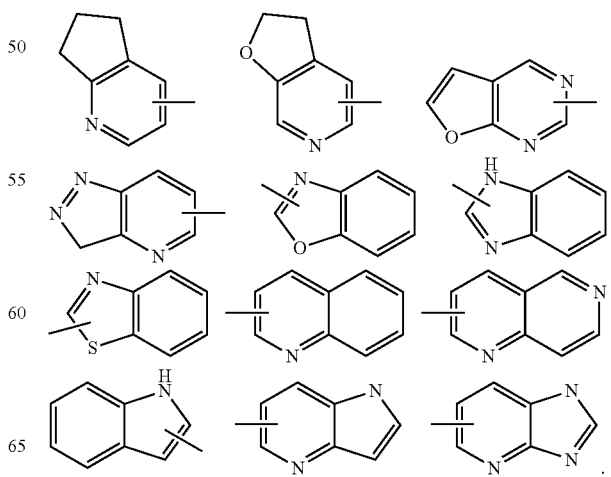

The heteroaryl can be optionally substituted or unsubstituted. When substituted, the substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkyloxy, heterocyclyloxy, cycloalkylthio, heterocyclylthio, —C(O)R$^8$, —C(O)OR$^8$ and —S(O)$_m$R$^8$.

The term "alkoxy" refers to an —O-(alkyl) or an —O-(unsubstituted cycloalkyl) group, wherein the alkyl is as defined above. Non-limiting examples include methoxy, ethoxy, propoxy, butoxy, cyclopropyloxy, cyclobutyloxy, cyclopentyloxy, cyclohexyloxy, and the like. The alkoxy can be optionally substituted or unsubstituted. When substituted, the substituent is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkyloxy, heterocyclyloxy, cycloalkylthio, heterocyclylthio, —C(O)R$^8$, —C(O)OR$^8$ and —S(O)$_m$R$^8$.

The term "alkylthio" refers to a —S-(alkyl) and —S-(unsubstituted cycloalkyl) group, wherein the alkyl is as defined above. Non-limiting examples of alkylthio include: methylthio, ethylthio, propylthio, butylthio, cyclopropylthio, cyclobutylthio, cyclopentylthio, cyclohexylthio. The alkylthio can be optionally substituted or unsubstituted. When substituted, the substituent is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkyloxy, heterocyclyloxy, cycloalkylthio, heterocyclylthio, —C(O)R$^8$, —C(O)OR$^8$ and —S(O)$_m$R$^8$.

The term "cycloalkyloxy" refers to a —O-cycloalkyl group, wherein the cycloalkyl is as defined above.

The term "haloalkyl" refers to an alkyl substituted by halogen(s), wherein the alkyl is as defined above.

The term "haloalkoxy" refers to an alkoxy substituted by halogen(s), wherein the alkoxy is as defined above.

The term "hydroxyalkyl" refers to an alkyl substituted by hydroxy(s), wherein the alkyl is as defined above.

The term "hydroxy" refers to an —OH group.

The term "halogen" refers to fluorine, chlorine, bromine or iodine.

The term "amino" refers to an —NH$_2$ group.

The term "cyano" refers to a —CN group.

The term "nitro" refers to an —NO$_2$ group.

The term "carboxy" refers to a —C(O)OH group.

The term "alkoxycarbonyl" refers to a —C(O)O(alkyl) or —C(O)O(cycloalkyl) group, wherein the alkyl and cycloalkyl are as defined above.

"Optional" or "optionally" means that the event or circumstance described subsequently can, but need not occur, and this description includes the situation in which the event or circumstance does or does not occur. For example, "the heterocyclic group optionally substituted by an alkyl" means that an alkyl group can be, but need not be, present, and this description includes the situation of the heterocyclic group being substituted by an alkyl and the heterocyclic group being not substituted by an alkyl.

"Substituted" refers to one or more hydrogen atoms in a group, preferably up to 5, more preferably 1 to 3 hydrogen atoms, independently substituted by a corresponding number of substituents. It goes without saying that the substituents only exist in their possible chemical positions. The person skilled in the art is able to determine whether the substitution is possible or impossible by experiments or theory without paying excessive efforts. For example, the combination of amino or hydroxy having free hydrogen and carbon atoms having unsaturated bonds (such as olefinic) can be unstable.

A "pharmaceutical composition" refers to a mixture of one or more of the compounds according to the present invention or physiologically/pharmaceutically acceptable salts or prodrugs thereof with other chemical ingredients, and other components such as physiologically/pharmaceutically acceptable carriers and excipients. The purpose of a pharmaceutical composition is to facilitate administration of a compound to an organism, which is conducive to the absorption of the active ingredient, thus displaying biological activity.

A "pharmaceutically acceptable salt" refers to a salt of the compound of the present invention, which is safe and effective in mammals and has the desired biological activity.

R$^8$ and m are as defined in formula (AI).

Synthesis Method of the Compound of the Present Invention

In order to achieve the object of the present invention, the present invention applies the following technical solutions.

Scheme 1

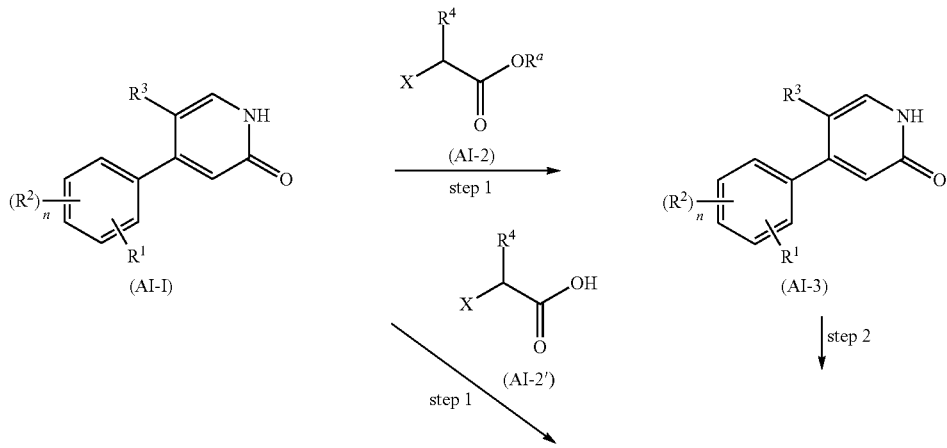

155

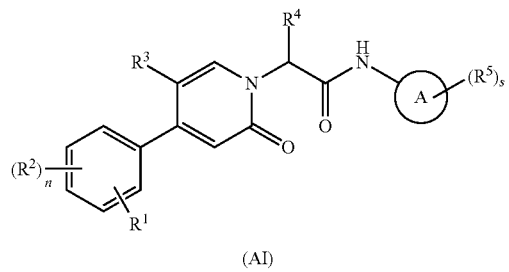

(AI)

156

-continued

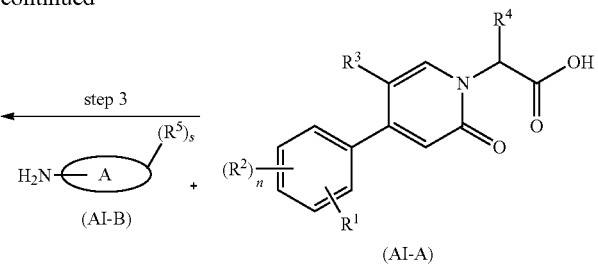

(AI-A)

A process for preparing a compound of formula (AI) of the present invention, or a tautomer, mesomer, racemate, enantiomer, diastereomer, or mixture thereof, or a pharmaceutically acceptable salt thereof, comprises the following steps:

wherein:

X is halogen, preferably bromine;

$R^a$ is alkyl, preferably methyl;

ring A, $R^1$~$R^5$, n and s are as defined in the formula (AI).

in the first step reaction, a compound of formula (AI-1) and a compound of formula (AI-2) are subjected to a nucleophilic substitution reaction under an alkaline condition in an organic solvent to obtain a compound of formula (AI-3); or a compound of formula (AI-1) and a compound of formula (AI-2') are subjected to a nucleophilic substitution reaction under an alkaline condition in an organic solvent to obtain a compound of formula (AI-A);

in the second step reaction, the compound of formula (AI-3) is hydrolyzed under an acidic condition to obtain a compound of (AI-A);

in the third step, the compound of formula (AI-A) and a compound of formula (AI-B) or a hydrochloride thereof are subjected to a condensation reaction under an alkaline condition, optionally the condensation product is hydrolyzed under an alkaline condition, to obtain the compound of formula (AI).

The reagents that provide an alkaline condition include organic bases and inorganic bases. The organic bases include, but are not limited to, triethylamine, N,N-diisopropylethylamine, n-butyllithium, lithium diisopropylamide, lithium bis(trimethylsilyl)amide, potassium acetate, sodium tert-butoxide and potassium tert-butoxide. The inorganic bases include, but are not limited to sodium hydride, potassium phosphate, sodium carbonate, potassium carbonate, cesium carbonate, sodium hydroxide and lithium hydroxide.

The reagents that provide an acidic condition include, but are not limited to, pyridine hydrobromide, trifluoroacetic acid, formic acid, acetic acid, hydrochloric acid, sulfuric acid and methanesulfonic acid, preferably pyridine hydrobromide or hydrochloric acid.

The condensing reagent includes, but is not limited to, 1-(3-dimethylaminopropyl)-3-ethylcarbodiimide hydrochloride, N,N'-dicyclohexylcarbodiimide, N,N'-diisopropylcarbodiimide, O-benzotriazole-N,N,N',N'-tetramethyluronium tetrafluoroborate, 1-hydroxybenzotriazole, 1-hydroxy-7-azobenzotriazole, O-benzotriazole-N,N,N',N'-tetramethyluronium hexafluorophosphate, 2-(7-oxobenzotriazole)-N,N,N',N'-tetramethyluronium hexafluorophosphate, 2-(7-azobenzotriazole)-N,N,N',N'-tetramethyluronium hexafluorophosphate, benzotriazol-1-yloxytris(dimethylamino)phosphonium hexafluorophosphate and benzotriazol-1-yl-oxytripyrrolidinylphosphonium phosphate, preferably 2-(7-oxobenzotriazole)-N,N,N',N'-tetramethyluronium hexafluorophosphate.

The above reaction is preferably carried out in a solvent. The solvent used includes, but is not limited to, acetic acid, methanol, ethanol, toluene, tetrahydrofuran, dichloromethane, dimethyl sulfoxide, 1,4-dioxane, water and N,N-dimethylformamide.

Scheme 2

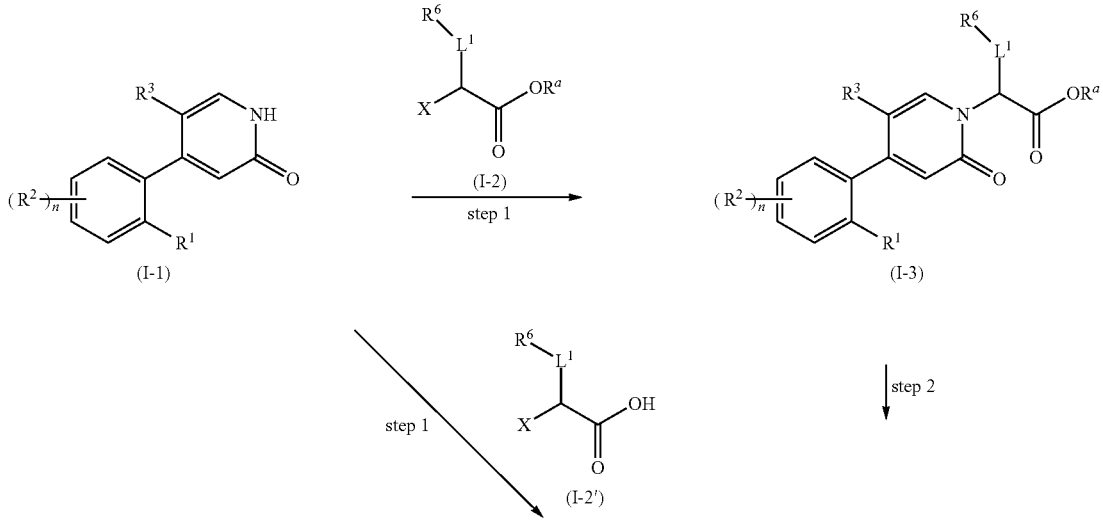

-continued

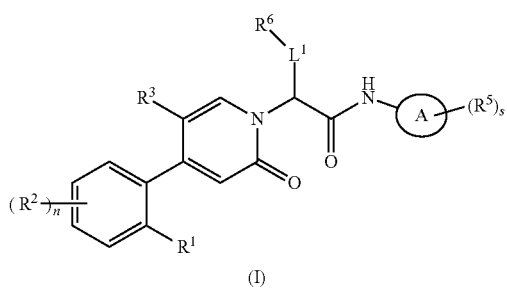

(I)

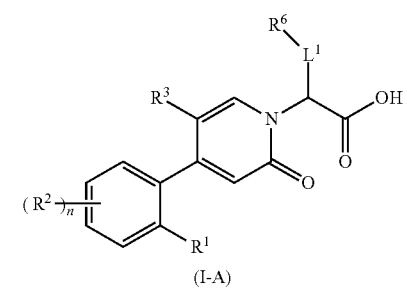

(I-A)

A process for preparing a compound of formula (I) of the present invention, or a tautomer, mesomer, racemate, enantiomer, diastereomer, or mixture thereof, or a pharmaceutically acceptable salt thereof, comprises the following steps:
wherein:
X is halogen, preferably bromine:
$R^a$ is alkyl, preferably methyl;
ring A, $L^1$, $R^1$~$R^3$, $R^5$—$R^6$, n and s are as defined in formula (I).

in the first step reaction, a compound of formula (I-1) and a compound of formula (I-2) are subjected to a nucleophilic substitution reaction under an alkaline condition in an organic solvent to obtain a compound of formula (I-3); or a compound of formula (I-1) and a compound of formula (I-2') are subjected to a nucleophilic substitution reaction under an alkaline condition in an organic solvent to obtain a compound of formula (I-A):

in the second step reaction, the compound of formula (I-3) is hydrolyzed under an acidic condition to obtain a compound of (I-A):

in the third step, the compound of formula (I-A) and a compound of formula (AI-B) or a hydrochloride thereof are subjected to a condensation reaction under an alkaline condition, optionally the condensation product is hydrolyzed under an alkaline condition, to obtain the compound of formula (I).

The reagents that provide an alkaline condition include organic bases and inorganic bases. The organic bases include, but are not limited to triethylamine, N,N-diisopropylethylamine, n-butyllithium, lithium diisopropylamide, lithium bis(trimethylsilyl)amide, potassium acetate, sodium tert-butoxide and potassium tert-butoxide. The inorganic bases include, but are not limited to sodium hydride, potassium phosphate, sodium carbonate, potassium carbonate, cesium carbonate, sodium hydroxide and lithium hydroxide.

The reagents that provide an acidic condition include, but are not limited to, pyridine hydrobromide, trifluoroacetic acid, formic acid, acetic acid, hydrochloric acid, sulfuric acid and methanesulfonic acid, preferably pyridine hydrobromide or hydrochloric acid.

The condensing reagent includes, but is not limited to, 1-(3-dimethylaminopropyl)-3-ethylcarbodiimide hydrochloride, N,N'-dicyclohexylcarbodiimide, N,N'-diisopropylcarbodiimide, O-benzotriazole-N,N,N',N'-tetramethyluronium tetrafluoroborate, 1-hydroxybenzotriazole, 1-hydroxy-7-azobenzotriazole, O-benzotriazole-N,N,N',N'-tetramethyluronium hexafluorophosphate, 2-(7-oxobenzotriazole)-N,N,N',N'-tetramethyluronium hexafluorophosphate, 2-(7-azobenzotriazole)-N,N,N',N'-tetramethyluronium hexafluorophosphate, benzotriazol-1-yloxytris(dimethylamino)phosphonium hexafluorophosphate and benzotriazol-1-yl-oxytripyrrolidinylphosphonium phosphate, preferably 2-(7-oxobenzotriazole)-N,N,N',N'-tetramethyluronium hexafluorophosphate.

The above reaction is preferably carried out in a solvent. The solvent used includes, but is not limited to, acetic acid, methanol, ethanol, toluene, tetrahydrofuran, dichloromethane, dimethyl sulfoxide, 1,4-dioxane, water and N,N-dimethylformamide.

Scheme 3

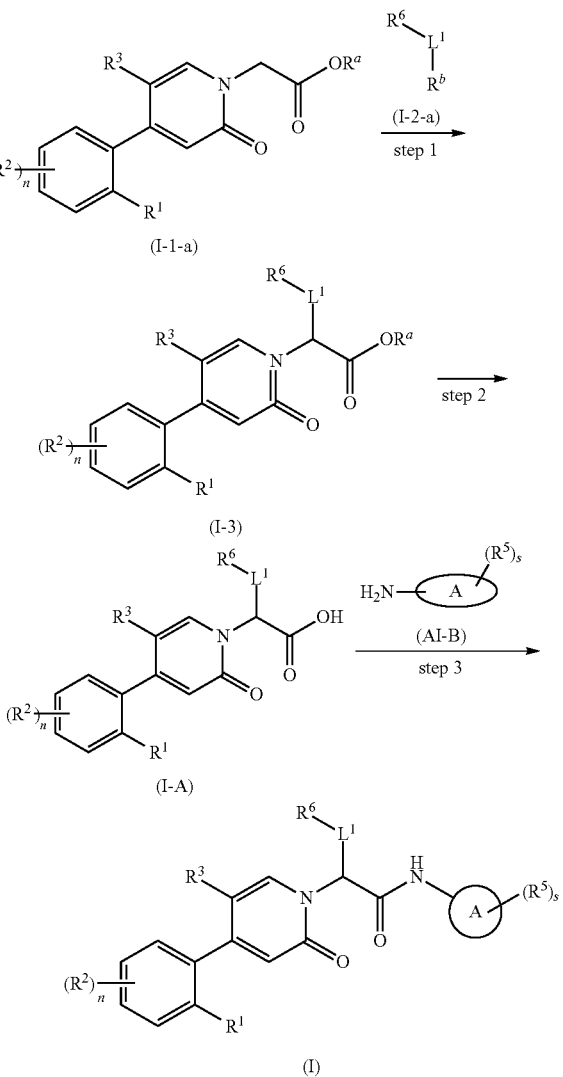

A process for preparing a compound of formula (I) of the present invention, or a tautomer, mesomer, racemate, enantiomer, diastereomer, or mixture thereof, or a pharmaceutically acceptable salt thereof, comprises the following steps:

wherein:

$R^a$ is alkyl, preferably methyl;

$R^b$ is a leaving group, preferably methanesulfonyloxy or trifluoromethanesulfonyloxy;

ring A, $L^1$, $R^1 \sim R^3$, $R^5 \sim R^6$, n and s are as defined in formula (I).

in the first step reaction, a compound of formula (I-1-a) and a compound of formula (I-2-a) are subjected to a nucleophilic substitution reaction under an alkaline condition in an organic solvent to obtain a compound of formula (I-3);

in the second step reaction, the compound of formula (I-3) is hydrolyzed under an acidic condition to obtain a compound of (I-A);

in the third step, the compound of formula (I-A) and a compound of formula (AI-B) or a hydrochloride thereof are subjected to a condensation reaction under an alkaline condition, optionally the condensation product is hydrolyzed under an alkaline condition, to obtain the compound of formula (I).

The reagents that provide an alkaline condition include organic bases and inorganic bases. The organic bases include, but are not limited to triethylamine, N,N-diisopropylethylamine, n-butyllithium, lithium diisopropylamide, lithium bis(trimethylsilyl)amide, potassium acetate, sodium tert-butoxide and potassium tert-butoxide. The inorganic bases include, but are not limited to sodium hydride, potassium phosphate, sodium carbonate, potassium carbonate, cesium carbonate, sodium hydroxide and lithium hydroxide.

The reagents that provide an acidic condition include, but are not limited to, pyridine hydrobromide, trifluoroacetic acid, formic acid, acetic acid, hydrochloric acid, sulfuric acid and methanesulfonic acid, preferably pyridine hydrobromide or hydrochloric acid.

The condensing reagent includes, but is not limited to, 1-(3-dimethylaminopropyl)-3-ethylcarbodiimide hydrochloride, N,N'-dicyclohexylcarbodiimide, N,N'-diisopropylcarbodiimide, O-benzotriazole-N,N,N',N'-tetramethyluronium tetrafluoroborate, 1-hydroxybenzotriazole, 1-hydroxy-7-azobenzotriazole, O-benzotriazole-N,N,N',N'-tetramethyluronium hexafluorophosphate, 2-(7-oxobenzotriazole)-N,N,N',N'-tetramethyluronium hexafluorophosphate, 2-(7-azobenzotriazole)-N,N,N',N'-tetramethyluronium hexafluorophosphate, benzotriazol-1-yloxytris(dimethylamino)phosphonium hexafluorophosphate and benzotriazol-1-yl-oxytripyrrolidinylphosphonium phosphate, preferably 2-(7-oxobenzotriazole)-N,N,N',N'-tetramethyluronium hexafluorophosphate.

The above reaction is preferably carried out in a solvent. The solvent used includes, but is not limited to, acetic acid, methanol, ethanol, toluene, tetrahydrofuran, dichloromethane, dimethyl sulfoxide, 1,4-dioxane, water and N,N-dimethylformamide.

Scheme 4

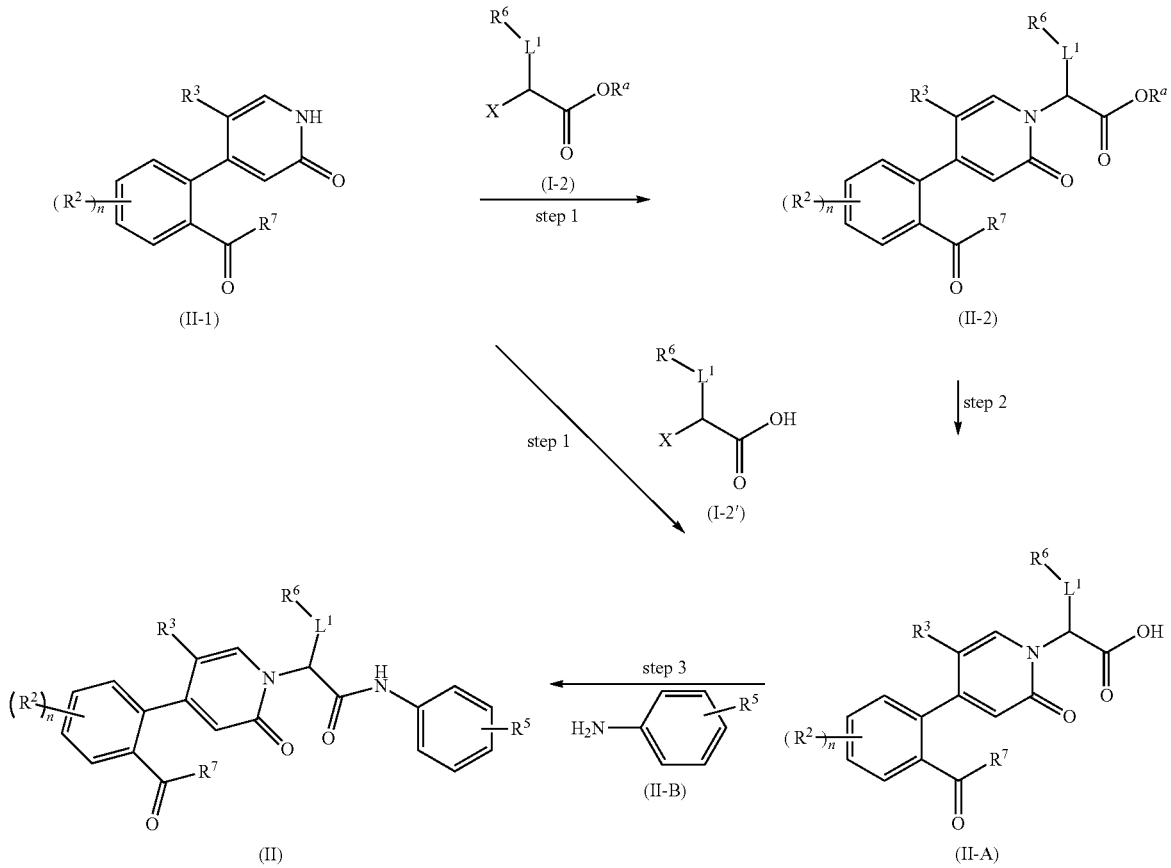

A process for preparing a compound of formula (II) of the present invention, or a tautomer, mesomer, racemate, enantiomer, diastereomer, or mixture thereof, or a pharmaceutically acceptable salt thereof, comprises the following steps:

wherein:

X is halogen, preferably bromine;

$R^a$ is alkyl, preferably methyl;

$L^1$, $R^2$, $R^3$, $R^5 \sim R^7$ and n are as defined in formula (II).

in the first step reaction, a compound of formula (II-1) and a compound of formula (I-2) are subjected to a nucleophilic substitution reaction under an alkaline condition in an organic solvent to obtain a compound of formula (II-2); or a compound of formula (II-1) and a compound of formula (I-2') are subjected to a nucleophilic substitution reaction under an alkaline condition in an organic solvent to obtain a compound of formula (II-A);

in the second step reaction, the compound of formula (II-2) is hydrolyzed under an acidic condition to obtain a compound of (II-A):

in the third step, the compound of formula (II-A) and a compound of formula (II-B) or a hydrochloride thereof are subjected to a condensation reaction under an alkaline condition, optionally the condensation product is hydrolyzed under an alkaline condition, to obtain the compound of formula (II).

The reagents that provide an alkaline condition include organic bases and inorganic bases. The organic bases include, but are not limited to triethylamine, N,N-diisopropylethylamine, n-butyllithium, lithium diisopropylamide, lithium bis(trimethylsilyl)amide, potassium acetate, sodium tert-butoxide and potassium tert-butoxide, preferably lithium bis(trimethylsilyl)amide. The inorganic bases include, but are not limited to sodium hydride, potassium phosphate, sodium carbonate, potassium carbonate, cesium carbonate, sodium hydroxide and lithium hydroxide, preferably potassium carbonate, sodium hydride or lithium hydroxide.

The reagents that provide an acidic condition include, but are not limited to, pyridine hydrobromide, trifluoroacetic acid, formic acid, acetic acid, hydrochloric acid, sulfuric acid and methanesulfonic acid, preferably pyridine hydrobromide or hydrochloric acid.

The condensing agent includes, but is not limited to, 1-(3-dimethylaminopropyl)-3-ethylcarbodiimide hydrochloride, N,N'-dicyclohexylcarbodiimide, N,N'-diisopropylcarbodiimide, O-benzotriazole-N,N,N',N-tetramethyluronium tetrafluoroborate, 1-hydroxybenzotriazole, 1-hydroxy-7-azobenzotriazole, O-benzotriazole-N,N,N',N'-tetramethyluronium hexafluorophosphate, 2-(7-oxobenzotriazole)-N,N,N',N'-tetramethyluronium hexafluorophosphate, 2-(7-azobenzotriazole)-N,N,N',N'-tetramethyluronium hexafluorophosphate, benzotriazol-1-yloxytris(dimethylamino)phosphonium hexafluorophosphate and benzotriazol-1-yl-oxytripyrrolidinylphosphonium phosphate, preferably 2-(7-oxobenzotriazole)-N,N,N',N'-tetramethyluronium hexafluorophosphate.

The above reaction is preferably carried out in a solvent. The solvent used includes, but is not limited to, acetic acid, methanol, ethanol, toluene, tetrahydrofuran, dichloromethane, dimethyl sulfoxide, 1,4-dioxane, water and N,N-dimethylformamide.

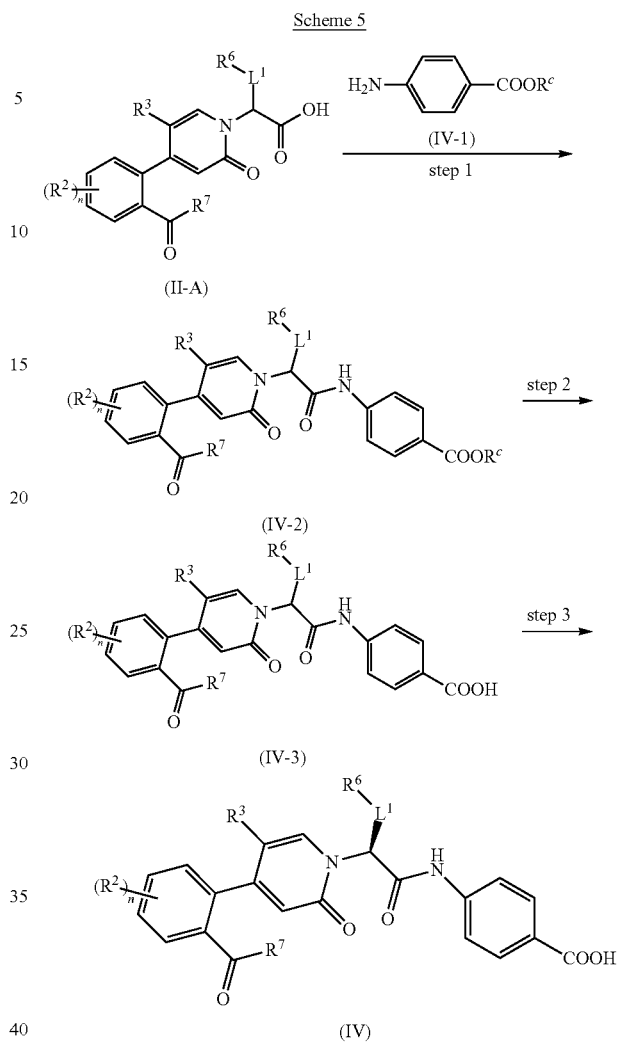

Scheme 5

A process for preparing a compound of formula (IV) of the present invention, or a tautomer, mesomer, racemate, enantiomer, diastereomer, or mixture thereof, or a pharmaceutically acceptable salt thereof, comprises the following steps:

wherein:

$R^c$ is alkyl, preferably methyl;

$L^1$, $R^2$, $R^1$, $R^6$, $R^7$ and n are as defined in formula (IV).

in the first step reaction, a compound of formula (II-A) and a compound of formula (IV-1) or a hydrochloride thereof are subjected to a condensation reaction under an alkaline condition to obtain a compound of formula (IV-2):

in the second step reaction, the compound of formula (IV-2) is hydrolyzed under an acidic condition to obtain a compound of (IV-3);

in the third step reaction, the compound of formula (IV-3) is subjected to a chiral preparation to obtain a compound of formula (IV).

The reagents that provide an alkaline condition include organic bases and inorganic bases. The organic bases include, but are not limited to triethylamine, N,N-diisopropylethylamine, n-butyllithium, lithium diisopropylamide, lithium bis(trimethylsilyl)amide, potassium acetate, sodium tert-butoxide and potassium tert-butoxide, preferably lithium bis(trimethylsilyl)amide. The inorganic bases include, but are not limited to sodium hydride, potassium phosphate, sodium carbonate, potassium carbonate, cesium carbonate, sodium hydroxide and lithium hydroxide, preferably potassium carbonate, sodium hydride or lithium hydroxide.

The reagents that provide an acidic condition include, but are not limited to, pyridine hydrobromide, trifluoroacetic acid, formic acid, acetic acid, hydrochloric acid, sulfuric acid and methanesulfonic acid, preferably pyridine hydrobromide or hydrochloric acid.

Conditions for the chiral preparation include, but are not limited to, a column being Superchiral S-AD (Chiralway), a mobile phase being carbon dioxide, ethanol and diethylamine.

The condensing reagent includes, but is not limited to, 1-(3-dimethylaminopropyl)-3-ethylcarbodiimide hydrochloride. N,N'-dicyclohexylcarbodiimide, N,N'-diisopropylcarbodiimide, O-benzotriazole-N,N,N',N'-tetramethyluronium tetrafluoroborate, 1-hydroxy benzotriazole, 1-hydroxy-7-azobenzotriazole, O-benzotriazole-N,N,N',N'-tetramethyluronium hexafluorophosphate, 2-(7-oxobenzotriazole)-N,N,N',N'-tetramethyluronium hexafluorophosphate, 2-(7-azobenzotriazole)-N,N,N',N'-tetramethyluronium hexafluorophosphate, benzotriazol-1-yloxytris(dimethylamino)phosphonium hexafluorophosphate and benzotriazol-1-yl-oxytripyrrolidinylphosphonium phosphate, preferably 2-(7-oxobenzotriazole)-N,N,N',N'-tetramethyluronium hexafluorophosphate.

The above reaction is preferably carried out in a solvent. The solvent used includes, but is not limited to, acetic acid, methanol, ethanol, toluene, tetrahydrofuran, dichloromethane, dimethyl sulfoxide, 1,4-dioxane, water and N,N-dimethylformamide.

As for the compound of each formula involved in the present invention, if a salt form of the compound is obtained during the synthesis, a free form of the compound can be further obtained by conventional experimental means; if the free form of the compound is obtained during the synthesis, a salt form of the compound can be further obtained by conventional experimental means.

PREFERRED EMBODIMENTS

The present invention will be further described with reference to the following examples, but the examples should not be considered as limiting the scope of the invention.

EXAMPLES

The structures of the compounds are identified by nuclear magnetic resonance (NMR) and/or mass spectrometry (MS). NMR chemical shifts (δ) are given in $10^{-6}$ (ppm). NMR is determined by a Bruker AVANCE-400 machine. The solvents for determination are deuterated-dimethyl sulfoxide (DMSO-$d_6$), deuterated-chloroform (CDCl$_3$) and deuterated-methanol (CD$_3$OD), and the internal standard is tetramethylsilane (TMS).

MS is determined by a FINNIGAN LCQAd (ESI) mass spectrometer (manufacturer: Thermo, type: Finnigan LCQ advantage MAX).

High performance liquid chromatography (HPLC) analysis is determined on an Agilent HPLC 1200DAD, Agilent HPLC 1200VWD and Waters HPLC e2695-2489 high pressure liquid chromatography spectrometer.

Chiral HPLC analysis is determined on an Agilent 1260 DAD high performance liquid chromatography spectrometer.

CombiFlash rapid preparation instrument is Combiflash Rf200 (TELEDYNE ISCO).

Yantai Huanghai HSGF254 or Qingdao GF254 silica gel plate is used for thin-layer silica gel chromatography (TLC). The dimension of the silica gel plate used in TLC is 0.15 mm to 0.2 mm, and the dimension of the silica gel plate used in product purification is 0.4 mm to 0.5 mm.

Yantai Huanghai 200 to 300 mesh silica gel is used as a carrier for column chromatography.

The average kinase inhibition rates and $IC_{50}$ values are determined by a NovoStar ELISA (BMG Co., Germany).

The known raw materials of the present invention can be prepared by conventional synthesis methods known in the art, or can be purchased from ABCR GmbH & Co. KG, Acros Organnics, Aldrich Chemical Company, Accela ChemBio Inc., or Dari chemical Company, etc.

Unless otherwise stated, the reactions are carried out under nitrogen atmosphere or argon atmosphere.

The term "nitrogen atmosphere" or "argon atmosphere" means that a reaction flask is equipped with a 1 L nitrogen or argon balloon.

The term "hydrogen atmosphere" means that a reaction flask is equipped with a 1 L hydrogen balloon.

Pressurized hydrogenation reactions are carried out with a Parr 3916EKX hydrogenation instrument and a QL-500 hydrogen generator or HC2-SS hydrogenation instrument.

In hydrogenation reactions, the reaction system is generally vacuumed and filled with hydrogen, and the above operation is repeated three times.

CEM Discover-S 908860 type microwave reactor is used in microwave reactions.

Unless otherwise stated, the solution refers to an aqueous solution.

Unless otherwise stated, the reaction temperature in the reactions refers to room temperature, ranging from 20° C. to 30° C.

The reaction process is monitored by thin layer chromatography (TLC), and the system of developing solvent, the elution system for purification of the compounds by column chromatography and thin layer chromatography include: A: dichloromethane and methanol system, B: n-hexane and ethyl acetate system, C: petroleum ether and ethyl acetate system, D: acetone, E: dichloromethane and acetone system, F: ethyl acetate and dichloromethane system. G: ethyl acetate, dichloromethane and n-hexane, H: ethyl acetate, dichloromethane and acetone, and I: petroleum ether, ethyl acetate and dichloromethane. The ratio of the volume of the solvents can be adjusted according to the polarity of the compounds, and sometimes a little alkaline reagent such as triethylamine or acidic reagent such as acetic acid can be added.

Example 1
5-(2-(4-(2-acetyl-5-chlorophenyl)-5-methoxy-2-oxopyridin-1(2H)-yl)-4-methoxybutanamido)-1H-indole-2-carboxylic acid
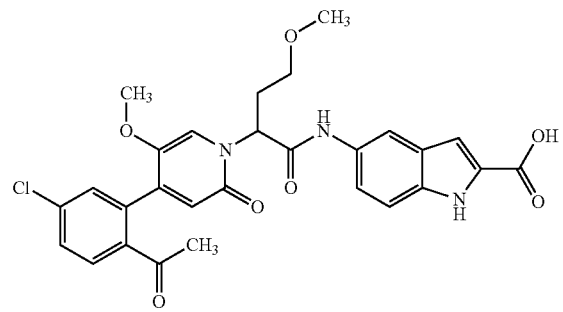
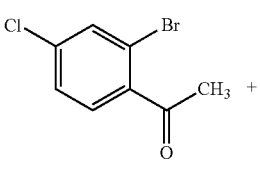
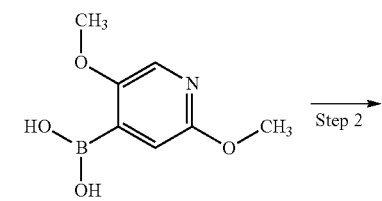
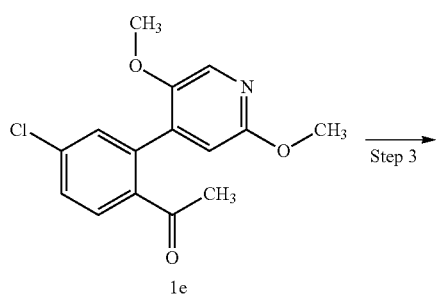
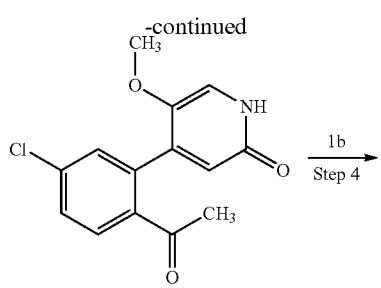
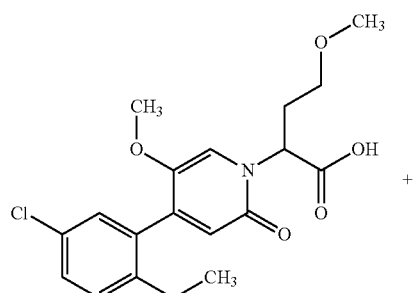
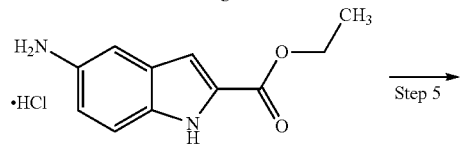
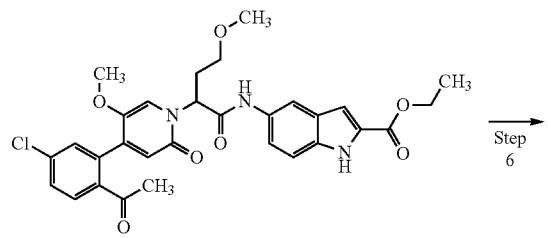
Step 1
methyl 2-bromo-4-methoxybutanoate 1b
Methyl 4-methoxybutanoate 1a (1.6 g, 12.1 mmol) was added to 50 mL of tetrahydrofuran, and the resulting solution was cooled to −78° C. in a dry ice-acetone bath. Lithium bis(trimethylsilyl)amide (12.7 mL, 12.7 mmol) was added slowly. After completion of the addition, the reaction solution was stirred for 1 hour, and then chlorotrimethylsilane (1.31 g, 12.1 mmol) was added. After stirring for 20 minutes, the reaction solution was added with N-bromosuccinimide (2.15 g, 12.1 mmol) and stirred for 2 hours. The dry ice-acetone bath was removed, and the temperature of the reaction solution was warmed up to room temperature. Saturated ammonium chloride solution was added to quench the reaction. The reaction solution was extracted with ethyl acetate (50 mL×3). The organic phases were combined, washed with water (50 mL) and saturated sodium chloride solution (50 mL) successively, dried over anhydrous sodium sulfate, and filtered. The filtrate was concentrated under reduced pressure, and the resulting residue was purified by silica gel column chromatography with elution system B to obtain the title compound 1b (900 mg, yield: 35.3%).

Step 2

1-(4-chloro-2-(2,5-dimethoxypyridin-4-yl)phenyl) ethanone 1e 1-(2-Bromo-4-chlorophenyl)ethanone 1c (1.27 g, 5.46 mmol), (2,5-dimethoxypyridin-4-yl)boronic acid 1d (1.0 g, 5.46 mmol, prepared by a method disclosed in the patent application "WO2015063093"), [1,1'-bis(diphenylphosphino)ferrocene]dichloropalladium (II) (230 mg, 0.32 mmol) and potassium carbonate (2.2 g, 16.38 mmol) were added to 25 mL of 1,4-dioxane. After completion of the addition, the reaction solution was heated to 110° C., stirred for 8 hours, and then cooled to room temperature naturally. The reaction solution was added with 50 mL of water, and extracted with ethyl acetate (50 mL×3). The organic phases were combined, washed with water (50 mL) and saturated sodium chloride solution (50 mL) successively, dried over anhydrous sodium sulfate and filtered. The filtrate was concentrated under reduced pressure, and the resulting residue was purified by silica gel column chromatography with elution system B to obtain the title compound 1e (1.0 g, yield: 63.3%).

MS m/z (ESI): 292.3 [M+1]

Step 3

4-(2-acetyl-5-chlorophenyl)-5-methoxypyridin-2 (1H)-one 1f

Compound 1e (1.0 g, 3.43 mmol) was added to 10 mL of N,N-dimethylformamide, and then pyridine hydrobromide (3.30 g, 20.6 mmol) was added. After completion of the addition, the reaction solution was heated to 105° C., and stirred for 3 hours. The reaction solution was added with 50 mL of water and extracted with ethyl acetate (50 mL×3). The organic phases were combined, washed with water (50 mL) and saturated sodium chloride solution (50 mL), dried over anhydrous sodium sulfated and filtered. The filtrate was concentrated under reduced pressure to obtain the title compound 1f (550 mg, yield: 57.8%).

MS m/z (ESI): 276.3 [M−1]

Step 4

2-(4-(2-acetyl-5-chlorophenyl)-5-methoxy-2-oxopyridin-1(2H)-yl)-4-methoxybutanoic acid 1g Compound 1f (350 mg, 1.28 mmol) was added to 10 mL of N,N-dimethylformamide, and then sodium hydride (153 mg, 3.84 mmol) was added slowly in an ice-water bath. After completion of the addition, the ice-water bath was removed, and the temperature of the reaction solution was warmed up to room temperature naturally. After stirring for 30 minutes, the reaction solution was added with compound 1b (350 mg, 1.66 mmol), and then stirred for 24 hours. The reaction solution was added with 50 mL of water, dropwise added with 1 M hydrochloric acid to adjust the pH to 3-4, and then extracted with ethyl acetate (50 mL×3). The organic phases were combined, washed with water (50 mL) and saturated sodium chloride (50 mL), dried over anhydrous sodium, and filtrated to remove the desiccant. The filtrate was concentrated under reduced pressure to obtain the crude title compound 1g (360 mg), which was directly used in the next reaction step without purification.

MS m/z (ESI): 394.4 [M+1]

Step 5 ethyl 5-(2-(4-(2-acetyl-5-chlorophenyl)-5-methoxy-2-oxopyridin-1(2H)-yl)-4-methoxybutanamido)-1H-indole-2-carboxylate 1i The crude product 1g (180 mg, 0.45 mmol) was added to 10 mL of N,N-dimethylformamide, followed by addition of 2-(7-oxobenzotriazole)-N,N,N',N'-tetramethyluronium hexafluorophosphate (313 mg, 0.82 mmol), N,N-diisopropylethylamine (0.22 mL, 1.35 mmol) and ethyl 5-amino-1H-indole-2-carboxylate hydrochloride 1h (129 mg, 0.54 mmol, prepared by a known method disclosed in "*Journal of Organic Chemistry*, 2012, 55(2), 766-782"). After completion of the addition, the reaction solution was heated to 50° C., and stirred for 16 hours. The reaction solution was added with 50 mL of water, and extracted with ethyl acetate (50 mL×3). The organic phases were combined, washed with water (50 mL) and saturated sodium chloride solution (50 mL), dried over anhydrous sodium sulfate, and filtrated to remove the desiccant. The filtrate was concentrated under reduced pressure, and the resulting residue was purified by silica gel column chromatography with elution system B to obtain the title compound 1i (60 mg, yield: 23.1%).

MS m/z (ESI): 580.4 [M+1]

Step 6

5-(2-(4-(2-acetyl-5-chlorophenyl)-5-methoxy-2-oxopyridin-1(2H)-yl)-4-methoxybutanamido)-1H-indole-2-carboxylic acid 1

Compound 1i (60 mg, 0.103 mmol) was added to 4 mL of a mixed solvent of tetrahydrofuran and methanol (V:V=3:1), followed by addition of 1 M lithium hydroxide solution (0.83 mL, 0.83 mmol). After completion of the addition, the reaction solution was stirred for 16 hours, and then the solvent was evaporated under reduced pressure. The resulting residue was added with 10 mL of water and stirred well. The reaction solution was added with 1 M hydrochloric acid to adjust the pH to 3-4, and then extracted with ethyl acetate (50 mL 3). The organic phases were combined, washed with water (50 mL) and saturated sodium chloride (50 mL), dried over anhydrous sodium sulfate and filtrated to remove the desiccant. The filtrate was concentrated under reduced pressure, and the resulting residue was purified by high performance liquid chromatography (Gilson-281, elution system: acetonitrile, water) to obtain the title compound 1 (4 mg, yield: 7.0%).

MS m/z (ESI): 552.4 [M+1]

$^1$H NMR (400 MHz, DMSO-d$_6$) δ 11.60 (s, 1H), 11.33 (s, 1H), 8.01 (s, 1H), 7.89-7.87 (d, 1H), 7.64-7.61 (dd, 1H), 7.47-7.46 (d, 1H), 7.37-7.32 (m, 3H), 6.97 (s, 1H), 6.40 (s, 1H), 5.79-5.75 (m, 1H), 3.54 (s, 3H), 3.22 (s, 3H), 2.42-2.31 (m, 2H)

Examples 2,3

(S)-5-(2-(4-(2-acetyl-5-chlorophenyl)-5-methoxy-2-oxopyridin-1(2H)-yl)-4-methoxybutanamido)-1H-indole-2-carboxylic acid 2

(R)-5-(2-(4-(2-acetyl-5-chlorophenyl)-5-methoxy-2-oxopyridin-1(2H)-yl)-4-methoxybutanamido)-1H-indole-2-carboxylic acid 3

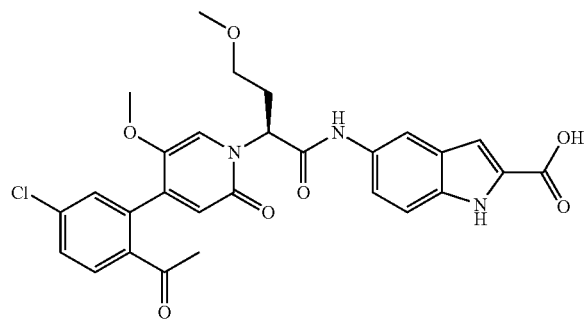

2

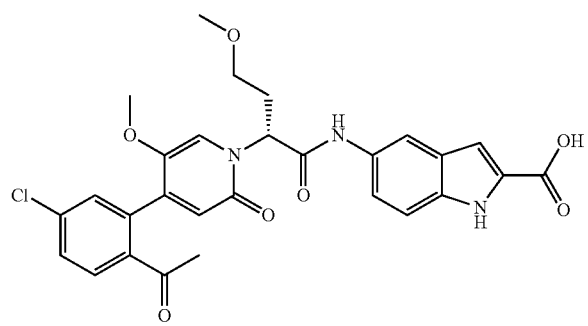

3

Compound 1 (100 mg, 0.18 mmol) was separated chirally (separation conditions: chiral preparative column CHIRAL PAK IE, 20*250 mm, 5 μm; mobile phase: mobile phase: ethanol (containing 0.01% trifluoroacetic acid)=100, flow rate: 8 mL/min). The corresponding fractions were collected and concentrated under reduced pressure to obtain the title compounds 2 (10 mg) and 3 (15 mg).

Compound 2:

MS m/z (ESI):552.5 [M+1]

Chiral HPLC analysis: retention time 8.907 minutes, chiral purity: 98% (chromatographic column: CHIRAL PAK IE, 4.6*150 mm, 5 μm; mobile phase: n-hexane/ethanol/trifluoroacetic acid=40/60/0.06(v/v/v)).

$^1$H NMR (400 MHz, DMSO-d$_6$) δ 11.60 (s, 1H), 11.33 (s, 1H), 8.01 (s, 1H), 7.89-7.87 (d, 1H), 7.64-7.61 (dd, 1H), 7.47-7.46 (d, 1H), 7.37-7.32 (m, 3H), 6.97 (s, 1H), 6.40 (s, 1H), 5.79-5.75 (m, 1H), 3.54 (s, 3H), 3.22 (s, 3H), 2.42-2.31 (m, 2H)

Compound 3:

MS m/z (ESI): 552.4 [M+1]

Chiral HPLC analysis: retention time 6.720 minutes, chiral purity: 98% (chromatographic column:CHIRAL PAK IE, 4.6*150 mm, 5 μm; mobile phase: n-hexane/ethanol/trifluoroacetic acid=40/60/0.06(v/v/v)).

$^1$H NMR (400 MHz, DMSO-d$_6$) δ 11.60 (s, 1H), 11.33 (s, 1H), 8.01 (s, 1H), 7.89-7.87 (d, 1H), 7.64-7.61 (dd, 1H), 7.47-7.46 (d, 1H), 7.37-7.32 (m, 3H), 6.97 (s, 1H), 6.40 (s, 1H), 5.79-5.75 (m, 1H), 3.54 (s, 3H), 3.22 (s, 3H), 2.42-2.31 (m, 2H)

Example 4

4-(2-(4-(2-acetyl-5-chlorophenyl)-5-methoxy-2-oxopyridin-1(2H)-yl)-3-phenylpropanamido)benzoic acid 4

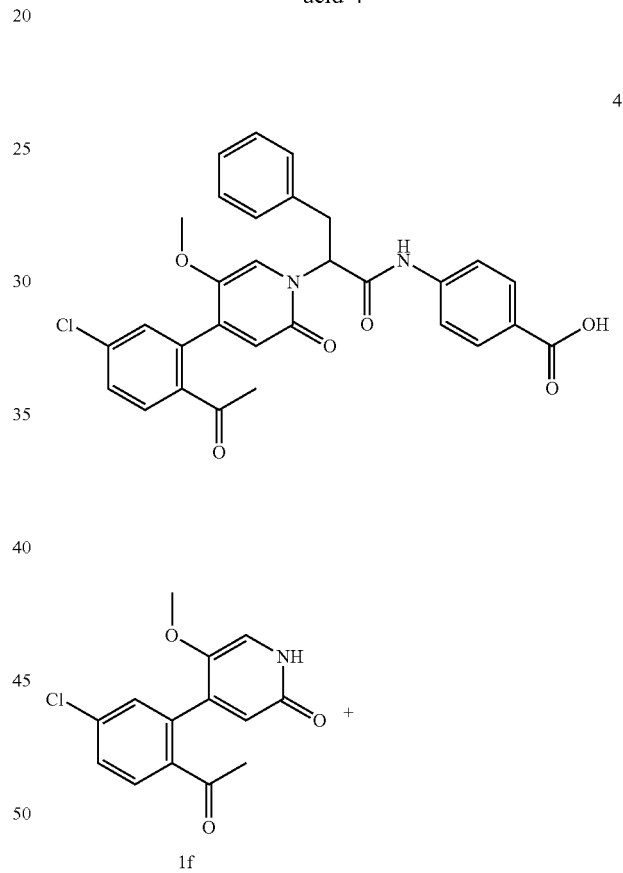

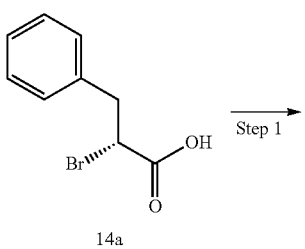

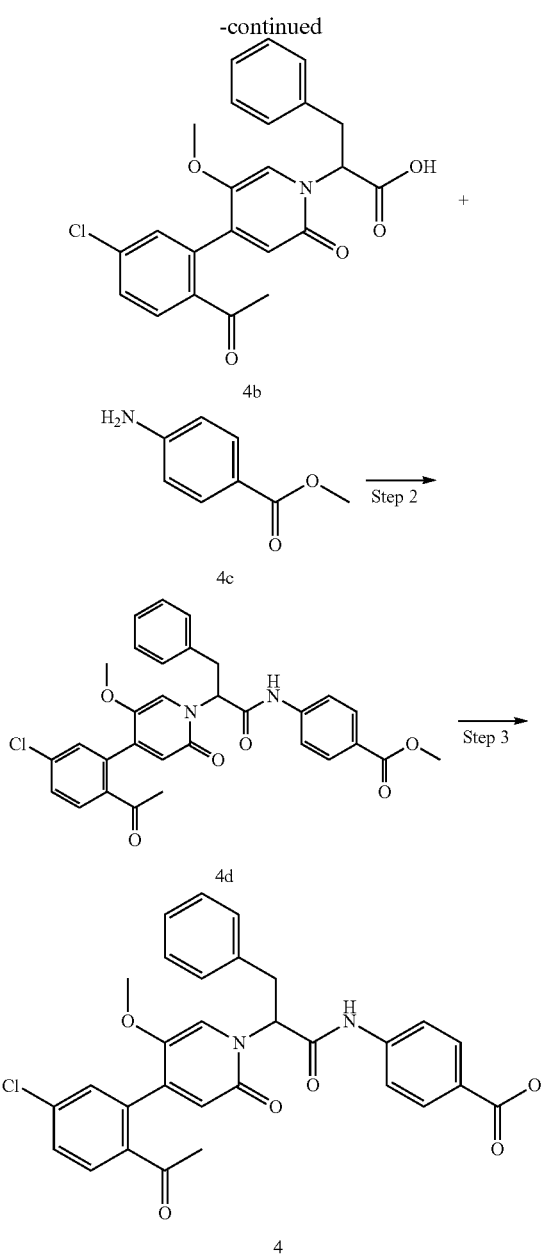

with ethyl acetate (50 mL 3). The organic phases were combined, dried over anhydrous sodium sulfate, and filtered. The filtrate was concentrated under reduced pressure, and the resulting residue was purified by high performance liquid chromatography (Gilson-281, elution system: acetonitrile, water) to obtain the title compound 4b (350 mg, yield: 20.5%).

MS m/z (ESI): 426.4 [M+1]

Step 2 methyl 4-(2-(4-(2-acetyl-5-chlorophenyl)-5-methoxy-2-oxopyridin-1(2H)-yl)-3-phenylpropanamido)benzoate 4d Compound 4b (350 mg, 0.82 mmol), methyl 4-aminobenzoate 4c (39.23 mg, 0.26 mmol, prepared by a known method disclosed in "*Chemical Communications (Cambridge, United Kingdom)*, 2015, 51(58), 11705-11708") and N,N-diisopropylethylamine (0.57 mL, 3.29 mmol) were successively dissolved in 30 mL of ethyl acetate, followed by dropwise addition of a solution of 2,4,6-tripropyl-1,3,5, 2,4,6-trioxatriphosphorinane-2,4,6-trioxide in ethyl acetate (50%, 1569 mg, 2.47 mmol). After completion of the addition, the reaction was warmed up to 60° C., and stirred for 2 hours. The reaction solution was cooled to room temperature, and concentrated under reduced pressure. The resulting residue was purified by silica gel column chromatography with elution system A to obtain the title compound 4d (140 mg, yield: 28.9%).

MS m/z (ESI): 559.5 [M+1]

Step 3

4-(2-(4-(2-acetyl-5-chlorophenyl)-5-methoxy-2-oxopyridin-1(2H)-yl)-3-phenylpropanamido)benzoic acid 4

Compound 4d (120 mg, 0.21 mmol) was dissolved in 4 mL of a mixed solvent of tetrahydrofuran and methanol (V/V=3:1), followed by addition of 1.28 mL of 1M lithium hydroxide solution. After completion of the addition, the reaction solution was stirred for 16 hours. The reaction solution was dropwise added with 10% hydrochloric acid to adjust the pH to 3-4, and extracted with ethyl acetate (50 mL×2). The organic phases were combined and concentrated under reduced pressure. The resulting residue was purified by high performance liquid chromatography (Gilson-281, elution system: acetonitrile, water) to obtain the title compound 4 (50 mg, yield: 42.7%).

MS m/z (ESI): 545.4 [M+1]

$^1$H NMR (400 MHz, DMSO-d$_6$) δ 10.81 (s, 1H), 7.92 (s, 1H), 7.90 (s, 1H), 7.83-7.81 (d, 1H), 7.74 (s, 1H), 7.72 (s, 1H), 7.62-7.59 (dd, 1H), 7.43 (s, 1H) 7.38 (s, 1H), 7.30-7.25 (m, 4H), 7.21-7.17 (m, 1H), 6.31 (s, 1H), 6.05-6.01 (m, 1H), 3.54 (s, 3H), 3.49-3.44 (m, 2H), 2.37 (s, 3H).

Step 1

2-(4-(2-acetyl-5-chlorophenyl)-5-methoxy-2-oxopyridin-1(2H)-yl)-3-phenylpropanoic acid 4b Magnesium tert-butoxide (701.62 mg, 7.2 mmol) was dissolved in 250 mL of tetrahydrofuran, and then (R)-2-bromo-3-phenylpropionic acid (1649.77 mg, 7.2 mmol, prepared by a known method disclosed in "*Chemical Communications (Cambridge, United Kingdom)*, 2014, 50(88), 13489-13491"), potassium tert-butoxide (404.07 mg, 3.6 mmol) and the crude compound 1f (1000 mg, 3.6 mmol) were added. The reaction solution was reacted for 16 hours at 60° C., cooled to room temperature, dropwise added with 1 M hydrochloric acid to adjust the pH to 3-4, and extracted

Examples 5, 6

(S)-4-(2-(4-(2-acetyl-5-chlorophenyl)-5-methoxy-2-oxopyridin-1(2H)-yl)-3-phenylpropanamido)benzoic acid 5

(R)-4-(2-(4-(2-acetyl-5-chlorophenyl)-5-methoxy-2-oxopyridin-1(2H)-yl)-3-phenylpropanamido)benzoic acid 6

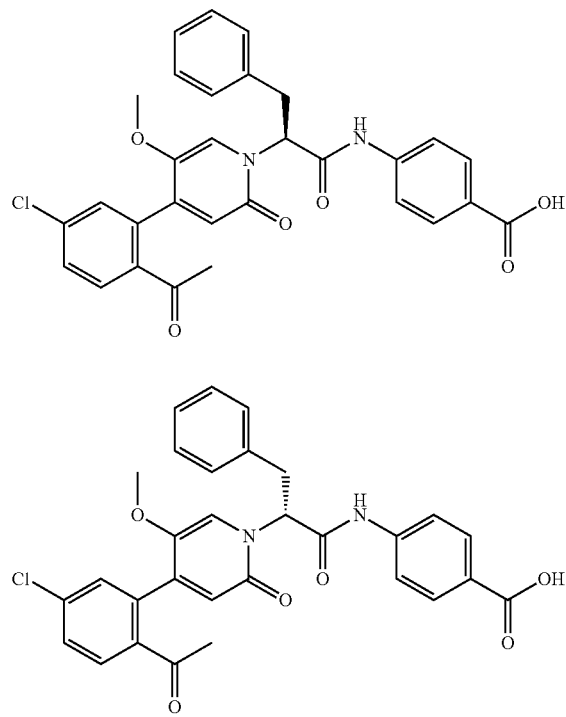

Compound 4 (900 mg, 1.62 mmol) was separated chirally (separation condition: chiral preparative column Superchiral S-AD(Chiralway), 2 cm I.D.*25 cm Length, 5 μm; mobile phase:carbon dioxide:ethanol:diethylamine=60:40:0.05, flow rate: 50 g/min). The corresponding fractions were collected and concentrated under reduced pressure to obtain the title compound 5 (421 mg) and 6 (405 mg).

Compound 5:

MS m/z (ESI): 545.4 [M+1];

Chiral HPLC analysis: retention time 4.138 minutes, chiral purity: 98% (chromatographic column: Superchiral S-AD(Chiralway), 2 cm I.D.*25 cm Length, 5 μm; mobile phase: ethanol/n-hexane/trifluoroacetic acid=50/50/0.05 (v/v/v)).

$^1$H NMR (400 MHz, DMSO-$d_6$) δ 10.81 (s, 1H), 7.92 (s, 1H), 7.90 (s, 1H), 7.83-7.81 (d, 1H), 7.74 (s, 1H), 7.72 (s, 1H), 7.62-7.59 (dd, 1H), 7.43 (s, 1H) 7.38 (s, 1H), 7.30-7.25 (m, 4H), 7.21-7.17 (m, 1H), 8.31 (s, 1H), 6.05-6.01 (m, 1H), 3.54 (s, 3H), 3.49-3.44 (m, 2H), 2.37 (s, 3H)

Compound 6:

MS m/z (ESI): 545.4 [M+1]

Chiral HPLC analysis: retention time 1.475 minutes, (chromatographic column: Superchiral S-AD(Chiralway), 2 cm I.D.*25 cm Length, 5 μm; mobile phase: ethanol/n-hexane/trifluoroacetic acid=50/50/0.05 (v/v/v)).

$^1$H NMR (400 MHz, DMSO-$d_6$) δ 10.81 (s, 1H), 7.92 (s, 1H), 7.90 (s, 1H), 7.83-7.81 (d, 1H), 7.74 (s, 1H), 7.72 (s, 1H), 7.62-7.59 (dd, 1H), 7.43 (s, 1H) 7.38 (s, 1H), 7.30-7.25 (m, 4H), 7.21-7.17 (m, 1H), 8.31 (s, 1H), 6.05-6.01 (m, 1H), 3.54 (s, 3H), 3.49-3.44 (m, 2H), 2.37 (s, 3H)

Example 7

4-(2-(4-(2-acetyl-5-chlorophenyl)-5-methoxy-2-oxopyridin-1(2H)-yl)-3-(thiophen-3-yl) propanamido)benzoic acid 7

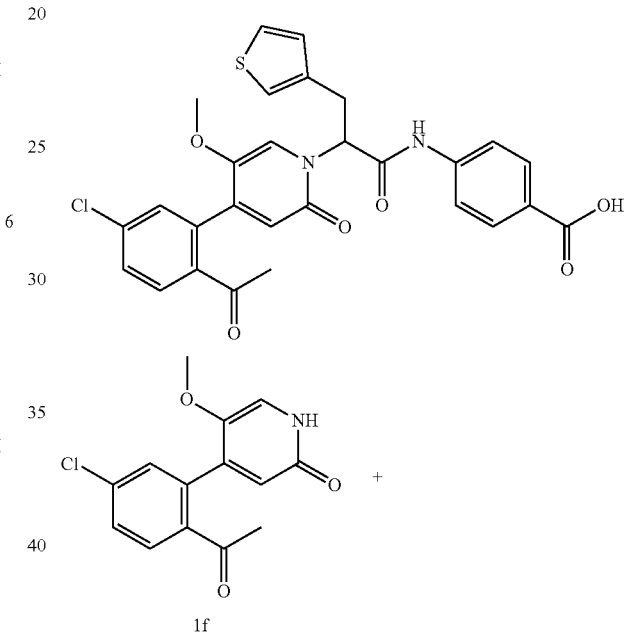

-continued

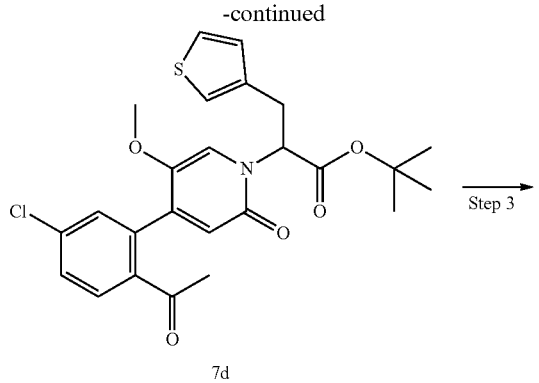

7d

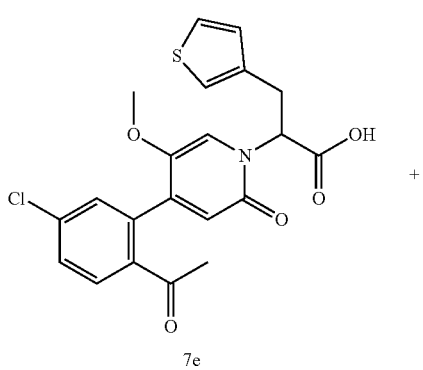

7e

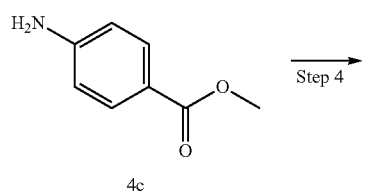

4c

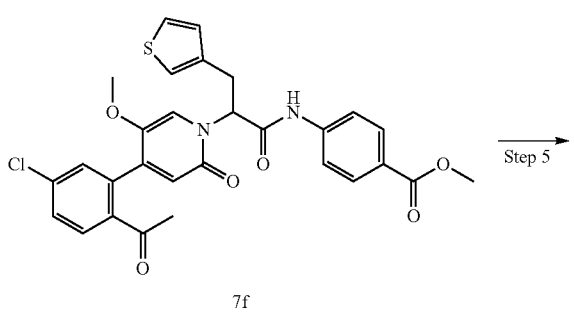

7f

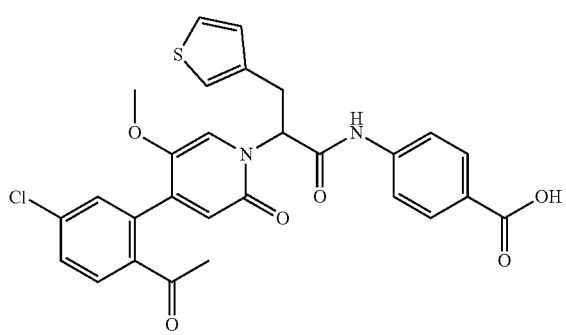

7

Step 1

Tert-Butyl 2-(4-(2-acetyl-5-chlorophenyl)-5-methoxy-2-oxopyridin-1(2H)-yl)acetate 7b Compound 1f (3.4 g, 12.24 mmol), cesium carbonate (11937.34 mg, 36.73 mmol) and tert-butyl 2-bromoacetate 7a (3.58 g, 18.37 mmol, prepared by a known method disclosed in "*Chemical Communications (Cambridge, United Kingdom)*, 2012, 48(22), 2803-2805") were successively dissolved in 40 mL N,N-dimethylformamide. After completion of the addition, the reaction solution was warmed up to 65° C. and stirred for 2 hours. The reaction solution was cooled to room temperature, added with 50 mL of water, extracted with ethyl acetate (50 mL×3), and the organic phase was washed with saturated sodium chloride solution (50 mL×3). The organic phases were combined, dried over anhydrous sodium sulfate, and filtered. The filtrate was concentrated under reduced pressure, and the resulting residue was purified by silica gel column chromatography with elution system I to obtain the title compound 7b (3.2 g, yield: 65.4%).

MS m/z (ESI): 392.1 [M+1]

Step 2

Tert-Butyl 2-(4-(2-acetyl-5-chlorophenyl)-5-methoxy-2-oxopyridin-1(2H)-yl)-3-(thiophen-3-yl) propanoate 7d Compound 7b (100 mg, 0.26 mmol) and 3-(bromomethyl) thiophene 7c (90.37 mg, 0.51 mmol, prepared by a known method disclosed in "*Journal of Organic Chemistry*, 2016, 81(22), 11035-11042") were successively dissolved in 10 mL of tetrahydrofuran. The reaction solution was cooled to −78° C., dropwise added with lithium diisopropylamide solution (1.53 mL, 1.02 mmol), and reacted for 2 hours. 1 mL of water was added slowly, and the temperature of the reaction solution was warmed up to room temperature naturally. The reaction solution was added with 10 mL of water, and then extracted with ethyl acetate (20 mL×3). The organic phase was washed with saturated sodium chloride solution (20 mL×2), and filtered. The filtrate was concentrated under reduced pressure, and the resulting residue was purified by silica gel column chromatography with elution system B to obtain the title compound 7d (84 mg, yield: 64.1%).

MS m/z (ESI): 488.4[M+1]

Step 3

2-(4-(2-acetyl-5-chlorophenyl)-5-methoxy-2-oxopyridin-1(2H)-yl)-3-(thiophen-3-yl)propanoic acid 7e Compound 7d (80 mg, 0.16 mmol) was dissolved in 4 mL of dichloromethane. The reaction solution was added with trifluoroacetic acid (0.5 mL, 0.78 mmol) and stirred for 5 hours. The reaction solution was evaporated under reduced pressure to obtain the crude title compound 7e (68 mg), which was directly used in the next reaction step without purification.

MS m/z (ESI): 432.3 [M+1]

Step 4 methyl 4-(2-(4-(2-acetyl-5-chlorophenyl)-5-methoxy-2-oxopyridin-1(2H)-yl)-3-(thiophen-3-yl) propanamido)benzoate 7f The crude compound 7e (67 mg, 0.16 mmol) and compound 4 (30.48 mg, 0.20 mmol) were dissolved in 6 mL of ethyl acetate, followed by successive addition of 0.5 mL of pyridine and 2,4,6-tripropyl-1,3,5,2,4,6-trioxatriphosphorinane-2,4,6-trioxide (197.44 mg, 0.62 mmol). After completion of the addition, the reaction was warmed up to 70° C., and stirred for 1.5 hours. The reaction solution was added with 15 mL of water, extracted with ethyl acetate (15 mL×2), washed with saturated sodium chloride solution (15 mL×2), dried over anhydrous sodium sulfate, and filtered. The filtrate was concentrated under reduced pressure, and the resulting residue was purified by silica gel column chromatography with elution system A to obtain the title compound 7f (80 mg), yield: 86.7%.

MS m/z (ESI): 565.5[M+1];

Step 5

4-(2-(4-(2-acetyl-5-chlorophenyl)-5-methoxy-2-oxopyridin-1(2H)-yl)-3-(thiophen-3-yl) propanamido)benzoic acid 7

Compound 7f (80 mg, 0.13 mmol) was dissolved in 3 mL of tetrahydrofuran, followed by addition of sodium hydroxide solution (1 N, 0.67 mL). After completion of the addition, the reaction solution was stirred for 12 hours, followed by addition of sodium hydroxide solution (1 N, 0.67 mL). The reaction solution was warmed up to 35° C., and stirred for 16 hours. The organic solvent was evaporated under reduced pressure. 15 mL of water were added, and then the reaction solution was added with 3 N hydrochloric acid to adjust the pH to 4-5, and filtered. The filter cake was collected, and the resulting residue was purified by silica gel column chromatography with elution system A to obtain the title compound 7 (50 mg, yield: 64.8%).

MS m/z (ESI):551.1 [M+1]
$^1$H NMR (400 MHz, DMSO-d$_6$) δ 12.76 (s, 1H), 10.81 (s, 1H), 7.92 (d, 2H), 7.84 (d, 1H), 7.75 (d, 2H), 7.62 (dd, 1H), 7.45 (dd, 1H), 7.40 (d, 2H), 7.22 (d, 1H), 7.01 (d, 1H), 6.34 (s, 1H), 5.99-5.95 (m, 1H), 3.58-3.52 (m, 1H), 3.53 (s, 3H), 3.46-3.41 (m, 1H), 2.41 (s, 3H)

Example 8

4-(2-(4-(5-chloro-2-propionylphenyl)-5-methoxy-2-oxopyridin-1(2H)-yl)-3-phenylpropanamido)benzoic acid 8

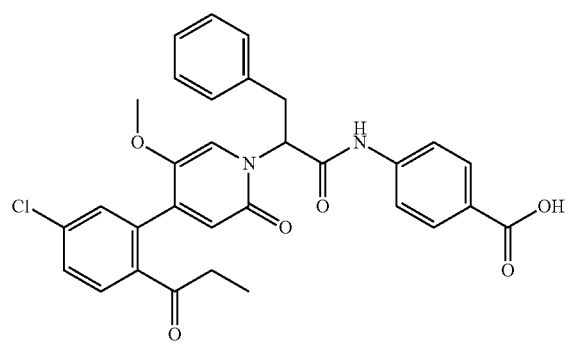

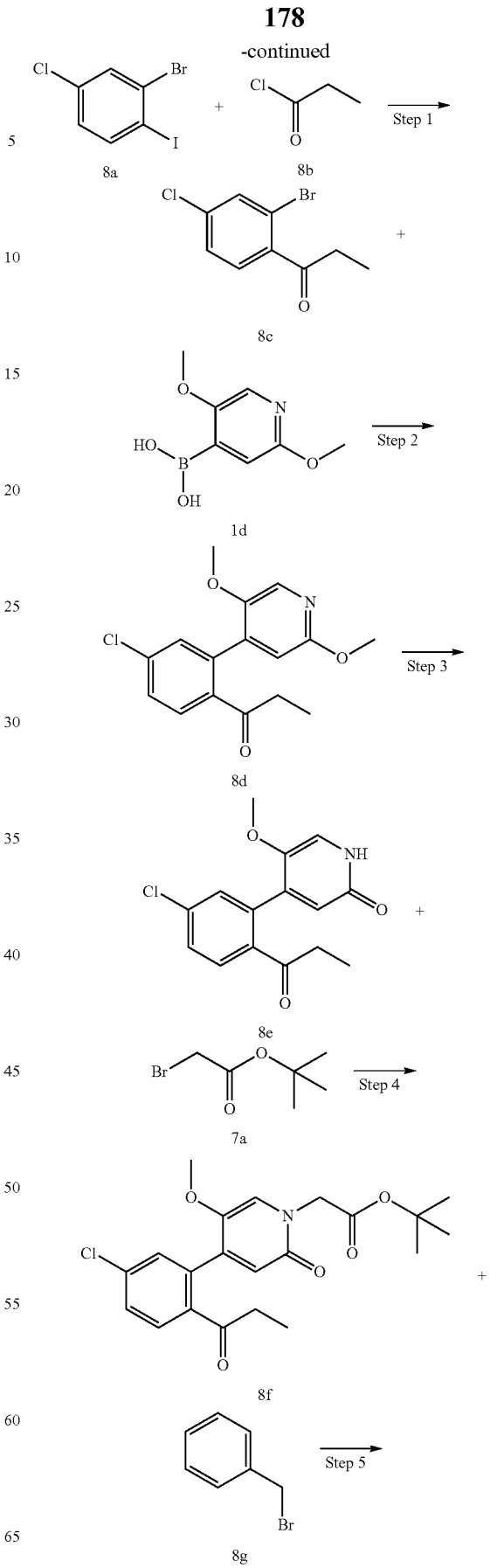

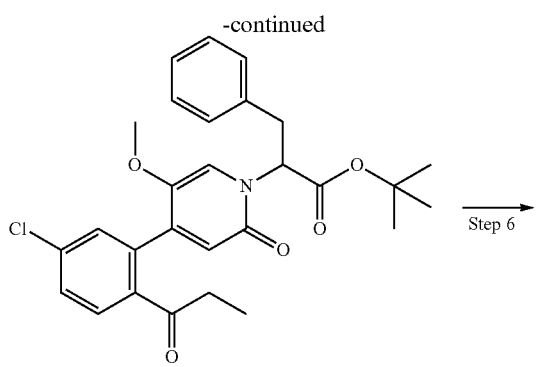

8h

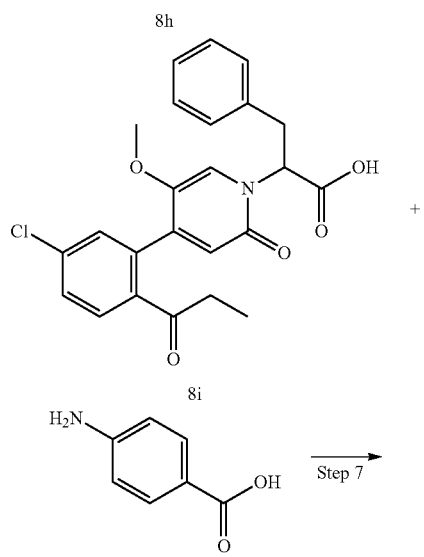

8i

+

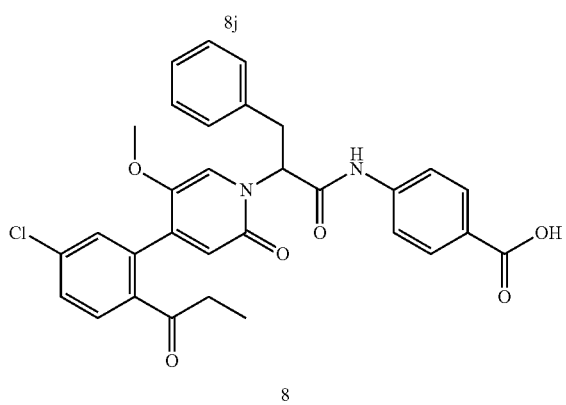

8j

8

Step 1

1-(2-bromo-4-chlorophenyl)propan-1-one 8c

2-Bromo-4-chloro-1-iodobenzene 8a (1.0 g, 3.15 mmol, prepared by a known method disclosed in "*Angewandie Chemie, International Edition,* 2010, 49(46), 8729-8732") was dissolved in 1 mL of tetrahydrofuran. The reaction solution was cooled to −20° C., added with isopropylmagnesium chloride (421.15 mg, 4.10 mmol), and pre-reacted for 1 hour. Propionyl chloride 8b (378.89 mg, 4.10 mmol), lithium chloride (11.42 mg, 189.00 μmol), cuprous chloride (9.36 mg, 94.50 μmol) and aluminum trichloride (12.61 mg, 94.50 μmol) were added to 1 mL of tetrahydrofuran, and stirred well at room temperature. The pre-reacted reaction solution was dropwise added to the above mixture, and reacted for 2 hours at room temperature. The reaction solution was added with 20 mL of saturated ammonium chloride solution to quench the reaction, and extracted with dichloromethane (20 mL×3). The organic phases were combined, dried over anhydrous sodium sulfate, and filtered. The filtrate was concentrated under reduced pressure, and the resulting residue was purified by CombiFlash rapid preparation instrument with elution system B to obtain the title compound 8c (640 mg, yield: 82.0%).

Step 2

1-(4-chloro-2-(2,5-dimethoxypyridin-4-yl)phenyl)propan-1-one 8d

Compound 8c (640 mg, 2.59 mmol), compound 1d (520.41 mg, 2.84 mmol), [1,1'-bis(diphenylphosphino)ferrocene]dichloropalladium (II) (191.8 mg, 0.259 mmol) and sodium carbonate (822.16 mg, 7.76 mmol) were added to a mixed solvent of 20 mL of 1,4-dioxane and 4 mL of water. After completion of the addition, the reaction solution was warmed up to 85° C., and stirred for 16 hours. After cooling to room temperature, the reaction solution was added with 20 mL of water, and extracted with ethyl acetate (20 mL×3). The organic phases were combined, washed with water (30 mL) and saturated sodium chloride solution (30 mL) successively, dried over anhydrous sodium sulfate, and filtered. The filtrate was concentrated under reduced pressure, and the resulting residue was purified by silica gel column chromatography with elution system B to obtain the title compound 8d (600 mg, yield: 75.9%).

MS m/z (ESI): 306.0 [M+1]

Step 3

4-(5-chloro-2-propionylphenyl)-5-methoxypyridin-2(1H)-one 8e

Compound 8d (600 mg, 1.96 mmol) was added to 10 mL of N,N-dimethylformamide, followed by addition of pyridine hydrobromide (1.51 g, 9.81 mmol). After completion of the addition, the reaction solution was heated to 100° C., and stirred for 3 hours. The reaction solution was cooled to room temperature, and concentrated under reduced pressure to remove the organic solvent. The resulting residue was added with 30 mL of water, and extracted with dichloromethane (20 mL 0.3). The organic phases were combined, dried over anhydrous sodium sulfate, and filtered. The filtrate was concentrated under reduced pressure to obtain the title compound 8e (550 mg), which was directly used in the next reaction step without purification.

Step 4 tert-butyl 2-(4-(5-chloro-2-propionylphenyl)-5-methoxy-2-oxopyridin-1(2H)-yl)acetate 8f The crude compound 8e (550 mg, 1.89 mmol), cesium carbonate (1.84 g, 5.67 mmol) and compound 7a (551.61 mg, 2.83 mmol) were dissolved in 10 mL of N,N-dimethylformamide. After completion of the addition, the reaction solution was warmed up to 65° C., and stirred for 2 hours. After cooling to room temperature, the reaction solution was added with 30 mL of water, and extracted with ethyl acetate (30 mL×3). The organic phases were combined, washed with saturated sodium chloride solution (30 mL×3), dried over anhydrous sodium sulfate, and filtered. The filtrate was concentrated under reduced pressure, and the resulting residue was purified by CombiFlash rapid preparation instrument with elution system B to obtain the title compound 8f (350 mg, yield: 51.0%).

MS m/z (ESI): 405.4 [M+1]

Step 5

Tert-Butyl 2-(4-(5-chloro-2-propionylphenyl)-5-methoxy-2-oxopyridin-1(2H)-yl)-3-phenylpropanoate 8h Compound 8f (122 mg, 302.37 μmol) was dissolved in 10 mL of tetrahydrofuran. The reaction solution was cooled to −78° C., added with 8g (103.43 mg, 604.74 μmol), followed by addition of a solution of lithium bis(trimethylsilyl)amide in tetrahydrofuran (1.21 mL, 1.21 mmol), and reacted for 2 hours. After warming up to room temperature, the reaction solution was added with 10 mL of water and extracted with ethyl acetate (20 mL×3). The organic phases were combined, washed with saturated sodium chloride solution (20 mL×2), dried over anhydrous sodium sulfate, and filtered. The filtrate was concentrated under reduced pressure, and the resulting residue was purified by silica gel column chromatography with elution system B to obtain the title compound 8h (75 mg, yield: 50.0%).

MS m/z (ESI): 496.2 [M+1]

Step 6

2-(4-(5-chloro-2-propionylphenyl)-5-methoxy-2-oxopyridin-1(2H)-yl)-3-phenylpropanoic acid 8i Compound 8h (75 mg, 0.15 mmol) was dissolved in 4 mL of dichloromethane, followed by dropwise addition of trifluoroacetic acid (0.5 mL). The reaction solution was stirred for 5 hours and concentrated under reduced pressure to obtain the crude title compound 8i (70 mg), which was directly used in the next reaction step without purification.

MS m/z (ESI): 439.9 [M+1]

Step 7

4-(2-(4-(5-chloro-2-propionylphenyl)-5-methoxy-2-oxopyridin-1(2H)-yl)-3-phenylpropanamido)benzoic acid 8

The crude compound 8i (70 mg, 159.13 mol) and 4-aminobenzoic acid 8j (32.73 mg, 237.70 μmol, prepared by a known method disclosed in "*Angewandte Chemie—International Edition*, 2012, 51(34), 8564-8567") was dissolved in 20 mL of ethyl acetate, followed by successive addition of triethylamine (64.41 mg, 636.53 μmol) and a solution of 2,4,6-tripropyl-1,3,5,2,4,6-trioxatriphosphorinane-2,4,6-trioxide in ethyl acetate (50%, 303.80 mg, 477.39 μmol). After completion of the addition, to the reaction solution was warmed up to 60° C., and stirred for 2 hours. After cooling to room temperature, the reaction solution was added with 15 mL of water, extracted with ethyl acetate (15 mL×2), washed with saturated sodium chloride (15 mL×2), dried over anhydrous sodium sulfate, and filtered. The filtrate was concentrated under reduced pressure, and the resulting residue was purified by silica gel column chromatography with elution system A to obtain the title compound 8 (30 mg, yield: 35.7%).

MS m/z (ESI): 559.4 [M+1]

$^1$H NMR (400 MHz, CDCl$_3$) δ 9.97 (s, 1H), 8.10 (d, 2H), 7.86 (d, 2H), 7.70 (d, 1H), 7.51-7.24 (m, 8H), 6.64 (s, 1H), 6.26 (s, 1H), 3.67-3.62 (m, 4H), 3.33-3.29 (m, 1H), 2.86 (s, 2H), 1.18-0.92 (m, 3H).

Examples 9, 10

(S)-4-(2-(4-(5-chloro-2-propionylphenyl)-5-methoxy-2-oxopyridin-1(2H)-yl)-3-phenylpropanamido)benzoic acid 9

(R)-4-(2-(4-(5-chloro-2-propionylphenyl)-5-methoxy-2-oxopyridin-1(2H)-yl)-3-phenylpropanamido)benzoic acid 10

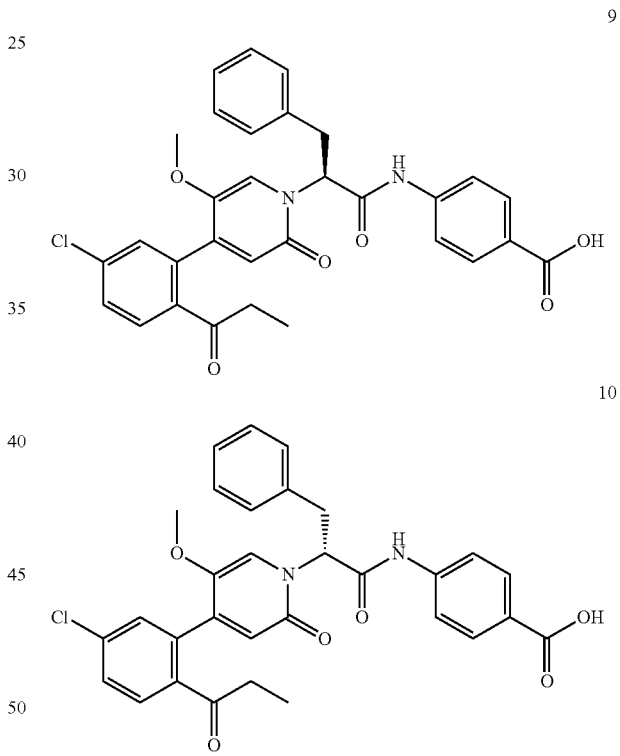

Compound 8 (1 g, 1.79 mmol) was separated chirally (separation conditions: chiral preparative column CHIRAL PAK IE 20*250 mm 5 μm; mobile phase: n-hexane:ethanol=55:45, flow rate: 7 mL/min). The corresponding fractions were collected and concentrated under reduced pressure to obtain the title compound 9 (300 mg) and compound 10 (400 mg).

Compound 9:

MS m/z (ESI): 559.5 [M+1]

Chiral HPLC analysis: retention time 11.267 minutes, (chromatographic column: CHIRAL PAK IE 4.6*150 mm 5 μm (with a guard column); mobile phase: ethanol/n-hexane=50/50(v/v)).

¹H NMR (400 MHz, CDCl₃) δ 9.88 (s, 1H), 8.10 (d, 2H), 7.85 (d, 2H), 7.69 (d, 1H), 7.48 (d, 1H), 7.40 (s, 7H), 6.62 (s, 1H), 6.22 (s, 1H), 3.65 (s, 3H), 3.60 (s, 1H), 3.31 (s, 1H), 2.85 (s, 2H), 1.15 (s, 3H).

Compound 10:

MS m/z (ESI): 559.5 [M+1]

Chiral HPLC analysis: retention time 4.836 minutes, (chromatographic column: CHIRAL PAK IE 4.6*150 mm 5 µm (with a guard column); mobile phase: ethanol/n-hexane=50/50(v/v)).

¹H NMR (400 MHz, CDCl₃) δ 9.88 (s, 1H), 8.10 (d, 2H), 7.85 (d, 2H), 7.69 (d, 1H), 7.48 (d, 1H), 7.40 (s, 7H), 6.62 (s, 1H), 6.22 (s, 1H), 3.65 (s, 3H), 3.60 (s, 1H), 3.31 (s, 1H), 2.85 (s, 2H), 1.15 (s, 3H).

Example 11

(S)-4-(2-(4-(2-acetyl-5-chlorophenyl)-5-methoxy-2-oxopyridin-1(2H)-yl)-3-phenylpropanamido)benzamide 11

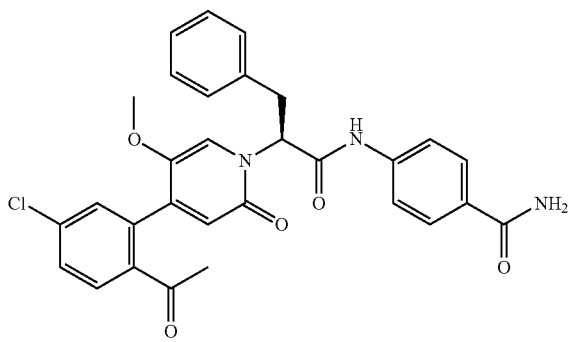

Compound 5 (54 mg, 99.09 mol) was dissolved in 5 mL of N,N-dimethylformamide, and then ammonium carbonate (64.03 mg, 495.43 µmol) and O-(7-azabenzotriazol-1-yl)-N,N,N',N'-tetramethyluronium hexafluorophosphate (112.96 mg, 297.26 µmol) were added. The reaction solution was stirred for 16 hours at room temperature, added with 20 mL of saturated sodium bicarbonate solution, and extracted with ethyl acetate (50 mL×2). The organic phases were combined, dried over anhydrous sodium sulfate, and filtered. The filtrate was concentrated under reduced pressure, and the resulting residue was purified by the elution system A to obtain the title compound 11 (40 mg, yield: 74.2%).

MS m/z (ESI): 544.2 [M+1]

¹H NMR (400 MHz, CD₃OD) δ 7.87-7.82 (m, 3H), 7.70-7.69 (m, 1H), 7.68-7.66 (m, 1H), 7.56-7.54 (dd, 1H), 7.36 (s, 1H), 7.32-7.31 (d, 1H), 7.29-7.25 (m, 4H), 7.24-7.19 (m, 1H), 6.41 (s, 1H), 5.89-5.85 (m, 1H), 3.65-3.60 (m, 1H), 3.59 (s, 3H), 3.50-3.45 (m, 1H), 2.46 (s, 3H).

Example 12

Methyl (S)-(4-(2-(4-(2-acetyl-5-chlorophenyl)-5-methoxy-2-oxopyridin-1(2H)-yl)-3-phenylpropanamido)phenyl)carbamate 12

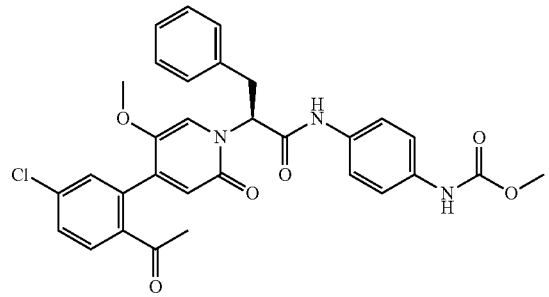

Compound 5 (100 mg, 183.83 µmol) was dissolved in 8 mL of toluene, followed by successive addition of triethylamine (65.1 mg, 643.39 µmol), diphenyl azidophosphate (60.71 mg, 220.59 µmol) and methanol (58.9 mg, 1.84 mmol). The reaction solution was warmed up to 100° C., and stirred for 2 hours. The reaction solution was cooled to room temperature, and concentrated under reduced pressure to remove the solvent. The resulting residue was added with 15 mL of saturated sodium bicarbonate solution, and extracted with ethyl acetate (50 mL×2). The organic phases were combined, dried over anhydrous sodium sulfate, and filtered. The filtrate was concentrated under reduced pressure, and the resulting residue was purified Silica gel column chromatography with elution system A to obtain the title compound 12 (75 mg, yield: 71.2%).

MS m/z (ESI): 574.2 [M+1]

¹H NMR (400 MHz, CDCl₃) δ 7.68-7.66 (d, 1H), 7.48-7.46 (d, 3H), 7.29-7.21 (m, 8H), 7.15-7.10 (m, 1H), 6.61-6.50 (m, 2H), 5.95-5.85 (m, 1H), 3.76 (s, 3H), 3.65-3.60 (m, 1H), 3.59 (s, 3H), 3.30-3.20 (m, 1H), 2.42 (s, 3H).

Example 13

(S)-4-(2-(4-(2-acetyl-5-chlorophenyl)-5-methoxy-2-oxopyridin-1(2H)-yl)-3-phenylpropanamido)-N-methylbenzamide 13

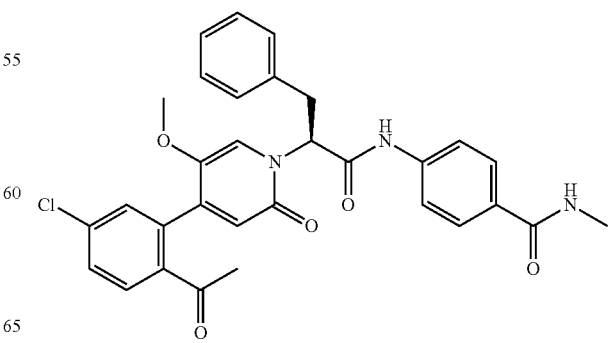

Compound 5 (70 mg, 128.44 μmol) was dissolved in 5 mL N,N-dimethylformamide, and then methylamine (11.97 mg, 385.33 μmol), N,N-diisopropylethylamine (66.4 mg, 513.78 μmol) and O-(7-azabenzotriazol-1-yl)-N,N,N',N'-tetramethyluronium hexafluorophosphate (97.62 mg, 256.89 μmol) was added successively. The reaction solution was stirred for 16 hours at room temperature, added with 50 mL of ethyl acetate, and washed with water (30 mL×2). The organic phases were combined, dried over anhydrous sodium sulfate, and filtered. The filtrate was concentrated under reduced pressure, and the resulting residue was purified by high performance liquid chromatography (Waters 2767-SQ detecor2, elution system: acetonitrile, water) to obtain the title compound 13 (45 mg, yield: 62.8%).

MS m/z (ESI): 558.1 [M+1]

$^1$H NMR (400 MHz, DMSO-$d_6$) δ 10.75 (s, 1H), 8.39-8.34 (m, 1H), 7.84-7.82 (m, 3H), 7.71 (d, 2H), 7.62 (dd, 1H), 7.44 (s, 1H), 7.38 (s, 1H), 7.31-7.26 (m, 4H), 7.22-7.18 (m, 1H), 6.31 (s, 1H), 6.04-6.01 (m, 1H), 3.54 (s, 3H), 3.49-3.39 (m, 2H), 2.77 (d, 3H), 2.38 (s, 3H).

Examples 14, 15

(R)-((ethoxycarbonyl)oxy)methyl 4-(2-(4-(2-acetyl-5-chlorophenyl)-5-methoxy-2-oxopyridin-1(2H)-yl)-3-phenylpropanamido)benzoate 14

(S)-((ethoxy carbonyl)oxy)methyl 4-(2-(4-(2-acetyl-5-chlorophenyl)-5-methoxy-2-oxopyridin-1(2H)-yl)-3-phenylpropanamido)benzoate 15

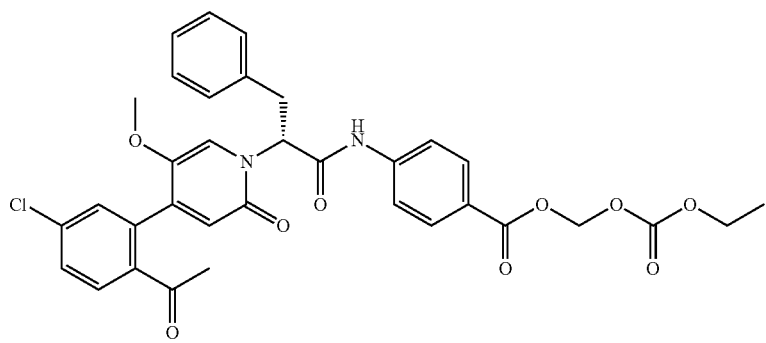

14

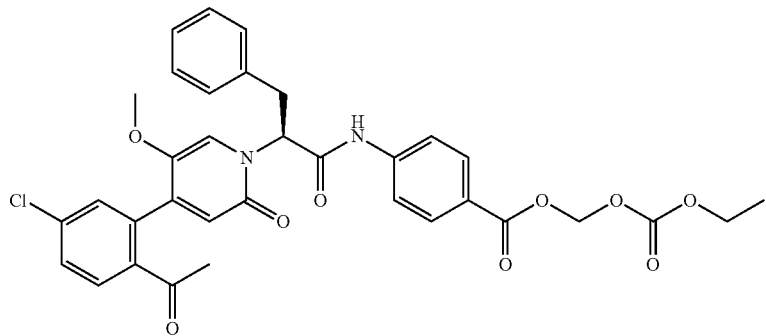

15

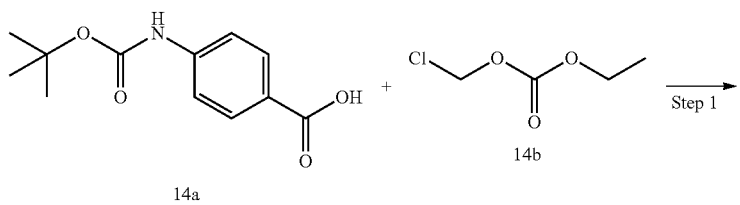

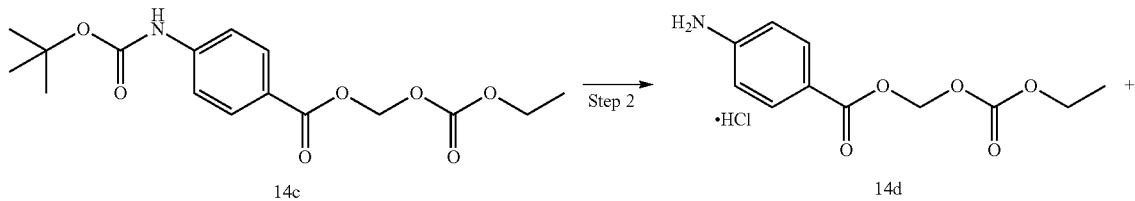

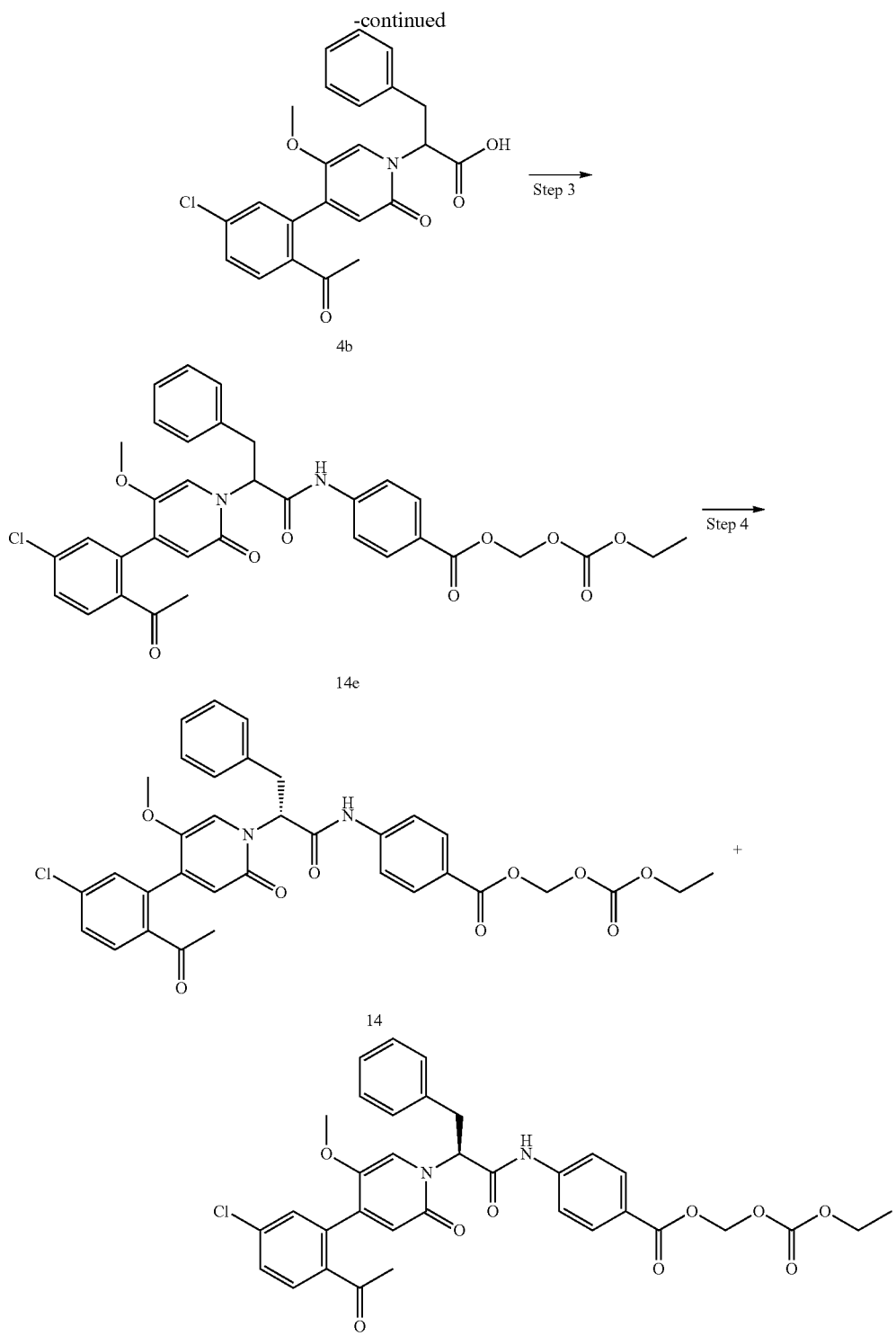

Step 1

((ethoxycarbonyl)oxy)methyl 4-((tert-butoxycarbonyl)amino)benzoate 14c 4-((tert-butoxycarbonyl)amino)benzoic acid 14a (4 g, 16.86 mmol, prepared by a known method disclosed in "*Journal of Medicinal Chemistry*, 2016, 59(22), 10299-10314"), potassium iodide (2.24 g, 13.49 mmol) and potassium carbonate (2.33 g, 16.86 mmol) were dissolved in 50 mL of N,N-dimethylformamide, followed by addition of chloromethyl ethyl carbonate 14b (3.5 g, 25.29 mmol, prepared by a known method disclosed in "*Tetrahedron Letters*, 2007, 48(1), 109-112") under argon atmosphere.

After completion of the addition, the reaction solution was warmed up to 50° C., stirred for 16 hours and cooled to room temperature. The reaction solution was added with 100 mL of ice water, and extracted with ethyl acetate (60 mL×3). The organic phases were combined, washed with 25 mL of saturated sodium chloride solution, dried over anhydrous sodium sulfate, and filtered. The filtrate was concentrated under reduced pressure, and the resulting residue was purified by silica gel column chromatography with elution system C to obtain the title compound 14c (5.3 g, yield: 88.0%).

MS m/z (ESI): 340.5 [M+1]

Step 2

((ethoxycarbonyl)oxy)methyl 4-aminobenzoate Hydrochloride 14d

A solution of hydrogen chloride in 1,4-dioxane (13.3 mL, 66.52 mmol) was added to 13 mL of tetrahydrofuran, followed by addition of compound 14c (2.7 g, 7.56 mmol). After completion of the addition, the reaction solution was warmed up to 50° C., stirred for 5 hours, cooled to room temperature, and concentrated under reduced pressure to remove the solvent. The resulting residue was added with 20 mL of a mixed solvent of ethyl acetate and hexane (V/V=1:9), stirred, and filtered. The filter cake was collected to obtain the crude title compound 14d (2 g), which was directly used in the next reaction step without purification.

MS m/z (ESI): 240.4 [M+1]

Step 3

((ethoxycarbonyl)oxy)methyl 4-(2-(4-(2-acetyl-5-chlorophenyl)-5-methoxy-2-oxopyridin-1(2H)-yl)-3-phenylpropanamido)benzoate 14e Compound 4b (250 mg, 0.59 mmol) was dissolved in 50 mL of ethyl acetate, followed by addition of N,N-diisopropylethylamine (303.48 mg, 2.35 mmol), the crude compound 14d (178.03 mg, 0.65 mmol) and a solution of 2,4,6-tripropyl-1,3,5,2,4,6-trioxatriphosphorinane-2,4,6-trioxide in ethyl acetate (50%, 747.14 mg, 1.17 mmol). After completion of the addition, the reaction solution was warmed up to 60° C., and stirred for 2 hours. After cooling to room temperature, the reaction solution was added with 25 mL of saturated sodium bicarbonate solution and extracted with ethyl acetate (50 mL×2). The organic phases were combined, dried over anhydrous sodium bicarbonate, and filtered. The filtrate was concentrated under reduced pressure, and the resulting residue was purified by the high performance liquid chromatography (Gilson-281, elution system: acetonitrile, water) to obtain the title compound 14e (230 mg, yield: 60.6%).

MS m/z (ESI): 647.5 [M+1]

Step 4

(R)-((ethoxycarbonyl)oxy)methyl 4-(2-(4-(2-acetyl-5-chlorophenyl)-5-methoxy-2-oxopyridin-1(2H)-yl)-3-phenylpropanamido)benzoate 14

(S)-((ethoxycarbonyl)oxy)methyl 4-(2-(4-(2-acetyl-5-chlorophenyl)-5-methoxy-2-oxopyridin-1(2H)-yl)-3-phenylpropanamido)benzoate 15

Compound 14e (230 mg, 0.36 mmol) was separated chirally (separation conditions: chromatographic column: Superchiral S-AD(Chiralway), 2 cm I.D.*25 cm Length, 5 μm; mobile phase: carbon dioxide:isopropanol=60:40, flow rate: 50 g/min). The corresponding fractions were collected and concentrated under reduced pressure to obtain the title compound 14 (84 mg) and compound 15 (76 mg).

Compound 14:

MS m/z (ESI): 647.5 [M+1]

Chiral HPLC analysis: retention time 5.297 minutes, (chromatographic column: CHIRAL PAK IE, 4.6*150 mm, 5 μm; flow rate: 1 mL/min; mobile phase: ethanol).

$^1$H NMR (400 MHz, CDCl$_3$) δ 9.70 (s, 1H), 8.03 (s, 1H), 8.01 (s, 1H), 7.70-7.69 (d, 1H), 7.64 (s, 1H), 7.62 (s, 1H), 7.48-7.46 (dd, 1H), 7.30-7.27 (m, 4H), 7.26-7.22 (m, 2H), 7.05-7.02 (m, 1H), 6.57 (s, 1H), 5.99 (s, 2H), 5.95-5.85 (m, 1H), 4.29-4.24 (m, 2H), 3.75-3.65 (m, 1H), 3.59 (s, 3H), 3.35-3.25 (m, 1H), 2.44 (s, 3H), 1.35-1.31 (m, 3H).

Compound 15:

MS m/z (ESI): 647.5 [M+1]

Chiral HPLC analysis: retention time 8.442 minutes, (chromatographic column: CHIRAL PAK IE, 4.6*150 mm, 5 μm; flow rate: 1 mL/min; mobile phase: ethanol).

$^1$H NMR (400 MHz, CDCl$_3$) δ 9.70 (s, 1H), 8.03 (s, 1H), 8.01 (s, 1H), 7.70-7.69 (d, 1H), 7.64 (s, 1H), 7.62 (s, 1H), 7.48-7.46 (dd, 1H), 7.30-7.27 (m, 4H), 7.26-7.22 (m, 2H), 7.05-7.02 (m, 1H), 6.57 (s, 1H), 5.99 (s, 2H), 5.95-5.85 (m, 1H), 4.29-4.24 (m, 2H), 3.75-3.65 (m, 1H), 3.59 (s, 3H), 3.35-3.25 (m, 1H), 2.44 (s, 3H), 1.35-1.31 (m, 3H).

Example 16

4-(2-(4-(2-acetyl-5-chlorophenyl)-5-methoxy-2-oxopyridin-1(2H)-yl)-3-(4-(cyclopropanecarboxamido)phenyl)propanamido)benzoic acid 16

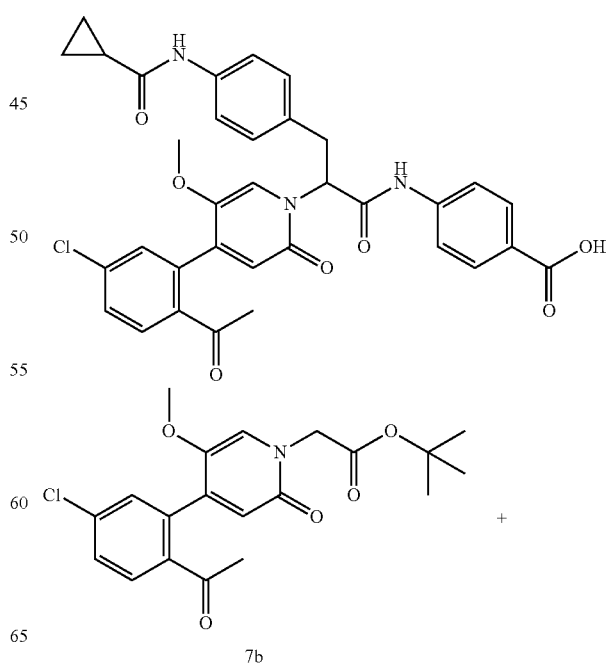

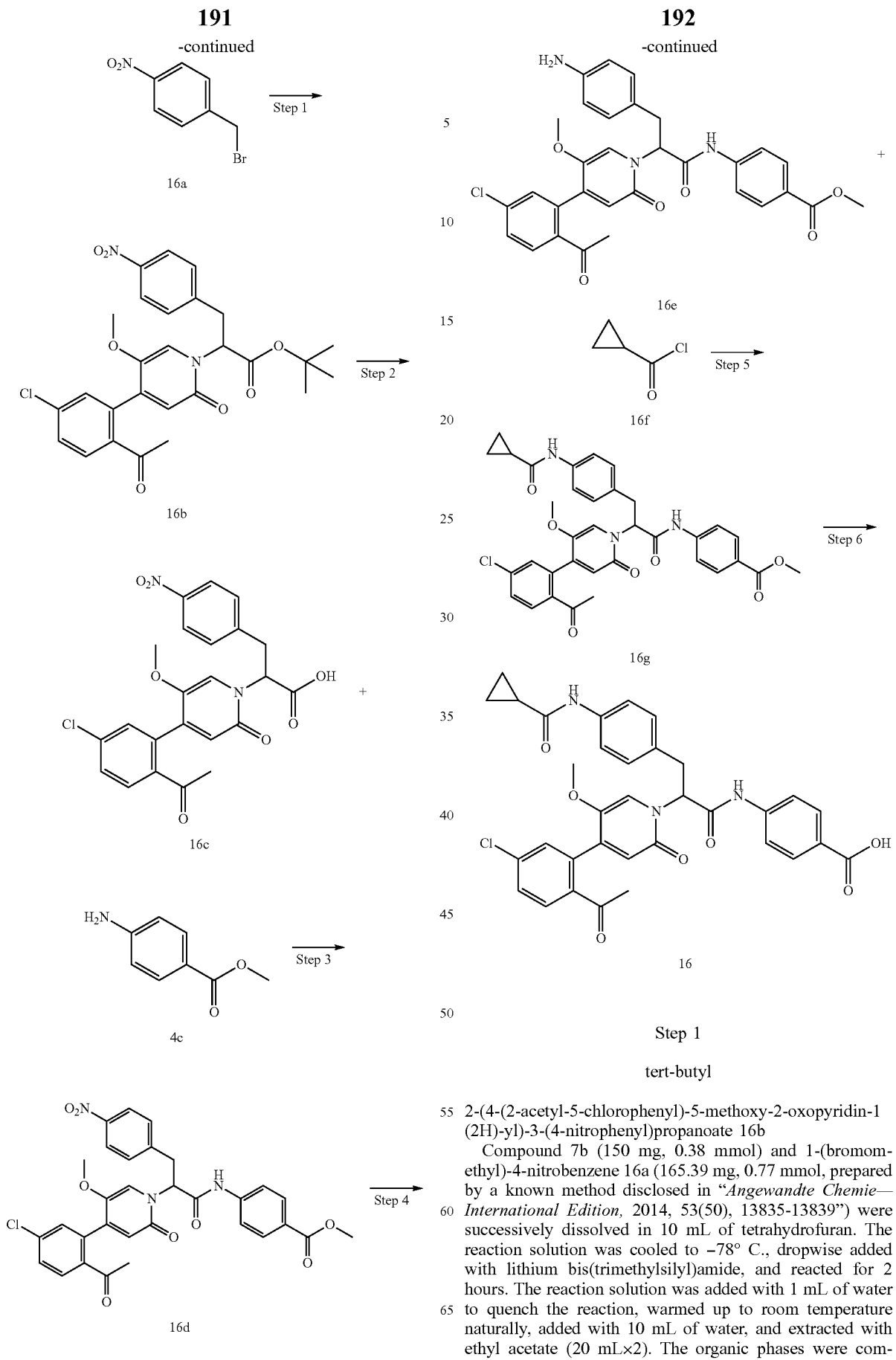

Step 1 tert-butyl 2-(4-(2-acetyl-5-chlorophenyl)-5-methoxy-2-oxopyridin-1 (2H)-yl)-3-(4-nitrophenyl)propanoate 16b Compound 7b (150 mg, 0.38 mmol) and 1-(bromomethyl)-4-nitrobenzene 16a (165.39 mg, 0.77 mmol, prepared by a known method disclosed in "*Angewandte Chemie— International Edition*, 2014, 53(50), 13835-13839") were successively dissolved in 10 mL of tetrahydrofuran. The reaction solution was cooled to −78° C., dropwise added with lithium bis(trimethylsilyl)amide, and reacted for 2 hours. The reaction solution was added with 1 mL of water to quench the reaction, warmed up to room temperature naturally, added with 10 mL of water, and extracted with ethyl acetate (20 mL×2). The organic phases were combined, washed with saturated sodium chloride solution (20 mL×2), dried over anhydrous sodium sulfate, and filtered. The filtrate was concentrated under reduced pressure, and the resulting residue was purified by silica gel column chromatography with elution system B to obtain the title compound 16b (180 mg, yield: 80.3%).

MS m/z (ESI): 527.4 [M+1]

Step 2

2-(4-(2-acetyl-5-chlorophenyl)-5-methoxy-2-oxopyridin-1(2H)-yl)-3-(4-nitrophenyl)propanoic acid 16c Compound 16b (180 mg, 0.34 mmol) was dissolved in 5 mL of dichloromethane, and then trifluoroacetic acid (0.5 mL) was dropwise added. The reaction solution was stirred for 5 hours, and then concentrated under reduced pressure to obtain the crude title compound 16c (166 mg), which was directly used in the next reaction step without purification.

MS m/z (ESI): 471.4 [M+1]

Step 3 methyl 4-(2-(4-(2-acetyl-5-chlorophenyl)-5-methoxy-2-oxopyridin-1(2H)-yl)-3-(4-nitrophenyl) propanamido)benzoate 16d The crude compound 16c (161 mg, 0.34 mmol) and compound 4c (67.19 mg, 0.44 mmol) were dissolved in 6 mL of ethyl acetate, followed by successive addition of 0.5 mL of pyridine and a solution of 2,4,6-tripropyl-1,3,5,2,4,6-trioxatriphosphorinane-2,4,6-trioxide in ethyl acetate (50%, 870.36 mg, 1.37 mmol). After completion of the addition, the reaction solution was warmed up to 70° C., and stirred for 1.5 hours. After cooling to room temperature, the reaction solution was added with 15 mL of water and extracted with ethyl acetate (15 mL×2). The organic phases were combined, washed with saturated sodium chloride (15 mL×2), dried over anhydrous sodium sulfate, and filtered. The filtrate was concentrated under reduced pressure, and the resulting residue was purified by silica gel column chromatography with elution system A to obtain the title compound 16d (130 mg, yield: 53.5%).

MS m/z (ESI): 604.4 [M+1]

Step 4 methyl 4-(2-(4-(2-acetyl-5-chlorophenyl)-5-methoxy-2-oxopyridin-1(2H)-yl)-3-(4-aminophenyl)propanamido)benzoate 16e The crude compound 16d (70 mg, 115.89 iµmol) was dissolved in 8 mL of tetrahydrofuran, and then platinum dioxide (5.26 mg, 23.18 iµmol) was added. The reaction system was purged with hydrogen twice. The reaction solution was stirred for 2.5 hours at room temperature, and then filtered. The filtrate was concentrated under reduced pressure to obtain the title compound 16e (66 mg), which was directly used in the next reaction step without purification.

Step 5 methyl 4-(2-(4-(2-acetyl-5-chlorophenyl)-5-methoxy-2-oxopyridin-1(2H)-yl)-3-(4-(cyclopropanecarboxamido)phenyl)propanamido)benzoate 16g The crude compound 16e (66 mg, 114.98 µmol) and triethylamine (290.87 mg, 2.87 mmol) were dissolved in 8 mL of tetrahydrofuran, and then cyclopropanoyl chloride (240.38 mg, 2.30 mmol) was added. The reaction solution was stirred for 16 hours, and then concentrated under reduced pressure. The resulting residue was added with 15 mL of water, and extracted with ethyl acetate (15 mL×2). The organic phases were combined, dried over anhydrous sodium sulfate, and filtered. The filtrate was concentrated under reduced pressure, and the resulting residue was purified by silica gel column chromatography with elution system A to obtain the title compound 16g (40 mg, yield: 54.2%).

MS m/z (ESI): 642.1 [M+1]

Step 6

4-(2-(4-(2-acetyl-5-chlorophenyl)-5-methoxy-2-oxopyridin-1(2H)-yl)-3-(4-(cyclopropanecarboxamido)phenyl)propanamido)benzoic acid 16

Compound 16g (40 mg, 62.3 µmol) was dissolved in 3 mL of methanol, and then sodium bicarbonate (12.46 mg, 311.48 µmol) was added. The reaction solution was warmed up to 50° C. and stirred for 5 hours. After cooling to room temperature, the reaction solution was added with 15 mL of water, followed by addition of 3M hydrochloric acid to adjust the pH to 5, and extracted with ethyl acetate (20 mL×2). The organic phases were combined, washed with saturated sodium chloride solution (20 mL×2), dried over anhydrous sodium sulfate, and filtered. The filtrate was concentrated under reduced pressure, and the resulting residue was purified by high performance liquid chromatography (Waters 2767-SQ detecor2, elution system: acetonitrile, water) to obtain the title compound 16 (16 mg, yield: 40.9%).

MS m/z (ESI): 628.5 [M+1]

$^1$H NMR (400 MHz, DMSO-d$_6$) δ 10.84 (s, 1H), 10.12 (s, 1H), 7.92 (d, 2H), 7.83 (d, 1H), 7.76 (d, 2H), 7.61 (dd, 1H), 7.48 (d, 2H), 7.41 (d, 2H), 7.18 (d, 2H), 6.30 (s, 1H), 6.00-5.96 (m, 1H), 3.55 (s, 3H), 3.42-3.36 (m, 2H), 2.39 (s, 3H), 1.76-1.70 (m, 1H), 0.76-0.74 (m, 4H).

Example 17

4-(2-(4-(2-acetyl-5-chlorophenyl)-5-methoxy-2-oxopyridin-1(2H)-yl)-3-(4'-cyano-2'-methyl-[1,1'-biphenyl]-4-yl)propanamido)benzoic acid 17

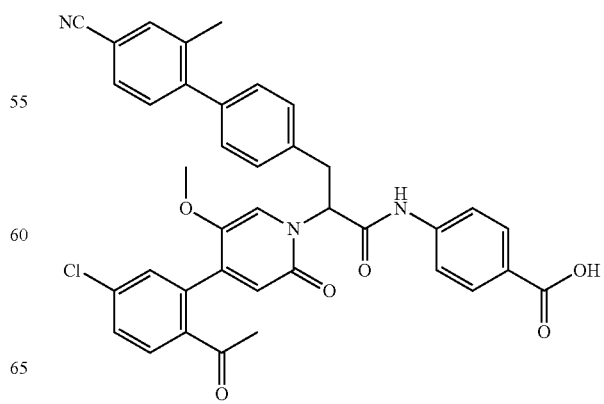

17

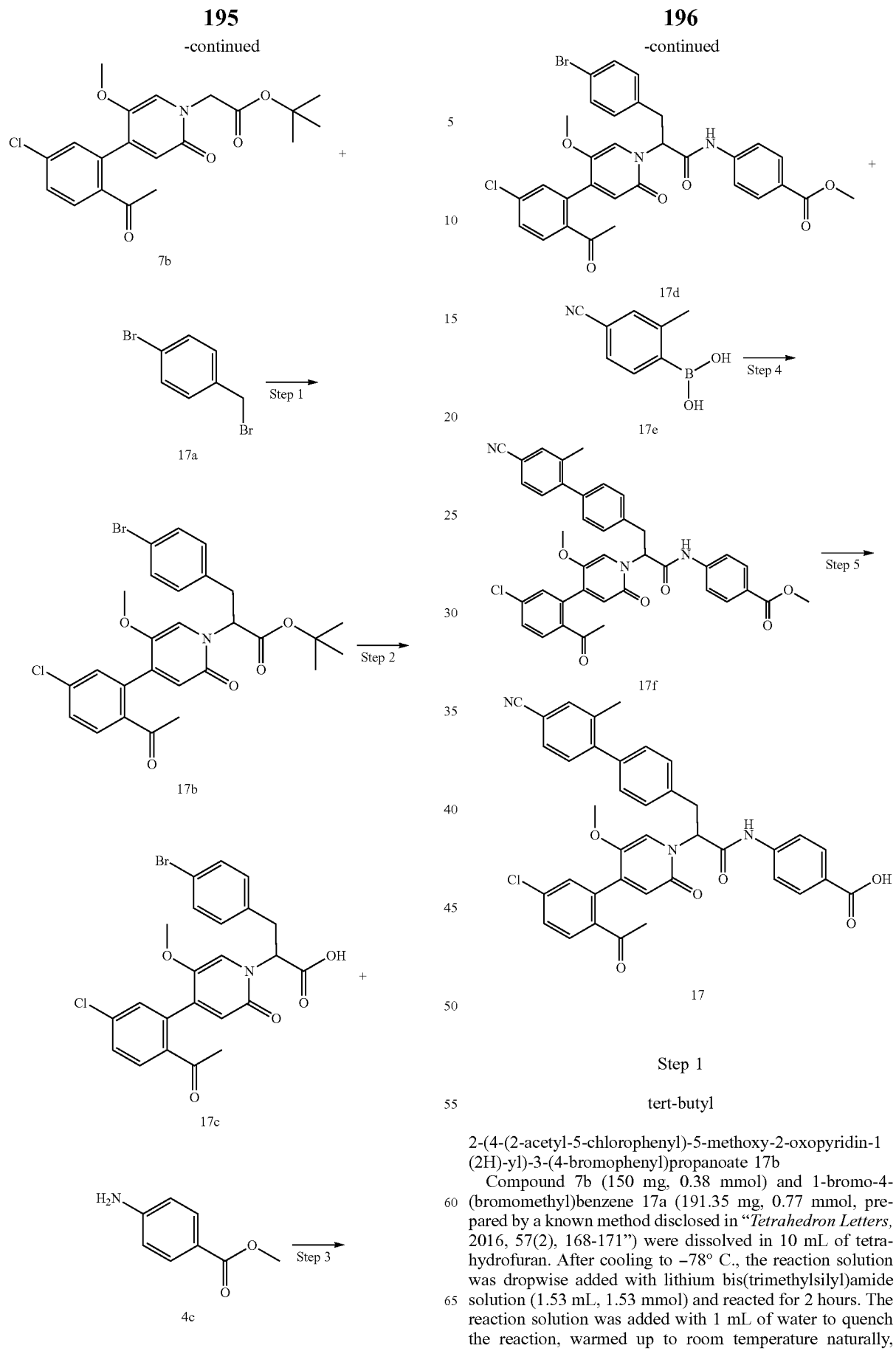

Step 1 tert-butyl 2-(4-(2-acetyl-5-chlorophenyl)-5-methoxy-2-oxopyridin-1(2H)-yl)-3-(4-bromophenyl)propanoate 17b Compound 7b (150 mg, 0.38 mmol) and 1-bromo-4-(bromomethyl)benzene 17a (191.35 mg, 0.77 mmol, prepared by a known method disclosed in "*Tetrahedron Letters,* 2016, 57(2), 168-171") were dissolved in 10 mL of tetrahydrofuran. After cooling to −78° C., the reaction solution was dropwise added with lithium bis(trimethylsilyl)amide solution (1.53 mL, 1.53 mmol) and reacted for 2 hours. The reaction solution was added with 1 mL of water to quench the reaction, warmed up to room temperature naturally, added with 10 mL of water, and extracted with ethyl acetate (20 mL×2). The organic phases were combined, washed with saturated sodium chloride solution (20 mL 2), dried over anhydrous sodium sulfate and filtered. The filtrate was concentrated under reduced pressure, and the resulting residue was purified by silica gel column chromatography with elution system B to obtain the title compound 17b (180 mg, yield: 79.6%).

MS m/z (ESI): 562.3 [M+1]

Step 2

2-(4-(2-acetyl-5-chlorophenyl)-5-methoxy-2-oxopyridin-1(2H)-yl)-3-(4-bromophenyl) propanoic acid 17c Compound 17b (180 mg, 0.30 mmol) was dissolved in 5 mL of dichloromethane, and then trifluoroacetic acid (0.5 mL) was added. The reaction solution was stirred for 5 hours, and then concentrated under reduced pressure to obtain the crude title compound 17c (160 mg), which was directly used in the next reaction step without purification.

MS m/z (ESI): 506.3 [M+1]

Step 3 methyl 4-(2-(4-(2-acetyl-5-chlorophenyl)-5-methoxy-2-oxopyridin-1(2H)-yl)-3-(4-bromophenyl)propanamido)benzoate 17d The crude compound 17c (154 mg, 0.31 mmol) and compound 4c (59.95 mg, 0.40 mmol) were dissolved in 6 mL of ethyl acetate, followed by successive addition of 0.5 mL of pyridine and a solution of 2,4,6-tripropyl-1,3,5,2,4,6-trioxatriphosphorinane-2,4,6-trioxide in ethyl acetate (50%, 776.60 mg, 1.22 mmol). After completion of the addition, the reaction solution was warmed up to 70° C., and stirred for 1.5 hours. The reaction solution was added with 15 mL of water and extracted with ethyl acetate (15 mL×2). The organic phases were combined, washed with saturated sodium chloride solution (15 mL×2), dried over anhydrous sodium sulfate and filtered. The filtrate was concentrated under reduced pressure, and the resulting residue was purified by silica gel column chromatography with elution system A to obtain the title compound 17d (180 mg, yield: 90.6%).

MS m/z (ESI): 639.3 [M+1]

Step 4 methyl 4-(2-(4-(2-acetyl-5-chlorophenyl)-5-methoxy-2-oxopyridin-1(2H)-yl)-3-(4'-cyano-2'-methyl-[1,1'-biphenyl]-4-yl) propanamido)benzoate 17f Compound 17d (180 mg, 0.28 mmol), (4-cyano-2-methylphenyl)boronic acid 17e (90.84 mg, 0.56 mmol, prepared by a known method disclosed in "Tetrahedron, 2011.67(52), 10082-10088"), [1,1'-bis(diphenylphosphino)ferrocene]dichloropalladium (II) (20.65 mg, 0.03 mmol) and sodium carbonate (89.73 mg, 0.85 mmol) were added to a mixed solvent of toluene (8 mL), ethanol (3 mL) and water (1 mL). After completion of the addition, the reaction solution was warmed up to 85° C., and stirred for 16 hours. After cooling to room temperature, the reaction solution was added with 15 mL of water, and extracted with ethyl acetate (20 mL×2). The organic phases were combined, washed with saturated sodium chloride solution (20 mL×2), dried over anhydrous sodium sulfate and filtered. The filtrate was concentrated under reduced pressure, and the resulting residue was purified by silica gel column chromatography with elution system A to obtain the title compound 17f (200 mg, yield: 31.5%).

MS m/z (ESI): 674.5 [M+1]

Step 5

4-(2-(4-(2-acetyl-5-chlorophenyl)-5-methoxy-2-oxopyridin-1(2H)-yl)-3-(4'-cyano-2'-methyl-[1,1'-biphenyl]-4-yl)propanamido)benzoic acid 17

Compound 17f (200 mg, 0.297 mmol) was dissolved in a mixed solvent of 2 mL of methanol and 2 mL of tetrahydrofuran, and then lithium hydroxide (29.9 mg, 0.71 mmol) was added. The reaction solution was stirred for 60 hours. The reaction solution was added with 15 mL of water, followed by dropwise addition of 3M hydrochloric acid to adjust the pH to 4-5, and extracted with ethyl acetate (20 mL×2). The organic phases were combined, washed with saturated sodium chloride solution (20 mL×2), dried over anhydrous sodium sulfate and filtered. The filtrate was concentrated under reduced pressure, and the resulting residue was purified by high performance liquid chromatography (Waters 2767-SQ detecor2, elution system: acetonitrile, water) to obtain the title compound 17 (10 mg, yield: 16.2%).

MS m/z (ESI): 660.5 [M+1]

$^1$H NMR (400 MHz, DMSO-d$_6$) δ 10.81 (s, 1H), 7.92 (d, 2H), 7.83 (d, 1H), 7.78-7.74 (m, 3H), 7.70 (dd, 1H), 7.61 (dd, 1H), 7.43-7.35 (m, 5H), 7.29 (d, 2H), 6.33 (s, 1H), 6.06-6.02 (m, 1H), 3.61-3.50 (m, 2H), 3.54 (s, 3H), 2.38 (s, 3H), 2.22 (s, 3H).

Example 18

2-(4-(2-acetyl-5-chlorophenyl)-5-methoxy-2-oxopyridin-1(2H)-yl)-N-(2-methyl-2H-indazol-5-yl)-3-phenylpropanamide 18

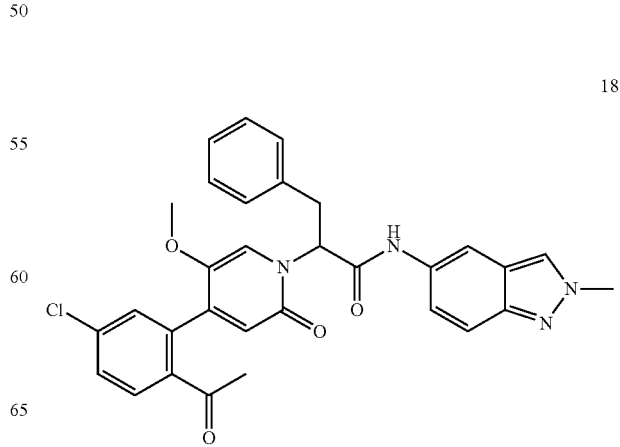

18

Examples 19, 20

(R)-2-(4-(2-acetyl-5-chlorophenyl)-5-methoxy-2-oxopyridin-1(2H)-yl)-N-(2-methyl-2H-indazol-5-yl)-3-phenylpropanamide 19

(S)-2-(4-(2-acetyl-5-chlorophenyl)-5-methoxy-2-oxopyridin-1(2H)-yl)-N-(2-methyl-2H-indazol-5-yl)-3-phenylpropanamide 20

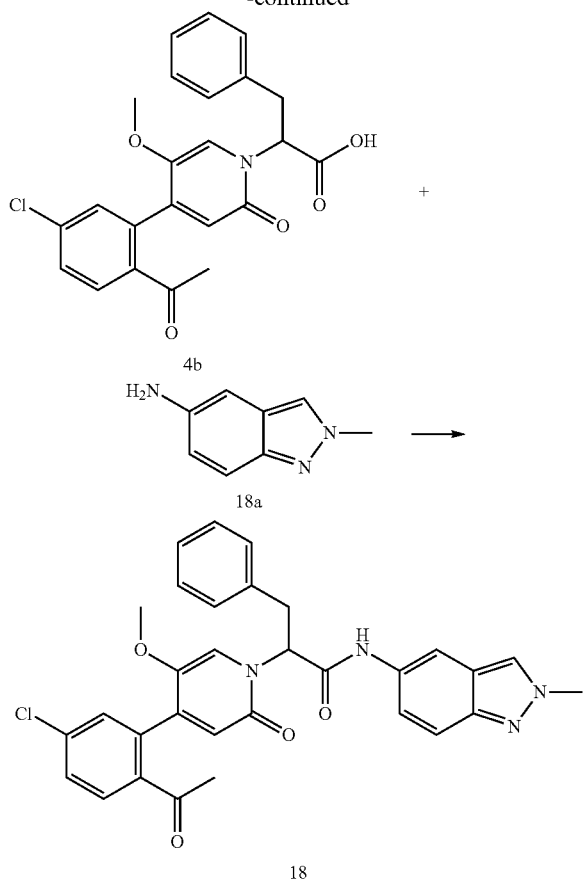
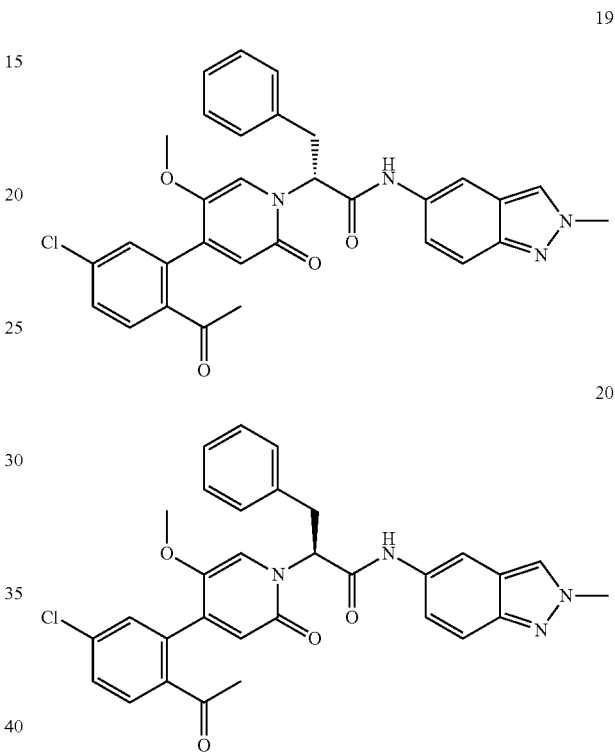

Compound 4b (90 mg, 211.34 µmol), 2-methyl-2H-indazol-5-amine 18a (34.21 mg, 232.47 mol, prepared by a known method disclosed in "*Journal of the American Chemical Society*, 2016, 138(14), 4730-4738") and N,N-diisopropylethylamine (273.14 mg, 2.11 mmol) were added to 15 mL of ethyl acetate, followed by addition of a solution of 2,4,6-tripropyl-1,3,5,2,4,6-trioxatriphosphorinane-2,4,6-trioxide in ethyl acetate (50%, 537.94 mg, 845.36 µmol). After completion of the addition, the reaction solution was warmed up to 75° C., and stirred for 2 hours. After cooling to room temperature, the reaction solution was added with 30 mL of water, followed by addition of 3M hydrochloric acid to adjust the pH to 5, and two phases were separated. The water phase was extracted with ethyl acetate (30 mL×2). The organic phases were combined, washed with saturated sodium chloride solution (35 mL×2), dried over anhydrous sodium sulfate, and filtered. The filtrate was concentrated under reduced pressure, and the resulting residue was purified by silica gel column chromatography with elution system A to obtain the title compound 18 (80 mg, yield: 68.2%).

MS m/z (ESI): 555.0 [M+1]

$^1$H NMR (400 MHz, DMSO-$d_6$) δ 10.49 (s, 1H), 8.27 (s, 1H), 8.16 (s, 1H), 7.83 (d, 1H), 7.61 (dd, 1H), 7.56 (d, 1H), 7.49 (s, 1H), 7.38 (s, 1H), 7.31-7.25 (m, 5H), 7.21-7.17 (m, 1H), 6.31 (s, 1H), 6.07-6.03 (m, 1H), 4.13 (s, 3H), 3.55 (s, 3H), 3.46 (d, 2H), 2.38 (s, 3H).

Compound 18 (75 mg, 135.13 µmol) was separated chirally (separation conditions: chiral preparative column Lux Cellulose-1 OD 21.2*250 mm 5 m; mobile phase: n-hexane:ethanol=60:40, flow rate: 8 mL/min). The corresponding fractions were collected and concentrated under reduced pressure to obtain the title compound 19 (28 mg) and compound 20 (27 mg).

Compound 19:

MS m/z (ESI): 555.5 [M+1]

Chiral HPLC analysis: retention time 5.816 minutes, chiral purity: 100% (chromatographic column: Lux Cellulose-1 OD 4.6*150 mm 5 µm (with a guard column): mobile phase: ethanol/hexane=30/70(v/v)).

$^1$H NMR (400 MHz, DMSO-$d_6$) δ 10.48 (s, 1H), 8.27 (s, 1H), 8.15 (s, 1H), 7.82 (d, 1H), 7.61 (d, 1H), 7.56 (d, 1H), 7.48 (s, 1H), 7.38 (s, 1H), 7.31-7.25 (m, 5H), 7.21-7.17 (m, 1H), 6.31 (s, 1H), 6.07-6.03 (m, 1H), 4.13 (s, 3H), 3.55 (s, 3H), 3.45 (d, 2H), 2.38 (s, 3H).

Compound 20:

MS m/z (ESI): 555.5 [M+1]

Chiral HPLC analysis: retention time 10.287 minutes, chiral purity: 100% (chromatographic column: Lux Cellulose-1 OD 4.6*150 mm 5 µm (with a guard column): mobile phase: ethanol/hexane=30/70(v/v)).

¹H NMR (400 MHz, DMSO-d₆) δ 10.48 (s, 1H), 8.27 (s, 1H), 8.15 (s, 1H), 7.83 (d, 1H), 7.61 (d, 1H), 7.56 (d, 1H), 7.48 (s, 1H), 7.38 (s, 1H), 7.31-7.25 (m, 5H), 7.21-7.17 (m, 1H), 6.31 (s, 1H), 6.07-6.03 (m, 1H), 4.13 (s, 3H), 3.55 (s, 3H), 3.45 (d, 2H), 2.38 (s, 3H).

Example 21

4-(2-(4-(2-butyryl-5-chlorophenyl)-5-methoxy-2-oxopyridin-1(2H)-yl)-3-phenylpropanamido)benzoic acid 21

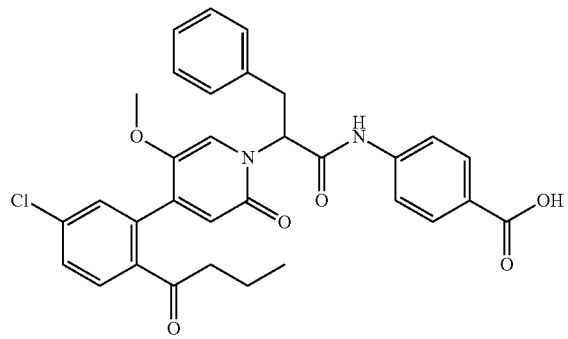

In accordance with the synthetic route of Example 8, the starting compound 8b was replaced with n-butyryl chloride, accordingly, the title compound 21 (95 mg) was prepared.
MS m/z (ESI): 573.2 [M+1]
¹H NMR (400 MHz, CDCl₃) δ 10.00 (s, 1H), 8.10-8.00 (d, 2H), 7.83-7.80 (d, 2H), 7.69-7.67 (d, 1H), 7.50-7.45 (dd, 1H), 7.34-7.25 (m, 7H), 6.65 (s, 1H), 6.29-6.19 (s, 3H), 3.64-3.58 (m, 4H), 3.30-3.22 (m, 1H), 2.80-2.70 (m, 2H), 1.70-1.60 (m, 2H), 0.94-0.89 (m, 3H).

Example 22

4-(2-(4-(2-acetyl-5-chlorophenyl)-5-methoxy-2-oxopyridin-1(2H)-yl)-3-phenylpropanamido)-2-fluorobenzamide 22

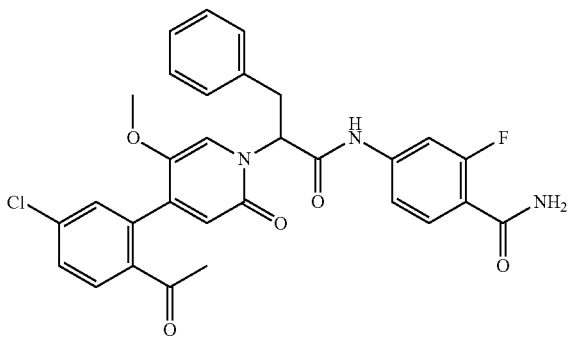

In accordance with the synthetic route of Example 18, the starting compound 18a was replaced with 4-amino-2-fluorobenzamide (prepared by a method disclosed in the patent application "WO 2013146963"), accordingly, the title compound 22 (30 mg) was prepared.
MS m/z (ESI): 562.5 [M+1]
¹H NMR (400 MHz; DMSO-d₆) δ 10.86 (s, 1H), 7.80 (d, 1H), 7.67-7.52 (m, 5H), 7.38-7.37 (m, 3H), 7.26-7.25 (m, 4H), 7.05-7.04 (m, 1H), 6.29 (s, 1H), 5.96-5.93 (m, 1H), 3.51 (s, 3H), 3.46-3.41 (m, 2H), 2.36 (s, 3H).

Example 23

2-(4-(5-chloro-2-propionylphenyl)-5-methoxy-2-oxopyridin-1(2H)-yl)-3-phenyl-N-(quinazolin-6-yl)propanamide 23

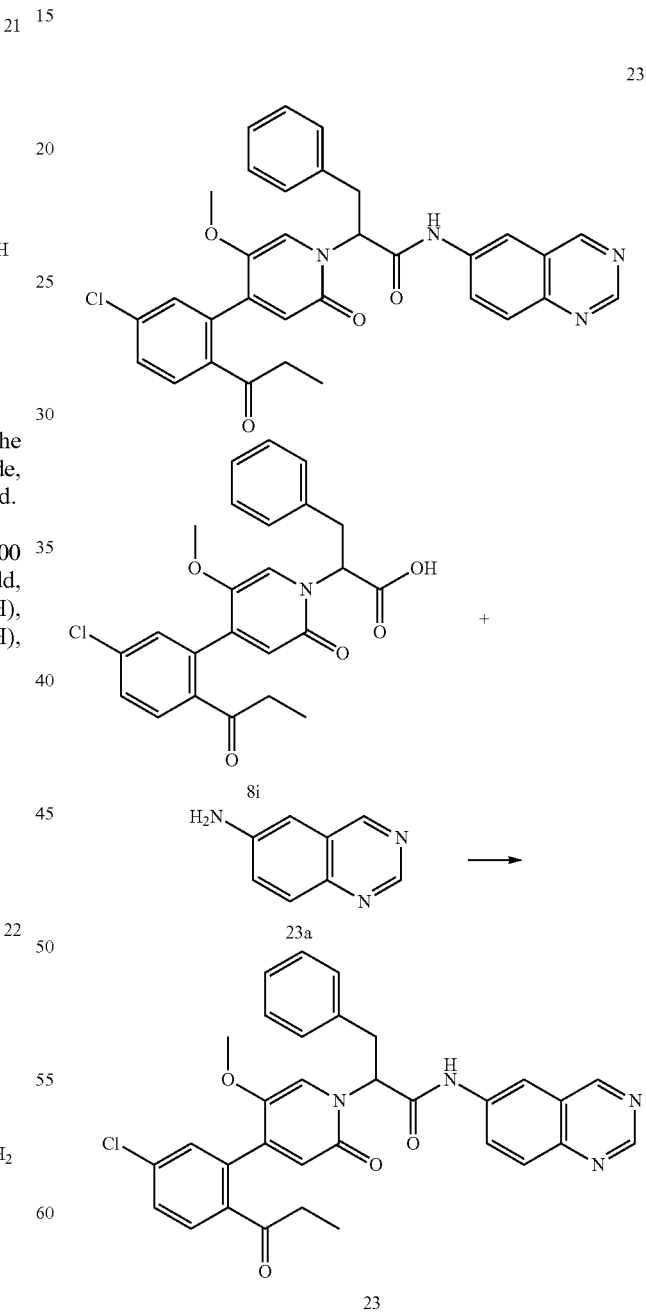

Compound 8i (90 mg, 204.6 μmol), quinazolin-6-amine 23a (32.67 mg, 225.06 μmol, prepared by a known method disclosed in "*Bioorganic & Medicinal Chemistry Letters*, 2015, 25(4), 803-806") and N,N-diisopropylethylamine (264.42 mg, 2.05 mmol) were added to 15 mL of ethyl acetate, followed by dropwise addition of a solution of 2,4,6-tripropyl-1,3,5,2,4,6-trioxatriphosphorinane-2,4,6-trioxide in ethyl acetate (50%, 537.94 mg, 845.36 μmol). After completion of the addition, the reaction solution was warmed up to 75° C., and stirred for 2 hours. After cooling to room temperature, the reaction solution was added with 30 mL of water, followed by addition of 3M hydrochloride to adjust the pH to 5, and two phases were separated. The water phase was extracted with ethyl acetate (30 mL×2). The organic phases were combined, and washed with the saturated sodium chloride solution (35 mL×2), dried over anhydrous sodium sulfate, and filtered. The filtrate was concentrated under reduced pressure, and the resulting residue was purified by silica gel column chromatography with elution system A to obtain the title compound 23 (50 mg, yield: 43.1%).

MS m/z (ESI): 567.5 [M+1]

$^1$H NMR (400 MHz, DMSO-d$_6$) δ 11.04 (s, 1H), 9.59 (s, 1H), 9.22 (s, 1H), 8.63 (s, 1H), 8.04 (q, 2H), 7.81 (d, 1H), 7.60 (d, 1H), 7.43 (s, 1H), 7.37 (s, 1H), 7.31-7.27 (m, 4H), 7.22-7.20 (m, 1H), 6.32 (s, 1H), 6.07-6.03 (m, 1H), 3.53 (s, 3H), 3.51-3.48 (m, 2H), 2.85-2.67 (m, 2H), 0.98 (t, 3H).

Example 24

4-(2-(4-(5-chloro-2-propionylphenyl)-5-methoxy-2-oxopyridin-1(2H)-yl)-3-phenylpropanamido)benzamide 24

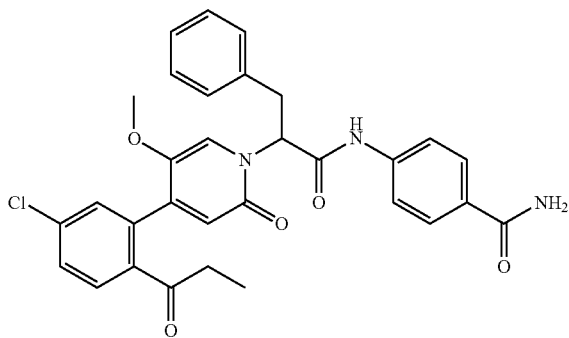

In accordance with the synthetic route of Example 23, the starting compound 23a was replaced with 4-aminobenzamide (prepared by a known method disclosed in "*Chemical Communications (Cambridge, United Kingdom)*, 2017, 53(35), 4807-4810"), accordingly, the title compound 24 (150 mg) was prepared.

MS m/z (ESI): 558.1 [M+1]

$^1$H NMR (400 MHz, CD$_3$OD) δ 7.89-7.86 (m, 2H), 7.82-7.81 (m, 1H), 7.77-7.70 (m, 2H), 7.58-7.55 (m, 1H), 7.34-7.29 (m, 7H), 7.25-7.23 (m, 1H), 6.43 (s, 1H), 5.92-5.89 (m, 1H), 3.63-3.58 (m, 1H), 3.57 (s, 3H), 3.47-3.41 (m, 2H), 1.12-1.09 (m, 3H).

Examples 25, 26

(R)-4-(2-(4-(5-chloro-2-propionylphenyl)-5-methoxy-2-oxopyridin-(2H)-yl)-3-phenylpropanamido)benzamide 25

(S)-4-(2-(4-(5-chloro-2-propionylphenyl)-5-methoxy-2-oxopyridin-(2H)-yl)-3-phenylpropanamido)benzamide 26

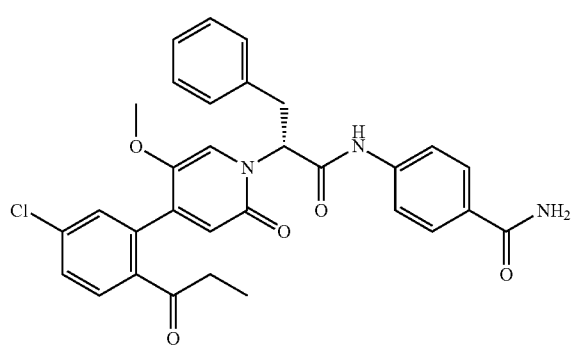

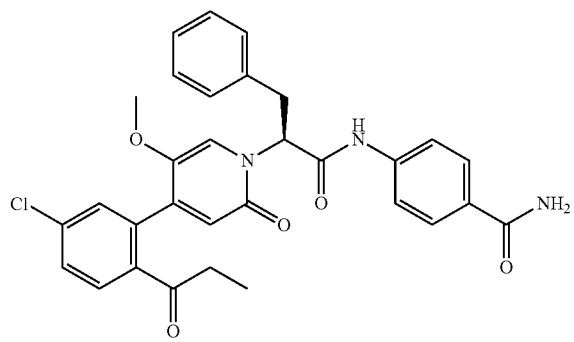

Compound 24 (150 mg, 268.81 μmol) was separated chirally (separation conditions: chiral preparative column CHIRALPAK IF 250*20 mm; mobile phase: A n-hexane:B ethanol=60:40, flow rate: 7.0 mL/min). The corresponding fractions were collected and concentrated under reduced pressure to obtain the title compound 25 (50 mg) and compound 26 (50 mg).

Compound 25:

MS m/z (ESI): 558.5 [M+1]

Chiral HPLC analysis: retention time 6.587 minutes, (chromatographic column: Lux Amylose-2 (AY) 4.6*150 mm 5 μm (with a guard column); mobile phase: ethanol/n-hexane=20/80 (v/v)).

$^1$H NMR (400 MHz, MeOH-d$_4$) δ 7.89-7.86 (m, 2H), 7.82-7.81 (m, 1H), 7.77-7.70 (m, 2H), 7.58-7.55 (m, 1H), 7.34-7.29 (m, 7H), 7.25-7.23 (m, 1H), 6.43 (s, 1H), 5.92-5.89 (m, 1H), 3.63-3.58 (m, 1H), 3.57 (s, 3H), 3.47-3.41 (m, 2H), 1.12-1.09 (m, 3H).

Compound 26:

MS m/z (ESI): 558.4 [M+1]

Chiral HPLC analysis: retention time 8.966 minutes, (chromatographic column: Lux Amylose-2 (AY) 4.6*150 mm 5 μm (with a guard column); mobile phase: ethanol/n-hexane=20/80 (v/v)).

$^1$H NMR (400 MHz, CD$_3$OD) δ 7.89-7.86 (m, 2H), 7.82-7.81 (m, 1H), 7.77-7.70 (m, 2H), 7.58-7.55 (m, 1H), 7.34-7.29 (m, 7H), 7.25-7.23 (m, 1H), 6.43 (s, 1H), 5.92-5.89 (m, 1H), 3.63-3.58 (m, 1H), 3.57 (s, 3H), 3.47-3.41 (m, 2H), 1.12-1.09 (m, 3H).

Example 27

2-(4-(5-chloro-2-propionylphenyl)-5-methoxy-2-oxopyridin-1(2H)-yl)-N-(1H-indazol-6-yl)-3-phenylpropanamide 27

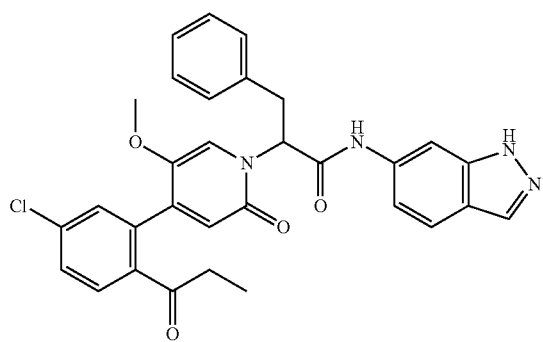

In accordance with the synthetic route of Example 23, the starting compound 23a was replaced with 6-aminoindazole (prepared by a known method disclosed in "*Tetrahedron Letters*, 2010, 51(5), 786-789"), accordingly, the title compound 27 (45 mg) was prepared.

MS m/z (ESI): 555.5 [M+1]

$^1$H NMR (400 MHz. DMSO-d$_6$) δ 12.95 (s, 1H), 10.68 (s, 1H), 8.14 (s, 1H), 7.99 (s, 1H), 7.80 (d, 1H), 7.70 (d, 1H) 7.60 (d, 1H), 7.45 (s, 1H), 7.38 (s, 1H), 7.30-7.26 (m, 4H), 7.21-7.16 (m, 2H), 6.30 (s, 1H), 6.07-6.03 (m, 1H), 3.53 (s, 3H), 3.50-3.47 (m, 2H), 2.85-2.67 (m, 2H), 0.97 (t, 3H).

Example 28

2-(4-(2-acetyl-5-chlorophenyl)-5-methoxy-2-oxopyridin-(2H)-yl)-N-(3-cyano-1H-indole-6-yl)-3-phenylpropanamide 28

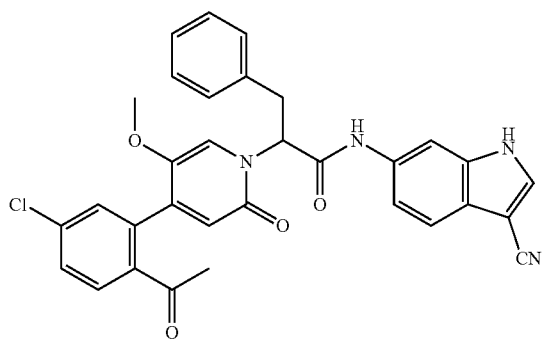

In accordance with the synthetic route of Example 18, the starting compound 18a was replaced with 6-amino-1H-indole-3-carbonitrile (prepared by a method disclosed in the patent application "US 20160271105"), accordingly, the title compound 28 (30 mg) was prepared.

MS m/z (ESI): 565.0 [M+1]

$^1$H NMR (400 MHz, CD$_3$OD) δ 8.03 (s, 1H), 7.91 (s, 1H), 7.82 (d, 1H), 7.55 (t, 2H), 7.41 (s, 1H), 7.31-7.15 (m, 7H), 6.42 (s, 1H), 5.96-5.93 (m, 1H), 3.58 (s, 3H), 3.43-3.38 (m, 2H), 2.44 (s, 3H).

Example 29

4-(2-(4-(2-acetyl-5-chlorophenyl)-5-methoxy-2-oxopyridin-1(2H)-yl)-3-phenylpropanamido)-3-fluorobenzoic acid 29

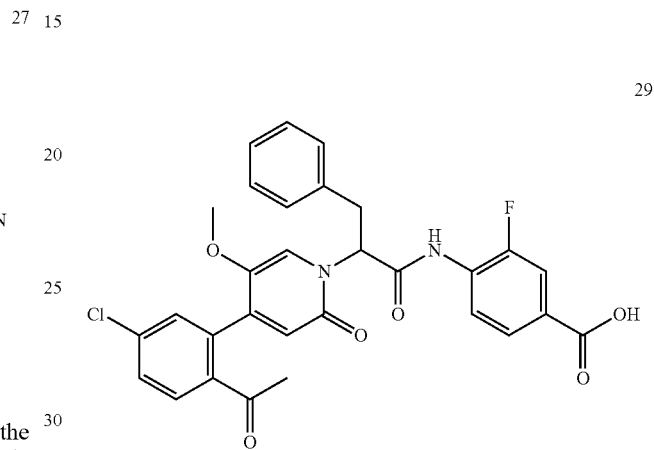

In accordance with the synthetic route of Example 4, the starting compound 4c used in Step 2 was replaced with methyl 4-amino-3-fluorobenzoate (prepared by a method disclosed in the patent application "WO 2012087519"), accordingly, the title compound 29 (20 mg) was prepared.

MS m/z (ESI): 563.4 [M+1]

$^1$H NMR (400 MHz, DMSO-d$_6$) δ 10.65 (s, 1H), 8.15-8.11 (m, 1H), 7.85-7.80 (d, 1H), 7.79-7.72 (m, 2H), 7.61-7.59 (dd, 1H), 7.38-7.37 (d, 2H), 7.34-7.32 (d, 2H), 7.29-7.25 (m, 2H), 7.20-7.17 (m, 1H), 6.31 (s, 1H), 6.23-6.19 (m, 1H), 3.57-3.45 (m, 5H), 2.36 (s, 3H).

Example 30

4-(2-(4-(6-acetyl-3-chloro-2-fluorophenyl)-5-methoxy-2-oxopyridin-1(2H)-yl)-3-phenylpropanamido)benzoic acid 30

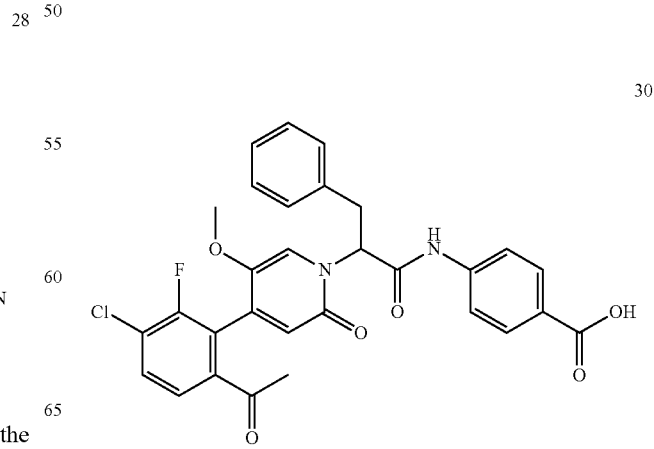

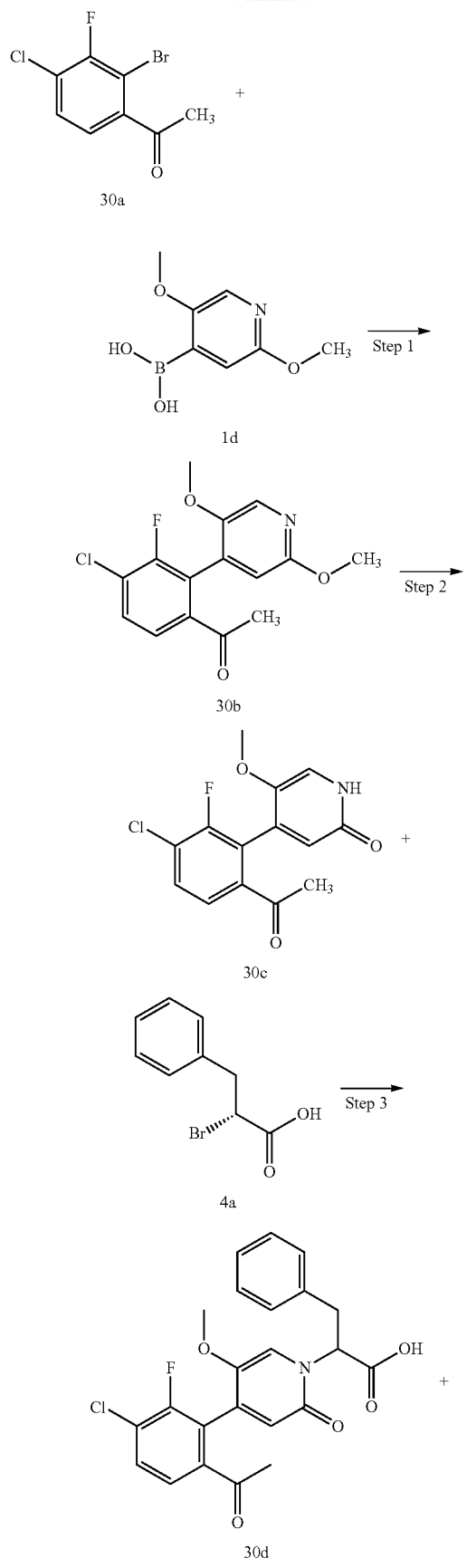

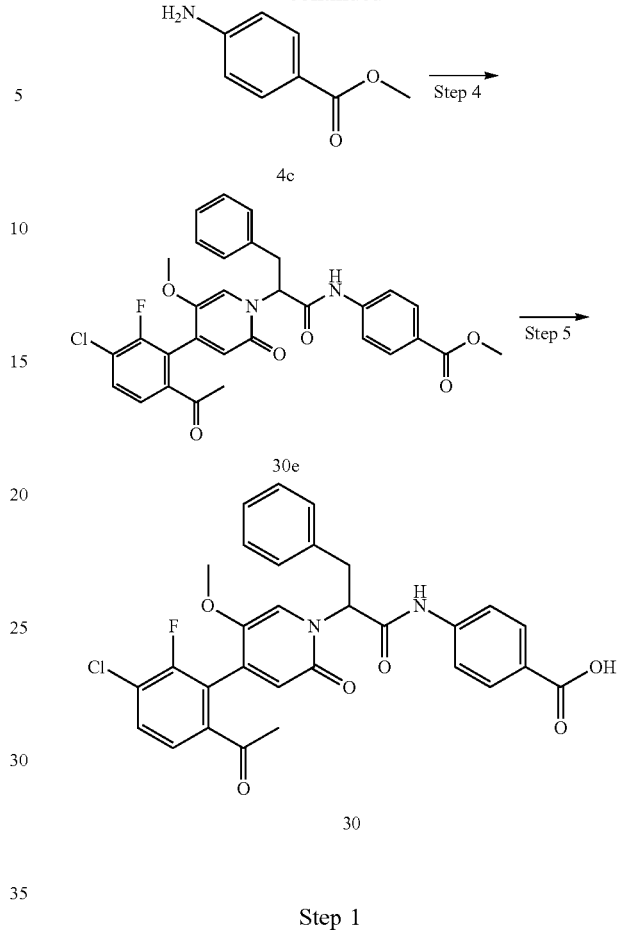

Step 1

1-(4-chloro-2-(2,5-dimethoxypyridin-4-yl)-3-fluorophenyl)ethanone 30b 1-(2-Bromo-4-chloro-3-fluorophenyl)ethanone 30a (630 mg, 2.51 mmol, prepared by a method disclosed in the patent application "WO2013056034"), compound 1d (550.05 mg, 3.01 mmol), tetrakis(triphenylphosphine)palladium (868.46 mg, 0.75 mmol) and sodium carbonate (796.57 mg, 7.52 mmol) were added to a mixed solvent of 3 mL of 1,4-dioxane and 1 mL of water. After completion of the addition, the reaction solution was heated to 95° C. and stirred for 16 hours. After cooling to room temperature naturally, the reaction solution was added with 50 mL of water and extracted with ethyl acetate (50 mL×2). The organic phases were combined, washed with saturated sodium chloride solution (50 mL), dried over anhydrous sodium sulfate and filtered. The filtrate was concentrated under reduced pressure, and the resulting residue was purified by silica gel column chromatography with elution system B to obtain the title compound 30b (650 mg, yield: 83.7%).

MS m/z (ESI): 310.3 [M+1]

Step 2

4-(6-acetyl-3-chloro-2-fluorophenyl)-5-methoxypyridin-2(1H)-one 30c

Compound 30b (650 mg, 2.1 mmol) was dissolved in 20 mL of 1,4-dioxane, followed by addition of concentrated hydrochloric acid (20 mL, 240 mmol). After completion of the addition, the reaction solution was heated to 110° C., and stirred for 16 hours. After cooling to room temperature, the reaction solution was concentrated under reduced pressure to remove the organic solvent. The resulting residue was added with 20 mL of water, neutralized with saturated sodium bicarbonate solution, and extracted with ethyl acetate (30 mL×3). The organic phases were combined, washed with saturated sodium chloride solution (50 mL), dried over anhydrous sodium sulfate, and filtered. The filtrate was concentrated under reduced pressure, and the resulting residue was purified by silica gel column chromatography with elution system A to obtain the title compound 30c (418 mg, yield: 67.4%).

MS m/z (ESI): 296.1 [M+1]

Step 3

2-(4-(6-acetyl-3-chloro-2-fluorophenyl)-5-methoxy-2-oxopyridin-(2H)-yl)-3-phenylpropanoic acid 30d Compound 30c (243 mg, 0.82 mmol) was dissolved in 50 mL of tetrahydrofuran, and then compound 4a (282.38 mg, 1.23 mmol), potassium tert-butoxide (404.07 mg, 3.6 mmol) and magnesium tert-butoxide (280.29 mg, 1.64 mmol) were added. The reaction solution was heated to 65° C. and stirred for 16 hours. After cooling to room temperature, the reaction solution was added with 1M hydrochloric acid to adjust the pH to 3, and extracted with ethyl acetate (150 mL×2). The organic phases were combined, dried over anhydrous sodium sulfate, and filtered. The filtrate was concentrated under reduced pressure, and the resulting residue was purified by silica gel column chromatography with elution system A to obtain the title compound 30d (200 mg, yield: 54.8%).

MS m/z (ESI): 444.4 [M+1]

Step 4 methyl 4-(2-(4-(6-acetyl-3-chloro-2-fluorophenyl)-5-methoxy-2-oxopyridin-(2H)-yl)-3-phenyl propanamido)benzoate 30e Compound 30d (200 mg, 0.45 mmol), compound 4c (68.11 mg, 0.45 mmol) and N,N-diisopropylethylamine (58.24 mg, 0.45 mmol) were dissolved in 5 mL of ethyl acetate, under ice bath, followed by dropwise addition of a solution of 2,4,6-tripropyl-1,3,5,2,4,6-trioxatriphosphorinane-2,4,6-trioxide in ethyl acetate (50%, 286.74 mg, 0.45 mmol) in an ice bath. After completion of the addition, the reaction solution was warmed up to 65° C., and stirred for 1 hour. After cooling to room temperature, the reaction solution was added with saturated sodium bicarbonate solution to quench the reaction, and extracted with ethyl acetate (150 mL×2). The organic phases were combined, dried over anhydrous sodium sulfate and filtered. The filtrate was concentrated under reduced pressure, and the resulting residue was purified by silica gel column chromatography with elution system A to obtain the title compound 30e (120 mg, yield: 46.2%).

MS m-z (ESI): 575.4 [M−1]

Step 5

4-(2-(4-(6-Acetyl-3-Chloro-2-Fluorophenyl)-5-Methoxy-2-Oxopyridin-1(2H)-yl)-3-phenylpropanamido)benzoic acid 30

Compound 30e (120 mg, 0.21 mmol) was dissolved in 8 mL of 1,2-dichloroethane, and then trimethyltin hydroxide (564.08 mg, 3.12 mmol) was added. The reaction solution was warmed up to 90° C., and stirred for 48 hours. After cooling to room temperature naturally, the reaction solution was filtered. The filtrate was concentrated under reduced pressure, and the resulting residue was purified by high pressure liquid chromatography (Waters 2767-SQ detecor2, elution system: acetonitrile, water) to obtain the title compound 30 (40 mg, yield: 32.8%).

MS m/z (ESI): 563.2 [M+1]

$^1$H NMR (400 MHz, CD$_3$OD) δ 8.00 (d, 2H), 7.75-7.67 (m, 4H), 7.45 (d, 1H), 7.31-7.29 (m, 4H), 7.26-7.22 (m, 1H), 6.40 (s, 1H), 5.97-5.91 (m, 1H), 3.63 (d, 3H), 3.61-3.40 (m, 2H), 2.45 (d, 3H).

Examples 31,32

(S)-4-(2-(4-(6-acetyl-3-chloro-2-fluorophenyl)-5-methoxy-2-oxopyridin-1(2H)-yl)-3-phenylpropanamido)benzoic acid 31

(R)-4-(2-(4-(6-acetyl-3-chloro-2-fluorophenyl)-5-methoxy-2-oxopyridin-1(2H)-yl)-3-phenylpropanamido)benzoic acid 32

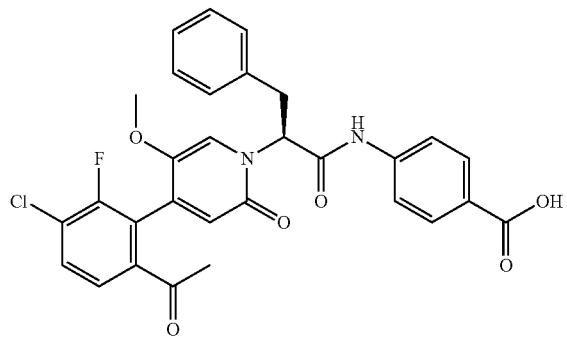

31

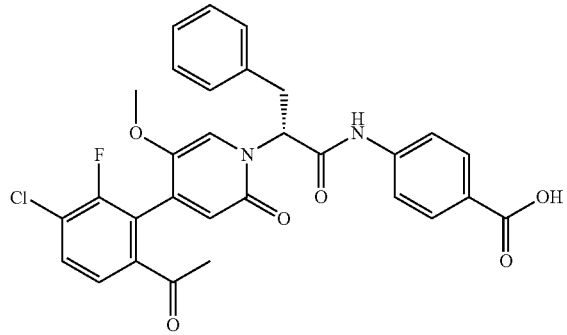

32

Compound 30 (35 mg, 0.06 mmol) was separated chirally (separation conditions: chiral preparative column CHIRALPAK ID, 5.0 cm I.D.*25 cm L, mobile phase: ethanol/dichloromethane/acetic acid=90/10/0.1(V/V/V), flow rate: 60 mL/min). The corresponding fractions were collected and concentrated under reduced pressure to obtain the title compound 31 (11 mg) and compound 32 (11 mg).

Compound 31:

MS m/z (ESI): 563.2 [M+1]

Chiral HPLC analysis: retention time 8.000 minutes, chiral purity: 98% (chromatographic column: CHIRAL PAK IE 4.6*150 mm 5 μm (with a guard column), mobile phase: ethanol (with 0.1% trifluoroacetic acid)/n-hexane=50/50(V/V/V), flow rate: 1.0 mL/min).

$^1$H NMR (400 MHz, CD$_3$OD) δ 8.00 (d, 2H), 7.75-7.67 (m, 4H), 7.45 (d, 1H), 7.31-7.29 (m, 4H), 7.26-7.22 (m, 1H), 6.40 (s, 1H), 5.97-5.91 (m, 1H), 3.63 (d, 3H), 3.61-3.40 (m, 2H), 2.45 (d, 3H).

Compound 32:

MS m/z (ESI): 563.2 [M+1]

Chiral HPLC analysis: retention time 3.777 minutes, chiral purity: 100% (chromatographic column: CHIRAL PAK IE 4.6*150 mm 5 μm (with a guard column), mobile phase: ethanol (with 0.1% trifluoroacetic acid)/n-hexane=50/50(V/V), flow rate: 1.0 mL/min)

$^1$H NMR (400 MHz, CD$_3$OD) δ 8.00 (d, 2H), 7.75-7.67 (m, 4H), 7.45 (d, 1H), 7.31-7.29 (m, 4H), 7.26-7.22 (m, 1H), 6.40 (s, 1H), 5.97-5.91 (m, 1H), 3.63 (d, 3H), 3.61-3.40 (m, 2H), 2.45 (d, 3H).

Example 33

2-(4-(2-acetyl-5-chlorophenyl)-5-methoxy-2-oxopyridin-1(2H)-yl)-N-(1H-imidazo[4,5-b]pyridin-5-yl)-3-phenylpropanamide

33

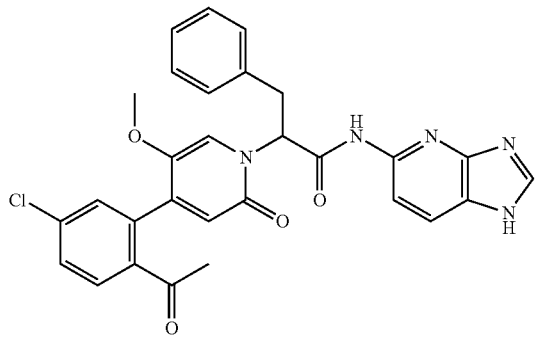

In accordance with the synthetic route of Example 18, the starting compound 18a was replaced with 1H-imidazo [4,5-b]pyridine-5-amine, accordingly, the title compound 33 (40 mg) was prepared.

MS m/z (ESI): 542.5 [M+1]

$^1$H NMR (400 MHz, CDCl$_3$) δ 10.55 (s, 1H), 8.18 (s, 1H), 8.08 (s, 2H), 7.71 (d, 1H), 7.52-7.50 (dd, 1H), 7.34 (d, 1H), 7.12 (m, 5H), 6.65 (s, 1H), 6.26 (s, 1H), 3.69 (s, 3H), 3.68-3.64 (m, 1H), 3.34-3.29 (m, 1H), 2.49 (s, 3H).

Example 34 methyl (S)-4-(2-(4-(2-acetyl-5-chlorophenyl)-5-methoxy-2-oxopyridin-1(2H)-yl)-3-phenylpropanamido)benzoate 34

34

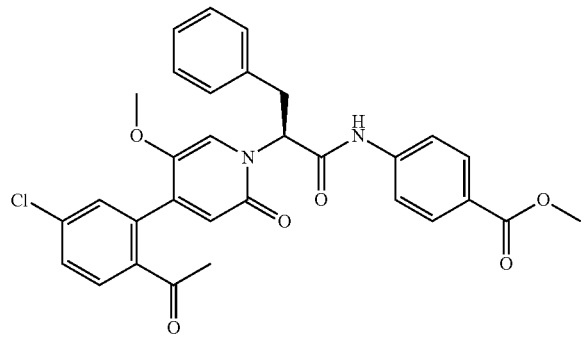

Compound 5 (60 mg, 110.10 mol) was dissolved in 5 mL of dichloromethane, and then methanol (35.27 mg, 1.1 mmol), 4-dimethylaminopyridine (20.34 mg, 165.14 μmol) and 1-(3-Dimethylaminopropyl)-3-ethylcarbodiimide hydrochloride (31.54 mg, 165.14 μmol) were added. After stirring for 16 hours, the reaction solution was added with 20 mL of saturated sodium bicarbonate solution, and extracted with dichloromethane (50 mL×2). The organic phases were combined, dried over anhydrous sodium sulfate, and filtered. The filtrate was concentrated under reduced pressure, and the resulting residue was purified by silica gel column chromatography with elution system B to obtain the title compound 34 (35 mg, yield: 56.9%).

MS m/z (ESI): 559.2 [M+1]

$^1$H NMR (400 MHz, DMSO-d$_6$) δ 10.88 (s, 1H), 7.97-7.96 (m, 1H), 7.95-7.94 (m, 1H), 7.83-7.81 (d, 1H), 7.80-7.79 (m, 1H), 7.78-7.77 (m, 1H), 7.62-7.59 (m, 1H), 7.43 (s, 1H), 7.38 (s, 1H), 7.30-7.25 (m, 4H), 7.21-7.17 (m, 1H), 6.31 (s, 1H), 6.05-6.01 (m, 1H), 3.83 (s, 3H), 3.53 (s, 3H), 3.52-3.42 (m, 2H), 2.37 (s, 3H).

Example 35

4-(2-(4-(5-chloro-2-(2,2,2-trifluoroacetyl)phenyl)-5-methoxy-2-oxopyridin-1(2H)-yl)-3-phenylpropanamido)benzoic acid 35

35

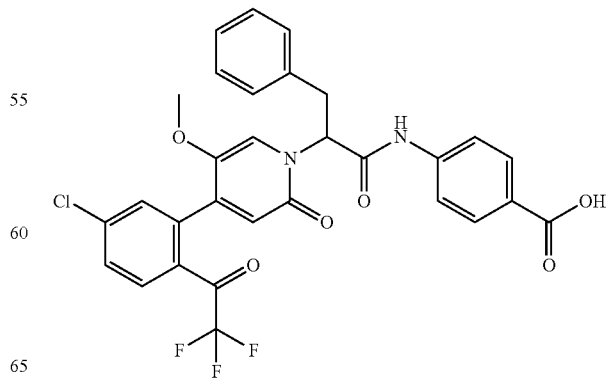

In accordance with the synthetic route of Example 8, the starting compound 8c was replaced with 1-(2-bromo-4-chlorophenyl)-2,2,2-trifluoroethanone (prepared by a method disclosed in the patent application "WO2011100285"), accordingly, the title compound 35 (10 mg) was prepared.

MS m/z (ESI): 599.4 [M+1]

$^1$H NMR (400 MHz, CDCl$_3$) δ 9.77 (s, 1H), 8.10-8.08 (m, 2H), 7.83-7.80 (m, 3H), 7.60-7.58 (m, 1H), 7.43 (s, 1H), 7.36-7.26 (m, 5H), 6.70 (s, 1H), 6.14 (br, 1H), 3.68-3.64 (m, 1H), 3.63 (s, 3H), 3.33-3.28 (m, 1H).

Example 36

2-(4-(2-acetyl-5-chlorophenyl)-5-methoxy-2-oxopyridin-1(2H)-yl)-N-(4-cyano-3-methoxyphenyl)-3-phenylpropanamide 36

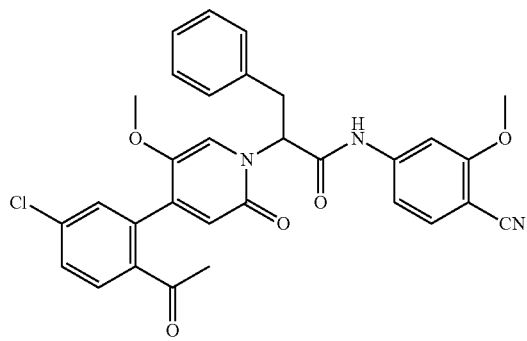

36

In accordance with the synthetic route of Example 18, the starting compound 18a was replaced with 4-amino-2-methoxybenzonitrile (prepared by a method disclosed in the patent application "WO 2013042782"), accordingly, the title compound 36 (40 mg) was prepared.

MS m/z (ESI): 556.5 [M+1]

$^1$H NMR (400 MHz, CDCl$_3$) δ 9.89 (s, 1H), 7.73 (d, 1H), 7.54-7.51 (dd, 1H), 7.48 (d, 1H), 7.41 (s, 1H), 7.29 (s, 4H), 7.21 (s, 1H), 7.09-7.06 (dd, 2H), 6.59 (s, 1H), 6.00 (s, 1H), 3.90 (s, 3H), 3.69-3.75 (m, 1H), 3.65 (s, 3H), 3.33-3.28 (m, 1H), 2.50 (s, 3H).

Example 37

(S)-4-(2-(4-(2-acetyl-5-chlorophenyl)-5-methoxy-2-oxopyridin-1(2H)-yl)-3-phenylpropanamido)-N-ethylbenzamide

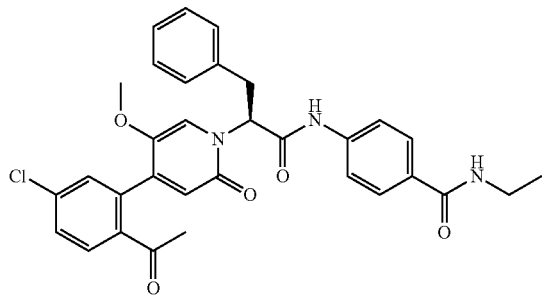

37

In accordance with the synthetic route of Example 13, the starting material methylamine was replaced with ethylamine, accordingly, the title compound 37 (40 mg) was prepared.

MS m/z (ESI): 572.1 [M+1]

$^1$H NMR (400 MHz, CDCl$_3$) δ 9.61 (br, 1H), 7.73-7.64 (m, 5H), 7.51 (d, 1H), 7.36-7.30 (m, 4H), 7.29-7.24 (m, 1H), 7.13 (s, 1H), 6.64 (s, 1H), 6.11 (s, 1H), 5.99-5.96 (m, 1H), 3.76-3.73 (m, 1H), 3.64 (s, 3H), 3.53-3.51 (m, 2H), 3.34-3.31 (m, 1H), 2.47 (s, 3H), 1.28 (t, 3H).

Example 38

N-(1H-benzo[d]imidazol-5-yl)-2-(4-(5-chloro-2-propionylphenyl)-5-methoxy-2-oxopyridin-1(2H)-yl)-3-phenylpropanamide 38

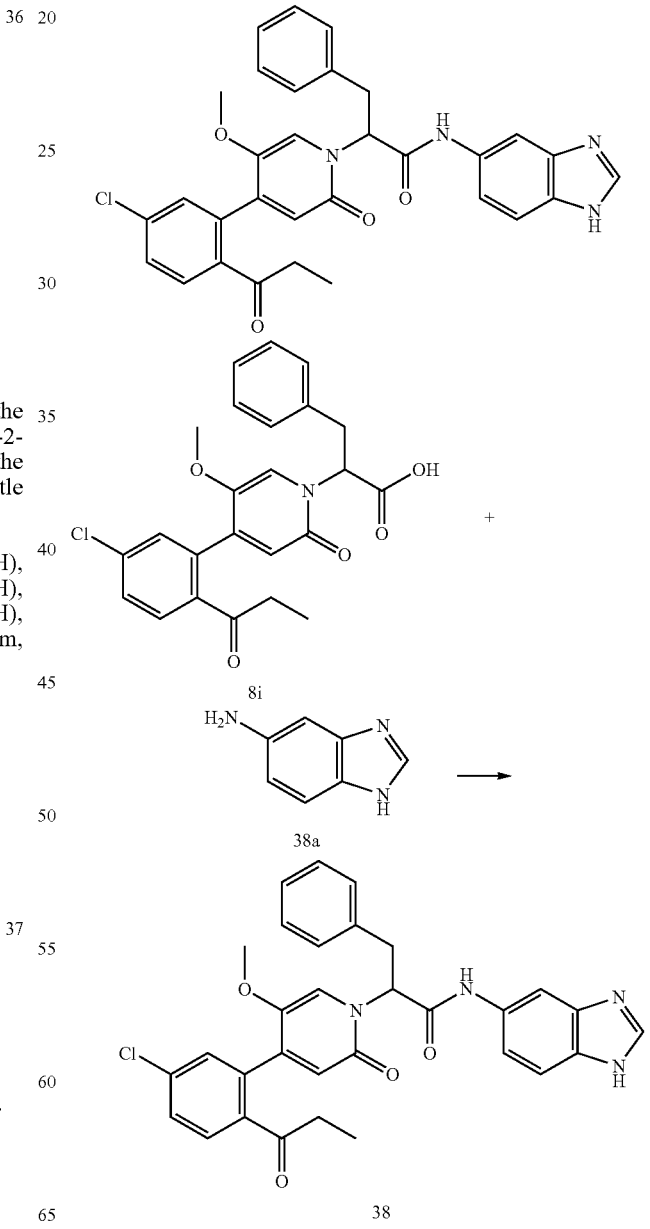

Compound 8i (80 mg, 181.86 μmol), 1H-benzo[d]imidazol-5-amine 38a (24.22 mg, 181.86 μmol, prepared by a known method disclosed in "*Chemical Communications (Cambridge, United Kingdom)*, 2011, 47(39), 10972-10974") and N,N-diisopropylethylamine (70.51 mg, 545.59 μmol) were added to 10 mL of tetrahydrofuran, followed by addition of a solution of 2,4,6-tripropyl-1,3,5,2,4,6-trioxatriphosphorinane-2,4,6-trioxide in ethyl acetate (50%, 231.34 mg, 363.73 iμmol). After completion of the addition, the reaction solution was warmed up to 50° C., and stirred for 1.5 hours. The reaction solution was cooled to room temperature and concentrated under reduced pressure. The resulting residue was added with 25 mL of saturated sodium bicarbonate solution, and extracted with ethyl acetate (50 mL×2). The organic phases were combined, dried over anhydrous sodium sulfate, and filtered. The filtrate was concentrated under reduced pressure, and the resulting residue was purified by the silica gel column with elution system A to obtain the title compound 38 (75 mg, yield: 74.3%).

MS m/z (ESI): 555.5 [M+1]

$^1$H NMR (400 MHz, DMSO-$d_6$) δ 10.84 (s, 1H), 9.05 (s, 1H), 9.14 (s, 1H), 8.27 (s, 1H), 7.79-7.77 (d, 1H), 7.72-7.69 (d, 1H), 7.59-7.52 (m, 2H), 7.41 (s, 1H), 7.34 (s, 1H), 7.30-7.24 (m, 4H), 7.19-7.17 (m, 1H), 6.30 (s, 1H), 6.03-5.99 (m, 1H), 3.52-3.50 (m, 4H), 3.48-3.44 (m, 1H), 2.85-2.75 (m, 2H), 1.25-1.18 (m, 3H).

Example 39

4-(2-(4-(5-chloro-2-(2-cyclopropylacetyl)phenyl)-5-methoxy-2-oxopyridin-1(2H)-yl)-3-phenylpropanamido)benzoic acid

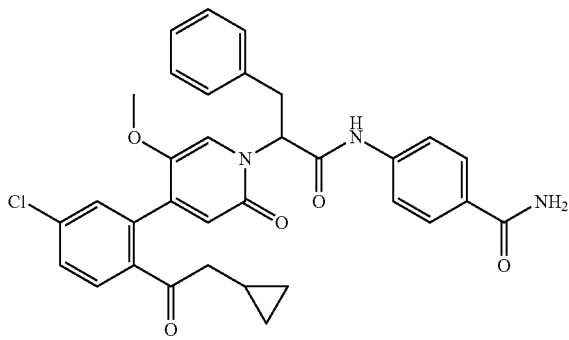

39

In accordance with the synthetic route of Example 8, the starting compound 8b was replaced with cyclopropylacetyl chloride (prepared by a method disclosed in the patent application "WO 2015110435"), the starting material cuprous chloride was replaced with cuprous iodide, accordingly, the title compound 39 (30 mg) was prepared.

MS m/z (ESI): 585.2 [M+1]

$^1$H NMR (400 MHz, CDCl$_3$) δ 9.93 (br, 1H), 8.10-8.08 (m, 2H), 7.85-7.83 (m, 2H), 7.69-7.67 (m, 1H), 7.51-7.48 (m, 1H), 7.35-7.26 (m, 6H), 6.63 (s, 1H), 6.22 (br, 1H), 3.69-3.64 (m, 4H), 3.62-3.29 (m, 1H), 2.74-2.72 (m, 2H), 1.07-1.05 (m, 1H), 0.61-0.59 (m, 2H), 0.15-0.14 (m, 2H).

Example 40

2-(4-(2-acetyl-5-chlorophenyl)-5-methoxy-2-oxopyridin-1(2H)-yl)-3-phenyl-N-(quinazolin-6-yl)propanamide 40

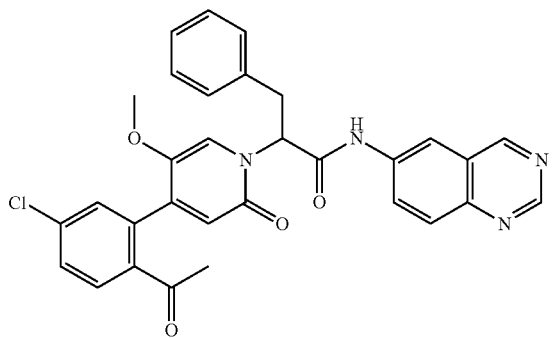

40

In accordance with the synthetic route of Example 18, the starting compound 18a was replaced with compound 23a, accordingly, the title compound 40 (80 mg) was prepared.

MS m/z (ESI): 553.1 [M+1]

$^1$H NMR (400 MHz, DMSO-$d_6$) δ 11.05 (s, 1H), 9.59 (s, 1H), 9.22 (s, 1H), 8.63 (s, 1H), 8.07-8.01 (m, 2H), 7.83 (d, 1H), 7.61 (dd, 1H), 7.46 (s, 1H), 7.38 (s, 1H), 7.32-7.26 (m, 4H), 7.22-7.18 (m, 1H), 6.33 (s, 1H), 6.10-6.06 (m, 1H), 3.56 (s, 3H), 3.52 (d, 2H), 2.40 (s, 3H).

Example 41

4-(2-(4-(5-chloro-2-(cyclopropanecarbonyl)phenyl)-5-methoxy-2-oxopyridin-1(2H)-yl)-3-phenylpropanamido)benzoic acid 41

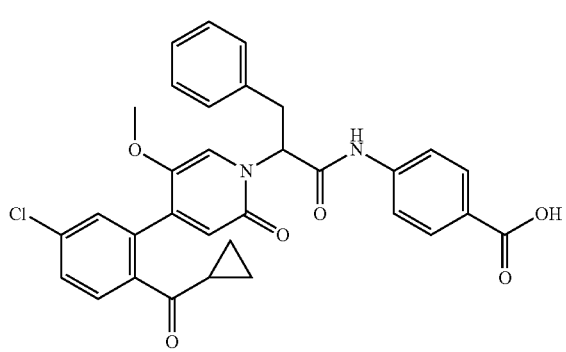

41

In accordance with the synthetic route of Example 8, the starting compound 8b was replaced with cyclopropanoyl chloride (prepared by a method disclosed in the patent application "WO 2015143380"), accordingly, the title compound 41 (60 mg) was prepared.

MS m/z (ESI): 571.2 [M+1]

$^1$H NMR (400 MHz, DMSO-$d_6$) δ 10.84 (s, 1H), 7.92 (d, 2H), 7.75-7.72 (m, 3H), 7.61 (dd, 1H), 7.38 (d, 2H), 7.31-

7.24 (m, 4H), 7.20-7.17 (m, 1H), 6.34 (s, 1H), 6.05-6.01 (m, 1H), 3.57-3.49 (m, 2H), 3.52 (s, 3H), 2.18-2.11 (m, 1H), 0.85-0.75 (m, 4H).

Example 42

2-(4-(2-acetyl-5-chlorophenyl)-5-methoxy-2-oxopyridin-1(2H)-yl)-N-(1H-indazol-6-yl)-3-phenyl-propanamide 42

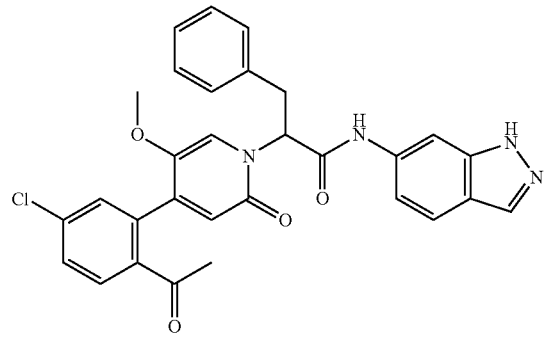

In accordance with the synthetic route of Example 18, the starting compound 18a was replaced with 6-aminocarbazole (prepared by a known method disclosed in "*Tetrahedron Letters*, 2010, 51(5), 786-789"), accordingly, the title compound 42 (83 mg) was prepared.

MS m/z (ESI): 541.4 [M+1]

$^1$H NMR (400 MHz, DMSO-d$_6$) δ 12.94 (s, 1H), 10.67 (s, 1H), 8.13 (s, 1H), 7.99 (s, 1H), 7.82 (d, 1H), 7.70 (d, 1H), 7.61 (d, 1H), 7.48 (s, 1H), 7.38 (s, 1H), 7.31-7.25 (m, 4H), 7.21-7.16 (m, 2H), 6.31 (s, 1H), 6.08-6.04 (m, 1H), 3.56 (s, 3H), 3.47 (d, 2H), 2.38 (s, 3H).

Example 43

(S)-4-(2-(4-(2-acetyl-5-chlorophenyl)-5-methoxy-2-oxopyridin-1(2H)-yl)-3-phenylpropanamido)-N-cyclopropylbenzamide 43

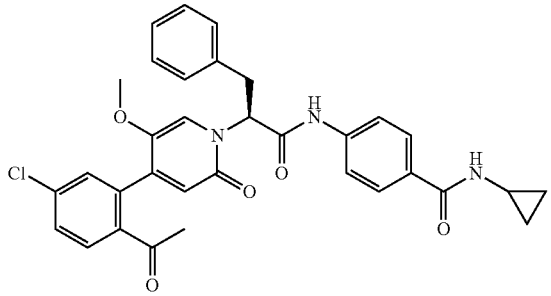

In accordance with the synthetic route of Example 13, the starting material methylamine is replaced with cyclopropylamine, accordingly, the title compound 43 (40 mg) was prepared.

MS m/z (ESI): 584.1 [M+1]

$^1$H NMR (400 MHz, DMSO-d$_6$) δ 10.75 (s, 1H), 8.37 (d, 1H), 7.84-7.80 (m, 3H), 7.70 (d, 2H), 7.61 (dd, 1H), 7.43 (s, 1H), 7.38 (s, 1H), 7.31-7.26 (m, 4H), 7.22-7.18 (m, 1H), 6.31 (s, 1H), 6.04-6.00 (m, 1H), 3.55 (s, 3H), 3.50-3.42 (m, 2H), 2.85-2.80 (m, 1H), 2.38 (s, 3H), 0.71-0.54 (m, 4H).

Example 44

4-(2-(4-(5-chloro-2-isobutyrylphenyl)-5-methoxy-2-oxopyridin-1(2H)-yl)-3-phenylpropanamido)benzoic acid 44

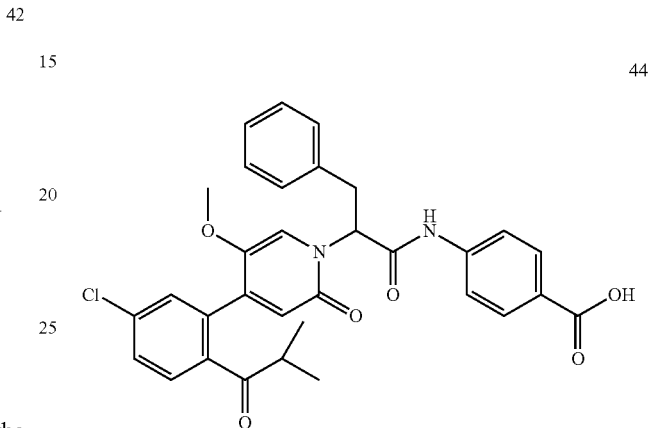

In accordance with the synthetic route of Example 8, the starting compound 8b was replaced with isobutyryl chloride (prepared by a known method disclosed in "*Organic Letters*, 2017, 19(7), 1768-1771"), accordingly, the title compound 44 (200 mg) was prepared.

MS m/z (ESI): 573.5 [M+1]

$^1$H NMR (400 MHz, CDCl$_3$) δ 9.99 (s, 1H), 8.10 (d, 2H), 7.86 (d, 2H), 7.72 (d, 1H), 7.52-7.29 (m, 8H), 6.59 (s, 1H), 6.28 (s, 1H), 3.67-3.62 (m, 4H), 3.33-3.23 (m, 2H), 1.15-1.12 (m, 6H).

Example 45

2-(4-(2-acetyl-5-chlorophenyl)-5-methoxy-2-oxopyridin-1(2H)-yl)-3-phenyl-N-(quinoxalin-6-yl)propanamide 45

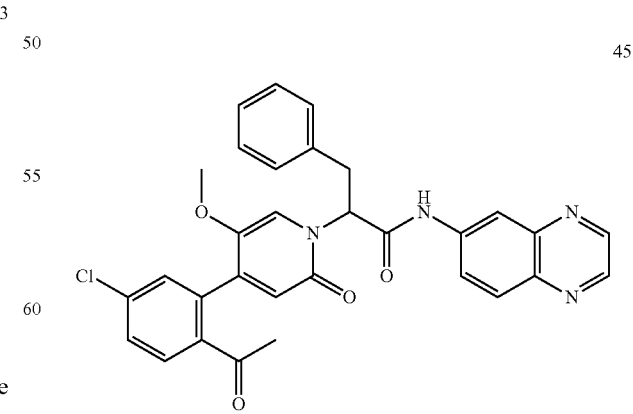

In accordance with the synthetic route of Example 18, the starting compound 18a was replaced with 6-aminoquinoxaline (prepared by a method disclosed in the patent application "WO2013006792"), accordingly, the title compound 45 (45 mg) was prepared.

MS m/z (ESI): 553.0 [M+1]

$^1$H NMR (400 MHz, CD$_3$OD) δ 8.85-8.83 (d, 1H), 8.83-8.80 (d, 1H), 8.61-8.57 (m, 1H), 8.08-8.04 (d, 1H), 8.02-7.94 (dd, 1H), 7.85-7.83 (d, 1H), 7.58-7.55 (dd, 1H), 7.39 (s, 1H), 7.33-7.27 (m, 5H), 7.23-7.20 (m, 1H), 6.43 (s, 1H), 6.00-5.95 (m, 1H), 3.65-3.60 (m, 1H), 3.59 (s, 3H), 3.50-3.45 (m, 1H), 2.46 (s, 3H).

Example 46

2-(4-(2-acetyl-5-chlorophenyl)-5-methoxy-2-oxopyridin-1(2H)-yl)-N-(isoquinolin-6-yl)-3-phenyl-propanamide 46

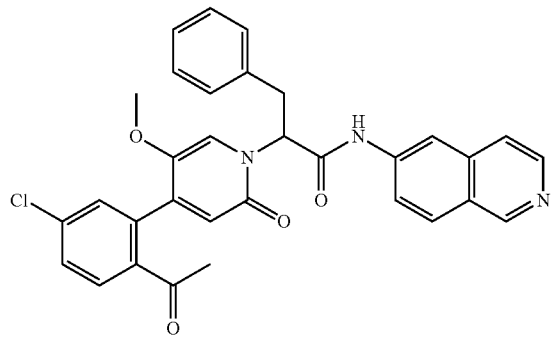

46

In accordance with the synthetic route of Example 18, the starting compound 18a was replaced with 6-aminoisoquinoline (prepared by a method disclosed in the patent application "WO 2010146881"), accordingly, the title compound 46 (88 mg) was prepared.

MS m/z (ESI): 552.5 [M+1]

$^1$H NMR (400 MHz, DMSO-d$_6$) δ 10.95 (s, 1H), 9.20 (s, 1H), 8.44-8.43 (m, 2H), 8.10 (d, 1H), 7.83 (d, 1H), 7.77-7.73 (m, 2H), 7.61 (d, 1H), 7.45 (s, 1H), 7.38 (s, 1H), 7.32-7.26 (m, 4H), 7.21-7.18 (m, 1H), 6.32 (s, 1H), 6.11-6.06 (m, 1H), 3.56 (s, 3H), 3.51 (d, 2H), 2.39 (s, 3H).

Example 47

2-(4-(2-acetyl-5-chlorophenyl)-5-methoxy-2-oxopyridin-1(2H)-yl)-N-(1H-benzo[d]imidazol-5-yl)-3-phenylpropanamide 47

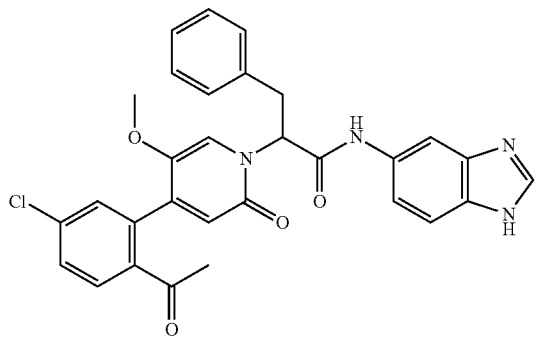

47

In accordance with the synthetic route of Example 18, the starting compound 18a was replaced with compound 38a, accordingly, the title compound 47 (10 mg) was prepared.

MS m/z (ESI): 541.2 [M+1]

$^1$H NMR (400 MHz, MeOH-d$_4$) δ 8.18 (s, 1H), 8.03 (s, 1H), 7.84-7.82 (d, 1H), 7.56-7.50 (d, 2H), 7.43 (s, 1H), 7.30-7.22 (m, 7H), 6.43 (s, 1H), 5.89-5.85 (m, 1H), 3.65-3.60 (m, 1H), 3.59 (s, 3H), 3.50-3.45 (m, 1H), 2.46 (s, 3H).

Example 48

2-(4-(2-acetyl-5-chlorophenyl)-5-methoxy-2-oxopyridin-(2H)-yl)-3-phenyl-N-(2-(trifluoromethyl)-1H-benzo[d]imidazol-5-yl)propanamide 48

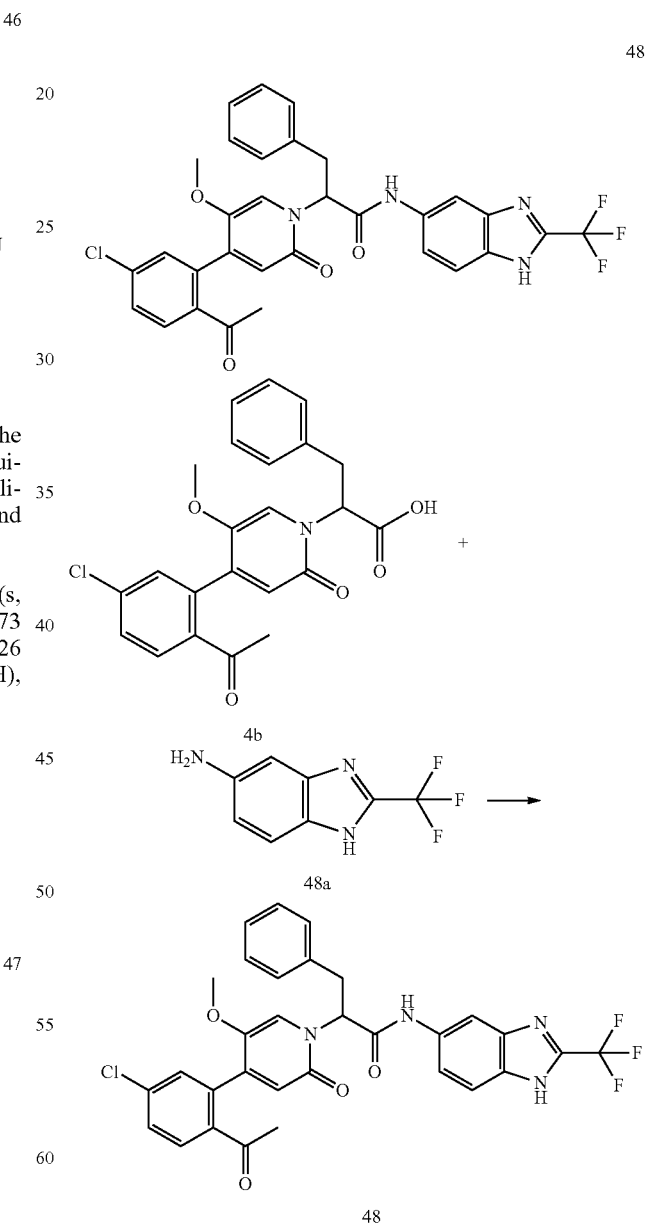

48

Compound 4b (43 mg, 100.97 μmol), 2-(trifluoromethyl)-H-benzo[d]imidazole-5-amine 48a (20.31 mg, 100.97 μmol, prepared by a known method disclosed in "*International*

*Journal of PharmTech Research*, 2009, 1(2), 277-281") and N,N-diisopropylethylamine (39.15 mg, 302.92 μmol) were added to 15 mL of tetrahydrofuran, followed by addition of 2,4,6-tripropyl-1,3,5,2,4,6-trioxatriphosphorinane-2,4,6-trioxide (64.22 mg, 201.94 μmol). After completion of the addition, the reaction solution was warmed up to 60° C., and stirred for 1 hour. The reaction solution was cooled to room temperature, and concentrated under reduced pressure. The resulting residue was added with 15 mL of saturated sodium bicarbonate solution, and extracted with ethyl acetate (50 mL×2). The organic phases were combined, dried over anhydrous sodium sulfate, and filtered. The filtrate was concentrated under reduced pressure, and the resulting residue was purified by silica gel column with elution system A to obtain the title compound 48 (50 mg).

MS m/z (ESI): 609.2 [M+1]

$^1$H NMR (400 MHz, DMSO-$d_6$) δ 13.93-13.83 (d, 1H), 10.74-10.65 (d, 1H), 8.25-8.15 (m, 1H), 7.84-7.82 (d, 1H), 7.78-7.74 (d, 1H), 7.62-7.60 (dd, 1H), 7.50-7.45 (m, 1H), 7.44-7.36 (m, 2H), 7.35-7.25 (m, 4H), 7.22-7.15 (m, 1H), 6.50 (s, 1H), 6.10-6.00 (m, 1H), 3.55 (s, 3H), 3.51-3.48 (m, 2H), 2.38 (s, 3H).

Example 49

2-(4-(2-acetyl-5-chlorophenyl)-5-methoxy-2-oxopyridin-1(2H)-yl)-N-(2-methyl-1H-benzo[d]imidazol-5-yl)-3-phenylpropanamide 49

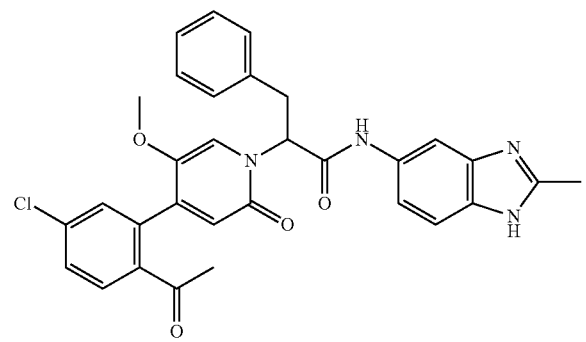

In accordance with the synthetic route of Example 48, the starting compound 48a was replaced with 2-methyl-1H-benzo[d]imidazole-5-amine (prepared by a method disclosed in the patent application "WO2012044090"), accordingly, the title compound 49 (40 mg) was prepared.

MS m/z (ESI):555.2 [M+1]

$^1$H NMR (400 MHz, DMSO-$d_6$) δ 10.58 (s, 1H), 7.86 (s, 1H), 7.88-7.81 (d, 1H), 7.61-7.59 (dd, 1H), 7.47 (s, 1H), 7.45-7.43 (d, 1H), 7.37 (s, 1H), 7.31-7.24 (m, 5H), 7.21-7.17 (m, 1H), 6.30 (s, 1H), 6.05-6.01 (m, 1H), 3.55 (s, 3H), 3.51-3.48 (m, 2H), 2.50 (s, 3H), 2.38 (s, 3H).

Example 50

(S)-4-(2-(4-(2-acetyl-5-chlorophenyl)-5-methoxy-2-oxopyridin-1(2H)-yl)-3-phenylpropanamido)-N,N-dimethylbenzamide 50

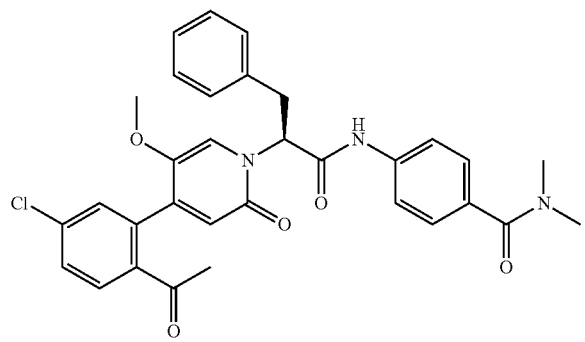

In accordance with the synthetic route of Example 13, the starting material methylamine was replaced with dimethylamine, accordingly, the title compound 50 (40 mg) was prepared.

MS m/z (ESI): 572.1 [M+1]

$^1$H NMR (400 MHz, DMSO-$d_6$) δ 10.72 (s, 1H), 7.84 (d, 1H), 7.82 (d, 2H), 7.70-7.68 (m, 1H), 7.44-7.40 (m, 4H), 7.31-7.28 (m, 4H), 7.21-7.18 (m, 1H), 6.31 (s, 1H), 6.04-6.00 (m, 1H), 3.55 (s, 3H), 3.52-3.47 (m, 2H), 2.96 (s, 6H), 2.38 (s, 3H).

Example 51

5-(2-(4-(2-acetyl-5-chlorophenyl)-5-methoxy-2-oxopyridin-1(2H)-yl)-3-phenylpropanamido)-2-picolinamide 51

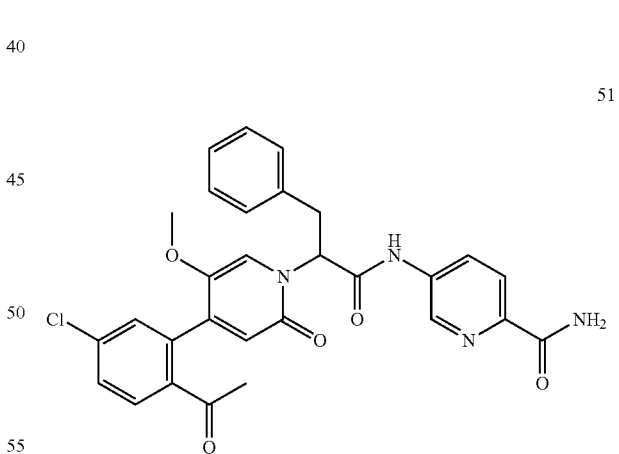

In accordance with the synthetic route of Example 18, the starting compound 18a was replaced with 5-amino-2-pyridinecarboxamide (prepared by a method disclosed in the patent application "WO2013146963"), accordingly, the title compound 51 (70 mg) was prepared.

MS m/z (ESI): 545.1 [M+1]

$^1$H NMR (400 MHz, CD$_3$OD) δ 8.83-8.82 (d, 1H), 8.23-8.20 (dd, 1H), 8.08-8.06 (d, 1H), 7.85-7.83 (d, 1H), 7.57-7.54 (dd, 1H), 7.32-7.29 (m, 1H), 7.28-7.25 (m, 5H), 7.23-7.20 (m, 1H), 6.41 (s, 1H), 5.89-5.85 (m, 1H), 3.65-3.60 (m, 1H), 3.59 (s, 3H), 3.50-3.45 (m, 1H), 2.46 (s, 3H).

Example 52

2-(4-(2-acetyl-5-chlorophenyl)-5-methoxy-2-oxopyridin-1(2H)-yl)-3-phenyl-N-(1H-pyrrolo[3,2-b]pyridin-6-yl)propanamide 52

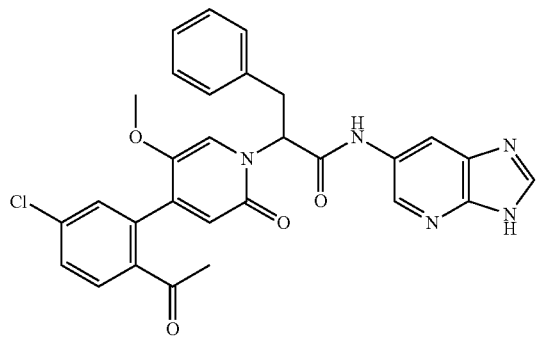

In accordance with the synthetic route of Example 18, the starting compound 18a was replaced with 1H-pyrrolo[3,2-b]pyridine-6-amine (Accela), accordingly, the title compound 52 (23 mg) was prepared.

MS m/z (ESI): 541.4 [M+1]

$^1$H NMR (400 MHz, DMSO-d$_6$) δ 8.94 (s, 1H), 8.69 (s, 1H), 8.08 (d, 1H), 7.86 (d, 1H), 7.58-7.55 (m, 1H), 7.32-7.18 (m, 7H), 6.82 (d, 1H), 6.45 (s, 1H), 5.76-5.73 (m, 1H), 3.63-3.61 (m, 1H), 3.51 (s, 3H), 3.50-3.48 (m, 1H), 2.48 (s, 3H).

Example 53 methyl 3-(2-(4-(2-acetyl-5-chlorophenyl)-5-methoxy-2-oxopyridin-1(2H)-yl)-3-phenylpropanamido)benzylcarbamate 53

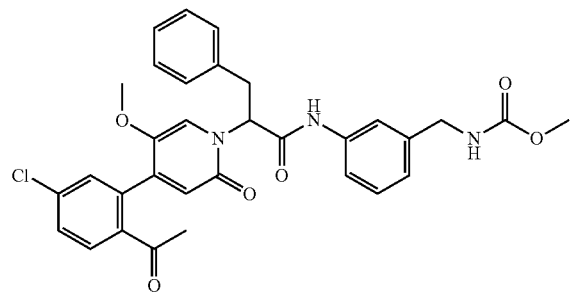

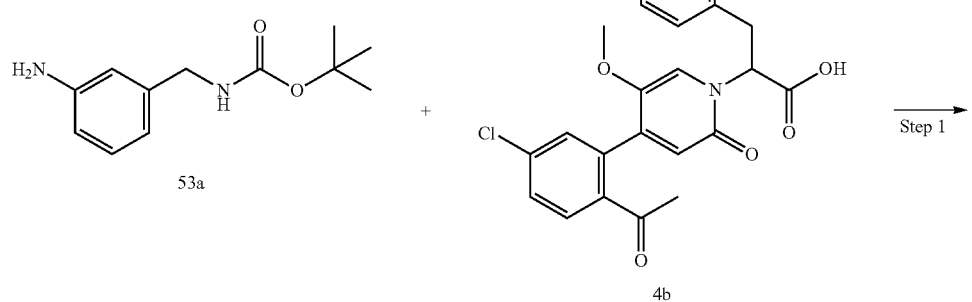

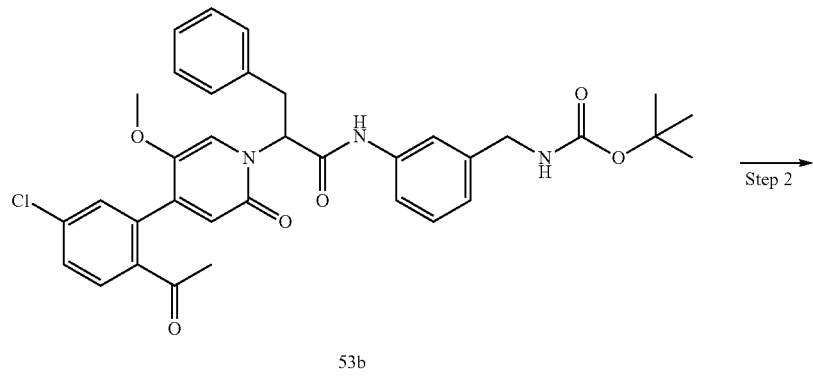

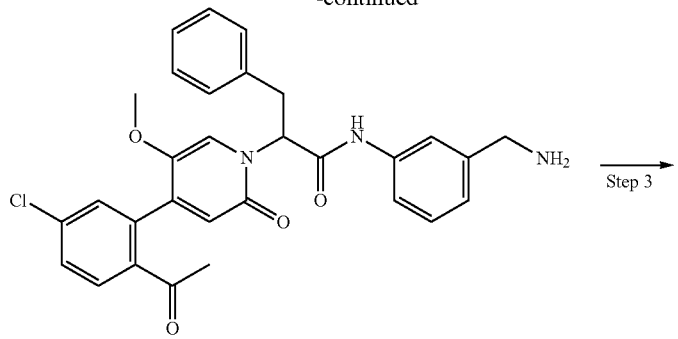

53c

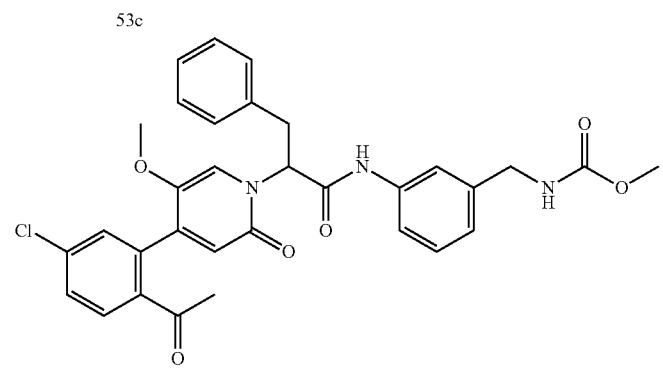

53

Step 1 tert-butyl 3-(2-(4-(2-acetyl-5-chlorophenyl)-5-methoxy-2-oxopyridin-1(2H)-yl)-3-phenylpropanamido)benzylcarbamate 53b Compound 4b (90 mg, 211.34 μmol), tert-butyl 3-aminobenzylcarbamate 53a (51.68 mg, 232.47 μmol, prepared by a known method disclosed in "*Chemical Communications (Cambridge, United Kingdom)*, 2014, 50 (97), 15305-15308") and N,N-diisopropylethylamine (273.14 mg, 2.11 mmol) were dissolved in 15 mL of ethyl acetate followed by addition of 2,4,6-tripropyl-1,3,5,2,4,6-trioxatriphosphorinane-2,4,6-trioxide (268.97 mg, 845.36 μmol). After completion of the addition, the reaction solution was warmed up to 75° C., and stirred for 2 hours. After cooling to room temperature, the reaction solution was added with 30 mL of water, followed by addition of 3M hydrochloric acid to adjust the pH to 5, and the two phases were separated. The water phase was extracted with ethyl acetate (30 mL×2), and the organic phases were combined, washed with saturated sodium chloride solution (35 mL×2), dried over anhydrous sodium sulfate, and filtered. The filtrate was concentrated under reduced pressure, and the resulting residue was purified by silica gel column with elution system A to obtain the title compound 53b (105 mg, yield: 78.85%).

MS m/z (ESI):630.1 [M+1]

Step 2

2-(4-(2-acetyl-5-chlorophenyl)-5-methoxy-2-oxopyridin-1(2H)-yl)-N-(3-(aminomethyl)phenyl)-3-phenylpropanamide 53c Compound 53b (105 mg, 166.63 μmol) was dissolved in 7 mL of dichloromethane, and then trifluoroacetic acid (1 mL) was added dropwise. The reaction solution was stirred for 1 hour, and then concentrated under reduced pressure to obtain the crude title compound 53c (80 mg), which was directly used in the next reaction step without purification.

MS m/z (ESI): 530.1 [M+1]

Step 3 methyl 3-(2-(4-(2-acetyl-5-chlorophenyl)-5-methoxy-2-oxopyridin-1(2H)-yl)-3-phenylpropanamido)benzylcarbamate 53

The crude compound 53c (80 mg, 105.94 μmol) was dissolved in 10 mL of dichloromethane, and then triethylamine (61.096 mg, 603.76 μmol) was added dropwise, followed by dropwise addition of methyl chloroformate (21.40 mg, 226.41 μmol) in an ice bath. After stirring for 2 hours at room temperature, the reaction solution was added with 25 ml of dichloromethane, washed with 0.5 M hydrochloric acid (15 mL), saturated sodium bicarbonate solution (15 mL) and saturated brine (15 mL) successively, dried over anhydrous sodium sulfate, and filtered. The filtrate was concentrated under reduced pressure, and the resulting residue was purified by high pressure liquid chromatography (Waters 2767-SQ detecor2, elution system: acetonitrile, water) to obtain the title compound 53 (35 mg, 39.4%).

MS m/z (ESI):588.3 [M+1]

$^1$H NMR (400 MHz, DMSO-d$_6$) δ 9.24 (s, 1H), 7.66 (d, 1H), 7.47 (dd, 1H), 7.43-7.41 (m, 2H), 7.28-7.20 (m, 7H), 7.12 (s, 1H), 7.04 (d, 1H), 6.55 (s, 1H), 6.00-5.91 (m, 1H), 5.08 (s, 1H), 4.31 (d, 2H), 3.72-3.65 (m, 1H), 3.68 (s, 3H), 3.60 (s, 3H), 3.28-3.23 (m, 1H), 2.43 (s, 3H).

Example 54

2-(4-(5-chloro-2-propionylphenyl)-5-methoxy-2-oxopyridin-1(2H)-yl)-N-(2-cyano-1H-indol-6-yl)-3-phenylpropanamide 54

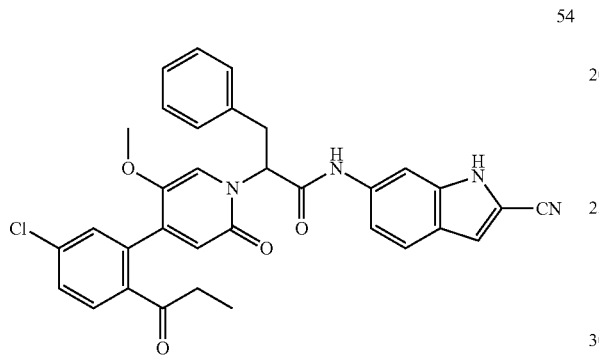

54

In accordance with the synthetic route of Example 38, the starting compound 38a was replaced with 6-amino-1H-indole-2-carbonitrile (prepared by a method disclosed in the patent application "US20160271105"), accordingly, the title compound 54 (30 mg) was prepared.

MS m/z (ESI): 579.1 [M+1]

$^1$H NMR (400 MHz, CD$_3$OD) δ 8.01 (s, 1H), 7.78-7.79 (d, 1H), 7.59-7.57 (d, 1H), 7.56-7.53 (dd, 1H), 7.38 (s, 1H), 7.33-7.25 (m, 5H), 7.25-7.18 (m, 1H), 7.16-7.15 (d, 1H), 7.14-7.12 (dd, 1H), 6.42 (s, 1H), 5.95-5.90 (m, 1H), 3.60-3.56 (m, 1H), 3.54 (s, 3H), 3.45-3.35 (m, 1H), 3.00-2.95 (m, 2H), 1.10-1.00 (m, 3H).

Example 55

2-(4-(2-acetyl-5-chlorophenyl)-5-methoxy-2-oxopyridin-1(2H)-yl)-N-(4-cyano-3-(trifluoromethyl)phenyl)-3-phenylpropanamide 55

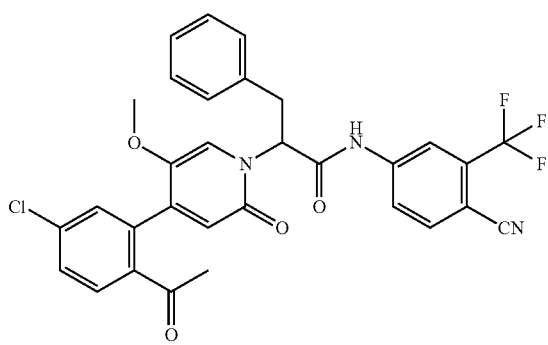

55

In accordance with the synthetic route of Example 18, the starting compound 18a was replaced with 4-amino-2-(trifluoromethyl)benzonitrile (prepared by a known method disclosed in "*Medicinal Chemistry Research*, 2016, 25(4), 539-552"), accordingly, the title compound 55 (40 mg) was prepared.

MS m/z (ESI): 594.4 [M+1]

$^1$H NMR (400 MHz, CDCl$_3$) δ 10.31 (s, 1H), 7.75-7.72 (m, 2H), 7.55-7.51 (m, 2H) 7.29-7.26 (m, 5H), 7.24-7.16 (m, 2H), 6.55 (s, 1H), 5.98 (s, 1H), 3.71-3.67 (m, 1H), 3.65 (s, 3H), 3.33-3.27 (m, 1H), 2.51 (m, 3H).

Example 56

2-(4-(2-acetyl-5-chlorophenyl)-5-methoxy-2-oxopyridin-1(2H)-yl)-N-(4-(methylsulfonyl)phenyl)-3-phenylpropanamide 56

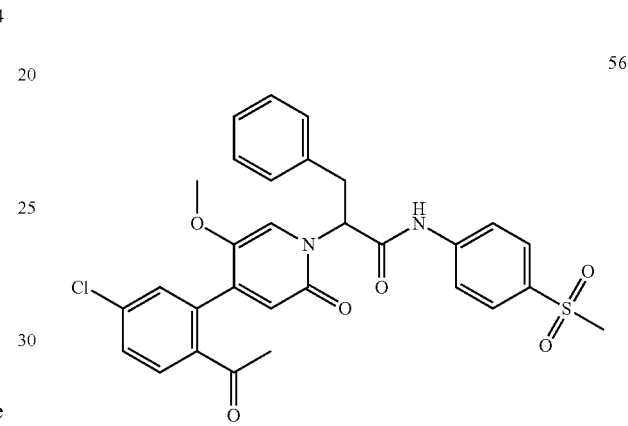

56

In accordance with the synthetic route of Example 18, the starting compound 18a was replaced with 4-(methylsulfonyl)aniline (prepared by a method disclosed in the patent application "WO2014100833"), accordingly, the title compound 56 (110 mg) was prepared.

MS m/z (ESI): 579.0 [M+1]

$^1$H NMR (400 MHz, DMSO-d$_6$) δ 10.96 (s, 1H), 7.91-7.86 (m, 4H), 7.83 (d, 1H), 7.61 (dd, 1H), 7.39 (d, 2H), 7.30-7.25 (m, 4H), 7.21-7.18 (m, 1H), 6.32 (s, 1H), 6.03-5.99 (m, 1H), 3.53 (s, 3H), 3.50-3.45 (m, 2H), 3.18 (s, 3H), 2.38 (s, 3H).

Example 57

2-(4-(2-acetyl-5-chlorophenyl)-5-methoxy-2-oxopyridin-1(2H)-yl)-N-(1,6-naphthyridin-3-yl)-3-phenylpropanamide 57

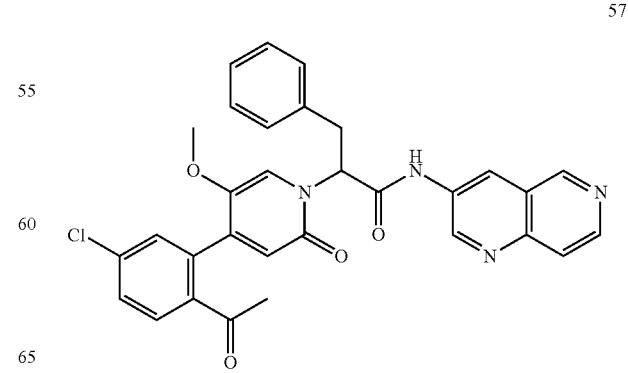

57

In accordance with the synthetic route of Example 48, the starting compound 48a was replaced with 1,6-naphthyridin-3-amine (prepared by a method disclosed in the patent application "WO2007048070"), accordingly, the title compound 57 (40 mg) was prepared.

MS m/z (ESI):553.2 [M+1]

$^1$H NMR (400 MHz, DMSO-d$_6$) δ 11.18 (s, 1H), 9.40 (s, 1H), 9.14 (s, 1H), 8.95 (s, 1H), 8.67-8.65 (d, 1H), 7.87-7.82 (m, 2H), 7.62-7.60 (d, 1H), 7.48 (s, 1H), 7.38 (s, 1H), 7.30-7.26 (m, 4H), 7.21-7.20 (m, 1H), 6.36 (s, 1H), 6.05-6.03 (m, 1H), 3.64-3.58 (m, 4H), 3.30-3.22 (m, 1H), 2.40 (s, 3H).

Example 58

2-(4-(2-acetyl-5-chlorophenyl)-5-methoxy-2-oxopyridin-1(2H)-yl)-3-phenyl-N-(4-sulfamoylphenyl)propanamide 58

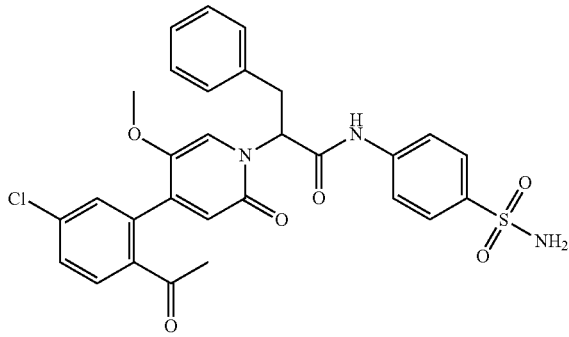

In accordance with the synthetic route of Example 18, the starting compound 18a was replaced with 4-(aminosulfonyl)aniline (prepared by a known method disclosed in "*Journal of Organic Chemistry*, 2014, 79 (19), 9433-9439"), accordingly, the title compound 58 (40 mg) was prepared.

MS m/z (ESI): 580.2 [M+1]

$^1$H NMR (400 MHz, CD$_3$OD) δ 7.85-7.82 (m, 3H), 7.76-7.74 (m, 2H), 7.56-7.54 (dd, 1H), 7.33-7.32 (m, 2H), 7.28-7.25 (m, 4H), 7.22-7.19 (m, 1H), 6.41 (s, 1H), 5.89-5.85 (m, 1H), 3.65-3.60 (m, 1H), 3.59 (s, 3H), 3.50-3.45 (m, 1H), 2.46 (s, 3H).

Example 59

2-(4-(2-acetyl-5-chlorophenyl)-5-methoxy-2-oxopyridin-1(2H)-yl)-N-(4-cyano-2-fluorophenyl)-3-phenylpropanamide 59

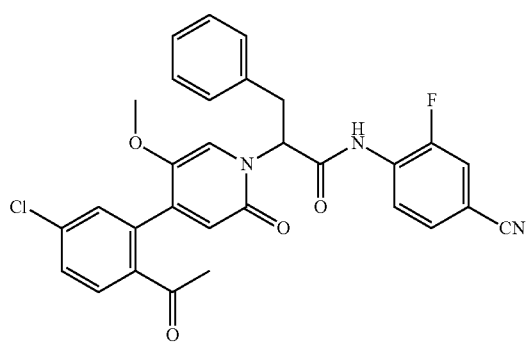

In accordance with the synthetic route of Example 18, the starting compound 18a was replaced with 4-amino-3-fluorobenzonitrile (prepared by a known method disclosed in "*Journal of Medicinal Chemistry*, 2005, 48 (18), 5823-5836"), accordingly, the title compound 59 (20 mg) was prepared.

MS m/z (ESI): 544.4 [M+1]

$^1$H NMR (400 MHz, CDCl$_3$) δ 9.83 (s, 1H), 8.53 (t, 1H), 7.72 (d, 1H), 7.53-7.50 (dd, 1H), 7.47 (d, 2H), 7.42-7.29 (dd, 1H), 7.37-7.32 (m, 4H), 7.30-7.26 (m, 1H), 6.92 (s, 1H), 6.65 (s, 1H), 5.86 (s, 1H), 3.82-3.74 (m, 1H), 3.61 (s, 3H), 3.37-3.32 (m, 1H), 2.49 (m, 3H).

Example 60

2-(4-(2-acetyl-5-chlorophenyl)-5-methoxy-2-oxopyridin-1(2H)-yl)-N-(3-oxo-3,4-dihydro-2H-benzo[b][1,4]oxazin-6-yl)-3-phenylpropanamide 60

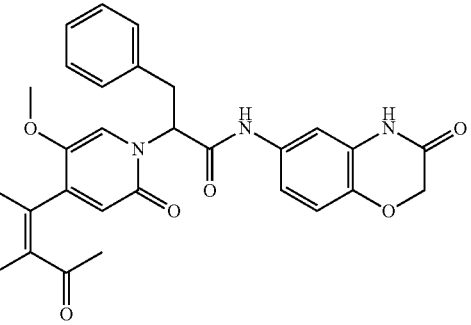

In accordance with the synthetic route of Example 18, the starting compound 18a was replaced with 6-amino-2H-benzo[b][1,4]oxazin-3(4H)-one (prepared by a method disclosed in the patent application "US20100216783"), accordingly, the title compound 60 (50 mg) was prepared.

MS m/z (ESI): 569.8 [M−1]

$^1$H NMR (400 MHz, CD$_3$OD) δ 10.10 (s, 1H), 7.85-7.83 (d, 1H), 7.58-7.55 (dd, 1H), 7.39 (s, 1H), 7.38-7.36 (m, 2H), 7.29-7.25 (m, 4H), 7.23-7.20 (m, 1H), 7.00-6.99 (dd, 1H), 6.91-6.81 (d, 1H), 6.43 (s, 1H), 5.89-5.85 (m, 1H), 4.54 (s, 2H), 3.65-3.60 (m, 1H), 3.59 (s, 3H), 3.50-3.45 (m, 1H), 2.46 (s, 3H).

Examples 61, 62

(S)-(5-methyl-2-oxo-1,3-dioxol-4-yl)methyl 4-(2-(4-(2-acetyl-5-chlorophenyl)-5-methoxy-2-oxopyridin-1(2H)-yl)-3-phenylpropanamido)benzoate 61

(R)-(5-methyl-2-oxo-1,3-dioxol-4-yl)methyl 4-(2-(4-(2-acetyl-5-chlorophenyl)-5-methoxy-2-oxopyridin-1(2H)-yl)-3-phenylpropanamido)benzoate 62

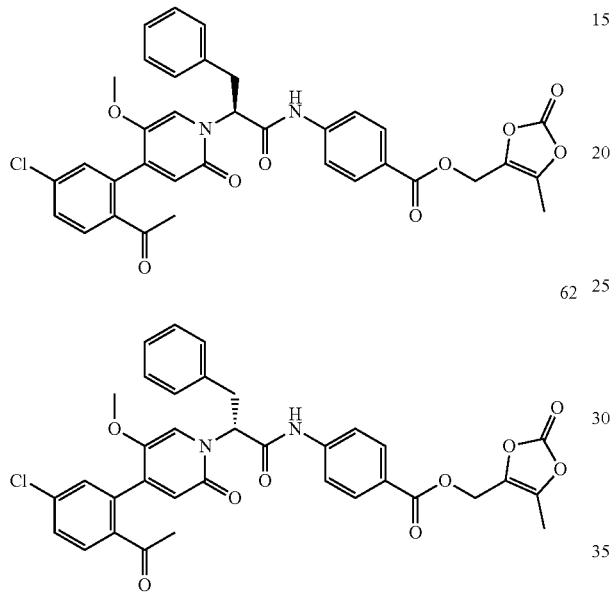

In accordance with the synthetic route of Examples 14, 15, the starting compound 14b was replaced with 4-(chloromethyl)-5-methyl-1,3-dioxol-2-one (prepared by a method disclosed in the patent application "CN103450146"). After chiral separation (separation conditions: chromatographic column: Superchiral S-AD (Chiralway), 2 cm ID*25 cm Length, 5 μm; mobile phase: carbon dioxide:isopropanol=60:40, flow rate: 50 g/min), the corresponding fractions were collected and concentrated under reduced pressure to obtain the title compound 61 (600 mg) and compound 62 (600 mg).

Compound 61
MS m/z (ESI): 657.5 [M+1]
Chiral HPLC analysis: retention time 7.283 minutes, chiral purity: 99.8% (chromatographic column: CHIRAL PAK IE 4.6*150 mm 5 μm (with a guard column); mobile phase: ethanol/methanol=50/50 (V/V), flow rate: 1.0 mL/min).
$^1$H NMR (400 MHz, DMSO-$d_6$) δ 10.91 (s, 1H), 7.98-7.97 (m, 1H), 7.96-7.95 (m, 1H), 7.83-7.79 (m, 3H), 7.62-7.59 (dd, 1H), 7.41 (s, 1H), 7.37 (s, 1H), 7.30-7.26 (m, 4H), 7.20-7.17 (m, 1H), 6.30 (s, 1H), 6.04-5.95 (m, 1H), 5.20 (s, 2H), 3.51 (s, 3H), 3.49-3.42 (m, 2H), 2.37 (s, 3H), 2.22 (s, 3H).

Compound 62
MS m/z (ESI): 657.2 [M+1]
Chiral HPLC analysis: retention time 5.342 minutes, chiral purity: 99.8% (chromatographic column: CHIRAL PAK IE 4.6*150 mm 5 μm (with a guard column); mobile phase: ethanol/methanol=50/50 (V/V), flow rate: 1.0 mL/min).
$^1$H NMR (400 MHz, DMSO-$d_6$) δ 10.92 (s, 1H), 7.98 (d, 2H), 7.84-7.80 (m, 3H), 7.63-7.60 (m, 1H), 7.40 (d, 2H), 7.30-7.26 (m, 4H), 7.22-7.18 (m, 1H), 6.31 (s, 1H), 6.04-6.01 (m, 1H), 5.20 (s, 2H), 3.54 (s, 3H), 3.51-3.43 (m, 2H), 2.38 (s, 3H), 2.22 (s, 3H).

Example 63

4-(2-(4-(2-acetyl-5-chlorophenyl)-5-methoxy-2-oxopyridin-1(2H)-yl)-3-(4-fluorophenyl)propanamido)benzoic acid 63

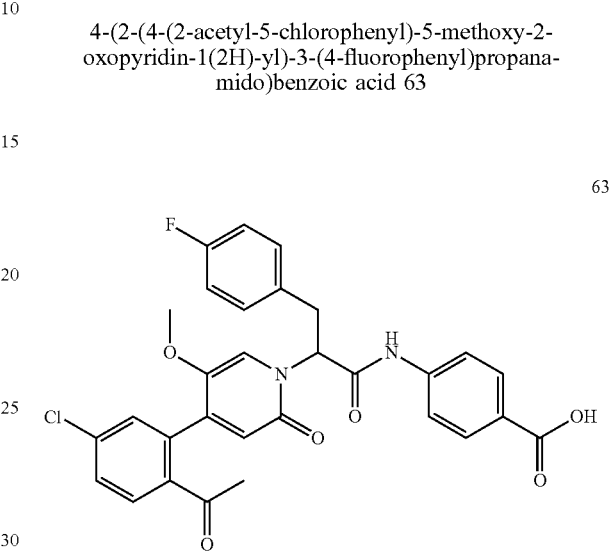

In accordance with the synthetic route of Example 4, the starting compound 4a was replaced with 2-bromo-3-(4-fluorophenyl)propionic acid (prepared by a method disclosed in the patent application "U.S. Pat. No. 5,981,529A"), accordingly, the title compound 63 (64 mg) was prepared.

MS m/z (ESI): 563.4 [M+1]
$^1$H NMR (400 MHz, DMSO-$d_6$) δ 10.79 (s, 1H), 7.90 (d, 2H), 7.84 (d, 1H), 7.71 (d, 2H), 7.61 (dd, 1H), 7.39 (s, 2H), 7.33-7.29 (m, 2H), 7.10 (t, 2H), 6.30 (s, 1H), 6.03-5.99 (m, 1H), 3.55 (s, 3H), 3.50-3.41 (m, 2H), 2.40 (s, 3H).

Example 64

4-(2-(4-(2-acetyl-5-chlorophenyl)-5-methoxy-2-oxopyridin-1(2H)-yl)-3-(2-bromophenyl)propanamido)benzoic acid 64

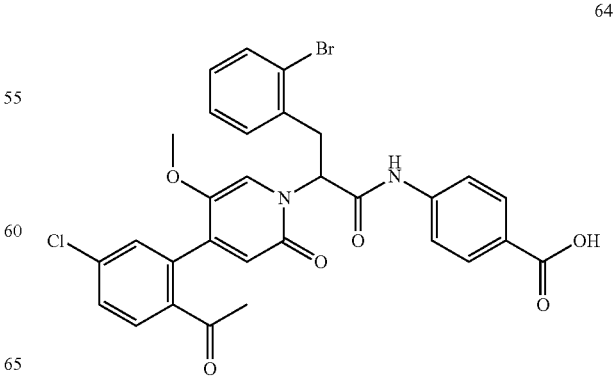

In accordance with the synthetic route of Example 7, the starting compound 7c was replaced with 1-bromo-2-(bromomethyl)benzene (prepared by a known method disclosed in "*Bioorganic & Medicinal Chemistry Letters,* 2014, 24(21), 5127-5133"), accordingly, the title compound 64 (8 mg) was prepared.

MS m/z (ESI): 625.3 [M+1]

$^1$H NMR (400 MHz, CD$_3$OD) δ 8.02-7.98 (m, 2H), 7.87 (d, 1H), 7.74-7.72 (m, 2H), 7.62-7.57 (m, 2H), 7.34 (d, 1H), 7.29-7.26 (m, 3H), 7.19-7.15 (m, 1H), 6.43 (s, 1H), 5.93-5.89 (m, 1H), 3.79-3.74 (m, 1H), 3.63-3.60 (m, 1H), 3.58 (s, 3H), 2.51 (s, 3H).

Example 65

4-(2-(4-(2-acetyl-5-chlorophenyl)-5-methoxy-2-oxopyridin-1(2H)-yl)-3-(2,4-difluorophenyl)propanamido)benzoic acid 65

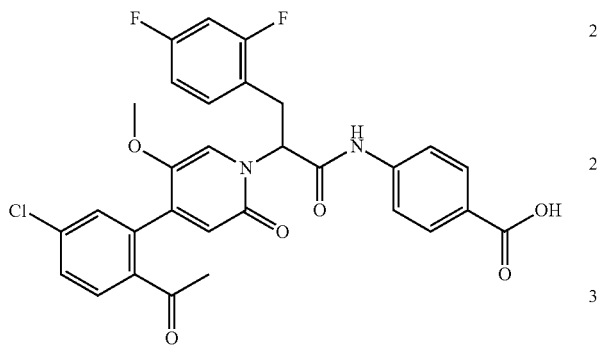

In accordance with the synthetic route of Example 7, the starting compound 7c was replaced with 1-(bromomethyl)-2,4-difluorobenzene (prepared by a method disclosed in the patent application "WO2012177638"), accordingly, the title compound 65 (8 mg) was prepared.

MS m/z (ESI): 581.4 [M+1]

$^1$H NMR (400 MHz, CD$_3$OD) δ 8.02-7.99 (m, 2H), 7.87 (d, 1H), 7.74-7.72 (m, 2H), 7.58 (dd, 1H), 7.36-7.28 (m, 3H), 6.98-6.90 (m, 2H), 6.41 (s, 1H), 5.91 (br, 1H), 3.63-3.59 (m, 4H), 3.52-3.46 (m, 1H), 2.52 (s, 3H).

Example 66

4-(2-(4-(2-acetyl-5-chlorophenyl)-5-methoxy-2-oxopyridin-1(2H)-yl)-3-(o-tolyl)propanamido)benzoic acid 66

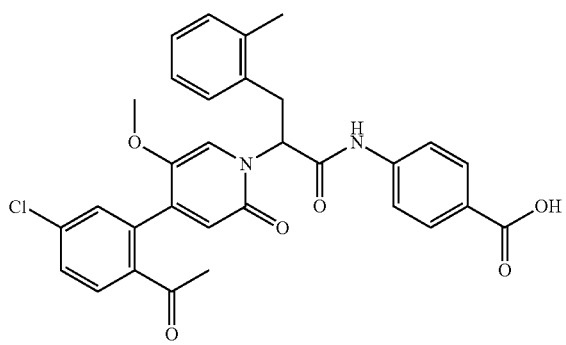

In accordance with the synthetic route of Example 7, the starting compound 7c was replaced with 1-(bromomethyl)-2-methylbenzene (prepared by a known method disclosed in "*Journal of Organic Chemistry,* 2014, 79(1), 223-229"), accordingly, the title compound 66 (60 mg) was prepared.

MS m/z (ESI): 559.2 [M+1]

$^1$H NMR (400 MHz, CDCl$_3$) δ 9.95 (s, 1H), 8.09 (d, 2H), 7.86 (d, 2H), 7.72 (d, 1H), 7.52-7.50 (m, 2H), 7.30 (s, 1H), 7.19-7.13 (m, 4H), 6.63 (s, 1H), 6.30 (s, 1H), 3.69-3.62 (m, 4H), 3.28-3.24 (m, 1H), 2.52-2.46 (m, 6H).

Example 67

4-(2-(4-(2-acetyl-5-chlorophenyl)-5-methoxy-2-oxopyridin-1(2H)-yl)-3-(m-tolyl)propanamido)benzoic acid 67

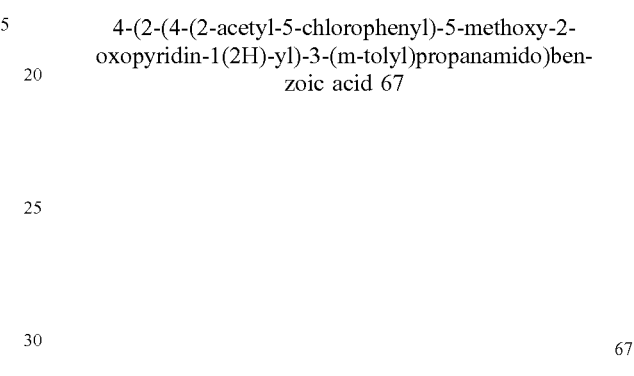

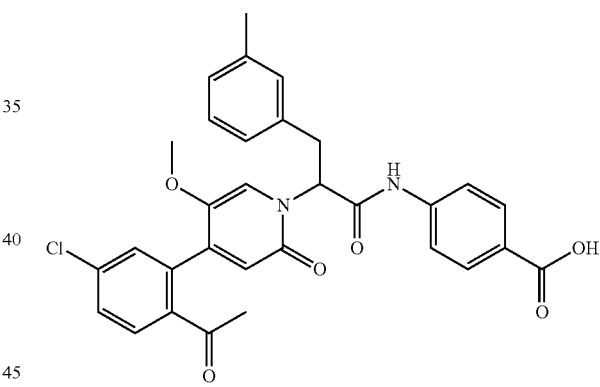

In accordance with the synthetic route of Example 7, the starting compound 7c was replaced with 1-(bromomethyl)-3-methylbenzene (prepared by a known method disclosed in "*Chemical Communications (Cambridge, United Kingdom),* 2014, 50 (28), 3692-3694), accordingly, the title compound 67 (80 mg) was prepared.

MS m/z (ESI): 559.2 [M+1]

$^1$H NMR (400 MHz, CDCl$_3$) δ 9.87 (s, 1H), 8.10 (d, 2H), 7.84-7.71 (m, 3H), 7.52-7.50 (m, 1H), 7.31 (s, 2H), 7.21-7.07 (m, 4H), 6.65 (s, 1H), 6.18 (s, 1H), 3.67-3.59 (m, 4H), 3.27-3.22 (m, 1H), 2.66 (s, 3H), 2.33 (s, 3H).

Example 68

4-(2-(4-(2-acetyl-5-chlorophenyl)-5-methoxy-2-oxopyridin-1(2H)-yl)-3-(2-fluorophenyl)propanamido)benzoic acid 68

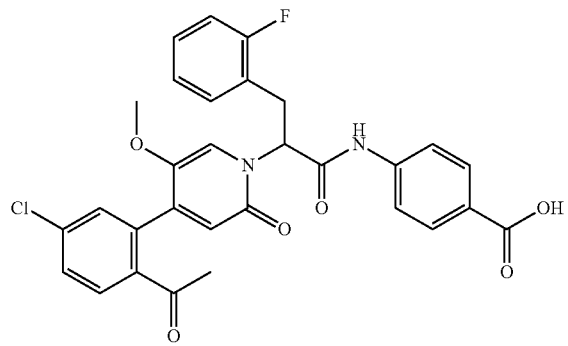

In accordance with the synthetic route of Example 7, the starting compound 7c was replaced with 1-(bromomethyl)-2-fluorobenzene (prepared by a known method disclosed in "*Tetrahedron Letters*, 2000, 41(27), 5161-5164"), accordingly, the title compound 68 (55 mg) was prepared.

MS m/z (ESI): 563.2 [M+1]

$^1$H NMR (400 MHz, DMSO-d$_6$) δ 10.73 (s, 1H), 7.90-7.89 (m, 1H), 7.90-7.89 (m, 1H), 7.84-7.82 (d, 1H), 7.73-7.72 (m, 1H), 7.71-7.70 (m, 1H), 7.62-7.60 (dd, 1H), 7.40-7.38 (d, 2H), 7.33-7.29 (m, 1H), 7.28-7.24 (m, 1H), 7.16-7.12 (m, 1H), 7.10-7.08 (m, 1H), 6.33 (s, 1H), 6.04-5.95 (m, 1H), 3.51 (s, 3H), 3.49-3.42 (m, 2H), 2.39 (s, 3H).

Example 69

4-(2-(4-(2-acetyl-5-chlorophenyl)-5-methoxy-2-oxopyridin-1(2H)-yl)-3-(4-chlorophenyl)propanamido)benzoic acid 69

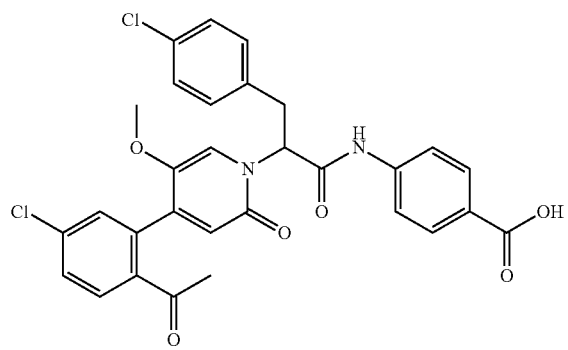

In accordance with the synthetic route of Example 4, the starting compound 4a was replaced with 2-bromo-3-(4-chlorophenyl)propionic acid (prepared by a method disclosed in the patent application "WO2012118216"), accordingly, the title compound 69 (15 mg) was prepared.

MS m/z (ESI): 579.5 [M+1]

$^1$H NMR (400 MHz, DMSO-d$_6$) δ 10.83 (s, 1H), 7.95-7.94 (m, 1H), 7.93-7.92 (n, 1H), 7.85-7.83 (d, 1H), 7.78-7.77 (m, 1H), 7.76-7.75 (m, 1H), 7.63-7.61 (n, 1H), 7.43-7.42 (m, 1H), 7.41-7.40 (m, 1H), 7.36-7.34 (m, 2H), 7.31-7.29 (m, 2H), 6.33 (s, 1H), 6.04-5.95 (m, 1H), 3.51 (s, 3H), 3.49-3.42 (m, 2H), 2.39 (s, 3H).

Example 70

4-(2-(4-(2-acetyl-5-chlorophenyl)-5-methoxy-2-oxopyridin-1(2H)-yl)-3-(2-chlorophenyl)propanamido)benzoic acid 70

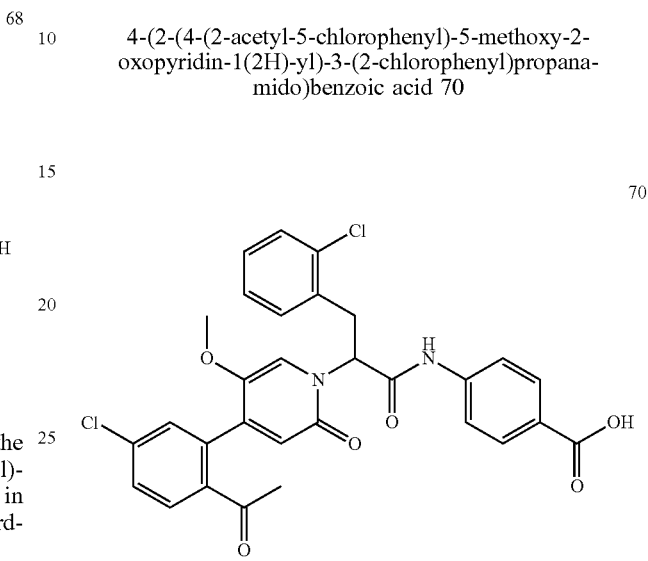

In accordance with the synthetic route of Example 7, the starting compound 7c was replaced with 1-(bromomethyl)-2-chlorobenzene (prepared by a known method disclosed in "*Tetrahedron Letters*, 2016, 57(2), 168-171"), accordingly, the title compound 70 (25 mg) was prepared.

MS m/z (ESI):579.2 [M+1]

$^1$H NMR (400 MHz, CDCl$_3$) δ 9.81 (s, 1H), 8.10 (d, 2H), 7.83 (d, 2H), 7.72 (d, 1H), 7.51 (d, 1H), 7.35-7.30 (m, 1H), 7.30-7.29 (m, 1H), 7.29-7.28 (m, 2H), 7.27-7.23 (m, 2H), 6.62 (s, 1H), 6.30 (s, 1H), 3.77-3.71 (m, 1H), 3.69 (s, 3H), 3.52-3.49 (m, 1H), 2.51 (s, 3H).

Example 71

4-(2-(4-(2-acetyl-5-chlorophenyl)-5-methoxy-2-oxopyridin-(2H)-yl)-3-(3-methoxyphenyl)propanamido)benzoic acid 71

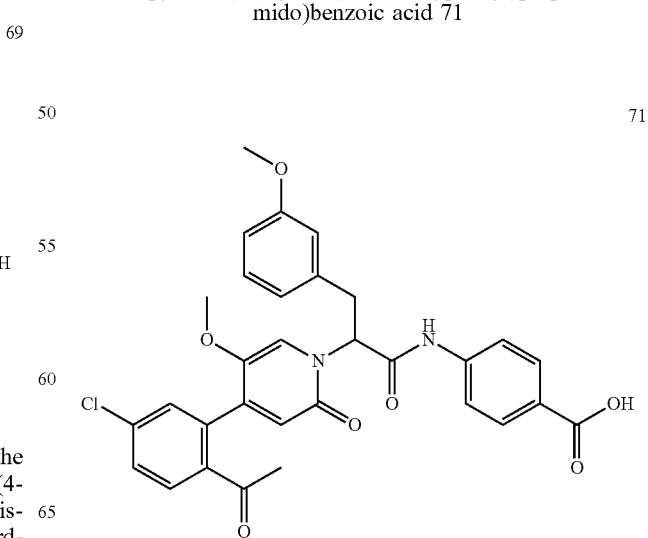

In accordance with the synthetic route of Example 7, the starting compound 7c was replaced with 1-(bromomethyl)-3-methoxybenzene (prepared by a method disclosed in the patent application "WO2014135095"), accordingly, the title compound 71 (48 mg) was prepared.

MS m/z (ESI):575.4 [M+1]

$^1$H NMR (400 MHz, DMSO-d$_6$) δ 10.83 (s, 1H), 7.91 (d, 2H), 7.82 (d, 1H), 7.73 (d, 2H), 7.61 (dd, 1H), 7.43 (s, 1H), 7.38 (s, 1H), 7.18 (t, 1H), 6.89-6.85 (m, 2H), 6.76 (dd, 1H), 6.32 (s, 1H), 6.06-6.02 (m, 1H), 3.70 (s, 3H), 3.54 (s, 3H), 3.47-3.44 (m, 2H), 2.37 (s, 3H).

Example 72

(S)-4-(2-(4-(2-acetyl-5-chlorophenyl)-5-methoxy-2-oxopyridin-1(2H)-yl)-3-(3-methoxyphenyl)propanamido)benzoic acid 72

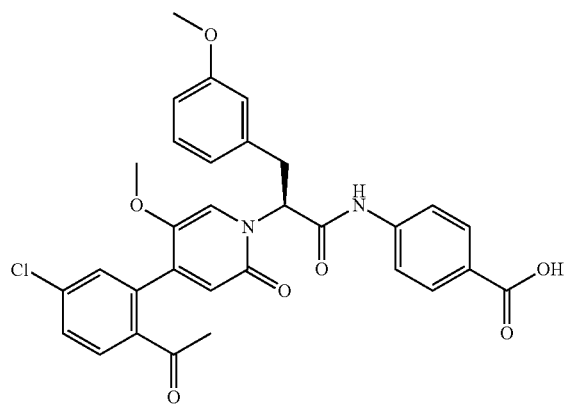

72

Compound 71 (48 mg, 83.48 μmol) was separated chirally (separation conditions: chiral preparative column CHIRAL PAK IF, 20*250 mm, 5 μm; mobile phase: ethanol (containing 0.01% trifluoroacetic acid)=100, flow rate: 7 mL/min). The corresponding fractions were collected and concentrated under reduced pressure to obtain the title compound 72 (18 mg).

MS m/z (ESI): 575.4 [M+1]

Chiral HPLC analysis: retention time 8.546 min, chiral purity: 98% (chromatographic column: Lux Amylose-1 (AD) 4.6*150 mm 5 μm (with a guard column); mobile phase: ethanol (containing 0.1% trifluoroacetic acid)/n-hexane=50/50 (v/v)).

$^1$H NMR (400 MHz, DMSO-d$_6$) δ 12.69 (s, 1H), 10.88 (s, 1H), 7.92 (d, 2H), 7.82 (d, 1H), 7.76 (d, 2H), 7.61 (dd, 1H), 7.42 (s, 1H), 7.38 (s, 1H), 7.18 (t, 1H), 6.90-6.86 (m, 2H), 6.76 (dd, 1H), 6.32 (s, 1H), 6.05-6.01 (m, 1H), 3.70 (s, 3H), 3.54 (s, 3H), 3.48-3.42 (m, 2H), 2.37 (s, 3H).

Example 73 methyl 4-(2-(4-(2-acetyl-5-chlorophenyl)-5-methoxy-2-oxopyridin-1 (2H)-yl)-3-(2-chlorophenyl)propanamido)benzoate 73

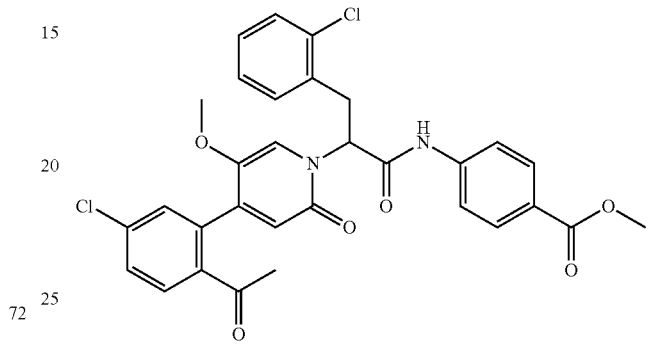

73

In accordance with the synthetic route of compound 7f, the starting compound 7c was replaced with 1-(bromomethyl)-2-chlorobenzene (prepared by a known method disclosed in "Tetrahedron Letters, 2016, 57(2), 168-171"), accordingly, the title compound 73 (70 mg) was prepared.

MS m/z (ESI):593.4 [M+1]

$^1$H NMR (400 MHz, CDCl$_3$) δ 10.17 (s, 1H), 8.00 (d, 2H), 7.69-7.62 (m, 3H), 7.49 (d, 1H), 7.31 (d, 2H), 7.25-7.16 (m, 4H), 6.47 (s, 1H), 6.23 (s, 1H), 3.93 (s, 3H), 3.76-3.74 (m, 1H), 3.65 (s, 3H), 3.55-3.52 (m, 1H), 2.48 (s, 3H).

Example 74

4-(2-(4-(2-acetyl-5-chlorophenyl)-5-methoxy-2-oxopyridin-1(2H)-yl)-3-(p-tolyl)propanamido)benzoic acid 74

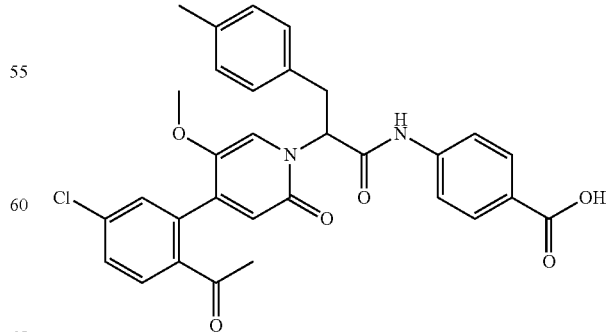

74

239
-continued

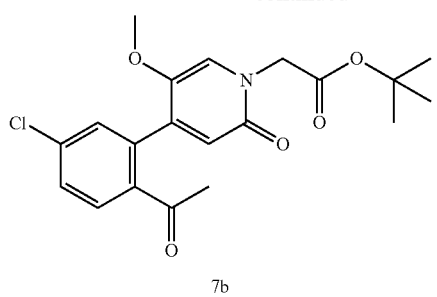
7b

+

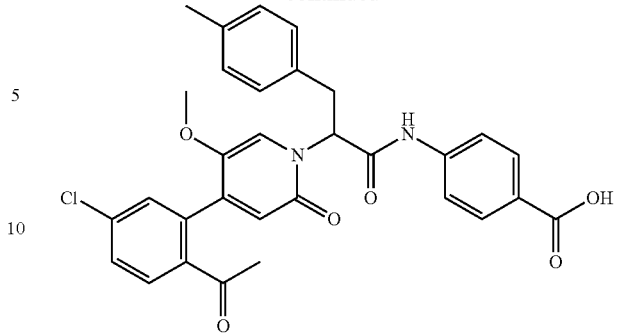
74

Step 1 tert-butyl 2-(4-(2-acetyl-5-chlorophenyl)-5-methoxy-2-oxopyridin-1(2H)-yl)-3-(p-tolyl)propanoate 74b Compound 7b (100 mg, 0.26 mmol) and 1-(bromomethyl)-4-methylbenzene 74a (94.45 mg, 0.51 mmol, prepared by a known method disclosed in "*Tetrahedron Letters*, 2016, 57(22), 2430-2433") were dissolved in 6 mL of tetrahydrofuran. The reaction solution was cooled to −78° C., dropwise added with lithium bis(trimethylsilyl)amide solution (1.02 mL, 1.02 mmol), and stirred for 2 hours. The reaction solution was added with 15 mL of saturated ammonium chloride solution to quench the reaction, and then warmed up to room temperature, and extracted with ethyl acetate (50 mL×2). The organic phases were combined, dried over anhydrous sodium sulfate, and filtered. The filtrate was concentrated under reduced pressure, and the resulting residue was purified by silica gel column chromatography with elution system B to obtain the title compound 74b (120 mg, yield: 94.8%).
MS m/z (ESI): 496.2 [M+1]

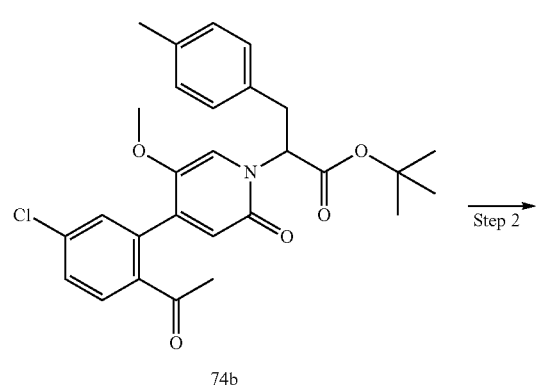
74b

Step 2

2-(4-(2-acetyl-5-chlorophenyl)-5-methoxy-2-oxopyridin-1(2H)-yl)-3-(p-tolyl)propanoic acid 74c Compound 74b (100 mg, 0.20 mmol) was dissolved in 4 mL of dichloromethane, and then trifluoroacetic acid (0.5 mL) was added dropwise. The reaction solution was stirred for 5 hours, and then concentrated under reduced pressure to obtain the crude title compound 74c (80 mg), which was directly used in the next reaction step without purification.
MS m/z (ESI): 440.0 [M+1]

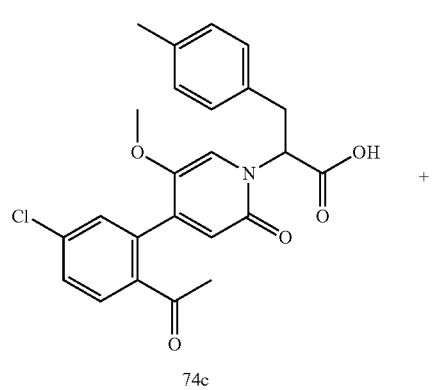
74c

+

8j

Step 3

Step 3

4-(2-(4-(2-acetyl-5-chlorophenyl)-5-methoxy-2-oxopyridin-1(2H)-yl)-3-(p-tolyl)propanamido)benzoic acid 74

The crude compound 74c (80 mg, 0.18 mmol) and compound 8j (68.52 mg, 0.27 mmol) were dissolved in 10 mL of ethyl acetate, and then N,N-diisopropylethylamine (112.43 mg, 0.87 mmol) and a solution of 2,4,6-tripropyl-1,3,5,2,4,6-trioxatriphosphorinane-2,4,6-trioxide in ethyl acetate (50%, 415.18 mg, 0.65 mmol) were added dropwise. After completion of the addition, the reaction solution was warmed up to 60° C., and stirred for 2 hours. The reaction solution was added with 15 mL of water, and extracted with ethyl acetate (15 mL×2). The organic phases were combined, washed with saturated sodium chloride solution (15 mL×2), dried over anhydrous sodium sulfate, and filtered. The filtrate was concentrated under reduced pressure, and the resulting residue was purified by high performance liquid chromatography (Waters 2767-SQ detecor2, elution system: acetonitrile, water) to obtain the title compound 74 (40 mg, yield: 39.4%).

MS m/z (ESI):559.1 [M+1]

$^1$H NMR (400 MHz, CDCl$_3$) δ 9.92 (s, 1H), 8.10 (d, 2H), 7.84 (d, 2H), 7.71 (d, 1H), 7.56-7.50 (m, 2H), 7.30 (s, 1H), 7.23-7.11 (m, 4H), 6.64 (s, 1H), 6.20 (s, 1H), 3.67-3.59 (m, 4H), 3.27-3.22 (m, 1H), 2.49 (s, 3H), 2.31 (s, 3H).

Example 75

4-(3-(4-acetamidophenyl)-2-(4-(2-acetyl-5-chlorophenyl)-5-methoxy-2-oxopyridin-1(2H)-yl)propanamido)benzoic acid 75

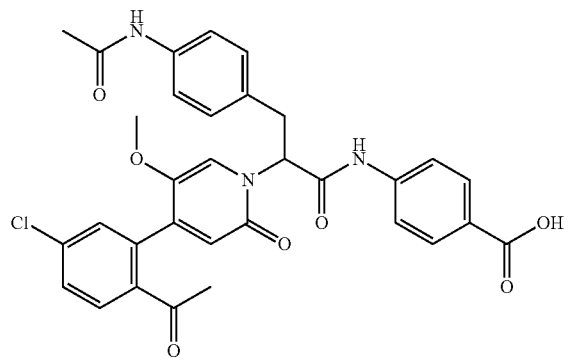

In accordance with the synthetic route of Example 16, the starting compound propionyl chloride was replaced with acetyl chloride, accordingly, the title compound 75 (10 mg) was prepared.

MS m/z (ESI): 602.4 [M+1]

$^1$H NMR (400 MHz, DMSO-d$_6$) δ 10.88 (s, 1H), 9.89 (s, 1H), 7.92 (d, 2H), 7.83 (d, 1H), 7.76 (d, 2H), 7.61 (dd, 1H), 7.46 (d, 2H), 7.41 (d, 2H), 7.18 (d, 2H), 6.30 (s, 1H), 6.00-5.96 (m, 1H), 3.55 (s, 3H), 3.42-3.39 (m, 2H), 2.39 (s, 3H), 2.00 (s, 3H).

Example 76

4-(2-(4-(2-acetyl-5-chlorophenyl)-5-methoxy-2-oxopyridin-1(2H)-yl)-3-(2,6-dichlorophenyl)propanamido)benzoic acid 76

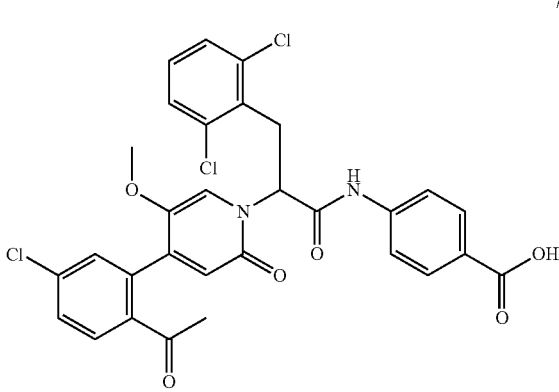

In accordance with the synthetic route of Example 74, the starting compound 74a was replaced with 2-(bromomethyl)-1,3-dichlorobenzene (prepared by a known method disclosed in "*Organic Letters*, 2017, 19(7), 1634-1637"), accordingly, the title compound 76 (20 mg) was prepared.

MS m/z (ESI):613.1 [M+1]

$^1$H NMR (400 MHz, CD$_3$OD) δ 8.00 (dd, 2H), 8.86-7.88 (m, 1H), 7.74-7.70 (m, 2H), 7.52-7.50 (m, 1H), 7.42-7.40 (m, 2H), 7.34 (d, 2H), 7.25 (t, 1H), 6.87 (s, 1H), 6.42 (s, 1H), 3.92-3.82 (m, 1H), 3.64-3.52 (m, 4H), 2.51 (d, 3H).

Example 77

4-(2-(4-(2-acetyl-5-chlorophenyl)-5-methoxy-2-oxopyridin-1 (2H)-yl)-3-(5-fluoro-2-methylphenyl)propanamido)benzoic acid 77

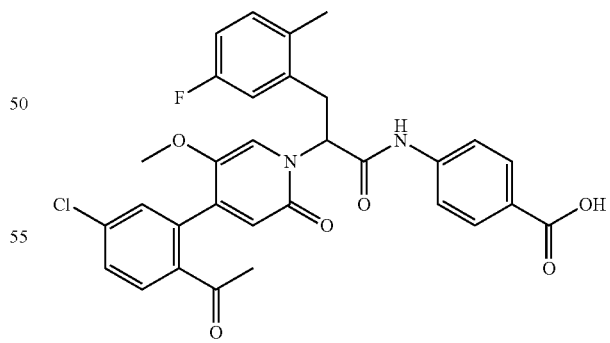

In accordance with the synthetic route of Example 7, the starting compound 7c was replaced with 2-(bromomethyl)-4-fluoro-1-methylbenzene (Adamas), accordingly, the title compound 77 (30 mg) was prepared.

MS m/z (ESI):577.2 [M+1]

$^1$H NMR (400 MHz, CDCl$_3$) δ 9.94 (s, 1H), 8.11 (d, 2H), 7.87 (d, 2H), 7.73 (d, 1H), 7.53-7.50 (m, 2H), 7.31 (s, 1H), 7.15-7.14 (m, 1H), 6.87-6.66 (m, 2H), 6.66 (s, 1H), 6.28 (s, 1H), 3.70-3.59 (m, 4H), 3.23-3.19 (m, 1H), 2.53 (s, 3H), 2.46 (s, 3H).

Example 78

4-(2-(4-(2-acetyl-5-chlorophenyl)-5-methoxy-2-oxopyridin-1(2H)-yl)-3-(2-methoxyphenyl)propanamido)benzoic acid 78

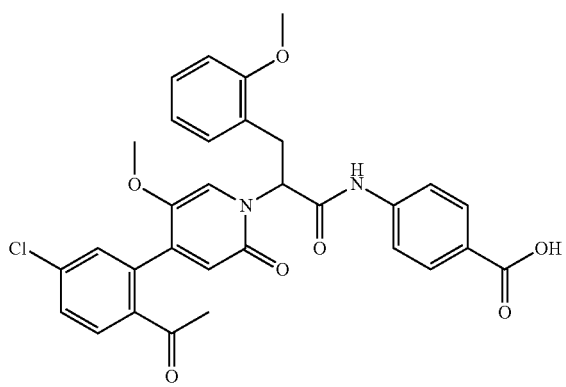

78

In accordance with the synthetic route of Example 74, the starting compound 74a was replaced with 1-(bromomethyl)-2-methoxybenzene (prepared by a known method disclosed in "*Journal of the American Chemical Society,* 2013, 135 (30), 10934-10937"), accordingly, the title compound 78 (60 mg) was prepared.

MS m/z (ESI):575.0 [M+1]

$^1$H NMR (400 MHz, DMSO-d$_6$) δ 7.90 (d, 2H), 7.82 (d, 1H), 7.73 (d, 2H), 7.60 (dd, 1H), 7.37 (s, 1H), 7.25 (s, 1H), 7.21-7.14 (m, 2H), 6.94 (d, 1H), 6.82 (t, 1H), 6.31 (s, 1H), 5.91-5.87 (m, 1H), 3.75 (s, 3H), 3.48 (s, 3H), 3.38 (d, 2H), 2.39 (s, 3H).

Example 79

4-(2-(4-(2-acetyl-5-chlorophenyl)-5-methoxy-2-oxopyridin-1(2H)-yl)-3-(pyridin-2-yl)propanamido)benzoic acid 79

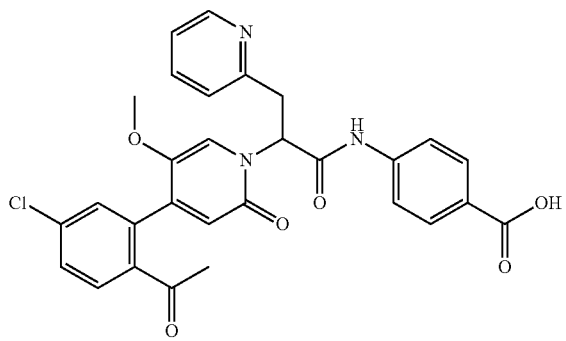

79

In accordance with the synthetic route of Example 74, the starting compound 74a was replaced with 2-(bromomethyl)pyridine (prepared by a known method disclosed in "*Journal of the American Chemical Society,* 2016, 138(26), 8253-8258"), accordingly, the title compound 79 (370 mg) was prepared.

MS m/z (ESI):546.4 [M+1]

$^1$H NMR (400 MHz, CD$_3$OD) δ 8.72 (d, 1H), 8.29-8.25 (m, 1H), 8.00 (d, 2H), 7.91 (d, 1H), 7.75-7.71 (m, 4H), 7.59 (dd, 1H), 7.35 (d, 1H), 7.25 (s, 1H), 6.40 (s, 1H), 6.09-5.87 (m, 1H), 3.98-3.94 (m, 1H), 3.80-3.76 (m, 1H), 3.59 (s, 3H), 2.56 (s, 3H).

Examples 80, 81

(S)-4(2-(4-(2-acetyl-5-chlorophenyl)-5-methoxy-2-oxopyridin-1(2H)-yl)-3-(pyridin-2-yl)propanamido)benzoic acid 80

(R)-4-(2-(4-(2-acetyl-5-chlorophenyl)-5-methoxy-2-oxopyridin-1(2H)-yl)-3-(pyridin-2-yl)propanamido)benzoic acid 81

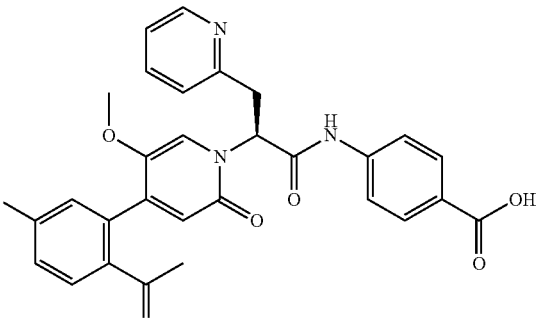

80

81

Compound 79 (370 mg, 677.69 μmol) was separated chirally (separation conditions: chiral preparative column CHIRAL PAK IF, 20*250 mm, 5 μm; mobile phase: n-hexane:ethanol=50:50, flow rate: 10.0 mL/min). The corresponding fractions were collected and concentrated under reduced pressure to obtain the title compound 80 (120 mg) and compound 81 (120 mg).

Compound 80:

MS m/z (ESI):546.2 [M+1]

Chiral HPLC analysis: retention time 9.971 minutes, (chromatographic column: Lux Amylose-1 (AD) 4.6*150 mm, 5 μm (with a guard column); mobile phase: n-hexane/ethanol (containing 0.1% trifluoroacetic acid)=50/50 (v/v)).

Compound 81:

MS m/z (ESI): 546.2 [M+1]

Chiral HPLC analysis: retention time 6.219 minutes, (chromatographic column: Lux Amylose-1 (AD) 4.6*150 mm, 5 μm (with a guard column): mobile phase: n-hexane/ethanol (containing 0.1% trifluoroacetic acid)=50/50 (v/v)).

Example 82

4-(2-(4-(2-acetyl-5-chlorophenyl)-5-methoxy-2-oxopyridin-1(2H)-yl)-3-(pyridin-3-yl)propanamido)benzoic acid 82

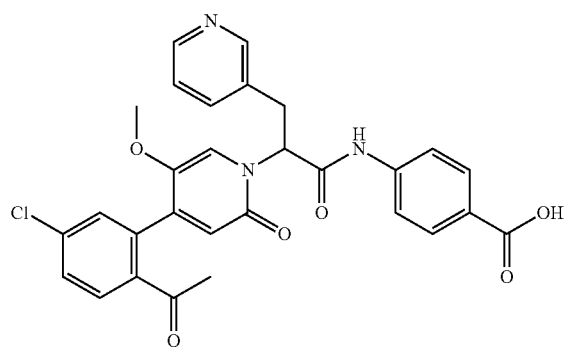

82

In accordance with the synthetic route of Example 74, the starting compound 74a was replaced with 3-(bromomethyl)pyridine (prepared by a known method disclosed in "*Chemical Communications* (*Cambridge, United Kingdom*), 2016, 52(82), 12159-12162"), accordingly, the title compound 82 (30 mg) was prepared.

MS m/z (ESI):546.2 [M+1]

$^1$H NMR (400 MHz, CD$_3$OD) δ 8.76-8.72 (m, 2H), 8.42 (d, 1H), 8.03-7.92 (m, 5H), 7.76 (d, 2H), 7.62-7.59 (m, 1H), 7.37 (s, 2H), 6.36 (s, 1H), 3.84-3.63 (m, 5H), 2.59 (s, 3H).

Examples 83, 84

(R)-4-(2-(4-(2-acetyl-5-chlorophenyl)-5-methoxy-2-oxopyridin-1(2H)-yl)-3-(pyridin-3-yl)propanamido)benzoic acid 83

(S)-4-(2-(4-(2-acetyl-5-chlorophenyl)-5-methoxy-2-oxopyridin-1(2H)-yl)-3-(pyridin-3-yl)propanamido)benzoic acid 84

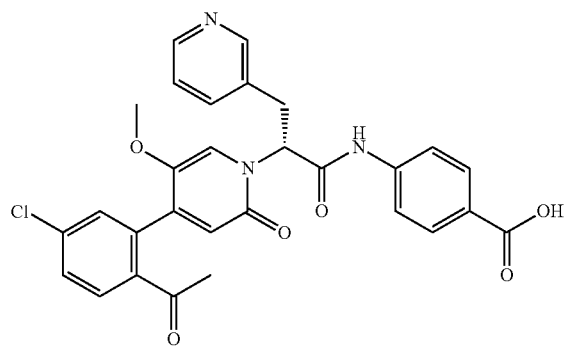

83

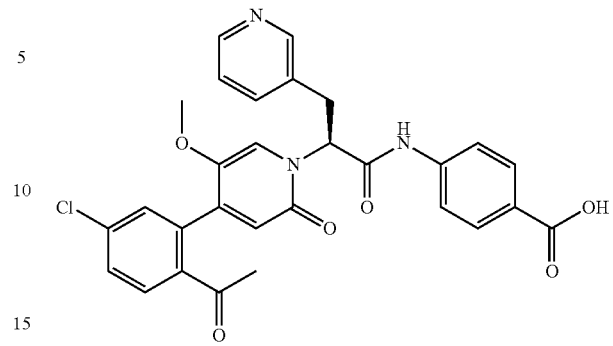

84

Compound 82 (30) mg, 549.48 μmol) was separated chirally (separation conditions: chiral preparative column CHIRAL PAK IF, 20*250 mm, 5 μm; mobile phase: n-hexane:ethanol (containing 0.01% trifluoroacetic acid)=50:50, Flow rate: 12.0 mL/min). The corresponding fractions were collected and concentrated under reduced pressure to obtain the title compound 83 (120 mg) and compound 84 (120 mg).

Compound 83:

MS m/z (ESI):546.1 [M+1]

Chiral HPLC analysis: retention time 3.723 minutes, (chromatographic column: CHIRAL PAK IF 4.6*150 mm, 5 μm (with a guard column); mobile phase: n-hexane/ethanol (containing 0.1% trifluoroacetic acid)=50/50 (v/v)).

Compound 84:

MS m/z (ESI): 546.1 [M+1]

Chiral HPLC analysis: retention time 7.315 minutes, (chromatographic column: CHIRAL PAK IF 4.6*150 mm, 5 μm (with a guard column), mobile phase: n-hexane/ethanol (containing 0.1% trifluoroacetic acid)=50/50 (vi v)).

$^1$H NMR (400 MHz; CD$_3$OD) δ 8.76-8.72 (m, 2H), 8.42 (d, 1H), 8.03-7.92 (m, 5H), 7.76 (d, 2H), 7.62-7.59 (m, 1H), 7.37 (s, 2H), 6.36 (s, 1H), 3.84-3.63 (m, 5H), 2.59 (s, 3H).

Example 85

(S)-4-(2-(4-(2-acetyl-5-chlorophenyl)-5-methoxy-2-oxopyridin-1(2H)-yl)-3-(pyridin-2-yl)propanamido)benzamide 85

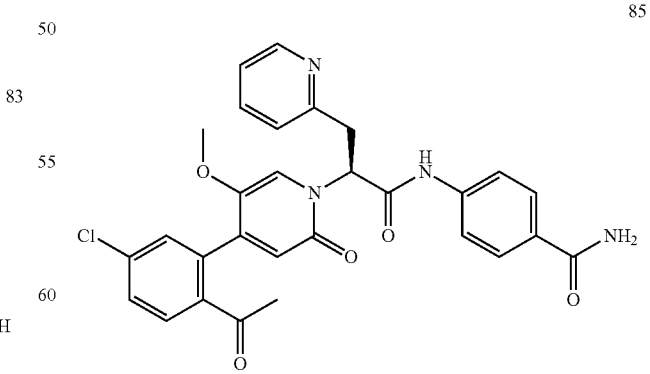

85

In accordance with the synthetic route of Example 11, the starting compound 5 was replaced with compound 80, accordingly, the title compound 85 (18 mg) was prepared.

MS m/z (ESI): 545.1 [M+1]
¹H NMR (400 MHz, CD₃OD) δ 8.51 (d, 1H), 7.88-7.84 (m, 3H), 7.78-7.74 (dd, 1H), 7.72 (d, 2H), 7.57-7.55 (dd, 1H), 7.35-7.32 (m, 3H), 7.30-7.27 (m, 1H), 6.39 (s, 1H), 6.06 (t, 1H), 3.79-3.74 (dd, 1H), 3.64-3.58 (m, 4H), 2.49 (m, 3H).

Example 86

4-(2-(4-(2-acetyl-5-chlorophenyl)-5-methoxy-2-oxopyridin-1(2H)-yl)-3-(pyridin-4-yl)propanamido)benzoic acid 86

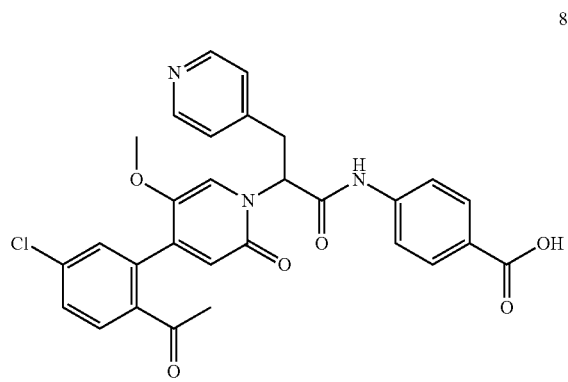

In accordance with the synthetic route of Example 74, the starting compound 74a was replaced with 4-(bromomethyl)pyridine hydrobromide (prepared by a known method disclosed in "*Chemical Communications* (*Cambridge, United Kingdom*), 2011, 47(5), 1482-1484"), accordingly, the title compound 86 (20 mg) was prepared.
MS m/z (ESI):546.2 [M+1]

Example 87

4-(2-(4-(2-acetyl-5-chlorophenyl)-5-methoxy-2-oxopyridin-1(2H)-yl)-3-(2-cyanophenyl)propanamido)benzoic acid 87

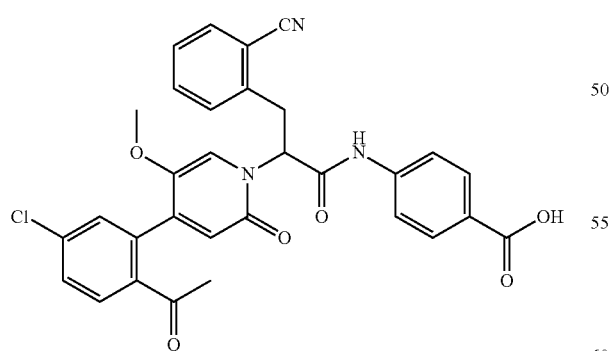

In accordance with the synthetic route of Example 7, the starting compound 7c was replaced with 2-(bromomethyl)benzonitrile (prepared by a known method disclosed in "*Journal of Organic Chemistry,* 2014, 79 (23), 11592-11608"), accordingly, the title compound 87 (15 mg) was prepared.

MS m/z (ESI):570.1 [M+1]
¹H NMR (400 MHz, DMSO-d₆) δ 12.75 (s, 1H), 10.69 (s, 1H), 7.92 (s, 1H), 7.90 (s, 1H), 7.86-7.84 (d, 1H), 7.83 (m, 1H), 7.74 (s, 1H), 7.72 (s, 1H), 7.64-7.60 (m, 2H), 7.45-7.41 (m, 2H), 7.39-7.38 (d, 1H), 7.30 (s, 1H), 6.33 (s, 1H), 6.04-5.95 (m, 1H), 3.76-3.70 (m, 1H), 3.59-3.54 (m, 1H), 3.51 (s, 3H), 2.43 (s, 3H).

Example 88

4-(2-(4-(2-acetyl-5-chlorophenyl)-5-methoxy-2-oxopyridin-1(2H)-yl)-3-(3-cyanophenyl)propanamido)benzoic acid 88

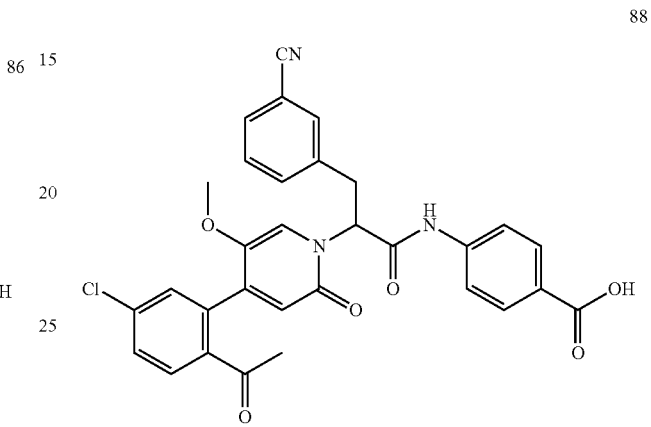

In accordance with the synthetic route of Example 7, the starting compound 7c was replaced with 3-(bromomethyl)benzonitrile (prepared by a known method disclosed in "*ChemMedChem,* 2015, 10(4), 688-714"), accordingly, the title compound 88 (25 mg) was prepared.
MS m/z (ESI):570.4 [M+1]
¹H NMR (400 MHz, DMSO-d₆) δ 10.78 (s, 1H), 7.94-7.93 (m, 1H), 7.92-7.91 (m, 1H), 7.86-7.84 (d, 1H), 7.77-7.68 (m, 4H), 7.62-7.60 (dd, 1H), 7.59-7.57 (d, 1H), 7.52-7.48 (m, 1H), 7.44 (s, 1H), 7.38 (s, 1H), 6.30 (s, 1H), 6.04-6.00 (m, 1H), 3.62-3.50 (m, 5H), 2.41 (s, 3H).

Example 89

(S)-4-(2-(4-(2-acetyl-5-chlorophenyl)-5-methoxy-2-oxopyridin-1(2H)-yl)-3-(3-cyanophenyl)propanamido)benzoic acid 89

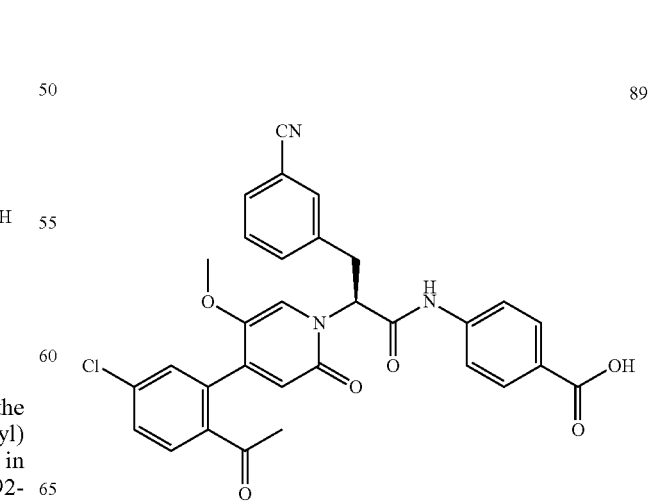

Compound 88 (350 mg, 614.04 μmol) was separated chirally (separation conditions: chiral preparative column CHIRAL PAK IF, 20*250 mm; mobile phase: n-hexane:ethanol:trifluoroacetic acid=50:50:0.06, flow rate: 10.0 mL/min), accordingly, the title compound 89 (60 mg) was prepared.

MS m/z (ESI): 570.1 [M+1]

Chiral HPLC analysis: retention time 12.723 minutes. (chromatographic column: CHIRALPAK IE 150*4.6 mm, 5 μm (with a guard column); mobile phase: n-hexane/ethanol (containing 0.01% trifluoroacetic acid)=50/50 (v/v)).

$^1$H NMR (400 MHz, CD$_3$OD) δ 8.01-8.00 (m, 1H), 7.98-7.97 (m, 1H), 7.87-7.85 (d, 1H), 7.73-7.71 (m, 1H), 7.70-7.69 (m, 2H), 7.61-7.55 (m, 3H), 7.50-7.46 (m, 1H), 7.38 (s, 1H), 7.34-7.33 (d, 1H), 6.39 (s, 1H), 5.95-5.85 (m, 1H), 3.65-3.60 (m, 1H) 3.59 (s, 3H), 3.50-3.45 (m, 1H), 2.46 (s, 3H).

Example 90

4-(2-(4-(2-acetyl-5-chlorophenyl)-5-methoxy-2-oxopyridin-1(2H)-yl)-3-(4-cyanophenyl)propanamido)benzoic acid 90

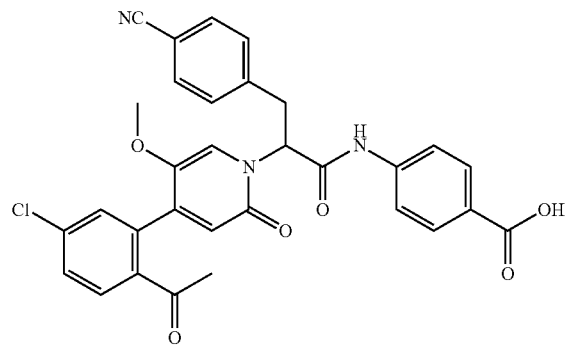

90

In accordance with the synthetic route of Example 74, the starting compound 74a was replaced with 4-(bromomethyl)benzonitrile (prepared by a known method disclosed in "*Organic & Biomolecular Chemistry*, 2017, 15(12), 2551-2561"), accordingly, the title compound 90 (15 mg) was prepared.

MS m/z (ESI):570.5 [M+1]

$^1$H NMR (400 MHz, DMSO-d$_6$) δ 10.82 (s, 1H), 7.94-7.93 (m, 1H), 7.92-7.91 (m, 1H), 7.85-7.83 (d, 1H), 7.77-7.74 (m, 4H), 7.62-7.59 (dd, 1H), 7.48 (s, 1H), 7.45 (s, 1H), 7.40-7.39 (m, 1H), 7.38-7.36 (d, 1H), 6.29 (s, 1H), 6.04-6.00 (m, 1H), 3.67-3.65 (m, 1H), 3.64-3.54 (m, 4H), 2.39 (s, 3H).

Example 91

4-(2-(4-(5-chloro-2-propionylphenyl)-5-methoxy-2-oxopyridin-(2H)-yl)-3-(1-cyclopropyl-1H-pyrazol-3-yl)propanamido)benzoic acid 91

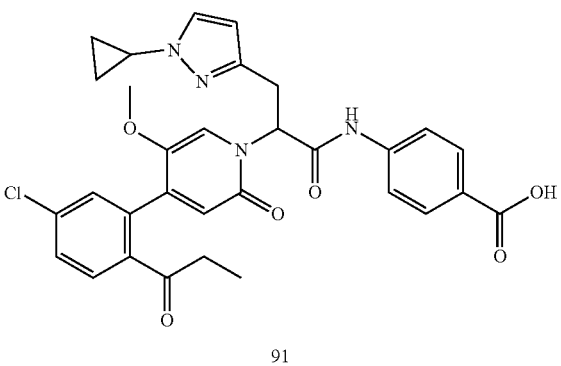

91

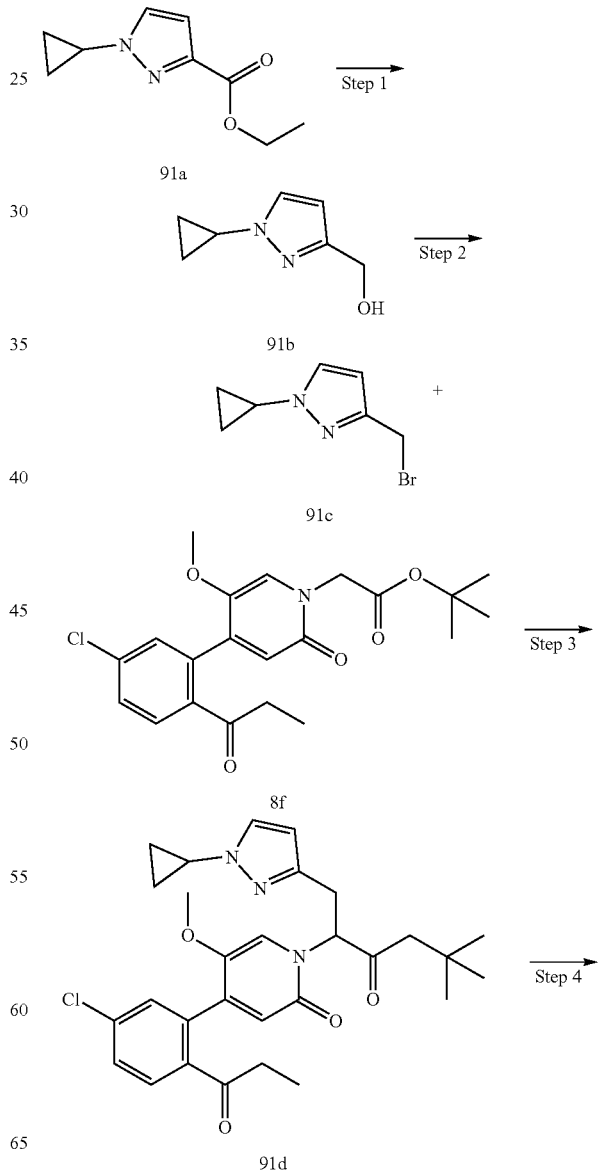

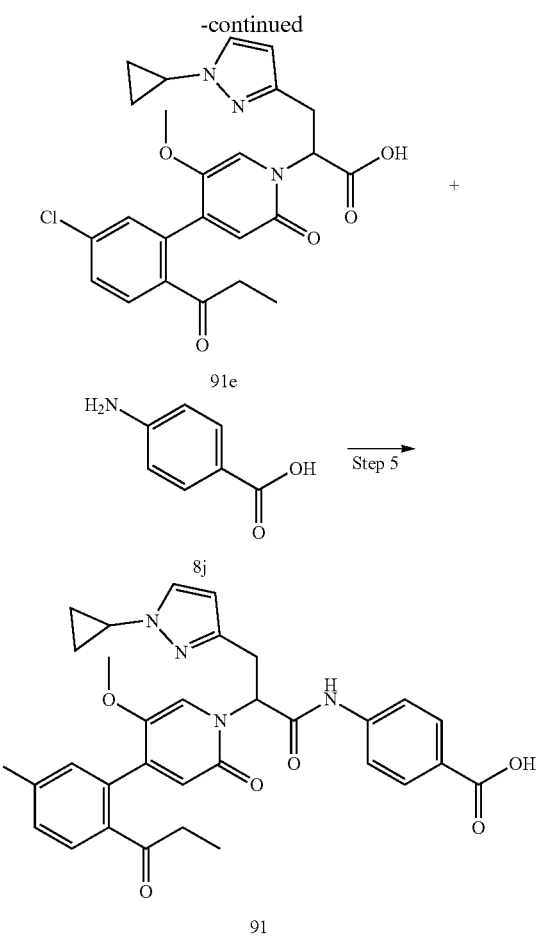

Step 1

(1-cyclopropyl-1H-pyrazol-3-yl)methanol 91b

Ethyl 1-cyclopropyl-1H-pyrazol-3-carboxylate 91a (500 mg, 2.77 mmol, prepared by a method disclosed in the patent application "US20140349990") was dissolved in 15 mL of tetrahydrofuran, and then lithium aluminum hydride (527.18 mg, 13.87 mmol) was added at 0° C. After stirring for 1 hour at 0° C., the reaction solution was added with 3 mL of sodium bicarbonate solution to quench the reaction, stirred until the gray solid disappeared, and filtered. The filtrate was dried over anhydrous sodium sulfate and concentrated under reduced pressure to obtain the crude title compound 91b (300 mg), which was directly used in the next reaction step without purification.
MS m/z (ESI):139.2 [M+1]

Step 2

3-(bromomethyl)-1-cyclopropyl-1H-pyrazole 91c

The crude compound 91b (350 mg, 2.53 mmol) was dissolved in dichloromethane (5 mL), and then phosphorus tribromide (2.06 g, 7.60 mmol) was added dropwise. After stirring for 16 hours, the reaction solution was added with 20 mL of saturated sodium bicarbonate solution to quench the reaction, and extracted with dichloromethane (20 mL×3). The organic phases were combined, dried over anhydrous sodium sulfate, and filtered. The filtrate was concentrated under reduced pressure to obtain the crude title compound 91c (400 mg), which was directly used in the next reaction step without purification.

Step 3 tert-butyl 2-(4-(5-chloro-2-propionylphenyl)-5-methoxy-2-oxopyridin-1(2H)-yl)-3-(1-cyclopropyl-1H-pyrazol-3-yl) propionate 91d Compound 8f (100 mg, 246.38 μmol) and the crude compound 91c (99.08 mg, 492.77 μmol) were dissolved in 10 mL of tetrahydrofuran. After cooling to −78° C., the reaction solution was dropwise added with lithium bis(trimethylsilyl)amide solution (0.985 mL, 985.53 μmol), and stirred for 6 hours. At −78° C., the reaction solution was slowly added with 2 mL of saturated ammonium chloride solution to quench the reaction, and then warmed up to room temperature naturally. The reaction solution was added with 10 mL of water, and extracted with ethyl acetate (20 mL×3). The organic phases were combined, washed with saturated sodium chloride solution (20 mL×2), dried over anhydrous sodium sulfate, and filtered. The filtrate was concentrated under reduced pressure, and the resulting residue was purified by silica gel column chromatography with elution system B to obtain the title compound 91d (90 mg, yield: 69.4°%).
MS m/z (ESI):526.2 [M+1]

Step 4

2-(4-(5-chloro-2-propionylphenyl)-5-methoxy-2-oxopyridin-1(2H)-yl)-3-(1-cyclopropyl-1H-pyrazol-3-yl)propionic acid 91e Compound 91d (90 mg, 171.1 μmol) was dissolved in 5 mL of dichloromethane, and then trifluoroacetic acid (195.09 mg, 1.71 mmol) was added dropwise. After stirring for 2 hours, the reaction solution was concentrated under reduced pressure to obtain the crude title compound 91e (80 mg), which was directly used in the next reaction step without purification.
MS m/z (ESI): 470.4 [M+1]

Step 5

44-(2-(4-(5-chloro-2-propionylphenyl)-5-methoxy-2-oxopyridin-1(2H)-yl)-3-(1-cyclopropyl-1H-pyrazol-3-yl)propanamido)benzoic acid 91

The crude compound 91e (90 mg, 191.52 μmol) and the compound 8j (31.52 mg, 229.83 μmol) were dissolved in 5 mL of ethyl acetate, followed by dropwise addition of N,N-diisopropylethylamine (123.76 mg, 957.62 μmol) and a solution of 2,4,6-tripropyl-1,3,5,2,4,6-trioxatriphosphorinane-2,4,6-trioxide in ethyl acetate (50%, 365.64 mg, 574.57 μmol). After completion of the addition, the reaction solution was warmed up to 60° C., and stirred for 2 hours. The reaction solution was added with 15 mL of water, and extracted with dichloromethane (15 mL×2). The organic phases were combined, washed with saturated sodium chloride solution (15 mL×2), dried over anhydrous sodium sulfate, and filtered. The filtrate was concentrated under reduced pressure, and the resulting residue was purified by high performance liquid chromatography (Waters 2767, elution system: acetonitrile, water) to obtain the title compound 91 (50 mg, yield: 44.3%).

MS m/z (ESI): 589.3 [M+1]

$^1$H NMR (400 MHz, CDCl$_3$) δ 9.96 (s, 1H), 8.13 (d, 2H), 7.85 (d, 2H), 7.70 (d, 1H), 7.50 (d, 1H), 7.37 (d, 2H), 6.65 (s, 1H), 6.28 (s, 1H), 6.15 (s, 1H), 3.77-3.42 (m, 6H), 2.91 (s, 2H), 1.18-1.15 (m, 3H), 1.10-1.05 (m, 4H).

Example 92

(S)-4-(2-(4-(5-chloro-2-propionylphenyl)-5-methoxy-2-oxopyridin-1(2H)-yl)-3-(1-cyclopropyl-1H-pyrazol-3-yl)propanamido)benzoic acid 92

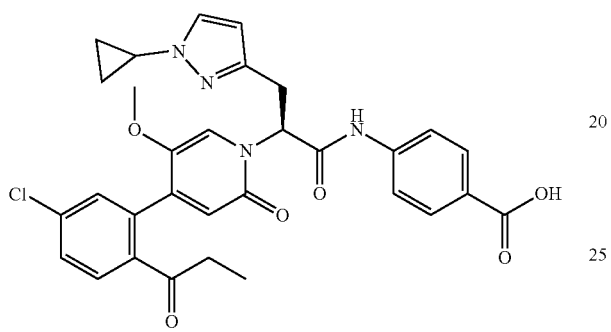

92

Compound 91 (32 mg, 54.33 μmol) was separated chirally (separation conditions: chiral preparative column CHIRAL PAK IE, 20*250 mm, 5 μm; mobile phase: n-hexane:ethanol (containing 0.01% trifluoroacetic acid)=40:60, flow rate: 10.0 mL/min). The corresponding fractions were collected and concentrated under reduced pressure to obtain the title compound 92 (10 mg).

MS m/z (ESI):589.2 [M+1]

Chiral HPLC analysis: retention time 13.016 min, (chromatographic column: CHIRAL PAK IE 4.6*150 mm 51 μm (with a guard column); mobile phase: n-hexane/ethanol (containing 0.1% trifluoroacetic acid)=50/50 (v/v)).

$^1$H NMR (400 MHz, CDCl$_3$) δ 10.07 (s, 1H), 8.12 (d, 2H), 7.87 (d, 2H), 7.70 (d, 1H), 7.50 (d, 1H), 7.37 (d, 1H), 7.30 (d, 1H), 6.60 (s, 1H), 6.25 (s, 1H), 6.12 (s, 1H), 3.72-3.68 (m, 4H), 3.59-3.58 (m, 1H), 3.44-3.41 (m, 1H), 2.88-2.86 (m, 2H), 1.18-1.15 (m, 3H), 1.10-1.05 (m, 4H).

Example 93

4-(2-(4-(2-acetyl-5-chlorophenyl)-5-methoxy-2-oxopyridin-1(2H)-yl)-3-(1-cyclopropyl-1H-pyrazol-3-yl)propanamido)benzoic acid 93

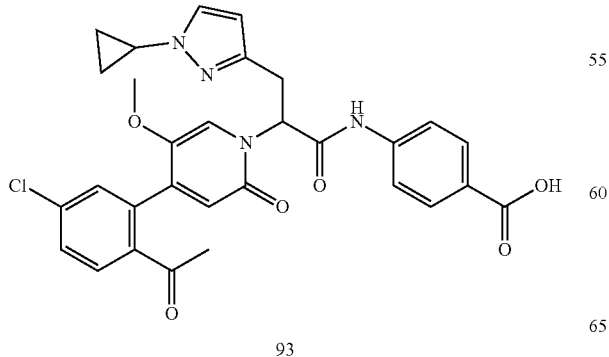

93

-continued

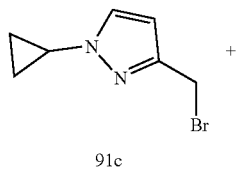

91c

+

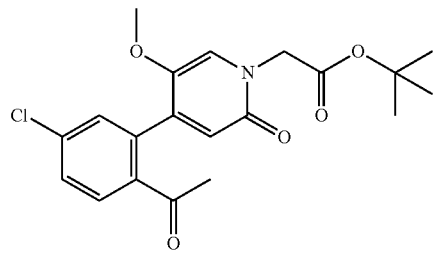

7b

Step 1 →

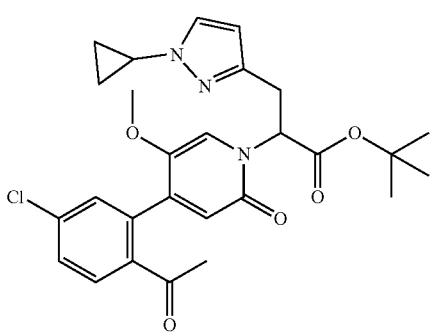

93a

Step 2 →

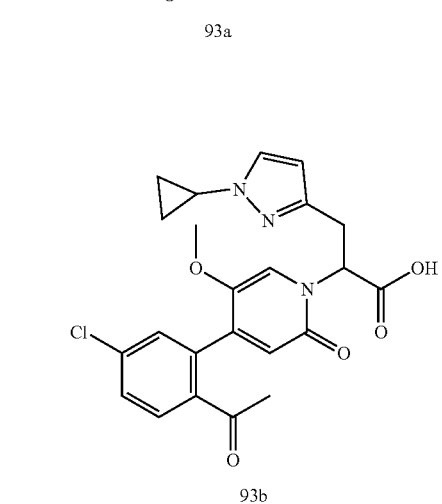

93b

+

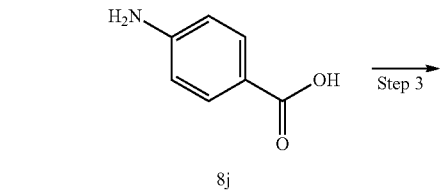

8j

Step 3 →

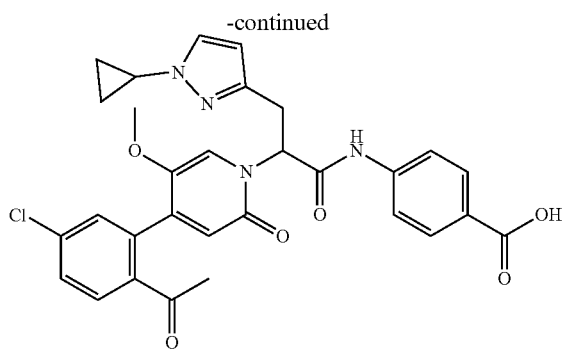

93

Step 1 tert-butyl 2-(4-(2-acetyl-5-chlorophenyl)-5-methoxy-2-oxopyridin-(2H)-yl)-3-(1-cyclopropyl-1H-pyrazol-3-yl)propionate 93a Compound 7b (100 mg, 255.20 μmol) and the crude compound 91c (102.62 mg, 510.40 μmol) were dissolved in 10 mL of tetrahydrofuran. The reaction solution was cooled to −78° C. and lithium bis(trimethylsilyl)amide solution (1.02 mL, 1.02 mmol) was added dropwise. After stirring for 6 hours, the reaction solution was slowly added with 2 mL of saturated ammonium chloride solution to quench the reaction, naturally warmed up to room temperature, added with 10 mL of water, and extracted with ethyl acetate (20 mL×3). The organic phases were combined, washed with saturated sodium chloride solution (20 mL×2) dried over anhydrous sodium sulfate, and filtered. The filtrate was concentrated under reduced pressure, and the resulting residue was purified by silica gel column chromatography with elution system B to obtain the title compound 93a (50 mg, yield: 38.3%).

MS m/z (ESI):512.3 [M+1]

Step 2

2-(4-(2-acetyl-5-chlorophenyl)-5-methoxy-2-oxopyridin-1(2H)-yl)-3-(1-cyclopropyl-1H-pyrazol-3-yl)propionic acid 93b Compound 93a (50 mg, 97.66 μmol) was dissolved in 5 mL of dichloromethane, and then trifluoroacetic acid (111.35 mg, 976.57 μmol) was added dropwise. After stirring for 16 hours, the reaction solution was concentrated under reduced pressure to obtain the crude title compound 93b (45 mg), which was directly used in the next reaction step without purification.

MS m/z (ESI): 456.2 [M+1]

Step 3

4-(2-(4-(2-acetyl-5-chlorophenyl)-5-methoxy-2-oxopyridin-1(2H)-yl)-3-(1-cyclopropyl-1H-pyrazol-3-yl)propanamido)benzoic acid 93

The crude compound 93b (45 mg, 98.71 μmol) and compound 8j (17.60 mg, 128.32 μmol) were dissolved in 5 mL of ethyl acetate, followed by dropwise addition of N,N-diisopropylethylamine (63.79 mg, 493.54 μmol) and a solution of 2,4,6-tripropyl-1,3,5,2,4,6-trioxatriphosphorinane-2,4,6-trioxide in ethyl acetate (50%, 188.44 mg, 296.12 μmol) successively, After completion of the addition, the reaction solution was warmed up to 60° C. and stirred for 2 hours. After cooling to room temperature, the reaction solution was added with 15 mL of water, and extracted with dichloromethane (15 mL×2). The organic phases were combined, washed with saturated sodium chloride solution (15 mL×2), dried over anhydrous sodium sulfate, and filtered. The filtrate was concentrated under reduced pressure, and the resulting residue was purified by high performance liquid chromatography (Waters 2767-SQ detecor2, elution system: acetonitrile, water) to obtain the title compound 93 (50 mg, yield: 88.2%).

MS m/z (ESI): 575.1 [M+1]

$^1$H NMR (400 MHz, CD$_3$OD) δ 8.00 (d, 2H), 7.86 (d, 1H), 7.73 (d, 2H), 7.59-7.55 (m, 2H), 7.37 (d, 2H), 6.44 (s, 1H), 6.13 (s, 1H), 5.97-5.93 (m, 1H), 3.64-3.47 (m, 5H), 3.16 (s, 1H), 2.51 (s, 3H), 1.02-0.98 (m, 4H).

Examples 94, 95

(S)-4-(2-(4-(2-acetyl-5-chlorophenyl)-5-methoxy-2-oxopyridin-1(2H)-yl)-3-(1-cyclopropyl-1H-pyrazol-3-yl)propanamido)benzoic acid 94

(R)-4-(2-(4-(2-acetyl-5-chlorophenyl)-5-methoxy-2-oxopyridin-1(2H)-yl)-3-(1-cyclopropyl-1H-pyrazol-3-yl)propanamido)benzoic acid 95

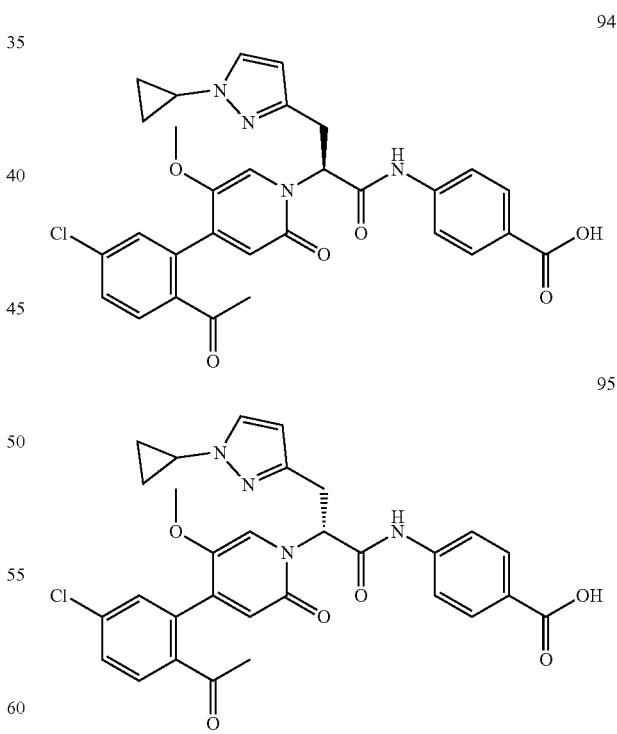

Compound 93 (60 mg, 104.35 μmol) was separated chirally (separation conditions: chiral preparative column CHIRAL PAK IE, 20*250 mm, 5 μm: mobile phase: n-hexane: ethanol (containing 0.01% trifluoroacetic acid)=30:70, flow rate: 7.0 mL/min). The corresponding fractions were collected and concentrated under reduced pressure to obtain the title compound 94 (15 mg) and Compound 95 (15 mg).

Compound 94:

MS m/z (ESI):575.2 [M+1]

Chiral HPLC analysis: retention time 15.655 min. (chromatographic column: CHIRAL PAK IE 4.6*150 mm 5 μm (with a guard column); mobile phase: n-hexane/ethanol (containing 0.1% trifluoroacetic acid)=50/50 (v/v)).

$^1$H NMR (400 MHz, CD$_3$OD) δ 8.00 (d, 2H), 7.86 (d, 1H), 7.73 (d, 2H), 7.59-7.55 (m, 2H), 7.37 (d, 2H), 6.44 (s, 1H), 6.13 (s, 1H), 5.97-5.93 (m, 1H), 3.64-3.47 (m, 5H), 3.16 (s, 1H), 2.51 (s, 3H), 1.02-0.98 (m, 4H).

Compound 95:

MS m/z (ESI):575.2 [M+1]

Chiral HPLC analysis: retention time 8.787 minutes, (chromatographic column: CHIRAL PAK IE 4.6*150 mm 5 μm (with a guard column); mobile phase: n-hexane/ethanol (containing 0.1% trifluoroacetic acid)=50/50 (v/v)).

$^1$H NMR (400 MHz, CD$_3$OD) δ 8.00 (d, 2H), 7.86 (d, 1H), 7.73 (d, 2H), 7.59-7.55 (m, 2H), 7.37 (d, 2H), 6.44 (s, 1H), 6.13 (s, 1H), 5.97-5.93 (m, 1H), 3.64-3.47 (m, 5H), 3.16 (s, 1H), 2.51 (s, 3H), 1.02-0.98 (m, 4H).

Example 96

2-(4-(2-acetyl-5-chlorophenyl)-5-methoxy-2-oxopyridin-1(2H)-yl)-3-(1-cyclopropyl-1H-pyrazol-3-yl)-N-(quinoxalin-6-yl)propanamide 96

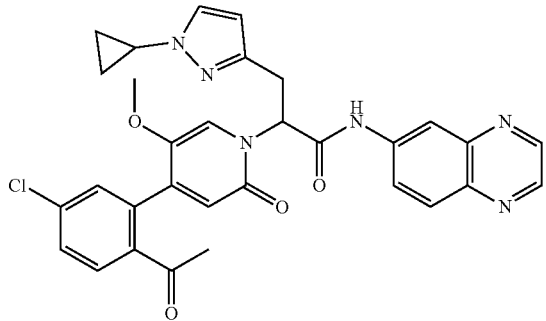

In accordance with the synthetic route of Example 93, the starting compound 8j was replaced with 6-aminoquinoxaline (prepared by a method disclosed in the patent application "WO2013006792"), accordingly, the title compound 96 (35 mg) was prepared.

MS m/z (ESI): 583.4 [M+1]

$^1$H NMR (400 MHz, CD$_3$OD) δ 8.80 (d, 2H), 8.55 (s, 1H), 8.06-7.98 (m, 2H), 7.76 (dd, 1H), 7.58-7.53 (m, 1H), 7.51 (d, 1H), 7.43 (s, 1H), 7.30 (s, 1H), 6.48 (s, 1H), 6.08 (s, 1H), 6.06-6.02 (m, 1H), 3.65 (s, 3H), 3.60-3.53 (m, 2H), 3.44-3.41 (m, 1H), 2.51 (s, 3H), 1.02-0.98 (m, 4H).

Example 97

2-(4-(2-acetyl-5-chlorophenyl)-5-methoxy-2-oxopyridin-(2H)-yl)-3-(1-cyclopropyl-1H-pyrazol-3-yl)-N-(2-methyl-2H-indazol-5-yl)propanamide 97

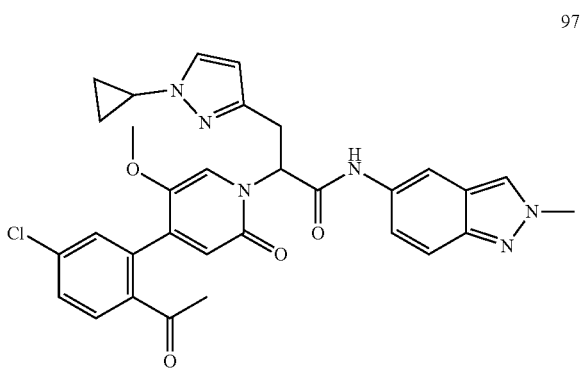 [SMILES: COc1cn(C(Cc2ccn(C3CC3)n2)C(=O)Nc2ccc3nn(C)cc3c2)c(=O)cc1-c1cc(Cl)ccc1C(C)=O]

In accordance with the synthetic route of Example 93, the starting compound 8j was replaced with 18a, accordingly, the title compound 97 (35 mg) was prepared.

MS m/z (ESI): 585.3 [M+1]

$^1$H NMR (400 MHz, CD$_3$OD) δ 8.16 (s, 1H), 8.11 (s, 1H), 7.86 (d, 1H), 7.59-7.55 (m, 3H), 7.42-7.33 (m, 3H), 6.46 (s, 1H), 6.15 (d, 1H), 6.00-5.96 (m, 1H), 4.21 (s, 3H), 3.64 (s, 3H), 3.58-3.53 (m, 3H), 2.52 (s, 3H), 1.02-0.98 (m, 4H).

Example 98

2-(4-(2-acetyl-5-chlorophenyl)-5-methoxy-2-oxopyridin-1(2H)-yl)-3-(1-cyclopropyl-1H-pyrazol-3-yl)-N-(quinazolin-6-yl)propanamide 98

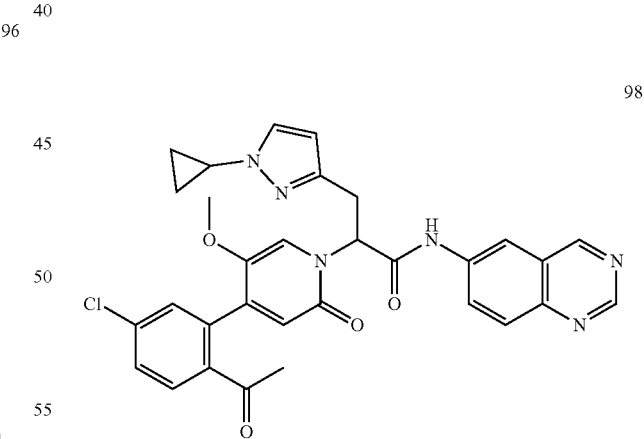

In accordance with the synthetic route of Example 93, the starting compound 8j was replaced with 23a, accordingly, the title compound 98 (30 mg) was prepared.

MS m/z (ESI): 583.2 [M+1]

$^1$H NMR (400 MHz. MeOH-d$_4$) δ 9.50 (s, 1H), 8.19 (s, 1H), 8.62 (d, 1H), 8.12 (d, 1H), 8.03 (d, 1H), 7.87 (d, 1H), 7.60-7.56 (m, 2H), 7.39-7.37 (m, 2H), 6.46 (s, 1H), 6.15 (d, 1H), 6.00-5.96 (m, 1H), 3.64 (s, 3H), 3.63-3.54 (m, 3H), 2.52 (s, 3H), 1.02-0.98 (m, 4H).

Example 99

4-(2-(4-(5-chloro-2-propionylphenyl)-5-methoxy-2-oxopyridin-1(2H)-yl)-3-(1-methyl-1H-pyrazol-3-yl)propanamido)benzoic acid 99

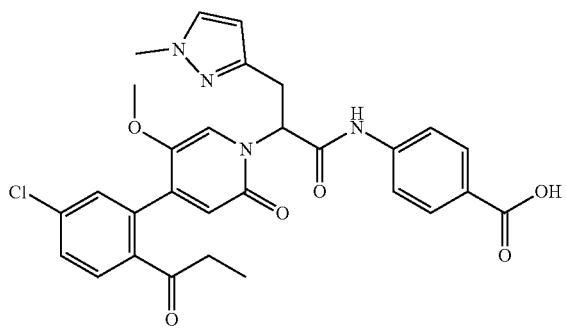

In accordance with the synthetic route of Example 8, the starting compound 8a was replaced with 3-(bromomethyl)-1-methyl-1H-pyrazole (prepared by a method disclosed in the patent application "WO2016045125"), accordingly, the title compound 99 (35 mg) was prepared.

MS m/z (ESI): 563.2 [M+1]

$^1$H NMR (400 MHz, CDCl$_3$) δ 9.96 (s, 1H), 8.13 (d, 2H), 7.87 (d, 2H), 7.71-7.69 (m, 1H), 7.52-7.49 (m, 1H), 7.35 (d, 1H), 7.31 (s, 1H), 6.64 (s, 1H), 6.29-6.27 (m, 1H), 6.17 (d, 1H), 3.93 (s, 3H), 3.79-3.73 (m, 4H), 3.47-3.45 (m, 1H), 2.91-2.89 (s, 2H), 1.19-1.15 (m, 3H).

Example 100

4-(2-(4-(2-acetyl-5-chlorophenyl)-5-methoxy-2-oxopyridin-(2H)-yl)-3-(1-methyl-1H-pyrazol-3-yl)propanamido)benzoic acid 100

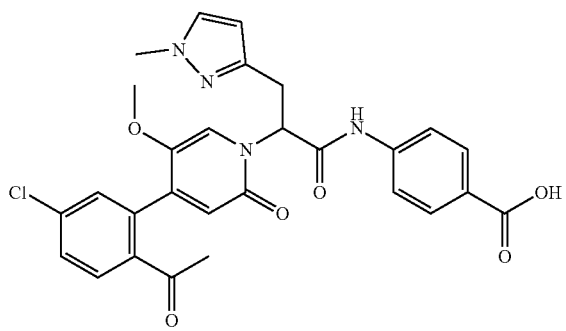

In accordance with the synthetic route of Example 74, the starting compound 74a was replaced with 3-(bromomethyl)-1-methyl-1H-pyrazole (prepared by a method disclosed in the patent application "WO2016045125"), accordingly, the title compound 100 (40 mg) was prepared.

MS m/z (ESI): 549.2 [M+1]

$^1$H NMR (400 MHz. CD$_3$OD) δ 8.00 (d, 2H), 7.87 (d, 1H), 7.76-7.73 (m, 2H), 7.60-7.59 (m, 1H), 7.58-7.57 (m, 1H), 7.39-7.37 (m, 2H), 6.46 (s, 1H), 6.15 (d, 1H), 5.96-5.94 (m, 1H), 3.64 (s, 3H), 3.63 (s, 3H), 3.55-3.51 (m, 1H), 3.49-3.46 (m, 1H), 2.52 (s, 3H).

Examples 101, 102

(S)-4-(2-(4-(2-acetyl-5-chlorophenyl)-5-methoxy-2-oxopyridin-1(2H)-yl)-3-(1-methyl-1H-pyrazol-3-yl)propanamido)benzoic acid 101

(R)-4-(2-(4-(2-acetyl-5-chlorophenyl)-5-methoxy-2-oxopyridin-1(2H)-yl)-3-(1-methyl-1H-pyrazol-3-yl)propanamido)benzoic acid 102

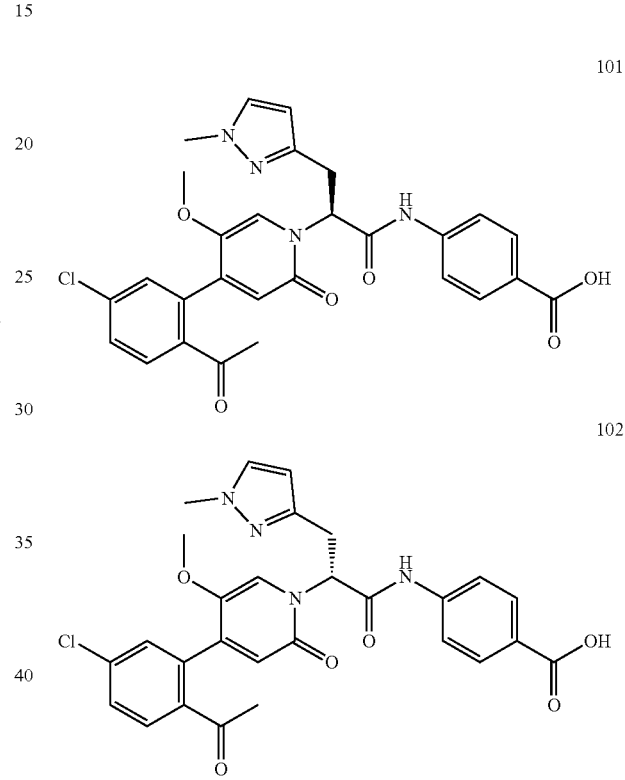

Compound 100 (40 mg, 72.86 μmol) was separated chirally (separation conditions: chiral preparative column CHIRAL PAK IE, 20*250 mm, 5 μm; mobile phase: n-hexane: ethanol (containing 0.01% trifluoroacetic acid)=30:70, flow rate: 7.0 mL/min) The corresponding fractions were collected and concentrated under reduced pressure to obtain the title compound 101 (15 mg) and compound 102 (15 mg).

Compound 101:

MS m/z (ESI):549.2 [M+1]

Chiral HPLC analysis: retention time 16.341 minutes, (chromatographic column: CHIRAL PAK IE 4.6*150 mm 5 μm (with a guard column): mobile phase: n-hexane/ethanol (containing 0.1% trifluoroacetic acid)=50/50 (v/v)).

$^1$H NMR (400 MHz, CDCl$_3$) δ 10.03 (s, 1H), 8.12 (d, 2H), 7.87 (d, 2H), 7.71 (d, 1H), 7.50 (d, 1H), 7.30-7.28 (m, 2H), 6.61 (s, 1H), 6.28-6.27 (m, 1H), 6.13 (s, 1H), 3.88 (s, 3H), 3.72-3.68 (m, 1H), 3.67 (s, 3H), 3.43-3.41 (m, 1H), 2.57 (s, 3H).

Compound 102:

MS m/z (ESI):549.2 [M+1]

Chiral HPLC analysis: retention time 9.904 minutes, (chromatographic column: CHIRAL PAK IE 4.6*150 mm 5

μm (with a guard column); mobile phase: n-hexane/ethanol (containing 0.1% trifluoroacetic acid)=50/50 (v/v)).

$^1$H NMR (400 MHz, CDCl$_3$) δ 10.03 (s, 1H), 8.12 (d, 2H), 7.87 (d, 2H), 7.71 (d, 1H), 7.50 (d, 1H), 7.30-7.28 (m, 2H), 6.61 (s, 1H), 6.28-6.27 (m, 1H), 6.13 (s, 1H), 3.88 (s, 3H), 3.72-3.68 (m, 1H), 3.67 (s, 3H), 3.43-3.41 (m, 1H), 2.57 (s, 3H).

Example 103

4-(2-(4-(2-acetyl-5-chlorophenyl)-5-methoxy-2-oxopyridin-1(2H)-yl)-3-(1-methyl-1H-pyrazol-4-yl)propanamido)benzoic acid 103

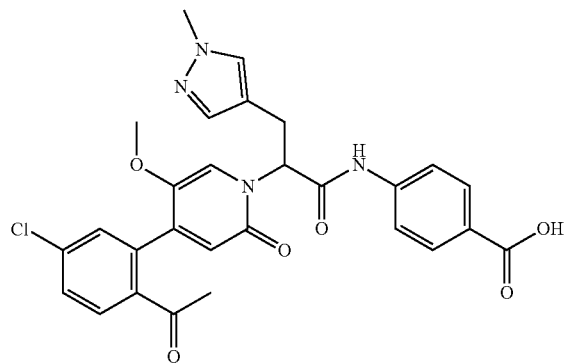

103

In accordance with the synthetic route of Example 74, the starting compound 74a was replaced with 4-(bromomethyl)-1-methyl-1H-pyrazole (prepared by a method disclosed in the patent application "WO 2015090599"), accordingly, the title compound 103 (40 mg) was prepared.

MS m/z (ESI): 549.2 [M+1]

$^1$H NMR (400 MHz, CDCl$_3$) δ 9.95 (s, 1H), 8.12 (d, 2H), 7.90 (d, 2H), 7.75 (d, 1H), 7.54-7.52 (m, 2H), 7.33-7.27 (m, 3H), 6.68 (s, 1H), 6.08 (s, 1H), 3.92 (s, 3H), 3.65 (s, 3H), 3.48-3.43 (m, 1H), 3.24 (s, 1H), 2.57 (s, 3H).

Examples 104, 105

(R)-4-(2-(4-(2-acetyl-5-chlorophenyl)-5-methoxy-2-oxopyridin-1(2H)-yl)-3-(1-methyl-1H-pyrazol-4-yl)propanamido)benzoic acid 104

(S)-4-(2-(4-(2-acetyl-5-chlorophenyl)-5-methoxy-2-oxopyridin-1(2H)-yl)-3-(1-methyl-1H-pyrazol-4-yl)propanamido)benzoic acid 105

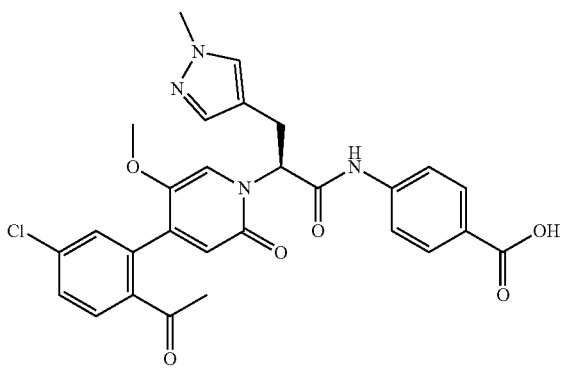

105

Compound 103 (300 mg, 546.47 μmol) was separated chirally (separation conditions: chiral preparative column CHIRAL PAK IE, 20*250 mm, 5 μm; mobile phase: ethanol (containing 0.01%)=100, flow rate: 7.0 mL/min). The corresponding fractions were collected and concentrated under reduced pressure to obtain the title compound 104 (120 mg) and compound 105 (120 mg).

Compound 104:

MS m/z (ESI): 549.2 [M+1]

Chiral HPLC analysis: retention time 3.778 minutes, (chromatographic column: CHIRAL PAK IE 4.6*150 mm 5 μm (with a guard column); mobile phase: ethanol (containing 0.1% trifluoroacetic acid)=100).

$^1$H NMR (400 MHz, DMSO-d$_6$) δ 10.82 (s, 1H), 7.93-7.88 (m, 3H), 7.76 (d, 2H), 7.65 (d, 1H), 7.48-7.45 (m, 3H), 7.25 (s, 1H), 6.37 (s, 1H), 5.82-5.80 (m, 1H), 3.97 (s, 3H), 3.76 (s, 3H), 3.45-3.24 (m, 2H), 2.49 (s, 3H).

Compound 105:

MS m/z (ESI): 549.2 [M+1]

Chiral HPLC analysis: retention time 5.535 minutes, (chromatographic column: CHIRAL PAK IE 4.6*150 mm 5 μm (with a guard column); mobile phase: ethanol (containing 0.1% trifluoroacetic acid)=100).

$^1$H NMR (400 MHz; DMSO-d$_6$) δ 10.82 (s, 1H), 7.93-7.88 (m, 3H), 7.76 (d, 2H), 7.65 (d, 1H), 7.48-7.45 (m, 3H), 7.25 (s, 1H), 6.37 (s, 1H), 5.82-5.80 (m, 1H), 3.97 (s, 3H), 3.76 (s, 3H), 3.45-3.24 (m, 2H), 2.49 (s, 3H).

Example 106

4-(2-(4-(2-acetyl-5-chlorophenyl)-5-methoxy-2-oxopyridin-1(2H)-yl)-3-(isoxazol-5-yl) propanamido)benzoic acid 106

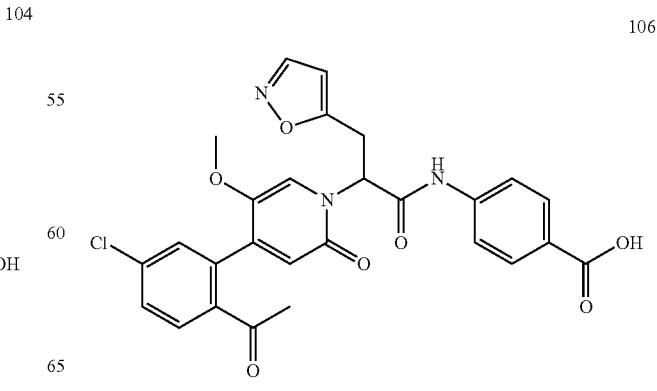

106

104

In accordance with the synthetic route of Example 74, the starting compound 74a was replaced with 5-bromomethyl-isoxazole (prepared by a known method disclosed in "*Journal of Medicinal Chemistry*, 2016, 59(7), 3471-3488"), accordingly, the title compound 106 (55 mg) was prepared.

MS m/z (ESI): 536.4 [M+1]

¹H NMR (400 MHz, DMSO-d₆) δ 10.84 (s, 1H), 8.47-8.46 (s, 1H), 7.93-7.94 (m, 1H), 7.92-7.91 (m, 1H), 7.86-7.85 (d, 1H), 7.77-7.76 (m, 1H), 7.75-7.74 (m, 1H), 7.64-7.61 (dd, 1H), 7.44-7.43 (d, 1H), 7.38 (s, 1H), 6.39 (s, 1H), 6.23-6.22 (d, 1H), 6.05-6.01 (m, 1H), 3.89-3.82 (m, 1H), 3.73-3.71 (m, 1H), 3.52 (s, 3H), 2.45 (s, 3H)

Example 107

4-(2-(4-(2-acetyl-5-chlorophenyl)-5-methoxy-2-oxopyridin-1(2H)-yl)-3-(thiazol-2-yl)propanamido)benzoic acid 107

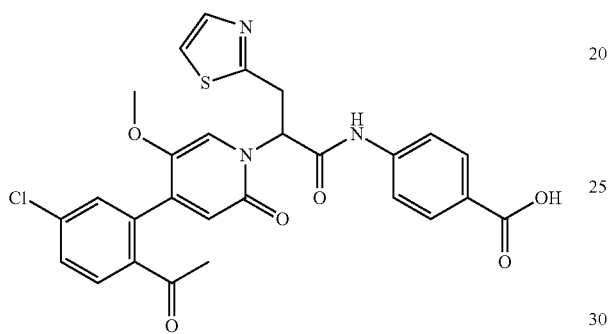

107

In accordance with the synthetic route of Example 74, the starting compound 74a was replaced with 2-bromomethyl-thiazole (prepared by a method disclosed in the patent application "WO2014065413"), accordingly, the title compound 107 (20 mg) was prepared.

MS m/z (ESI): 551.9 [M+1]

¹H NMR (400 MHz, CD₃OD) δ 7.98 (d, 2H), 7.86 (d, 1H), 7.75-7.71 (m, 3H), 7.57 (dd, 1H), 7.52 (d, 1H), 7.37-7.36 (m, 2H), 6.47 (s, 1H), 6.06-6.02 (m, 1H), 4.06-3.91 (m, 2H), 3.60 (s, 3H), 2.51 (s, 3H).

Examples 108, 109

(S)-4-(4-(tert-butoxy)-2-(4-(5-chloro-2-propionylphenyl)-5-methoxy-2-oxopyridin-1(2H)-yl)butanamido)benzoic acid 108

(R)-4-(4-(tert-butoxy)-2-(4-(5-chloro-2-propionylphenyl)-5-methoxy-2-oxopyridin-1(2H)-yl)butanamido)benzoic acid 109

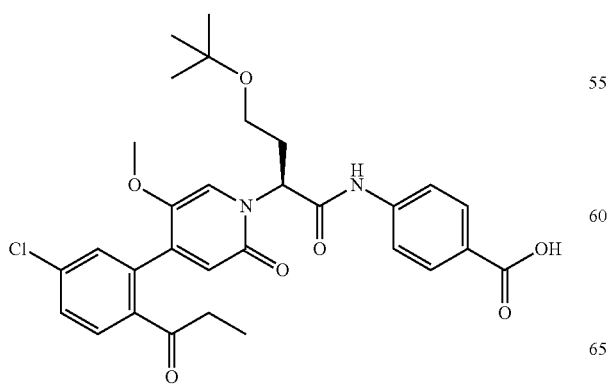

108

-continued

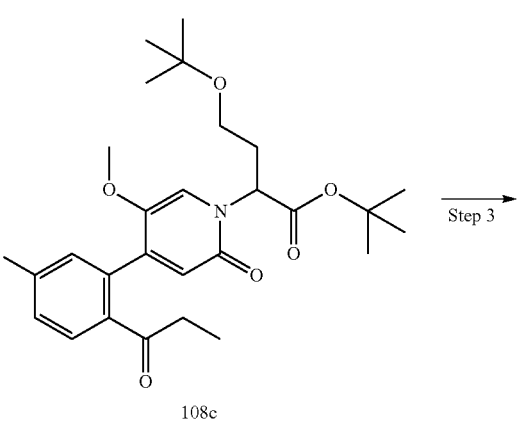

109

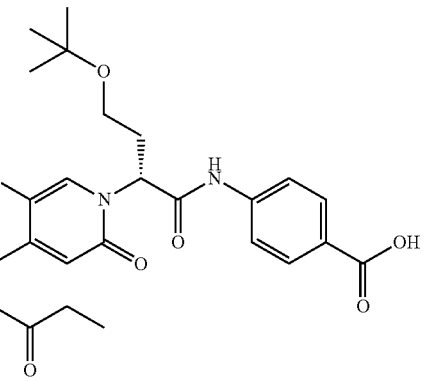

108a    108b

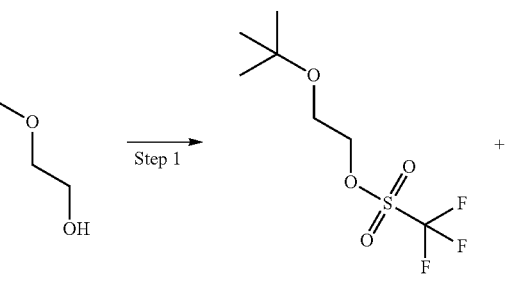

8f

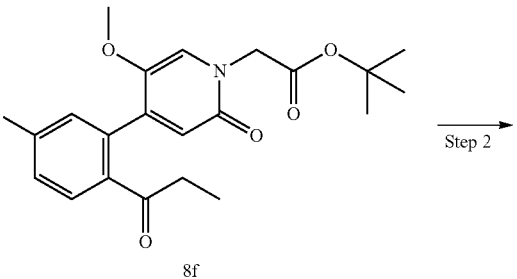

108c

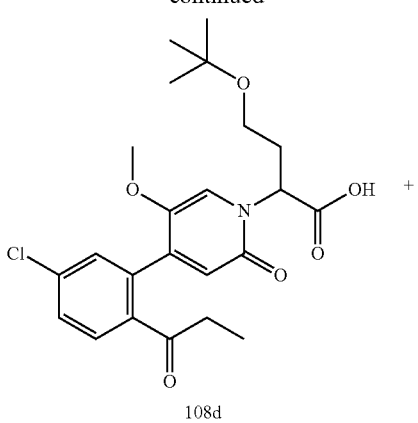

108d

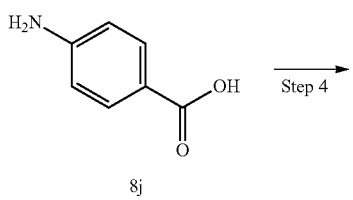

8j

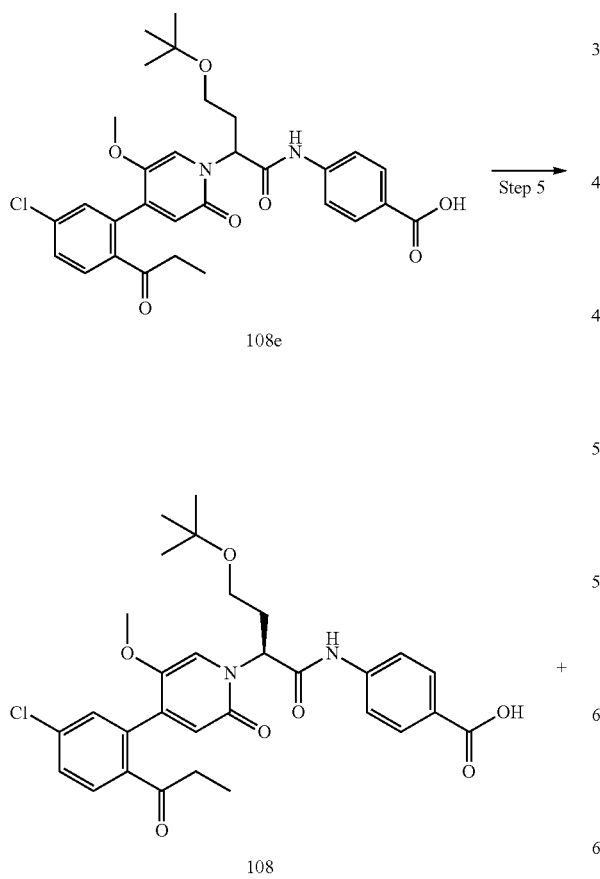

108e

108

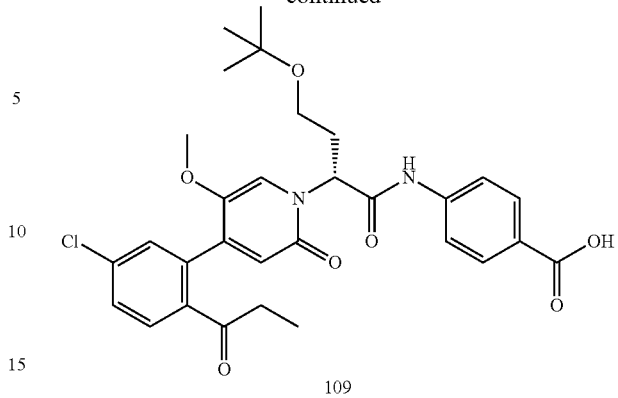

109

Step 1

2-(tert-butoxy)ethyl trifluoromethanesulfonate 108b 2-tert-butoxyethanol 108a (300 mg, 2.54 mmol) was dissolved in 8 mL of dichloromethane, and then 2,6-dimethylpyridine (299.22 mg, 2.79 mmol) was added in an ice bath, and trifluoromethanesulfonic anhydride (787.87 mg, 2.79 mmol) was added dropwise. After completion of the addition, the reaction solution was stirred for 1 hour in an ice bath, naturally warmed up to room temperature and stirred for 1 hour. The reaction solution was added with 30 mL of dichloromethane, and washed with 20 mL of water. The organic phase was dried over anhydrous sodium sulfate and filtered. The filtrate was concentrated under reduced pressure to obtain the crude title compound 108b (550 mg), which was directly used in the next reaction step without purification.

Step 2 tert-butyl 4-(tert-Butoxy)-2-(4-(5-chloro-2-propionylphenyl)-5-methoxy-2-oxopyridin-(2H)-yl)butyrate 108c Compound 8f (148 mg, 364.65 μmol) and the crude compound 108b (182.50 mg, 729.30 μmol) were dissolved in 15 mL of tetrahydrofuran. The reaction solution was cooled to −78° C. dropwise added with lithium bis(trimethylsilyl)amide solution (1.46 mL, 1.46 mmol), and stirred for 2 hours. The reaction solution was added with 5 mL of water at −78° C. to quench the reaction, naturally warmed up to room temperature, added with 20 mL of water, and extracted with ethyl acetate (35 mL×3). The organic phases were combined, washed with saturated sodium chloride solution (25 mL×2), dried over anhydrous sodium sulfate, and filtered. The filtrate was concentrated under reduced pressure, and the resulting residue was purified by silica gel column chromatography with elution system A to obtain the title compound 108c (120 mg, yield: 65.0%).

MS m/z (ESI): 506.5 [M+1]

Step 3

4-(tert-butoxy)-2-(4-(5-chloro-2-propionylphenyl)-5-methoxy-2-oxopyridin-(2H)-yl)butyric acid 108d Compound 108c (120 mg, 237.14 μmol) was dissolved in a mixed solvent of 8 mL of ethanol and 4 mL of tetrahydrofuran, and lithium hydroxide (49.75 mg, 1.19 mmol) was added. The reaction solution was warmed up to 50° C. and stirred for 2 hours. After cooling to room temperature, the reaction solution was concentrated under reduced pressure to remove most of the organic solvents, added with 15 mL of water, added with 3M hydrochloric acid to adjust the pH to 6, and extracted with ethyl acetate (20 mL×3). The organic phases were combined, washed with saturated sodium chloride (20 mL: 2), dried over anhydrous sodium sulfate, and filtered. The filtrate was concentrated under reduced pressure to obtain the title compound 108d (106 mg), which was directly used in the next reaction step without purification.

MS m/z (ESI):450.4 [M+1]

Step 4

4-(4-(tert-butoxy)-2-(4-(5-chloro-2-propionylphenyl)-5-methoxy-2-oxopyridin-1(2H)-yl)butanamido)benzoic acid 108e The crude compound 108d (106 mg, 235.59 μmol) was dissolved in 15 mL of ethyl acetate, and then N,N-diisopropylethylamine (304.48 mg, 2.36 mmol), compound 8j (35.54 mg, 259.16 μmol) and a solution of 2,4,6-tripropyl-1,3,5,2,4,6-trioxatriphosphorinane-2,4,6-trioxide in ethyl acetate (50%, 599.70 mg, 942.38 μmol) were added. After completion of the addition, the reaction solution was warmed up to 80° C., and stirred for 2 hours. After cooling to room temperature, the reaction solution was added with 20 mL of water, added with 3M hydrochloric acid to adjust the pH to 5, and extracted with ethyl acetate (20 mL×3). The organic phases were combined, washed with saturated sodium chloride solution (20 mL×2), dried over anhydrous sodium sulfate, and filtered. The filtrate was concentrated under reduced pressure, and the resulting residue was purified by high performance liquid chromatography (Waters 2767-SQ detecor2, acetonitrile, water) to obtain the title compound 108e (60 mg, yield: 44.8%).

MS m/z (ESI):569.5 [M+1]

Step 5

(S)-4-(4-(tert-Butoxy)-2-(4-(5-chloro-2-propionylphenyl)-5-methoxy-2-oxopyridin-1 (2H)-yl)butanamido)benzoic acid 108

(R)-4-(4-(tert-butoxy)-2-(4-(5-chloro-2-propionylphenyl)-5-methoxy-2-oxopyridin-1(2H)-yl)butanamido)benzoic acid 109

Compound 108e (60 mg, 105.44 μmol) was separated chirally (separation conditions: chromatographic column Superchiral S-AD (Chiralway), 2 cm ID*25 cm Length, 5 μm; mobile phase: carbon dioxide:ethanol:diethylamine=60:40:0.05, flow rate: 50 g/min). The corresponding fractions were collected and concentrated under reduced pressure to obtain title compound 108 (22 mg) and compound 109 (22 mg).

Compound 108:

MS m/z (ESI):569.5 [M+1]

Chiral HPLC analysis: retention time 8.518 minutes, chiral purity 100% (chromatographic column: CHIRAL PAK IE 4.6*150 mm 5 μm (with a guard column); mobile phase: n-hexane/ethanol (containing 0.1% trifluoroacetic acid)=50/50(v/v)).

$^1$H NMR (400 MHz, DMSO-d$_6$) δ 12.70 (s, 1H), 10.73 (s, 1H), 7.90 (d, 2H), 7.86 (d, 1H), 7.78 (d, 2H), 7.62 (dd, 1H), 7.41 (s, 1H), 7.27 (s, 1H), 6.39 (s, 1H), 5.76-5.72 (m, 1H), 3.52 (s, 3H), 3.39-3.36 (m, 2H), 2.99-2.86 (m, 2H), 2.36-2.27 (m, 2H), 1.06 (s, 9H), 1.00 (t, 3H).

Compound 109:

MS m/z (ESI):569.4 [M+1]

Chiral HPLC analysis: retention time 5.172 minutes, chiral purity 99.7% (chromatographic column: CHIRAL PAK IE 4.6*150 mm 5 μm (with a guard column): mobile phase: n-hexane/ethanol (containing 0.1% trifluoroacetic acid)=50/50(v/v)).

$^1$H NMR (400 MHz, DMSO-d$_6$) δ 10.71 (s, 1H), 7.91-7.84 (m, 3H), 7.77 (d, 2H), 7.62 (dd, 1H), 7.41 (s, 1H), 7.27 (s, 1H), 6.39 (s, 1H), 5.76-5.72 (m, 1H), 3.52 (s, 3H), 3.39-3.36 (m, 2H), 2.99-2.86 (m, 2H), 2.36-2.27 (m, 2H), 1.06 (s, 9H), 1.00 (t, 3H).

Example 110

4-(2-(4-(2-acetyl-5-chlorophenyl)-5-methoxy-2-oxopyridin-1(2H)-yl)-4-(tert-butoxy)butanamido)benzoic acid 110

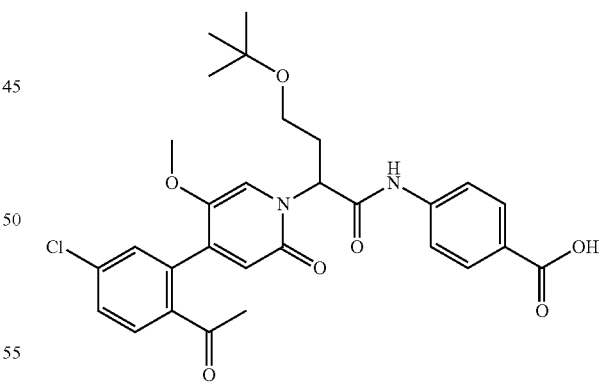

110

In accordance with the synthetic route of compound 108e in Example 108, the starting compound 8f was replaced with the starting compound 7b, accordingly, the title compound 110 (30 mg) was prepared.

MS m/z (ESI): 555.1 [M+1]

$^1$H NMR (400 MHz, CD$_3$OD) δ 8.01 (d, 2H), 7.88 (d, 1H), 7.75 (d, 2H), 7.58 (dd, 1H), 7.37 (d, 1H), 7.36 (s, 1H), 6.52 (s, 1H), 5.90-5.87 (m, 1H), 3.65 (s, 3H), 3.57-3.43 (m, 2H), 2.55 (s, 3H), 2.49-2.36 (m, 2H), 1.18 (s, 9H).

Examples 111, 112

(S)-4-(2-(4-(2-acetyl-5-chlorophenyl)-5-methoxy-2-oxopyridin-1(2H)-yl)-4-(tert-butoxy)butanamido)benzoic acid 111

(R)-4-(2-(4-(2-acetyl-5-chlorophenyl)-5-methoxy-2-oxopyridin-(2H)-yl)-4-(tert-butoxy)butanamido)benzoic acid 112

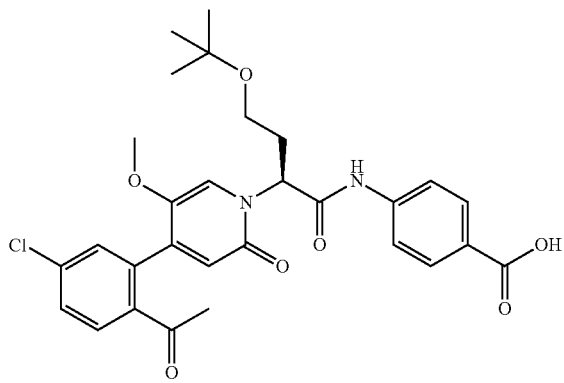

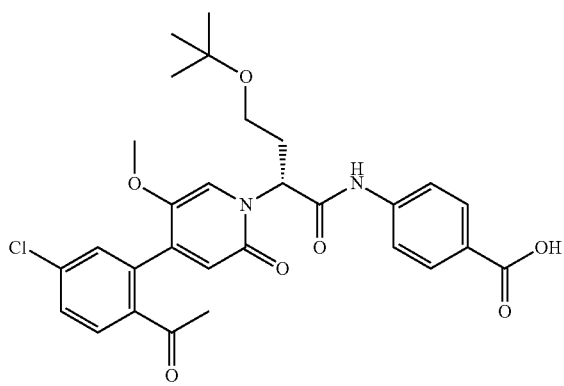

Compound 110 (1.2 g, 2.16 mmol) was separated chirally (separation conditions: chromatographic column: Superchiral S-AD (Chiralway), 2 cm ID*25 cm Length, 5 μm; mobile phase: carbon dioxide:ethanol:diethylamine=60:40:0.05, flow rate: 50 g/min). The corresponding fractions were collected and concentrated under reduced pressure to obtain the title compound 111 (500 mg) and compound 112 (450 mg).

Compound 111:

MS m/z (ESI):555.1 [M+1]

Chiral HPLC analysis: retention time 16.803 minutes, chiral purity 100% (chromatographic column: CHIRAL PAK IE 4.6*150 mm 5 μm (with a guard column); mobile phase: n-hexane/ethanol (containing 0.1% trifluoroacetic acid)=70/30 (v/v)).

$^1$H NMR (400 MHz, CD$_3$OD) δ 8.03-7.99 (m, 2H), 7.89 (d, 1H), 7.76-7.74 (m, 2H), 7.60 (dd, 1H), 7.39 (d, 1H), 7.36 (s, 1H), 6.52 (s, 1H), 5.91-5.87 (m, 1H), 3.66 (s, 3H), 3.60-3.54 (m, 1H), 3.47-3.42 (m, 1H), 2.55 (s, 3H), 2.52-2.45 (m, 1H), 2.42-2.37 (m, 1H), 1.18 (s, 9H).

Compound 112:

MS m/z (ESI):555.1 [M+1]

Chiral HPLC analysis: retention time 4.247 minutes, chiral purity 100% (chromatographic column: CHIRAL PAK IE 4.6*150 mm 5 μm (with a guard column); mobile phase: n-hexane/ethanol (containing 0.1% trifluoroacetic acid)=70/30 (v/v)).

$^1$H NMR (400 MHz, CD$_3$OD) δ 8.03-7.99 (m, 2H), 7.89 (d, 1H), 7.76-7.74 (m, 2H), 7.60 (dd, 1H), 7.39 (d, 1H), 7.36 (s, 1H), 6.52 (s, 1H), 5.91-5.87 (m, 1H), 3.66 (s, 3H), 3.60-3.54 (m, 1H), 3.47-3.42 (m, 1H), 2.55 (s, 3H), 2.52-2.45 (m, 1H), 2.42-2.37 (m, 1H), 1.18 (s, 9H).

Example 113

4-(tert-butoxy)-2-(4-(5-chloro-2-propionylphenyl)-5-methoxy-2-oxopyridin-1(2H)-yl)-N-quinoxalin-6-yl)butanamide 113

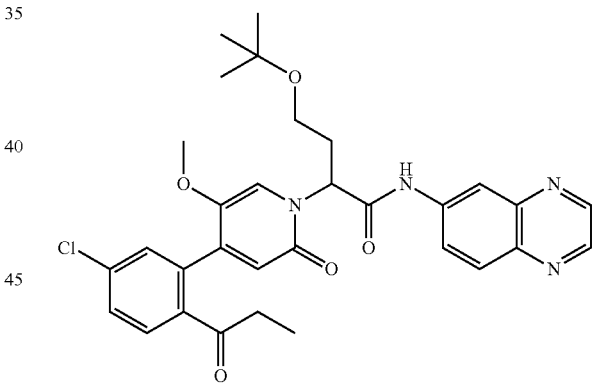

In accordance with the synthetic route of compound 108e in Example 108, the starting compound 8j used in Step 4 was replaced with 6-aminoquinoxaline (prepared by a method disclosed in the patent application "WO2013006792"), accordingly, the title compound 113 (35 mg) was prepared.

MS m/z (ESI): 577.3 [M+1]

$^1$H NMR (400 MHz, CD$_3$OD) δ 8.85-8.83 (d, 1H), 8.80-8.79 (d, 1H), 8.61-8.60 (m, 1H), 8.08-8.06 (d 1H), 8.02-7.97 (dd, 1H), 7.85-7.83 (d, 1H), 7.58-7.55 (dd, 1H), 7.40-7.35 (m, 2H), 6.50 (s, 1H), 5.95-5.85 (m, 1H), 3.65-3.60 (m, 1H), 3.60-3.55 (s, 3H), 3.50-3.40 (m, 1H), 3.00-2.95 (m, 2H), 2.50-2.40 (m, 1H), 2.35-2.25 (m, 1H), 1.17 (s, 9H), 1.10-1.00 (m, 3H)

Examples 114, 115

(S)-4-(tert-butoxy)-2-(4-(5-chloro-2-propionylphenyl)-5-methoxy-2-oxopyridin-1(2H)-yl)-N-(quinoxalin-6-yl)butanamide 114

(R)-4-(tert-butoxy)-2-(4-(5-chloro-2-propionylphenyl)-5-methoxy-2-oxopyridin-(2H)-yl)-N-(quinoxalin-6-yl)butanamide 115

114

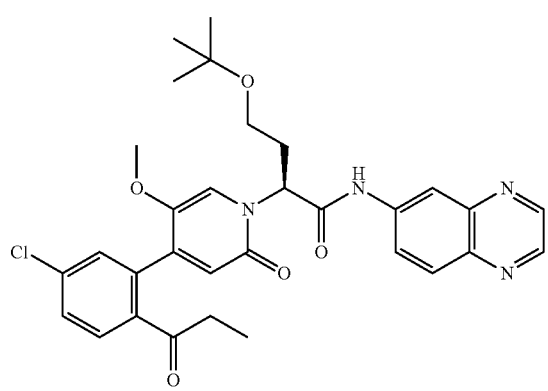

115

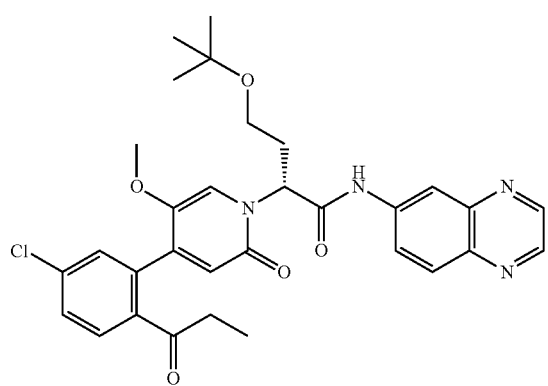

Compound 113 (65 mg, 112.64 μmol) was separated chirally (separation conditions: chromatographic column Superchiral S-AD (Chiralway), 2.1 cm ID*25 cm Length, 5 μm; mobile phase: ethanol:acetonitrile:diethylamine=15:85:0.05, flow rate: 1.0 mL/min). The corresponding fractions were collected and concentrated under reduced pressure to obtain the title compound 114 (20 mg) and compound 115 (20 mg).

Compound 114:

MS m/z (ESI):577.3 [M+1]

Chiral HPLC analysis: retention time 17.031 minutes, (chromatographic column: CHIRAL PAK IE 4.6*150 mm 5 μm (with a guard column); mobile phase: n-hexane/ethanol (containing 0.1% trifluoroacetic acid)=30/70 (v/v)).

$^1$H NMR (400 MHz, CD$_3$OD) δ 10.50 (s, 1H), 8.85-8.83 (d, 1H), 8.80-8.79 (d, 1H), 8.61-8.60 (m, 1H), 8.08-8.06 (d, 1H), 8.02-7.97 (dd, 1H), 7.85-7.83 (d, 1H), 7.58-7.55 (dd, 1H), 7.40-7.35 (m, 2H), 6.50 (s, 1H), 5.95-5.85 (m, 1H), 3.65-3.60 (s, 3H), 3.60-3.55 (m, 1H), 3.50-3.40 (m, 1H), 3.00-2.95 (m, 2H), 2.50-2.40 (m, 1H), 2.35-2.25 (m, 1H), 1.17 (s, 9H), 1.10-1.00 (m, 3H).

Compound 115:

MS m/z (ESI):577.3 [M+1]

Chiral HPLC analysis: retention time 7.416 minutes, (chromatographic column: CHIRAL PAK IE 4.6*150 mm 5 μm (with a guard column): mobile phase: n-hexane/ethanol (containing 0.1% trifluoroacetic acid)=30/70 (v/v)).

$^1$H NMR (400 MHz, CD$_3$OD) δ 10.50 (s, 1H), 8.85-8.83 (d, 1H), 8.80-8.79 (d, 1H), 8.61-8.60 (m, 1H), 8.08-8.06 (d, 1H), 8.02-7.97 (dd, 1H), 7.85-7.83 (d, 1H), 7.58-7.55 (dd, 1H), 7.40-7.35 (m, 2H), 6.50 (s, 1H), 5.95-5.85 (m, 1H), 3.65-3.60 (m, 1H), 3.60-3.55 (s, 3H), 3.50-3.40 (m, 1H), 3.00-2.95 (m, 2H), 2.50-2.40 (m, 1H), 2.35-2.25 (m, 1H), 1.17 (s, 9H), 1.10-1.00 (m, 3H).

Example 116

2-(4-(2-acetyl-5-chlorophenyl)-5-methoxy-2-oxopyridin-1(2H)-yl)-4-(tert-butoxy)-N-(1-oxoisoindolin-5-yl)butanamide 116

116

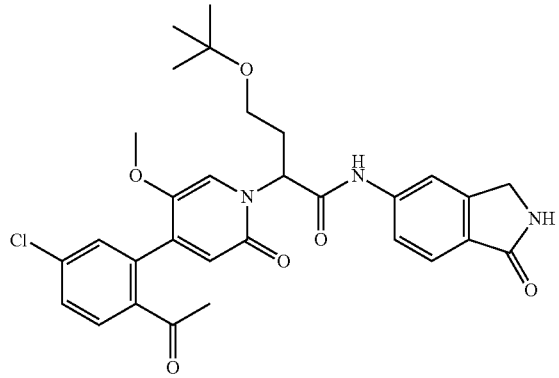

In accordance with the synthetic route of compound 108e in Example 108, the starting compound 8f used in Step 2 was replaced with the starting compound 7b, and the starting compound 8j used in Step 4 was replaced with 5-aminoisoindoline-1-one (prepared by a method disclosed in the patent application "WO 2012092880"), accordingly, the title compound 116 (35 mg) was prepared.

MS m/z (ESI): 566.1 [M+1]

$^1$H NMR (400 MHz, CD$_3$OD) δ 8.04 (s, 1H), 7.89 (d, 1H), 7.76 (d, 1H), 7.65 (d, 1H), 7.59 (d, 1H), 7.39 (s, 1H), 7.37 (s, 1H), 6.52 (m, 1H), 5.91-5.87 (m, 1H), 4.46 (s, 2H), 3.66 (s, 3H), 3.41-3.58 (m, 2H), 2.55 (s, 3H), 2.30-2.51 (m, 2H), 1.18 (s, 9H).

Examples 117, 118

(R)-2-(4-(2-acetyl-5-chlorophenyl)-5-methoxy-2-oxopyridin-1(2H)-yl)-4-methoxy-N-(1'-oxo-1'H-spiro[cyclobutane-1,3'-oxazolo[3,4-a]indol]-7'-yl)butanamide 117

(S)-2-(4-(2-acetyl-5-chlorophenyl)-5-methoxy-2-oxopyridin-1(2H)-yl)-4-methoxy-N-(1'-oxo-1'H-spiro[cyclobutane-1,3'-oxazolo[34-a]indol]-7'-yl)butanamide 118

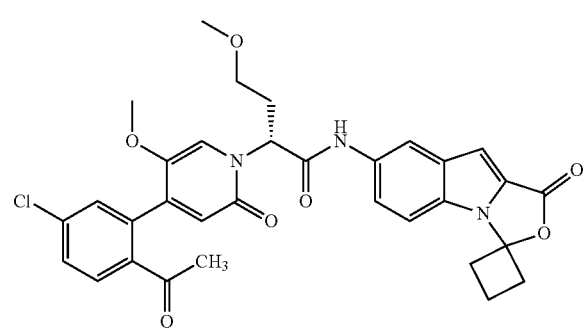

117

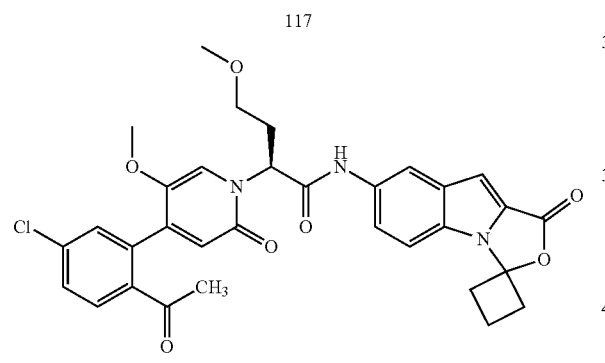

118

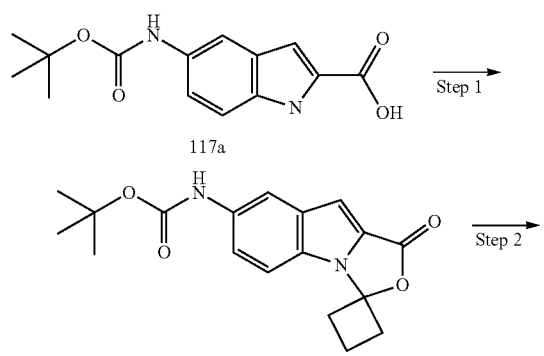

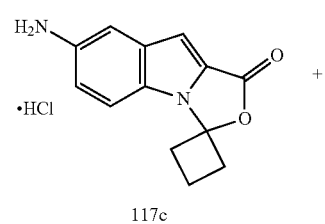

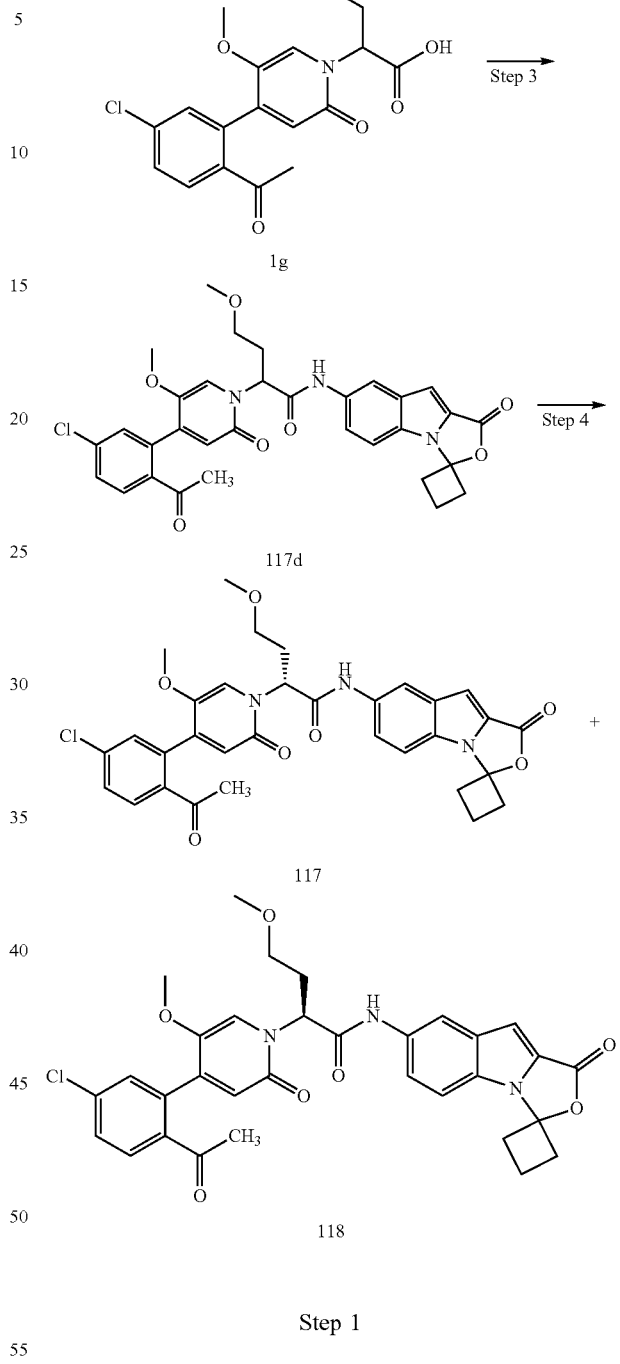

Step 1 tert-butyl (1'-oxo-1'H-spiro[cyclobutane-1,3'-oxazolo[3,4-a]indol]-7'-yl)carbamate 117b 5-((tert-Butoxycarbonyl)amino)-1H-indole-2-carboxylic acid 117a (4.5 g, 16.29 mmol, prepared by a method disclosed in the patent application "WO2012162482") was dissolved in 160 mL of tetrahydrofuran. N,N-carbonyldiimidazole (5.82 g, 32.57 mmol) was added in an ice bath, and the mixture was warmed up to room temperature and stirred for 1.5 hours. After cooling to 0° C., the reaction solution was dropwise added with cyclobutanone (2.85 g, 40.72 mmol) and 1,8-diazabicyclo[5.4.0]undec-7-ene (6.44 g, 42.35 mmol), and stirred for 30 minutes at 0° C. The reaction solution was warmed up to room temperature, and stirred for 2 hours. The reaction solution was concentrated under reduced pressure to remove most of the tetrahydrofuran. The residue was poured into 150 mL of ice water, added with 3M hydrochloric acid to adjust the pH to about 5, and extracted with ethyl acetate (50 mL×3). The organic phases were combined, washed with saturated sodium chloride solution (40 mL×2), dried over anhydrous sodium sulfate, and filtered. The filtrate was concentrated under reduced pressure, and the resulting residue was purified by silica gel column chromatography with elution system B to obtain the title compound 117b (2.7 g, yield: 50.5%).

MS m/z (ESI): 329.5 [M+1]

Step 2

7'-amino-1'H-spiro[cyclobutane-1,3'-oxazolo[3,4-a]indol]-1'-one hydrochloride 117c Compound 117b (4.9 g, 14.92 mmol) was dissolved in 30 mL of tetrahydrofuran, and then 4M a solution of hydrogen chloride in 1,4-dioxane (22.38 mL, 89.54 mmol) was added. The reaction solution was warmed up to 45° C. and stirred for 5 hours. The reaction solution was concentrated under reduced pressure. The resulting residue was added with 40 mL of a mixed solvent of ethyl acetate and n-hexane (V/V=1:5), stirred, and filtered. The filter cake was collected to obtain the crude title compound 117c (3.9 g), which was directly used in the next reaction step without purification.

MS m/z (ESI): 229.4 [M+1]

Step 3

2-(4-(2-acetyl-5-chlorophenyl)-5-methoxy-2-oxopyridin-1(2H)-yl)-4-methoxy-N-(1'-oxo-1'H-spiro[cyclobutane-1,3'-oxazolo[3,4-a]indol]-7'-yl)butanamide 117d Compound 1g (400 mg, 1.02 mmol) was added to 12 mL of N,N-dimethylformamide, followed by addition of O-(7-azabenzotriazol-1-yl)-N,N,N',N'-tetramethyluronium hexafluorophosphate (578.94 mg, 1.52 mmol), N,N-diisopropylethylamine (0.708 mL, 4.06 mmol) and the crude compound 117c (268.86 mg, 1.02 mmol). After completion of the addition, the reaction solution was heated to 40° C. and stirred for 16 hours. The reaction solution was added with 50 mL of saturated sodium bicarbonate solution, and extracted with ethyl acetate (100 mL×2). The organic phases were combined, washed with saturated sodium chloride solution (50 mL×3), dried over anhydrous sodium sulfate, and filtered. The filtrate was concentrated under reduced pressure, and the resulting residue was purified by silica gel chromatography with elution system A to obtain the title compound 117d (400 mg, yield: 58.7%).

MS m/z (ESI): 604.5 [M+1]

Step 4

(R)-2-(4-(2-acetyl-5-chlorophenyl)-5-methoxy-2-oxopyridin-1(2H)-yl)-4-methoxy-N-(1'-oxo-1'H-spiro[cyclobutane-1,3'-oxazolo[3,4-a]indol]-7'-yl)butanamide 117

(S)-2-(4-(2-acetyl-5-chlorophenyl)-5-methoxy-2-oxopyridin-1(2H)-yl)-4-methoxy-N-(1'-oxo-1'H-spiro[cyclobutane-1,3'-oxazolo[3,4-a]indol]-7'-yl)butanamide 118

Compound 117d (510 mg, 0.84 mmol) was separated chirally (separation conditions: chiral preparative column CHIRAL PAK IE, 20*250 mm, 5 µm; mobile phase: ethanol=100, flow rate: 8.0 mL/min). The corresponding fractions were collected and concentrated under reduced pressure to obtain the title compound 117 (150 mg) and compound 118 (135 mg).

Compound 117:

MS m/z (ESI):604.6 [M+1]

Chiral HPLC analysis: retention time 8.666 minutes, (chromatographic column: CHIRAL PAK IE 4.6*150 mm 5 µm (with a guard column); mobile phase: ethanol).

¹H NMR (400 MHz, CDCl₃) δ 9.55 (s, 1H), 8.20 (s, 1H), 7.70-7.68 (d, 1H), 7.54-7.49 (m, 2H), 7.48-7.47 (dd, 1H), 7.29-7.28 (d, 1H), 7.05 (s, 1H), 7.00 (s, 1H), 6.67 (s, 1H), 5.95-5.80 (m, 1H), 3.60 (s, 3H), 3.57-3.54 (m, 2H), 3.37 (s, 3H), 3.06-3.02 (m, 2H), 2.92-2.87 (m, 2H), 2.72-2.62 (m, 1H), 2.50 (s, 3H), 2.35-2.15 (m, 3H).

Compound 118:

MS m/z (ESI):604.5 [M+1]

Chiral HPLC analysis: retention time 11.473 minutes, (chromatographic column: CHIRAL PAK IE 4.6*150 mm 5 µm (with a guard column); mobile phase: ethanol).

¹H NMR (400 MHz. CDCl₃) δ 9.55 (s, 1H), 8.20 (s, 1H), 7.70-7.68 (d, 1H), 7.54-7.49 (m, 2H), 7.48-7.47 (dd, 1H), 7.29-7.28 (d, 1H), 7.05 (s, 1H), 7.00 (s, 1H), 6.67 (s, 1H), 5.95-5.80 (m, 1H), 3.60 (s, 3H), 3.57-3.54 (m, 2H), 3.37 (s, 3H), 3.06-3.02 (m, 2H), 2.92-2.87 (m, 2H), 2.72-2.62 (m, 1H), 2.50 (s, 3H), 2.35-2.15 (m, 3H).

Example 119

5-(4-(tert-butoxy)-2-(4-(5-chloro-2-propionylphenyl)-5-methoxy-2-oxopyridin-1(2H)-yl)butanamido)-1H-indole-2-carboxylic acid 119

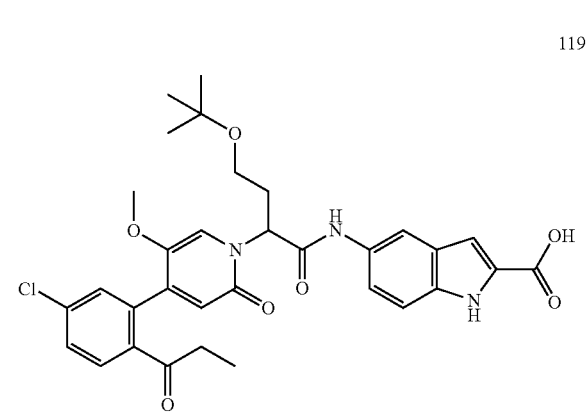 [SMILES: CCC(=O)c1ccc(Cl)cc1-c1cc(=O)n(C(CCOC(C)(C)C)C(=O)Nc2ccc3[nH]c(C(=O)O)cc3c2)cc1OC]

In accordance with the synthetic route of compound 108e in Example 108, the starting compound 8j was replaced with 5-amino-1H-indole-2-carboxylic acid (prepared by a known method disclosed in "Journal of the American Chemical Society, 2006, 128 (37), 12162-12168"), accordingly, the title compound 119 (20 mg) was prepared.

MS m/z (ESI): 608.6 [M+1]

¹H NMR (400 MHz, DMSO-d₆) δ 11.32 (s, 1H), 10.25 (s, 1H), 7.96 (s, 1H), 7.85 (d, 1H), 7.62 (dd, 1H), 7.41 (s, 1H), 7.35-7.28 (m, 3H), 6.80 (s, 1H), 6.39 (s, 1H), 5.78-5.74 (m, 1H), 3.52 (s, 3H), 3.29-3.25 (m, 2H), 2.98-2.85 (m, 2H), 2.35-2.23 (m, 2H), 1.08 (s, 9H), 1.00 (t, 3H).

Example 120

44-(2-(4-(6-acetyl-3-chloro-2-fluorophenyl)-5-methoxy-2-oxopyridin-1(2H)-yl)-4-(tert-butoxy)butanamido)benzoic acid 120

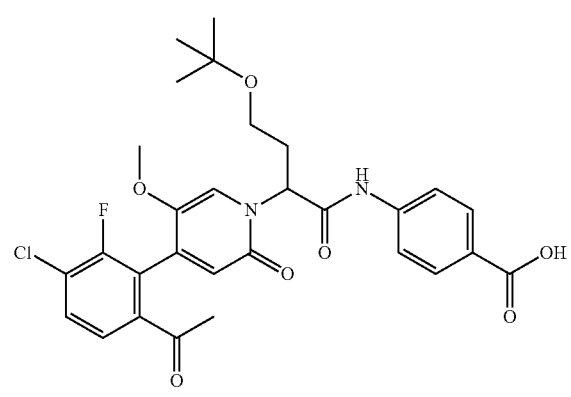

120

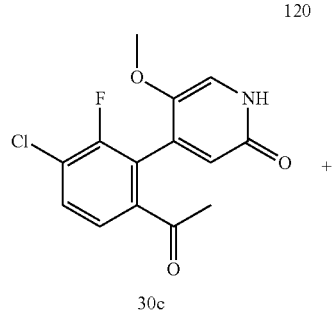

30c

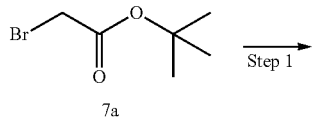

7a

Step 1

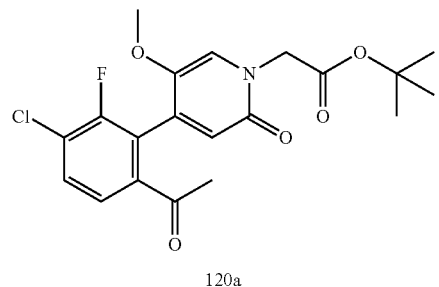

120a

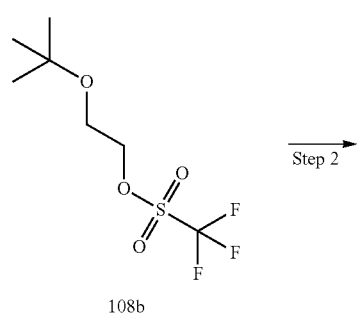

108b

Step 2

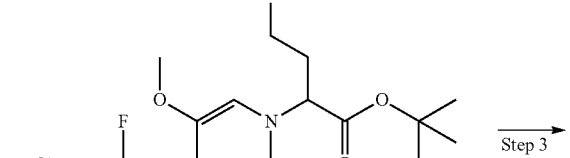

120b

Step 3

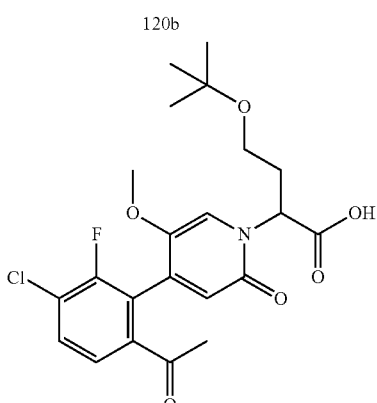

120c

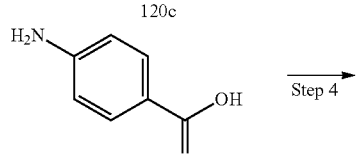

8j

Step 4

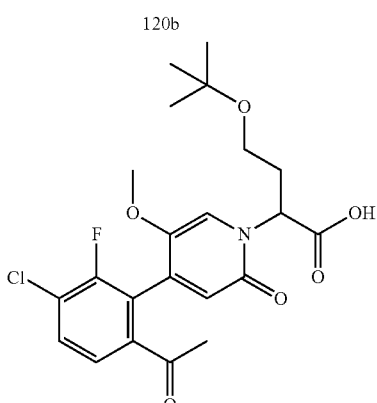

120

Step 1

2-(4-(6-Acetyl-3-chloro-2-fluorophenyl)-5-methoxy-2-oxopyridin-1(2H)-yl)acetate 120a Compound 30c (300 mg, 1.01 mmol), compound 7a (217.68 mg, 1.12 mmol) and cesium carbonate (661.13 mg, 2.03 mmol) were dissolved in 10 mL of N,N-dimethylformamide. The reaction solution was warmed up to 65° C. and stirred for 2 hours. After cooling to room temperature, the reaction solution was added with 20 mL of water, and extracted with ethyl acetate (20 mL×3). The organic phases were combined, washed with saturated sodium chloride solution (20 mL×2), dried over anhydrous sodium sulfate, and filtered. The filtrate was concentrated under reduced pressure, and the resulting residue was purified by silica gel column chromatography with elution system C to obtain the title compound 120a (300 mg, yield: 72.1%).

MS m/z (ESI): 410.4 [M+1]

Step 2 to Step 4

In accordance with the synthetic route of the compound 108e in Example 108, the starting compound 8f was replaced with 120a, accordingly, the title compound 120 (35 mg) was prepared.

MS m/z (ESI): 573.5 [M+1]

$^1$H NMR (400 MHz, DMSO-$d_6$) δ 10.77 (s, 1H), 7.91-7.89 (m, 2H), 7.83-7.76 (m, 4H), 7.37 (d, 1H), 6.40 (d, 1H), 5.82-5.76 (m, 1H), 3.59 (s, 3H), 3.41-3.36 (m, 1H), 3.29-3.23 (m, 1H), 2.47 (d, 3H), 2.38-2.32 (m, 2H), 1.04 (d, 9H).

Example 121

4-(tert-butoxy)-2-(4-(5-chloro-2-propionylphenyl)-5-methoxy-2-oxopyridin-1(2H)-yl)-N-(quinazolin-6-yl)butanamide 121

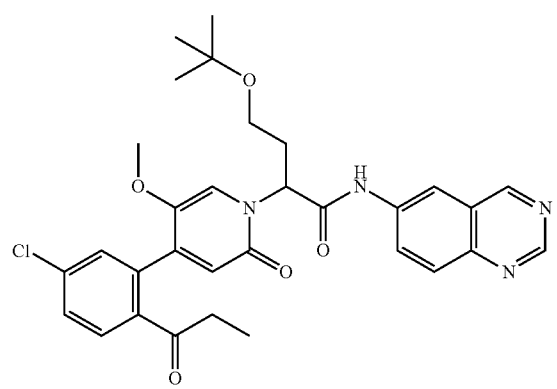

In accordance with the synthetic route of compound 108e in Example 108, the starting compound 8j was replaced with compound 23a, accordingly, the title compound 121 (20 mg) was prepared.

MS m/z (ESI): 577.1 [M+1]

$^1$H NMR (400 MHz; CD$_3$OD) δ 8.57 (s, 1H), 7.93 (dd, 1H), 7.87 (d, 1H), 7.80-7.73 (m, 1H), 7.60 (dd, 1H), 7.39-7.38 (m, 1H), 7.34 (s, 1H), 7.31 (d, 1H), 6.51 (s, 1H), 6.21 (s, 1H), 5.83-5.78 (m, 1H), 3.65 (s, 3H), 3.58-3.40 (m, 2H), 3.03-2.97 (m, 2H), 2.54-2.40 (m, 2H), 1.18 (s, 9H), 1.12 (t, 3H).

Example 122

(S)-4-(2-(4-(2-acetyl-5-chlorophenyl)-5-methoxy-2-oxopyridin-1(2H)-yl)-4-(tert-butoxy)butanamido)benzamide 122

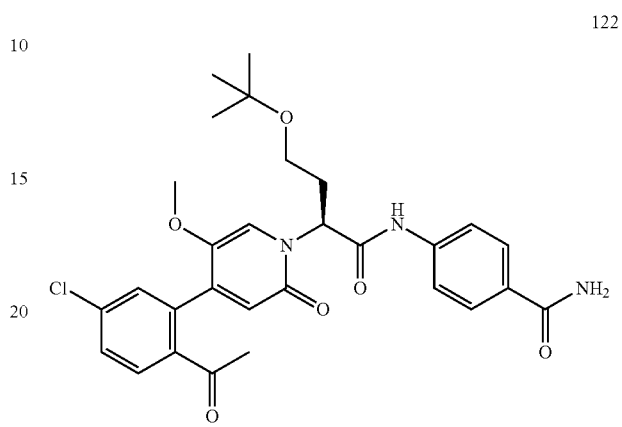

In accordance with the synthetic route of Example 11, the starting compound 5 was replaced with compound 111, accordingly, the title compound 122 (40 mg) was prepared.

MS m/z (ESI): 554.1 [M+1]

$^1$H NMR (400 MHz, DMSO-$d_6$) δ 10.63 (s, 1H), 7.90-7.83 (m, 4H), 7.73 (d, 2H), 7.63 (dd, 1H), 7.42 (s, 1H), 7.29-7.27 (m, 2H), 6.41 (s, 1H), 5.79-5.76 (m, 1H), 3.55 (s, 3H), 3.30-3.28 (m, 2H), 2.55 (s, 3H), 2.36-2.28 (m, 2H), 1.07 (s, 9H).

Example 123

(S)-4-(2-(4-(2-acetyl-5-chlorophenyl)-5-methoxy-2-oxopyridin-(2H)-yl)-4-(tert-butoxy)butanamido)-N-methylbenzamide 123

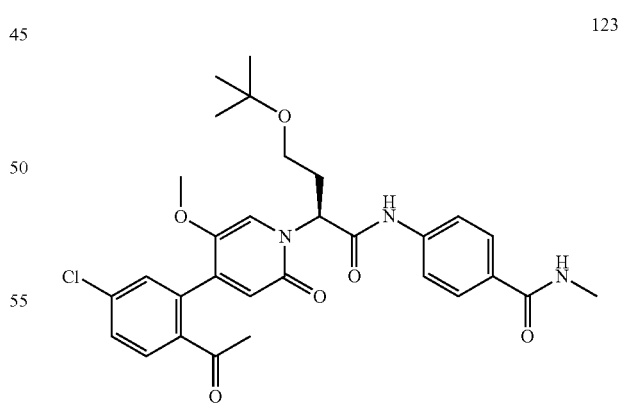

In accordance with the synthetic route of Example 13, the starting compound 5 was replaced with compound 111, accordingly, the title compound 123 (40 mg) was prepared.

MS m/z (ESI): 568.1 [M+1]

$^1$H NMR (400 MHz, CDCl$_3$) δ 9.73 (br, 1H), 7.76-7.65 (m, 4H), 7.51 (d, 1H), 7.32-7.31 (m, 1H), 6.98 (s, 1H), 6.66 (s, 1H), 6.26-6.24 (m, 1H), 5.84-5.79 (m, 1H), 3.62 (s, 3H), 3.54-3.52 (m, 2H), 3.03 (d, 1H), 2.66-2.61 (m, 1H), 2.53 (s, 3H), 2.33-2.25 (m, 2H), 1.20 (s, 9H).

Example 124

4-(tert-butoxy)-2-(4-(5-chloro-2-propionylphenyl)-5-methoxy-2-oxopyridin-1(2H)-yl)-N-(2,3-dimethylquinoxalin-6-yl)butanamide 124

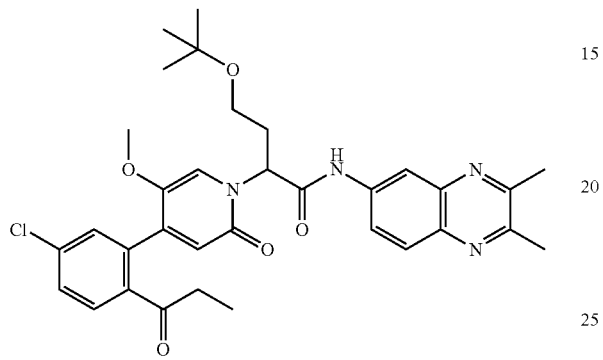

In accordance with the synthetic route of compound 108e in Example 108, the starting compound 8j used in Step 4 was replaced with 2,3-dimethyl-6-quinoxalinamine (prepared by a known method disclosed in "*Bioorganic & Medicinal Chemistry Letters*, 2012, 20(7), 2227-2234"), accordingly, the title compound 124 (15 mg) was prepared.

MS m/z (ESI): 605.3 [M+1]

$^1$H NMR (400 MHz, CD$_3$OD) δ 8.45-8.42 (d, 1H), 7.92-7.90 (d, 1H), 7.90-7.86 (dd, 1H), 7.85-7.82 (d, 1H), 7.57-7.52 (dd, 1H), 7.37 (s, 2H), 6.50 (s, 1H), 5.95-5.85 (m, 1H), 3.65-3.60 (s, 3H), 3.60-3.55 (m, 1H), 3.50-3.40 (m, 1H), 3.00-2.95 (m, 2H), 2.70 (s, 6H), 2.50-2.40 (m, 1H), 2.35-2.25 (m, 1H), 1.17 (s, 9H), 1.10-1.00 (m, 3H).

Example 125

4-(tert-butoxy)-2-(4-(5-chloro-2-propionylphenyl)-5-methoxy-2-oxopyridin-(2H)-yl)-N-(2-cyano-1H-indol-6-yl)butanamide 125

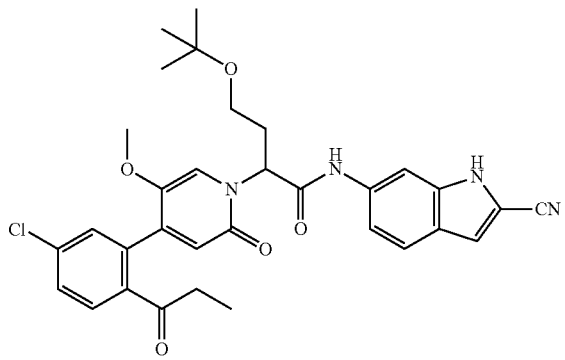

In accordance with the synthetic route of compound 108e in Example 108, the starting compound 8j was replaced with 6-amino-1H-indole-2-carbonitrile (prepared according to the patent application "US20160271105"), accordingly, the title compound 125 (30 mg) was prepared.

MS m/z (ESI): 589.5 [M+1]

$^1$H NMR (400 MHz, CD$_3$OD) δ 8.04 (s, 1H), 7.85-7.83 (d, 1H), 7.61-7.59 (d, 1H), 7.58-7.57 (dd, 1H), 7.38-7.37 (d, 1H), 7.36 (s, 1H), 7.25-7.18 (dd, 1H), 7.16-7.15 (d, 1H), 6.50 (s, 1H), 5.95-5.90 (m, 1H), 3.63 (s, 3H), 3.60-3.55 (m, 1H), 3.50-3.40 (m, 1H), 3.00-2.95 (m, 2H), 2.50-2.40 (m, 1H), 2.35-2.25 (m, 1H), 1.17 (s, 9H), 1.10-1.00 (m 3H).

Example 126

N-(Benzo[d]thiazol-5-yl)-4-(tert-butoxy)-2-(4-(5-chloro-2-propionylphenyl)-5-methoxy-2-oxopyridin-1(2H)-yl)butanamide 126

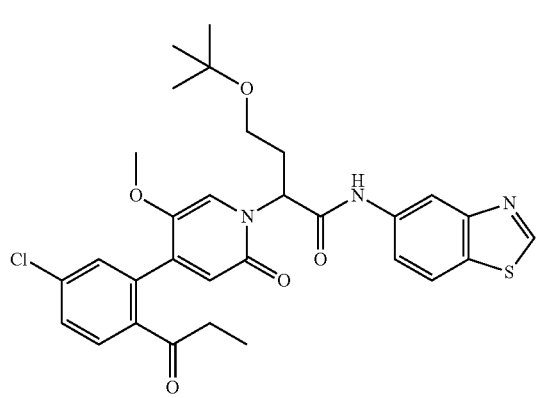

In accordance with the synthetic route of compound 108e in Example 108, the starting compound 8j was replaced with benzo[d]thiazol-5-amine (prepared according to the patent application "WO2013142266"), accordingly, the title compound 126 (35 mg) was prepared.

MS m/z (ESI): 582.2 [M+1]

$^1$H NMR (400 MHz, CD$_3$OD) δ 9.24 (s, 1H), 8.50 (s, 1H), 8.03-8.00 (d, 1H), 7.84-7.82 (d, 1H), 7.68-7.69 (d, 1H), 7.57-7.54 (dd, 1H), 7.38-7.35 (m, 2H), 6.50 (s, 1H), 5.95-5.85 (m, 1H), 3.62 (s, 3H), 3.60-3.55 (m, 1H), 3.50-3.40 (m, 1H), 3.00-2.80 (m, 2H), 2.50-2.40 (m, 1H), 2.35-2.25 (m, 1H), 1.17 (s, 9H), 1.11-1.09 (m, 3H).

Example 127

4-(4-(tert-butoxy)-2-(4-(5-chloro-2-propionylphenyl)-5-methoxy-2-oxopyridin-1(2H)-yl)butanamido)thiophene-2-carboxylic acid 127

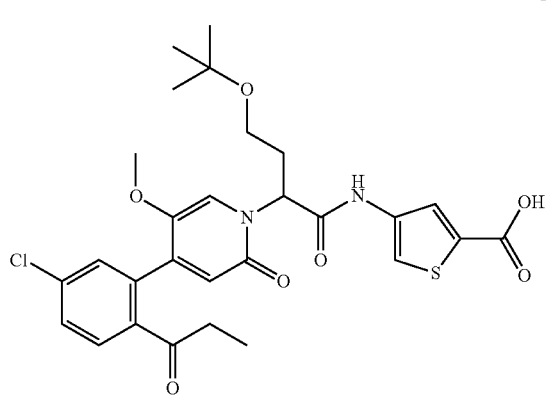

127

In accordance with the synthetic route of compound 108e in Example 108, the starting compound 8j was replaced with 4-aminothiophene-2-carboxylic acid (prepared according to the patent application "*Journal of the American Chemical Society*, 1999, 121 (34), 7751-7759"), accordingly, the title compound 127 (20 mg) was prepared.

MS m/z (ESI): 575.3 [M+1]

$^1$H NMR (400 MHz, CD$_3$OD) δ 7.85 (s, 1H), 7.85-7.84 (d, 1H), 7.82-7.80 (d, 1H), 7.58-7.55 (d, 1H), 7.38-7.36 (d, 1H), 7.33-7.31 (s, 1H), 6.48 (s, 1H), 5.95-5.85 (m, 1H), 3.65-3.60 (m, 3H), 3.60-3.55 (m, 1H), 3.50-3.40 (m, 1H), 3.00-2.95 (m, 2H), 2.50-2.40 (m, 1H), 2.35-2.25 (m, 1H), 1.17 (s, 9H), 1.10-1.00 (m, 3H).

Example 128

2-(4-(2-acetyl-5-chlorophenyl)-5-methoxy-2-oxopyridin-1(2H)-yl)-4-(tert-butoxy)-N-(3,4-dihydro-2H-benzo[b][1,4]oxazin-6-yl)butanamide 128

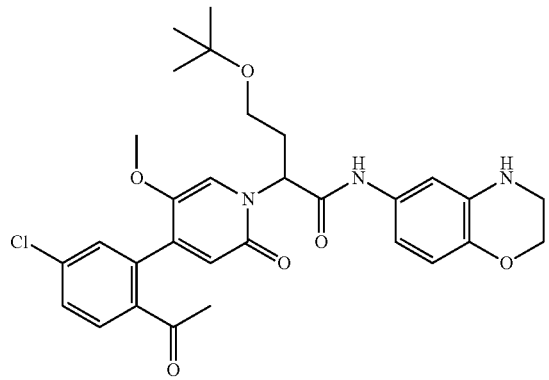

128

In accordance with the synthetic route of compound 108e in Example 108, the starting compound 8f was replaced with the starting compound 7b, and the starting compound 8j was replaced with 3,4-dihydro-2H-benzo[b][1,4]oxazin-6-amine (prepared by a known method disclosed in "*Bioorganic & Medicinal Chemistry Letters*, 2015, 25 (10), 2122-2128"), accordingly, the title compound 128 (23 mg) was prepared.

MS m/z (ESI): 568.1 [M+1]

$^1$H NMR (400 MHz, CDCl$_3$) δ 8.98 (s, 1H), 7.69 (d, 1H), 7.51-7.48 (dd, 1H), 7.32 (d, 1H), 7.07 (d, 1H), 6.95 (s, 1H), 6.75-6.71 (m, 2H), 6.60 (s, 1H), 5.80 (s, 1H), 4.25 (t, 2H), 3.59 (s, 3H), 3.52 (t, 2H), 3.43 (t, 2H), 2.63-2.59 (m, 1H), 2.50 (s, 3H), 2.22-2.18 (m, 1H), 1.22 (s, 9H).

Example 129

2-(4-(2-acetyl-5-chlorophenyl)-5-methoxy-2-oxopyridin-1(2H)-yl)-4-(tert-butoxy)-N-(3-fluorophenyl)butanamide 129

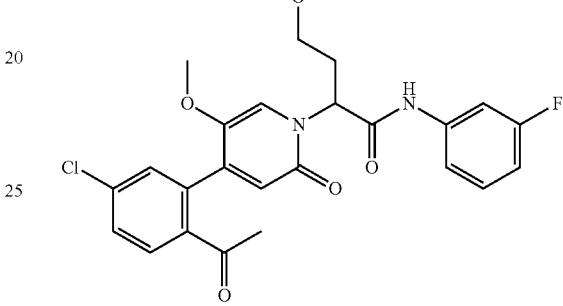

129

In accordance with the synthetic route of the compound 108e in Example 108, the starting compound 8f was replaced with the starting compound 7b, and the starting compound 8j was replaced with 3-fluoroaniline, accordingly, the title compound 129 (20 mg) was prepared.

MS m/z (ESI): 529.2 [M+1]

$^1$H NMR (400 MHz, CDCl$_3$) δ 9.67 (br, 1H), 8.01-8.00 (m, 1H), 7.75-7.70 (m, 2H), 7.52-7.45 (m, 2H), 7.40-7.38 (m, 1H), 7.34-7.33 (m, 1H), 6.91 (s, 1H), 6.64 (s, 1H), 5.79 (br, 1H), 3.61 (s, 3H), 3.56-3.53 (m, 2H), 2.70-2.62 (m, 1H), 2.53 (s, 3H), 2.27-2.23 (m, 1H), 1.22 (m, 9H).

Example 130

2-(4-(2-acetyl-5-chlorophenyl)-5-methoxy-2-oxopyridin-1(2H)-yl)-4-(tert-butoxy)-N-(5-chloropyridin-3-yl)butanamide 130

130

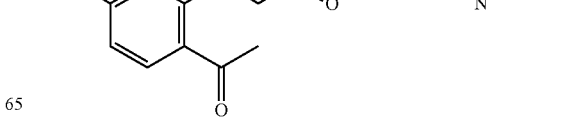

In accordance with the synthetic route of compound 108e in Example 108, the starting compound 8f was replaced with the starting compound 7b, and the starting compound 8j was replaced with 5-chloropyridin-3-amine (prepared by a method disclosed in the patent application "WO2006067445"), accordingly, the title compound 130 (25 mg) was prepared.

MS m/z (ESI): 546.0 [M+1]

¹H NMR (400 MHz, CD₃OD) δ 8.68 (d, 1H), 8.33 (m, 1H), 8.31 (d, 1H), 7.89 (d, 1H), 7.58 (dd, 1H), 7.38 (d, 1H), 7.33 (s, 1H), 6.51 (s, 1H), 5.86-5.81 (m, 1H), 3.65 (s, 3H), 3.58-3.40 (m, 2H), 2.56 (s, 3H), 2.53-2.39 (m, 2H), 1.18 (s, 9H).

Example 131

2-(4-(2-acetyl-5-chlorophenyl)-5-methoxy-2-oxopyridin-1(2H)-yl)-4-(tert-butoxy)-N-(5-fluoro-pyridin-3-yl)butanamide 131

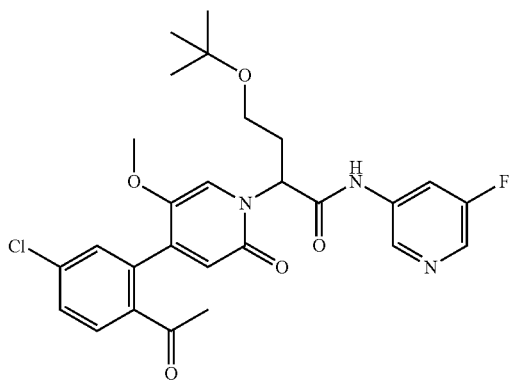

131

In accordance with the synthetic route of compound 108e in Example 108, the starting compound 8f was replaced with the starting compound 7b, and the starting compound 8j was replaced with 5-fluoropyridin-3-amine (prepared by a known method disclosed in "*Journal of Medicinal Chemistry*, 1999, 42 (18), 3701-3710"), accordingly, the title compound 131 (25 mg) was prepared.

MS m/z (ESI): 530.1 [M+1]

¹H NMR (400 MHz, CD₃OD) δ 8.59 (s, 1H), 8.24 (d, 1H), 8.18-8.14 (m, 1H), 7.89 (d, 1H), 7.59 (dd, 1H), 7.38 (d, 1H), 7.33 (s, 1H), 6.51 (s, 1H), 5.86-5.81 (m, 1H), 3.65 (s, 3H), 3.58-3.40 (m, 2H), 2.56 (s, 3H), 2.53-2.39 (m, 2H), 1.18 (s, 9H).

Example 132

2-(4-(2-acetyl-5-chlorophenyl)-5-methoxy-2-oxopyridin-1(2H)-yl)-4-(tert-butoxy)-N-(4-fluoro-phenyl)butanamide 132

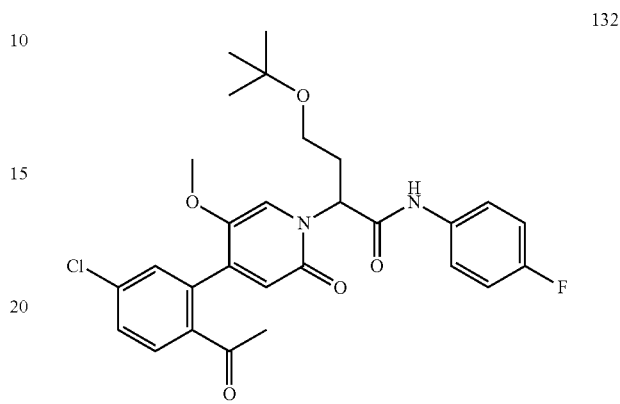

132

In accordance with the synthetic route of compound 108e in Example 108, the starting compound 8f used in Step 2 was replaced with the starting compound 7b, and the starting compound 8j used in Step 4 was replaced with 4-fluoroaniline, accordingly, the title compound 132 (20 mg) was prepared.

MS m/z (ESI): 529.2 [M+1]

¹H NMR (400 MHz, CDCl₃) δ 9.37 (br, 1H), 7.72-7.70 (d, 1H), 7.59-7.56 (m, 2H), 7.52-7.49 (m, 1H), 7.33-7.32 (m, 1H), 7.07-7.02 (m, 2H), 6.95 (s, 1H), 6.62 (s, 1H), 5.78 (br, 1H), 3.60 (s, 3H), 3.54-3.52 (m, 2H), 2.66-2.60 (m, 1H), 2.52 (s, 3H), 2.26-2.21 (m, 1H), 1.22 (m, 9H).

Example 133

2-(4-(2-acetyl-5-chlorophenyl)-5-methoxy-2-oxopyridin-1 (2H)-yl)-4-(tert-butoxy)-N-(3,4-di-hydro-2H-benzo[b][1,4]oxazin-7-yl)butanamide 133

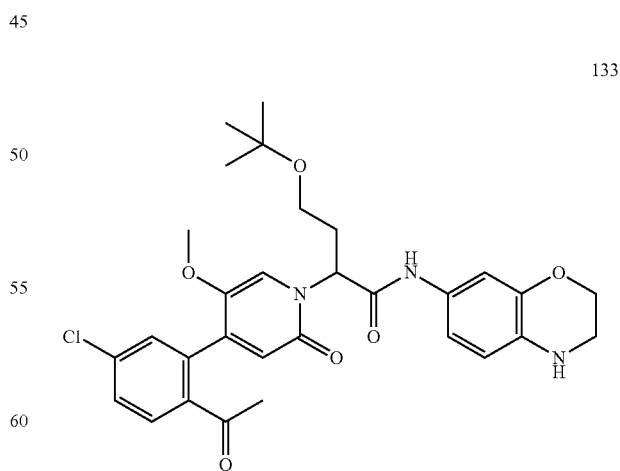

133

In accordance with the synthetic route of compound 108e in Example 108, the starting compound 8f was replaced with the starting compound 7b, and the starting compound 8j was replaced with 3,4-dihydro-2H-benzo[b][1,4]oxazin-7-amine (prepared by a known method disclosed in "*Journal of Medicinal Chemistry.*, 2005, 48(1), 71-90"), accordingly, the title compound 133 (19 mg) was prepared.

MS m/z (ESI): 568.5 [M+1]

¹H NMR (400 MHz, CDCl₃) δ 8.91 (s, 1H), 7.69 (d, 1H), 7.50-7.48 (dd, 1H), 7.32 (d, 1H), 7.09 (d, 1H), 6.97 (s, 1H), 6.94 (d, 1H), 6.60 (s, 1H), 6.56 (d, 1H), 5.78 (s, 1H), 4.26 (t, 2H), 3.59 (s, 3H), 3.42 (t, 2H), 3.51 (t, 2H), 2.60-2.57 (m, 1H), 2.50 (s, 3H), 2.27-2.24 (m, 1H), 1.22 (s, 9H).

Example 134

2-(4-(2-acetyl-5-chlorophenyl)-5-methoxy-2-oxopyridin-1(2H)-yl)-4-(tert-butoxy)-N-(6-methoxy pyridin-3-yl)butanamide 134

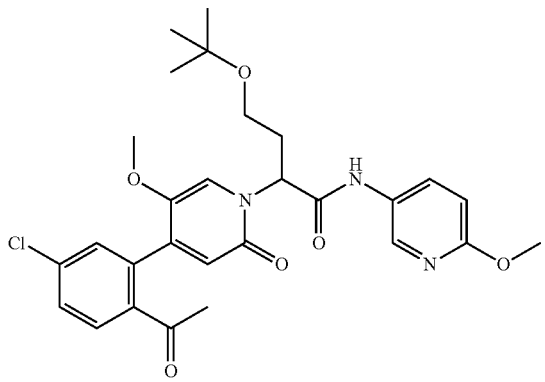

134

In accordance with the synthetic route of compound 108e in Example 108, the starting compound 8f was replaced with the starting compound 7b, and the starting compound 8j was replaced with 6-methoxypyridin-3-amine (prepared by a known method disclosed in "*Tetrahedron Letters,* 2010, 51 (5), 786-789"), accordingly, the title compound 134 (25 mg) was prepared.

MS m/z (ESI): 542.1 [M+1]

¹H NMR (400 MHz, CD₃OD) δ 8.38 (s, 1H), 7.95-7.91 (m, 1H), 7.89 (d, 1H), 7.59 (dd, 1H), 7.38 (d, 1H), 7.34 (s, 1H), 6.83 (d, 1H), 6.52 (s, 1H), 5.85-5.82 (m, 1H), 3.91 (s, 3H), 3.65 (s, 3H), 3.58-3.40 (m, 2H), 2.55 (s, 3H), 2.51-2.33 (m, 2H), 1.19 (s, 9H).

Example 135

2-(4-(2-acetyl-5-chlorophenyl)-5-methoxy-2-oxopyridin-1(2H)-yl)-4-(tert-butoxy)-N-(3-(trifluoromethyl)phenyl)butanamide 135

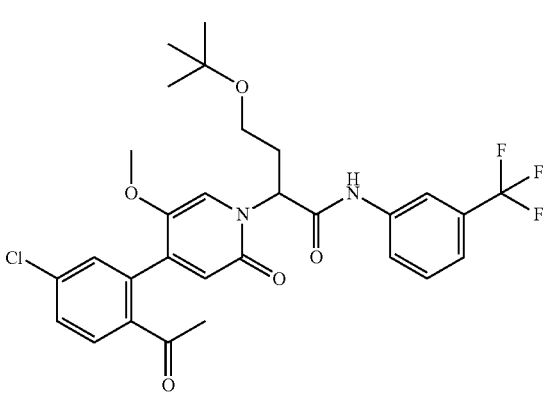

135

In accordance with the synthetic route of compound 108e in Example 108, the starting compound 8f was replaced with the starting compound 7b, and the starting compound 8j was replaced with 3-(trifluoromethyl)aniline (prepared by a known method disclosed in "*Journal of Organic Chemistry,* 2016, 81 (12), 5120-5127"), accordingly, the title compound 135 (15 mg) was prepared.

MS m/z (ESI): 579.2 [M+1]

¹H NMR (400 MHz, CDCl₃) δ 9.53 (br, 1H), 7.72-7.70 (m, 1H), 7.61-7.58 (m, 1H), 7.52-7.49 (m, 1H), 7.33-7.32 (m, 1H), 7.30-7.21 (m, 2H), 6.92 (s, 1H), 6.86-6.82 (m, 1H), 6.63 (s, 1H), 5.78 (br, 1H), 3.60 (s, 3H), 3.55-3.52 (m, 2H), 2.68-2.60 (m, 1H), 2.52 (s, 3H), 2.26-2.21 (m, 1H), 1.22 (s, 9H).

Example 136

2-(4-(2-acetyl-5-chlorophenyl)-5-methoxy-2-oxopyridin-1(2H)-yl)-4-(tert-butoxy)-N-(4-(trifluoromethyl)phenyl)butanamide 136

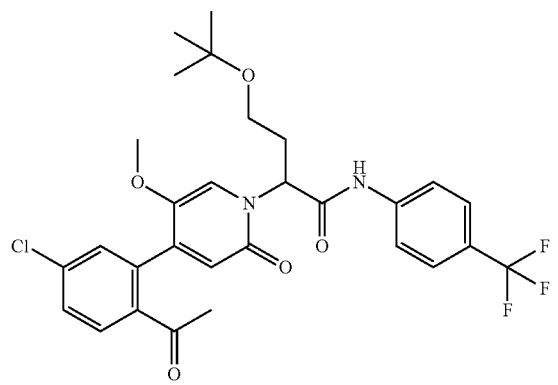

136

In accordance with the synthetic route of compound 108e in Example 108, the starting compound 8f was replaced with the starting compound 7b, and the starting compound 8j was replaced with 4-(trifluoromethyl)aniline (prepared by a known method disclosed in "*Journal of Organic Chemistry,* 2009, 74 (12), 4542-4546"), accordingly, the title compound 136 (20 mg) was prepared.

MS m/z (ESI): 579.2 [M+1]

¹H NMR (400 MHz, CDCl₃) δ 9.70 (br, 1H), 7.76-7.72 (m, 3H), 7.62-61 (m, 2H), 7.52-7.51 (m, 1H), 7.34-7.32 (m, 1H), 6.92-6.90 (m, 1H), 6.65-6.63 (m, 1H), 5.80-5.77 (m, 1H), 3.61-3.60 (m, 3H), 3.54 (br, 2H), 2.67-2.66 (m, 1H), 2.54-2.52 (m, 3H), 2.28-2.24 (m, 1H), 1.23-1.21 (m, 9H).

Example 137

2-(4-(2-acetyl-5-chlorophenyl)-5-methoxy-2-oxopyridin-1(2H)-yl)-4-(tert-butoxy)-N-(2,3-dihydrobenzo[b][1,4]dioxin-5-yl)butanamide 137

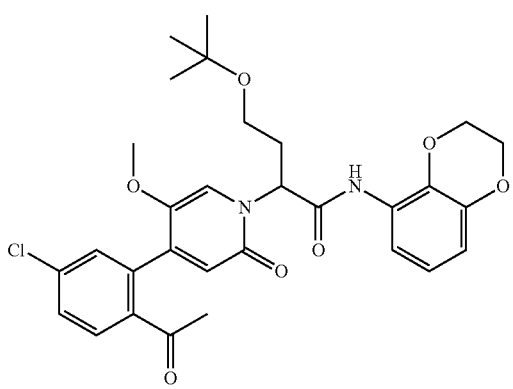

In accordance with the synthetic route of compound 108e in Example 108, the starting compound 8f was replaced with the starting compound 7b, and the starting compound 8j was replaced with 2,3-dihydrobenzo[b][1,4]dioxin-5-amine (prepared by a method disclosed in the patent application "WO2012092880"), accordingly, the title compound 137 (30 mg) was prepared.

MS m/z (ESI): 569.2 [M+1]

$^1$H NMR (400 MHz, CDCl$_3$) δ 8.90 (s, 1H), 7.90 (d, 1H), 7.69 (d, 1H), 7.48 (d, 1H), 7.33 (d, 1H), 7.00 (s, 1H), 6.82 (t, 1H), 6.67 (dd, 1H), 6.61 (s, 1H), 5.89-5.85 (m, 1H), 4.42-4.39 (m, 2H), 4.32-4.30 (m, 2H), 3.60 (s, 3H), 3.52-3.49 (m, 2H), 2.61-2.57 (m, 1H), 2.51 (s, 3H), 2.25-2.12 (m, 1H), 1.21 (m, 9H).

Example 138

2-(4-(2-acetyl-5-chlorophenyl)-5-methoxy-2-oxopyridin-1(2H)-yl)-4-(tert-butoxy)-N-(3,4-dihydro-2H-benzo[b][1,4]oxazin-5-yl)butanamide 138

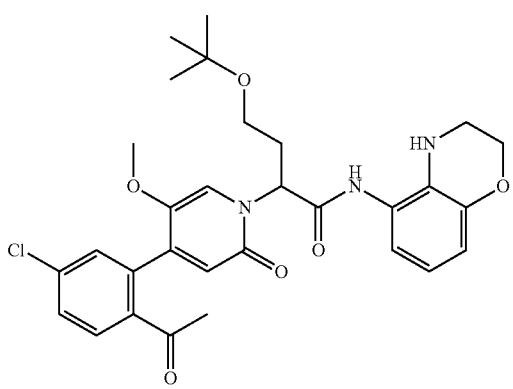

In accordance with the synthetic route of compound 108e in Example 108, the starting compound 8f was replaced with the starting compound 7b, and the starting compound 8j was replaced with 3,4-dihydro-2H-benzo[b][1,4]oxazin-5-amine (prepared by a known method disclosed in "Journal of Medicinal Chemistry, 2017, 60 (6), 2401-2410"), accordingly, the title compound 138 (21 mg) was prepared.

MS m/z (ESI): 568.1 [M+1]

$^1$H NMR (400 MHz, CDCl$_3$) δ 8.76 (s, 1H), 7.70 (d, 1H), 7.52-7.49 (dd, 1H), 7.32 (d, 1H), 7.13-7.11 (m, 1H), 6.94 (s, 1H), 6.72-6.70 (m, 2H), 6.61 (s, 1H), 5.70 (s, 1H), 4.23-4.19 (m, 2H), 3.60 (s, 3H), 3.58-3.55 (m, 2H), 3.48 (s, 2H), 2.68-2.62 (m, 1H), 2.52 (s, 3H), 2.28-2.22 (m, 1H), 1.23 (s, 9H).

Example 139

2-(4-(2-acetyl-5-chlorophenyl)-5-methoxy-2-oxopyridin-1(2H)-yl)-4-(tert-butoxy)-N-(2,3-dihydrobenzo[b][1,4]dioxin-6-yl)butanamide 139

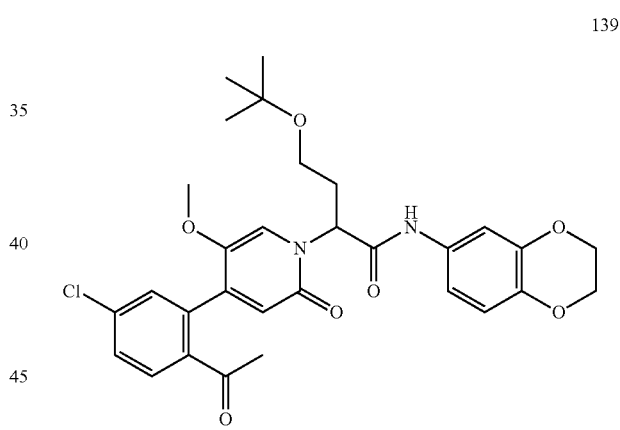

In accordance with the synthetic route of compound 108e in Example 108, the starting compound 8f was replaced with the starting compound 7b, and the starting compound 8j was replaced with 2,3-dihydrobenzo[b][14]dioxin-6-amine (prepared by a well-known method disclosed in "Chemical Communications, 2012, 48 (64), 7982-7984"), accordingly, the title compound 139 (30 mg) was prepared.

MS m/z (ESI): 569.2 [M+1]

$^1$H NMR (400 MHz, CDCl$_3$) δ 9.05 (s, 1H), 7.70 (d, 1H), 7.50 (d, 1H), 7.33 (s, 1H), 7.26 (s, 1H), 6.98 (d, 1H), 6.94 (s, 1H), 6.82 (d, 1H), 6.61 (s, 1H), 5.78-5.77 (m, 1H), 4.27 (s, 4H), 3.60 (s, 3H), 3.51-3.52 (m, 2H), 2.61-2.62 (m, 1H), 2.51 (s, 3H), 2.22-2.26 (s, 1H), 1.22 (m, 9H).

Example 140

2-(4-(2-acetyl-5-chlorophenyl)-5-methoxy-2-oxopyridin-(2H)-yl)-N-(benzo[d][1,3]dioxol-5-yl)-4-(tert-butoxy)butanamide 140

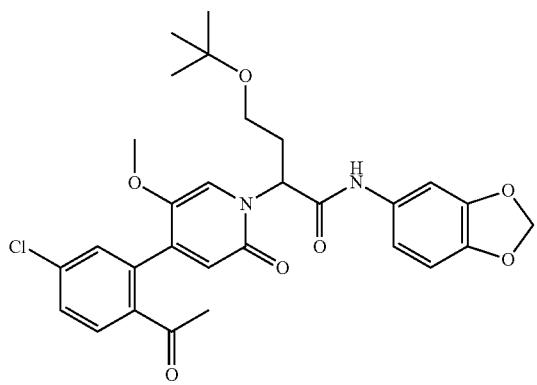

140

In accordance with the synthetic route of compound 108e in Example 108, the starting compound 8f used in Step 2 was replaced with the starting compound 7b, and the starting compound 8j used in Step 4 was replaced with benzo[d][1,3]dioxol-5-amine (prepared by a method disclosed in the patent application "CN105348251"), accordingly, the title compound 140 (25 mg) was prepared.

MS m/z (ESI): 555.1 [M+1]
$^1$H NMR (400 MHz, CD$_3$OD) δ 7.89 (d, 1H), 7.59 (d, 1H), 7.39 (s, 1H), 7.35 (s, 1H), 7.06 (s, 1H), 6.97 (d, 1H), 6.79 (d, 1H), 6.52 (s, 1H), 5.85-5.81 (m, 1H), 3.65 (s, 3H), 3.55-3.42 (m, 2H), 2.55 (s, 3H), 2.44-2.34 (m, 2H), 1.19 (s, 9H).

Example 141

4-(tert-butoxy)-2-(4-(5-chloro-2-propionylphenyl)-5-methoxy-2-oxopyridin-1(2H)-yl)-N-(2-methyl-2H-carbazol-5-yl)butanamide 141

141

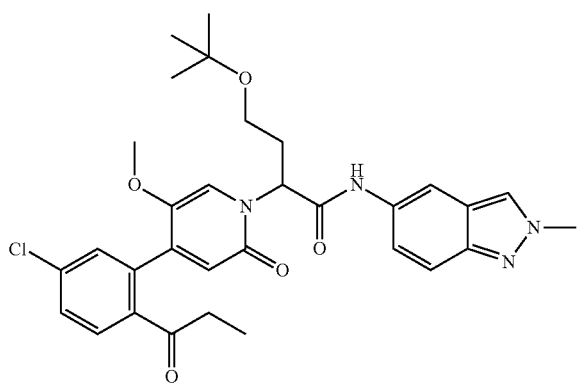

In accordance with the synthetic route of compound 108e in Example 108, the starting compound 8j was replaced with compound 18a, accordingly, the title compound 141(25 mg) was prepared.

MS m/z (ESI): 579.1 [M+1]
$^1$H NMR (400 MHz, CD$_3$OD) δ 7.89 (d, 1H), 7.60 (d, 1H), 7.41-7.39 (m, 2H), 7.35 (s, 1H), 7.21 (d, 1H), 7.12 (d, 1H), 6.52 (s, 1H), 5.87-5.84 (m, 1H), 3.66 (s, 3H), 3.62-3.52 (m, 1H), 3.51 (s, 2H), 3.47-3.43 (m, 1H), 2.55 (s, 3H), 2.53-2.37 (m, 2H), 1.35-1.31 (m, 2H), 1.19 (s, 9H).

Example 142

2-(4-(2-acetyl-5-chlorophenyl)-5-methoxy-2-oxopyridin-1(2H)-yl)-4-(tert-butoxy)-N-(1H-indol-4-yl)butanamide 142

142

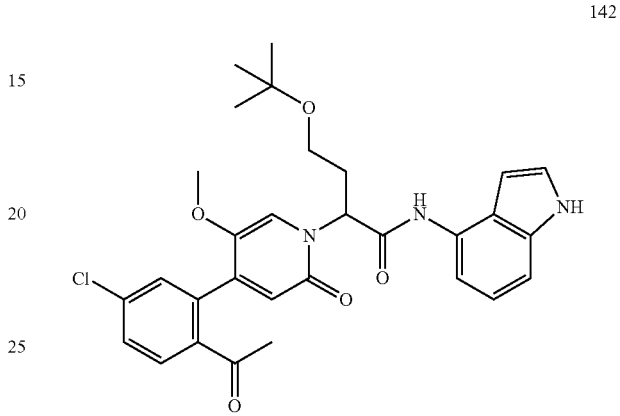

In accordance with the synthetic route of compound 108e in Example 108, the starting compound 8f was replaced with the starting compound 7b, and the starting compound 8j was replaced with 1H-indole-4-amine (prepared by a known method disclosed in "*Journal of Medicinal Chemistry*, 2005, 48 (9), 3417-3427"), accordingly, the title compound 142 (25 mg) was prepared.

MS m/z (ESI): 550.1 [M+1]
$^1$H NMR (400 MHz, CD$_3$OD) δ 7.89 (d, 1H), 7.59 (d, 1H), 7.45 (d, 1H), 7.40 (s, 1H), 7.38 (d, 2H), 7.28-7.26 (m, 2H), 7.10 (t, 1H), 6.63-6.61 (m, 1H), 6.57 (s, 1H), 6.03-5.99 (m, 1H), 3.66 (s, 3H), 3.62-3.47 (m, 2H), 2.55 (s, 3H), 2.54-2.40 (m, 2H), 1.20 (s, 9H).

Example 143

2-(4-(2-acetyl-5-chlorophenyl)-5-methoxy-2-oxopyridin-1(2H)-yl)-4-(tert-butoxy)-N-(1-oxo-1,2,3,4-tetrahydroisoquinolin-6-yl)butanamide 143

143

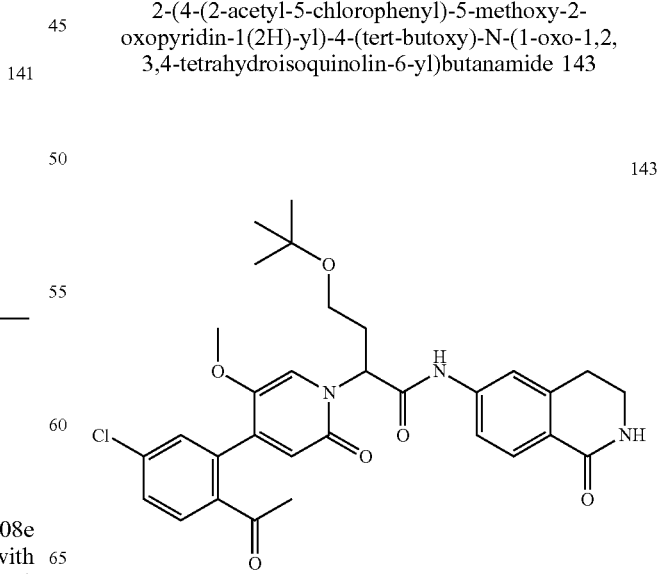

In accordance with the synthetic route of compound 108e in Example 108, the starting compound 8f was replaced with the starting compound 7b, and the starting compound 8j was replaced with 6-amino-3,4-dihydroisoquinolin-1(2H)-one (prepared by a method disclosed in the patent application "CN103804358"), accordingly, the title compound 143 (20 mg) was prepared.

MS m/z (ESI): 580.6 [M+1]

$^1$H NMR (400 MHz, CDCl$_3$) δ 9.69 (s, 1H), 8.05 (d, 1H), 7.70 (d, 1H), 7.64 (d, 1H), 7.51-7.47 (m, 2H), 7.32 (d, 1H), 6.91 (s, 1H), 6.62 (s, 1H), 5.91 (s, 1H), 5.79 (s, 1H), 3.60 (s, 3H), 3.59-3.52 (m, 4H), 3.01 (t, 2H), 2.68-2.60 (m, 1H), 2.52 (s, 3H), 2.28-2.20 (m, 1H), 1.22 (s, 9H).

Example 144

2-(4-(2-acetyl-5-chlorophenyl)-5-methoxy-2-oxopyridin-1(2H)-yl)-4-(tert-butoxy)-N-(2-oxoindo-lin-6-yl)butanamide 144

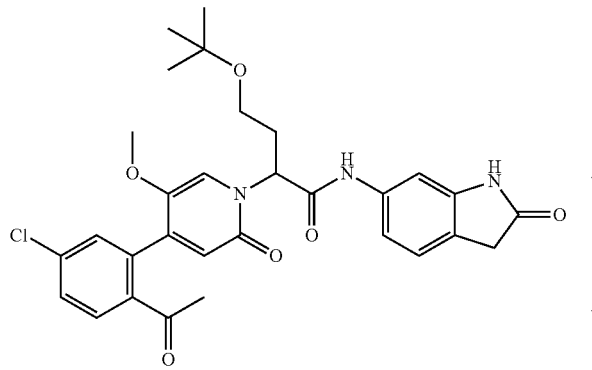

In accordance with the synthetic route of compound 108e in Example 108, the starting compound 8f was replaced with the starting compound 7b, and the starting compound 8j was replaced with 6-aminoindol-2-one (prepared by a method disclosed in the patent application "WO2009079767"), accordingly, the title compound 144 (25 mg) was prepared.

MS m/z (ESI): 566.1 [M+1]

$^1$H NMR (400 MHz, CD$_3$OD) δ 8.18 (s, 1H), 8.13 (s, 1H), 7.86 (d, 1H), 7.60-7.57 (m, 2H), 7.39-7.37 (m, 3H), 6.52 (s, 1H), 5.90-5.86 (m, 1H), 4.21 (s, 3H), 3.65 (s, 3H), 3.58-3.46 (m, 2H), 2.98 (s, 2H), 2.47-2.32 (m, 2H), 1.20 (s, 9H).

Example 145

2-(4-(2-acetyl-5-chlorophenyl)-5-methoxy-2-oxopyridin-1(2H)-yl)-4-(tert-butoxy)-N-(2-oxoindo-lin-5-yl)butanamide 145

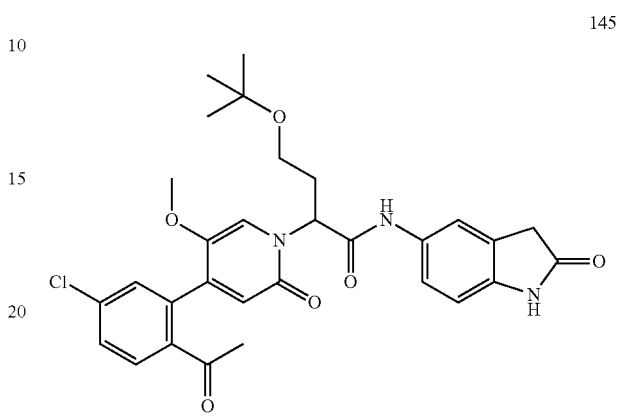

In accordance with the synthetic route of compound 108e in Example 108, the starting compound 8f was replaced with the starting compound 7b, and the starting compound 8j was replaced with 5-aminoindol-2-one (prepared by a known method disclosed in "*Bioorganic and Medicinal Chemistry*, 2013, 21 (7), 1724-1734"), accordingly, the title compound 145 (25 mg) was prepared.

MS m/z (ESI): 566.1 [M+1]

$^1$H NMR (400 MHz, CD$_3$OD) δ 7.89 (d, 1H), 7.59 (d, 1H), 7.56 (s, 1H), 7.41-7.39 (m, 2H), 7.36 (s, 1H), 6.87 (d, 1H), 6.51 (s, 1H), 5.87-5.82 (m, 1H), 3.65 (s, 3H), 3.55 (s, 2H), 3.54-3.43 (m, 2H), 2.55 (s, 3H), 2.53-2.36 (m, 2H), 1.19 (s, 9H).

Example 146

4-(2-(4-(6-acetyl-3-chloro-2-fluorophenyl)-5-methoxy-2-oxopyridin-1(2H)-yl)-4-methoxybutana-mido)benzoic acid 146

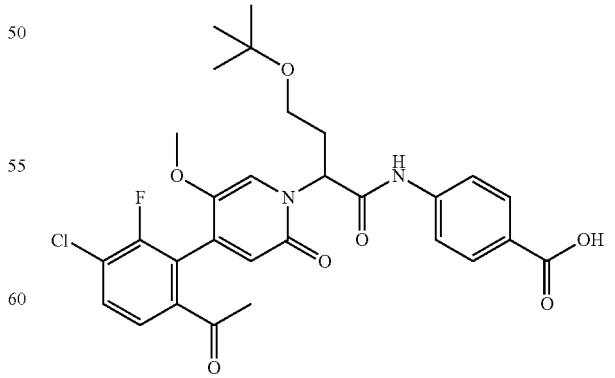

In accordance with the synthetic route in Example 30, the starting compound 4a was replaced with compound 1b, accordingly, the title compound 146 (35 mg) was prepared.

MS m/z (ESI): 531.4 [M+1]

¹H NMR (400 MHz, CD₃OD) δ 8.03-7.99 (m, 2H), 7.78-7.68 (m, 4H), 7.46 (d, 1H), 6.51 (s, 1H), 5.89-5.77 (m, 1H), 3.69 (d, 3H), 3.58-3.53 (m, 1H), 3.47-3.40 (m, 1H), 3.36 (s, 3H), 2.59-2.51 (m, 4H), 2.44-2.38 (m, 1H).

Example 147

4-(2-(4-(2-acetyl-5-chlorophenyl)-5-methoxy-2-oxopyridin-1(2H)-yl)-4-methoxybutanamido)benzoic acid 147

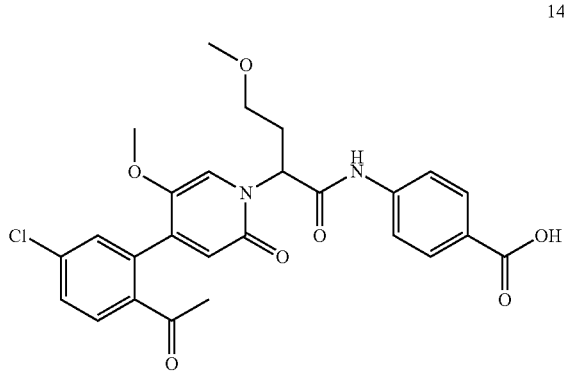

147

In accordance with the synthetic route in Example 1, the starting compound 1h was replaced with compound 4c, accordingly, the title compound 147 (20 mg) was prepared.

MS m/z (ESI): 513.4 [M+1]

¹H NMR (400 MHz, DMSO-d₆) δ 10.73 (s, 1H), 7.89-7.87 (m, 3H), 7.76 (s, 1H), 7.74 (s, 1H), 7.64-7.61 (dd, 1H), 7.46-7.45 (d, 1H), 7.29 (s, 1H), 6.40 (s, 1H), 5.72-5.70 (m, 1H), 3.53 (s, 3H), 3.27-3.25 (m, 2H), 3.22 (s, 3H), 2.50 (s, 3H), 2.33-2.30 (m, 2H).

Example 148

4-(2-(4-(2-acetyl-5-chlorophenyl)-5-methoxy-2-oxopyridin-1(2H)-yl)-4-methoxybutanamido)-2-fluorobenzoic acid 148

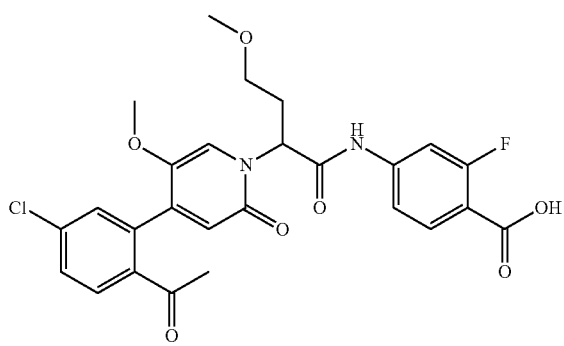

148

In accordance with the synthetic route of Example 1, the starting compound 1h was replaced with methyl 4-amino-2-fluorobenzoate (prepared by a method disclosed in the patent application "WO2013068467"), accordingly, the title compound 148 (15 mg) was prepared.

MS m/z (ESI): 531.5 [M+1]

¹H NMR (400 MHz, DMSO-d₆) δ 10.79 (s, 1H), 7.89-7.87 (d, 1H), 7.76-7.72 (m, 1H), 7.64-7.62 (dd, 1H), 7.61-7.58 (d, 1H), 7.47-7.45 (d, 1H), 7.40-7.38 (d, 1H), 7.28 (s, 1H), 6.40 (s, 1H), 5.72-5.70 (m, 1H), 3.53 (s, 3H), 3.27-3.25 (m, 2H), 3.22 (s, 3H), 2.50 (s, 3H), 2.33-2.30 (m, 2H).

Example 149

4-(2-(4-(2-acetyl-5-chlorophenyl)-5-methoxy-2-oxopyridin-1(2H)-yl)-4-methoxybutanamido)-2-methoxybenzoic acid 149

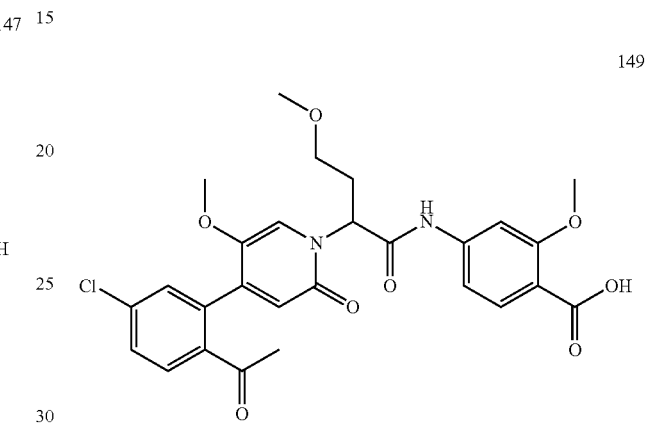

149

In accordance with the synthetic route of Example 1, the starting compound 1h was replaced with methyl 4-amino-2-methoxybenzoate (prepared by a method disclosed in the patent application "WO 2016053794"), accordingly, the title compound 149 (42 mg) was prepared.

MS m/z (ESI): 543.5 [M+1]

¹H NMR (400 MHz, DMSO-d₆) δ 10.67 (s, 1H), 7.89 (d, 1H), 7.63 (d, 2H), 7.53 (s, 1H), 7.46 (s, 1H), 7.28 (s, 1H), 7.23 (d, 1H), 6.41 (s, 1H), 5.74-5.70 (m, 1H), 3.77 (s, 3H), 3.54 (s, 3H), 3.30-3.27 (m, 2H), 3.22 (s, 3H), 2.53 (s, 3H), 2.38-2.36 (m, 2H)

Example 150

2-(4-(2-acetyl-5-chlorophenyl)-5-methoxy-2-oxopyridin-1(2H)-yl)-N-(2,2-dimethyl-3-oxo-3,4-dihydro-2H-benzo[b][1,4]oxazin-6-yl)-4-methoxybutanamide 150

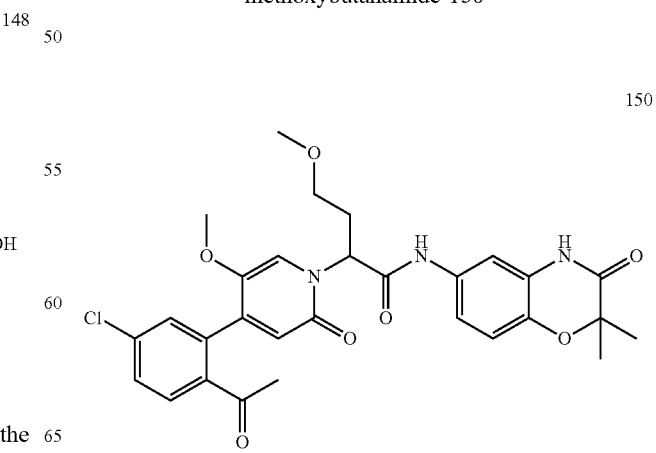

150

In accordance with the synthetic route of Example 117, the starting compound 117c was replaced with 6-amino-2,2-dimethyl-2H-benzo[b][1,4]oxazin-3(4H)-one (prepared by a method disclosed in the patent application "JP 2008013527"), accordingly, the title compound 150 (40 mg) was prepared.

MS m/z (ESI): 566.4 [M+1]

$^1$H NMR (400 MHz, DMSO-$d_6$) δ 10.64 (s, 1H), 10.42 (s, 1H), 7.89-7.87 (d, 1H), 7.64-7.62 (dd, 1H), 7.47-7.46 (d, 1H), 7.39-7.38 (d, 1H), 7.29 (s, 1H), 7.12-7.09 (dd, 1H), 6.88-6.86 (d, 1H), 6.40 (s, 1H), 5.72-5.70 (m, 1H), 3.53 (s, 3H), 3.27-3.25 (m, 2H), 3.22 (s, 3H), 2.50 (s, 3H), 2.33-2.30 (m, 2H), 1.37 (s, 6H)

Example 151

1-((ethoxycarbonyl)oxy)ethyl 5-((R)-2-(4-(2-acetyl-5-chlorophenyl)-5-methoxy-2-oxopyridin-1(2H)-yl)-4-methoxybutanamido)-1H-indole-2-carboxylate 151

1-((ethoxycarbonyl)oxy)ethyl 5-((S)-2-(4-(2-acetyl-5-chlorophenyl)-5-methoxy-2-oxopyridin-(2H)-yl)-4-methoxybutanamido)-1H-indole-2-carboxylate 152

After chiral separation (separation conditions: chromatographic column Superchiral S-AD (Chiralway), 2 cm ID*25 cm Length, 5 μm; mobile phase: carbon dioxide:isopropanol=70:30, flow rate: 50 g/min), the corresponding fractions were collected and concentrated under reduced pressure to obtain the title compounds 151 (90 mg) and 152 (96 mg).

Compound 151:

MS m/z (ESI):668.6 [M+1]

Chiral HPLC analysis: retention time 25.596 minutes, chiral purity 99.3% (chromatographic column: Lux® Amylose-1 (AD) 4.6*150 mm 5 μm (with a guard column): flow rate: 1 mL/min; mobile phase: ethanol/n-hexane=50/50 (v/v)).

$^1$H NMR (400 MHz, DMSO-$d_6$) δ 11.98 (s, 1H), 10.41 (s, 1H), 10.22 (s, 1H), 8.09 (s, 1H), 7.90-7.88 (d, 1H), 7.64-7.61 (dd, 1H), 7.48-7.46 (d, 1H), 7.44-7.40 (m, 1H), 7.34 (s, 1H), 7.21-7.20 (d, 1H), 6.93-6.89 (m, 1H), 6.40 (s, 1H), 5.80-5.70 (m, 1H), 4.19-4.14 (m, 2H), 3.55 (s, 3H), 3.27-3.25 (m, 2H), 3.23 (s, 3H), 2.50 (s, 3H), 2.40-2.30 (m, 2H), 1.60 (d, 3H), 1.24-1.20 (m, 3H)

Compound 152:

MS m/z (ESI): 668.5 [M+I]

Chiral HPLC analysis: retention time 11.905 minutes, chiral purity 100%0/(chromatographic column: Lux® Amylose-1 (AD) 4.6*150 mm 5μm (with a guard column); flow

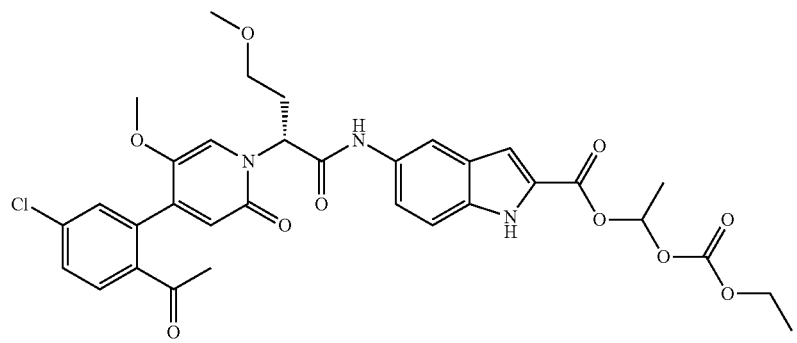

151

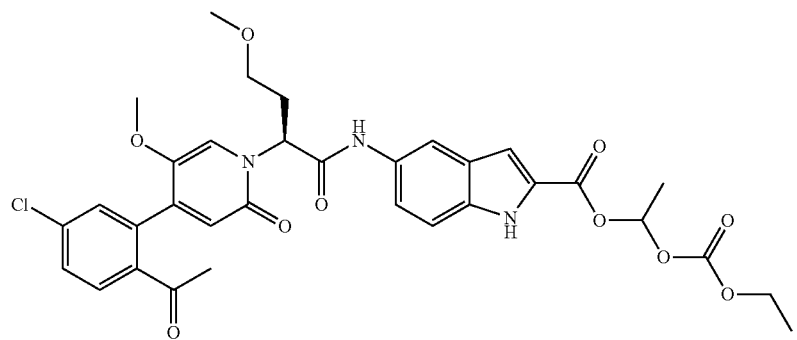

152

In accordance with the synthetic route of Examples 14, 15, the starting compound 14a was replaced with 5-nitro-1H-indole-2-carboxylic acid (prepared by a method disclosed in the patent application "US20160282369"), the starting compound 14b was replaced with 1-chloroethyl-ethyl carbonate (prepared by a known method disclosed in "Tetrahedron Letters, 2016, 57 (14), 1619-1621"), and the starting compound 4b was replaced with compound 1g.

rate: 1 mL/min: mobile phase: ethanol/n-hexane=50/50 (v/v)).

$^1$H NMR (400 MHz, DMSO-$d_6$) δ 11.98 (s, 1H), 10.41 (s, 1H), 10.22 (s, 1H), 8.09 (s, 1H), 7.90-7.88 (d, 1H), 7.64-7.61 (dd, 1H), 7.48-7.46 (d, 1H), 7.44-7.40 (m, 1H), 7.34 (s, 1H), 7.21-7.20 (d, 1H), 6.93-6.89 (m, 1H), 6.40 (s, 1H), 5.80-5.70 (m, 1H), 4.19-4.14 (m, 2H), 3.55 (s, 3H), 3.27-3.25 (m, 2H), 3.23 (s, 3H), 2.50 (s, 3H), 2.40-2.30 (m, 2H), 1.60 (d, 3H), 1.24-1.20 (m, 3H)

Examples 153, 154

(5-methyl-2-oxo-1,3-dioxol-4-yl)methyl (R)-5-(2-(4-(2-acetyl-5-chlorophenyl))-5-methoxy-2-oxopyridin-1(2H)-yl)-4-methoxybutanamido)-1H-indole-2-carboxylate 153

(5-methyl-2-oxo-1,3-dioxol-4-yl)methyl (S)-5-(2-(4-(2-acetyl-5-chlorophenyl))-5-methoxy-2-oxopyridin-1(2H)-yl)-4-methoxybutanamido)-1H-indole-2-carboxylate 154

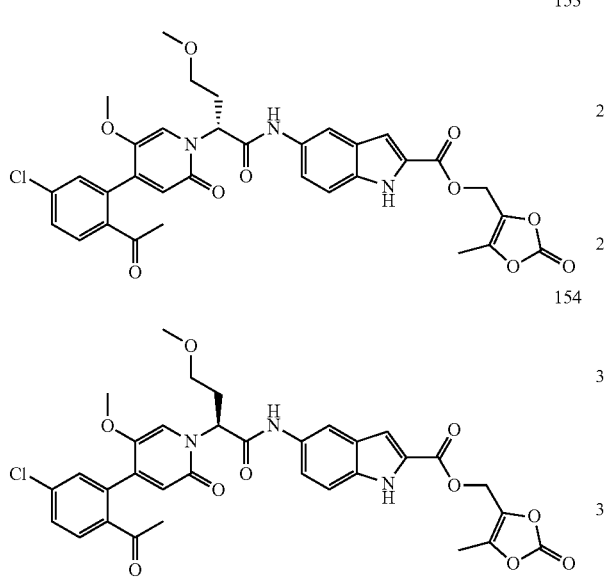

In accordance with the synthetic route of Examples 14, 15, the starting compound 14a was replaced with 5-((tert-butoxycarbonyl)amino)-1H-indole-2-carboxylic acid (prepared by a known method disclosed in "*Journal of the American Chemical Society,* 2007, 129 (17), 5384-5390"), the starting compound 14b is replaced with 4-(chloromethyl)-5-methyl-1,3-dioxol-2-one (prepared by a method disclosed in the patent application "CN103450146"), and the starting compound 4b is replaced with the compound 1g. After chiral separation (separation conditions: chiral preparation column CHIRAL PAK IE, 20*250 mm, 5 μm; mobile phase: methanol:ethanol=50:50, flow rate: 10 mL/min), the corresponding fractions were collected and concentrated under reduced pressure to obtain the title compounds 153 (60 mg) and 154 (25 mg).

Compound 153:

MS m/z (ESI): 664.5 [M+1]

Chiral HPLC analysis: retention time 7.129 minutes, (chromatographic column: CHIRAL PAK IE 4.6*150 mm 5 μm (with a guard column); flow rate: 1 mL/min; mobile phase: methanol/ethanol=50/50 (v/v)).

$^1$H NMR (400 MHz, DMSO-$d_6$) δ 11.95 (s, 1H), 10.39 (s, 1H), 8.08 (s, 1H), 7.89-7.87 (d, 1H), 7.64-7.61 (dd, 1H), 7.47-7.45 (d, 1H), 7.44-7.41 (dd, 1H), 7.40-7.38 (d, 1H), 7.34 (s, 1H), 7.19-7.18 (d, 1H), 6.40 (s, 1H), 5.80-5.70 (m, 1H), 5.23 (s, 2H), 3.53 (s, 3H), 3.27-3.25 (m, 2H), 3.22 (s, 3H), 2.50 (s, 3H), 2.40-2.30 (m, 2H), 2.23 (s, 3H)

Compound 154:

MS m/z (ESI): 664.5 [M+I]

Chiral HPLC analysis: retention time 8.579 min, (chromatographic column: CHIRAL PAK IE, 4.6*150 mm, 5 μm; flow rate: 1 mL/min; mobile phase: methanol/ethanol=50/50 (v/v)).

$^1$H NMR (400 MHz, DMSO-$d_6$) δ 11.95 (s, 1H), 10.39 (s, 1H), 8.08 (s, 1H), 7.89-7.87 (d, 1H), 7.64-7.61 (dd, 1H), 7.47-7.457 (d, 1H), 7.44-7.41 (dd, 1H), 7.40-7.38 (d, 1H), 7.34 (s, 1H), 7.19-7.18 (d, 1H), 6.40 (s, 1H), 5.80-5.70 (m, 1H), 5.23 (s, 2H), 3.53 (s, 3H), 3.27-3.25 (m, 2H), 3.22 (s, 3H), 2.50 (s, 3H), 2.40-2.30 (m, 2H), 2.23 (s, 3H)

Example 155

4-(2-(4-(2-acetyl-5-chlorophenyl)-5-methoxy-2-oxopyridin-1(2H)-yl)hexanamido)benzoic acid 155

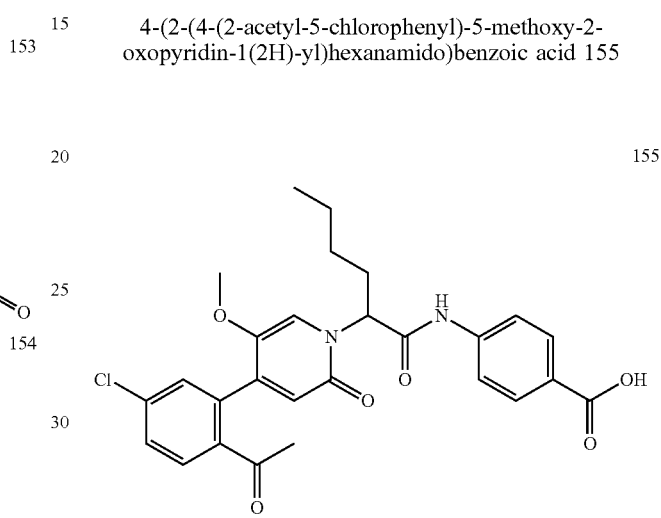

In accordance with the synthetic route of Example 7, the starting compound 7c was replaced with butyl trifluoromethanesulfonate (prepared by a known method disclosed in "*Perkin* 1,2000, (4), 571-574"), accordingly, the title compound 155 (25 mg) was prepared.

MS m/z (ESI): 511.4 [M+1]

$^1$H NMR (400 MHz, CD$_3$OD) δ 8.01 (d, 2H), 7.88 (d, 1H), 7.75 (d, 2H), 7.58 (dd, 1H), 7.41 (d, 1H), 7.38 (s, 1H), 6.53 (s, 1H), 5.80-5.76 (m, 1H), 3.65 (s, 3H), 2.55 (s, 3H), 2.28-2.14 (m, 2H), 1.50-1.37 (m, 4H), 0.98 (t, 3H).

Example 156

4-(2-(4-(2-acetyl-5-chlorophenyl)-5-methoxy-2-oxopyridin-1(2H)-yl)propanamido)benzoic acid 156

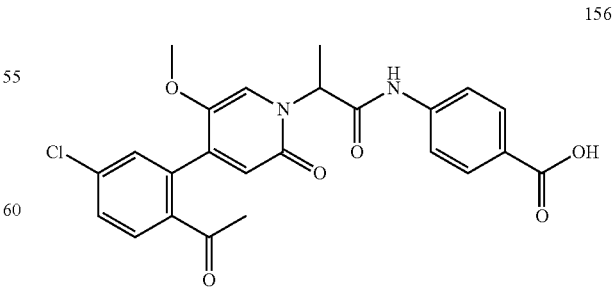

In accordance with the synthetic route of Example 7, the starting compound 7c was replaced with iodomethane, accordingly, the title compound 156 (30 mg) was prepared.

MS m/z (ESI): 469.1 [M+1]
¹H NMR (400 MHz, CDCl₃) δ 10.03 (s, 1H), 8.13 (d, 2H), 7.90 (d, 2H), 7.73 (d, 1H), 7.53-7.50 (m, 1H), 7.34 (s, 1H), 7.18 (s, 1H), 6.71 (s, 1H), 6.11-6.06 (m, 1H), 3.65 (s, 3H), 2.55 (s, 3H), 1.77-1.75 (m, 3H).

Example 157

4-(2-(4-(2-acetyl-5-chlorophenyl)-5-methoxy-2-oxopyridin-1(2H)-yl)butanamido)benzoic acid 157

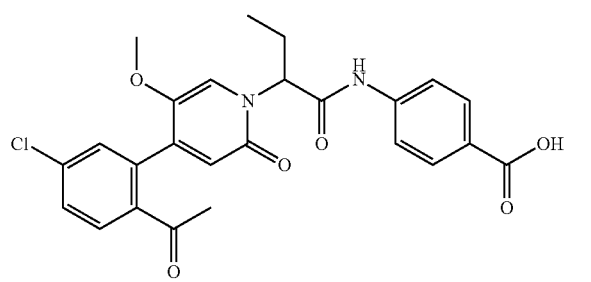

157

In accordance with the synthetic route of Example 7, the starting compound 7c was replaced with iodoethane, accordingly, the title compound 157 (6 mg) was prepared.

MS m/z (ESI): 483.2 [M+1]
¹H NMR (400 MHz, CDCl₃) δ 10.04 (s, 1H), 8.15 (d, 2H), 7.93 (d, 2H), 7.73 (d, 1H), 7.53-7.50 (m, 1H), 7.34-7.29 (m, 2H), 6.72 (s, 1H), 5.93-5.89 (m, 1H), 3.65 (s, 3H), 2.54 (s, 3H), 2.39-2.30 (m, 1H), 2.08-2.03 (m, 1H), 1.12-1.08 (m, 3H).

Example 158

4-(2-(4-(2-acetyl-5-chlorophenyl)-5-methoxy-2-oxopyridin-(2H)-yl)-3-(1-methylcyclopropyl)propanamido)benzoic acid 158

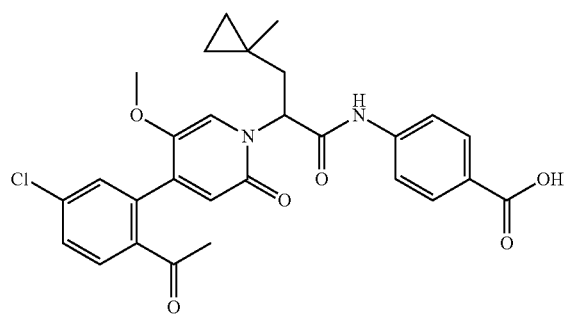

158

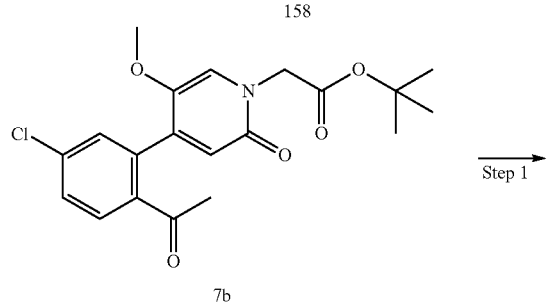

7b

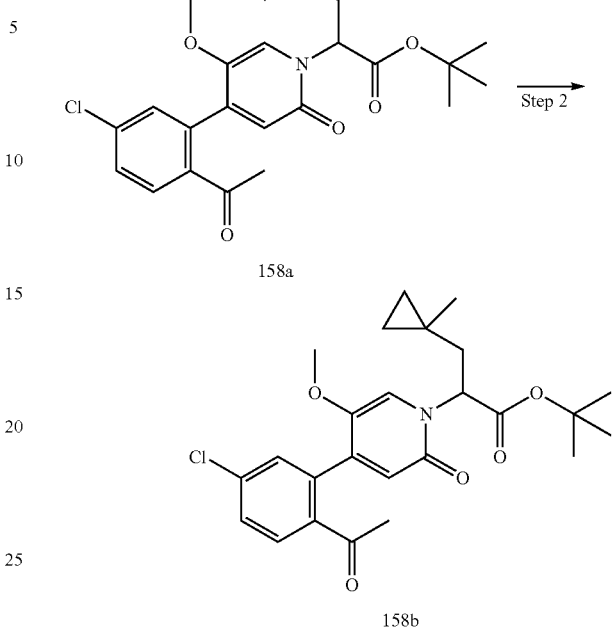

158a

158b

Step 1 tert-butyl 2-(4-(2-acetyl-5-chlorophenyl)-5-methoxy-2-oxopyridin-1(2H)-yl)-4-methylpent-4-enoate 158a Compound 7b (250 mg, 638.01 μmol) was dissolved in 10 mL of tetrahydrofuran. After cooling to −78° C., the reaction solution was added with 3-bromo-2-methylpropene (172.26 mg, 1.28 mmol) and a solution of lithium bis(trimethylsilyl)amide (427.02 mg, 2.55 mmol) in tetrahydrofuran and stirred for 1 hour at −78° C. The reaction solution was added with saturated ammonium chloride solution to quench the reaction, and extracted with ethyl acetate. The organic phase was concentrated under reduced pressure and purified by silica gel column chromatography with elution system B to obtain the title compound 158a (250 mg, yield: 87.87%).

Step 2 tert-butyl 2-(4-(2-acetyl-5-chlorophenyl)-5-methoxy-2-oxopyridin-1(2H)-yl)-3-(1-methylcyclopropyl)propanoate 158b In an ice bath, diethyl zinc (2.69 mmol, 2.69 mL) was dissolved in 15 mL of dichloromethane, and then a solution of trifluoroacetic acid (306.82 mg, 2.69 mmol) in dichloromethane was slowly added dropwise, followed by dropwise addition of a solution of diiodomethane (720.72 mg, 2.69 mmol) in dichloromethane and a final solution of the pre-prepared compound 158a (60 mg, 134.55 μmol) in dichloromethane. After stirring for 24 hours at room temperature, the reaction solution was cooled in an ice bath, added with 10 mL of hydrochloric acid, and extracted with ethyl acetate (50 mL×3). The organic phases were combined, dried over anhydrous sodium sulfate, and filtered. The filtrate was concentrated under reduced pressure to obtain the crude title compound 158b (50 mg), which was directly used in the next reaction step without purification.

In accordance with the synthetic route of Example 7, the starting compound 7d was replaced with crude compound 158b, accordingly, the title compound 158 (10 mg) was prepared.

MS m/z (ESI): 523.4 [M+1]

$^1$H NMR (400 MHz, CD$_3$OD) δ 10.52 (s, 1H), 8.01-8.00 (m, 1H), 7.98-7.97 (m, 1H), 7.87-7.85 (d, 1H), 7.77-7.76 (d, 1H), 7.75-7.74 (d, 1H), 7.59-7.56 (dd, 1H), 7.40 (s, 1H), 7.39-7.38 (d, 1H), 6.51 (s, 1H), 6.01-5.95 (m, 1H), 3.60 (s, 3H), 2.50 (s, 3H), 2.35-2.25 (m, 1H), 2.00-1.90 (m, 1H), 1.18 (s, 3H), 0.42-0.38 (m, 1H), 0.35-0.31 (m, 1H), 0.30-0.25 (m, 2H).

Example 159

4-(2-(4-(6-acetyl-3-chloro-2-fluorophenyl)-5-methoxy-2-oxopyridin-1(2H)-yl)-3-cyclobutylpropanamido)benzoic acid 159

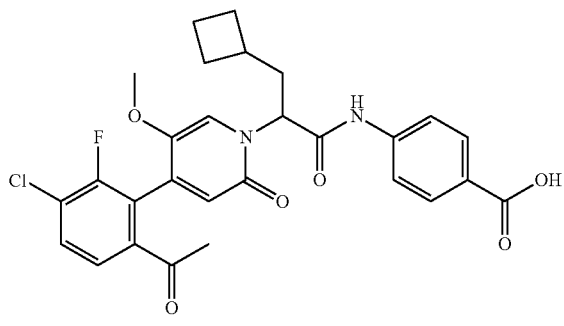

159

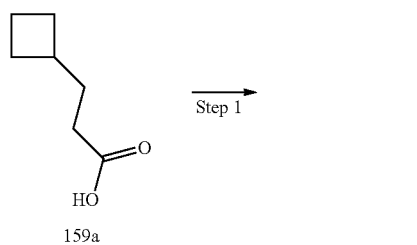

159a

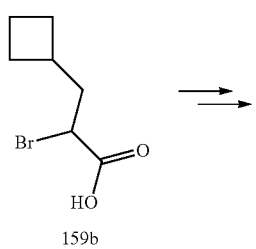

159b

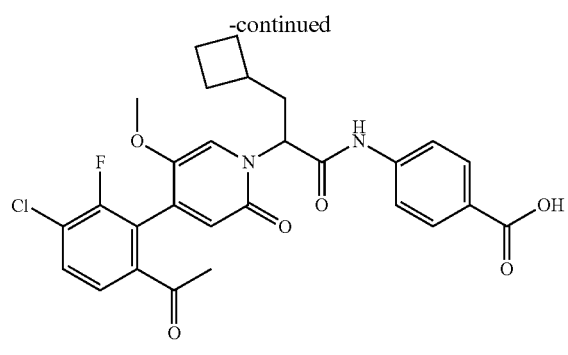

159

3-Cyclobutylpropionic acid 159a (500 mg, 3.90 mmol, prepared by a known method disclosed in "*Organic Process Research & Development*, 2008, 12 (2), 183-191") was dissolved in 5 mL of carbon tetrachloride, and then phosphorus tribromide (1.06 g, 3.90 mmol) and bromine (1.56 g, 9.75 mmol) were added. The reaction solution was heated to 85° C. and stirred for 12 hours. The reaction solution was cooled to room temperature and washed with saturated sodium bisulfate solution. The organic phase was dried over anhydrous sodium sulfate, and filtered. The filtrate was concentrated under reduced pressure, and purified by silica gel column chromatography with elution system B to obtain the title compound 159b (300 mg, yield: 37.14%).

In accordance with synthetic route in Example 30, the starting compound 4a was replaced with compound 159b, accordingly, the title compound 159 (60 mg) was prepared.

MS m/z (ESI): 541.1 [M+1]

$^1$H NMR (400 MHz; DMSO-d$_6$) δ 12.74 (br, 1H), 10.82 (s, 1H), 7.93-7.90 (m, 2H), 7.85-7.75 (m, 4H), 7.42 (d, 1H), 6.41 (d, 1H), 5.72-5.66 (m, 1H), 3.65 (d, 3H), 2.49 (s, 3H), 2.27-2.18 (m, 3H), 2.01-1.91 (m, 2H), 1.79-1.66 (m, 4H).

Examples 160, 161

(R)-4-(2-(4-(6-acetyl-3-chloro-2-fluorophenyl)-5-methoxy-2-oxopyridin-1(2H)-yl)-3-cyclobutylpropanamido)benzoic acid 160

(S)-4-(2-(4-(6-acetyl-3-chloro-2-fluorophenyl)-5-methoxy-2-oxopyridin-1(2H)-yl)-3-cyclobutylpropanamido)benzoic acid 161

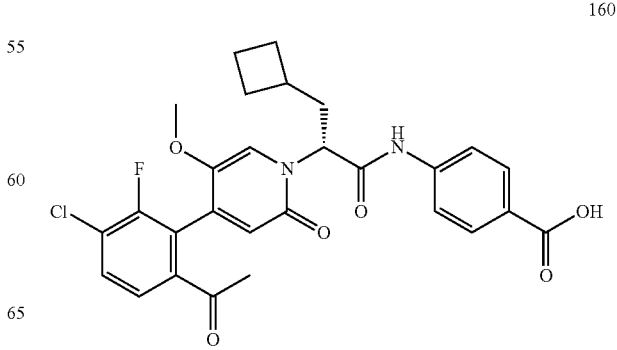

160

305
-continued

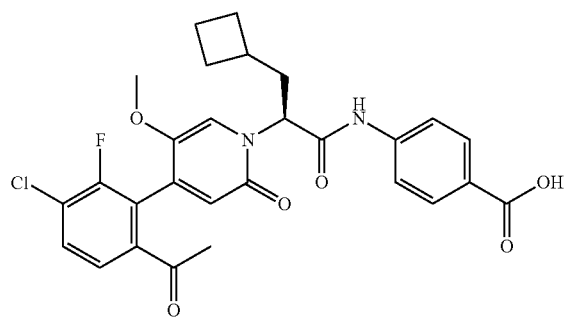

161

Compound 159 (50 mg, 92.43 μmol) was separated chirally (separation conditions: chromatographic column: Superchiral S-AD (Chiralway), 0.46 cm ID*15 cm Length, 5 μm; mobile phase: carbon dioxide:ethanol:diethylamine=60:40:0.05, flow rate: 50 g/min). The corresponding fractions were collected and concentrated under reduced pressure to obtain the title compound 160 (20 mg) and compound 161 (20 mg).

Compound 160:

MS m/z (ESI): 541.2 [M+1]

Chiral HPLC analysis: retention time 6.264 minutes, (chromatographic column: Lux Amylose-1 (AD) 4.6*150 mm 5 μm (with a guard column): mobile phase: n-hexane/ethanol (containing 0.1% trifluoroacetic acid)=70/30 (v/v)).

$^1$H NMR (400 MHz, CD$_3$OD) δ 7.97 (d, 2H), 7.73-7.63 (m, 4H), 7.46 (d, 1H), 6.47 (s, 1H), 5.76-5.70 (m, 1H), 3.65 (d, 3H), 2.34 (d, 3H), 2.29-2.21 (m, 3H), 2.06-1.43 (m, 6H).

Compound 161:

MS m/z (ESI):541.4 [M+1]

Chiral HPLC analysis: retention time 9.045 minutes, (chromatographic column: Lux Amylose-1 (AD) 4.6*150 mm 5 μm (with a guard column); mobile phase: n-hexane/ethanol (containing 0.1% trifluoroacetic acid)=70/30 (v/v)).

$^1$H NMR (400 MHz, CD$_3$OD) δ 7.97 (d, 2H), 7.73-7.63 (m, 4H), 7.46 (d, 1H), 6.47 (s, 1H), 5.76-5.70 (m, 1H), 3.65 (d, 3H), 2.34 (d, 3H), 2.29-2.21 (m, 3H), 2.06-1.43 (m, 6H).

Example 162

4-(2-(4-(2-acetyl-5-chlorophenyl)-5-methoxy-2-oxopyridin-(2H)-yl)-4-cyclobutoxybutanamido)benzoic acid 162

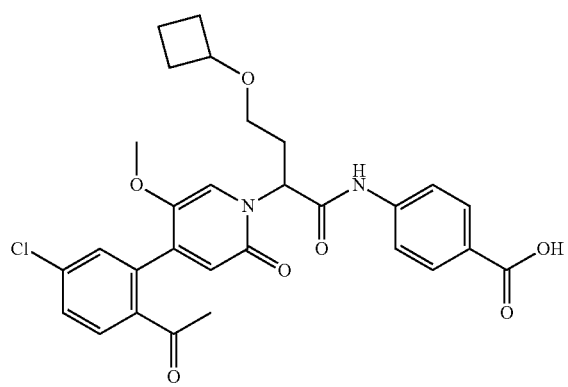

162

306
-continued

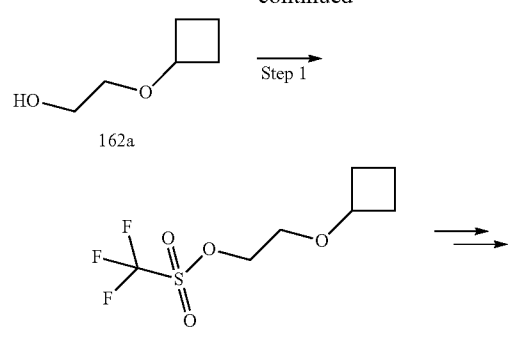

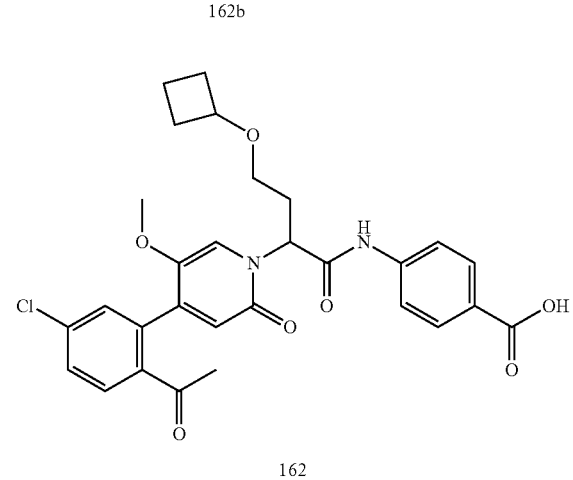

162

2-(Cyclobutoxy)ethanol 162a (224 mg, 1.93 mmol, prepared by a method disclosed in the patent application "WO 2015120786") was dissolved in 10 mL of dichloromethane, and then 2,6-dimethyl pyridine (206.64 mg, 1.93 mmol) was added, followed by dropwise addition of trifluoromethanesulfonic anhydride (598.49 mg, 2.12 mmol). After stirring for 2 hours, the reaction solution was added with 15 mL of water, and two phases were separated. The water phase was extracted with 15 mL of dichloromethane. The organic phases were combined, washed with saturated sodium chloride solution (15 mL×2), dried over anhydrous sodium sulfate, and filtered. The filtrate was concentrated under reduced pressure to obtain the crude title compound 162b (420 mg), which was directly used in the next reaction step without purification.

In accordance with synthetic route in Example 7, the starting compound 7c was replaced with the crude compound 162b, accordingly, the title compound 162 (35 mg) was prepared.

MS m/z (ESI): 553.4 [M+1]

$^1$H NMR (400 MHz, DMSO-d$_6$) δ10.75 (s, 1H), 7.91-7.87 (m, 3H), 7.76 (d, 2H), 7.63 (dd, 1H), 7.44 (d, 1H), 7.29 (s, 1H), 6.42 (s, 1H), 5.79-5.75 (m, 1H), 3.87-3.80 (m, 1H), 3.54 (s, 3H), 3.33-3.31 (m, 1H), 3.24-3.22 (m, 1H), 2.49 (s, 3H), 2.41-2.28 (m, 2H), 2.10-2.01 (m, 2H), 1.82-1.68 (m, 2H), 1.60-1.52 (m, 1H), 1.44-1.34 (m, 1H).

Examples 163, 164

(R)-4-(2-(4-(2-acetyl-5-chlorophenyl)-5-methoxy-2-oxopyridin-1(2H)-yl)-4-cyclobutoxybutanamido)benzoic acid 163

(S)-4-(2-(4-(2-acetyl-5-chlorophenyl)-5-methoxy-2-oxopyridin-1(2H)-yl)-4-cyclobutoxybutanamido)benzoic acid 164

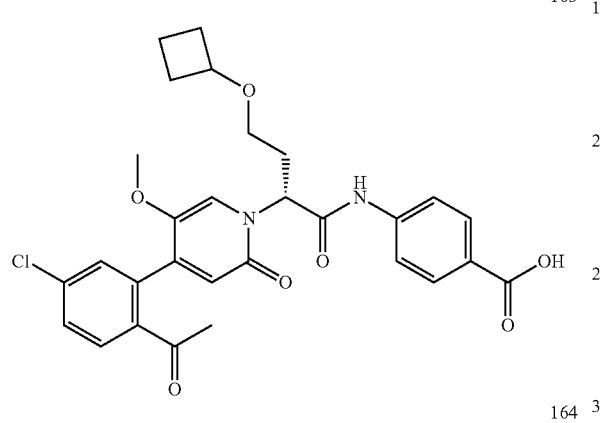

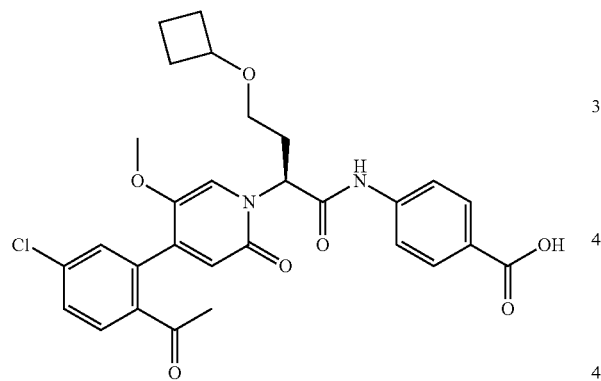

Compound 162 (32 mg, 57.87 μmol) was separated chirally (separation conditions: chiral preparative column CHIRAL PAK IF, 20*250 mm, 5 μm; mobile phase: n-hexane:ethanol (containing 0.01% trifluoroacetic acid)=50:50, flow rate: 6.0 mL/min). The corresponding fractions were collected and concentrated under reduced pressure to obtain the title compound 163 (15 mg) and compound 164 (15 mg).

Compound 163:

MS m/z (ESI):553.4 [M+1]

Chiral HPLC analysis: retention time 3.577 minutes, (chromatographic column: CHIRALPAK IF 150*4.6 mm 5 μm (with a guard column); mobile phase: n-hexane/ethanol (containing 0.1% trifluoroacetic acid)=50/50 (v/v)).

$^1$H NMR (400 MHz, DMSO-$d_6$) δ 10.77 (s, 1H), 7.91-7.87 (m, 3H), 7.77 (d, 2H), 7.63 (dd, 1H), 7.44 (d, 1H), 7.29 (s, 1H), 6.42 (s, 1H), 5.79-5.75 (m, 1H), 3.87-3.80 (m, 1H), 3.54 (s, 3H), 3.33-3.31 (m, 1H), 3.24-3.16 (m, 1H), 2.49 (s, 3H), 2.38-2.30 (m, 2H), 2.10-2.02 (m, 2H), 1.79-1.71 (m, 2H), 1.59-1.50 (m, 1H), 1.44-1.36 (m, 1H).

Compound 164:

MS m/z (ESI):553.4 [M+1]

Chiral HPLC analysis: retention time 8.134 minutes, (chromatographic column: CHIRALPAK IF 150*4.6 mm 5 μm (with a guard column); mobile phase: n-hexane/ethanol (containing 0.1% trifluoroacetic acid)=50/50 (v/v)).

$^1$H NMR (400 MHz, DMSO-$d_6$) δ 12.77 (s, 1H), 10.79 (s, 1H), 7.91-7.87 (m, 3H), 7.77 (d, 2H), 7.63 (dd, 1H), 7.44 (d, 1H), 7.29 (s, 1H), 6.42 (s, 1H), 5.78-5.75 (m, 1H), 3.87-3.80 (n, 1H), 3.54 (s, 3H), 3.33-3.31 (m, 1H), 3.24-3.18 (m, 1H), 2.49 (s, 3H), 2.40-2.28 (m, 2H), 2.10-2.01 (m, 2H), 1.81-1.68 (m, 2H), 1.59-1.52 (m, 1H), 1.46-1.36 (m, 1H).

Example 165

4-(2-(4-(2-acetyl-5-chlorophenyl)-5-methoxy-2-oxopyridin-1(2H)-yl)-3-((1R,4R)-4-hydroxycyclohexyl)propanamido)benzoic acid 165

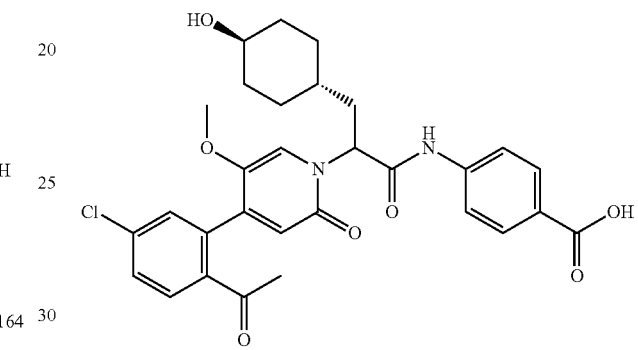

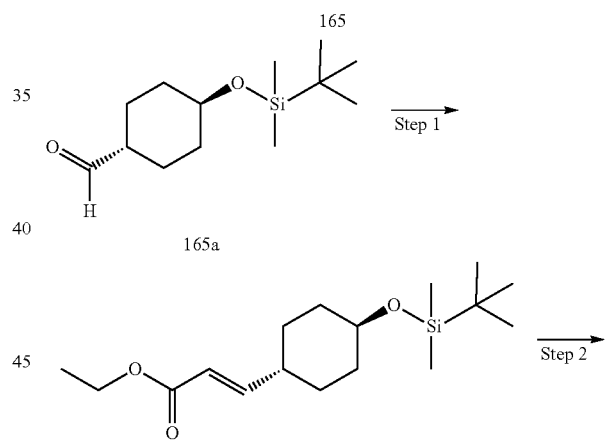

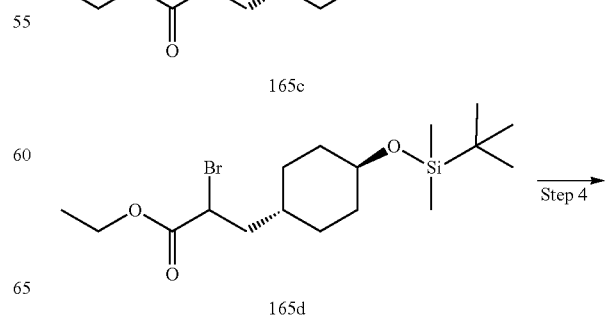

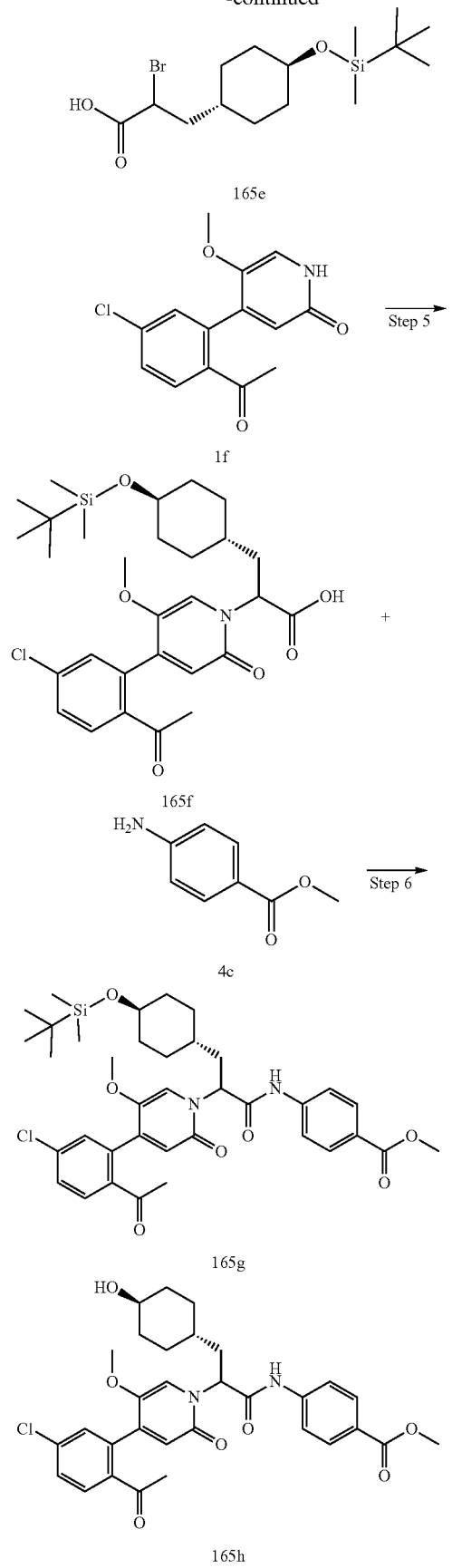

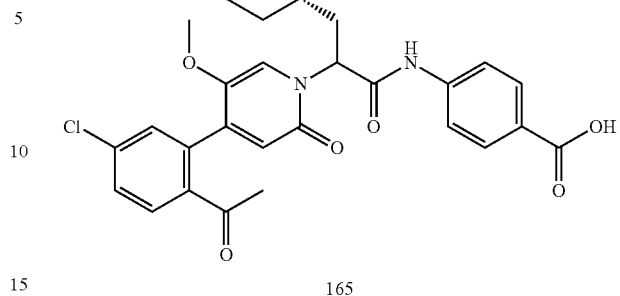

Step 1

Ethyl 3-((1R,4R)-4-((tert-butyldimethylsilyl)oxy)cyclohexyl)acrylate 165b (1R,4R)-4-((tert-Butyldimethylsilyl)oxy)cyclohexane-1-carbaldehyde 165a (3.2 g, 13.2 mmol, prepared b a known method disclosed in "*Bioorganic Chemistry Letters,* 2016 26(14), 3213-3215") was dissolved in 50 mL of toluene, and then (carbethoxmethylene)triphenylphosphorane (5.518 g, 15.84 mmol) was added. The reaction solution was warmed up to 100° C. and stirred for 16 hours. The reaction solution was cooled to room temperature, and concentrated under reduced pressure. The resulting residue was added with 50 mL of saturated sodium bicarbonate solution, and extracted with ethyl acetate (100 mL×2). The organic phases were combined, dried over anhydrous sodium sulfate, and filtered. The filtrate was concentrated under reduced pressure, and the resulting residue was purified by silica gel column chromatography with elution system B to obtain the title compound 165b (3.2 g, yield: 73.69%)

Step 2

Ethyl 3-((1R,4R)-4-((tert-butyldimethylsilyl)oxy)cyclohexyl)propanoate 165c

Compound 165b (1.5 g, 4.8 mmol) was dissolved in 30 mL of ethyl acetate, and then palladium on carbon (51.08 mg, 0.48 mmol) was added. The reaction system was purged with hydrogen three times. The reaction solution was stirred for 3 hours at room temperature, and then filtered. The filtrate was concentrated under reduced pressure and purified by silica gel column chromatography with elution system B to obtain the title compound 165c (1.509 g, yield: 94.96%).

Step 3

2-bromo-3-((1R,4R)-4-((tert-butyldimethylsilvl)oxy)cyclohexyl)propanoate 165d

Compound 165c (1.11 g, 3.53 mmol) was dissolved in 40 mL of tetrahydrofuran The reaction solution was cooled to −78° C., added with lithium bis(trimethylsilyl)amide (620.03 mg, 3.71 mmol) in batches, and stirred for 60 min, followed by addition of trimethylchlorosilane (383.39 mg, 3.53 mmol) and N-bromosuccinimide (628.08 mg, 3.53 mmol). After stirring for 2 hours, the reaction solution was warmed up to room temperature and then stirred for 1 hour.

The reaction solution was added with 50 mL of saturated sodium chloride solution, and extracted with ethyl acetate (50 mL×3). The organic phases were combined, dried over anhydrous sodium sulfate, and filtered. The filtrate was concentrated under reduced pressure, and purified by silica gel column chromatography with elution system B to obtain the title compound 165d (260 mg, yield: 17.79%).

Step 4

2-bromo-3-((1R,4R)-4-((tert-butyldimethylsilyl)oxy)cyclohexyl)propanoic acid 165e Compound 165d (260 mg, 0.66 mmol) was dissolved in 4 mL of tetrahydrofuran, and then lithium hydroxide monohydrate (83.19 mg, 1.98 mmol) was added. After stirring for 2 hours, the reaction solution was added dropwise with 10% citric acid solution to adjust the pH to 3 to 4, and extracted with ethyl acetate (25 mL×2). The organic phases were combined, washed with 50 mL of saturated sodium chloride solution, dried over anhydrous sodium sulfate, and filtered. The filtrate was concentrated under reduced pressure to obtain the crude title compound 165e (240 mg), which was directly used in the next reaction step without purification.

Step 5

2-(4-(2-acetyl-5-chlorophenyl)-5-methoxy-2-oxopyridin-1(2H)-yl)-3-((1R,4R)-4-((tert- butyldimethylsilyl)oxy)cyclohexyl)propionic acid 165f Magnesium tert-butoxide (171.41 mg, 1.01 mmol) was dissolved in 30 mL of tetrahydrofuran, and then the crude compound 165e (239.46 mg, 0.66 mmol), potassium tert-butoxide (59.4 mg, 0.53 mmol) and compound 1f (140 mg, 0.5 mmol) were added. After stirring for 16 hours at 60° C., the reaction solution was cooled to room temperature, added dropwise with 1 M hydrochloric acid to adjust the pH to 3-4, and extracted with ethyl acetate (100 mL×2). The organic phases were combined, dried over anhydrous sodium sulfate, and filtered. The filtrate was concentrated under reduced pressure and purified by silica gel column chromatograph with elution system A to obtain the title compound 165f (283 mg, yield: 24.96%).

Step 6 methyl 4-(2-(4-(2-acetyl-5-chlorophenyl)-5-methoxy-2-oxopyridin-1(2H)-yl)-3-((1R,4R)-4-((tert- butyldimethylsilyl)oxy)cyclohexyl)propanamido)benzoate 165g Compound 165f (300 mg, 0.53 mmol) was dissolved in 20 mL of ethyl acetate. The reaction solution was added with compound 4c (80.67 mg, 0.53 mmol) and N,N-diisopropylethylamine (0.28 mL, 1.6 mmol), and then a solution of 4,6-tripropyl-1,3,5,2,4,6-trioxatriphosphooxatriphosphornane-2,4,6-trioxide in ethyl acetate (50%, 679.18 mg, 1.07 mmol). The reaction solution was warmed up to 60° C., and stirred for 2 hours. The reaction solution was cooled to room temperature and concentrated under reduced pressure. The resulting residue was purified by silica gel column chromatography with elution system B to obtain the title compound 165g (60 mg, yield: 15.36%).

Step 7 methyl 4-(2-(4-(2-acetyl-5-chlorophenyl)-5-methoxy-2-oxopyridin-1(2H)-yl)-3-((1R,4R)-4-hydroxycyclohexyl)propanamido)benzoate 165h Compound 165g (60 mg, 0.09 mmol) was dissolved in 10 mL of tetrahydrofuran, and then tetrabutylammonium fluoride (180.49 mg, 0.69 mmol) was added. The reaction solution was warmed up to 66° C. and stirred for 8 hours. After cooling to room temperature, the reaction solution was added with 20 mL of water, and extracted with ethyl acetate (25 mL×4). The organic phases were combined, washed with water (25 mL×4) and saturated sodium chloride (25 mL) successively, dried over anhydrous sodium sulfate, and filtered. The filtrate was concentrated under reduced pressure, and the resulting residue was purified by silica gel column chromatography with elution system A to obtain the title compound 165h (26 mg, yield: 49.78%).

Step 8

4-(2-(4-(2-acetyl-5-chlorophenyl)-5-methoxy-2-oxopyridin-1(2H)-yl)-3-((1R,4R)-4-hydroxycyclohexyl)propanamido)benzoic acid 165

Compound 165h (25 mg, 0.04 mmol) was dissolved in 3.63 mL of a mixed solvent of tetrahydrofuran and methanol (V/V=10:1), and then 0.33 mL of 1 M lithium hydroxide solution was added. After stirring for 16 hours, the reaction solution was dropwise added with 10% hydrochloric acid to adjust the pH to 3-4, and extracted with ethyl acetate (50 mL×2). The organic phases were combined, dried over anhydrous sodium sulfate, and filtered. The filtrate was concentrated under reduced pressure, and the resulting residue was purified by high performance liquid chromatography (Waters 2767-SQ detecor2, elution system: acetonitrile, water) to obtain the title compound 165 (8 mg, yield: 32.46%).

MS m/z (ESI):567.5 [M+1]

$^1$H NMR (400 MHz. DMSO-$d_6$) δ 10.78 (s, 1H), 7.91-7.87 (m, 3H), 7.75 (s, 1H), 7.73 (s, 1H), 7.64-7.62 (dd, 1H), 7.48-7.47 (d, 1H), 7.28 (s, 1H), 6.42 (s, 1H), 5.95-5.83 (m, 1H), 4.46 (m, 1H), 3.54 (s, 3H), 2.48 (s, 3H), 2.09-2.07 (m, 1H), 2.01-1.99 (m, 1H), 1.90-1.84 (m, 1H), 1.82-1.72 (m, 4H), 1.08-0.96 (m, 4H).

Example 166

4-(2-(4-(5-chloro-2-propionylphenyl)-5-methoxy-2-oxopyridin-1(2H)-yl)-3-(tetrahydro-2H-pyran)-2-yl)propanamido)benzoic acid 166

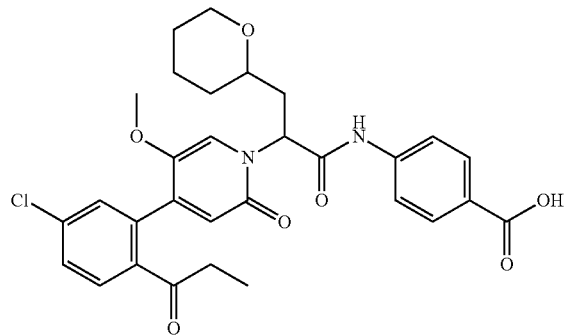

166

In accordance with the synthetic route of Example 8, the compound 8g was replaced with (tetrahydro-2H-pyran-2-yl)methyl trifluoromethanesulfonate (prepared by a method disclosed in the patent application "WO2016046159"), accordingly, the title compound 166 (30 mg) was prepared.

MS m/z (ESI):567.4 [M+1]

$^1$H NMR (400 MHz, CD$_3$OD) δ 8.01-7.97 (m, 2H), 7.86-7.82 (m, 1H), 7.75-7.70 (m, 2H), 7.58-7.55 (m, 1H), 7.41-7.38 (dd, 1H), 7.36-7.30 (m, 1H), 6.49-6.48 (d, 1H), 5.91-5.60 (m, 1H), 4.00-3.94 (m, 1H), 3.62 (s, 3H), 3.44-3.39 (m, 1H), 3.25-3.21 (m, 1H), 3.00-2.95 (m, 2H), 2.50-2.27 (m, 2H), 1.85-1.74 (m, 1H), 1.71-1.68 (m, 1H), 1.66-1.45 (m, 3H), 1.42-1.38 (m, 1H), 1.13-1.08 (m, 3H)

Example 167

4-(2-(4-(2-acetyl-5-chlorophenyl)-5-methoxy-2-oxopyridin-1(2H)-yl)-3-cyclopropylpropanamido)benzoic acid 167

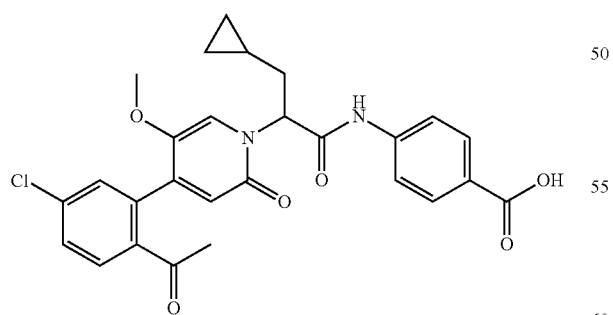

167

In accordance with the synthetic route of Example 7, the starting compound 7c was replaced with bromomethylcyclopropane (prepared by a method disclosed in the patent application "CN106242941"), accordingly, the title compound 167 (18 mg) was prepared.

MS m/z (ESI):509.4 [M+1]

$^1$H NMR (400 MHz. DMSO-d$_6$) δ 10.79 (s, 1H), 7.93-7.88 (m, 3H), 7.76 (s, 1H), 7.74 (s, 1H), 7.64-7.62 (d, 1H), 7.46 (s, 1H), 7.33 (s, 1H), 6.42 (s, 1H), 5.81-5.77 (m, 1H), 3.55 (s, 3H), 2.50 (s, 3H), 2.22-2.14 (m, 1H), 1.91-1.83 (m, 1H), 0.68-0.64 (m, 1H), 0.49-0.42 (m, 1H), 0.40-0.33 (m, 1H), 0.30-0.20 (m, 2H).

Example 168

(S)-4-(2-(4-(2-acetyl-5-chlorophenyl)-5-methoxy-2-oxopyridin-1(2H)-yl)-3-cyclopropylpanamido)benzoic acid 168

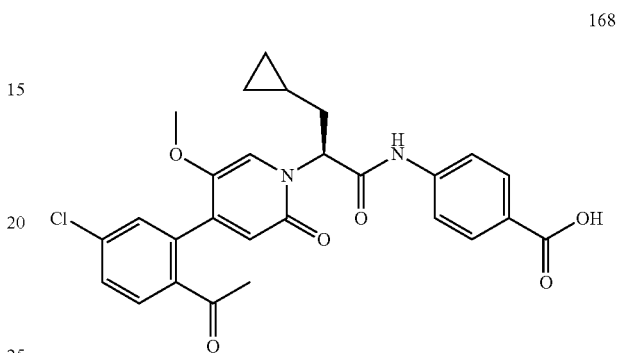

168

Compound 167 (180 mg, 353.77 μmol) was separated chirally (separation conditions: chiral preparative column: Lux Amylose-1 (AD) 21.2*250 mm 5 μm; mobile phase: n-hexane:ethanol (containing 0.01% trifluoroacetic acid) =30:70, flow rate: 10.0 mL/min). The corresponding fractions were collected and concentrated under reduced pressure to obtain the title compound 168 (40 mg).

MS m/z (ESI): 509.4 [M+1]

Chiral HPLC analysis: retention time 11.482 minutes, (chromatographic column: Lux Amylose-1 (AD) 4.6*150 mm 5 μm (with a guard column); mobile phase: n-hexane/ethanol (containing 0.1% trifluoroacetic acid)=70/30 (v/v)).

$^1$H NMR (400 MHz, CD$_3$OD) δ 8.01-8.00 (m, 1H), 7.98-7.97 (m, 1H), 7.90-7.85 (d, 1H), 7.75-7.74 (m, 1H), 7.73-7.71 (m, 1H), 7.59-7.56 (dd, 1H), 7.40 (s, 1H), 7.39-7.38 (d, 1H), 6.51 (s, 1H), 5.84-5.80 (m, 1H), 3.60 (s, 3H), 2.50 (s, 3H), 2.20-2.00 (m, 2H), 0.85-0.75 (m, 1H), 0.55-0.45 (m, 2H), 0.35-0.25 (m, 2H)

Example 169

4-(2-(4-(6-acetyl-3-chloro-2-fluorophenyl)-5-methoxy-2-oxopyridin-1(2H)-yl)-3-cyclopropylpropanamido)benzoic acid 169

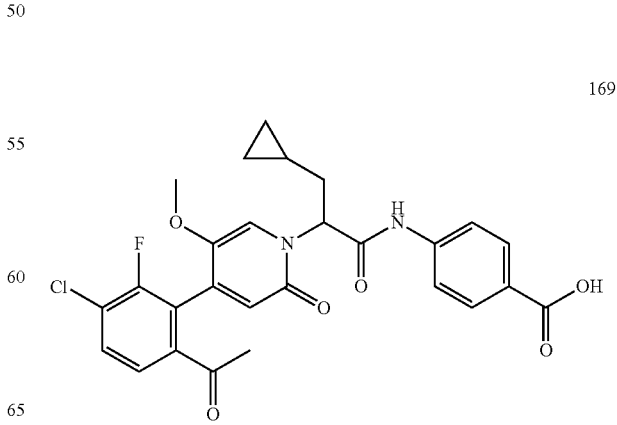

169

In accordance with the synthetic route of Example 30, the starting compound 4a was replaced with (bromomethyl)cyclopropane to obtain the title compound 169 (20 mg).
MS m/z (ESI): 527.2 [M+1]
¹H NMR (400 MHz. CD₃OD) δ 8.01-8.00 (d, 1H), 7.99-7.98 (d, 1H), 7.76-7.67 (m, 4H), 7.49-7.46 (d, 1H), 6.48 (s, 1H), 5.90-5.80 (m, 1H), 3.66 (s, 3H), 2.53-2.48 (m, 3H), 2.15-2.05 (m, 2H), 0.80-0.75 (m, 1H), 0.55-0.45 (m, 2H), 0.25-0.20 (m, 2H)

Example 170

4-(2-(4-(2-acetyl-5-chlorophenyl)-5-methoxy-2-oxopyridin-1(2H)-yl)-3-cyclobutylpropanamido)benzoic acid 170

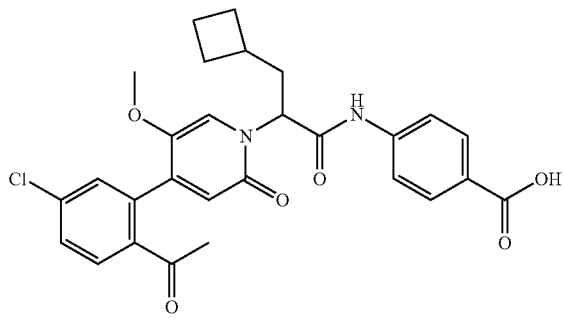

170

In accordance with the synthetic route of Example 4, the starting compound 4a was replaced with compound 159b, accordingly, the title compound 170 (42 mg) was prepared.
MS m/z (ESI): 523.2 [M+1]
¹H NMR (400 MHz, CD₃OD) δ 8.02-8.00 (m, 2H), 7.89 (d, 1H), 7.77-7.74 (m, 2H), 7.59 (dd, 1H), 7.41 (d, 1H), 7.38 (s, 1H), 6.51 (s, 1H), 5.76-5.72 (m, 1H), 3.66 (s, 3H), 2.56 (s, 3H), 2.36-2.23 (m, 3H), 2.20-2.10 (m, 2H), 1.96-1.77 (m, 4H).

Examples 171, 172

(S)-4-(2-(4-(2-acetyl-5-chlorophenyl)-5-methoxy-2-oxopyridin-1(2H)-yl)-3-cyclobutylpropanamido)benzoic acid 171

(R)-4-(2-(4-(2-acetyl-5-chlorophenyl)-5-methoxy-2-oxopyridin-1(2H)-yl)-3-cyclobutylpropanamido)benzoic acid 172

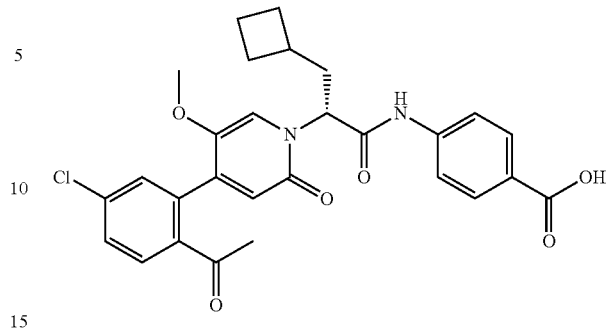

172

Compound 170 (38 mg, 0.07 mmol) was separated chirally (separation conditions: chiral preparative column CHIRAL PAK IE, 20*250 mm, 5 μm; mobile phase: ethanol (containing 0.01% trifluoroacetic acid)=100, flow rate: 6.0 mL/min). The corresponding fractions were collected and concentrated under reduced pressure to obtain the title compound 171 (18 mg) and compound 172 (18 mg).

Compound 171:
MS m/z (ESI):523.2 [M+1]
Chiral HPLC analysis: retention time 9.644 minutes, (chromatographic column: CHIRAL PAK IE 4.6*150 mm 5 μm (with a guard column); mobile phase: n-hexane/ethanol (containing 0.1% trifluoroacetic acid)=40/60 (v/v)).
¹H NMR (400 MHz, CD₃OD) δ 8.02-8.00 (m, 2H), 7.89 (d, 1H), 7.77-7.74 (m, 2H), 7.59 (dd, 1H), 7.41 (d, 1H), 7.38 (s, 1H), 6.51 (s, 1H), 5.76-5.72 (m, 1H), 3.66 (s, 3H), 2.56 (s, 3H), 2.36-2.23 (m, 3H), 2.20-2.10 (m, 2H), 1.96-1.77 (m, 4H).

Compound 172:
MS m/z (ESI):523.2 [M+1]
Chiral HPLC analysis: retention time 3.831 minutes, (chromatographic column: CHIRAL PAK IE 4.6*150 mm 5 μm (with a guard column): mobile phase: n-hexane/ethanol (containing 0.1% trifluoroacetic acid)=40/60 (v/v)).
¹H NMR (400 MHz, CD₃OD) δ 8.02-8.00 (m, 2H), 7.89 (d, 1H), 7.77-7.74 (m, 2H), 7.59 (dd, 1H), 7.41 (d, 1H), 7.38 (s, 1H), 6.51 (s, 1H), 5.76-5.72 (m, 1H), 3.66 (s, 3H), 2.56 (s, 3H), 2.36-2.23 (m, 3H), 2.20-2.10 (m, 2H), 1.96-1.77 (m, 4H).

Example 173

4-(2-(4-(2-acetyl-5-chlorophenyl)-5-methoxy-2-oxopyridin-1(2H)-yl)-3-(3,3-dimethylcyclobutyl)propanamido)benzoic acid 173

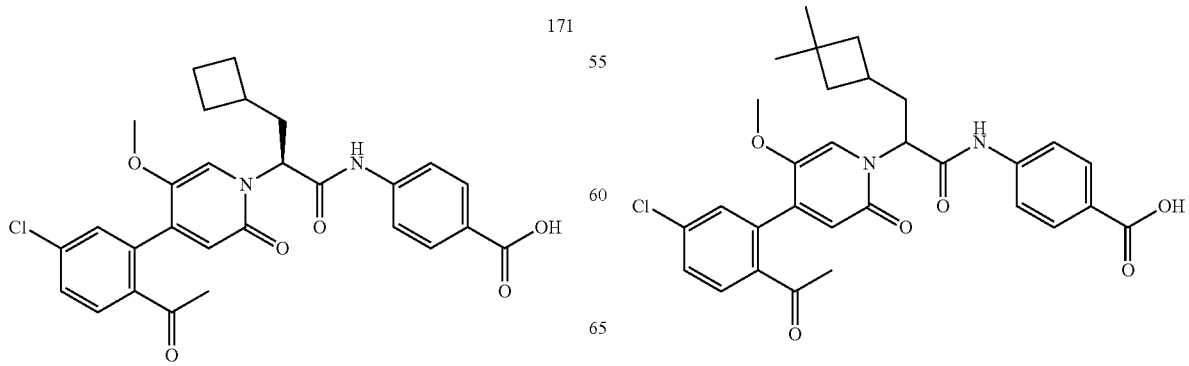

173

In accordance with the synthetic route of Example 165, the starting compound 165a was replaced with 3,3-dimethylcyclobutane-1-carbaldehyde (prepared by a method disclosed in the patent application "WO2015129926"), accordingly, the title compound 173 (25 mg) was prepared.

MS m/z (ESI): 551.2 [M+1]

¹H NMR (400 MHz, CD₃OD) δ 8.00) (s, 1H), 7.98 (s, 1H), 7.88-7.86 (d, 1H), 7.74 (s, 1H), 7.72 (s, 1H), 7.59-7.26 (dd, 1H), 7.40-7.39 (d, 1H), 7.37 (s, 1H), 6.49 (s, 1H), 5.71-5.69 (m, 1H), 3.64 (s, 3H), 2.53 (s, 3H), 2.30-2.25 (m, 3H), 1.95-1.85 (m, 2H), 1.65-1.60 (m, 1H), 1.55-1.50 (m, 1H), 1.26 (s, 3H), 1.06 (s, 3H).

Example 174

4-(2-(4-(2-acetyl-5-chlorophenyl)-5-methoxy-2-oxopyridin-1(2H)-yl)-3-(tetrahydrofuran-2-yl) propanamido)benzoic acid 174

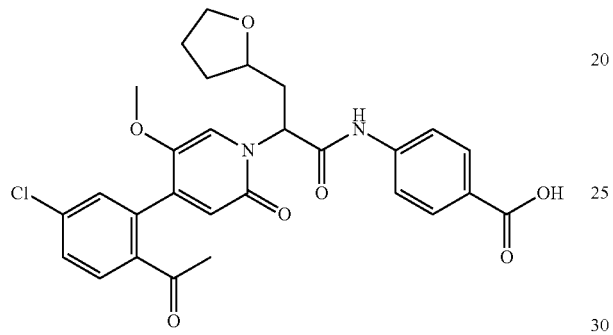

174

In accordance with the synthetic route of Example 7, the starting compound 7c was replaced with (tetrahydrofuran-2-yl)methyl trifluoromethanesulfonate (prepared by a method disclosed in the patent application "WO2003095438"), accordingly, the title compound 174 (15 mg) was prepared.

MS m/z (ESI): 539.1 [M+1]

¹H NMR (400 MHz, CD₃OD) δ 8.01-8.00 (m, 1H), 7.98-7.97 (m, 1H), 7.90-7.85 (m, 1H), 7.75-7.71 (m, 2H), 7.59-7.56 (dt, 1H), 7.40-7.38 (m, 1H), 7.37-7.34 (m, 1H), 6.52-6.48 (m, 1H), 5.70-5.60 (m, 1H), 3.95-3.85 (m, 2H), 3.75-3.70 (m, 1H), 3.64 (s, 3H), 2.54 (s, 2H), 2.51 (s, 1H), 2.50-2.22 (m, 2H), 2.16-2.10 (m, 1H), 2.00-1.95 (m, 2H), 1.65-1.60 (m, 1H).

Example 175

4-(2-(4-(2-acetyl-5-chlorophenyl)-5-methoxy-2-oxopyridin-1(2H)-yl)-3-(4-methoxycyclohexyl)propanamido)benzoic acid 175

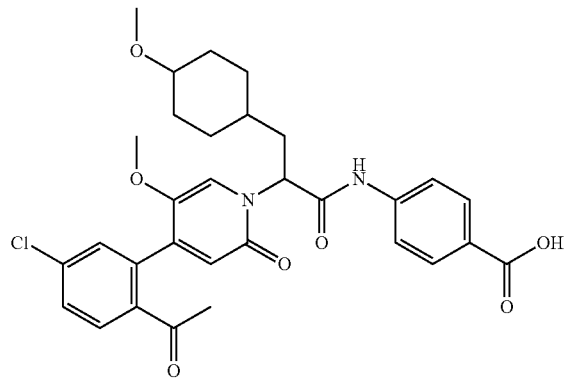

175

In accordance with the synthetic route of Example 165, the starting compound 165a was replaced with 4-methoxycyclohexane-1-carboxaldehyde (prepared by a method disclosed in the patent application "WO2016044626"), accordingly, the title compound 175 (8 mg) was prepared.

MS m/z (ESI): 581.2 [M+1]

¹H NMR (400 MHz. CD₃OD) δ 8.00-7.37 (m, 8H), 6.78-6.53 (m, 1H), 5.95 (s, 1H), 3.89-3.82 (m, 1H), 3.66-3.62 (m, 3H), 3.48-3.16 (m, 3H), 2.68-2.54 (m, 3H), 2.09-1.90 (m, 5H), 1.66-1.14 (m, 6H).

Example 176

4-(2-(4-(2-acetyl-5-chlorophenyl)-5-methoxy-2-oxopyridin-1(2H)-yl)-3-(tetrahydro-2H-pyran)-2-yl) propanamido)benzoic acid 176

176

In accordance with the synthetic route of Example 7, the starting compound 7c was replaced with (tetrahydro-2H-pyran-2-yl)methyl trifluoromethanesulfonate, accordingly, the title compound 176 (15 mg) was prepared.

MS m/z (ESI): 553.4 [M+1]

¹H NMR (400 MHz, DMSO-d₆) δ 10.66 (s, 1H), 7.92-7.87 (m, 3H), 7.79-7.75 (m, 2H), 7.64-7.61 (dd, 1H), 7.47-7.45 (dd, 1H), 7.31-7.27 (d, 1H), 6.39 (s, 1H), 5.72-5.65 (m, 1H), 3.90-3.85 (m, 1H), 3.54 (s, 3H), 3.31-3.08 (m, 2H), 2.50 (s, 3H), 2.25-2.35 (m, 1H), 2.22-2.15 (m, 1H), 2.10-2.00 (m, 1H), 1.80-1.70 (m, 1H), 1.65-1.55 (m, 1H), 1.50-1.35 (m, 3H).

Examples 177, 178
4-[[(2S)-4-tert-butoxy-2-[4-(5-chloro-2-propionyl-phenyl)-2-oxo-5-(trideuteromethoxy)-1-pyridyl]butyryl]amino]benzoic acid 177
4-[[(2R)-4-tert-butoxy-2-[4-(5-chloro-2-propionyl-phenyl)-2-oxo-5-(trideuteromethoxy)-1-pyridyl]butyryl]amino]benzoic acid 178
177
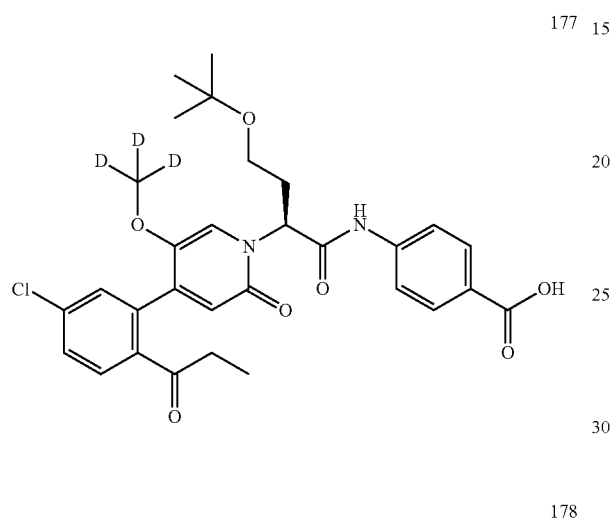
178
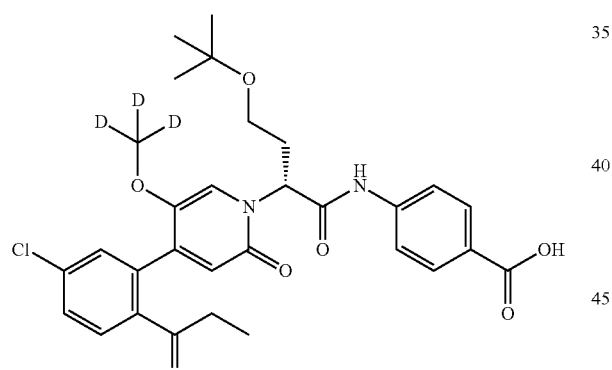
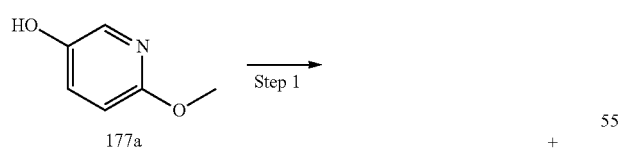
177a
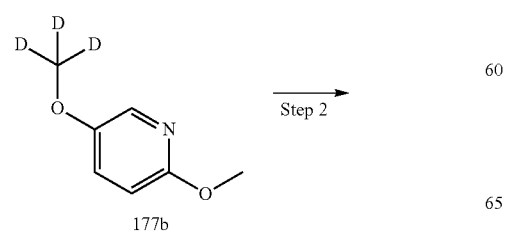
177b
-continued
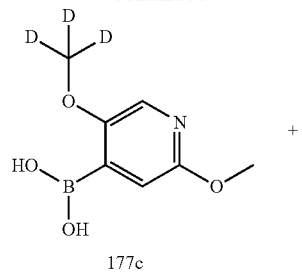
177c
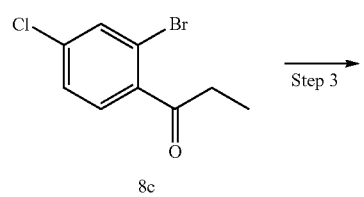
8c
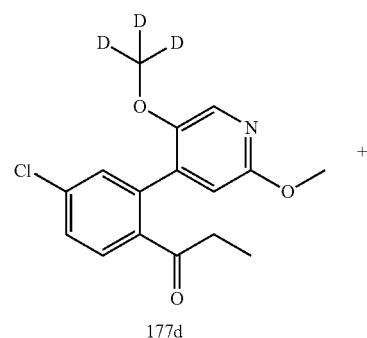
177d
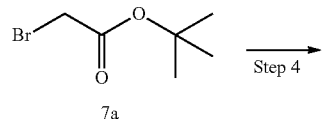
7a
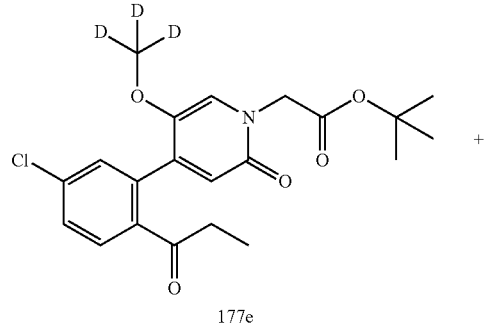
177e
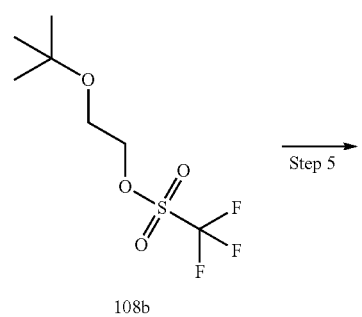
108b

321
-continued

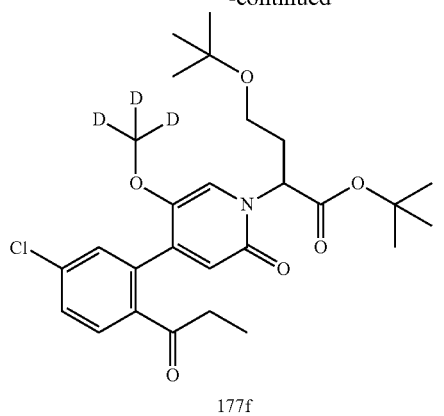

177f

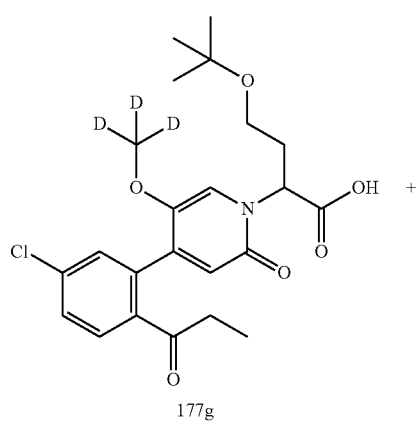

177g

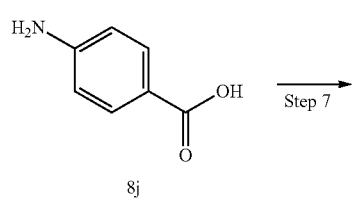

8j

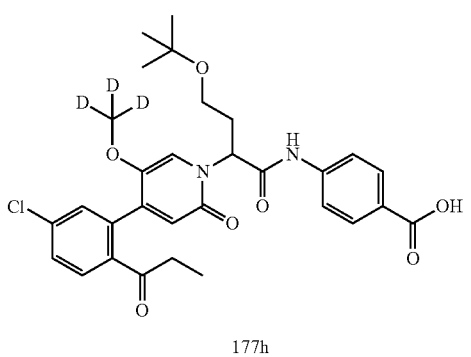

177h

322
-continued

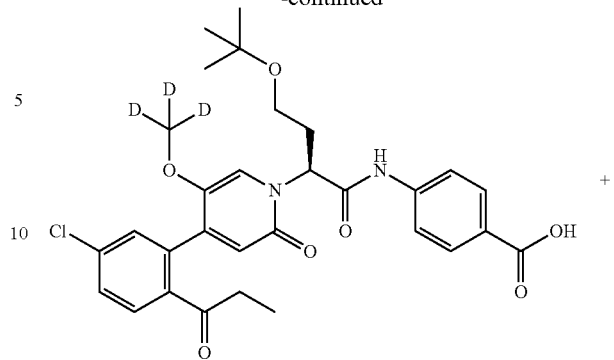

177

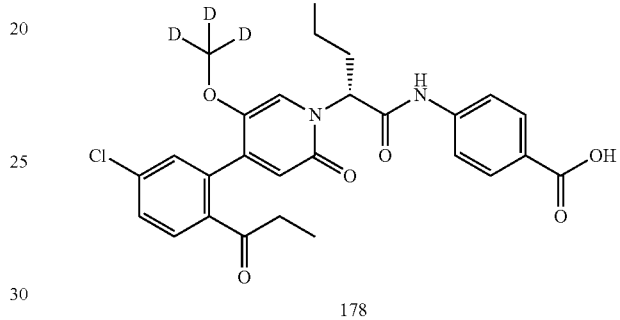

178

Step 1

2-methoxy-5-(trideuteromethoxy)pyridine 177b

6-Methoxypyridin-3-ol 177a (4.0 g, 31.97 mmol, prepared by a known method disclosed in "*Medicinal Chemistry Research*, 2013, 22(4), 1825-1836") was dissolved in 50 mL of N,N-dimethylformamide, and then potassium carbonate (13.25 g, 95.90 mmol) was added. Trideuteroiodomethane (6.95 g, 47.95 mmol) was added dropwise in an ice bath, and the internal temperature of the reaction solution was controlled to not exceed 20° C. during the dropwise addition. The dropwise addition was completed within 1 hour, and the reaction solution was warmed up to room temperature and stirred for 3 hours. The reaction solution was added with 100 mL of water, extracted with ethyl acetate (300 mL×1), separated, washed with water (100 mL×5) and saturated sodium chloride solution (100 mL), dried over anhydrous sodium sulfate and filtered. The filtrate was concentrated under reduced pressure to obtain the crude title compound 177b (4.4 g), which was directly used in the next reaction step without purification.

Step 2

[2-methoxy-5-(trideuteromethoxy)-4-pyridyl]boronic acid 177c

The crude compound 177b (4.40 g, 30.95 mmol) was dissolved in 50 mL of tetrahydrofuran. The reaction solution was cooled to −78° C., and 2M a solution of lithium diisopropylamide in tetrahydrofuran/n-heptane/ethylbenzene (30.95 mL, 61.90 mmol) was added dropwise. During the dropwise addition, the internal temperature of the reaction solution is controlled to not exceed −65° C. After completion of the addition, the reaction solution was stirred for 0.5 hour at −78° C., and then triisopropyl borate (6.63 g, 61.90 mmol) is slowly added dropwise, and the internal temperature of the reaction solution was controlled not to exceed −65 OC during the dropwise addition. After completion of the addition, the reaction solution was stirred for 2 hours at −78° C. The reaction solution was added with 80 mL of water to quench the reaction, added with ethyl acetate (80 mL), and two phases were separated. The water phase was added with 6M hydrochloric acid to adjust the pH to 3-4. A solid was precipitated, and the mixture was filtered. The filter cake was collected and naturally dried to obtain the crude title compound 177c (2.5 g), which was directly used in the next reaction step without purification.

Step 3

1-[4-chloro-2-[2-methoxy-5-(trideuteromethoxy)-4-pyridyl]phenyl]propan-1-one 177d Compound 8c (400 mg, 1.62 mmol) was dissolved in 13 mL of a mixed solvent of 1,4-dioxane and water (V:V=10:3), and then the crude compound 177c (300.57 mg, 1.62 mmol), [1,1'-bis(diphenylphosphino)ferrocene]dichloropalladium (II) (59.94 mg, 80.80 μmol) and sodium carbonate (513.91 mg, 4.85 mmol) were added. The reaction solution was warmed up to 85° C., and stirred for 16 hours. The reaction solution was naturally cooled to room temperature and filtered. The filtrate was added with 30 mL of water, and extracted with ethyl acetate (80 mL×2). The organic phases were combined, washed with saturated sodium chloride solution (50 mL), dried over anhydrous sodium sulfate, and filtered. The filtrate was concentrated under reduced pressure, and the resulting residue was purified by silica gel column chromatography with elution system B to obtain the title compound 177d (353 mg, yield: 70.74%).

Step 4 tert-butyl

2-[4-(5-chloro-2-propionyl-phenyl)-2-oxo-5-(trideuteromethoxy)-1-pyridyl]acetate 177e Compound 177d (352 mg, 1.14 mmol) and compound 7a (667.08 mg, 3.42 mmol) were mixed, heated to 100° C. and stirred for 2 hours. The reaction solution was cooled to room temperature. The resulting residue was purified by silica gel column chromatography with elution system B to obtain the title compound 177e (252 mg, yield: 54.06%).

Step 5 tert-butyl 4-tert-butoxy-2-[4-(5-chloro-2-propionylphenyl)-2-oxo-5-(trideuteromethoxy)-1-pyridyl]butyrate 177f Compound 177e (252 mg, 616.30 μmol) and compound 108b (462.66 mg, 1.85 mmol) were dissolved in 15 mL of tetrahydrofuran, and the reaction solution was cooled to −78° C., followed by dropwise addition of lithium bis (trimethylsilyl)amide solution (2.47 mL, 2.47 mmol). After stirring for 2 hours, the reaction solution was slowly added with 50 mL of water to quench the reaction at −78° C. The reaction solution was warmed up to room temperature, and extracted with ethyl acetate (60 mL×2). The organic phases were combined and washed with saturated sodium chloride solution (50 mL), dried over anhydrous sodium sulfate, and filtered. The filtrate was concentrated under reduced pressure, and the resulting residue was purified by silica gel column chromatography with elution system B to obtain the title compound 177f (80 mg, yield: 25.5%).

Step 6

4-tert-butoxy-2-[4-(5-chloro-2-propionyl-phenyl)-2-oxo-5-(trideuteromethoxy)-1-pyridyl]butyric acid 177 g Compound 177f (80 mg, 157.16 μol) was dissolved in a mixed solvent of 2 mL of water, 2 mL of methanol and 10 mL of tetrahydrofuran, and then lithium hydroxide monohydrate (33 mg, 785.78 μmol) was added. After stirring for 16 hours, the reaction solution was dropwise added with 1M hydrochloric acid to adjust the pH to 3-4, and extracted with ethyl acetate (50 mL×2). The organic phases were combined, washed with saturated sodium chloride solution (30 mL), dried over anhydrous sodium sulfate, and filtered. The filtrate was concentrated under reduced pressure to obtain the crude title compound 177g (60 mg), which was directly used in the next reaction step without purification.

Step 7

4-[[4-tert-butoxy-2-[4-(5-chloro-2-propionyl-phenyl)-2-oxo-5-(trideuteromethoxy)-1-pyridyl]butyryl] amino]benzoic acid 177h The crude compound 177g (60.09 mg, 132.66 μmol) was dissolved in 20 mL of tetrahydrofuran, and then N,N-diisopropylethylamine (68.58 mg, 530.63 μmol) and a solution of 2,4,6-tripropyl-1,3,5,2,4,6-trioxatriphosphorinane-2,4,6-trioxide in ethyl acetate (50%, 168.74 mg, 265.31 μmol) were added successively. After stirring for 10 minutes, the reaction solution was added with compound 8j (19.10 mg, 139.29 μmol), and stirred for 3 hours. The reaction solution was added with 30 mL of water, and extracted with ethyl acetate (50 mL×2). The organic phases were combined, and washed with saturated sodium chloride solution (30 mL), dried over anhydrous sodium sulfate, and filtered. The filtrate was concentrated under reduced pressure, and purified by high performance liquid chromatography (Waters 2767, elution system: acetonitrile, water, 0.05% trifluoroacetic acid) to obtain the title compound 177h (30 mg, yield: 39.53%).

MS m/z (ESI): 572.1 [M+1]

Step 8

4-[[(2S)-4-tert-butoxy-2-[4-(5-chloro-2-propionyl-phenyl)-2-oxo-5-(trideuteromethoxy)-1-pyridyl]butyryl]amino]benzoic acid 177

4-[[(2R)-4-tert-butoxy-2-[4-(5-chloro-2-propionyl-phenyl)-2-oxo-5-(trideuteromethoxy)-1-pyridyl]butyryl]amino]benzoic acid 178

Compound 177h (30 mg, 52.44 μmol) was separated chirally (separation conditions: chiral preparative column: Daicel IE 20*250 mm 5 μm; mobile phase: n-hexane/ethanol=50/50 (v/v), flow rate: 20 mL/min). The corresponding fractions were collected and concentrated under reduced pressure to obtain the title compound 177 (8 mg) and compound 178 (8 mg).

Compound 177:

MS m/z (ESI):572.1 [M+1]

Chiral HPLC analysis: retention time 7.640 minutes, (chromatographic column: CHIRAL PAK IE 4.6*150 mm 5 μm; mobile phase: n-hexane/ethanol (containing 0.1% trifluoroacetic acid)=50/50 (v/v)).

$^{1}$H NMR (400 MHz, CD$_{3}$OD) δ 8.02-8.01 (m, 2H), 7.83-7.76 (m, 3H), 7.57 (s, 1H), 7.36 (m, 2H), 6.52 (s, 1H), 5.88-5.87 (m, 1H), 3.55-3.45 (m, 2H), 3.01-2.97 (m, 2H), 2.48-2.40 (m, 2H), 1.18-1.12 (m, 12H).

Compound 178:

MS m/z (ESI):572.1 [M+1]

Chiral HPLC analysis: retention time 4.703 minutes, (chromatographic column: CHIRAL PAK IE 4.6*150 mm 5 μm; mobile phase: n-hexane/ethanol (containing 0.1% trifluoroacetic acid)=50/50 (v/v)).

$^{1}$H NMR (400 MHz, CD$_{3}$OD) δ 8.02-8.01 (m, 2H), 7.83-7.76 (m, 3H), 7.57 (s, 1H), 7.36 (m, 2H), 6.52 (s, 1H), 5.88-5.87 (m, 1H), 3.55-3.45 (m, 2H), 3.01-2.97 (m, 2H), 2.48-2.40 (m, 2H), 1.18-1.12 (m, 12H).

Examples 179, 180

4-[[(2S)-2-[4-(2-acetyl-5-chloro-phenyl)-2-oxo-5-(trideuteromethoxy)-1-pyridyl]-3-phenyl-propionyl]amino]benzoic acid 179

4-[[(2R)-2-[4-(2-acetyl-5-chloro-phenyl)-2-oxo-5-(trideuteromethoxy)-1-pyridyl]-3-phenyl-propionyl]amino]benzoic acid 180

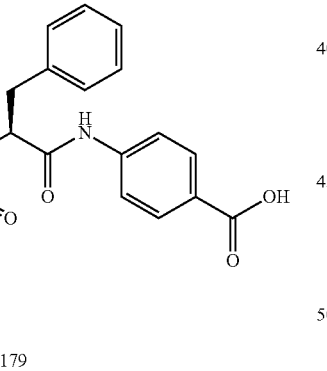

179

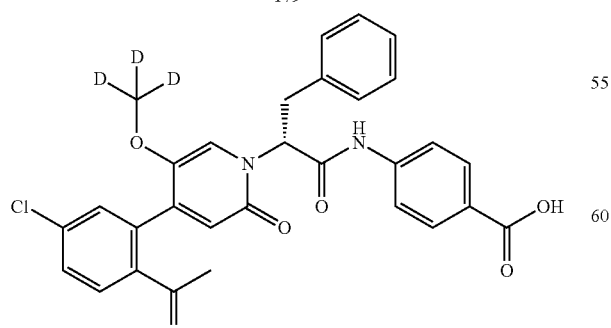

180

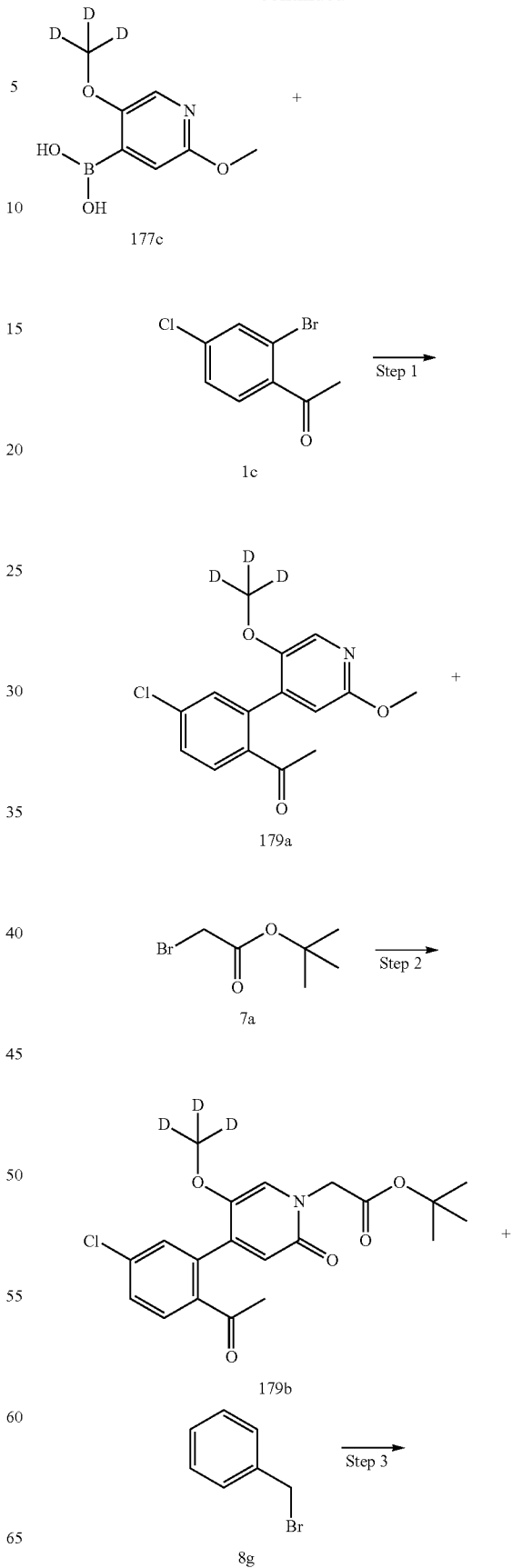

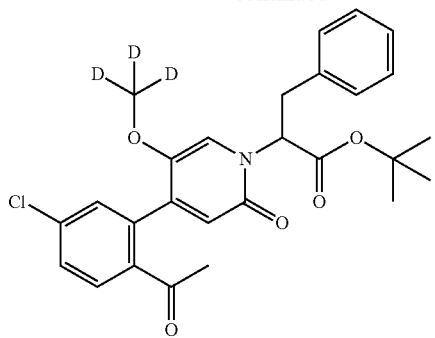

179c

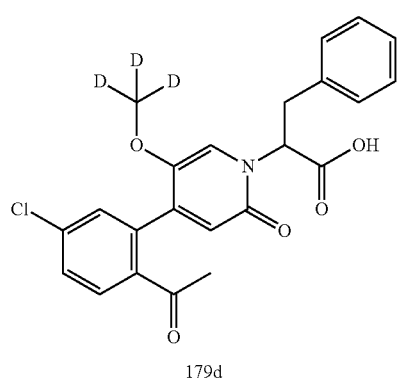

179d

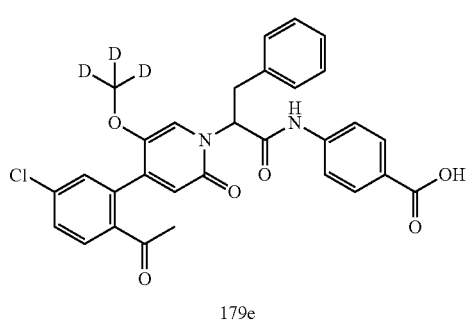

179e

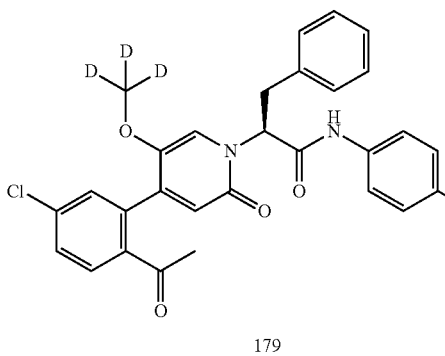

179

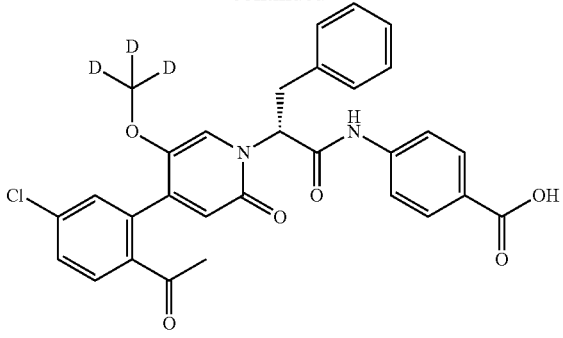

180

Step 1 to Step 5

4-[[2-[4-(2-acetyl-5-chloro-phenyl)-2-oxo-5-(trideuteromethoxy)-1-pyridyl]-3-phenyl-propionyl]amino]benzoic acid 179e In accordance with the synthetic route of compound 177h in Examples 177, 178, the starting compound 8c was replaced with the compound 1c, and the compound 108b was replaced with the compound 8g, accordingly, the title compound 179e (200 mg) was prepared.

Step 6

4-[[(2S)-2-[4-(2-acetyl-5-chloro-phenyl)-2-oxo-5-(trideuteromethoxy)-1-pyridyl]-3-phenyl-propionyl]amino]benzoic acid 179

4-[[(2R)-2-[4-(2-acetyl-5-chloro-phenyl)-2-oxo-5-(trideuteromethoxy)-1-pyridyl]-3-phenyl-propionyl]amino]benzoic acid 180

Compound 179e (200 mg, 364.96 μmol) was separated chirally (separation conditions: chiral preparative column: Daicel IE 20*250 mm 5 μm; mobile phase: n-hexane/ethanol (containing 0.1% trifluoroacetic acid)=50/50 (v/v), flow rate: 20 mL/min). The corresponding fractions were collected and concentrated under reduced pressure to obtain the title compound 179 (35 mg) and compound 180 (35 mg).

Compound 179:

MS m/z (ESI): 548.0 [M+1]

Chiral HPLC analysis: retention time 13.346 minutes, (chromatographic column: CHIRAL PAK IE 4.6*150 mm 5 μm; mobile phase: n-hexane/ethanol (containing 0.1% trifluoroacetic acid)=50/50 (v/v)).

$^1$H NMR (400 MHz, DMSO-$d_6$) δ 10.84 (s, 1H), 7.93 (d, 2H), 7.83 (d, 1H), 7.76 (d, 2H), 7.61 (d, 1H), 7.39 (d, 2H), 7.26-7.30 (m, 4H), 7.18-7.22 (m, 1H), 6.32 (s, 1H), 6.02-6.06 (m, 1H), 3.47-3.50 (m, 2H), 2.38 (s, 3H).

Compound 180:

MS m/z (ESI): 548.0 [M+1]

Chiral HPLC analysis: retention time 4.909 minutes, (chromatographic column: CHIRAL PAK IE 4.6*150 mm 5 μm; mobile phase: n-hexane/ethanol (containing 0.1% trifluoroacetic acid)=50/50 (v/v)).

$^1$H NMR (400 MHz, DMSO-$d_6$) δ 10.84 (s, 1H), 7.93 (d, 2H), 7.83 (d, 1H), 7.76 (d, 2H), 7.61 (d, 1H), 7.39 (d, 2H), 7.26-7.30 (m, 4H), 7.18-7.22 (m, 1H), 6.32 (s, 1H), 6.02-6.06 (n, 1H), 3.47-3.50 (m, 2H), 2.38 (s, 3H).

329
Examples 181, 182
4-[[(2S)-2-[4-(2-acetyl-5-chloro-phenyl)-5-methoxy-2-oxo-1-pyridyl]-3,3-dideutero-3-(2,3,4,5,6-penta-deuterophenyl)propionyl]amino]benzoic acid 181
4-[[(2R)-2-[4-(2-acetyl-5-chloro-phenyl)-5-methoxy-2-oxo-1-pyridyl]-3,3-dideutero-3-(2,3,4,5,6-penta-deuterophenyl)propionyl]amino]benzoic acid 182
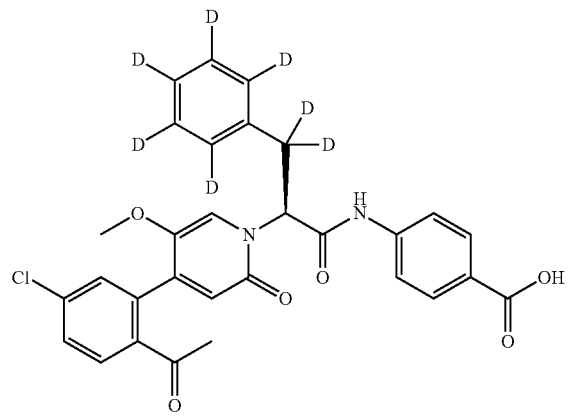
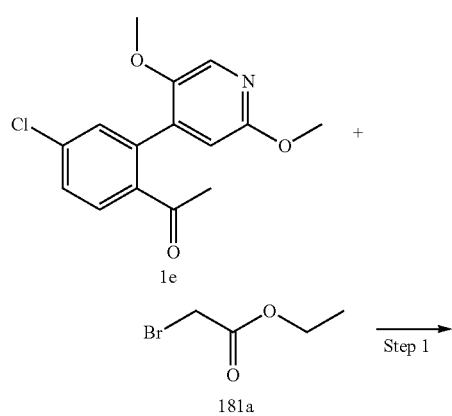
330
-continued
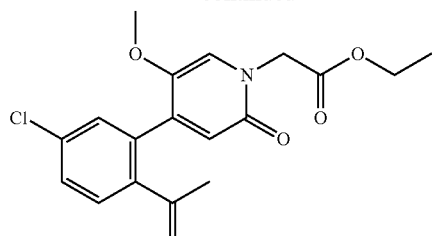
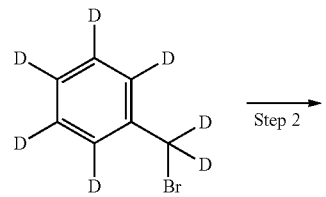
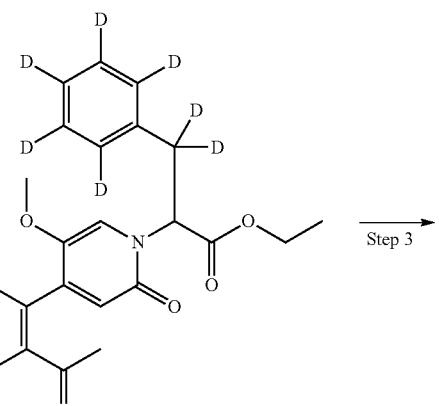
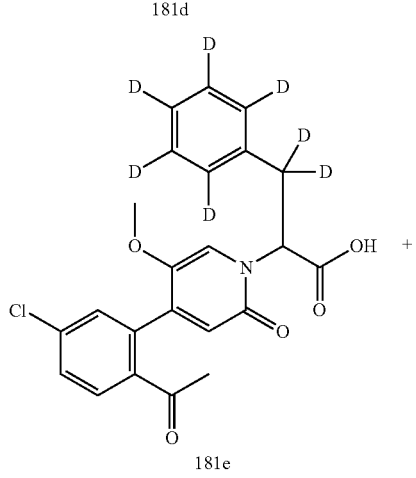
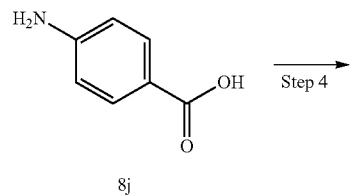

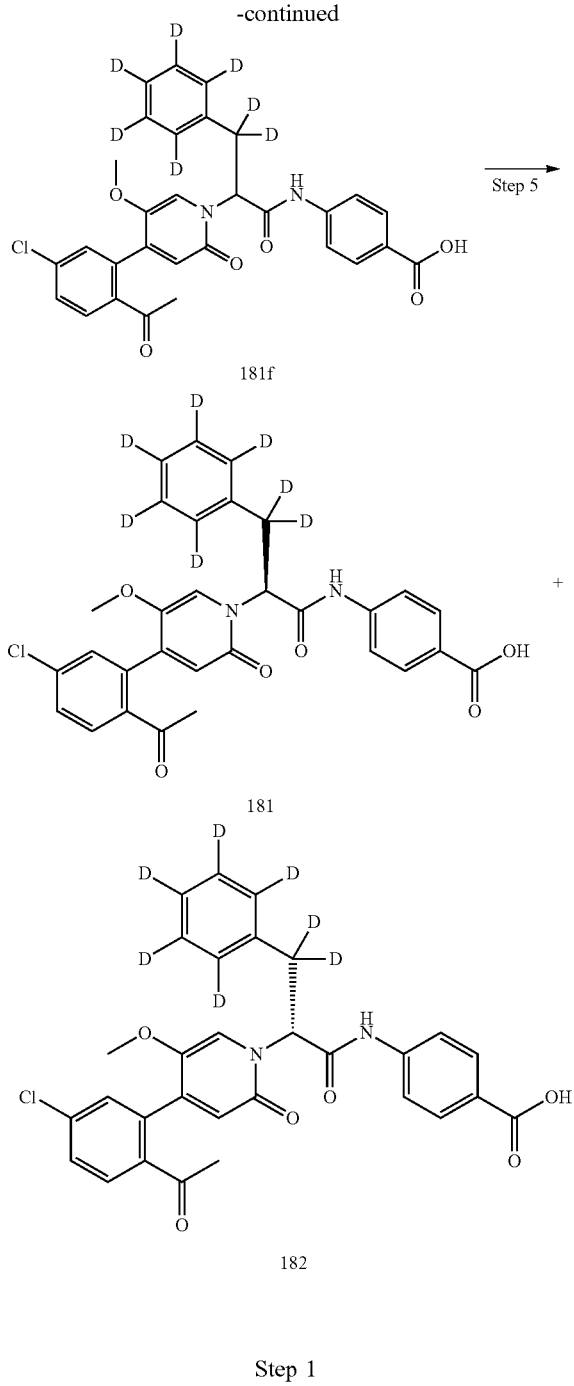

181f

181

182

Step 1 ethyl 2-(4-(2-acetyl-5-chlorophenyl)-5-methoxy-2-oxopyridin-1(2H)-yl)acetate 181b Compound 1e (20.3 g, 69.59 mmol) and ethyl 2-bromoacetate 181a (34.86 g, 208.76 mmol, prepared by a known method disclosed in "*European Journal of Organic Chemistry*, 2002, (17), 3015-3023") were mixed. The reaction solution was warmed up to 100° C. and stirred for 3 hours. After cooling to room temperature, the reaction solution was added with 50 mL of isopropanol, stirred for 16 hours to precipitate a large amount of solid, and filtered. The filter cake was washed with isopropanol (10 mL×2) and n-hexane (10 mL×2) successively. The filter cake was collected and dried in vacuo to obtain the crude title compound 181 (18.5 g), which was directly used in the next reaction step without purification.

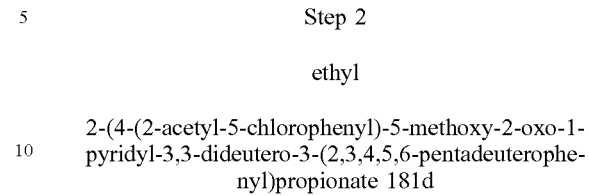

Step 2 ethyl 2-(4-(2-acetyl-5-chlorophenyl)-5-methoxy-2-oxo-1-pyridyl-3,3-dideutero-3-(2,3,4,5,6-pentadeuterophenyl)propionate 181d The crude compound 181b (18.5 g, 50.85 mm ol) was dissolved in dichloromethane (250 mL), and then 1-[bromo (dideutero)methyl]-2,3,4,5,6-pentadeutero-benzene 181c (22.64 g, 127.13 mmol, prepared by a known method disclosed in "*Angeandte Chemie-International Edition*, 2015, 54 (18), 5478-5482") was added. Under an argon atmosphere, the reaction solution was cooled to −78° C., added dropwise with lithium bis(trimethylsilyl)amide solution (25.27 m, 25.27 mm mmol), and stirred for 2 hours. The low temperature bath was removed, and the reaction solution was slowly added dropwise with 100 mL of saturated ammonium chloride solution to quench the reaction. The reaction solution was naturally warmed up to room temperature, added with 30 mL of water, and two phases were separated. The water phase was extracted with ethyl acetate (100 mL×3). The organic phases were combined, washed with saturated sodium chloride solution (100 mL), dried over anhydrous sodium sulfate, and filtered. The filtrate was concentrated under reduced pressure to obtain the crude title compound 181d (30 g), which was directly used in the next reaction step without purification.

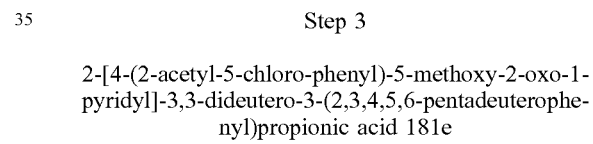

Step 3

2-[4-(2-acetyl-5-chloro-phenyl)-5-methoxy-2-oxo-1-pyridyl]-3,3-dideutero-3-(2,3,4,5,6-pentadeuterophenyl)propionic acid 181e The crude compound 181d (23.44 g, 50.85 mmol) was dissolved in 100 mL of THF, and then 1M sodium hydroxide solution (71.19 mL, 71.19 mmol) was added. After stirring for 16 hours, the reaction solution was concentrated under reduced pressure to remove tetrahydrofuran, and the resulting residue was extracted with methyl tert-butyl ether (100 mL×3). The water phase was added with concentrated hydrochloric acid to adjust the pH to 2-3, and extracted with ethyl acetate (100 mL×3). The organic phases were combined, dried over anhydrous sodium sulfate, and filtered. The filtrate was concentrated under reduced pressure, and the resulting residue was purified by silica gel column chromatography with elution system C to obtain the title compound 181e (11.7 g, yield: 53.15%).

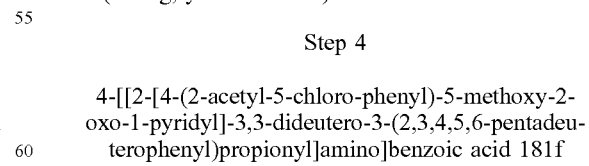

Step 4

4-[[2-[4-(2-acetyl-5-chloro-phenyl)-5-methoxy-2-oxo-1-pyridyl]-3,3-dideutero-3-(2,3,4,5,6-pentadeuterophenyl)propionyl]amino]benzoic acid 181f Compound 181e (11.7 g, 27.03 mmol) was dissolved in 60 mL of tetrahydrofuran, and then a solution of 2,4,6-tripropyl-1,3,5,2,4,6-trioxatriphosphorinane-2,4,6-trioxide (50%, 25.8 g, 40.54 mmol) in ethyl acetate was added in an ice bath. The reaction solution was stirred well, added with N,N-diisopropylethylamine (10.48 g, 81.08 mmol), stirred for 10 minutes in an ice bath, and added with compound 8j (3.71 g, 27.03 mmol) in batches. The reaction solution was warmed up to room temperature and stirred for 0.5 hour. The reaction solution was added with 100 mL of water to quench the reaction, stirred for 10 minutes, and two phases were separated. The water phase was extracted with ethyl acetate (50 mL×3). The organic phases were combined, concentrated under reduced pressure to remove the organic solvent, added with 200 mL of ethyl acetate, washed with saturated sodium chloride solution (50 mL), and concentrated under reduced pressure. The resulting residue was added to 100 mL of isopropanol, warmed up to 90° C. and stirred for 20 minutes, cooled to room temperature and stirred for 16 hours, and filtered. The filter cake was washed with isopropanol (20 mL×2) and methyl tert-butyl ether (20 mL×2) successively, and the filter cake was collected to obtain the crude title compound 181f (13.4 g), which was directly used in the next reaction step without purification.

Step 5

4-[[(2S)-2-[4-(2-acetyl-5-chloro-phenyl)-5-methoxy-2-oxo-1-pyridyl]-3,3-dideutero-3-(2,3,4,5,6-pentadeuterophenyl)propionyl]amino]benzoic acid 181

4-[[(2R)-2-[4-(2-acetyl-5-chloro-phenyl)-5-methoxy-2-oxo-1-pyridyl]-3,3-dideutero-3-(2,3,4,5,6-pentadeuterophenyl)propionyl]amino]benzoic acid 182

Compound 181f (13.4 g, 24.27 mmol) was separated chirally (separation conditions: chiral preparative column: CHIRAL PAK AD 5.0*250 mm; mobile phase: carbon dioxide/(70% ethanol/30% acetonitrile/0.1% diethylamine)=60/40 (v/v), flow rate: 59 mL/min). The corresponding fractions were collected, and concentrated under reduced pressure. The resulting residue was dissolved in 100 mL of dichloromethane, dropwise added with 50 mL of 0.5 M hydrochloric acid in an ice bath, stirred for 15 minutes at room temperature, and extracted with dichloromethane (30 mL×2). The organic phases were combined, dried over anhydrous sodium sulfate, and filtered. The filtrate was concentrated under reduced pressure. The resulting residue was added to 100 mL of methanol and stirred for 1 hour, and filtered. The filter cake was collected, washed with methanol (10 mL) and methyl tert-butyl ether (10 mL×2) successively, and dried in vacuum to obtain the title compound 181 (5.5 g) and compound 182 (4.8 g).

Compound 181:
MS m/z (ESI):552.6 [M+1]
Chiral HPLC analysis: retention time 12.738 min, chiral purity 99.8%/(chromatographic column: CHIRAL PAK IE 4.6*150 mm 5 μm; mobile phase: n-hexane/ethanol (containing 0.1% trifluoroacetic acid)=50/50 (v/v)).
$^1$H NMR (400 MHz, DMSO-$d_6$) δ 12.77 (s, 1H), 10.83 (s, 1H), 7.92 (d, 2H), 7.82 (d, 1H), 7.76 (d, 2H), 7.60 (d, 1H), 7.42 (s, 1H), 7.37 (s, 1H), 6.30 (s, 1H), 6.01 (s, 1H), 3.54 (s, 3H), 2.37 (s, 3H).

Compound 182:
MS m/z (ESI):552.6 [M+1]
Chiral HPLC analysis: retention time 4.902 minutes, chiral purity 99.1% (chromatographic column: CHIRAL PAK IE 4.6*150 mm 5 μm; mobile phase: n-hexane/ethanol (containing 0.1% trifluoroacetic acid)=50/50 (v/v))).
$^1$H NMR (400 MHz, DMSO-$d_6$) δ 12.78 (s, 1H), 10.83 (s, 1H), 7.92 (d, 2H), 7.82 (d, 1H), 7.76 (d, 2H), 7.60 (d, 1H), 7.42 (s, 1H), 7.37 (s, 1H), 6.30 (s, 1H), 6.01 (s, 1H), 3.54 (s, 3H), 2.37 (s, 3H).

Examples 183, 184

4-[[(2S)-2-[4-[5-chloro-2-(2,2,2-trideuteroacetyl)phenyl]-5-methoxy-2-oxo-1-pyridyl]-3-phenyl-propionyl]amino]benzoic acid 183

4-[[(2R)-2-[4-[5-chloro-2-(2,2,2-trideuteroacetyl)phenyl]-5-methoxy-2-oxo-1-pyridyl]-3-phenyl-propionyl]amino]benzoic acid 184

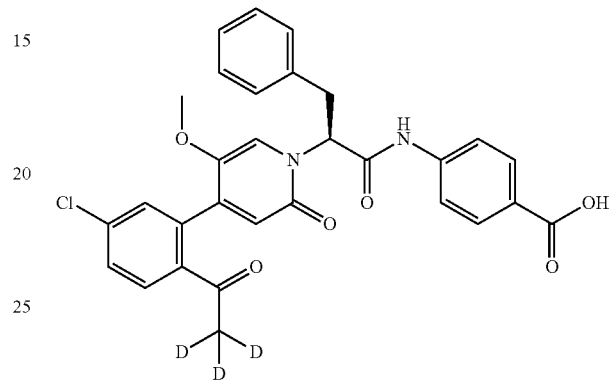

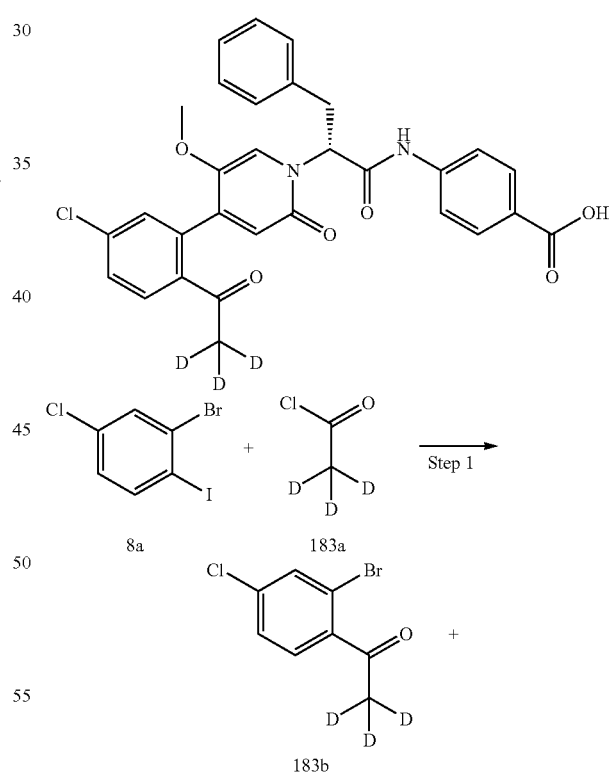

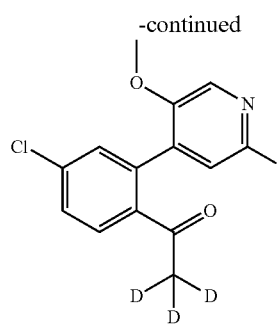
183c
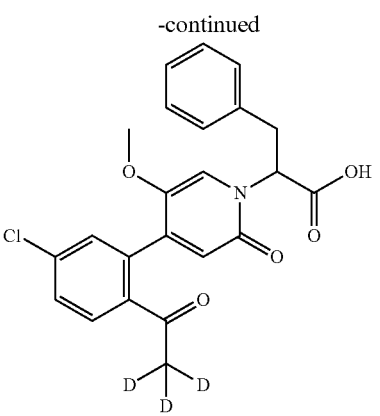
183f
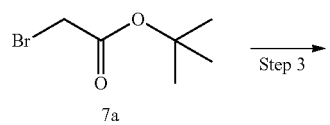
7a
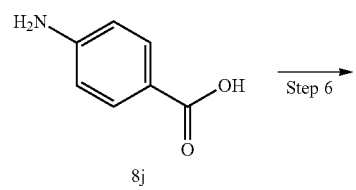
8j
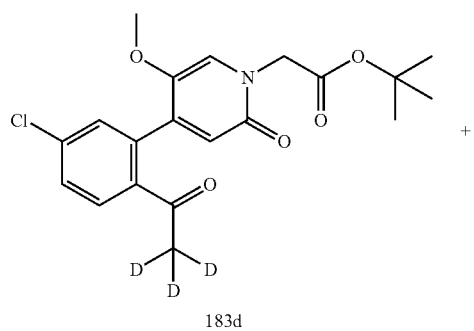
183d
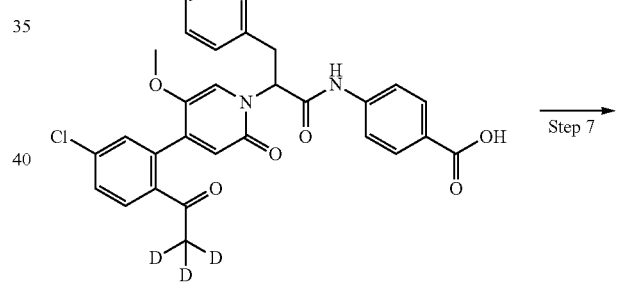
183g
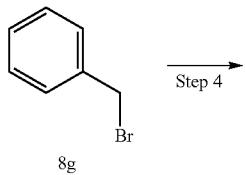
8g
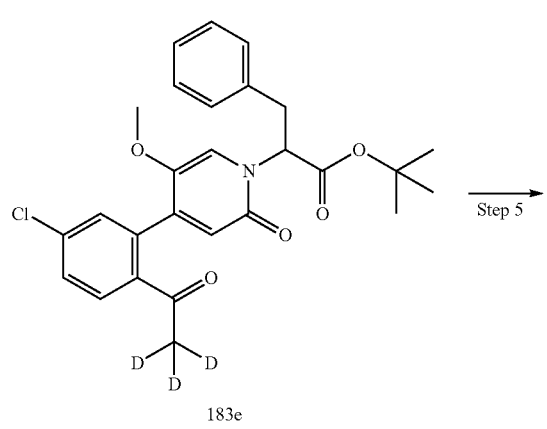
183e
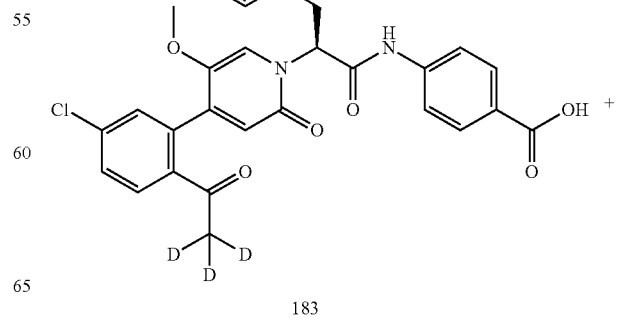
183

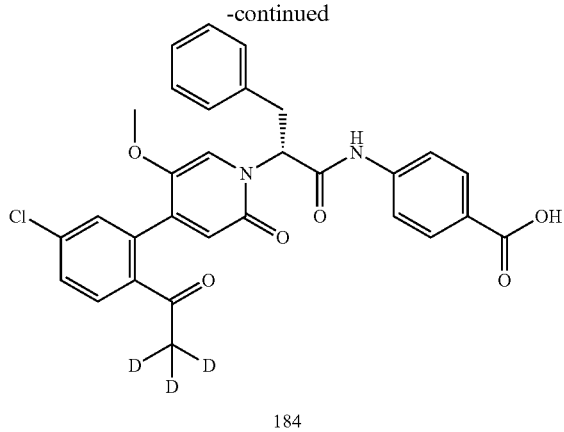

184

Step 1

1-(2-bromo-4-chloro-phenyl)-2,2,2-trideutero-ethanone 183b

Compound 8a (3.8 g, 11.97 mmol) was dissolved in 50 mL of tetrahydrofuran. The reaction solution was cooled to −10° C., slowly dropwise added with isopropylmagnesium chloride (1.6 g, 15.57 mmol), and pre-reacted for 0.5 hour, 2,2,2-Trideuteroacetyl chloride 183a (1.27 g, 15.57 mmol), lithium chloride (21.70 mg, 359.23 μmol), cuprous chloride (35.56 mg, 359.23 μmol) and aluminum trichloride (47.90 mg, 359.23 μmol) were added to 50 mL of tetrahydrofuran, and the mixture was uniformly stirred at room temperature. The reaction solution which had been pre-reacted for 0.5 hour was added to the above mixture, and reacted for 0.5 hour at room temperature. The reaction solution was washed with 50 mL of 3M hydrochloric acid, and the water phase was extracted with ethyl acetate (100 mL). The organic phase was washed with saturated sodium chloride solution (60 mL), dried over anhydrous sodium sulfate, and filtered. The filtrate was concentrated under reduced pressure to obtain the crude title compound 183b (2.5 g), which was directly used in the next reaction step without purification.

Step 2

1-[4-chloro-2-(2,5-dimethoxy-4-pyridyl)]phenyl-2,2,2-trideutero-ethanone 183c

Compound 183b (400 mg, 1.69 mmol) and compound 1d (309.45 mg, 1.69 mmol) were dissolved in a mixed solvent of 8 mL of 1,4-dioxane and 1 mL of deuteroxide, and then [1,1'-bis(diphenylphosphino)ferrocene]dichloropalladium (II) (61.88 mg, 84.56 μmol) and sodium carbonate (537.83 mg, 5.07 mmol) were added. The reaction solution was heated to 85° C. and stirred for 5 hours. The reaction solution was naturally cooled to room temperature, added with 30 mL of water, and extracted with ethyl acetate (50 mL×2). The organic phases were combined, washed with water (40 mL) and saturated sodium chloride solution (40 mL) successively, dried over anhydrous sodium sulfate, and filtered. The filtrate was concentrated under reduced pressure, and the resulting residue was purified by silica gel column chromatography with elution system B to obtain the title compound 183c (400 mg, yield: 80.24%).

MS m/z (ESI):295.4 [M+1]

Step 3 tert-butyl 2-[4-[5-chloro-2-(2,2,2-trideuteroacetyl)phenyl]-5-methoxy-2-oxo-1-pyridyl]acetate 183d Compound 183c (400 mg, 1.36 mmol) and compound 7a (794.12 mg, 4.07 mmol) were mixed, warmed up to 100° C. and stirred for 2 hours. The reaction solution was cooled to room temperature. The resulting residue was purified by silica gel column chromatography with elution system B to obtain the title compound 183d (480 mg, yield: 89.57%).

Step 4 tert-butyl 2-[4-[5-chloro-2-(2,2,2-trideuteroacetyl)phenyl]-5-methoxy-2-oxo-1-pyridyl]-3-phenyl-propionate 183e Compound 183d (480 mg, 1.22 mmol) was dissolved in 20 mL of tetrahydrofuran. After cooling to −78° C., the reaction solution was added with compound 8g (623.73 mg, 3.65 mmol), dropwise added with a solution of lithium bis(trimethylsilyl)amide in tetrahydrofuran (4.86 mL, 4.86 mmol), and stirred at −78° C. for 1.5 hours. The reaction solution was added with 4.0 mL of deuteroxide to quench the reaction, warmed up to room temperature, and extracted with ethyl acetate (50 mL×2). The organic phases were combined, washed with saturated sodium chloride solution (20 mL×2), dried over anhydrous sodium sulfate, and filtered. The filtrate was concentrated under reduced pressure, and the resulting residue was purified by silica gel column with elution system A to obtain the title compound 183e (494 mg, yield: 83.79%).

Step 5

2-[4-[5-chloro-2-(2,2,2-trideuteroacetyl)phenyl]-5-methoxy-2-oxo-1-pyridyl]-3-phenylpropionic acid 183f Compound 183e (494 mg, 1.02 mmol) was dissolved in 10 mL of dichloromethane, and then trifluoroacetic acid (2.3 g, 20.33 mmol) was added dropwise. After stirring for 2 hours, the reaction solution was concentrated under reduced pressure to obtain the crude title compound 183f (430 mg), which was directly used in the next reaction step without purification.

Step 6

4-[[2-[4-[5-chloro-2-(2,2,2-trideuteroacetyl)phenyl]-5-methoxy-2-oxo-1-pyridine]-3-phenyl-propionyl]amino]benzoic acid 183g The crude compound 183f (430 mg, 990.95 μmol) was dissolved in 10 mL of tetrahydrofuran, and then N,N-diisopropylethylamine (512 mg, 3.96 mmol) and a solution of 2,4,6-tripropyl-1,3,5,2,4,6-trioxatriphosphorinane-2,4,6-trioxide in ethyl acetate (50%, 1.51 g, 1.98 mmol) were added in an ice bath. After stirring for 10 minutes in an ice bath, the reaction solution was added with compound 8j (136 mg, 991.72 μmol), warmed up to room temperature and stirred for 2 hours. The reaction solution was added with 25 mL of ethyl acetate, washed with water (15 mL) and saturated sodium chloride solution (15 mL) successively, dried over anhydrous sodium sulfate, and filtered. The filtrate was concentrated under reduced pressure, and the resulting residue was purified by silica gel column chromatography with elution system A to obtain the title compound 183g (512 mg, yield: 94.28%).

Step 7

4-[[(2S)-2-[4-[5-chloro-2-(2,2,2-trideuteroacetyl)phenyl]-5-methoxy-2-oxo-1-pyridyl]-3-phenyl-propionyl]amino]benzoic acid 183

4-[[(2R)-2-[4-[5-chloro-2-(2,2,2-trideuteroacetyl)phenyl]-5-methoxy-2-oxo-1-pyridyl]-3-phenyl-propionyl]amino]benzoic acid 184

Compound 183g (512 mg, 934.31 μmol) was separated chirally (separation conditions: chiral preparative column Daicel IE 20*250 mm 5 μm; mobile phase: n-hexane:ethanol=60:40, flow rate: 20 mL/min). The corresponding fractions were collected and concentrated under reduced pressure to obtain the title compound 183 (200 mg) and compound 184 (200 mg).

Compound 183:
MS m/z (ESI): 548.0 [M+1]
Chiral HPLC analysis: retention time 12.947 minutes, (chromatographic column: CHIRAL PAK IE 4.6*150 mm 5 μm (with a guard column); mobile phase: ethanol (containing 0.1% trifluoroacetic acid)/n-hexane=50/50 (v/v)).
$^1$H NMR (400 MHz, DMSO-d$_6$) δ 12.77 (br, 1H), 10.85 (s, 1H), 7.93 (d, 2H), 7.83 (d, 1H), 7.77 (d, 2H), 7.62 (d, 1H), 7.41 (d, 2H), 7.32-7.26 (m, 4H), 7.22-7.18 (m, 1H), 6.32 (s, 1H), 6.06-6.02 (m, 1H), 3.55 (s, 3H), 3.50-3.43 (m, 2H).

Compound 184:
MS m/z (ESI): 548.0 [M+1]
Chiral HPLC analysis: retention time 4.840 minutes, (chromatographic column: CHIRAL PAK IE 4.6*150 mm 5 μm (with a guard column): mobile phase: ethanol (containing 0.1% trifluoroacetic acid)/n-hexane=50/50 (v/v)).
$^1$H NMR (400 MHz, DMSO-d$_6$) δ 12.77 (br, 1H), 10.85 (s, 1H), 7.93 (d, 2H), 7.83 (d, 1H), 7.77 (d, 2H), 7.62 (d, 1H), 7.41 (d, 2H), 7.32-7.26 (m, 4H), 7.22-7.18 (m, 1H), 6.32 (s, 1H), 6.06-6.02 (m, 1H), 3.55 (s, 3H), 3.50-3.43 (m, 2H).

Comparative Example 1 (Example 185)

(S)-4-(2-(4-(5-chloro-2-cyanophenyl)-5-methoxy-2-oxopyridin-1(2H)-yl)-3-(pyridin-4-yl)propanamido)benzoic acid

185

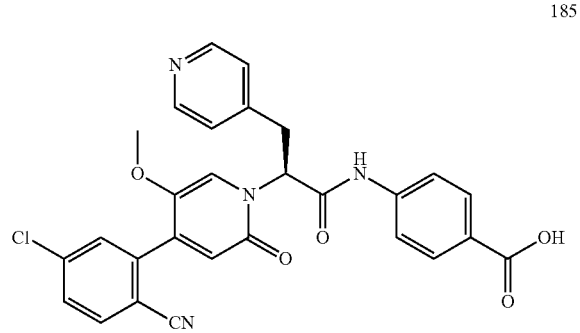

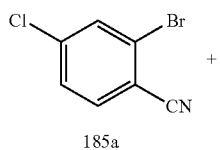
185a

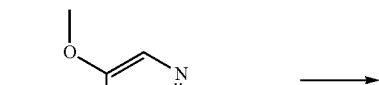
1d

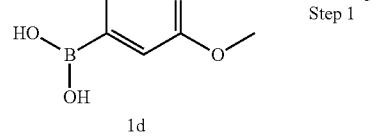
185b

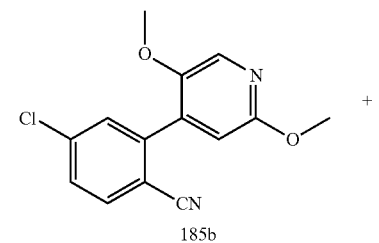
7a

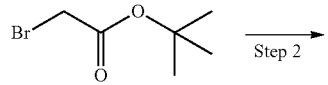
185c

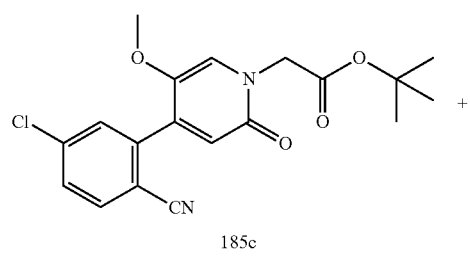
185d

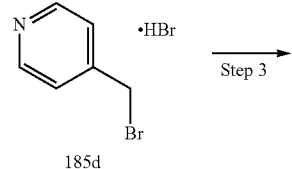
185e

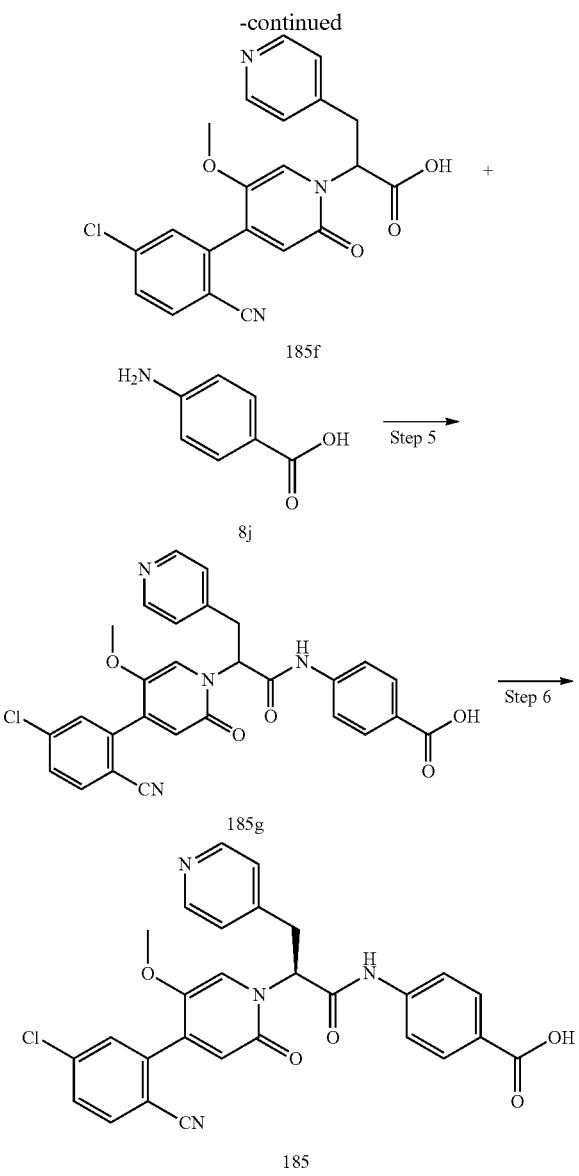

Step 1

4-chloro-2-(2,5-dimethoxypyridin-4-yl)benzonitrile 185b

2-Bromo-4-chloro-benzonitrile 185a (5.92 g, 27.33 mmol, prepared by a known method disclosed in "*Angewandte Chemie, International Edition*, 2017, 56(9), 2473-2477") was dissolved in 180 mL 1,4-dioxane, and then compound 1d (5 g, 27.33 mmol), [1,1'-bis(diphenylphosphino)ferrocene]dichloropalladium (II) (2.03 g, 2.73 mmol) and potassium carbonate (11.33 g, 81.98 mmol) were added. Under an argon atmosphere, the reaction solution was warmed up to 110° C., and stirred for 16 hours. The reaction solution was naturally cooled to room temperature, and filtered. The filtrate was concentrated under reduced pressure, and the resulting residue was purified by silica gel column with elution system B to obtain the title compound 185b (6.5 g, yield: 86.59%).

Step 2 tert-butyl 2-(4-(5-chloro-2-cyanophenyl)-5-methoxy-2-oxopyridin-1(2H)-yl)acetate 185c Compound 185b (5 g, 18.20 mmol) and compound 7a (21.30 g, 109.21 mmol) were mixed. The reaction solution was heated to 100° C., and stirred for 3 hours. The reaction solution was cooled to 90° C. and stirred for 4 hours. The reaction solution was cooled to room temperature. The resulting residue was purified by elution system B to obtain the title compound 185c (5 g, yield: 73.29%).

Step 3 tert-butyl 2-(4-(5-chloro-2-cyanophenyl)-5-methoxy-2-oxopyridin-1(2H)-yl)-3-(pyridin-4-yl)propionate 185e Compound 185c (200 mg, 533.39 μmol) and 4-(bromomethyl)pyridine hydrobromide 185d (269.92 mg, 1.07 mmol, prepared by a known method disclosed in "*Chemical Communications (Cambridge, United Kingdom)*, 2011, 47 (5), 1482-1484") were dissolved in 10 mL of tetrahydrofuran. The reaction solution was cooled to −78° C., dropwise added with lithium bis(trimethylsilyl)amide solution (3.2 mL, 3.2 mmol), and stirred for 2 hours. At −78° C., the reaction solution was slowly added with 10 mL of water to quench the reaction, and then added with 10 mL of saturated sodium chloride solution. The reaction solution was naturally warmed up to room temperature, and extracted with ethyl acetate (20 mL×3). The phases were combined, washed with saturated sodium chloride solution (20 mL×2), dried over anhydrous sodium sulfate, and filtered. The filtrate was concentrated under reduced pressure, and the resulting residue was purified by silica gel column chromatography with elution system A to obtain the title compound 185e (240 mg, yield: 96.53%).

Step 4

2-(4-(5-chloro-2-cyanophenyl)-5-methoxy-2-oxopyridin-1(2H)-yl)-3-(pyridin-4-yl)propanoic acid 185f Compound 185e (240 mg, 515.10 μmol) was dissolved in 6 mL of dichloromethane, and then trifluoroacetic acid (1 mL, 515.1 μmol) was added. The reaction solution was stirred for 16 hours, and then concentrated under reduced pressure to obtain the title compound 185f (211.1 mg), which was directly used in the next reaction step without purification.

Step 5

4-(2-(4-(5-chloro-2-cyanophenyl)-5-methoxy-2-oxopyridin-1(2H)-yl)-3-(pyridin-4-yl)propanamido)benzoic acid 185g The crude compound 185f (211 mg, 514.86 μmol) was dissolved in 10 mL of ethyl acetate, and then compound 8j (70.61 mg, 514.86 μmol), N,N-diisopropylethylamine (665.40 mg, 5.15 mmol) and a solution of 2,4,6-tripropyl-1,3,5,2,4,6-trioxatriphosphorinane-2,4,6-trioxide in ethyl acetate (50%, 982.90 mg, 1.54 mmol) were added. The reaction solution was warmed up to 68° C. and stirred for 1.5 hours. The reaction solution was cooled to room temperature, and concentrated under reduced pressure. The resulting residue was added with 20 mL of water, added with 3M hydrochloric acid to adjust the pH to 5. A solid was precipitated, and the mixture was filtered. The filter cake was collected and purified by silica gel column chromatography with elution system A to obtain the title compound 185g (35 mg, yield: 12.85%).

Step 6

(S)-4-(2-(4-(5-chloro-2-cyanophenyl)-5-methoxy-2-oxopyridin-1(2H)-yl)-3-(pyridin-4-yl)propanamido) benzoic acid 185

Compound 185g (33 mg, 62.39 μmol) was separated chirally (separation conditions: chiral preparative column: CHIRAL PAK 1G 2.5*250 mm; mobile phase: ethanol/acetic acid=100/0.1 (v/v), flow rate: 30 mL/min). The corresponding fractions were collected and concentrated under reduced pressure to obtain the title compound 185 (14 mg).

MS m/z (ESI):529.5 [M+1]

Chiral HPLC analysis: retention time 9.464 minutes, chiral purity 97.5% (chromatographic column: CHIRAL PAK IE 4.6*150 mm 5 μm; mobile phase: n-hexane/ethanol (containing 0.1% trifluoroacetic acid)=50/50 (v/v)).

$^1$H NMR (400 MHz, DMSO-$d_6$) δ 10.80 (s, 1H), 8.43-8.32 (m, 2H), 7.98-7.91 (m, 3H), 7.70-7.55 (m, 5H), 7.27-7.16 (m, 2H), 6.41-6.38 (m, 1H), 6.11-6.05 (m, 1H), 3.68-3.59 (m, 4H), 3.56-3.49 (m, 1H).

Comparative Example 2 (Example 186)

(S)-4-(tert-butoxy)-2-(4-(5-chloro-2-(3-methyl-1,2,4-oxadiazol-5-yl)phenyl)-5-methoxy-2-oxopyridin-1 (2H)-yl)-N-(quinoxalin-6-yl)butanamide 186

186

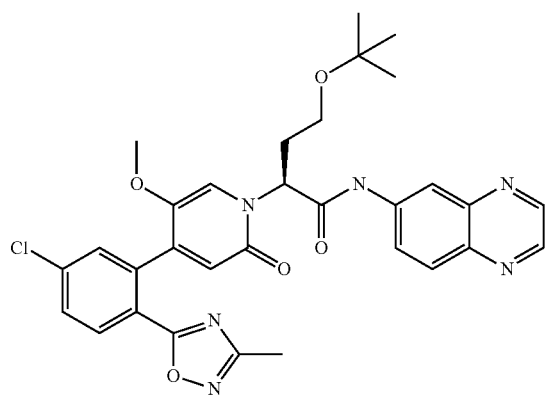

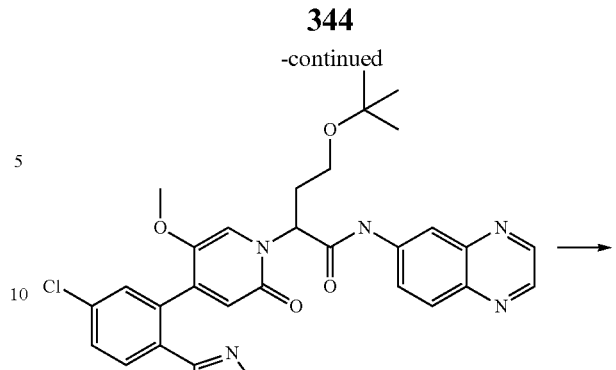

186a

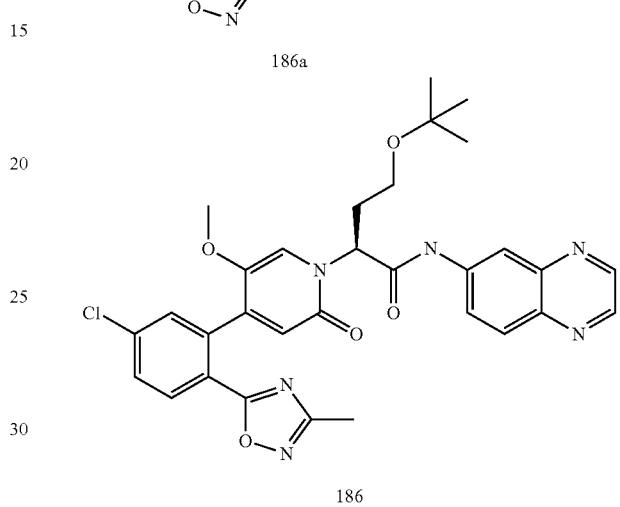

186

Compound 186a (80 mg, 132.65 μmol, prepared by a method disclosed in the patent application "WO2017005725") was separated chirally (separation conditions: chiral preparative column: Daicel IE 20*250 mm, 5 μm; mobile phase: ethanol/n-hexane=40/60 (v/v), flow rate: 15 mL/min). The corresponding fractions were collected and concentrated under reduced pressure to obtain the title compound 186 (30 mg).

MS m/z (ESI):603.2 [M+1]

Chiral HPLC analysis: retention time 9.362 minutes (chromatographic column: CHIRAL PAK IE 4.6*150 mm 5 μm; mobile phase: n-hexane/ethanol (containing 0.1% trifluoroacetic acid)=30/70 (v/v)).

$^1$H NMR (400 MHz, CD$_3$OD) δ 10.80 (s, 1H), 8.85-8.83 (m, 1H), 8.80-8.79 (m, 1H), 8.61-8.60 (m, 1H), 8.08-8.07 (m, 2H), 8.06 (s, 1H), 7.70-7.69 (m, 1H), 7.68-7.65 (m, 1H), 7.57-7.50 (m, 1H), 6.61 (s, 1H), 6.00-5.90 (m, 1H), 3.60-3.59 (m, 1H), 3.57-3.47 (s, 3H), 3.50-3.40 (m, 1H), 2.53-2.52 (m, 1H), 2.51-2.49 (m, 1H), 2.43-2.34 (m, 3H) 1.17 (s, 9H)

Biological Assay

The present invention will be further described with reference to the following test examples, but the examples should not be considered as limiting the scope of the invention.

The experimental methods in the following examples for which no specific conditions are indicated will be carried out according to conventional conditions or recommended conditions of the raw materials and the product manufacturer.

The experimental reagents for which no specific sources are indicated will be conventional reagents generally purchased from market.

Test Example 1: Biological Activity of the Compounds of the Present Invention on the Inhibition of Factor XIa Detected by Absorption Photometry 1. Experimental Materials Enzyme: Coagulation Factor XIa protease (Abcam, Art. No ab62411)

Substrate: Coagulation Factor XIa specific substrate (HY-PHEN1310 med, Art. No. Biophen cs-21(66))

Buffer: 100 mM tris-HCl, 200 mM NaCl, 0.02% Tween20, pH 7.4

2. Experimental Procedure 20 mM of test compound dissolved in 100% DMSO was diluted to 200, 20, 2, 0.2, 0.02, 0.002 μM with 100% DMSO; 1 μl of the compound was added to each well in a 384-well plate, blank and control wells were replaced with DMSO. The plate was centrifuged to remove the compound to the bottom, 10 μl (2.5 μg/ml) of FXIa enzyme solution was added to each well, and 10 μl of buffer was added to the blank well. The plate was centrifuged to remove the enzyme solution to the bottom.

Finally, 10 μl of 2 mM substrate were added to each well, and the plate was centrifuged to remove the substrate solution to the bottom.

The plate was incubated for 10 minutes at 37° C.; and then the absorbance was measured at 405 nm. The absorbance was curve-fitted by graphpad and the $IC_{50}$ obtained is shown in Table 1.

TABLE 1

$IC_{50}$ of the compounds of the present invention on the inhibition of factor XIa

| Compound No. | $IC_{50}$(FXIa)/(nM) |
| --- | --- |
| 1 | 34 |
| 2 | 19 |
| 3 | 1741 |
| 4 | 39 |
| 5 | 16 |
| 6 | 1817 |
| 7 | 34 |
| 8 | 17 |
| 9 | 14 |
| 11 | 13 |
| 12 | 42 |
| 13 | 46 |
| 16 | 100 |
| 18 | 56 |
| 19 | 5690 |
| 20 | 36 |
| 21 | 36 |
| 23 | 24 |
| 24 | 36 |
| 25 | 1523 |
| 26 | 21 |
| 27 | 66 |
| 29 | 90 |
| 37 | 29 |
| 38 | 30 |
| 39 | 38 |
| 40 | 38 |
| 41 | 39 |
| 42 | 40 |
| 43 | 47 |
| 44 | 53 |
| 45 | 69 |
| 46 | 71 |
| 47 | 82 |
| 63 | 55 |
| 64 | 58 |
| 65 | 43 |
| 66 | 34 |
| 67 | 35 |
| 68 | 47 |
| 69 | 49 |
| 70 | 54 |
| 71 | 46 |
| 72 | 21 |
| 74 | 100 |
| 75 | 100 |
| 76 | 100 |
| 78 | 72 |
| 79 | 45 |
| 80 | 40 |
| 81 | 2678 |
| 82 | 68 |
| 83 | >10000 |
| 84 | 42 |
| 85 | 92 |
| 86 | 99 |
| 87 | 73 |
| 88 | 74 |
| 89 | 42 |
| 90 | 100 |
| 91 | 50 |
| 92 | 21 |
| 93 | 42 |
| 94 | 24 |
| 95 | 7513 |
| 96 | 32 |
| 97 | 36 |
| 98 | 40 |
| 99 | 29 |
| 100 | 35 |
| 101 | 23 |
| 102 | 8213 |
| 103 | 70 |
| 104 | 8146 |
| 105 | 30 |
| 108 | 12 |
| 109 | 5456 |
| 110 | 53 |
| 111 | 18 |
| 112 | >10000 |
| 113 | 33 |
| 114 | 27 |
| 115 | >10000 |
| 119 | 45 |
| 120 | 49 |
| 121 | 67 |
| 122 | 100 |
| 123 | 100 |
| 124 | 100 |
| 141 | 66 |

TABLE 1-continued

IC$_{50}$ of the compounds of the present invention on the inhibition of factor XIa

| Compound No. | IC$_{50}$(FXIa)/(nM) |
|---|---|
| 146 | 37 |
| 147 | 56 |
| 155 | 81 |
| 158 | 46 |
| 159 | 33 |
| 160 | 68 |
| 161 | 13110 |
| 162 | 35 |
| 163 | 9114 |
| 164 | 30 |
| 166 | 42 |
| 167 | 92 |
| 168 | 43 |
| 171 | 35 |
| 172 | 8918 |
| 173 | 100 |
| 176 | 71 |
| 177 | 27 |
| 178 | 7956 |
| 179 | 31 |
| 180 | 4834 |

Conclusion: The compounds of the present invention have significant inhibition effects on FXIa.

Test Example 2: Determination of In Vitro Anticoagulant Effect of the Compounds of the Present Invention on Human Blood 1. Experimental Materials Plasma: Human blood was collected in blood collection tubes containing no anticoagulant, and then 3.8% sodium citrate (volume ratio 1:9) was added. The tubes were centrifuged at 2500 rpm for 10 minutes at room temperature, and then the plasma was collected and stored at −80° C.:

Reagents: APTT reagent (Activated partial thromboplastin time assay kit, SIEMENS, Art. No. B4218-1), calcium chloride solution;

Instrument: Coagulation instrument (SYSMEX, CA-500).

2. Experimental Testing

The divided plasma was melted at room temperature and mixed well. 10000 μM the test compound dissolved in 100% DMSO was diluted to 3000, 300, 200, 150, 75, 30, 10, 3, 0.3 μM with 100% DMSO, and the blank was 100% DMSO. The reagent, plasma, and compound were placed in corresponding positions in the coagulation instrument, and APTT detection of the compound was carried out.

3. Data Analysis

Curve fitting was carried out by graphpad and CT2 was calculated, i.e., the concentration of the compound corresponding to 2 times the APTT of the blank control. The results are shown in Table 2.

TABLE 2

CT2 of anticoagulant effect in vitro of the compounds of the present invention on human blood

| Compound No. | Inhibition of platelet aggregation CT$_2$ (μM) |
|---|---|
| 1 | 4.4 |
| 2 | 2.9 |
| 3 | >10000 |
| 5 | 2.0 |
| 6 | >10000 |
| 8 | 6.4 |
| 9 | 2.4 |
| 11 | 4.2 |
| 13 | 6.0 |
| 20 | 6.5 |
| 31 | 8.5 |
| 37 | 7.8 |
| 39 | 8.3 |
| 80 | 7.9 |
| 81 | >10000 |
| 85 | 6.5 |
| 89 | 5.7 |
| 91 | 2.1 |
| 92 | 1.2 |
| 93 | 2.9 |
| 94 | 2.2 |
| 96 | 6.7 |
| 97 | 5.4 |
| 98 | 7.6 |
| 99 | 3.5 |
| 100 | 3.3 |
| 104 | >10000 |
| 105 | 6.9 |
| 108 | 1.4 |
| 109 | >10000 |
| 111 | 3.2 |
| 112 | >10000 |
| 114 | 3.6 |
| 160 | 3.8 |
| 163 | >10000 |
| 164 | 6.4 |
| 166 | 7.2 |
| 177 | 1.5 |
| 178 | >10000 |
| 179 | 3.3 |
| 180 | >10000 |
| 181 | 2.3 |
| 183 | 2.6 |
| 184 | >10000 |

TABLE 3

Comparison of CT2 of anticoagulant effect in vitro of the compounds of the present invention with similar compounds in the published patents on human blood

| Compound No. | Inhibition of platelet aggregation CT$_2$ (μM) |
|---|---|
| 114 | 2.9 |
| Comparative Example 2 | 13.1 |

Conclusion: It can be seen from Table 2 that the compounds of the present invention have significant anticoagulant effect on human blood. It can be seen from Table 3 that the CT2 value of Example 114 of the present invention is 4.5 times that of comparative Example 2 (Example 186). The structural difference between the two compounds only lies in that the substituents on position R$^1$ are different, fully indicating that R$^1$ in formula (AI) being —C(O)R$^7$ has an unexpected effect on the anticoagulant effect of the entire molecular structure.

Pharmacokinetics Evaluation

Test Example 3. Pharmacokinetics Assay of the Compounds of the Present Invention 1. Abstract Rats were used as test animals. The drug concentration in plasma at different time points was determined by LC/MS/MS after intragastrical administration of the compounds of Example 5, Example 9, Example 1, Example 13, Example 29, Example 31, Example 80. Example 84, Example 108, Example 111, Example 114, Example 160, Example 171 and Comparative Example 1 to the rats. The pharmacokinetic behavior of the compounds of the present invention was studied and evaluated in rats.

2. Test Protocol 2.1 Test Compounds

Compounds of Example 5, Example 9, Example 11, Example 13, Example 29, Example 31, Example 80, Example 84, Example 108, Example 111, Example 114, Example 160, Example 171 and Comparative Example 1.

2.2 Test Animals 56 healthy adult Sprague-Dawley (SD) rats, half male and half female, were purchased from SINO-BRITSH SIPPR/BK LAB. ANIMAL LTD., CO, with License No.: SCXK (Shanghai) 2008-0016.

3. Process

The rats were intragastrically administered the test compounds of Example 5, Example 9. Example 11, Example 13, Example 29, Example 31, Example 80, Example 84, Example 108. Example 111, Example 114, Example 160. Example 171 and Comparative Example 1. Blood (0.2 mL) was taken from the orbital sinus before administration and at 0.5, 1.0, 2.0, 4.0, 6.0, 8.0, 11.0 and 24.0 hours after administration. The samples were stored in heparin anticoagulation tubes, and centrifuged for 10 minutes at 3500 rpm at 4° C. to separate the blood plasma. The plasma samples were stored at −20° C. The rats were fed 2 hours after administration.

The content of the test compound in the plasma of rats after intragastric administration of different concentrations of the drug was determined: 25 μL of rat plasma at each time after administration was taken and added with 30 μL (100 ng/mL) of the internal standard solution of camptothecin and 200 μL of acetonitrile, shaken vertically for 5 minutes, and centrifuged for 10 minutes (4000 rpm). 3.0 μL of the supernatant was taken from the plasma samples for LC/MS/MS analysis.

4. Results of Pharmacokinetic Parameters

Pharmacokinetic parameters of the compounds of the present invention in rats are shown below.

| | Pharmacokinetics Experiment 2 mg/kg | | | | | |
|---|---|---|---|---|---|---|
| Example No. | Plasma Concentration Cmax (ng/mL) | Area Under Curve AUC (ng/mL*h) | Half-Life T½ (h) | Mean Residence Time MRT (b) | Clearance CLz/F (ml/min/kg) | Apparent Distribution Volume Vz/F (ml/kg) |
| 5 | 244 ± 77 | 518 ± 63 | 0.89 ± 0.08 | 6.64 ± 1.77 | 65.1 ± 8.1 | 4981 ± 291 |
| 9 | 128 ± 50 | 701 ± 615 | 5.55 ± 1.79 | 6.78 ± 2.36 | 69.8 ± 35.2 | 31483 ± 16061 |
| 11 | 73.1 ± 32.3 | 125 ± 50 | 1.53 ± 0.33 | 2.12 ± 0.17 | 299 ± 110.9 | 40229 ± 18630 |
| 15 | 119 ± 78.0 | 241 ± 168 | 1.67 ± 0.48 | 2.36 ± 1.05 | 217 ± 151 | 26944 ± 14004 |
| 29 | 167 ± 45 | 382 ± 98 | 6.06 ± 2.99 | 5.00 ± 2.57 | 92.5 ± 28.3 | 45447 ± 16465 |
| 31 | 234 ± 66 | 414 ± 77 | 3.20 ± 1.41 | 3.24 ± 0.93 | 82.5 ± 14.6 | 21574 ± 6313 |
| 80 | 126 ± 50.0 | 158 ± 45.0 | 0.85 ± 0.14 | 1.85 ± 0.76 | 222 ± 55.7 | 15822 ± 2288 |
| 108 | 105 ± 23 | 452 ± 44 | 6.98 ± 1.22 | 7.33 ± 0.48 | 74.3 ± 6.9 | 44364 ± 3451 |
| 111 | 252 ± 56 | 378 ± 98 | 4.94 ± 2.33 | 4.41 ± 1.99 | 94.1 ± 30.8 | 36730 ± 13669 |
| 114 | 91.2 ± 51.3 | 168 ± 102 | 1.11 ± 0.25 | 1.67 ± 0.23 | 278 ± 182 | 24049 ± 11053 |
| 160 | 53.9 ± 20.3 | 365 ± 52 | 4.34 ± 0.35 | 8.30 ± 1.33 | 92.5 ± 12.3 | 34577 ± 4126 |
| 171 | 462 ± 116 | 701 ± 175 | 1.45 ± 0.32 | 1.71 ± 0.32 | 49.9 ± 12.5 | 6236 ± 2146 |
| 84 | 48.8 ± 8.8 | 54.6 ± 19.1 | 0.68 ± 0.14 | 1.20 ± 0.20 | 673 ± 235.2 | 37947 ± 8230 |
| Comparative Example 1 | 7.02 ± 2.97 | 7.27 ± 3.37 | — | — | — | — |

2.3 Preparation of the Test Compounds

A certain amount of the test compound was weighed, and added with 5% by volume of DMSO, 5% by volume of Tween 80 and 90% normal saline to prepare a 0.2 mg/mL colorless, clear and transparent solution.

2.4 Administration

After an overnight fast, SD rats were intragastrically administered at a dose of 2.0 mg/kg and an administration volume of 10.0 mL/kg.

Conclusion: The pharmacological absorption of the compounds of the present invention in rats is good, especially in the comparison of Example 84 with Comparative Example 1 (Example 185), the Cmax difference of the two is 6.9 times, and the AUC difference is 7.5 times. The structural difference of the two is mainly at $R^1$ position, i.e., the corresponding position in Example 84 is an acetyl group, and the corresponding position in Comparative Example 1 is a cyano group, fully indicating that $R^1$ in formula (AI) of the present invention being —C(O)$R^7$ remarkably improves the pharmacological absorption of the compound. Therefore, the compounds of the present invention have pharmacokinetic advantages.

Test Example 4: Determination of APTT Value and Pharmacokinetic Assay in Cynomolgus Monkey 1. Test Purposes Cynomolgus monkeys were used as test animals, and the APTT value at different times after the oral administration of the compound of Example 5 and the compound of Example 108 was measured by a coagulation instrument, and the pharmacodynamic properties were evaluated.

Cynomolgus monkeys were used as test animals. The drug concentration in plasma at different time points was determined by LC/MS/MS after intragastrical administration of the compounds of Example 5 and Example 108 to the cynomolgus monkey. The pharmacokinetic behavior of the compounds of the present invention was studied and evaluated in the cynomolgus monkeys.

2. Test Animals

Six male cynomolgus monkeys (101, 102, 103, 201, 202 and 203) were purchased from Guangxi Xiongsen Primate Experimental Animal Breeding Development Co., Ltd.

3. Test Compounds

Compounds of Example 5 and Example 108.

4. Preparation of the Test Compounds

A certain amount of the test compound was weighed, and added with 2% by volume of DMSO, 78% by volume of PEG400 and 20% CMC-Na (0.5%) to prepare a 3.0 mg/mL colorless, clear and transparent solution.

5. Administration

After an overnight fast, cynomolgus monkeys were intragastrically administered at a dose of 15.0 mg/kg and an administration volume of 5.0 mL/kg.

6. Test Protocol for Determination of APTT Value in Cynomolgus Monkeys 6.1 Experimental Materials Reagents: APTT reagent (Activated partial thromboplastin time assay kit, SIEMENS, Art. No. B4218-1), PEG-400 and CMC-Na:

Instrument: Coagulation instrument (SYSMEX, CA-500).

6.2 Collection and Processing of APTT Plasma Sample

Blood was taken before administration and at 1 hour, 2 hours, 4 hours, 8 hours and 12 hours after administration. About 1.8 mL of blood was taken through femoral vein puncture in each animal for each time. Anticoagulated sodium citrate was added. After the blood sample was collected, it was placed in a pre-labeled centrifuge tube, and the plasma was separated by centrifugation (centrifugation conditions: 3500 rpm, 10 minutes, 2-8° C.). The plasma was stored in a −80° C. refrigerator for APTT assay.

6.3 APTT Assay Results in Cynomolgus Monkeys

TABLE 4

Determination results of APTT value of the compounds of the present invention in cynomolgus monkeys

| No. | Animal | Before Administration | APTT (sec) | | | | |
|---|---|---|---|---|---|---|---|
| | | | 1 hour | 2 hours | 4 hours | 8 hours | 12 hours |
| Example 5 | 101 | 17.3 | 25.9 | 31.4 | 26.1 | 32.5 | 23.8 |
| | 102 | 19.1 | — | 27.2 | 22.2 | 24.8 | 23.9 |
| | 103 | 17.2 | 36.8 | 33.3 | 28.3 | 27.3 | 28.6 |
| Example 108 | 201 | 17.5 | 26.3 | 27.5 | 28.7 | 26.9 | 27.3 |
| | 202 | 18.5 | 31.2 | 27.1 | 24.1 | 20.3 | 19 |
| | 203 | 17.6 | 31.9 | 28.5 | 28.6 | 26.3 | 21.5 |

Conclusion: The compounds of the present invention has a significant prolongation of the APTT value in cynomolgus monkeys, indicating that the compounds of the present invention have a good anticoagulant effect.

7. Test Protocol of Pharmacokinetics Assay in Cynomolgus Monkeys 7.1 Experimental Process The cynomolgus monkeys were intragastrically administered the compounds of Example 5 and Example 9. 1.0 mL of blood was taken from the forelimb vein before administration and at 0.25, 0.5, 1, 2, 4, 6, 8, 12 and 24 hours after administration. The samples were stored in heparin anticoagulation tubes, and centrifuged for 10 minutes at 3500 rpm to separate the blood plasma. The plasma samples were stored at −80° C. The rats were fed 2 hours after administration.

The content of the test compound in the plasma of cynomolgus monkeys after intragastric administration of different concentrations of the drug was determined: 25 μL of cynomolgus monkey plasma at each time after administration was taken and added with 30 μL (100 ng/mL) of the internal standard solution of camptothecin and 225 μL of acetonitrile, shaken vertically for 5 minutes, and centrifuged for 10 minutes (4000 rpm). 1.0 μL of the supernatant was taken from the plasma samples for LC/MS/MS analysis.

7.2. Results of Pharmacokinetic Parameters in Cynomolgus Monkeys

Pharmacokinetic parameters of the compounds of the present invention in cynomolgus monkeys are shown below.

| Pharmacokinetics Experiment 15 mg/kg | | | | | |
|---|---|---|---|---|---|
| No. | Plasma Concentration Cmax (ng/mL) | Area Under Carve AUC (ng/mL*h) | Half-Life T½ (b) | Mean Residence Time MRT (h) | Clearance CLz/F (ml/min/kg) | Apparent Distribution Volume Vz/F (ml/kg) |
| Example 5 | 688 ± 560 | 4953 ± 2881 | 5.86 ± 1.10 | 9.63 ± 0.78 | 62 ± 32 | 30409 ± 12559 |
| Example 108 | 295 ± 102 | 2701 ± 1344 | 6.32 ± 1.47 | 8.81 ± 3.65 | 120 ± 83 | 59145 ± 26224 |

Conclusion: The compounds of the present invention have good pharmacological absorption in cynomolgus monkeys and have pharmacokinetic advantages.

What is claimed is:

1. A compound that is (S)-4-(2-(4-(2-acetyl-5-chlorophenyl)-5-methoxy-2-oxopyridin-1(2H)-yl)-3-phenylpropanamido)benzoic acid:

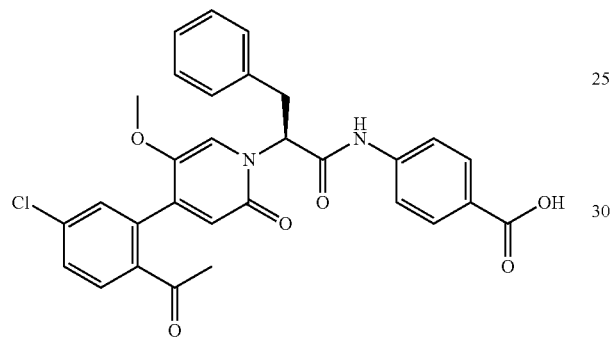

5 or a tautomer, mesomer, racemate, enantiomer, diastereomer, or mixture thereof, or a pharmaceutically acceptable salt thereof.

2. A compound that is (S)-4-(4-(tert-butoxy)-2-(4-(5-chloro-2-propionylphenyl)-5-methoxy-2-oxopyridin-1(2H)-yl)butanamido)benzoic acid:

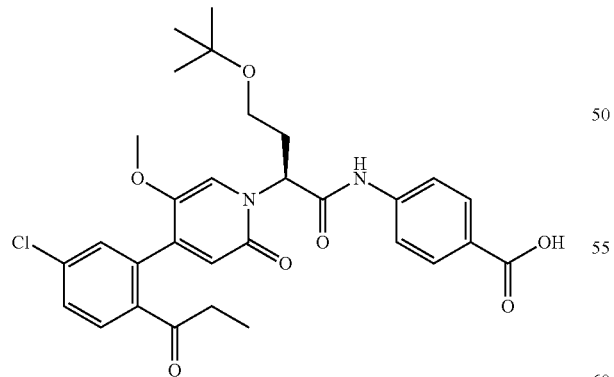

108 or a tautomer, mesomer, racemate, enantiomer, diastereomer, or mixture thereof, or a pharmaceutically acceptable salt thereof.

3. A pharmaceutical composition comprising (S)-4-(2-(4-(2-acetyl-5-chlorophenyl)-5-methoxy-2-oxopyridin-1(2H)-yl)-3-phenylpropanamido)benzoic acid:

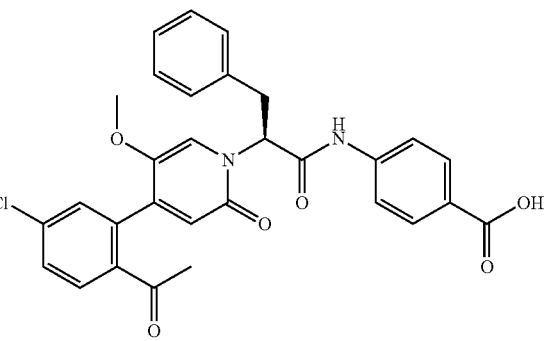

5 or a tautomer, mesomer, racemate, enantiomer, diastereomer, or mixture thereof, or a pharmaceutically acceptable salt thereof and a pharmaceutically acceptable carrier.

4. A pharmaceutical composition comprising (S)-4-(4-(tert-butoxy)-2-(4-(5-chloro-2-propionylphenyl)-5-methoxy-2-oxopyridin-1(2H)-yl)butanamido)benzoic acid:

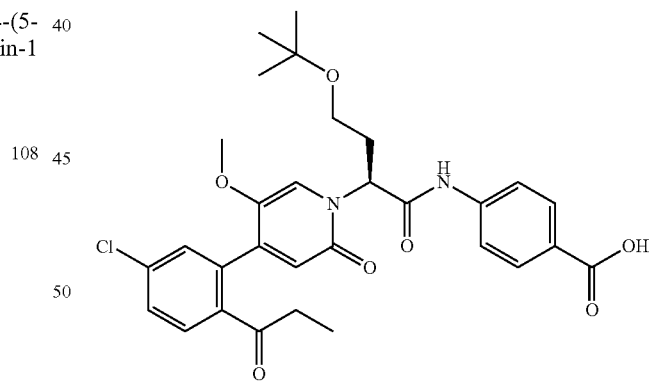

108 or a tautomer, mesomer, racemate, enantiomer, diastereomer, or mixture thereof, or a pharmaceutically acceptable salt thereof and a pharmaceutically acceptable carrier.

5. A method for preventing and/or treating a factor XIa mediated disease, comprising administering to a patient in need thereof an effective amount of the pharmaceutical composition according to claim 3.

6. A method for preventing and/or treating a cardiovascular and cerebrovascular disease, comprising administering to a patient in need thereof an effective amount of the pharmaceutical composition according to claim 3.

7. A method for preventing and/or treating a factor XIa mediated disease, comprising administering to a patient in need thereof an effective amount of the pharmaceutical composition according to claim 4.

8. A method for preventing and/or treating a cardiovascular and cerebrovascular disease, comprising administering to a patient in need thereof an effective amount of the pharmaceutical composition according to claim 4.

* * * * *